(12) United States Patent
Baiazitov et al.

(10) Patent No.: US 10,584,115 B2
(45) Date of Patent: Mar. 10, 2020

(54) SUBSTITUTED PYRIDINE AND PYRAZINE BMI-1 INHIBITORS

(71) Applicant: PTC Therapeutics, Inc., South Plainfield, NJ (US)

(72) Inventors: Ramil Baiazitov, East Brunswick, NJ (US); Soongyu Choi, Princeton, NJ (US); Wu Du, Cranbury, NJ (US); Seongwoo Hwang, Edison, NJ (US); Chang-Sun Lee, Belle Mead, NJ (US); Ronggang Liu, Berwyn, PA (US); Young-Choon Moon, Belle Mead, NJ (US); Steven D. Paget, Hillsborough, NJ (US); Hongyu Ren, Dayton, NJ (US); Nadiya Sydorenko, Princeton, NJ (US); Richard Gerald Wilde, Somerville, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

(21) Appl. No.: 15/037,514

(22) PCT Filed: Nov. 21, 2013

(86) PCT No.: PCT/US2013/071142
§ 371 (c)(1),
(2) Date: May 18, 2016

(87) PCT Pub. No.: WO2015/076800
PCT Pub. Date: May 28, 2015

(65) Prior Publication Data
US 2016/0280685 A1 Sep. 29, 2016

(51) Int. Cl.
| | |
|---|---|
| C07D 403/04 | (2006.01) |
| C07D 401/14 | (2006.01) |
| C07F 5/04 | (2006.01) |
| A61K 31/69 | (2006.01) |
| C07D 471/04 | (2006.01) |
| A61K 31/519 | (2006.01) |
| C07D 405/14 | (2006.01) |
| C07D 417/14 | (2006.01) |
| C07D 401/04 | (2006.01) |
| A61K 31/4985 | (2006.01) |
| C07D 413/04 | (2006.01) |
| C07D 403/14 | (2006.01) |
| A61K 45/06 | (2006.01) |
| C07D 487/04 | (2006.01) |
| A61K 31/497 | (2006.01) |
| C07D 513/04 | (2006.01) |

(52) U.S. Cl.
CPC .......... *C07D 403/04* (2013.01); *A61K 31/497* (2013.01); *A61K 31/4985* (2013.01); *A61K 31/519* (2013.01); *A61K 31/69* (2013.01); *A61K 45/06* (2013.01); *C07D 401/04* (2013.01); *C07D 401/14* (2013.01); *C07D 403/14* (2013.01); *C07D 405/14* (2013.01); *C07D 413/04* (2013.01); *C07D 417/14* (2013.01); *C07D 471/04* (2013.01); *C07D 487/04* (2013.01); *C07D 513/04* (2013.01); *C07F 5/04* (2013.01)

(58) Field of Classification Search
CPC .................................................. C07D 403/04
USPC .......................................................... 514/64
See application file for complete search history.

(56) References Cited

U.S. PATENT DOCUMENTS

| | | | |
|---|---|---|---|
| 3,978,055 A | 8/1976 | Fauran et al. | |
| 5,750,531 A | 5/1998 | Lee et al. | |
| 7,226,927 B2 | 6/2007 | Cai et al. | |
| 7,282,504 B2 | 10/2007 | Armistead et al. | |
| 7,494,997 B2 | 2/2009 | Asaki et al. | |
| 7,582,630 B2 | 9/2009 | Dickerson et al. | |
| 7,803,801 B2 | 9/2010 | Kodama et al. | |
| 7,855,205 B2 | 12/2010 | Huang et al. | |
| 7,968,556 B2 | 6/2011 | Mortensen et al. | |
| 8,222,262 B2 | 7/2012 | Eriksen et al. | |
| 8,329,737 B2* | 12/2012 | Styles .................. | C07D 235/30 514/394 |
| 8,383,634 B2 | 2/2013 | Mortensen et al. | |
| 8,415,358 B2* | 4/2013 | Eriksen ................ | C07D 401/04 514/255.05 |
| 2002/0052386 A1 | 5/2002 | Armistead et al. | |
| 2003/0004174 A9 | 1/2003 | Armistead et al. | |
| 2003/0055044 A1 | 3/2003 | Davies et al. | |
| 2003/0060629 A1 | 3/2003 | Kuo et al. | |
| 2003/0199534 A1 | 10/2003 | Armistead et al. | |
| 2004/0043388 A1 | 3/2004 | Come et al. | |
| 2004/0097503 A1 | 5/2004 | Cai et al. | |

(Continued)

FOREIGN PATENT DOCUMENTS

| | | |
|---|---|---|
| CA | 2755935 A1 | 8/2010 |
| CA | 2805435 C | 5/2017 |

(Continued)

OTHER PUBLICATIONS

Compound (CAS RN 1380971-24-3) (2012).*

(Continued)

*Primary Examiner* — Yong L Chu
(74) *Attorney, Agent, or Firm* — Hoffmann & Baron, LLP

(57) ABSTRACT

Amine substituted pyridine and pyrazine compounds and forms thereof that inhibit the function and reduce the level of B-cell specific Moloney murine leukemia virus integration site 1 (Bmi-1) protein and methods for their use to inhibit Bmi-1 function and reduce the level of Bmi-1 to treat a cancer mediated by Bmi-1 are described herein.

17 Claims, No Drawings

(56) References Cited

U.S. PATENT DOCUMENTS

| | | |
|---|---|---|
| 2004/0110821 A1 | 6/2004 | Konkel et al. |
| 2005/0113342 A1 | 5/2005 | Honold et al. |
| 2005/0203114 A1 | 9/2005 | Armistead et al. |
| 2008/0182852 A1 | 7/2008 | Johnson et al. |
| 2009/0042890 A1 | 2/2009 | Mortensen et al. |
| 2009/0325989 A1 | 12/2009 | Eriksen et al. |
| 2010/0204230 A1* | 8/2010 | Blurton ............... C07D 213/74 514/235.8 |
| 2010/0286161 A1 | 11/2010 | Eriksen et al. |
| 2010/0292262 A1 | 11/2010 | Dorsch et al. |
| 2011/0039873 A1 | 2/2011 | Gaeta et al. |
| 2011/0098301 A1 | 4/2011 | Dixon et al. |
| 2011/0190239 A1 | 8/2011 | Moon et al. |
| 2011/0224217 A1 | 9/2011 | Mortensen et al. |
| 2012/0171245 A1 | 7/2012 | Charifson et al. |
| 2013/0035331 A1 | 2/2013 | Moussy et al. |

FOREIGN PATENT DOCUMENTS

| | | |
|---|---|---|
| CN | 1155281 A | 7/1997 |
| CN | 1429222 A | 7/2003 |
| CN | 101516873 A | 8/2009 |
| CN | 101679432 A | 3/2010 |
| EP | 2454257 B1 | 8/2013 |
| JP | 2006-045119 A | 2/2006 |
| JP | 201136925 A | 7/2011 |
| WO | 96/05177 A1 | 2/1996 |
| WO | 98/43968 A1 | 10/1998 |
| WO | 00/29403 A1 | 5/2000 |
| WO | 2001/014375 A1 | 3/2001 |
| WO | 01/30778 A1 | 5/2001 |
| WO | 2001/060816 A1 | 8/2001 |
| WO | 2001/072745 A1 | 10/2001 |
| WO | 02/22608 A1 | 3/2002 |
| WO | 02/066481 A1 | 8/2002 |
| WO | 2002/066480 A2 | 8/2002 |
| WO | 03/004492 A1 | 1/2003 |
| WO | 2003/000682 A1 | 1/2003 |
| WO | 03/011837 A1 | 2/2003 |
| WO | 03/075828 A2 | 9/2003 |
| WO | 2004/005282 A1 | 1/2004 |
| WO | 2004/007407 A1 | 1/2004 |
| WO | 2004/021989 A1 | 3/2004 |
| WO | 2005/095400 A1 | 10/2005 |
| WO | 2008/040753 A1 | 4/2008 |
| WO | 2008/079933 A1 | 7/2008 |
| WO | 2008/132502 A1 | 11/2008 |
| WO | 2009/013614 A1 | 1/2009 |
| WO | 2009/064835 A1 | 5/2009 |
| WO | 2009/071701 A1 | 6/2009 |
| WO | 2009/092431 A1 | 7/2009 |
| WO | 2009/093049 A1 | 7/2009 |
| WO | 2009/131687 A2 | 10/2009 |
| WO | 2010/002985 A1 | 1/2010 |
| WO | 2010/026087 A1 | 3/2010 |
| WO | 2010/110685 A2 | 9/2010 |
| WO | 2010/138575 A1 | 12/2010 |
| WO | 2011/005119 A1 | 1/2011 |
| WO | 2011/008830 A1 | 1/2011 |
| WO | 2011/008915 A1 | 1/2011 |
| WO | 2011/101161 A1 | 8/2011 |
| WO | 2011/121418 A1 | 10/2011 |
| WO | 2012/035023 A1 | 3/2012 |
| WO | 2012/050884 A1 | 4/2012 |
| WO | 2012/078777 A1 | 6/2012 |
| WO | 2012/115478 A1 | 8/2012 |
| WO | 2012/115480 A1 | 8/2012 |
| WO | 2013/004332 A1 | 1/2013 |
| WO | 2014/081906 A1 | 5/2014 |
| WO | 2014/081944 A2 | 5/2014 |
| WO | 2014/081955 A1 | 5/2014 |

OTHER PUBLICATIONS

Compound (CAS RN 1348721-67-4) (2011).*
Kassis et al., European Journal of Medicinal Chemistry (2011), 46, p. 5416-5434.*
Kassis et al. Euro. J. of Med. Chem., (2011), 46(11), p. 5416-5434.*
Suzuki et al., Structure-Activity Relationships of Pyrazine-Based CK2 Inhibitors: Synthesis and Evaluation of 2,6-Disubstituted Pyrazines and 4,6-DisubstitutedPyramidines. Archiv der Pharmazie 341(9):554-561, 2008. Abstract only.
International Search Report in PCT/US2013/071142, dated May 20, 2014.
Written Opinion of the International Searching Authority in PCT/US2013/071142, dated May 20, 2014.
Examination Report for Australian Patent Application No. 2013399092, dated Dec. 1, 2017.
Johns, B. A. et al., "Pyrazolopyridine antiherpetics: SAR of C2' and C7 amine substituents", Bioorg. Med. Chem., 2005, vol. 13, pp. 2397-2411.
Vilchis-Reyes, M. A. et al., "Synthesis and cytotoxic activity of 2-methylimidazo[1,2-a]pyridine- and quinoline-substituted 2-aminopyrimdine derivatives", European Journal of Medinical Chemistry, 2010, vol. 45, pp. 379-386.
Shapiro et al., "Guanamines. IV. Pyridylguanamines", J. Org. Chem., 1960, vol. 25(3):384-387.
Blaine R. Copenheaver, International Search Report in PCT/US2013/071153, 5 pages, dated May 20, 2014, USPTO, Alexandria, Virginia, 22313-1450.
Blaine R. Copenheaver, Written Opinion of the International Searching Authority in PCT/US2013/071153, 7 pages, dated May 20, 2014, USPTO, Alexandria, Virginia, 22313-1450.
Supporting Information (2 parts, pp. 1-54) for "Whitten et al., "Rapid Microscale Synthesis, a New Method for Lead Optimization Using Robotics and Solution Phase Chemistry: Application to the Synthesis and Optimization of Corticotropin-Releasing Factor1 Receptor Antagonists", 1996, vol. 39(22):4354-4357."
Examiner's Search Strategy and Results in U.S. Appl. No. 15/038,039, dated May 5, 2017, 139 results, 805 pages.
Excerpts from "Examiners Search Strategy and Results in U.S. Appl. No. 15/038,039, dated May 5, 2017, 139 results, 305 pages", dated Nov. 13, 2017, 6 pages.
Thirumurthy Madhavan, et al., "3D-QSAR studies of JNK1 inhibitors utilizing various alignment methods", 2011, Chemical Biology & Drug Design, vol. 79 (1), p. 53-67.
Phuong T. Le, et al., "Design and synthesis of a novel pyrrolidinyl pyrido pyrimidinone derivative as a potent inhibitor of PI3Kα and mTOR", Bioorganic & Medicinal Chemistry Letters, 2012, vol. 22 (15), p. 5098-5103.
Kirk E. Hevener, et al., "Discovery of a Novel and Potent Class of F. tularensis Enoyl-Reductase (FabI) Inhibitors by Molecular Shape and Electrostatic Matching", Journal of Medicinal Chemistry, Jan. 12, 2012, vol. 55 (1), p. 268-279.
Daniel Moser, et al., "Dual-Target Virtual Screening by Pharmacophore Elucidation and Molecular Shape Filtering", ACS Medicinal Chemistry Letters, 2012, vol. 3 (2), p. 155-158.
Junji Miyata, et al., "Orally available pyridinylpyrimidine derivatives as novel RANKL-induced osteoclastogenesis inhibitors", Bioorganic & Medicinal Chemistry Letters, 2012, vol. 22 (17), p. 5681-5684.
International Search Report for PCT/US2013/071132, dated May 20, 2014.
Written Opinion for PCT/US2013/071132, dated May 20, 2014.
Bregman et al., "Identification of a Potent, State-Dependent Inhibitor of Nav 1.7 With Oral Efficacy in the Formalin Model of Persistent Pain", Journal of Medicinal Chemistry, 2011, vol. 54(13):4427-4445.
"Ma et al., "Combinatorial Synthesis of Substituted Biaryls and Heterocyclic Arylamines", Journal of Combinatorial Chemistry, 2004, vol. 6(3):426-430".
Sabat et al., "The Development of 2-Benzimidazole Substituted Pyrimidine Based Inhibitors of Lymphocyte Specific Kinase (LCK)", Bioorganic & Medicinal Chemistry Letters, Sep. 25, 2006, vol. 16(23):5973-5977.
Sirisoma et al., "Discovery of substituted 4-anilino-2-(2-pyridyl)pyrimidines as a new series of apoptosis inducers using a

(56) References Cited

OTHER PUBLICATIONS cell- and caspase-based high throughput screening assay. Part 1: Structure-activity relationships of the 4-anilino group", Bioorganic & Medicinal Chemistry, Aug. 21, 2006, vol. 14(23):7761-7773.
CAS Reg. No. 396135-22-1, Feb. 27, 2002.
CAS Reg. No. 79871-84-4, Nov. 16, 1984.
CAS Reg. No. 79871-85-5, Nov. 16, 1984.
CAS Registry No. 1203795-20-3; STN Entry Date Jan. 27, 2010; 1,4-Benzenediamine, N1,N1-dimethyl-N4-[4-(2-methylimidazo[1,2-a]pyrimidin-3-yl)-2-pyrimidinyl].
CAS Registry No. 1203795-19-0; STN Entry Date Jan. 27, 2010; 2-Pyrimidinamine, N-(4-methoxyphenyl)-4-(2-methylimidazo[1,2-a]pryimidin-3-yl)-.
Sagi, et al., "Synthesis and biological evaluation of novel pyrimidine derivatives as sub-micromolar affinity ligands of GalR2", Bioorganic & Medicinal Chemistry Letters, Sep. 12, 2011, vol. 1(23):7210-7215.
Paul, et al., "Preparation of Substituted N-Phenyl-4-aryl-2-pyrimidinamines as Mediator Release Inhibitors", Journal of Medicinal Chemistry, Sep. 17, 1993, vol. 36(19):216-2725.
Johns, et al., "Pyrazolo[5-a]pyridines: synthetic approaches to a novel class of Antiherpetics", Tetrahedron, Nov. 3, 2003, vol. 59(45):9001-9011.

Choung et al., "4-(Isoxazol-3-yl)pyrimidines from Pryimidinyl Nitrile Oxides", Synlett, Jan. 1, 2008, vol. 19, pp. 3036-3040.
Blaine R. Copenheaver, International Search Report in PCT/US2013/071216, 4 pages, dated May 20, 2014, USPTO, Alexandria, VA.
Blaine R. Copenheaver, Written Opinion of the International Searching Authority in PCT/US2013/071216, 7 pages, dated May 20, 2014, USPTO, Alexandria, VA.
N. Sirisoma, et al., "Discovery of substituted 4-anilino-2-arylpyrimidines as a new series of apoptosis inducers using a cell- and caspase-based high throughput screening assay. 2. Structure-activity relationships of the 2-aryl group", Bioorg. Med. Chem. Lett. 19, 2009, 2305-2309.
Y. V. V. Srikanth, 2011 PhD Thesis: "Synthesis of Bisindole Conjugates and 2-Anilinonicotinyl Linked Oxadiazoles/2-Aminobenzothiazoles/Triazolobenzothiadiazines as Potential Anticancer Agents" Acharya Nagarjuna University, Jun. 2011.
Chen, et al., "Development of pyrimidine-based inhibitors of Janus tyrosine kinase 3", Bioorganic & Medicinal Chemistry Letters 16 (2006) 5633-5638.
V. Chubanov et al., "Natural and synthetic modulators of SK (Kca2) potassium channels inhibit magnesium-dependent activity of the kinase-coupled cation channel TRPM7", 2012, British Journal of Pharmacology, vol. 166, pp. 1357-1376.

* cited by examiner

SUBSTITUTED PYRIDINE AND PYRAZINE BMI-1 INHIBITORS

INTRODUCTION

Substituted pyridine and pyrazine compounds that inhibit the function of the B-cell specific Moloney murine leukemia virus integration site 1 (Bmi-1) protein and reduce the level thereof and methods of using such compounds to treat a cancer mediated by Bmi-1 are described. More particularly, amine substituted pyridine and pyrazine compounds that inhibit Bmi-1 function and reduce the level of Bmi-1 are useful for treating a cancer mediated by Bmi-1.

BACKGROUND

Bmi-1 was originally identified by its over-expression in various leukemias and lymphomas. Subsequently, Bmi-1 has been shown to have oncogenic activity when overexpressed in normal cells and to play a role in the maintenance of cancer stem cell populations. Bmi-1 is elevated in many tumor types and is important in hematologic cancers and many solid tumors, including brain cancers. Reduction of Bmi-1 levels in tumor cells by siRNA causes apoptosis and/or cell senescence and increases susceptibility to cytotoxic agents. Bmi-1 serves as the key regulatory component of the PRC1 complex (polycomb repressive complex-1), but has no enzymatic activity. Therefore, targeting Bmi-1 by traditional drug discovery methods has been problematic.

Since Bmi-1 levels within cells are tightly regulated through both transcriptional and post-transcriptional mechanisms, this regulation can be exploited to target this important protein. Accordingly, there remains a need to provide compounds that inhibit Bmi-1 function and reduce the level of Bmi-1 to treat a cancer mediated by Bmi-1.

SUMMARY

Certain amine substituted pyridine and pyrazine compounds that inhibit Bmi-1 function and reduce the level of Bmi-1 and methods for their use to treat a cancer mediated by Bmi-1 are described herein.

A compound of Formula (I) is described:

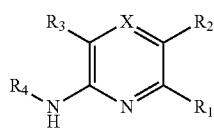

(I)

wherein X, $R_1$, $R_2$, $R_3$ and $R_4$ are as defined herein, including forms and pharmaceutical compositions thereof, and methods of using such compounds, forms or compositions thereof to treat a cancer mediated by Bmi-1 in a human subject in need thereof.

DETAILED DESCRIPTION

Amine substituted pyridine and pyrazine compounds for use in inhibiting Bmi-1 function and reducing the level of Bmi-1 and in methods for treating a cancer mediated by Bmi-1 thereby are described.

In one embodiment is a compound of Formula (I):

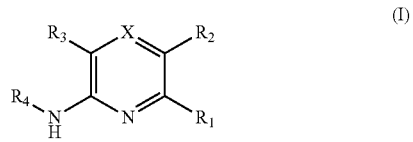

(I)

or a form thereof, wherein
X is C—$R_5$ or N—$R_8$;
$R_1$ is heteroaryl or heterocyclyl optionally substituted on a carbon atom ring member with one, two, three or four $R_6$ substituents or on a nitrogen atom ring member with an oxygen atom substituent to form an N-oxide;
$R_2$ and $R_3$ are independently hydrogen, cyano, halo, $C_{1-8}$alkyl, amino, $C_{1-8}$alkyl-amino or $(C_{1-8}$alkyl$)_2$-amino;
$R_4$ is $C_{3-14}$cycloalkyl, aryl, heteroaryl or heterocyclyl, each optionally substituted with one, two, three or four $R_7$ substituents;
$R_5$ is hydrogen, cyano, halo, hydroxyl, nitro, $C_{1-8}$alkyl, hydroxyl-$C_{1-8}$alkyl, $C_{1-8}$alkoxy, amino, $C_{1-8}$alkyl-amino, $(C_{1-8}$alkyl$)_2$-amino, hydroxyl-amino, hydroxyl-$C_{1-8}$alkyl-amino, $C_{1-8}$alkoxy-$C_{1-8}$alkyl-amino, $C_{1-8}$alkyl-thio, $C_{1-8}$alkyl-carbonyl, $C_{1-8}$alkyl-carbonyl-amino, amino-carbonyl, $C_{1-8}$alkyl-amino-carbonyl, $(C_{1-8}$alkyl$)_2$-amino-carbonyl, amino-carbonyl-amino, $C_{1-8}$alkyl-amino-carbonyl-amino, $(C_{1-8}$alkyl$)_2$-amino-carbonyl-amino, $C_{1-8}$alkoxy-carbonyl, $C_{1-8}$alkoxy-carbonyl-amino, amino-sulfonyl, $C_{1-8}$alkyl-amino-sulfonyl, $(C_{1-8}$alkyl$)_2$-amino-sulfonyl, amino-sulfonyl-amino, $C_{1-8}$alkyl-amino-sulfonyl-amino, $(C_{1-8}$alkyl$)_2$-amino-sulfonyl-amino, $P(O)(R_9)_2$-amino or heteroaryl, wherein heteroaryl is optionally substituted with one, two, three or four $C_{1-8}$alkyl substituents;
$R_6$ is independently selected from cyano, halo, nitro, oxo, hydroxyl, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino, $C_{1-8}$alkyl-thio, $C_{1-8}$alkyl-carbonyl, $C_{1-8}$alkyl-carbonyl-amino, $C_{1-8}$alkyl-carbonyl-oxy, $C_{1-8}$alkyl-carbonyl-oxy-$C_{1-8}$alkyl, $C_{1-8}$alkoxy-carbonyl, $C_{1-8}$alkoxy-carbonyl-$C_{1-8}$ alkyl, $C_{1-8}$alkoxy-carbonyl-amino, $C_{1-8}$alkyl-sulfonyl, $C_{3-14}$cycloalkyl, aryl, aryl-$C_{1-8}$alkyl, aryl-amino, aryl-$C_{1-8}$ alky-amino, heteroaryl, heteroaryl-$C_{1-8}$ alkyl or heterocyclyl, wherein $C_{3-14}$cycloalkyl, aryl, heteroaryl or heterocyclyl and the aryl and heteroaryl portions of aryl-$C_{1-8}$alkyl, aryl-amino, aryl-$C_{1-8}$alky-amino and heteroaryl-$C_{1-8}$alkyl are each optionally substituted with one, two, three or four halo, $C_{1-8}$alkyl, halo-$C_{1-}$salkyl, hydroxyl-$C_{1-8}$alkyl, $C_{1-8}$alkoxy, halo-$C_{1-8}$alkoxy, hydroxyl-$C_{1-8}$alkoxy or carboxyl substituents;
$R_7$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{1-8}$alkoxy-$C_{2-8}$ alkenyl, $C_{2-8}$alkynyl, $C_{1-8}$alkoxy-$C_{2-8}$alkynyl, carboxyl, formyl, formyl-oxy, $C_{1-8}$alkyl-carbonyl, halo-$C_{1-8}$ alkyl-carbonyl, $C_{1-8}$alkyl-thio, halo-$C_{1-8}$alkyl-thio, amino, $C_{1-8}$alkyl-amino, $(C_{1-8}$alkyl$)_2$-amino, $C_{1-8}$alkyl-carbonyl, $C_{1-8}$alkyl-carbonyl-oxy, $C_{1-8}$alkyl-carbonyl-oxy-$C_{1-8}$alkyl, $C_{1-8}$alkoxy-carbonyl, halo-$C_{1-8}$alkoxy-carbonyl, $C_{1-8}$alkoxy-carbonyl-$C_{1-8}$alkyl, $C_{1-8}$alkoxy-carbonyl-amino, $C_{1-8}$alkoxy-carbonyl-amino-$C_{1-8}$alkyl, amino-carbonyl, $C_{1-8}$alkyl-amino-carbonyl, $(C_{1-8}$alkyl$)_2$-amino-carbonyl, $C_{1-8}$alkyl-carbonyl-amino, $C_{1-8}$alkyl-carbonyl-amino-$C_{1-8}$alkyl, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$alkyl-amino, $(C_{1-8}$alkyl$)_2$-amino-$C_{1-8}$ alkyl-amino, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$ alkyl-amino, imino-$C_{1-8}$alkyl, hydroxyl-imino-$C_{1-8}$alkyl, $C_{1-8}$alkoxy-imino-$C_{1-8}$alkyl, $C_{1-8}$alkyl-sulfonyl, halo-$C_{1-8}$alkyl-sulfonyl, amino-sulfonyl, $C_{1-8}$alkyl-amino-sulfonyl, $(C_{1-8}$alkyl$)_2$-amino-sulfonyl, $B(OR_{10})_2$, $C_{3-14}$cycloalkyl, heterocyclyl, aryl or heteroaryl, wherein $C_{3-14}$cycloalkyl, heterocyclyl, aryl and heteroaryl are each optionally substituted with one, two, three or four halo or $C_{1-8}$alkyl substituents;

$R_8$ is absent or an oxygen atom, wherein, when present, the oxygen atom forms an N-oxide with the nitrogen atom of attachment;

$R_9$ is independently hydroxyl or $(C_{1-8}$alkoxy$)_n$, wherein n represents an integer from 1 to 5; and, $R_{10}$ is independently hydrogen or $C_{1-8}$alkyl, wherein $C_{1-8}$alkyl optionally forms a heterocyclyl ring system with the oxygen atoms of attachment.

Another embodiment includes a compound of Formula (I), wherein X is C—$R_5$.

Another embodiment includes a compound of Formula (I), wherein X is N—$R_8$.

Another embodiment includes a compound of Formula (I), wherein $R_1$ is optionally substituted heteroaryl or heterocyclyl selected from 1H-pyrazolyl, 1H-imidazolyl, 1,2-oxazolyl, pyridinyl, 1H-indolyl, 2H-indazolyl, 4,5,6,7-tetrahydro-2H-indazolyl, 1H-benzimidazolyl, imidazo[2,1-b][1,3]thiazolyl, pyrazolo[1,5-a]pyridinyl, pyrazolo[1,5-c]pyrimidinyl, imidazo[1,2-a]pyridinyl, 5,6,7,8-tetrahydroimidazo[1,2-a]pyridinyl, 1H-imidazo[4,5-b]pyridinyl, 1H-imidazo[4,5-c]pyridinyl, 4,5,6,7-tetrahydro-3H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl or heterocyclyl selected from 1H-pyrazolyl, 1H-imidazolyl, 1,2-oxazolyl, pyridinyl, 1H-indolyl, 2H-indazolyl, 4,5,6,7-tetrahydro-2H-indazolyl, 1H-benzimidazolyl, imidazo[2,1-b][1,3]thiazolyl, pyrazolo[1,5-a]pyridinyl, imidazo[1,2-a]pyridinyl, 5,6,7,8-tetrahydroimidazo[1,2-a]pyridinyl, 1H-imidazo[4,5-b]pyridinyl, 1H-imidazo[4,5-c]pyridinyl, 4,5,6,7-tetrahydro-3H-imidazo[4,5-c]pyridinyl, 7H-purinyl or quinolinyl.

Another embodiment includes a compound of Formula (I), wherein $R_1$ is optionally substituted heteroaryl or heterocyclyl selected from 1H-pyrazolyl, 1H-imidazolyl, 1,2-oxazolyl, pyridinyl, 1H-indolyl, 2H-indazolyl, 4,5,6,7-tetrahydro-2H-indazolyl, 1H-benzimidazolyl, imidazo[2,1-b][1,3]thiazolyl, pyrazolo[1,5-a]pyridinyl, imidazo[1,2-a]pyridinyl, 5,6,7,8-tetrahydroimidazo[1,2-a]pyridinyl, 1H-imidazo[4,5-b]pyridinyl, 1H-imidazo[4,5-c]pyridinyl, 4,5,6,7-tetrahydro-3H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl or heterocyclyl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-3-yl, 1H-indol-4-yl, 2H-indazol-3-yl, 4,5,6,7-tetrahydro-2H-indazol-3-yl, 1H-benzimidazol-1-yl, imidazo[2,1-b][1,3]thiazol-5-yl, pyrazolo[1,5-a]pyridin-2-yl, pyrazolo[1,5-a]pyridin-3-yl, pyrazolo[1,5-a]pyridin-7-yl, pyrazolo[1,5-c]pyrimidin-3-yl, imidazo[1,2-a]pyridin-2-yl, imidazo[1,2-a]pyridin-3-yl, imidazo[1,2-a]pyridin-5-yl, 5,6,7,8-tetrahydroimidazo[1,2-a]pyridin-3-yl, 1H-imidazo[4,5-b]pyridin-1-yl, 1H-imidazo[4,5-c]pyridin-1-yl, 4,5,6,7-tetrahydro-3H-imidazo[4,5-c]pyridin-3-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl or heterocyclyl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 4,5,6,7-tetrahydro-2H-indazol-3-yl, 1H-benzimidazol-1-yl, imidazo[2,1-b][1,3]thiazol-5-yl, pyrazolo[1,5-a]pyridin-3-yl, pyrazolo[1,5-a]pyridin-7-yl, imidazo[1,2-a]pyridin-3-yl, imidazo[1,2-a]pyridin-5-yl, 5,6,7,8-tetrahydroimidazo[1,2-a]pyridin-3-yl, 1H-imidazo[4,5-b]pyridin-1-yl, 1H-imidazo[4,5-c]pyridin-1-yl, 4,5,6,7-tetrahydro-3H-imidazo[4,5-c]pyridin-3-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl or heterocyclyl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 4,5,6,7-tetrahydro-2H-indazol-3-yl, 1H-benzimidazol-1-yl, imidazo[2,1-b][1,3]thiazol-5-yl, pyrazolo[1,5-a]pyridin-3-yl, pyrazolo[1,5-a]pyridin-7-yl, imidazo[1,2-a]pyridin-3-yl, imidazo[1,2-a]pyridin-5-yl, 5,6,7,8-tetrahydroimidazo[1,2-a]pyridin-3-yl, 1H-imidazo[4,5-b]pyridin-1-yl, 1H-imidazo[4,5-c]pyridin-1-yl, 4,5,6,7-tetrahydro-3H-imidazo[4,5-c]pyridin-3-yl, 7H-purin-7-yl or quinolin-4-yl.

Another embodiment includes a compound of Formula (I), wherein $R_1$ is optionally substituted heteroaryl selected from 1H-pyrazolyl, 1H-imidazolyl, 1,2-oxazolyl, pyridinyl, 1H-indolyl, 2H-indazolyl, 1H-benzimidazolyl, imidazo[2,1-b][1,3]thiazolyl, pyrazolo[1,5-a]pyridinyl, pyrazolo[1,5-c]pyrimidinyl, imidazo[1,2-a]pyridinyl, 1H-imidazo[4,5-b]pyridinyl, 1H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl selected from 1H-pyrazolyl, 1H-imidazolyl, 1,2-oxazolyl, pyridinyl, 1H-indolyl, 2H-indazolyl, 1H-benzimidazolyl, imidazo[2,1-b][1,3]thiazolyl, pyrazolo[1,5-a]pyridinyl, imidazo[1,2-a]pyridinyl, 1H-imidazo[4,5-b]pyridinyl, 1H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl selected from 1H-pyrazolyl, 1H-imidazolyl, 1,2-oxazolyl, pyridinyl, 1H-indolyl, 2H-indazolyl, 1H-benzimidazolyl, imidazo[2,1-b][1,3]thiazolyl, pyrazolo[1,5-a]pyridinyl, imidazo[1,2-a]pyridinyl, 1H-imidazo[4,5-b]pyridinyl, 1H-imidazo[4,5-c]pyridinyl, 7H-purinyl or quinolinyl.

Another embodiment includes a compound of Formula (I), wherein $R_1$ is optionally substituted heteroaryl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-3-yl, 1H-indol-4-yl, 2H-indazol-3-yl, 1H-benzimidazol-1-yl, imidazo[2,1-b][1,3]thiazol-5-yl, pyrazolo[1,5-a]pyridin-2-yl, pyrazolo[1,5-a]pyridin-3-yl, pyrazolo[1,5-a]pyridin-7-yl, pyrazolo[1,5-c]pyrimidin-3-yl, imidazo[1,2-a]pyridin-2-yl, imidazo[1,2-a]pyridin-3-yl, imidazo[1,2-a]

pyridin-5-yl, 1H-imidazo[4,5-b]pyridin-1-yl, 1H-imidazo[4,5-c]pyridin-1-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 1H-benzimidazol-1-yl, imidazo[2,1-b][1,3]thiazol-5-yl, pyrazolo[1,5-a]pyridin-3-yl, pyrazolo[1,5-a]pyridin-7-yl, imidazo[1,2-a]pyridin-3-yl, imidazo[1,2-a]pyridin-5-yl, 1H-imidazo[4,5-b]pyridin-1-yl, 1H-imidazo[4,5-c]pyridin-1-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 1H-benzimidazol-1-yl, imidazo[2,1-b][1,3]thiazol-5-yl, pyrazolo[1,5-a]pyridin-7-yl, imidazo[1,2-a]pyridin-5-yl, 1H-imidazo[4,5-b]pyridin-1-yl, 1H-imidazo[4,5-c]pyridin-1-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heterocyclyl selected from 4,5,6,7-tetrahydro-2H-indazolyl, 5,6,7,8-tetrahydroimidazo[1,2-a]pyridinyl or 4,5,6,7-tetrahydro-3H-imidazo[4,5-c]pyridinyl.

Another embodiment includes a compound of Formula (I), wherein $R_1$ is optionally substituted heterocyclyl selected from 4,5,6,7-tetrahydro-2H-indazol-3-yl, 5,6,7,8-tetrahydroimidazo[1,2-a]pyridin-3-yl or 4,5,6,7-tetrahydro-3H-imidazo[4,5-c]pyridin-3-yl.

Another embodiment includes a compound of Formula (I), wherein $R_2$ and $R_3$ are hydrogen.

Another embodiment includes a compound of Formula (I), wherein $R_2$ and $R_3$ are independently cyano, halo, $C_{1-8}$alkyl, amino, $C_{1-8}$alkyl-amino or $(C_{1-8}$alkyl$)_2$-amino.

Another embodiment includes a compound of Formula (I), wherein $R_2$ and $R_3$ are independently cyano, halo, $C_{1-8}$alkyl or amino.

Another embodiment includes a compound of Formula (I), wherein $R_4$ is optionally substituted $C_{3-14}$cycloalkyl selected from 2,3-dihydro-1H-indenyl; or, optionally substituted aryl selected from phenyl or naphthyl; or, optionally substituted heteroaryl selected from 1,3-thiazolyl, 1,2-oxazolyl, pyridinyl, pyrimidinyl, 1H-indolyl, benzofuranyl, benzooxazolyl, 1,3-benzothiazolyl, quinolinyl or isoquinolinyl; or, optionally substituted heterocyclyl selected from 1,3-benzodioxolyl or 2,3-dihydro-1,4-benzodioxinyl.

Another embodiment includes a compound of Formula (I), wherein $R_4$ is optionally substituted $C_{3-14}$cycloalkyl selected from 2,3-dihydro-1H-indenyl.

Another embodiment includes a compound of Formula (I), wherein $R_4$ is optionally substituted $C_{3-14}$cycloalkyl selected from 2,3-dihydro-1H-inden-2-yl.

Another embodiment includes a compound of Formula (I), wherein $R_4$ is optionally substituted aryl selected from phenyl or naphthyl.

Another embodiment includes a compound of Formula (I), wherein $R_4$ is optionally substituted heteroaryl selected from 1,3-thiazolyl, 1,2-oxazolyl, pyridinyl, pyrimidinyl, 1H-indolyl, benzofuranyl, benzooxazolyl, 1,3-benzothiazolyl, quinolinyl or isoquinolinyl; or, optionally substituted heterocyclyl selected from 1,3-benzodioxolyl or 2,3-dihydro-1,4-benzodioxinyl.

Another embodiment includes a compound of Formula (I), wherein $R_4$ is optionally substituted heteroaryl selected from 1,3-thiazol-2-yl, 1,2-oxazol-5-yl, pyridin-2-yl, pyridin-3-yl, pyrimidin-5-yl, 1H-indol-5-yl, benzofuran-5-yl, benzooxazol-5-yl, 1,3-benzothiazol-2-yl, quinolin-3-yl, quinolin-6-yl or isoquinolin-3-yl; or, optionally substituted heterocyclyl selected from 1,3-benzodioxol-5-yl or 2,3-dihydro-1,4-benzodioxin-6-yl.

Another embodiment includes a compound of Formula (I), wherein $R_4$ is optionally substituted heteroaryl selected from 1,3-thiazolyl, 1,2-oxazolyl, pyridinyl, pyridinyl, pyrimidinyl, 1H-indolyl, benzofuranyl, benzooxazolyl, 1,3-benzothiazolyl, quinolinyl or isoquinolinyl.

Another embodiment includes a compound of Formula (I), wherein $R_4$ is optionally substituted heteroaryl selected from 1,3-thiazol-2-yl, 1,2-oxazol-5-yl, pyridin-2-yl, pyridin-3-yl, pyrimidin-5-yl, 1H-indol-5-yl, benzofuran-5-yl, benzooxazol-5-yl, 1,3-benzothiazol-2-yl, quinolin-3-yl, quinolin-6-yl or isoquinolin-3-yl.

Another embodiment includes a compound of Formula (I), wherein $R_4$ is optionally substituted heterocyclyl selected from 1,3-benzodioxolyl or 2,3-dihydro-1,4-benzodioxinyl.

Another embodiment includes a compound of Formula (I), wherein $R_4$ is optionally substituted heterocyclyl selected from 1,3-benzodioxol-5-yl or 2,3-dihydro-1,4-benzodioxin-6-yl.

Another embodiment includes a compound of Formula (I), wherein $R_5$ is cyano, halo, hydroxyl, nitro, $C_{1-8}$alkyl, hydroxyl-$C_{1-8}$alkyl, $C_{1-8}$alkoxy, amino, $C_{1-8}$alkyl-amino, $(C_{1-8}$alkyl$)_2$-amino, hydroxyl-amino, hydroxyl-$C_{1-8}$alkyl-amino, $C_{1-8}$alkoxy-$C_{1-8}$alkyl-amino, $C_{1-8}$alkyl-thio, $C_{1-8}$alkyl-carbonyl, $C_{1-8}$alkyl-carbonyl-amino, amino-carbonyl, $C_{1-8}$alkyl-amino-carbonyl, $(C_{1-8}$alkyl$)_2$-amino-carbonyl, amino-carbonyl-amino, $C_{1-8}$alkyl-amino-carbonyl-amino, $(C_{1-8}$alkyl$)_2$-amino-carbonyl-amino, $C_{1-8}$alkoxy-carbonyl, $C_{1-8}$alkoxy-carbonyl-amino, amino-sulfonyl, $C_{1-8}$alkyl-amino-sulfonyl, $(C_{1-8}$alkyl$)_2$-amino-sulfonyl, amino-sulfonyl-amino, $C_{1-8}$alkyl-amino-sulfonyl-amino, $(C_{1-8}$alkyl$)_2$-amino-sulfonyl-amino, $P(O)(R_9)_2$-amino or heteroaryl, wherein heteroaryl is optionally substituted with one, two, three or four $C_{1-8}$alkyl substituents.

Another embodiment includes a compound of Formula (I), wherein $R_5$ is cyano, halo, nitro, $C_{1-8}$alkyl, hydroxyl-$C_{1-8}$alkyl, $C_{1-8}$alkoxy, amino, hydroxyl-amino, hydroxyl-$C_{1-8}$alkyl-amino, $C_{1-8}$alkoxy-$C_{1-8}$alkyl-amino, $C_{1-8}$alkyl-thio, amino-carbonyl, amino-carbonyl-amino, $C_{1-8}$alkoxy-carbonyl-amino, amino-sulfonyl-amino or heteroaryl, wherein heteroaryl is optionally substituted with one, two, three or four $C_{1-8}$alkyl substituents.

Another embodiment includes a compound of Formula (I), wherein $R_5$ is cyano, halo, hydroxyl, nitro, $C_{1-8}$alkyl, hydroxyl-$C_{1-8}$alkyl, $C_{1-8}$alkoxy, amino, $C_{1-8}$alkyl-amino, $(C_{1-8}$alkyl$)_2$-amino, hydroxyl-amino, hydroxyl-$C_{1-8}$alkyl-amino, $C_{1-8}$alkoxy-$C_{1-8}$alkyl-amino, $C_{1-8}$alkyl-thio, $C_{1-8}$alkyl-carbonyl, $C_{1-8}$alkyl-carbonyl-amino, amino-carbonyl, $C_{1-8}$alkyl-amino-carbonyl, $(C_{1-8}$alkyl$)_2$-amino-carbonyl, amino-carbonyl-amino, $C_{1-8}$alkyl-amino-carbonyl-amino, $(C_{1-8}$alkyl$)_2$-amino-carbonyl-amino, $C_{1-8}$alkoxy-carbonyl, $C_{1-8}$alkoxy-carbonyl-amino, amino-sulfonyl, $C_{1-8}$alkyl-amino-sulfonyl, $(C_{1-8}$alkyl$)_2$-amino-sulfonyl, amino-sulfonyl-amino, $C_{1-8}$alkyl-amino-sulfonyl-amino, $(C_{1-8}$alkyl$)_2$-amino-sulfonyl-amino or $P(O)(R_9)_2$-amino.

Another embodiment includes a compound of Formula (I), wherein $R_5$ is cyano, halo, nitro, $C_{1-8}$alkyl, hydroxyl-$C_{1-8}$alkyl, $C_{1-8}$alkoxy, amino, hydroxyl-amino, hydroxyl-$C_{1-8}$alkyl-amino, $C_{1-8}$alkoxy-$C_{1-8}$alkyl-amino, $C_{1-8}$alkyl-thio, amino-carbonyl, amino-carbonyl-amino, $C_{1-8}$alkoxy-carbonyl-amino or amino-sulfonyl-amino.

Another embodiment includes a compound of Formula (I), wherein $R_5$ is heteroaryl, wherein heteroaryl is optionally substituted with one, two, three or four $C_{1-8}$alkyl substituents.

Another embodiment includes a compound of Formula (I), wherein $R_5$ heteroaryl is optionally substituted 1H-pyrrolyl.

Another embodiment includes a compound of Formula (I), wherein $R_5$ heteroaryl is optionally substituted 1H-pyrrol-1-yl.

Another embodiment includes a compound of Formula (I), wherein $R_6$ is independently selected from cyano, halo, hydroxyl, nitro, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, carboxyl, amino, $C_{1-8}$alkyl-amino, $C_{1-8}$alkyl-amino-$C_{1-8}$alkyl, hydroxyl-$C_{1-8}$alkyl-amino, $C_{1-8}$alkyl-thio, $C_{1-8}$alkyl-carbonyl, $C_{1-8}$alkyl-carbonyl-oxy-$C_{1-8}$alkyl, $C_{1-8}$alkoxy-carbonyl, $C_{1-8}$alkyl-sulfonyl, $C_{3-14}$cycloalkyl, aryl-$C_{1-8}$alkyl, aryl-amino, aryl-$C_{1-8}$alky-amino, heteroaryl or heteroaryl-$C_{1-8}$alkyl, wherein heteroaryl and the aryl and heteroaryl portions of aryl-$C_{1-8}$alkyl, aryl-amino, aryl-$C_{1-8}$alky-amino and heteroaryl-$C_{1-8}$alkyl are each optionally substituted with one, two, three or four halo or halo-$C_{1-8}$alkoxy substituents.

Another embodiment includes a compound of Formula (I), wherein $R_6$ is independently selected from cyano, halo, hydroxyl, nitro, oxo, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino-$C_{1-8}$alkyl-amino, $C_{1-8}$alkyl-thio, $C_{1-8}$alkyl-carbonyl, $C_{1-8}$alkyl-carbonyl-amino, $C_{1-8}$alkyl-carbonyl-oxy, $C_{1-8}$alkyl-carbonyl-oxy-$C_{1-8}$alkyl, $C_{1-8}$alkoxy-carbonyl, $C_{1-8}$alkoxy-carbonyl-$C_{1-8}$alkyl, $C_{1-8}$alkoxy-carbonyl-amino or $C_{1-8}$alkyl-sulfonyl.

Another embodiment includes a compound of Formula (I), wherein $R_6$ is independently selected from cyano, halo, hydroxyl, nitro, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, carboxyl, amino, $C_{1-8}$alkyl-amino, $C_{1-8}$alkyl-amino-$C_{1-8}$alkyl, hydroxyl-$C_{1-8}$alkyl-amino, $C_{1-8}$alkyl-thio, $C_{1-8}$alkyl-carbonyl, $C_{1-8}$alkyl-carbonyl-oxy-$C_{1-8}$alkyl, $C_{1-8}$alkoxy-carbonyl or $C_{1-8}$alkyl-sulfonyl.

Another embodiment includes a compound of Formula (I), wherein $R_6$ is independently selected from optionally substituted $C_{3-14}$cycloalkyl selected from cyclopropyl or cyclobutyl; or, aryl, aryl-$C_{1-8}$alkyl, aryl-amino or aryl-$C_{1-8}$alky-amino optionally substituted on aryl and the aryl portions, wherein aryl is selected from phenyl; and, wherein the optional substituents are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents; or, heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents.

Another embodiment includes a compound of Formula (I), wherein $R_6$ is independently selected from optionally substituted $C_{3-14}$cycloalkyl selected from cyclopropyl or cyclobutyl; or, aryl-$C_{1-8}$alkyl, aryl-amino or aryl-$C_{1-8}$alky-amino optionally substituted on the aryl portions, wherein aryl is selected from phenyl; and, wherein the optional substituents are selected from one, two, three or four halo or halo-$C_{1-8}$alkoxy substituents; or, heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents are selected from one, two, three or four halo or halo-$C_{1-8}$alkoxy substituents.

Another embodiment includes a compound of Formula (I), wherein $R_6$ is independently selected from optionally substituted $C_{3-14}$cycloalkyl selected from cyclopropyl or cyclobutyl.

Another embodiment includes a compound of Formula (I), wherein $R_6$ is independently selected from aryl, aryl-$C_{1-8}$alkyl, aryl-amino or aryl-$C_{1-8}$alky-amino optionally substituted on aryl and the aryl portions, wherein aryl is selected from phenyl; and, wherein the optional substituents are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents.

Another embodiment includes a compound of Formula (I), wherein $R_6$ is independently selected from aryl-$C_{1-8}$alkyl, aryl-amino or aryl-$C_{1-8}$alky-amino optionally substituted on the aryl portions, wherein aryl is selected from phenyl; and, wherein the optional substituents are selected from one, two, three or four halo or halo-$C_{1-8}$alkoxy substituents.

Another embodiment includes a compound of Formula (I), wherein $R_6$ is independently selected from heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents.

Another embodiment includes a compound of Formula (I), wherein $R_6$ is independently selected from heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents are selected from one, two, three or four halo or halo-$C_{1-8}$alkoxy substituents.

Another embodiment includes a compound of Formula (I), wherein $R_6$ is independently selected from heteroaryl or heteroaryl-$C_{1-8}$alkyl optionally substituted on heteroaryl and the heteroaryl portion, wherein heteroaryl is selected from 2H-tetrazol-2-yl, tetrazol-1-yl, pyridin-2-yl, pyridin-3-yl or pyridin-4-yl; and, wherein the optional substituents are selected from one, two, three or four halo or halo-$C_{1-8}$alkoxy substituents.

Another embodiment includes a compound of Formula (I), wherein $R_7$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{2-8}$alkynyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-carbonyl, $C_{1-8}$alkoxy-carbonyl, amino-carbonyl, $C_{1-8}$alkyl-amino-carbonyl, amino-$C_{1-8}$alkyl, $(C_{1-8}$alkyl$)_2$-amino-$C_{1-8}$alkyl-amino, hydroxyl-$C_{1-8}$alkyl-amino, hydroxyl-imino-$C_{1-8}$alkyl, $C_{1-8}$alkyl-sulfonyl, $B(OR_{10})_2$, $C_{3-14}$cycloalkyl, heterocyclyl, aryl or heteroaryl, wherein $C_{3-14}$cycloalkyl, heterocyclyl, aryl and heteroaryl are each optionally substituted with one, two, three or four halo or $C_{1-8}$alkyl substituents.

Another embodiment includes a compound of Formula (I), wherein $R_7$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-amino, ($C_{1-8}$alkyl)$_2$-amino, $C_{1-8}$alkyl-carbonyl, $C_{1-8}$alkyl-carbonyl-oxy, $C_{1-8}$alkyl-carbonyl-oxy-$C_{1-8}$alkyl, $C_{1-8}$alkoxy-carbonyl, halo-$C_{1-8}$alkoxy-carbonyl, $C_{1-8}$alkoxy-carbonyl-$C_{1-8}$alkyl, $C_{1-8}$alkoxy-carbonyl-amino, $C_{1-8}$alkoxy-carbonyl-amino-$C_{1-8}$alkyl, amino-carbonyl, $C_{1-8}$alkyl-amino-carbonyl, ($C_{1-8}$alkyl)$_2$-amino-carbonyl, $C_{1-8}$alkyl-carbonyl-amino, $C_{1-8}$alkyl-carbonyl-amino-$C_{1-8}$alkyl, amino-$C_{1-8}$alkyl, $C_{1-8}$alkyl-amino-$C_{1-8}$alkyl, ($C_{1-8}$ alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino, imino-$C_{1-8}$alkyl, hydroxyl-imino-$C_{1-8}$alkyl, $C_{1-8}$alkoxy-imino-$C_{1-8}$alkyl, $C_{1-8}$alkyl-sulfonyl, halo-$C_{1-8}$alkyl-sulfonyl, amino-sulfonyl, $C_{1-8}$alkyl-amino-sulfonyl, ($C_{1-8}$alkyl)$_2$-amino-sulfonyl or B(OR$_{10}$)$_2$.

Another embodiment includes a compound of Formula (I), wherein $R_7$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{2-8}$alkynyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-carbonyl, $C_{1-8}$alkoxy-carbonyl, amino-carbonyl, $C_{1-8}$alkyl-amino-carbonyl, amino-$C_{1-8}$alkyl, ($C_{1-8}$alkyl)$_2$-amino-$C_{1-8}$ alkyl-amino, hydroxyl-$C_{1-8}$alkyl-amino, hydroxyl-imino-$C_{1-8}$alkyl, $C_{1-8}$alkyl-sulfonyl, $C_{1-8}$alkyl-amino-sulfonyl or B(OR$_{10}$)$_2$.

Another embodiment includes a compound of Formula (I), wherein $R_7$ is independently selected from $C_{3-14}$cycloalkyl, heterocyclyl, aryl or heteroaryl, wherein $C_{3-14}$cycloalkyl, heterocyclyl, aryl and heteroaryl are each optionally substituted with one, two, three or four halo or $C_{1-8}$alkyl substituents.

Another embodiment includes a compound of Formula (I), wherein $R_7$ is independently selected from $C_{3-14}$cycloalkyl or heterocyclyl, wherein $C_{3-14}$cycloalkyl and heterocyclyl are each optionally substituted with two $C_{1-8}$alkyl substituents.

Another embodiment includes a compound of Formula (I), wherein $R_7$ optionally substituted $C_{3-14}$cycloalkyl is selected from cyclopropyl; optionally substituted heterocyclyl is selected from morpholinyl or 1,3,2-dioxaborolanyl; optionally substituted aryl is selected from phenyl; or, optionally substituted heteroaryl is selected from 1H-pyrazolyl.

Another embodiment includes a compound of Formula (I), wherein $R_7$ optionally substituted $C_{3-14}$cycloalkyl is selected from cyclopropyl.

Another embodiment includes a compound of Formula (I), wherein $R_7$ optionally substituted heterocyclyl is selected from morpholinyl or 1,3,2-dioxaborolanyl.

Another embodiment includes a compound of Formula (I), wherein $R_7$ optionally substituted heterocyclyl is selected from morpholin-4-yl or 1,3,2-dioxaborolan-2-yl.

Another embodiment includes a compound of Formula (I), wherein $R_7$ optionally substituted heterocyclyl is 1,3,2-dioxaborolanyl optionally substituted with one, two, three or four halo or $C_{1-8}$alkyl substituents.

Another embodiment includes a compound of Formula (I), wherein $R_7$ optionally substituted heterocyclyl is 1,3,2-dioxaborolan-2-yl optionally substituted with one, two, three or four halo or $C_{1-8}$alkyl substituents.

Another embodiment includes a compound of Formula (I), wherein $R_7$ optionally substituted aryl is selected from phenyl.

Another embodiment includes a compound of Formula (I), wherein $R_7$ optionally substituted heteroaryl is selected from 1H-pyrazolyl.

Another embodiment includes a compound of Formula (I), wherein $R_7$ optionally substituted heteroaryl is selected from 1H-pyrazol-1-yl.

Another embodiment includes a compound of Formula (I), wherein $R_8$ is absent.

Another embodiment includes a compound of Formula (I), wherein $R_8$ is an oxygen atom, wherein, when present, the oxygen atom forms an N-oxide with the nitrogen atom of attachment.

Another embodiment includes a compound of Formula (I), wherein $R_9$ is hydroxyl.

Another embodiment includes a compound of Formula (I), wherein $R_9$ is ($C_{1-8}$alkoxy)$_n$, wherein n represents an integer from 1 to 5.

Another embodiment includes a compound of Formula (I), wherein $R_{10}$ is hydrogen.

Another embodiment includes a compound of Formula (I), wherein $R_{10}$ is $C_{1-8}$alkyl.

Another embodiment includes a compound of Formula (I) or a form thereof, wherein the form of the compound of Formula (I) is selected from a free acid, free base, salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof, wherein the form of the compound of Formula (I) is selected from a free acid, free base, ester, hydrate, solvate, chelate, clathrate, polymorph, isotopologue, stereoisomer, racemate, enantiomer, diastereomer or tautomer thereof.

Another embodiment includes a compound of Formula (I) or a form thereof, wherein the form of the compound of Formula (I) is selected from a salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof, wherein the form of the compound of Formula (I) is selected from a free acid, free base, salt, ester, hydrate, solvate or polymorph thereof.

Another embodiment includes a compound of Formula (I) or a form thereof, wherein the form of the compound of Formula (I) is selected from a free acid, free base, salt, hydrate or polymorph thereof.

Another embodiment includes a compound of Formula (I) or a form thereof, wherein the form of the compound of Formula (I) is selected from a free acid, free base, hydrate, solvate or polymorph thereof.

Another embodiment includes a compound of Formula (I) or a form thereof, wherein the form of the compound of Formula (I) is selected from a salt, hydrate, solvate or polymorph thereof.

Another embodiment includes a compound of Formula (I) or a form thereof, wherein the form of the compound of Formula (I) is selected from a free acid, free base or salt thereof.

Another embodiment includes a compound of Formula (I) or a form thereof, wherein the form of the compound of Formula (I) is selected from a free acid or free base thereof.

Another embodiment includes a compound of Formula (I) or a form thereof, wherein the form of the compound of Formula (I) is selected from a salt thereof.

Another embodiment includes a compound of Formula (I) or a form thereof, wherein the form of the compound of Formula (I) is selected from a polymorph thereof.

Another embodiment includes a compound of Formula (I) or a form thereof, wherein the form of the compound of Formula (I) is pharmaceutically acceptable.

Another embodiment includes a compound of Formula (I) or a form thereof, wherein the form of the compound of Formula (I) is isolated.

Another embodiment includes a compound of Formula (I) or a form thereof, wherein the compound is a compound of Formula (II), Formula (III), Formula (IV) or Formula (V):

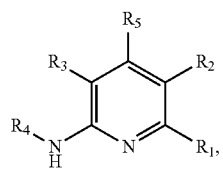

Formula (II)

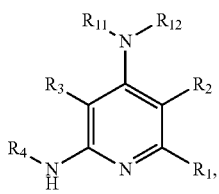

Formula (III)

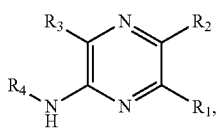

Formula (IV)

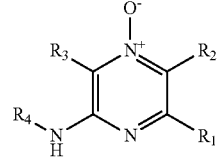

Formula (V)

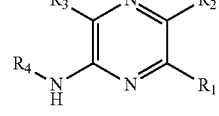

or a form thereof, wherein
$R_{11}$ and $R_{12}$ are independently hydrogen, hydroxyl, $C_{1-8}$alkyl, hydroxyl-$C_{1-8}$alkyl, $C_{1-8}$alkoxy-$C_{1-8}$alkyl, $C_{1-8}$alkyl-carbonyl, amino-carbonyl, $C_{1-8}$alkyl-amino-carbonyl, ($C_{1-8}$ alkyl)$_2$-amino-carbonyl, $C_{1-8}$alkoxy-carbonyl, amino-sulfonyl, $C_{1-8}$ alkyl-amino-sulfonyl, ($C_{1-8}$alkyl)$_2$-amino-sulfonyl or P(O)(R$_9$)$_2$.

Another embodiment includes a compound of Formula (III), wherein one of $R_{11}$ and $R_{12}$ is hydrogen and the other is hydroxyl, $C_{1-8}$alkyl, hydroxyl-$C_{1-8}$alkyl, $C_{1-8}$alkoxy-$C_{1-8}$ alkyl, $C_{1-8}$alkyl-carbonyl, amino-carbonyl, $C_{1-8}$alkyl-amino-carbonyl, ($C_{1-8}$alkyl)$_2$-amino-carbonyl, $C_{1-8}$alkoxy-carbonyl, amino-sulfonyl, $C_{1-8}$alkyl-amino-sulfonyl, ($C_{1-8}$ alkyl)$_2$-amino-sulfonyl or P(O)(R$_9$)$_2$.

Another embodiment includes a compound of Formula (I) or a form thereof, wherein the compound is a compound of Formula (Ia), Formula (IIa), Formula (IIIa), Formula (IV) or Formula (Va):

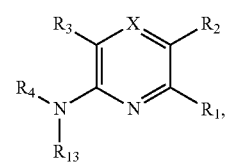

Formula (Ia)

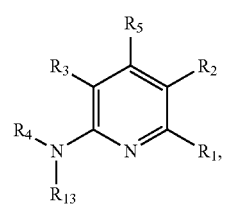

Formula (IIa)

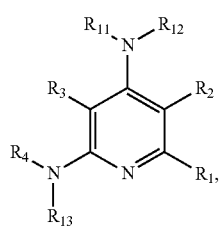

Formula (IIIa)

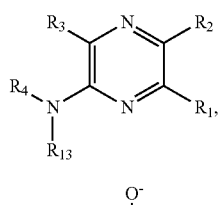

Formula (IVa)

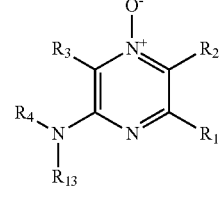

Formula (Va)

or a form thereof, wherein $R_2$, $R_3$, $R_5$, $R_{11}$, $R_{12}$ or $R_{13}$ are independently deuterium.

Another embodiment includes a compound of Formula (I) or a form thereof selected from the group consisting of:

1

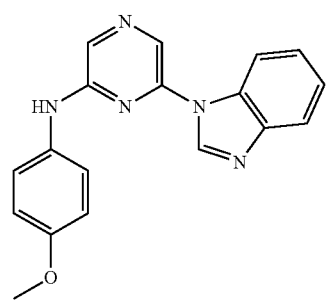

-continued
2
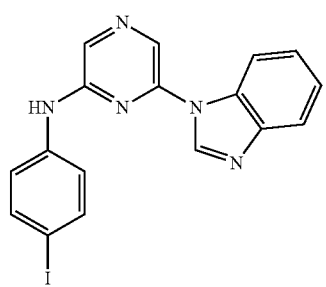
3
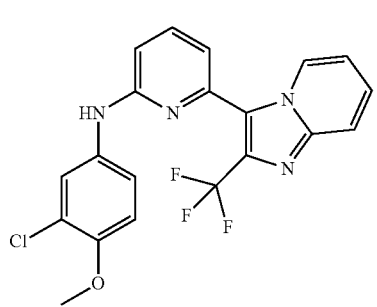
4
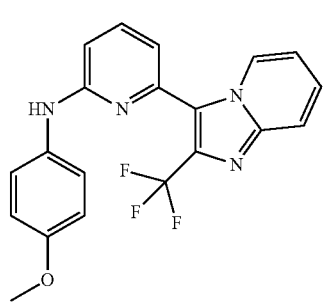
5
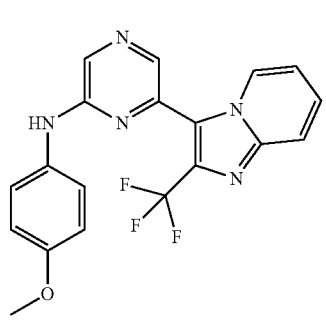
6
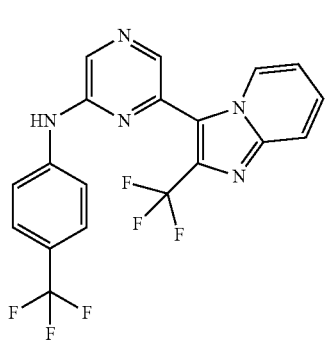
-continued
7
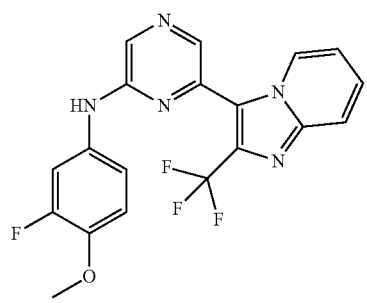
8
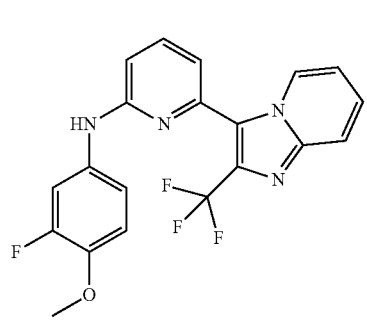
9
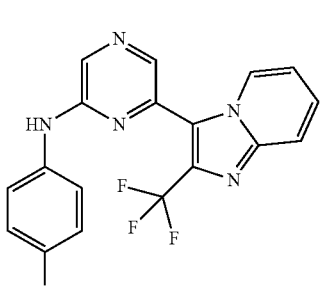
10
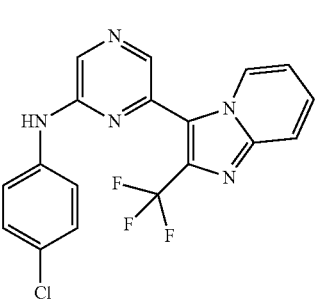
11
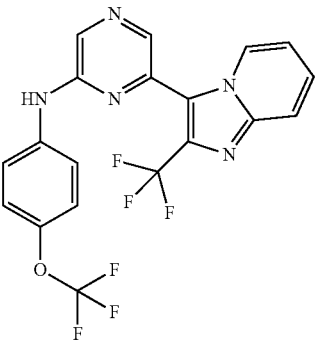

-continued
12
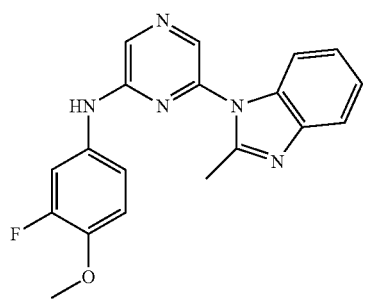
13
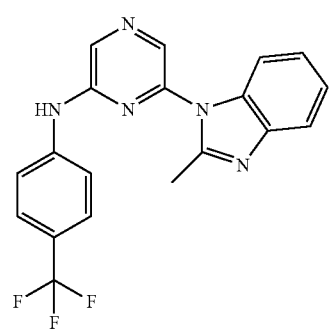
14
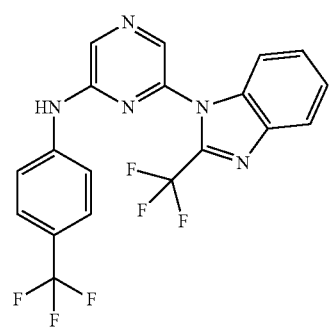
15
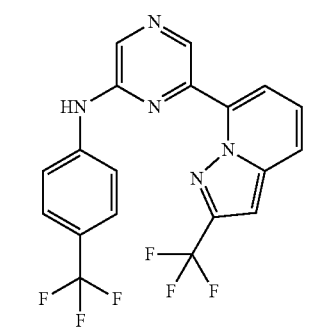
16
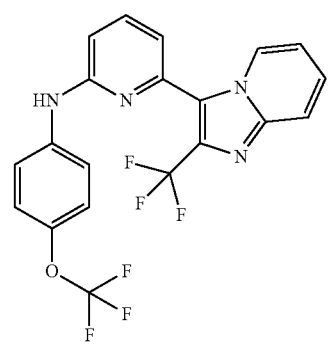
-continued
17
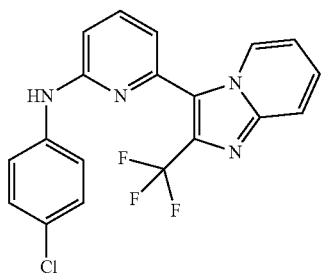
18
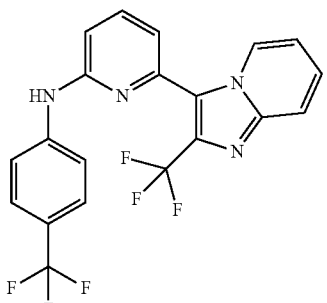
19
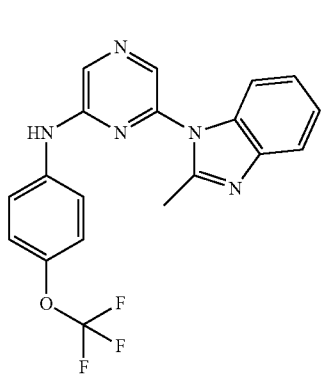
20
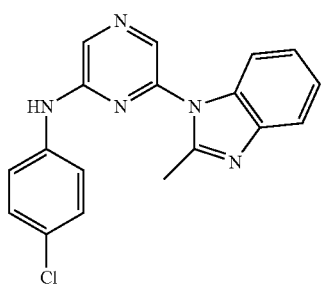
21
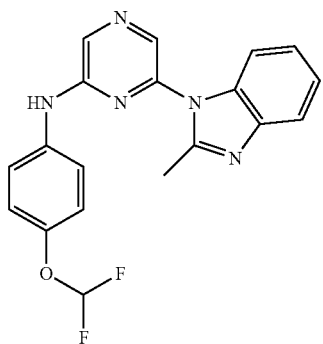

22
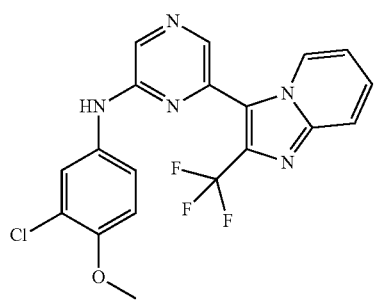
23
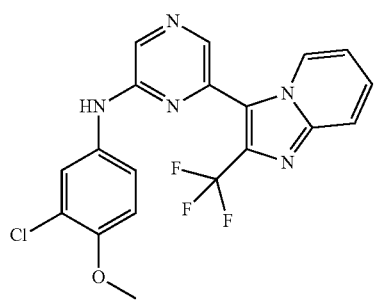
24
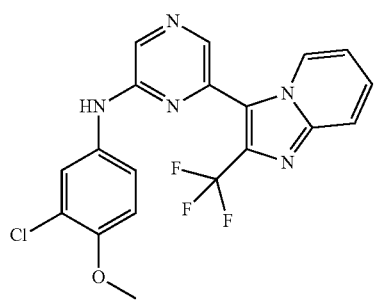
25
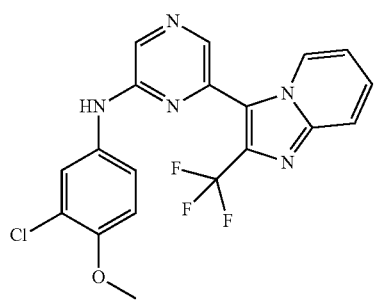
26
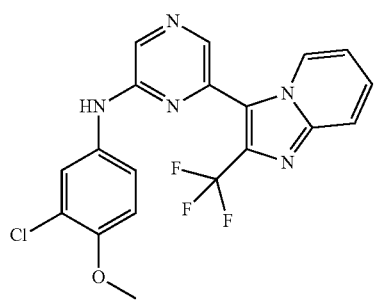
27
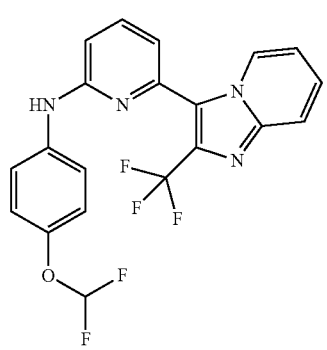
28
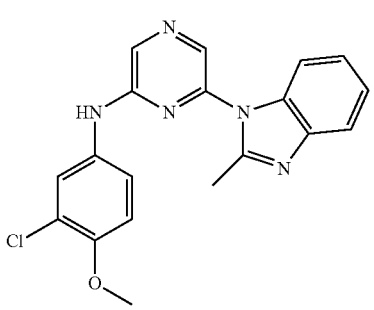
29
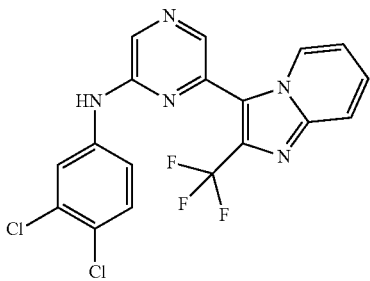
30
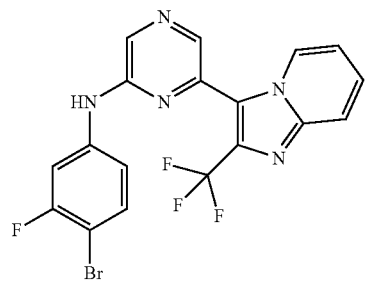
31
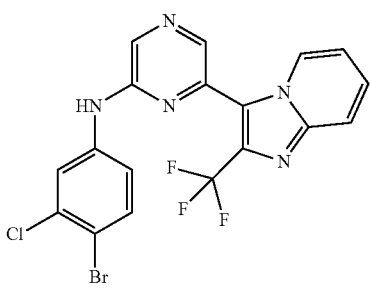

-continued
32
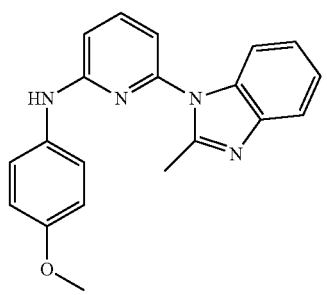
33
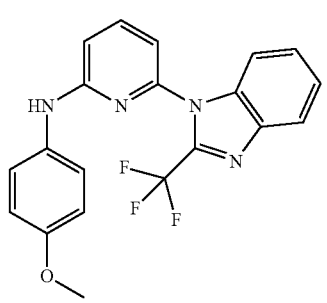
34
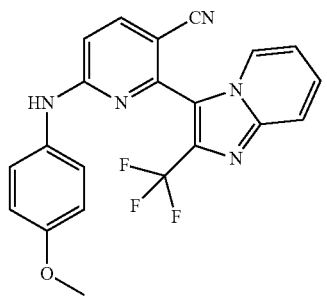
35
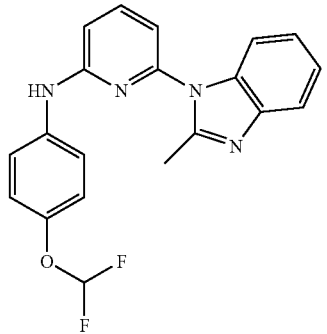
36
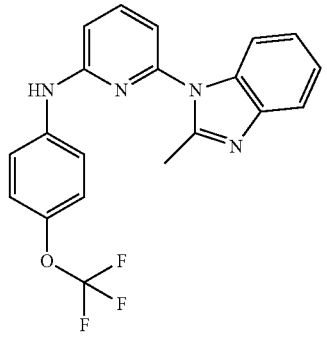
-continued
37
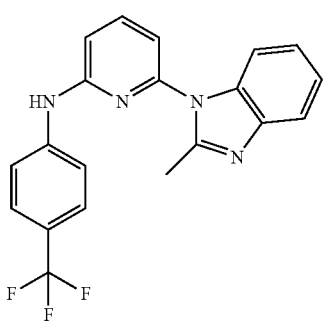
38
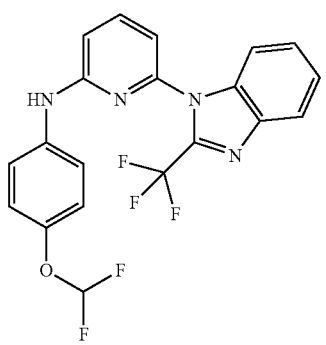
39
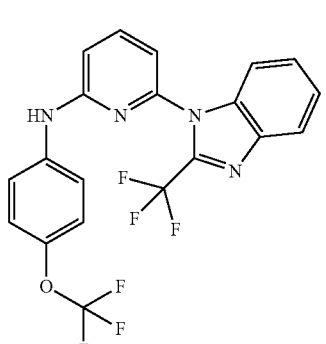
40
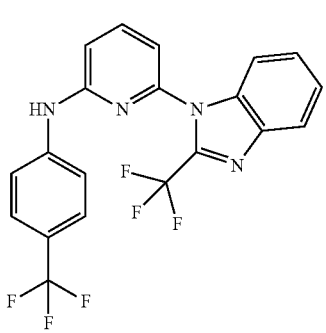
41
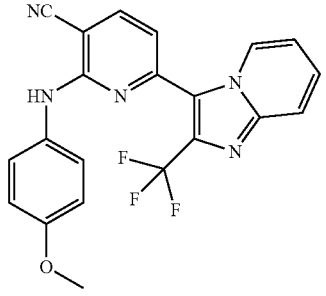

42
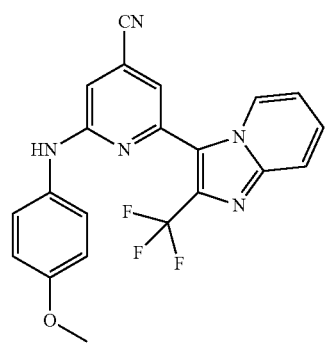
43
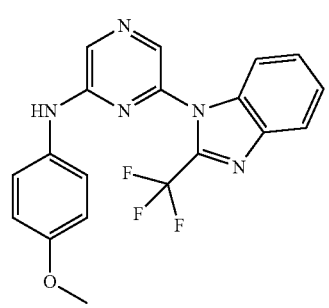
44
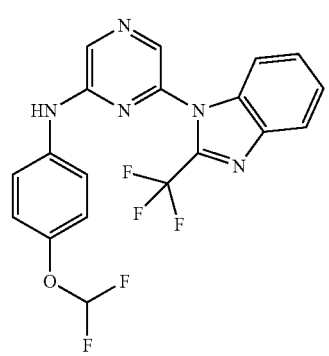
45
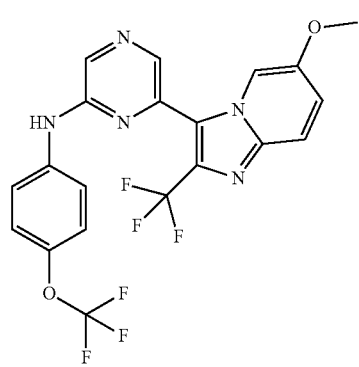
46
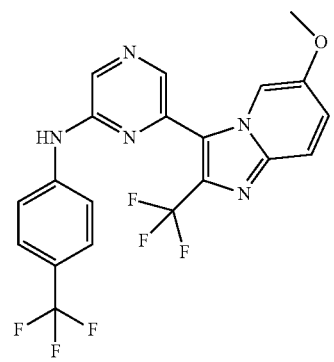
47
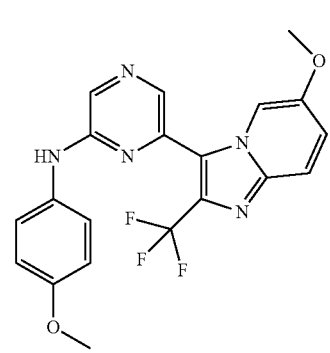
48
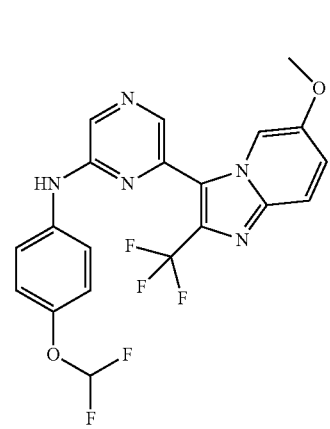
49
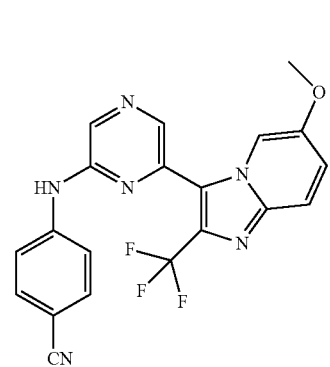

50
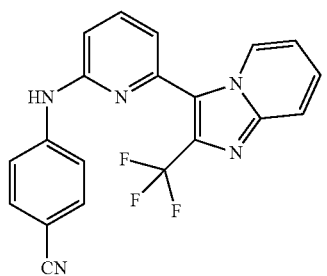
51
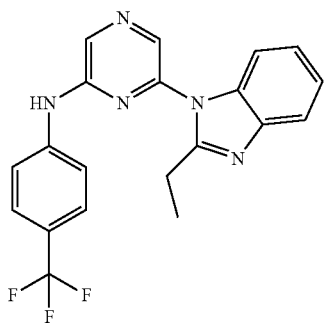
52
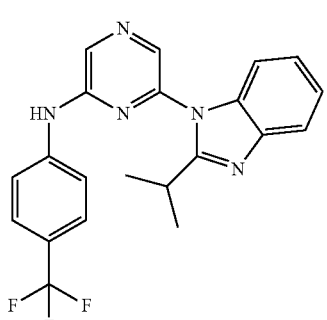
53
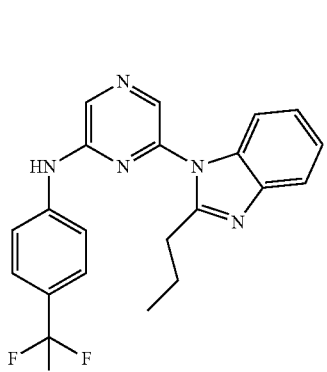
54
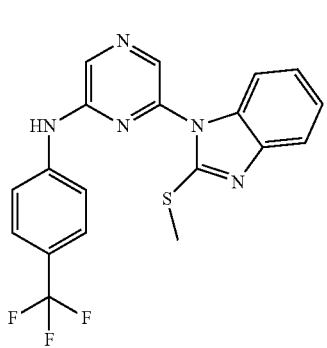
55
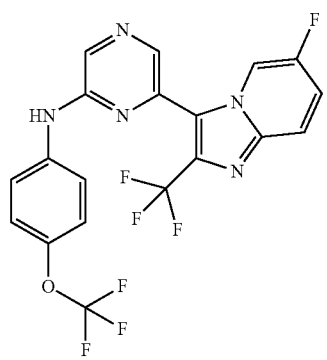
56
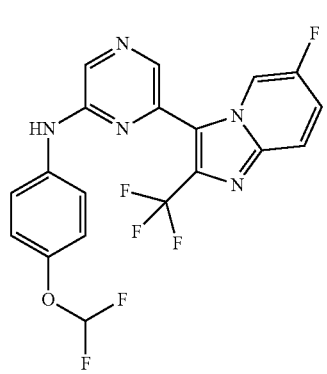
57
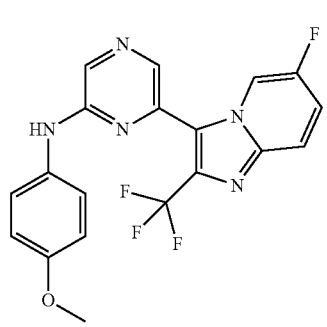
58
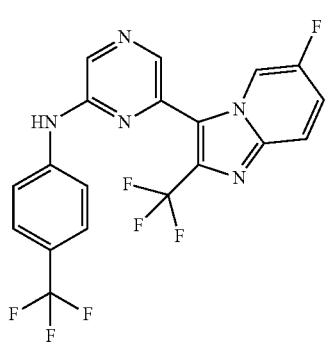

59
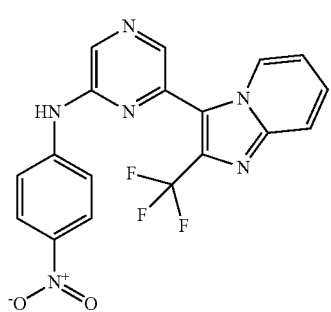
60
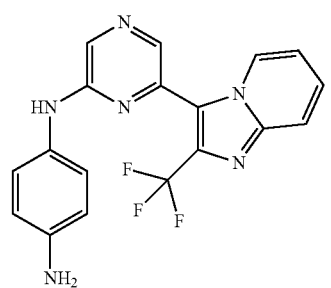
61
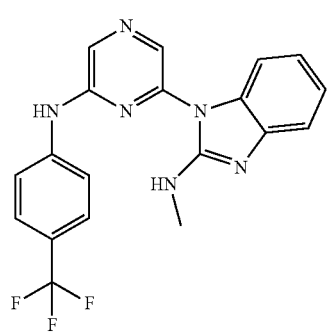
62
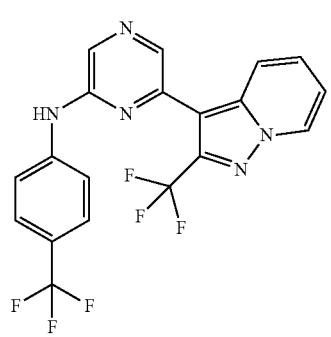
63
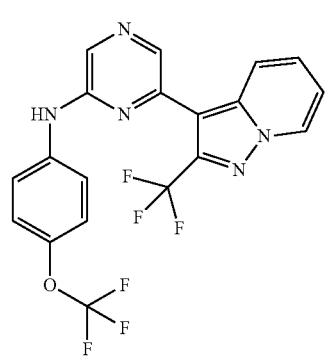
64
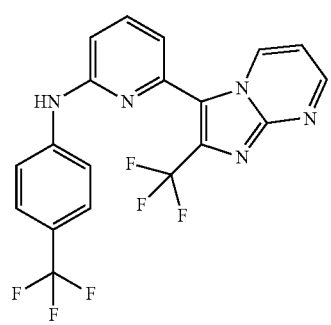
65
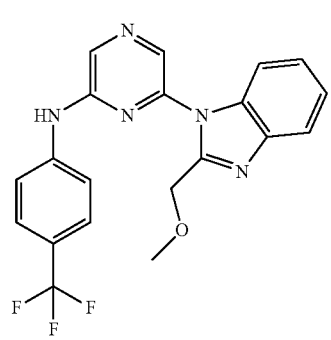
66
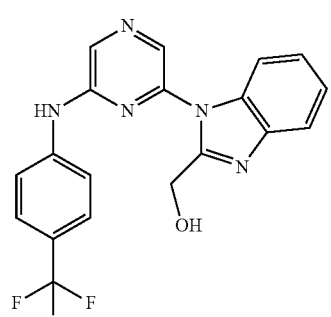
67
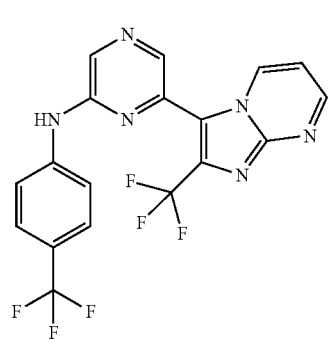
68
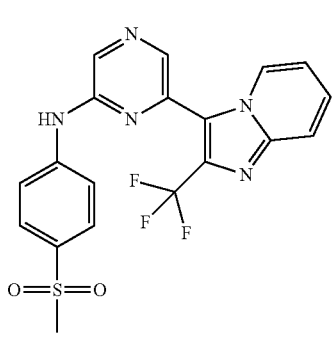

69
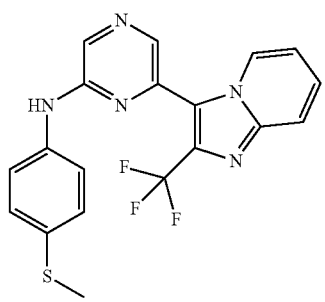
70
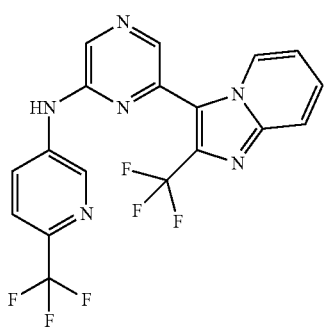
71
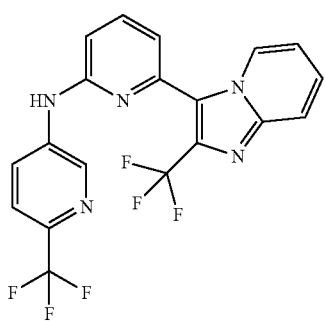
72
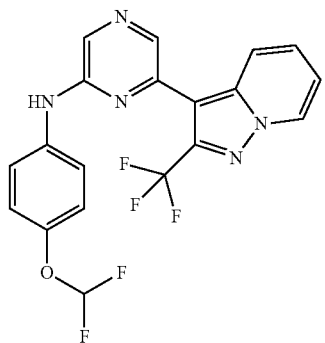
73
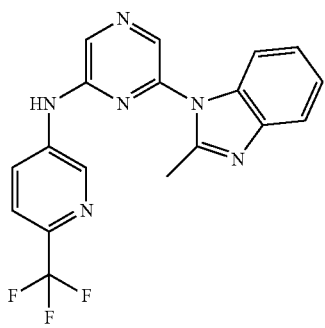
74
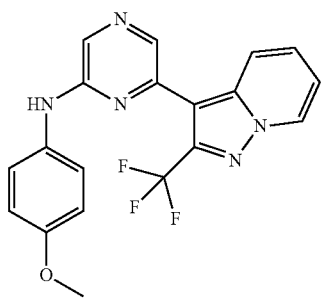
75
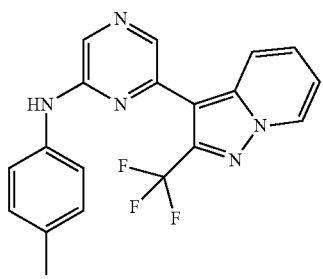
76
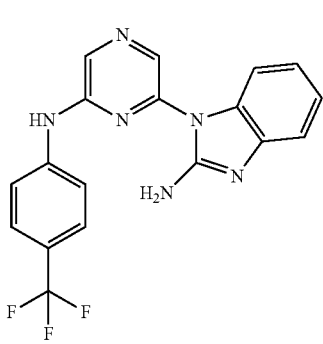
77
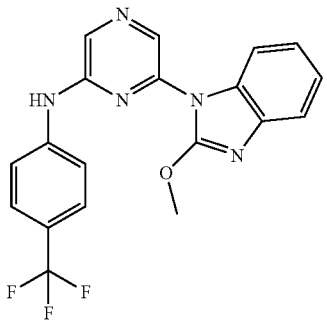
78
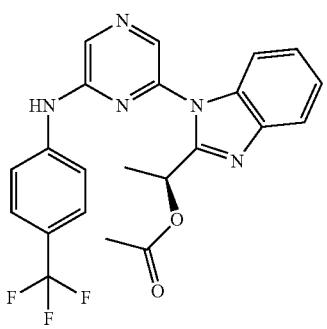

79 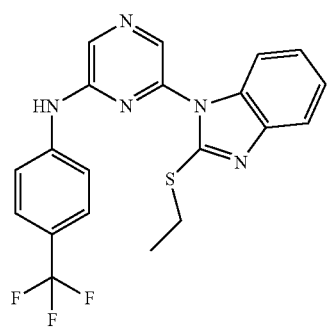
80 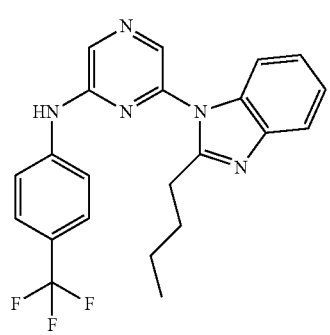
81 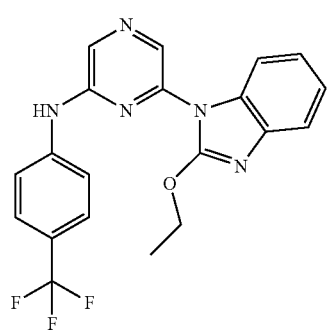
82 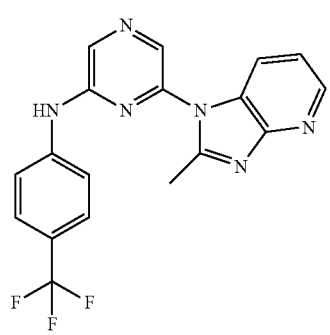
83 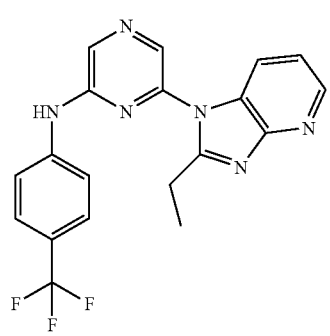
84 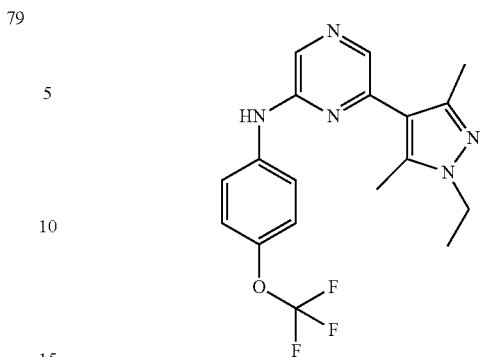
85 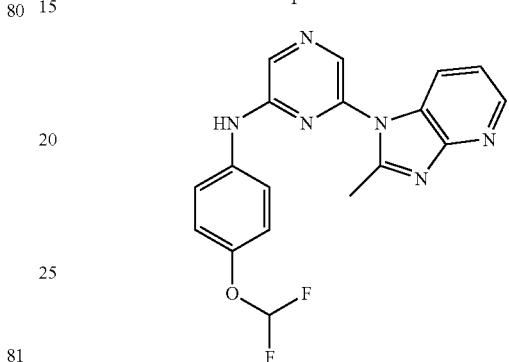
86 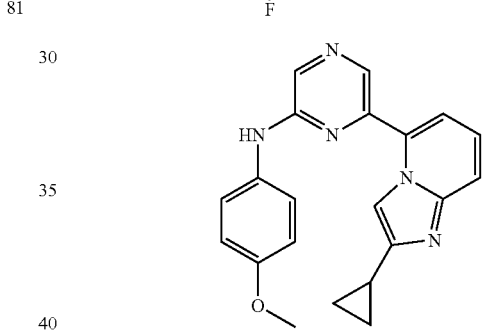
87 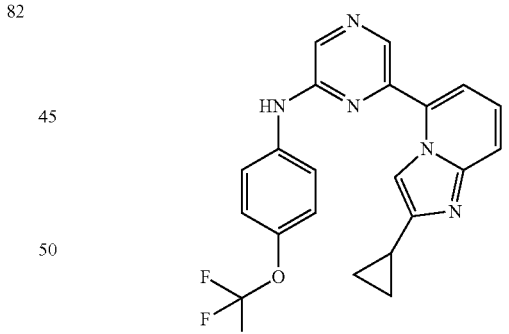
88 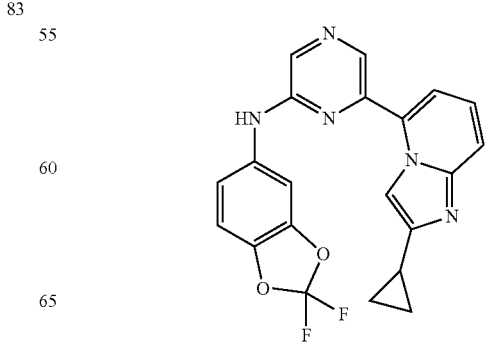

89 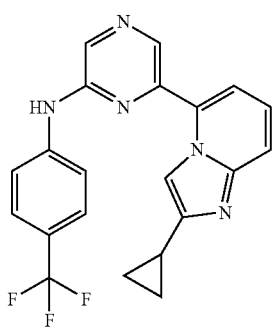
90 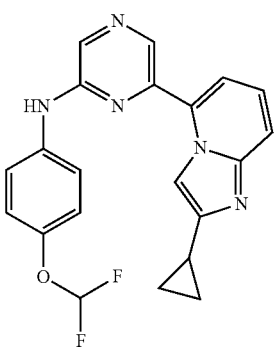
91 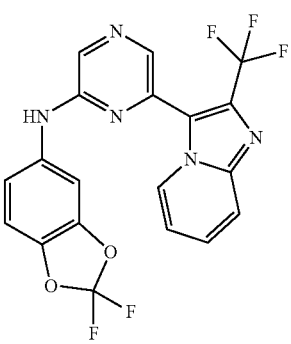
92 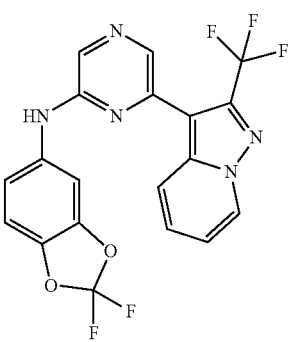
93 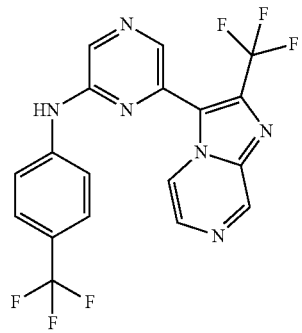
94 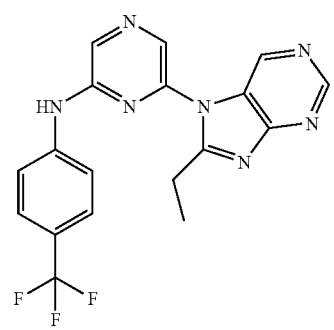
95 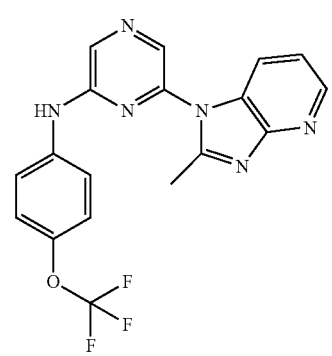
96 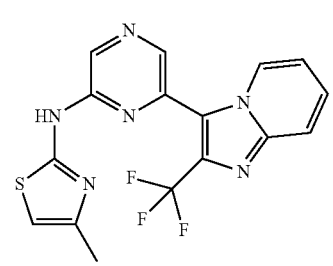
97 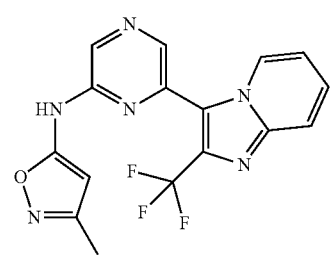

98
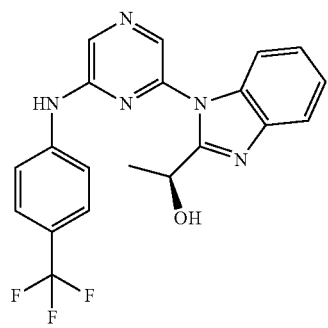
99
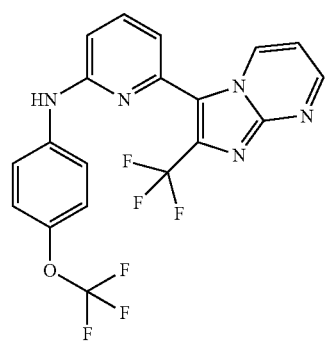
100
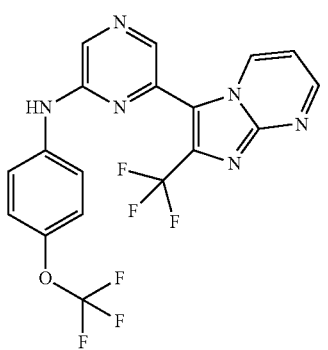
101
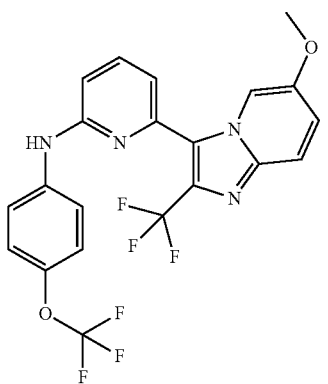
102
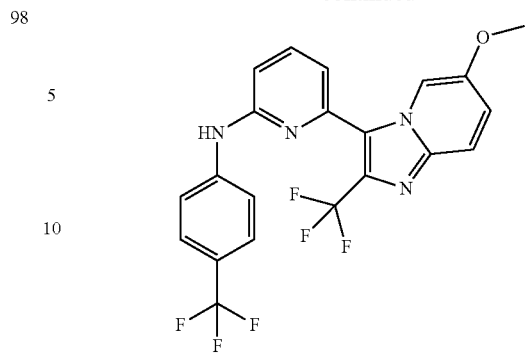
103
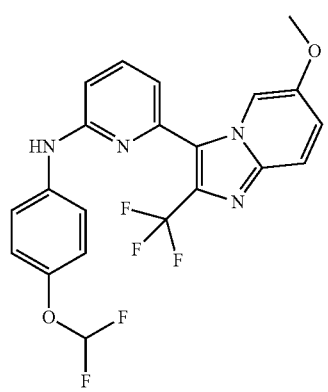
104
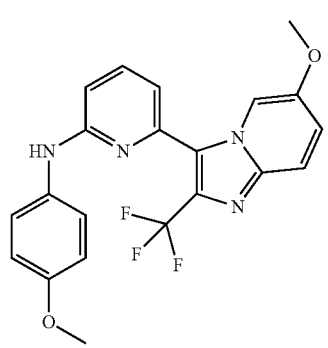
105
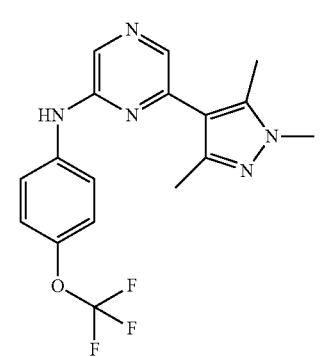

106 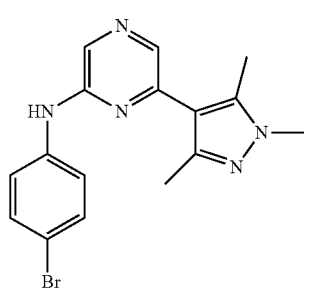
107 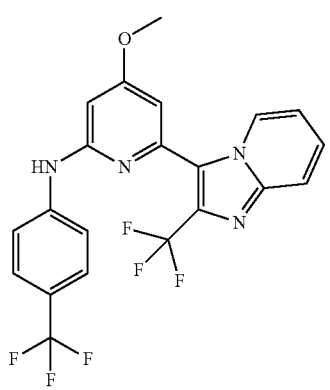
108 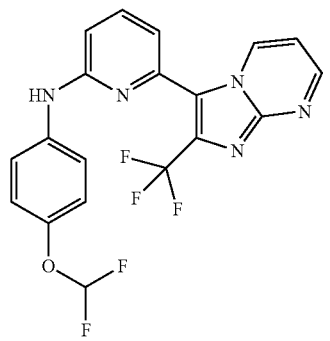
109 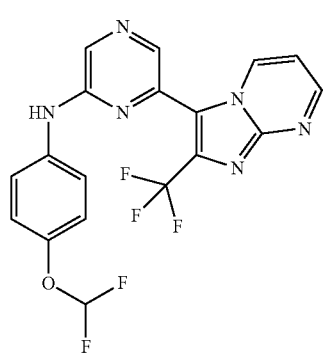
110 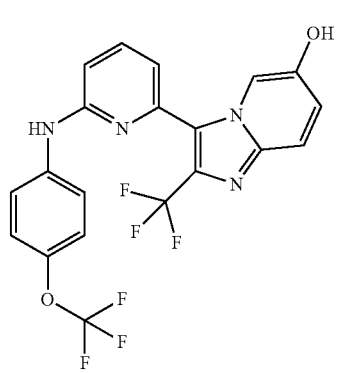
111 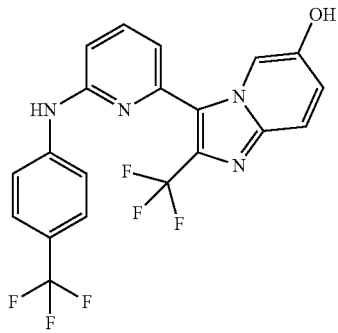
112 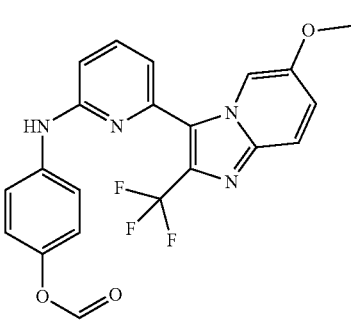
113 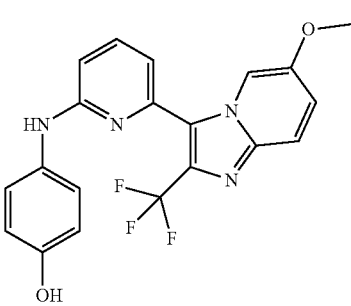
114 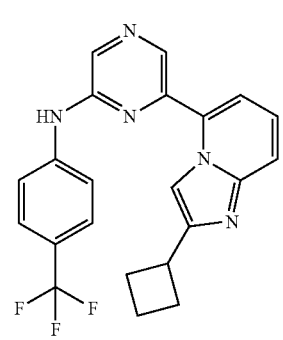

115 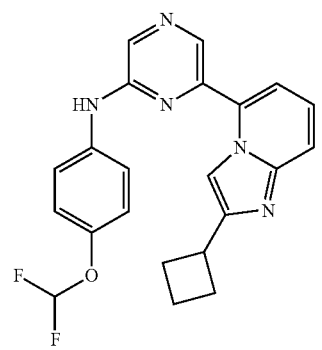
116 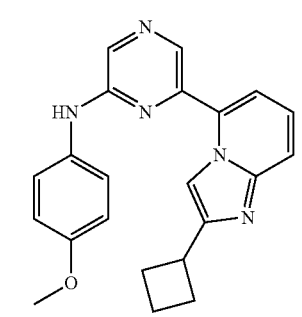
117 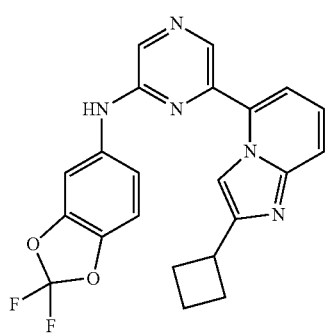
118 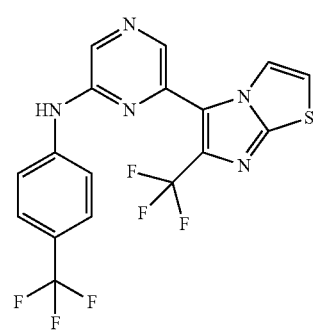
119 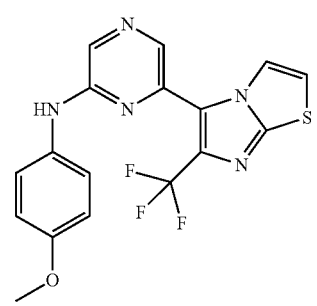
120 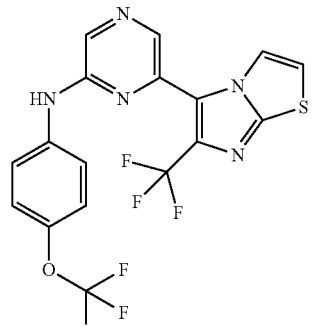
121 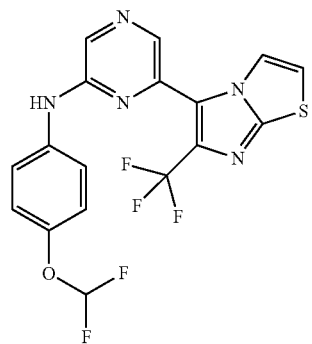
122 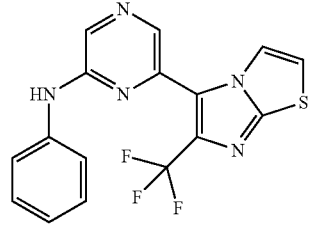
123 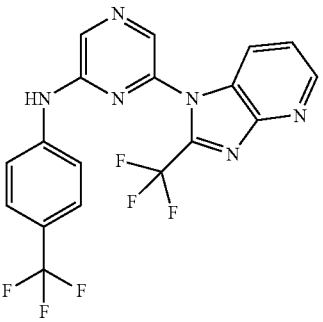
124 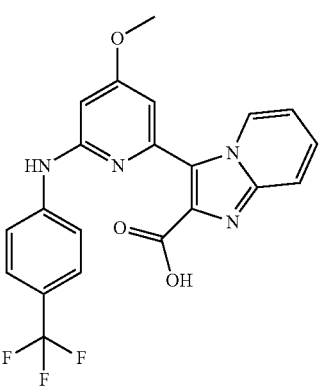

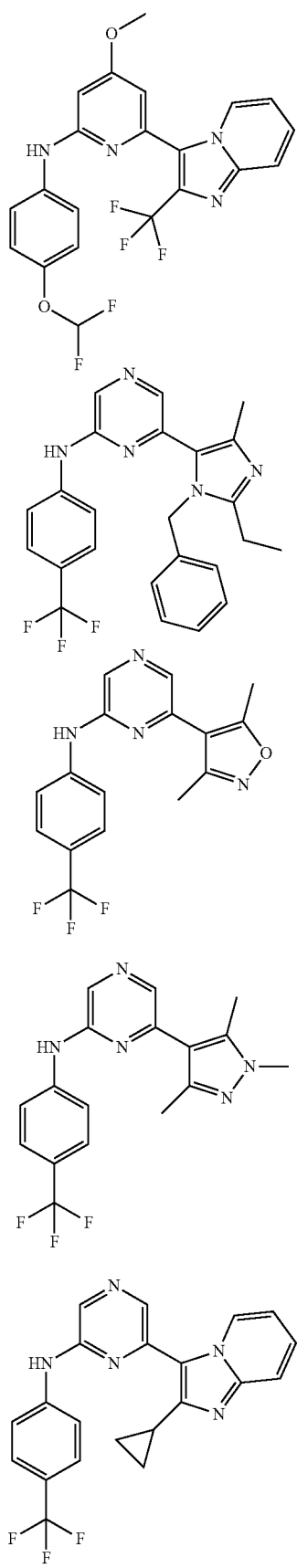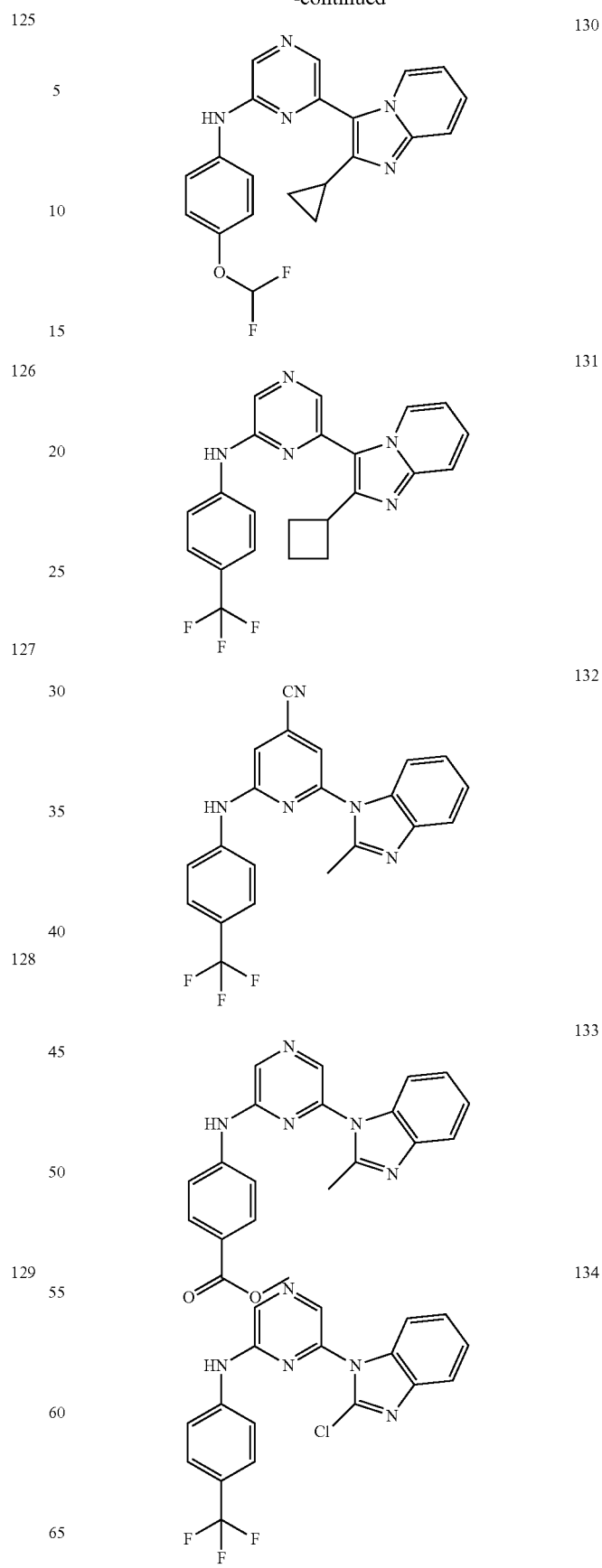

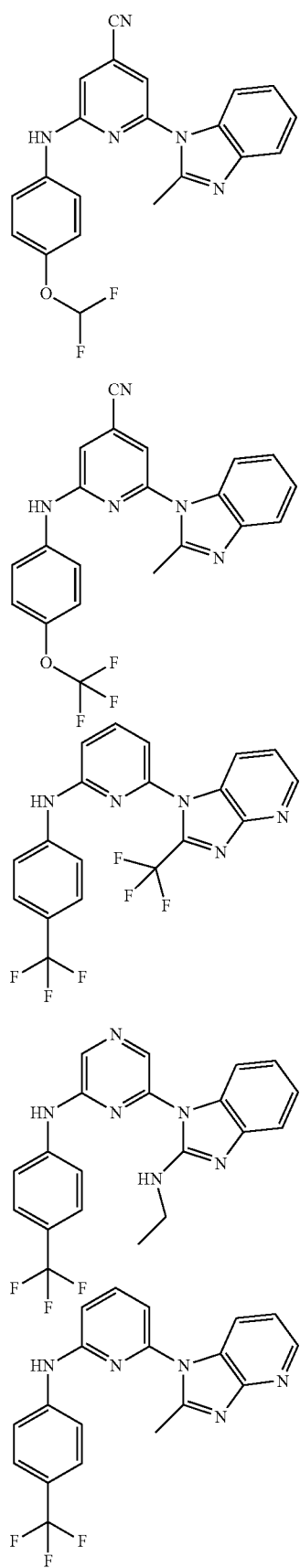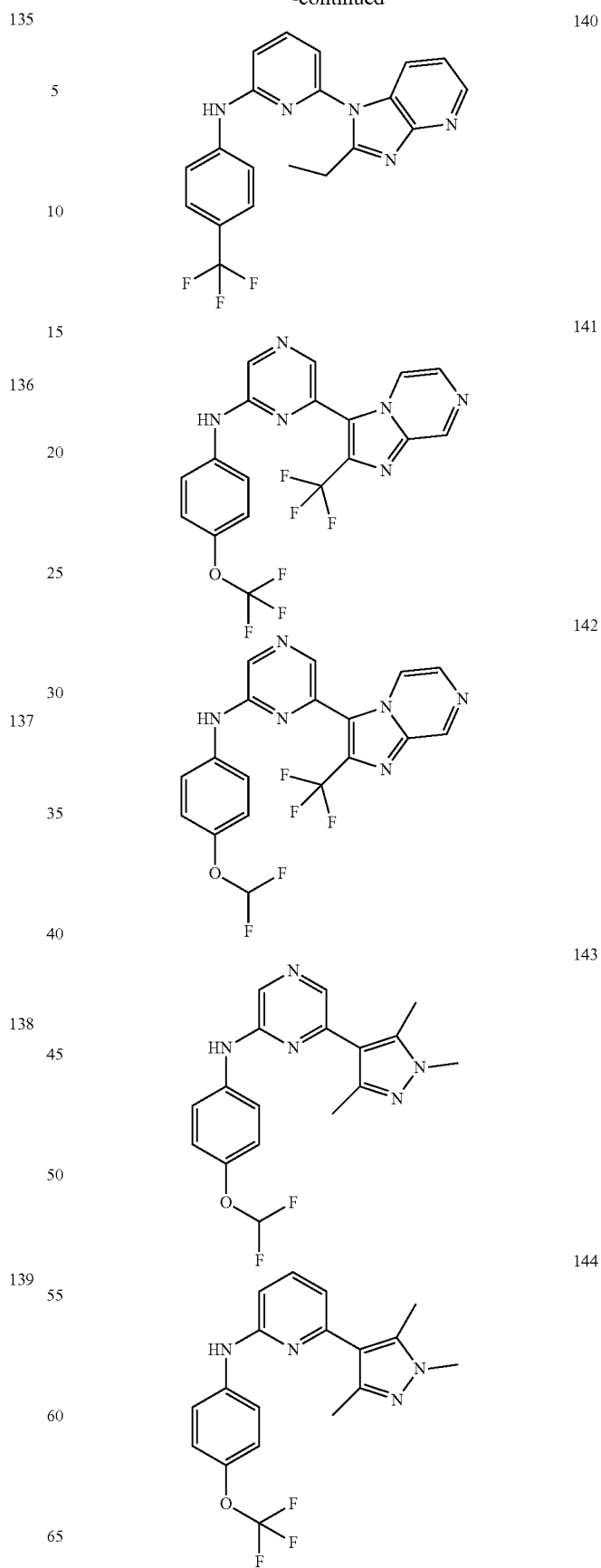

145 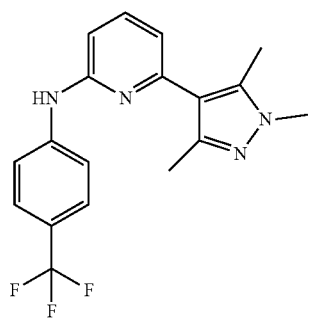
146 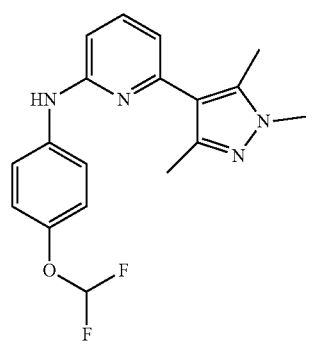
147 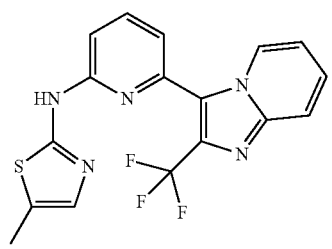
148 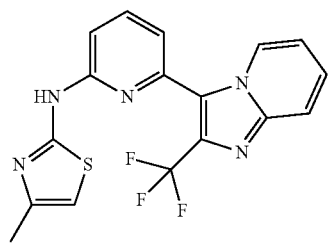
149 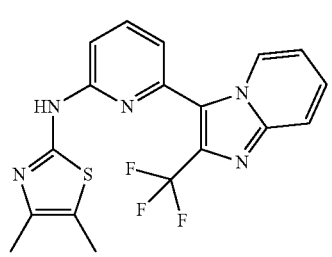
150 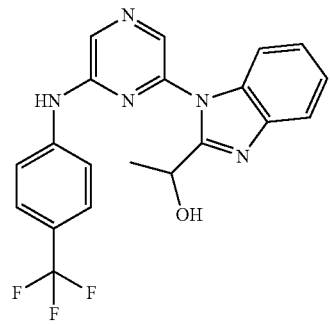
151 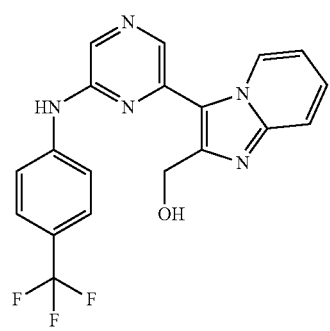
152 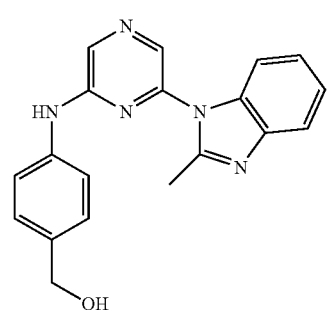
153 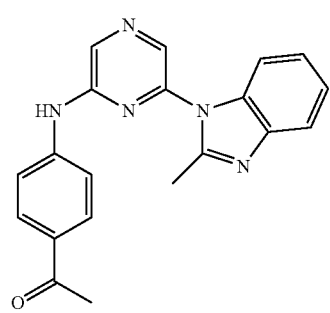
154 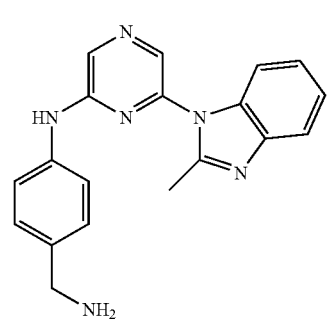

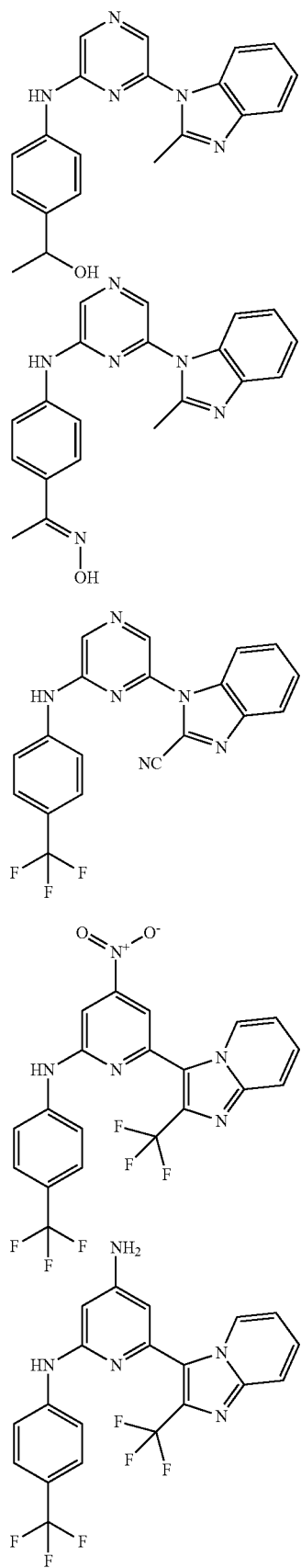
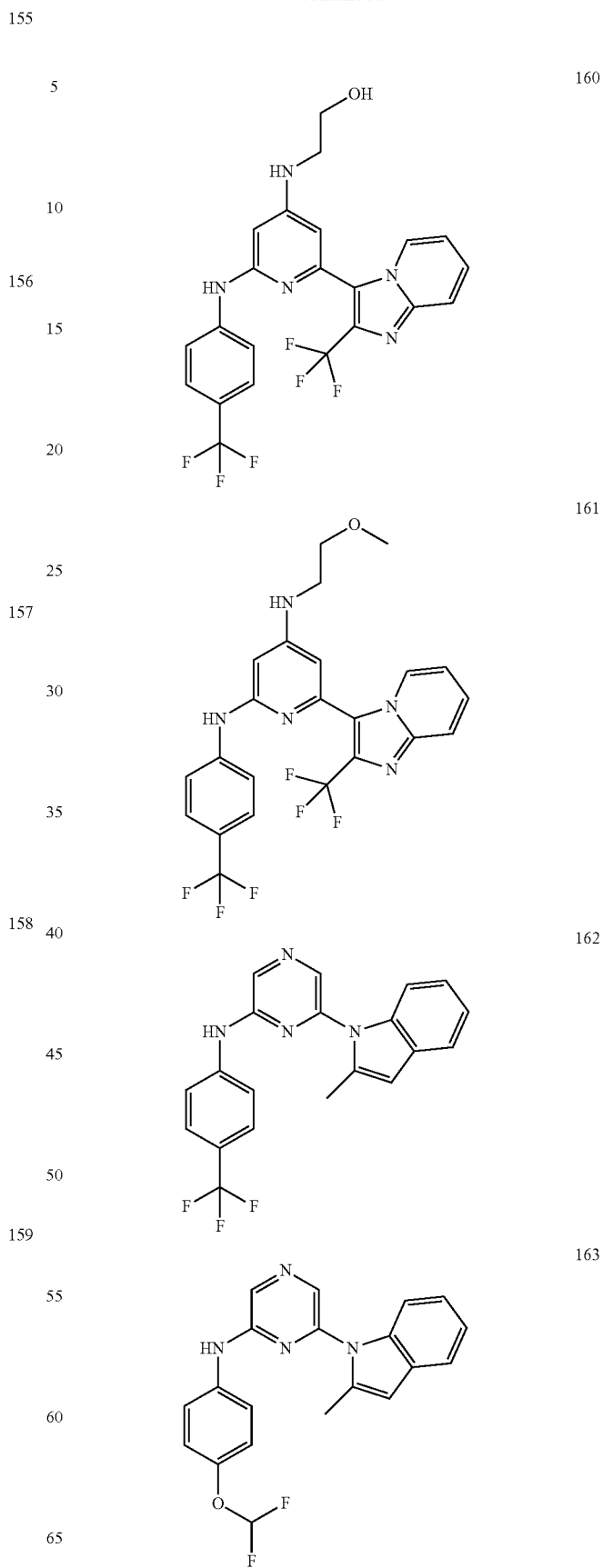

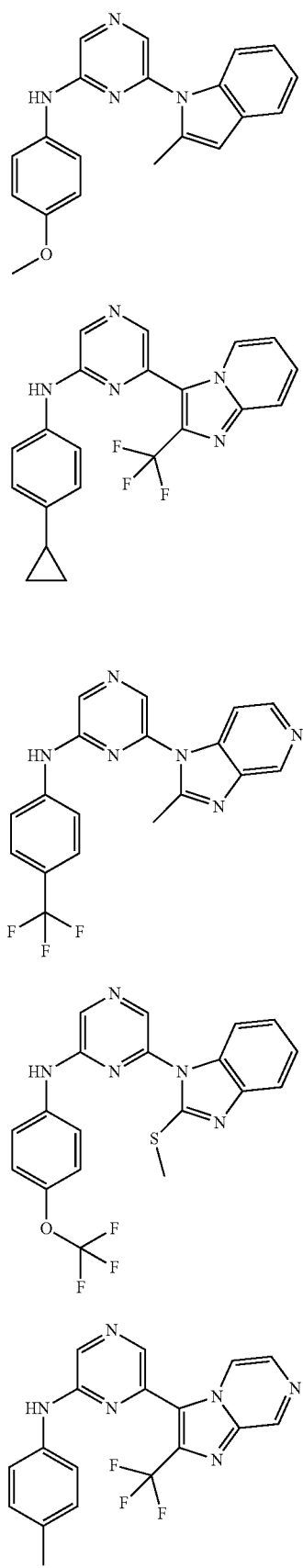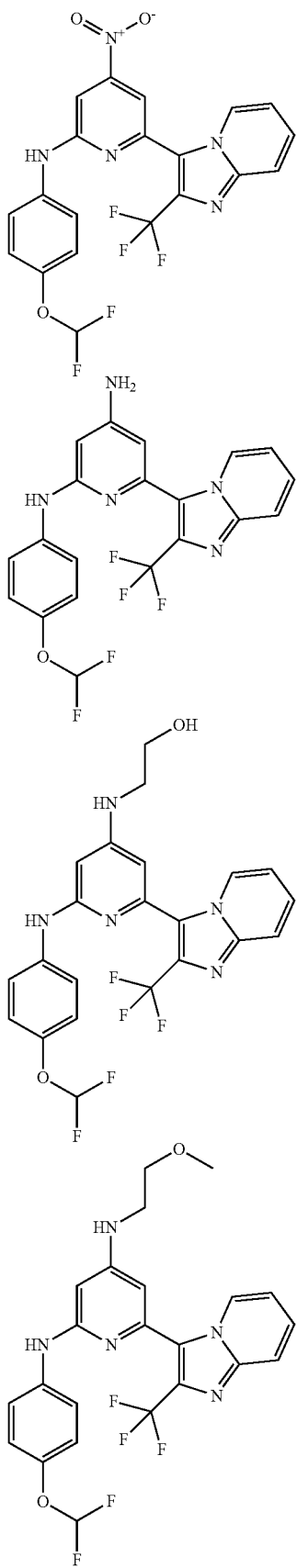

173 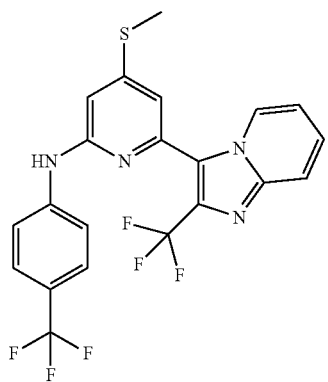
174 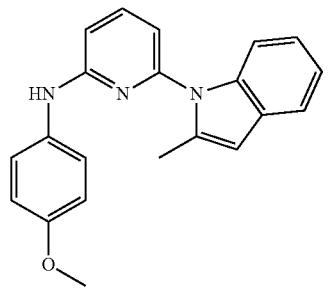
175 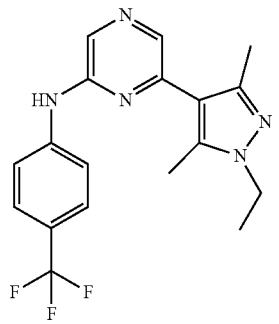
176 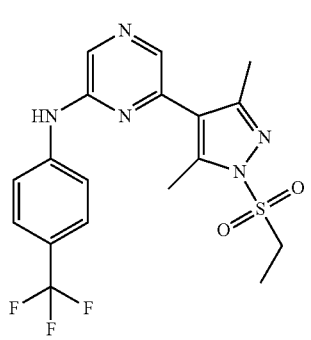
177 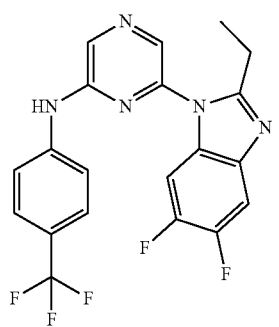
178 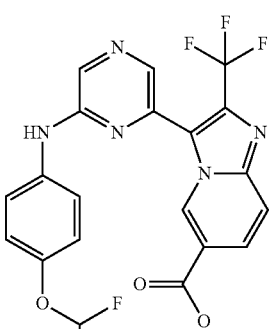
179 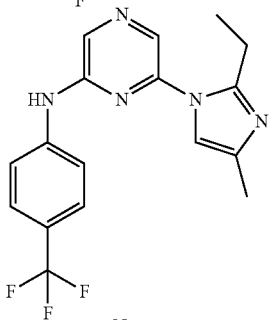
180 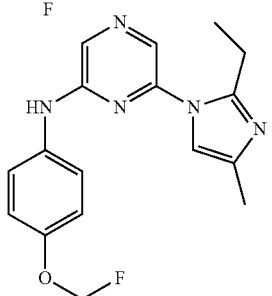
181 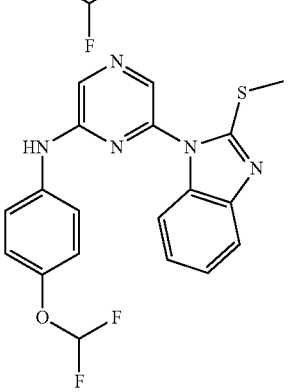
182 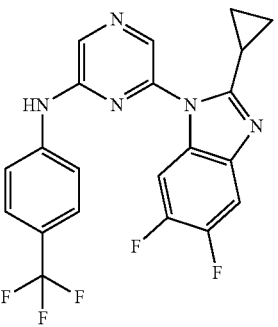

183 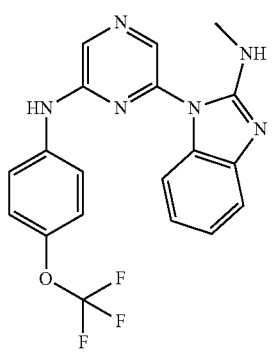
184 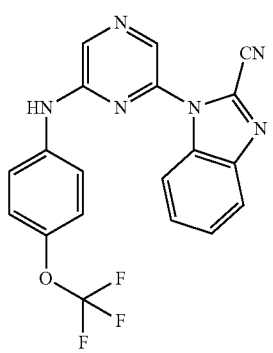
185 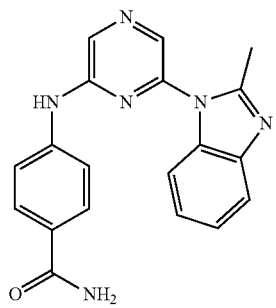
186 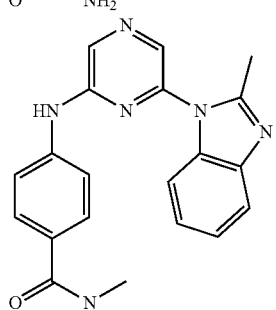
187 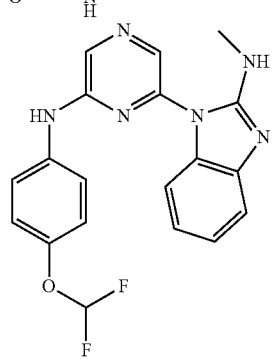
188 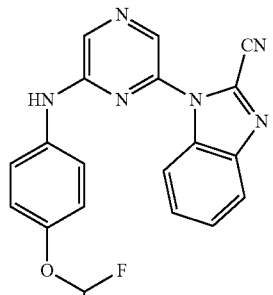
189 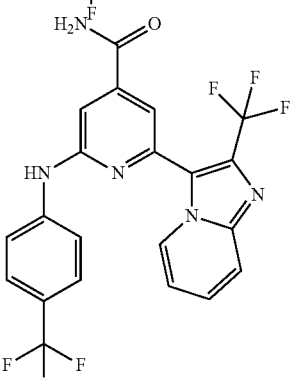
190 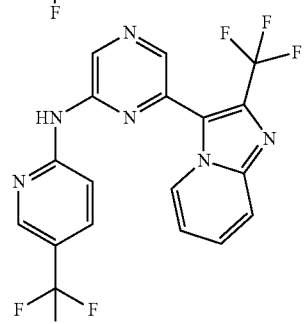
191 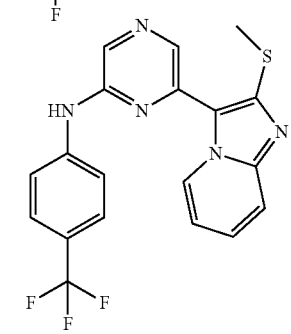
192 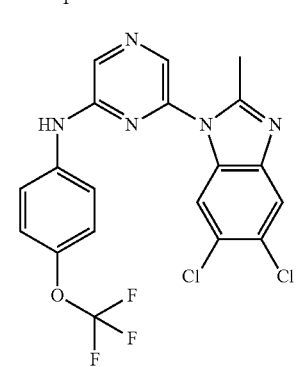

193 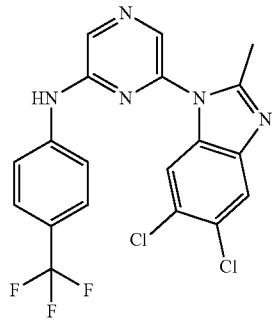
194 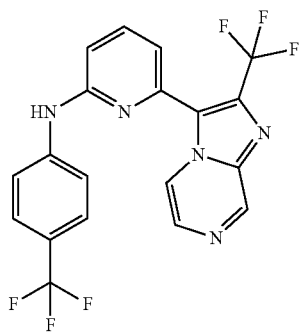
195 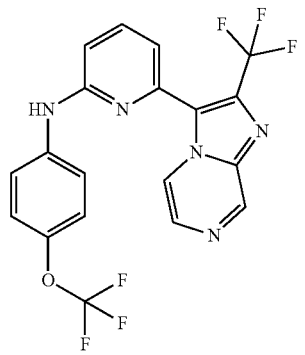
196 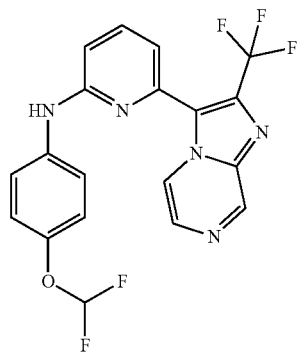
197 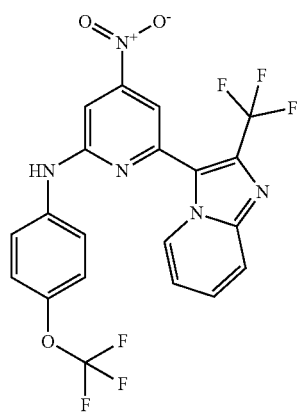
198 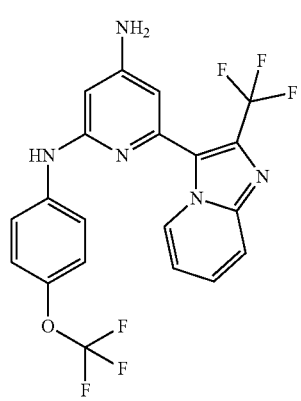
199 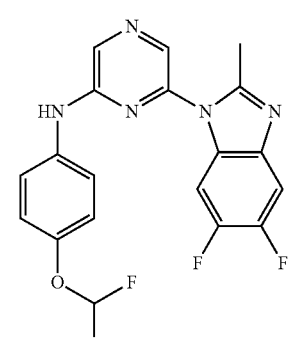
200 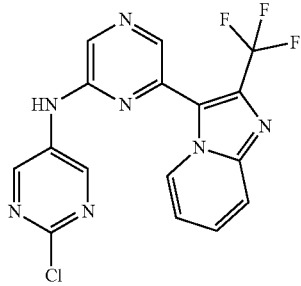

201 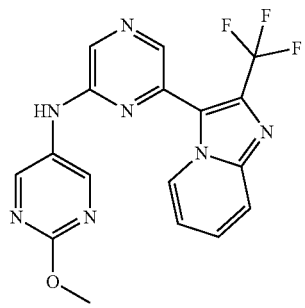
202 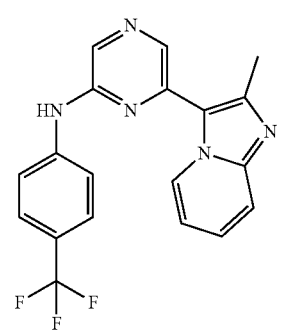
203 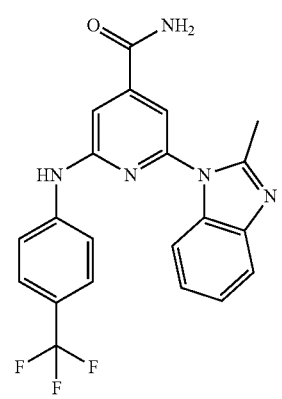
204 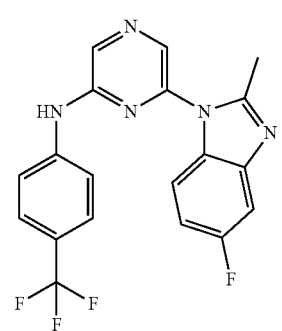
205 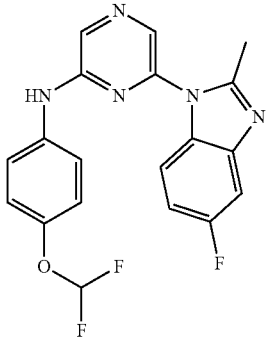
206 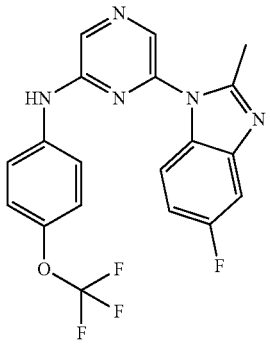
207 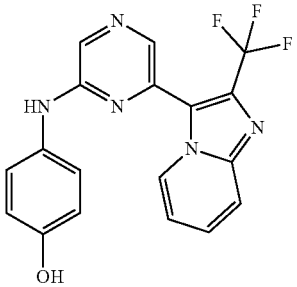
208 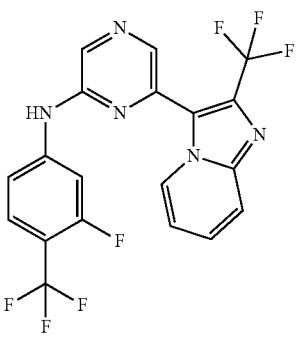
209 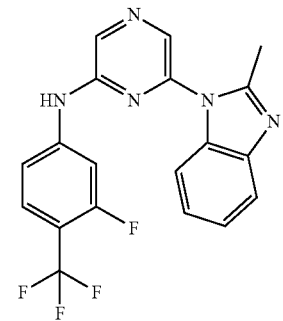

210 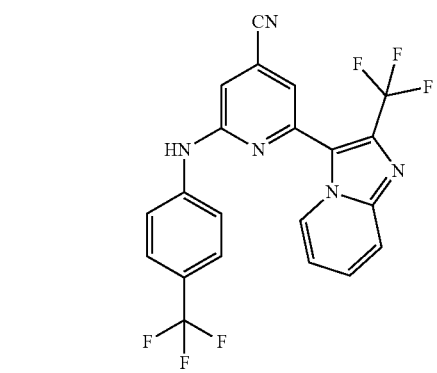
lp;3p
211 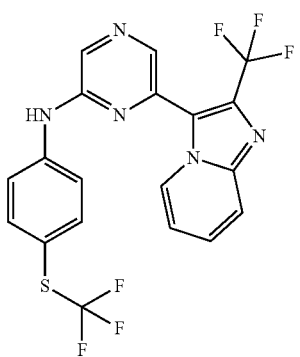
212 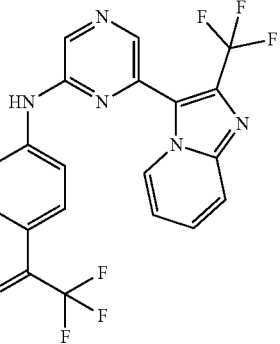
213 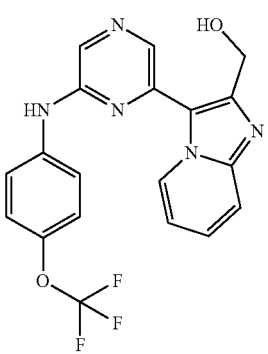
214 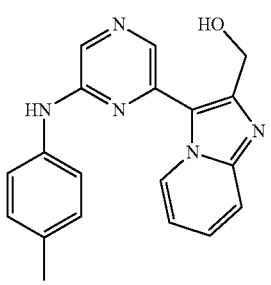
215 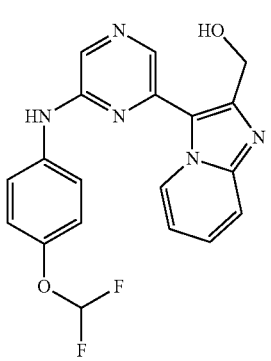
216 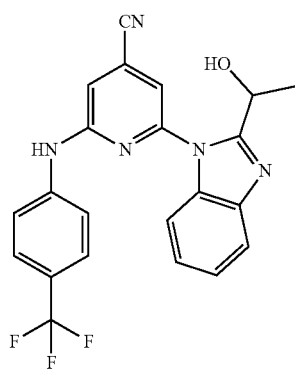
217 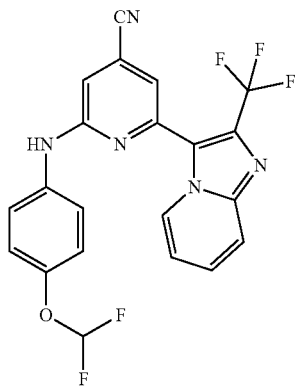

218 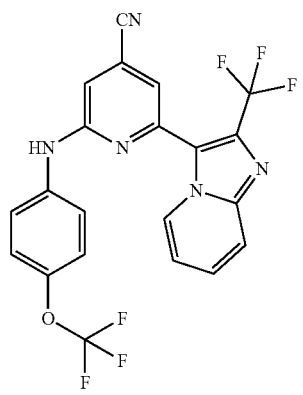
219 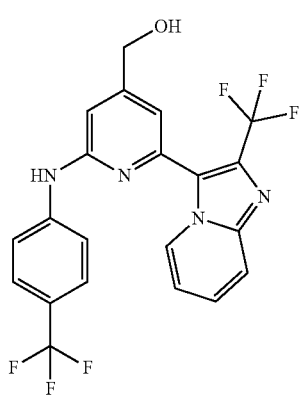
220 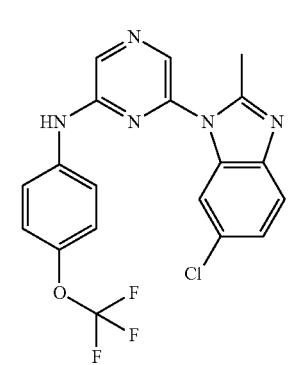
221 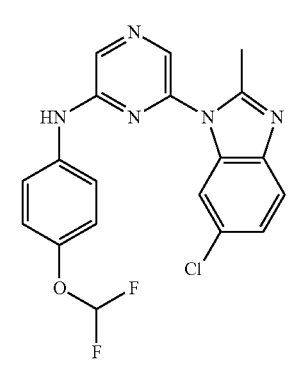
222 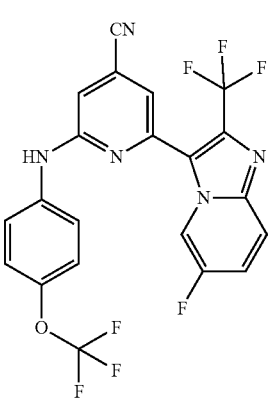
223 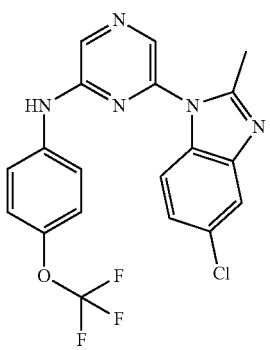
224 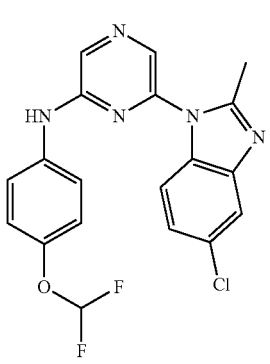
225 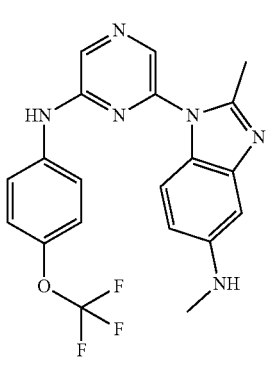

226 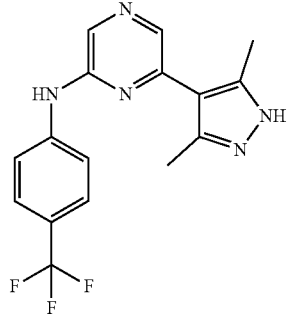
227 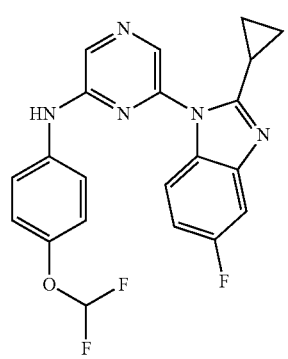
228 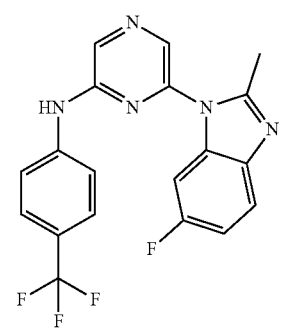
229 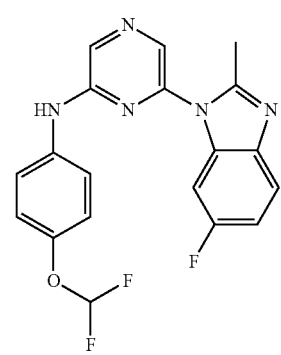
230 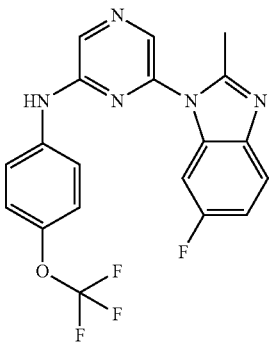
231 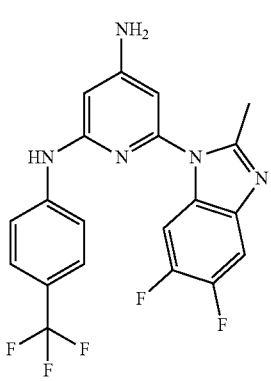
232 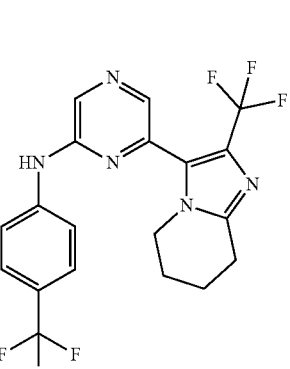
233 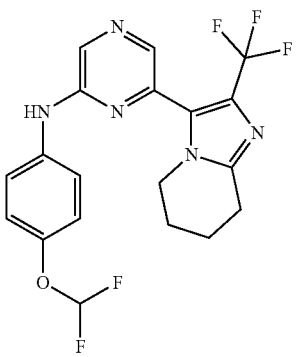

234 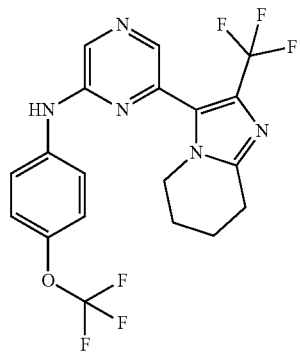
235 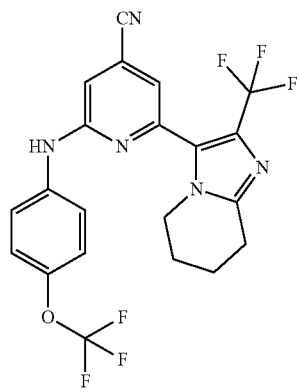
236 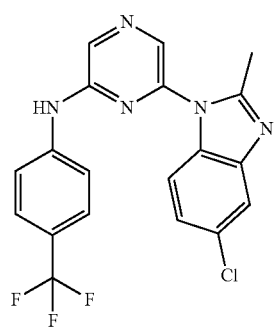
237 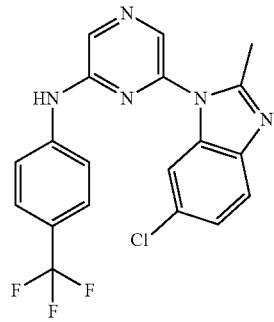
238 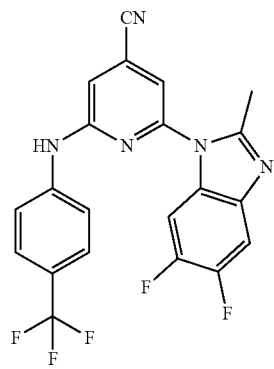

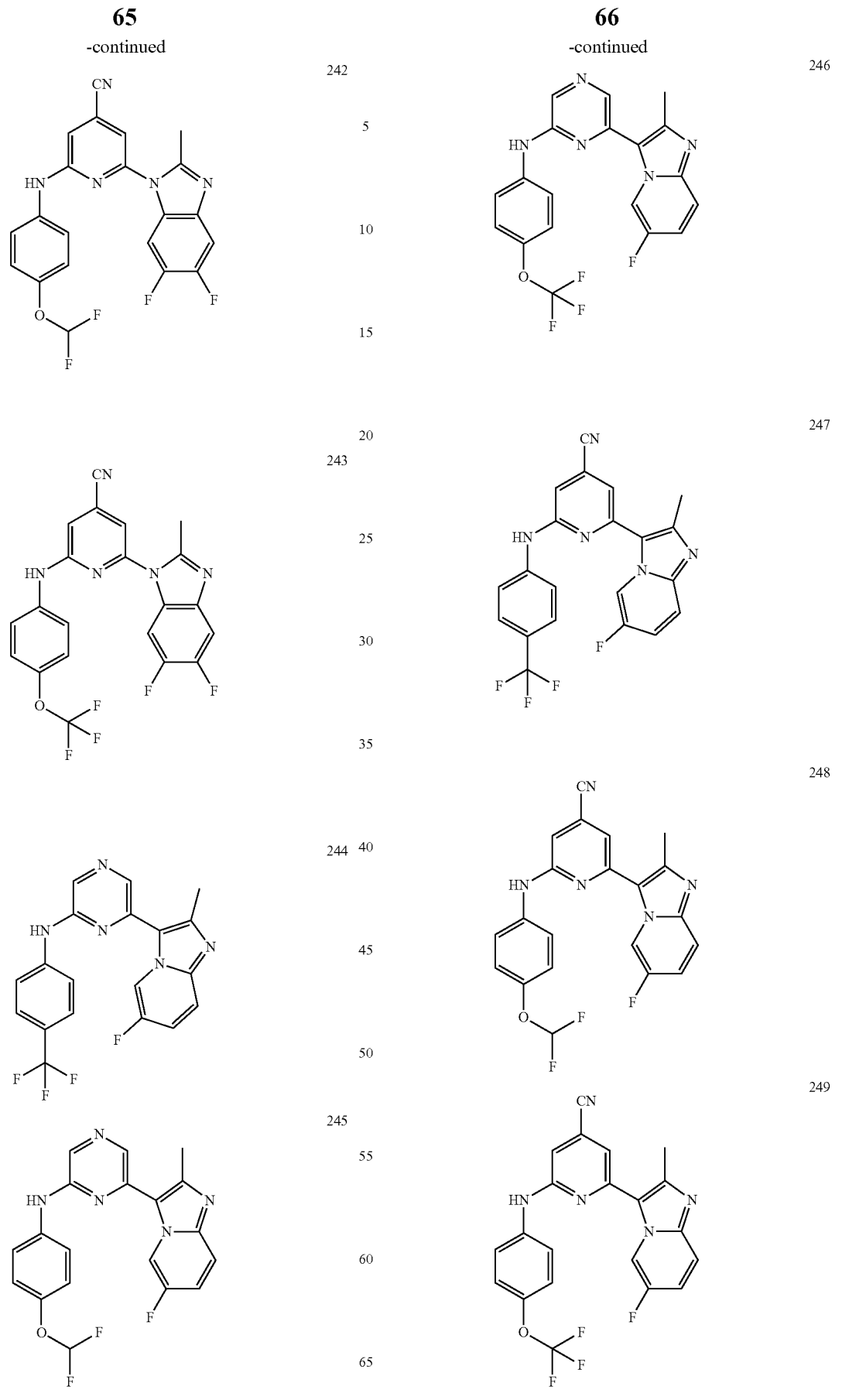

242

243

244

245

246

247

248

249

-continued
250
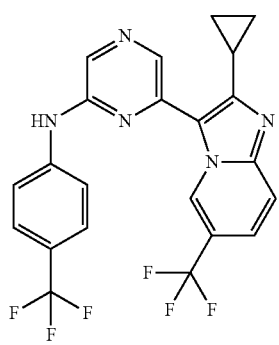
251
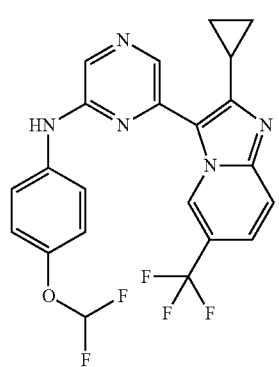
252
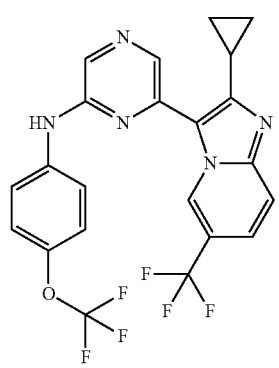
253
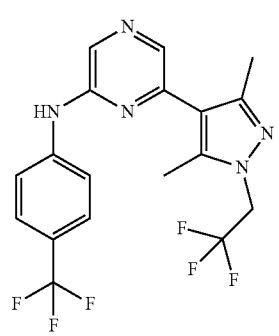
-continued
254
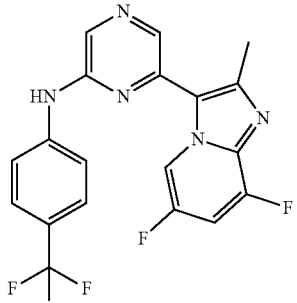
255
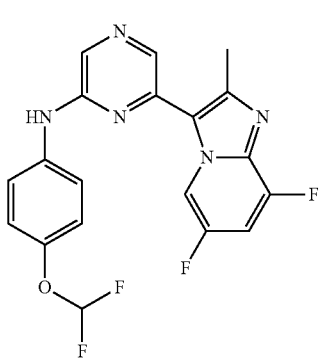
256
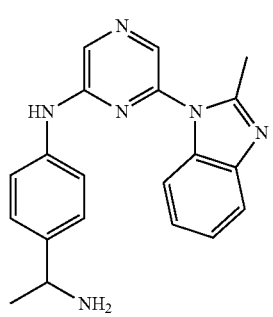
257
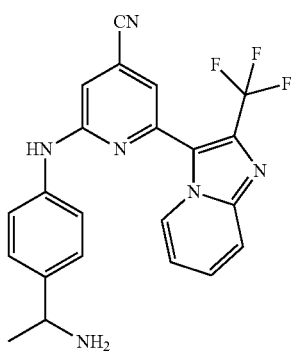

258 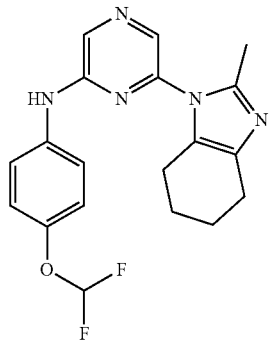
259 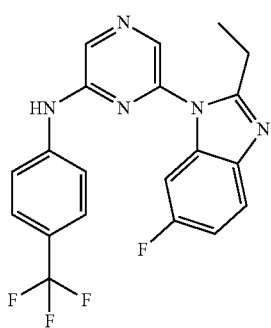
260 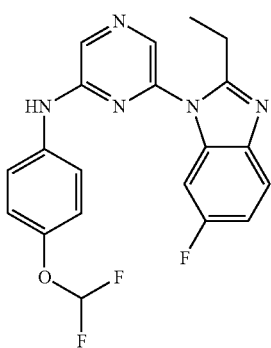
261 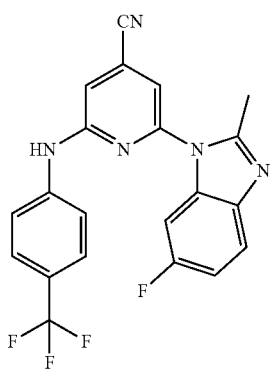
262 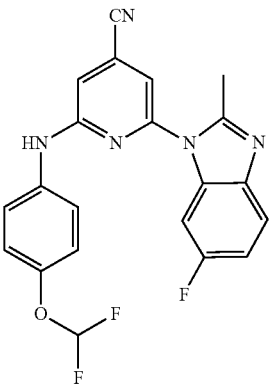
263 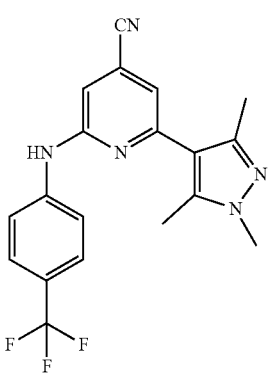
264 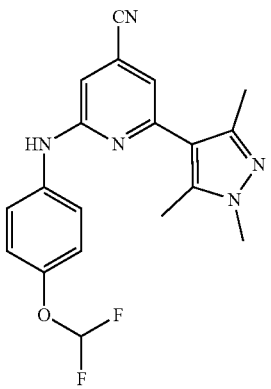
265 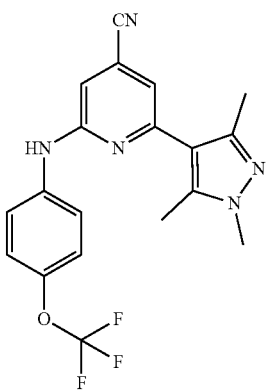

266 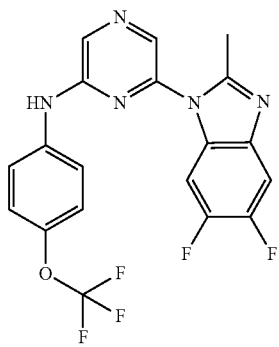
267 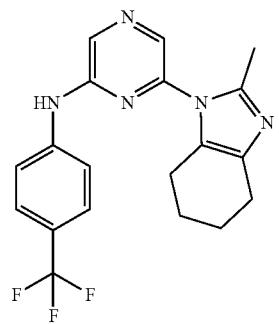
268 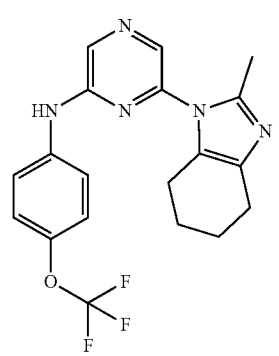
269 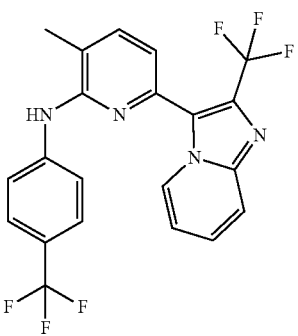
270 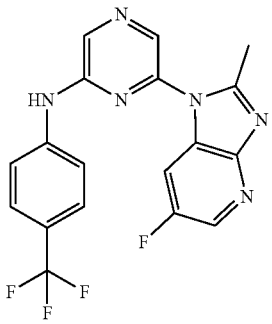
271 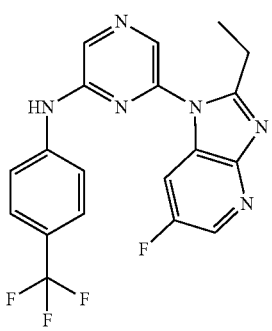
272 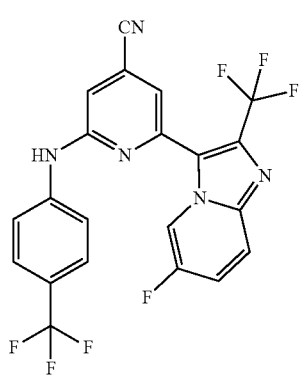
273 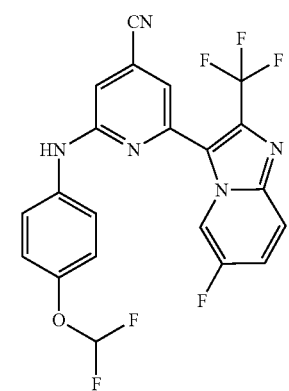

-continued
274 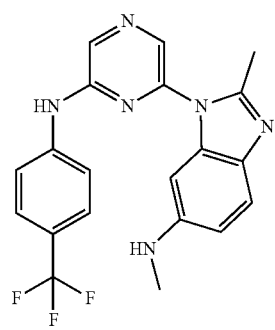
275 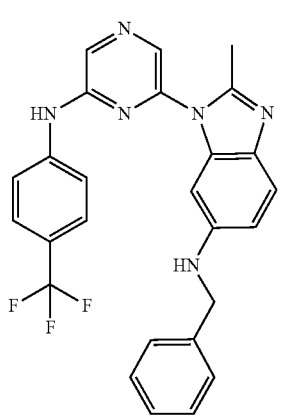
276 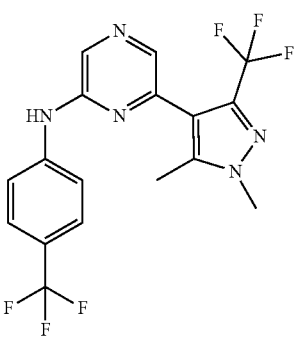
277 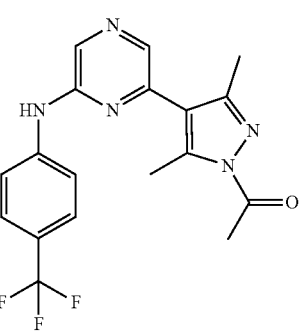
-continued
278 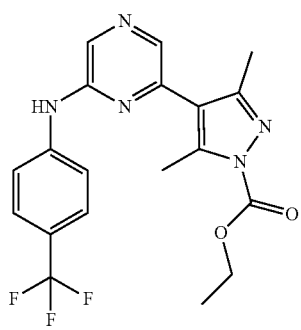
279 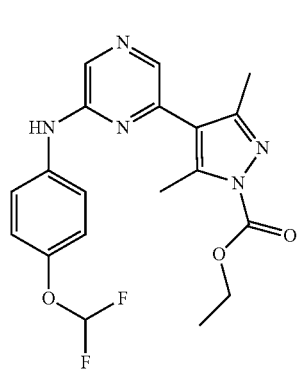
280 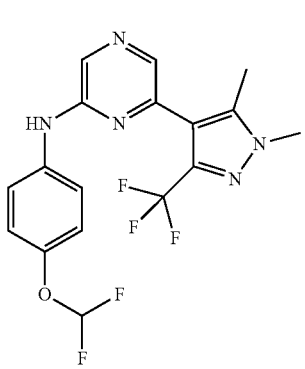
281 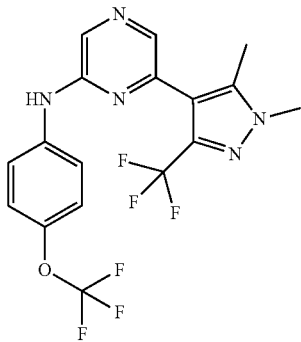

282 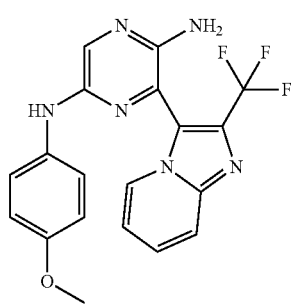
283 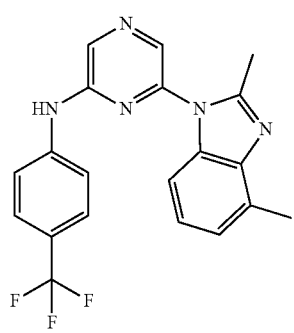
284 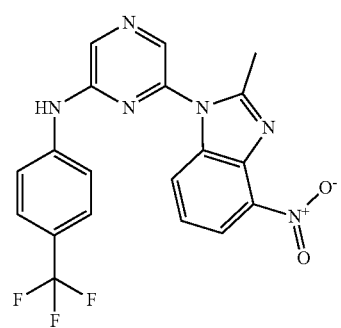
285 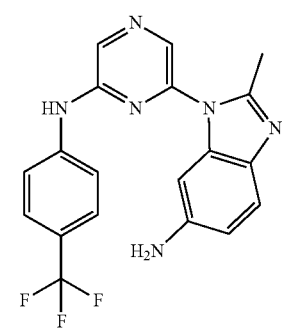
286 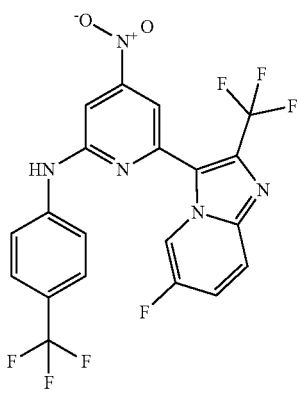
287 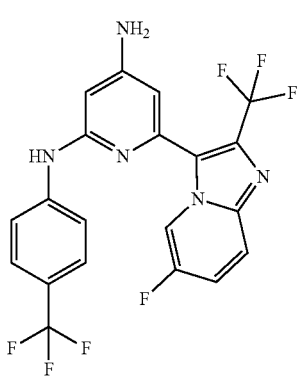
288 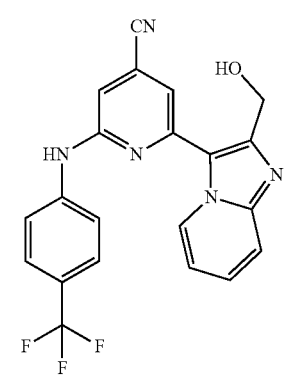
289 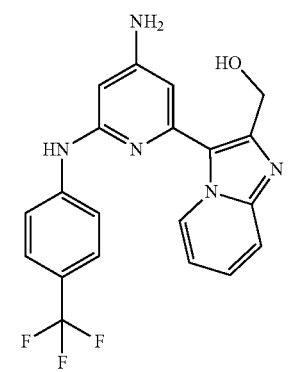

290 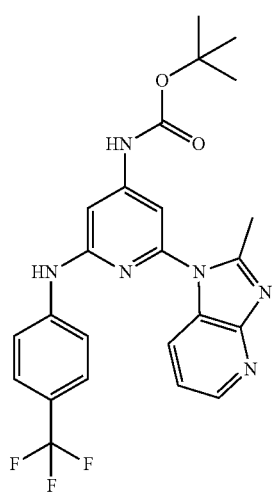
291 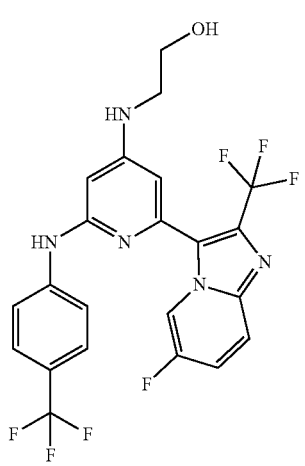
292 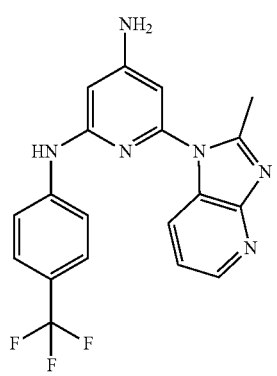
293 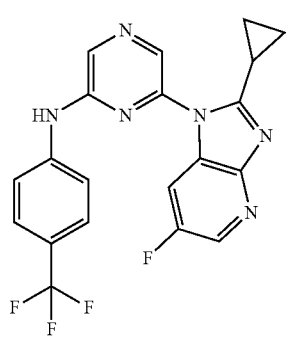
294 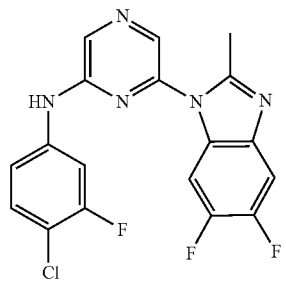
295 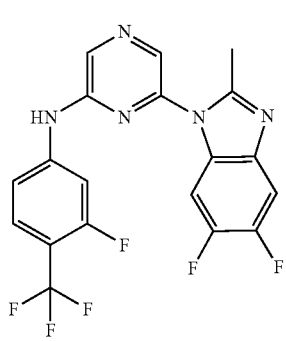
296 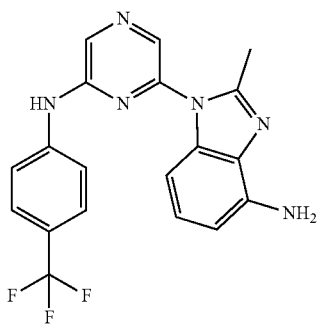
297 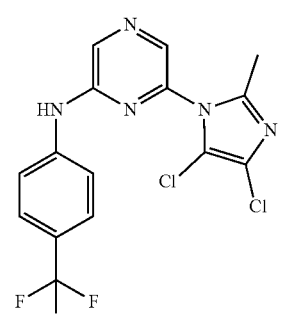
298 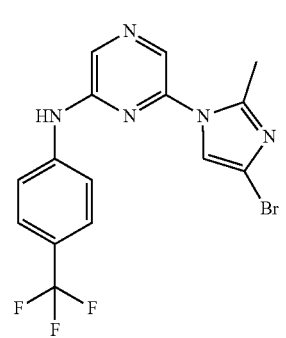

-continued
299 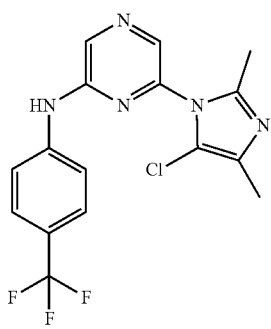
300 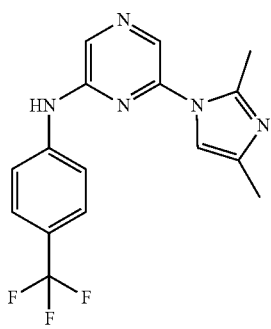
301 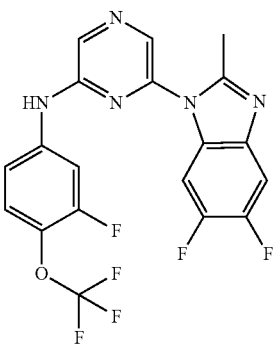
302 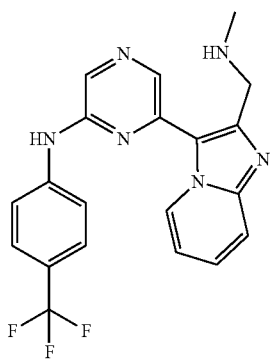
-continued
303 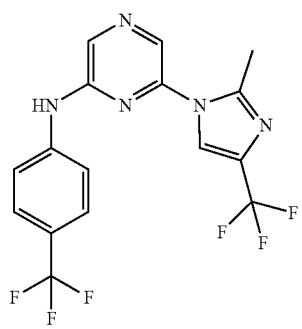
304 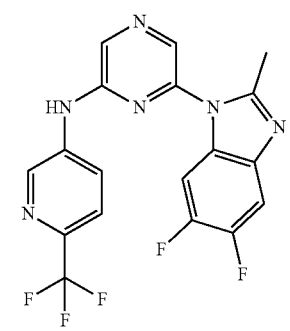
305 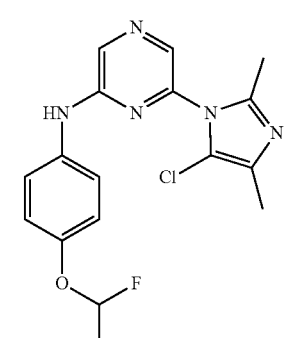
306 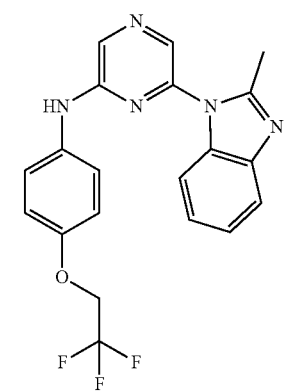

307 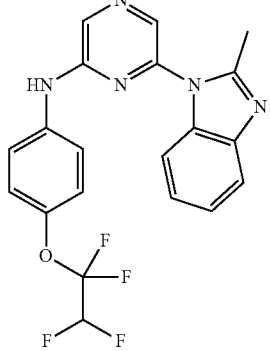
308 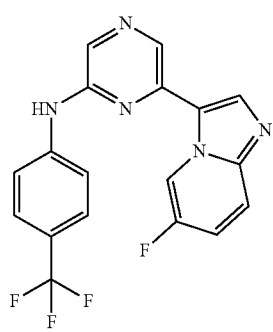
309 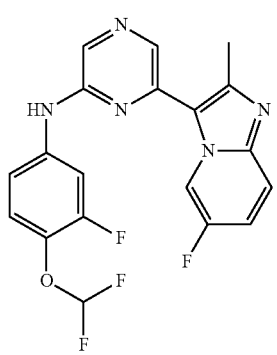
310 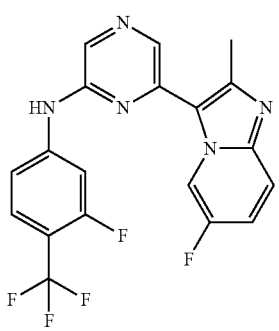
311 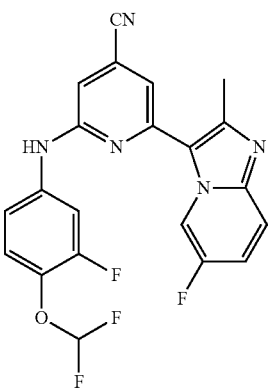
312 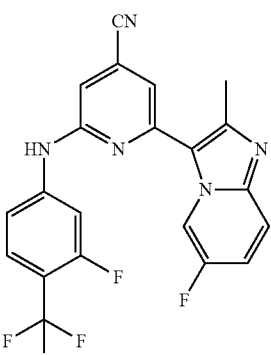
313 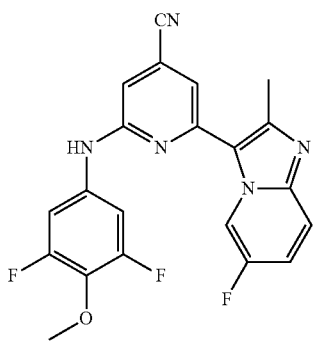
314 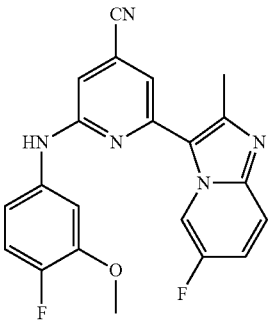

315 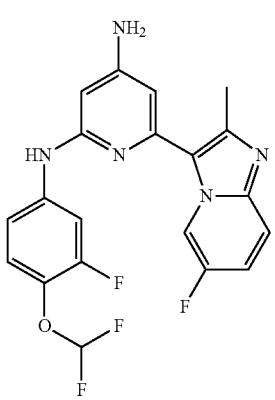
316 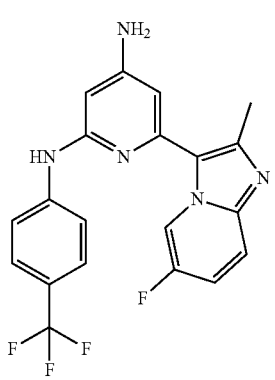
317 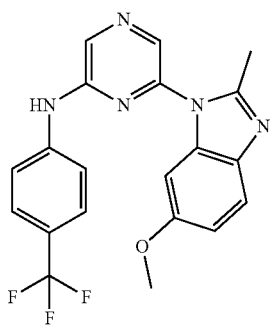
318 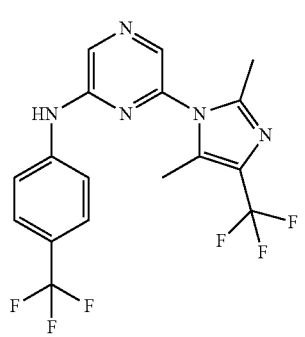
319 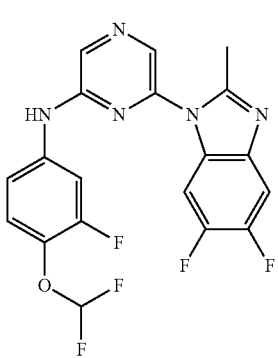
320 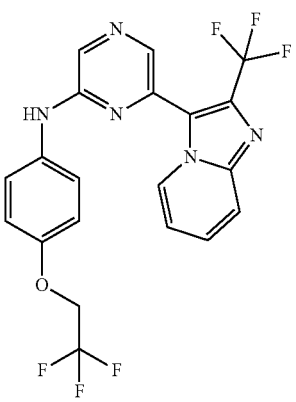
321 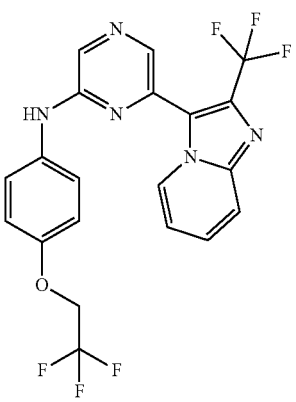
322 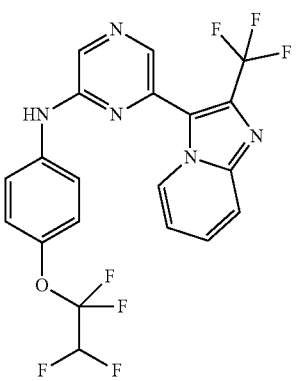

-continued
323 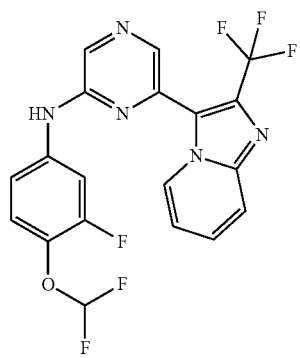
324 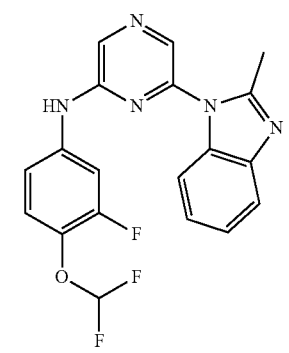
325 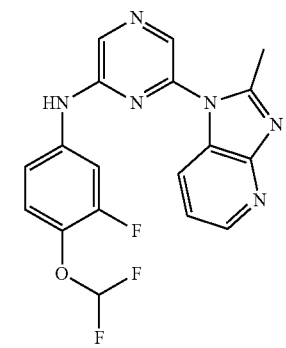
326 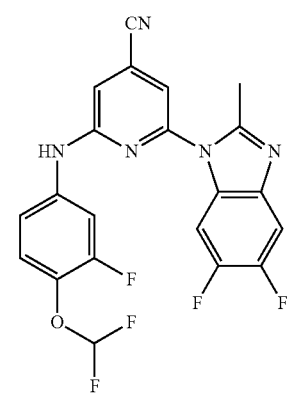
-continued
327 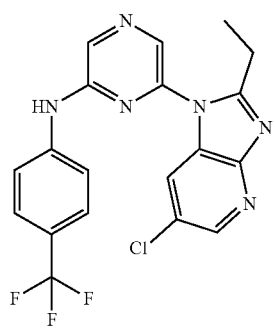
328 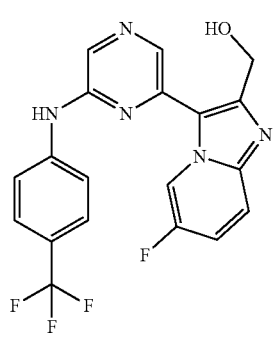
329 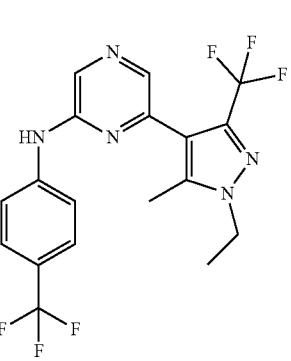
330 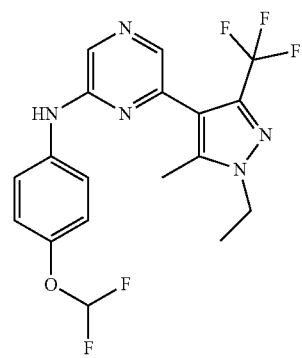

| 331 | 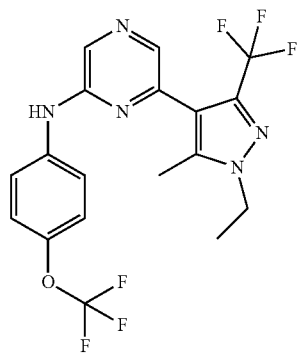 | 335 | 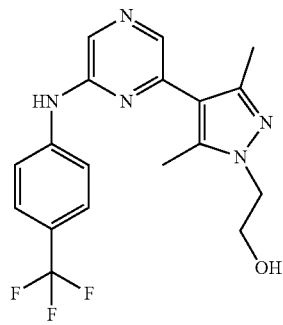 |
| 332 | 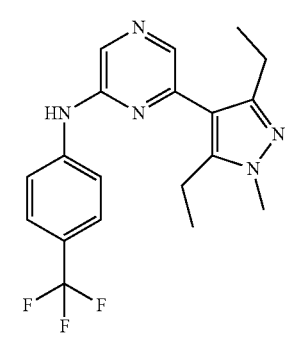 | 336 | 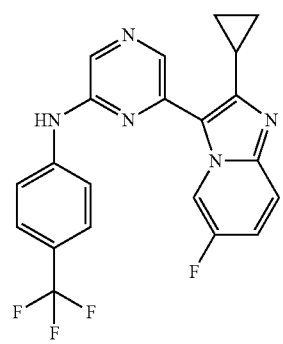 |
| 333 | 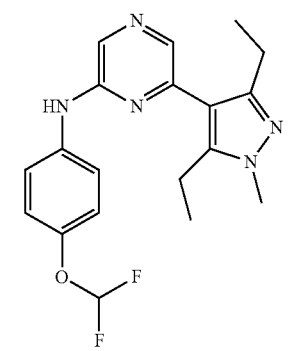 | 337 | 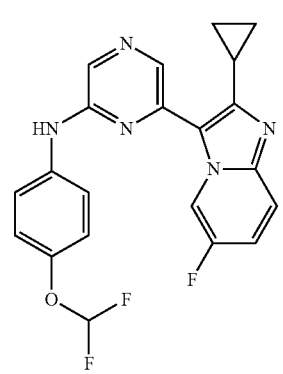 |
| 334 | 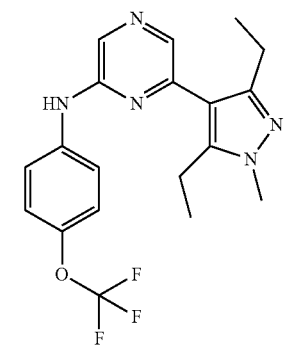 | 338 | 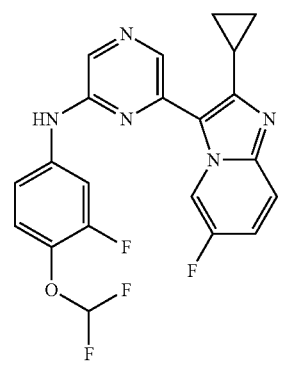 |

339 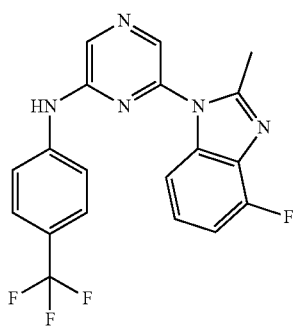
340 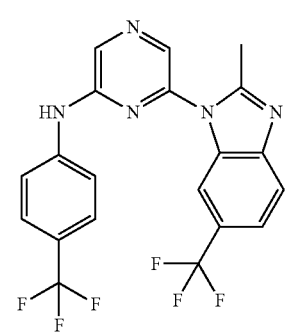
341 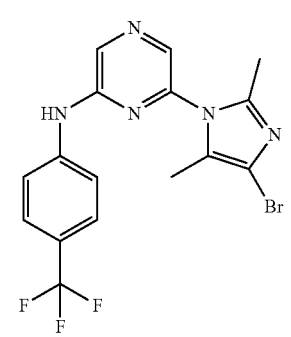
342 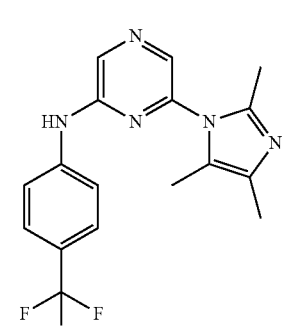
343 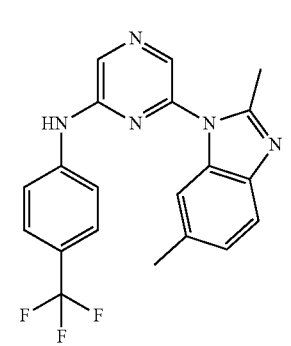
344 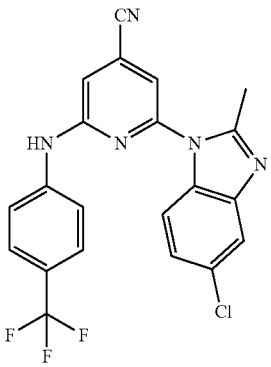
345 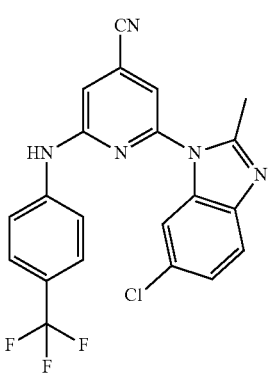
346 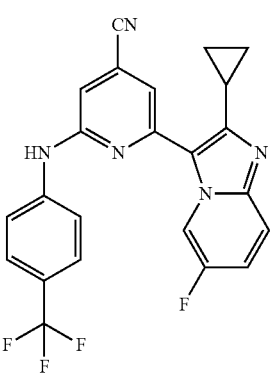
347 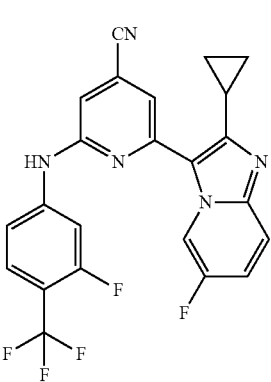

348 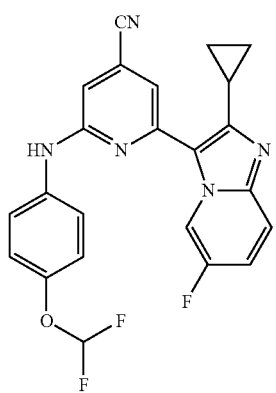
349 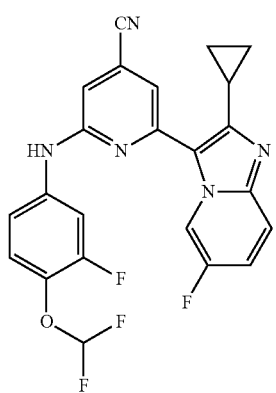
350 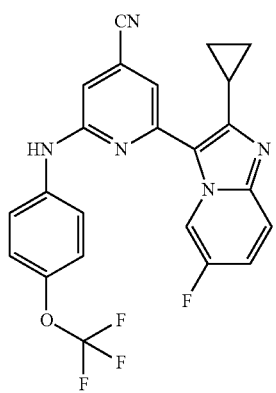
351 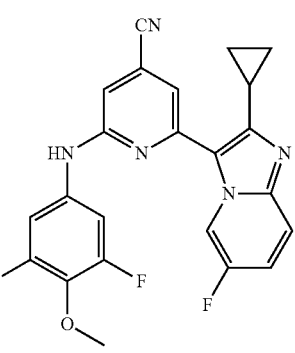
352 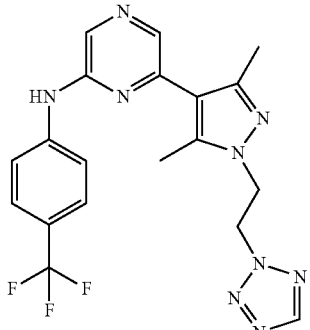
353 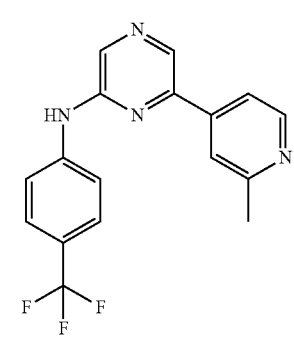
354 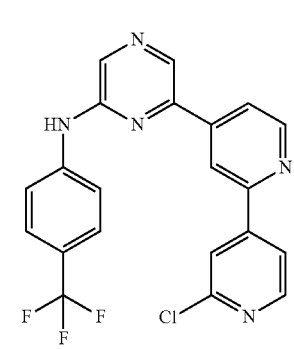
355 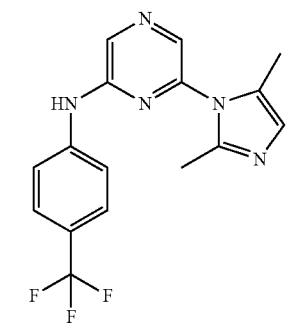

-continued
| | |
|---|---|
| 356 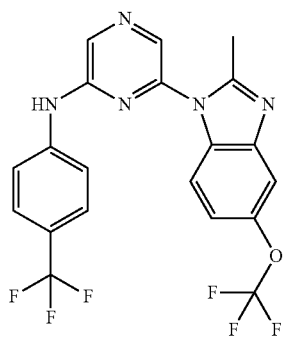 | 360 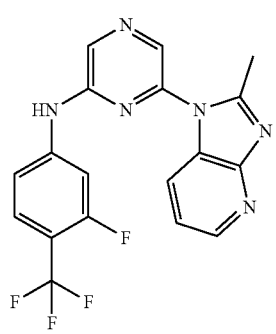 |
| 357 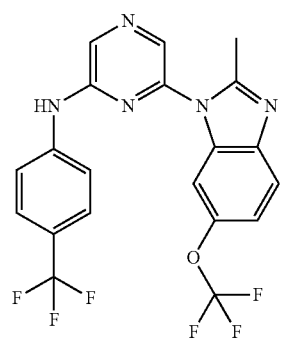 | 361 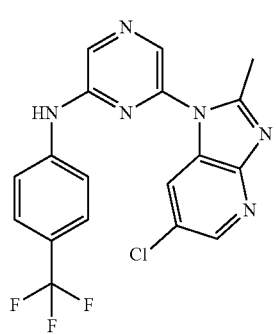 |
| 358 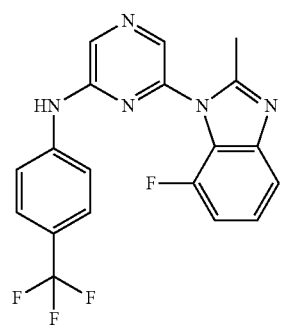 | 362 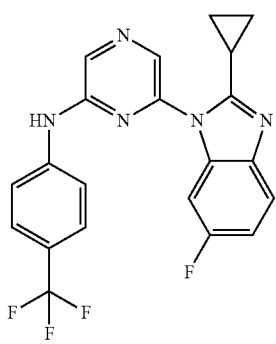 |
| 359 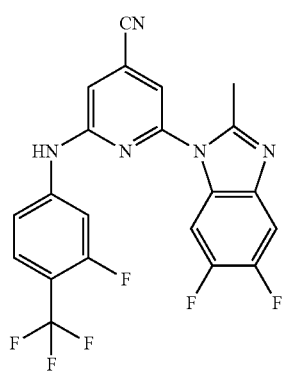 | 363 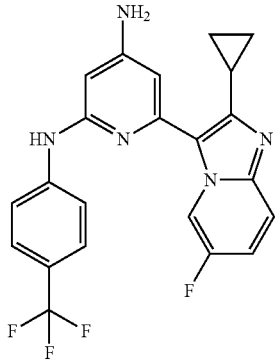 |

364 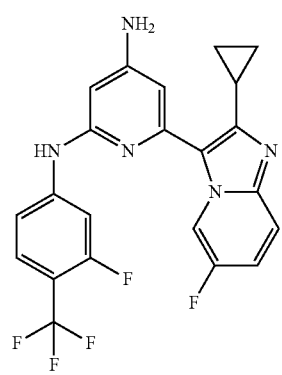
365 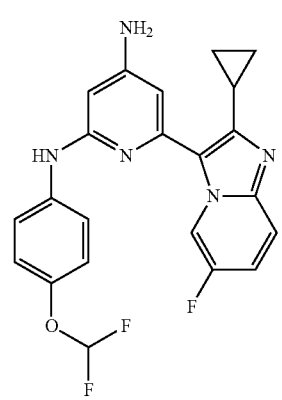
366 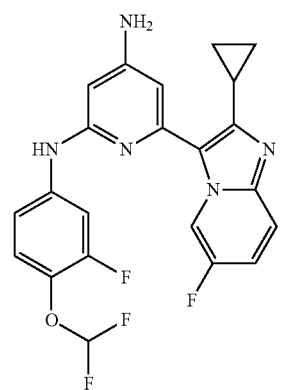
367 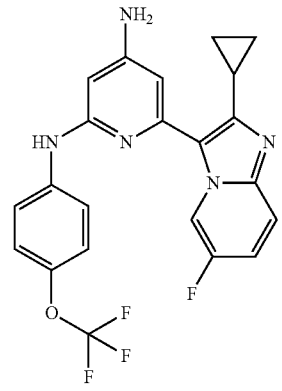
368 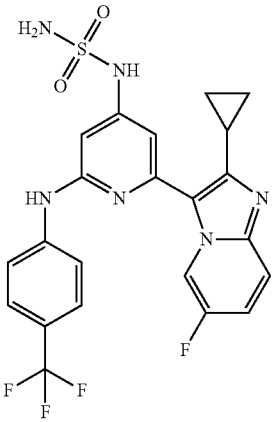
369 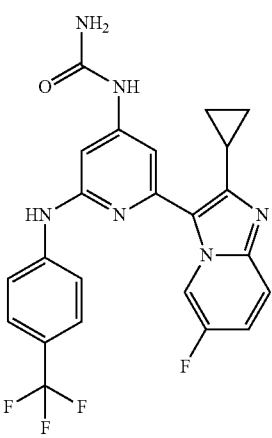
370 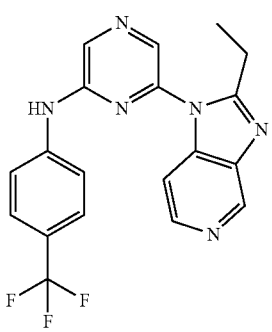
371 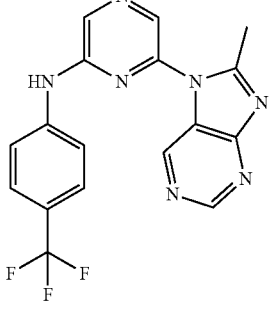

| | |
|---|---|
| 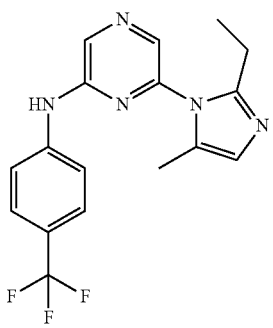 372 | 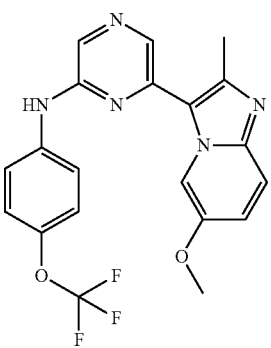 377 |
| 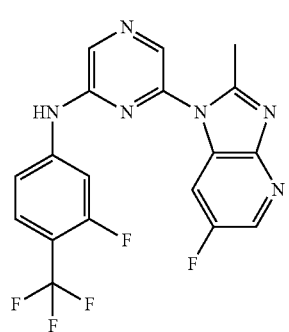 373 | 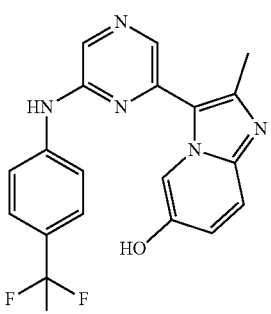 378 |
| 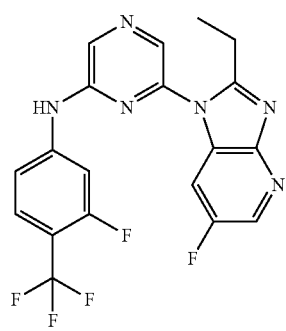 374 | 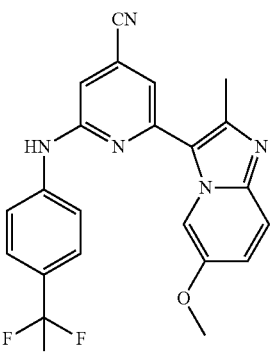 379 |
| 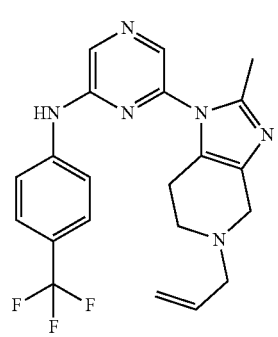 375 | 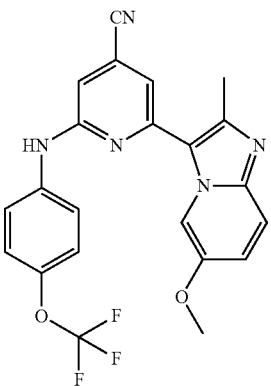 380 |
| 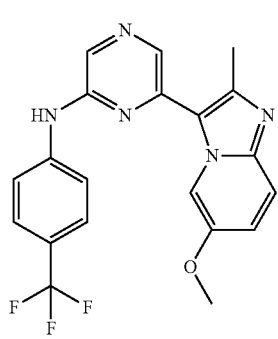 376 | |

381 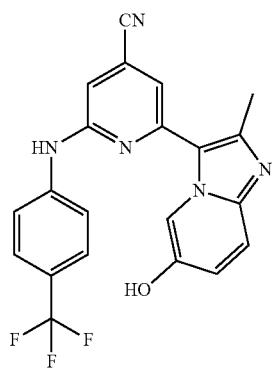
382 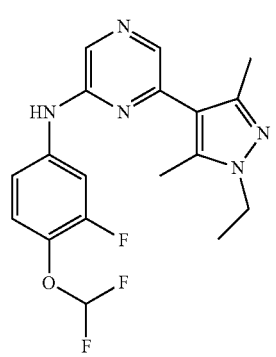
383 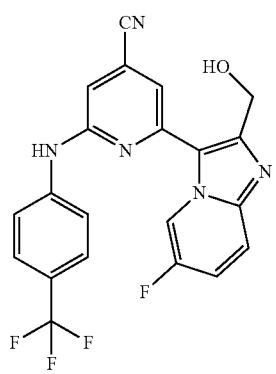
384 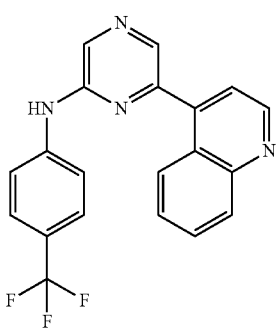
385 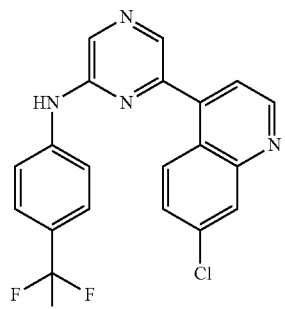
386 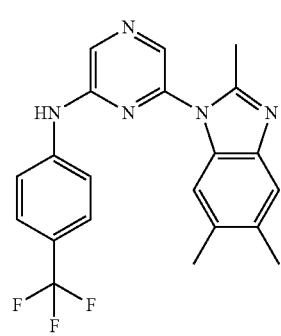
387 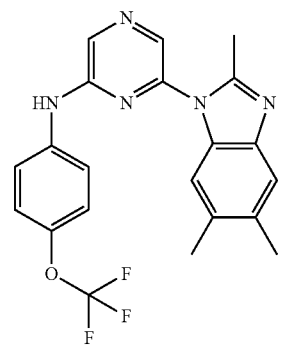
388 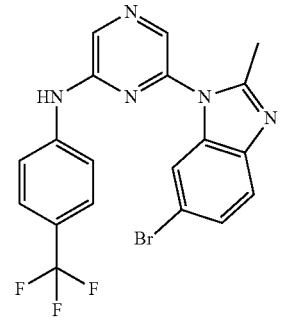

389 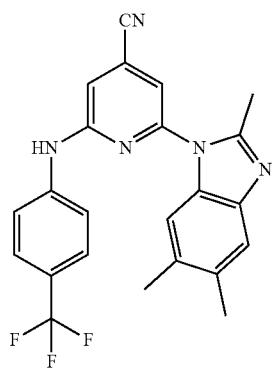
390 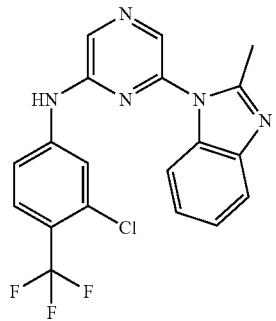
391 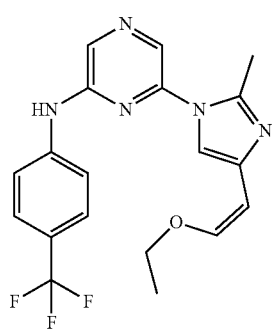
392 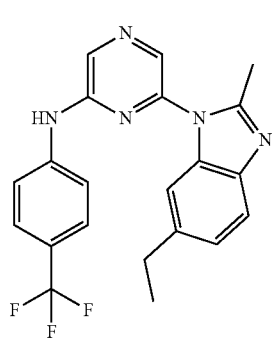
393 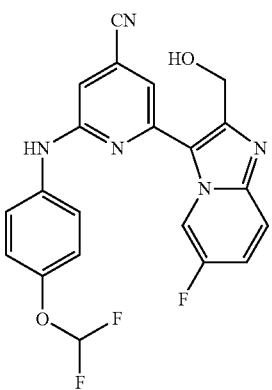
394 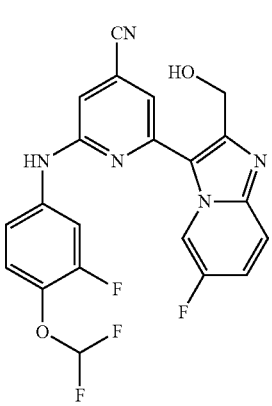
395 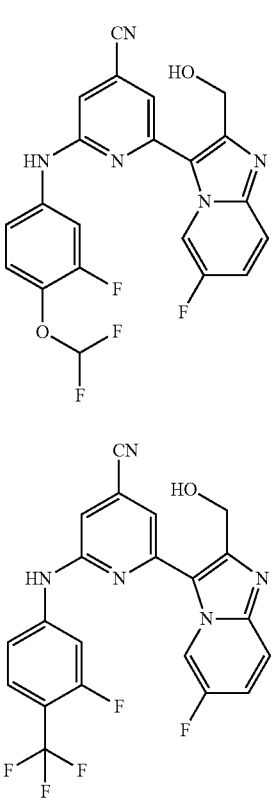
396 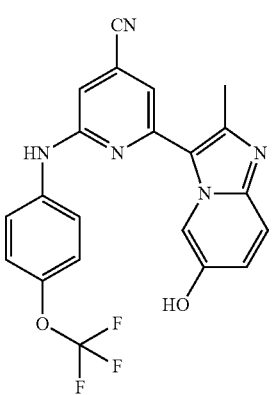

| 397 | 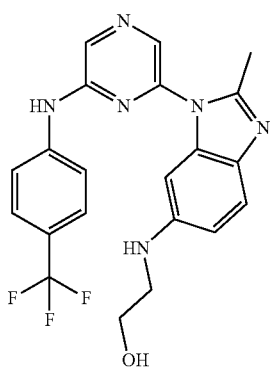 | 401 | 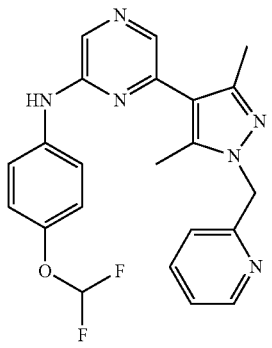 |
| 398 | 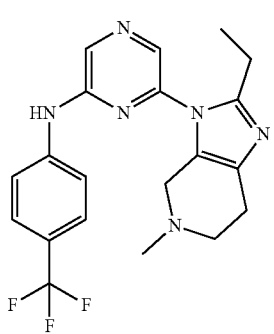 | 402 | 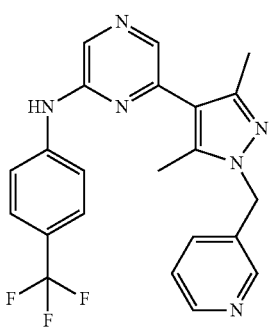 |
| | | 403 | 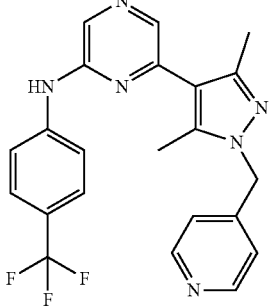 |
| 399 | 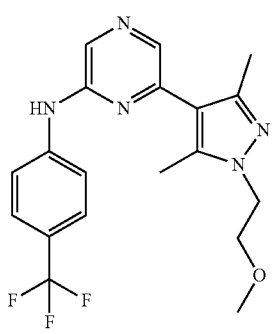 | 404 | 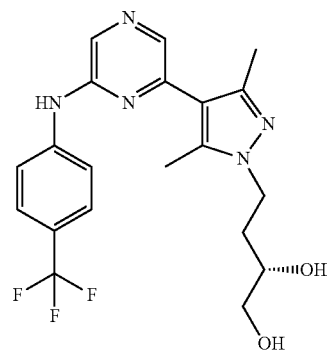 |
| 400 | 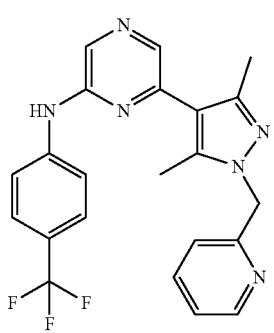 | 405 | 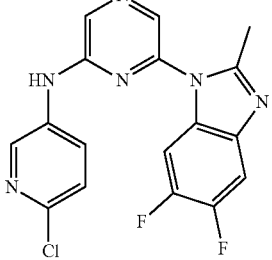 |

406 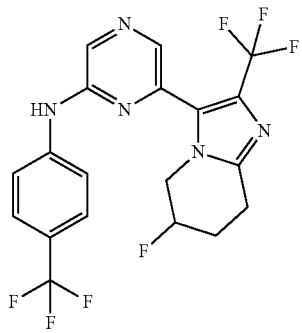
407 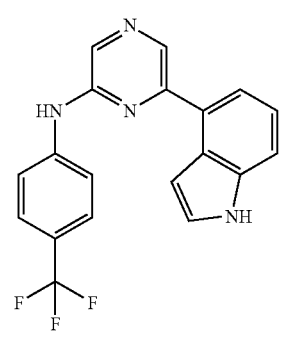
408 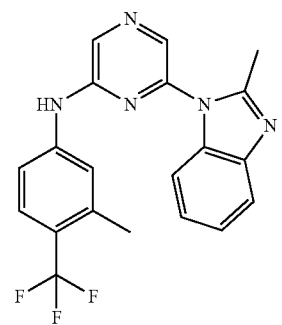
409 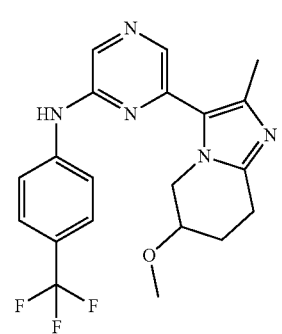
410 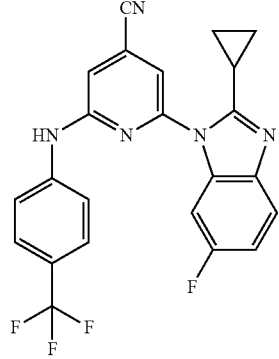
411 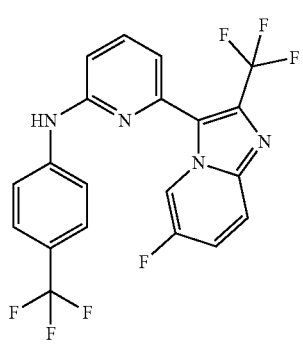
412 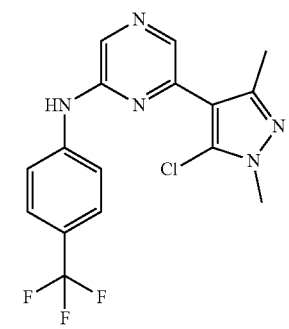
413 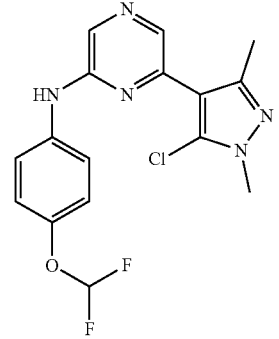

414 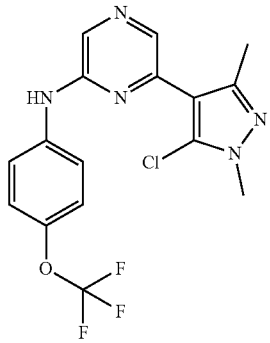
415 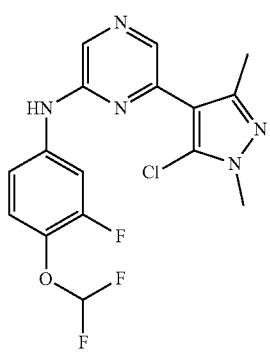
416 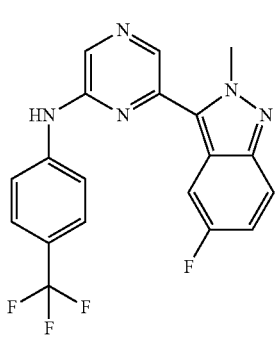
417 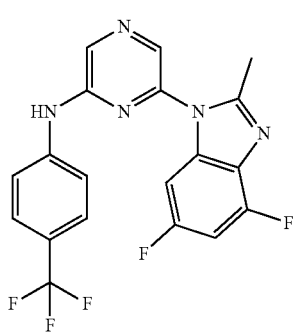
418 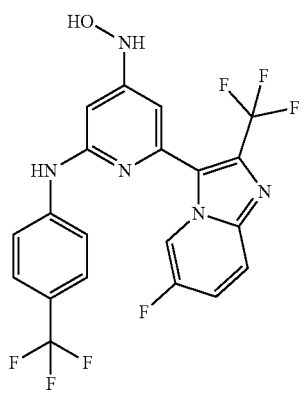
419 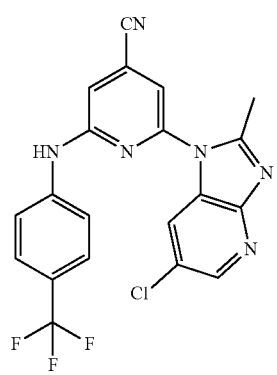
420 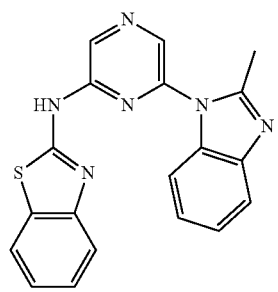
421 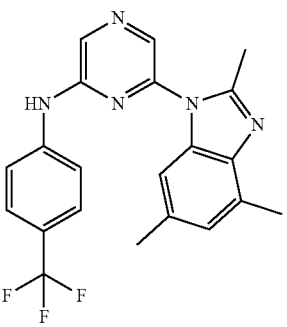

| | | |
|---|---|---|
| 422 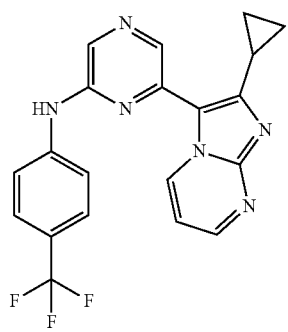 | 427 | 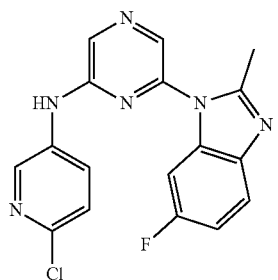 |
| 423 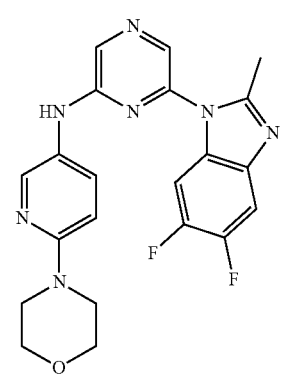 | 428 | 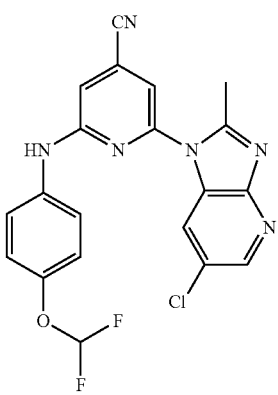 |
| 424 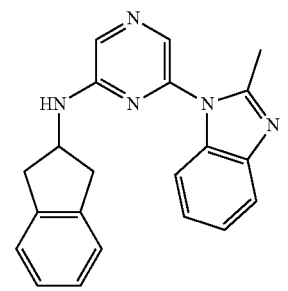 | | |
| 425 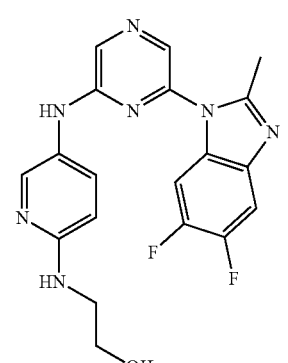 | 429 | 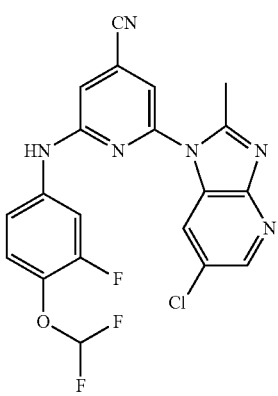 |
| 426 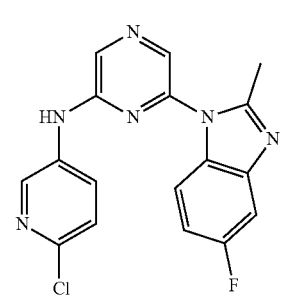 | 430 | 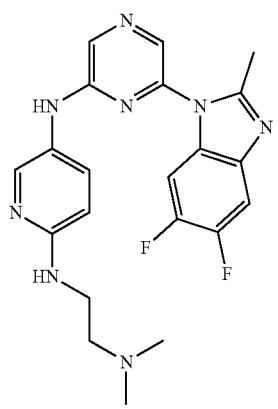 |

431 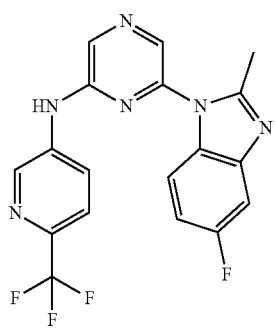
432 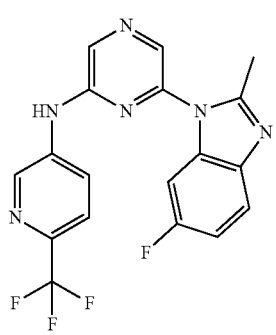
433 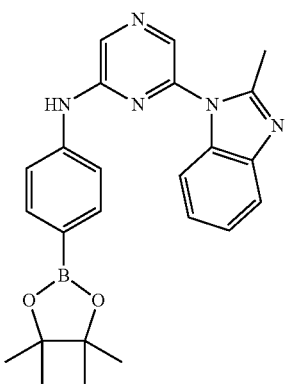
434 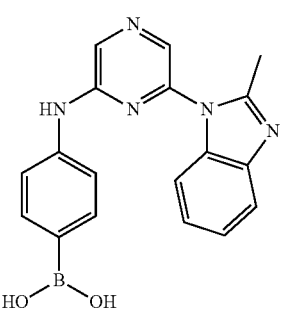
435 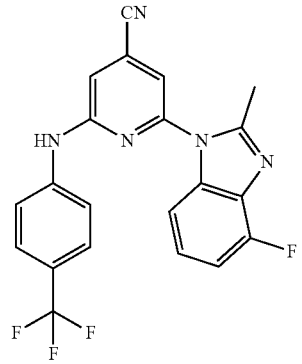
436 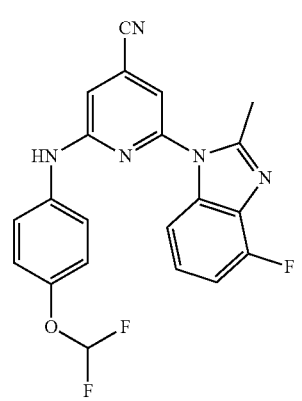
437 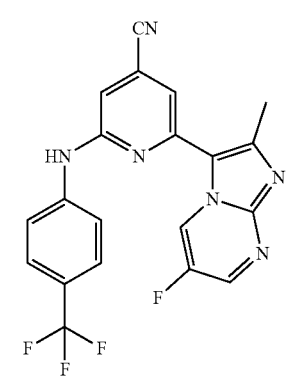
438 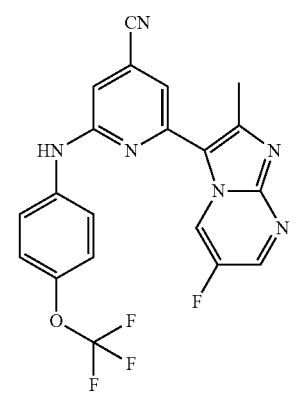

| 439 | 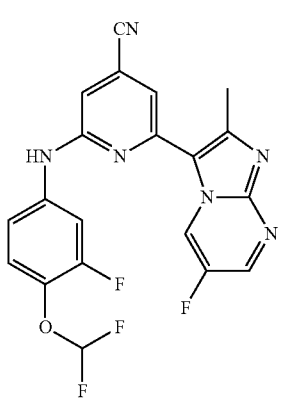 | 443 | 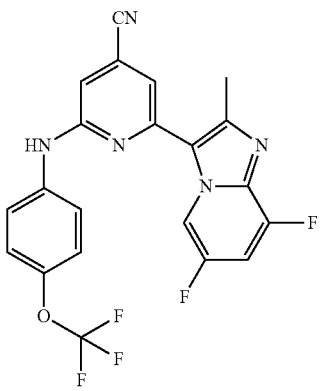 |
| 440 | 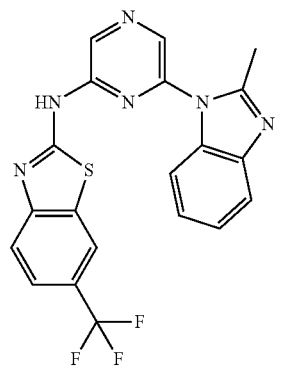 | 444 | 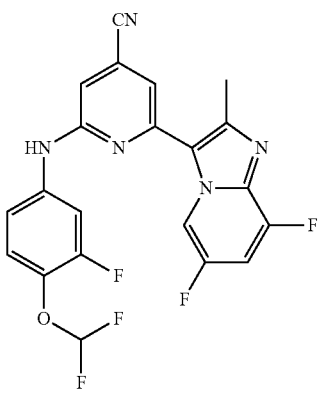 |
| 441 | 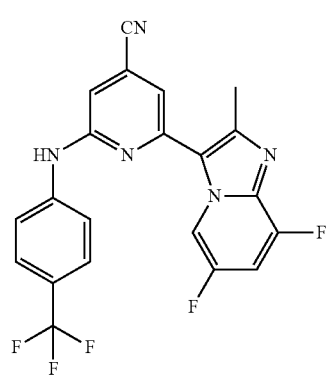 | 445 | 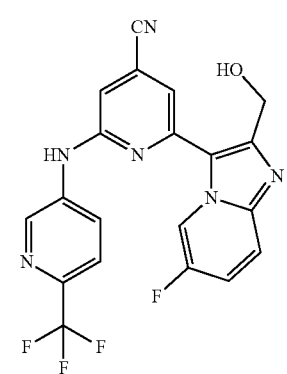 |
| 442 | 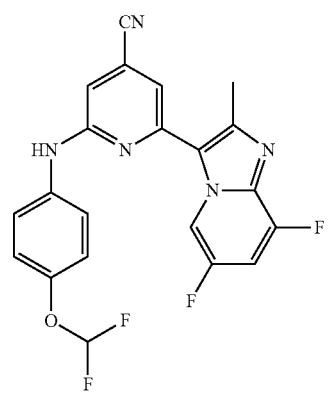 | 446 | 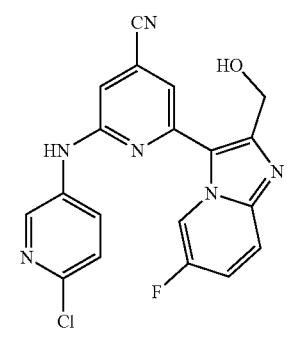 |

447 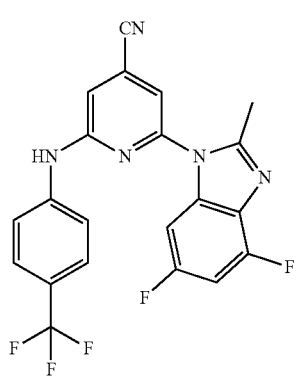
448 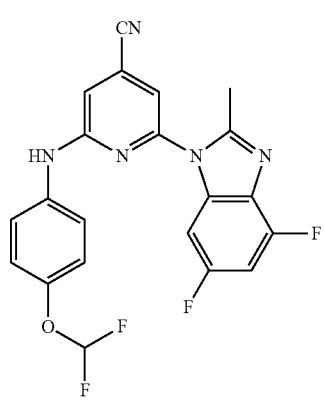
449 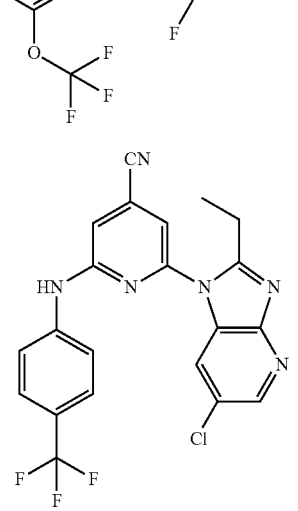
450
451 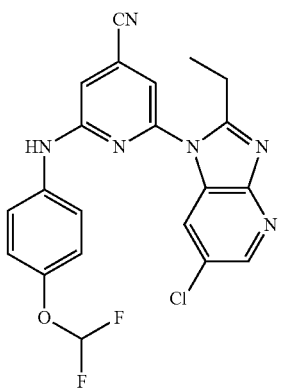
452 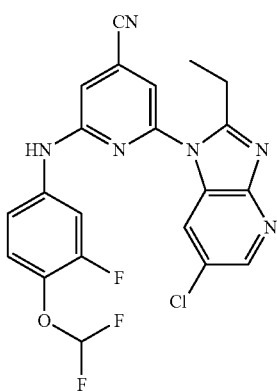
453 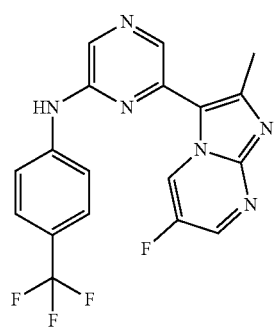
454 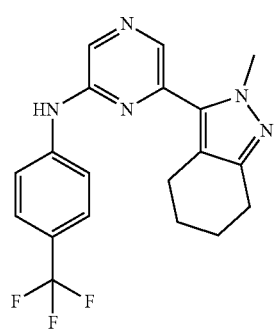

| 455 | 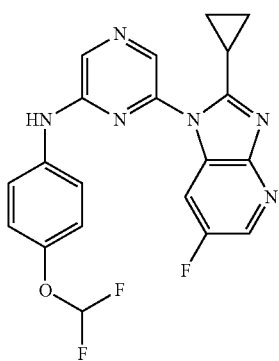 | 459 | 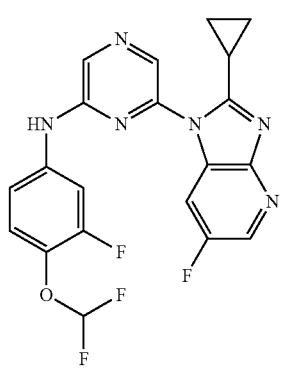 |
| 456 | 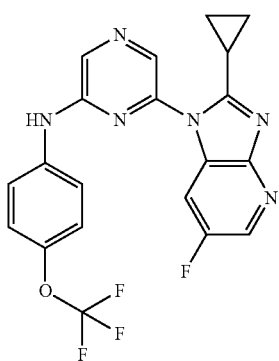 | 460 | 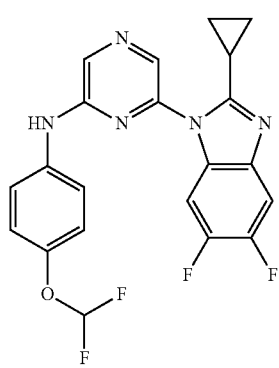 |
| 457 | 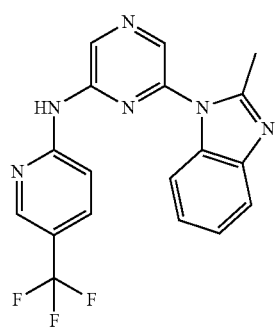 | 461 | 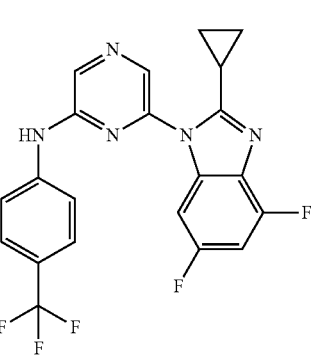 |
| 458 | 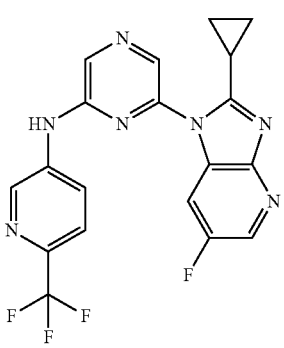 | 462 | 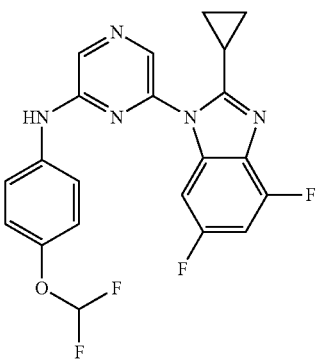 |

-continued
463 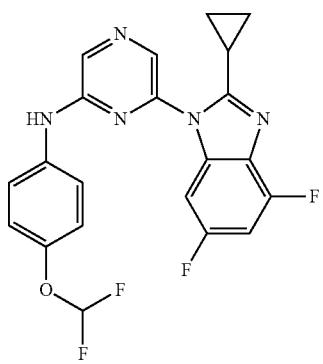
464 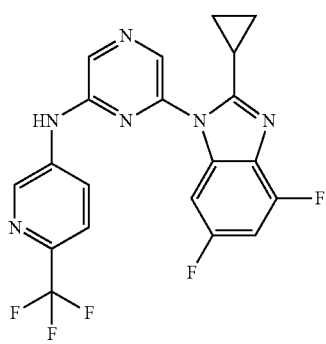
465 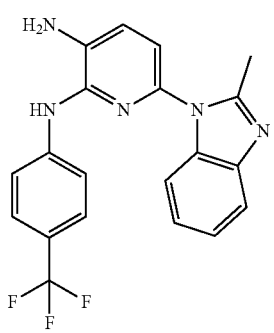
466 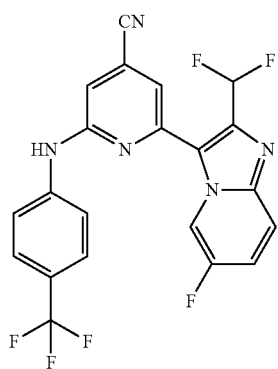
-continued
467 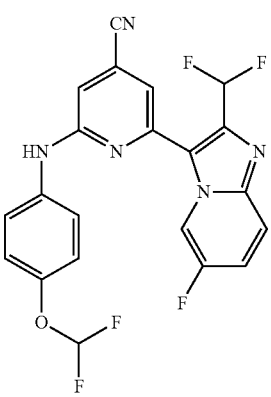
468 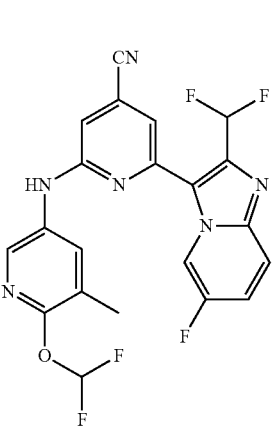
469 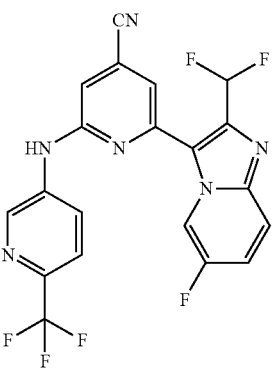
470 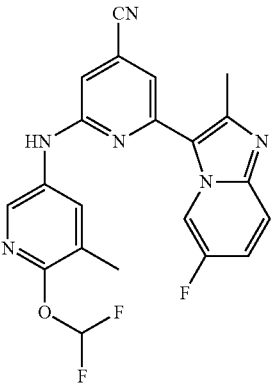

471 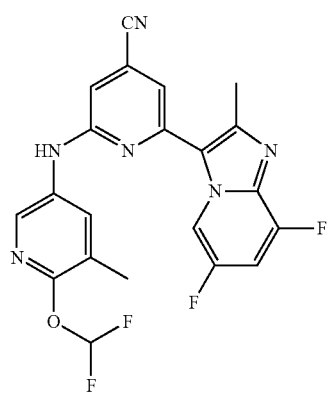
472 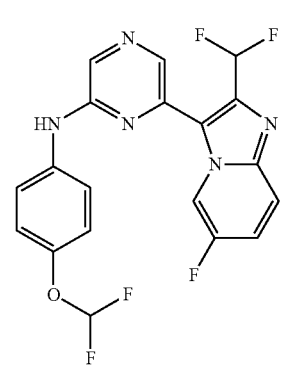
473 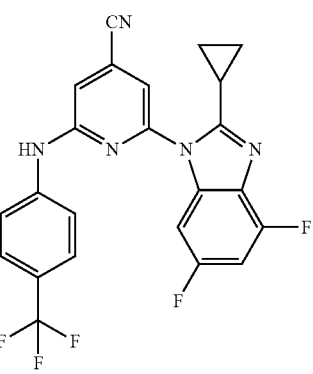
474 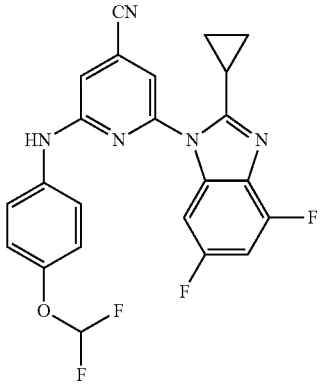
475 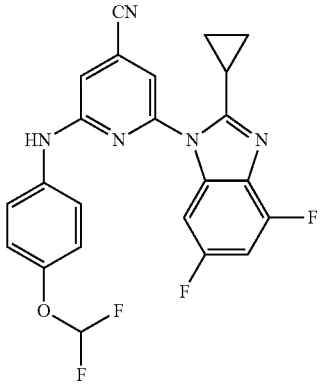
476 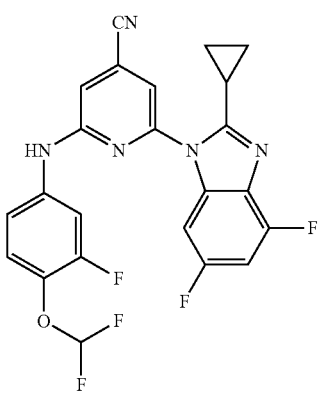
477 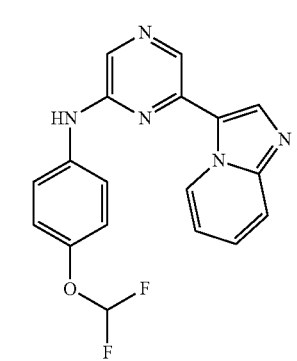
478 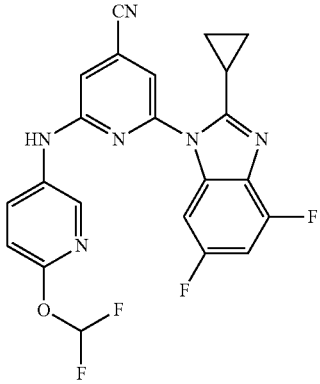

| | | |
|---|---|---|
| 479 | 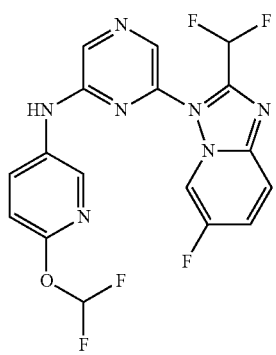 | 483 | 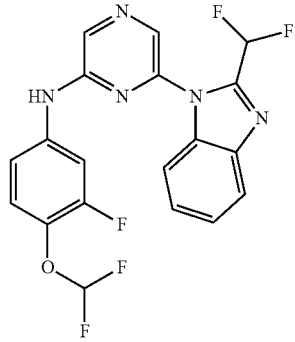 |
| 480 | 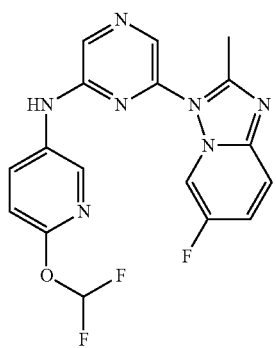 | 484 | 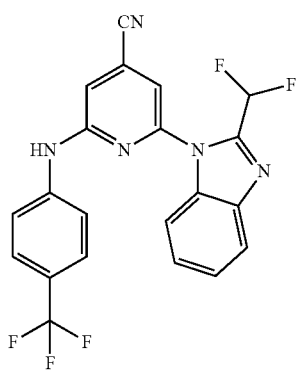 |
| 481 | 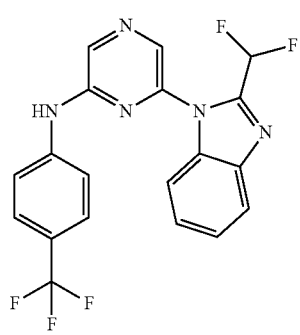 | 485 | 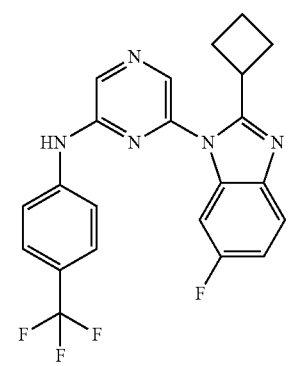 |
| 482 | 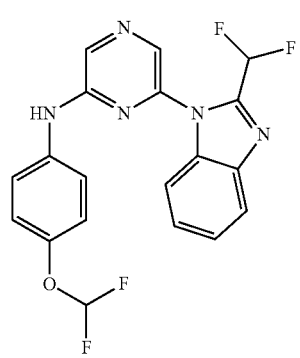 | 486 | 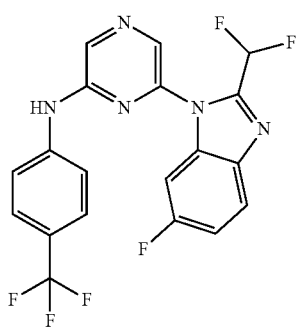 |

| 487 | 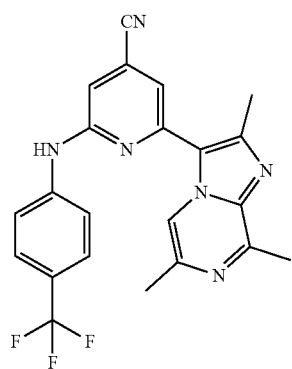 | 491 | 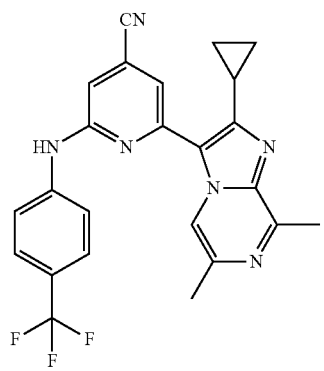 |
| 488 | 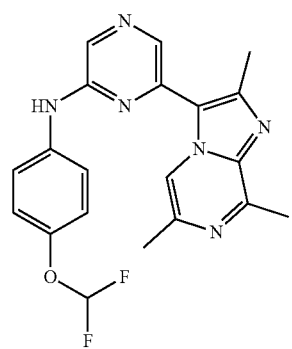 | 492 | 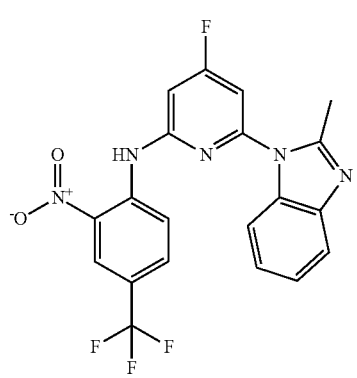 |
| 489 | | 493 | |
| 490 | 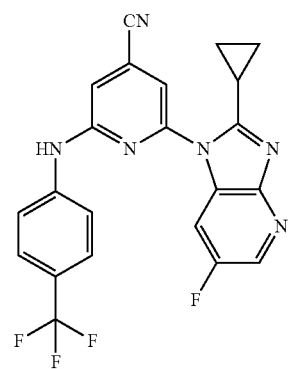 | 494 | 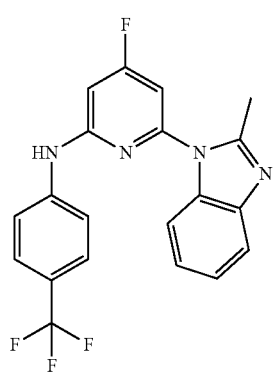 |

495 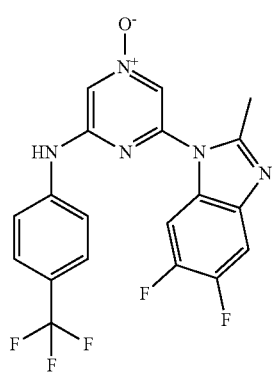
496 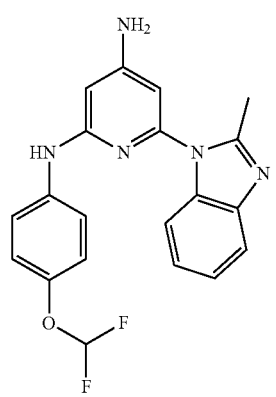
497 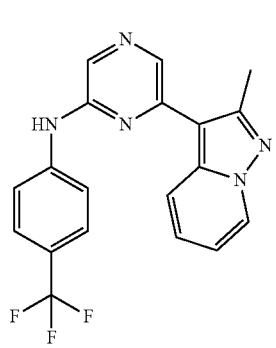
498 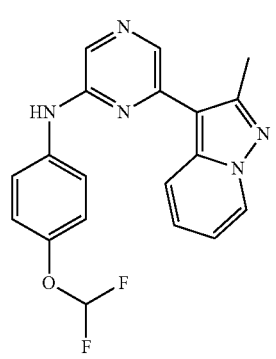
499 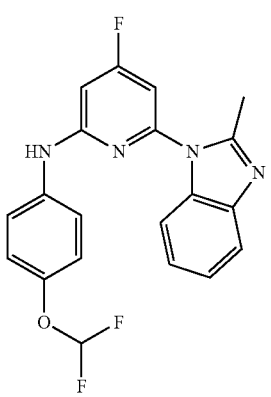
500 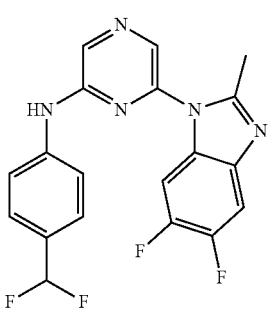
501 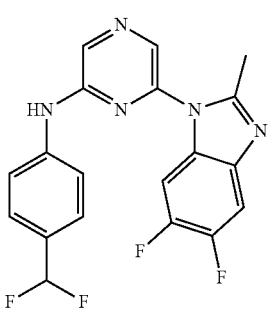
502 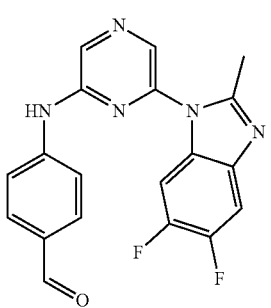

-continued
503
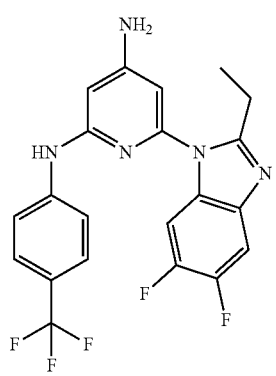
504
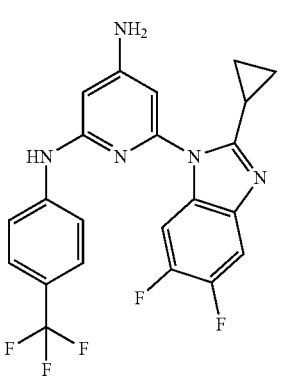
505
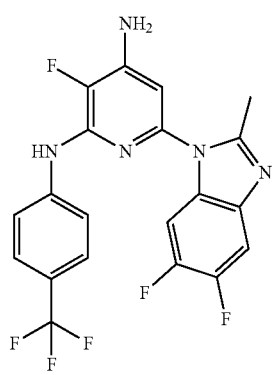
506
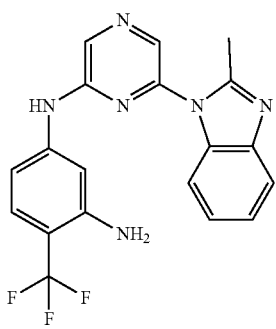
-continued
507
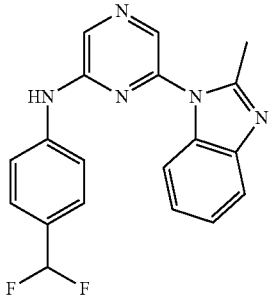
508
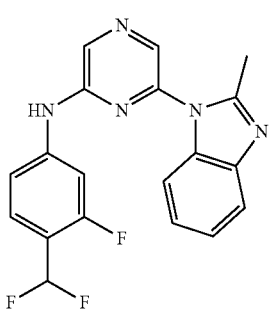
509
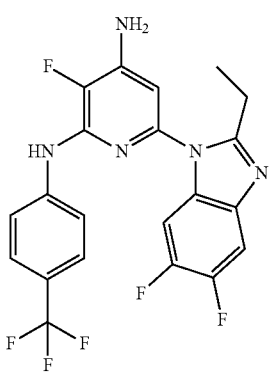
510
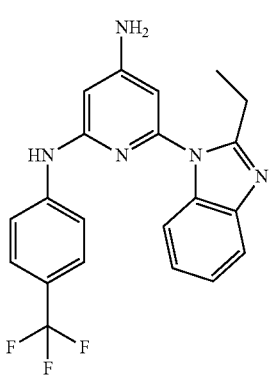

-continued
511
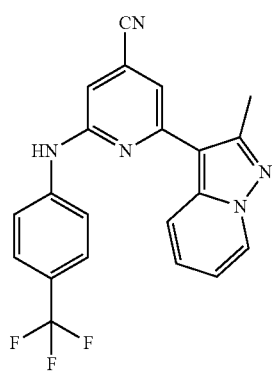
512
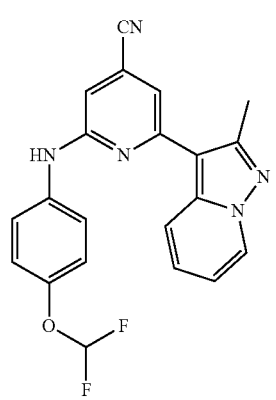
513
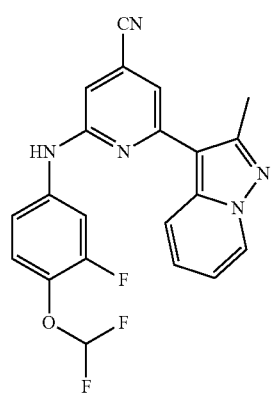
514
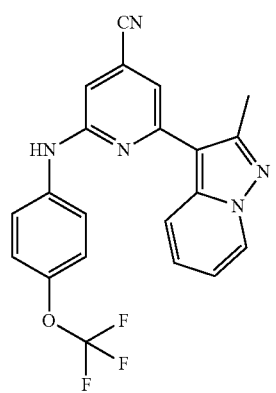
-continued
515
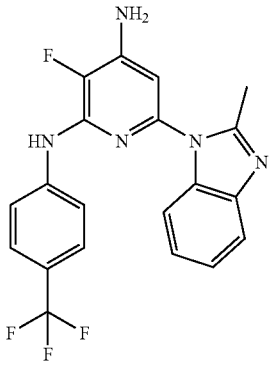
516
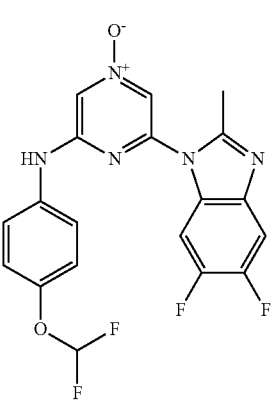
517
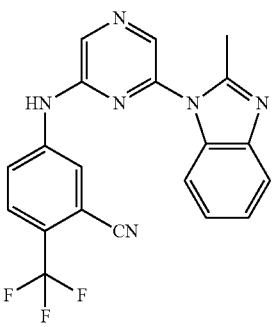
518
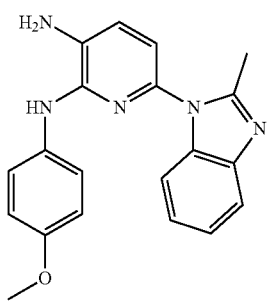

| 519 | 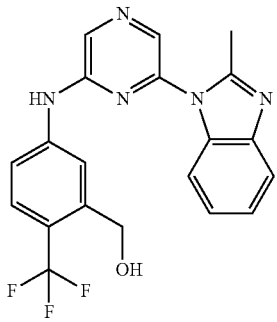 | 523 | 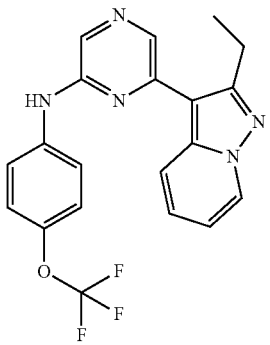 |
| 520 | 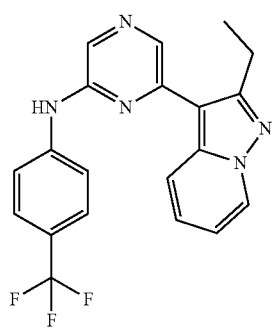 | 524 | 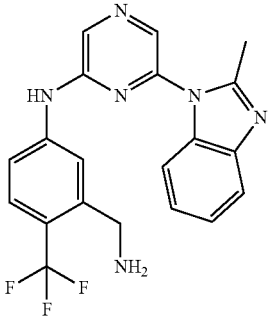 |
| 521 | 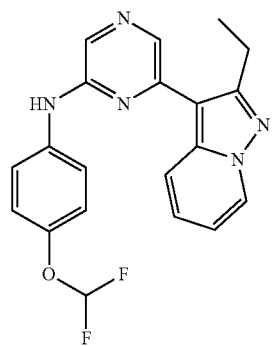 | 525 | 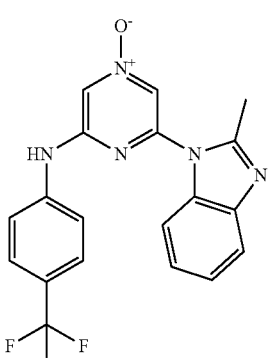 |
| 522 | 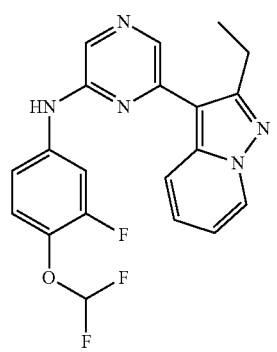 | 526 | 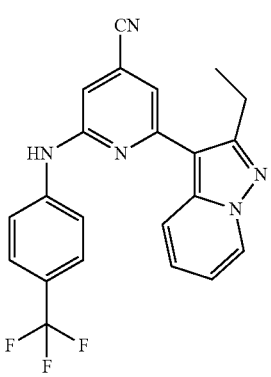 |

| | |
|---|---|
| 527 | 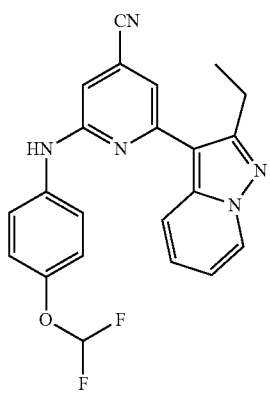 |
| 528 | 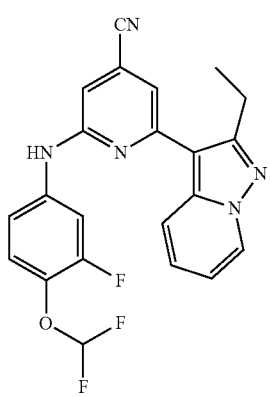 |
| 529 | 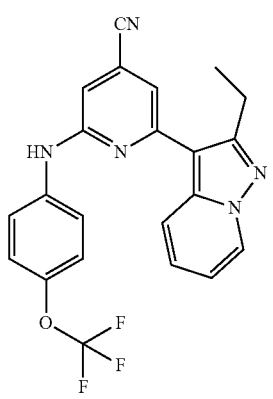 |
| 530 | 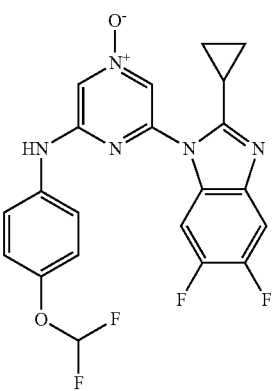 |
| 531 | 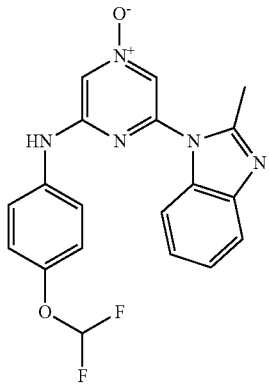 |
| 532 | 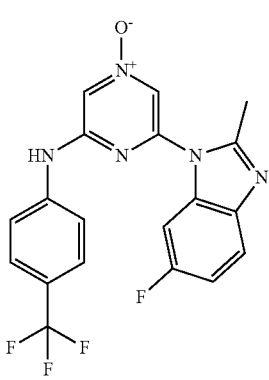 |
| 533 | 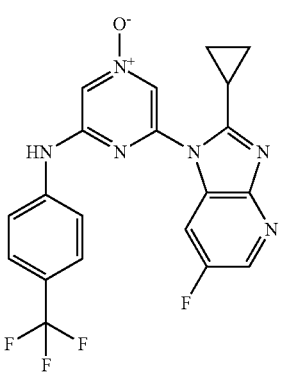 |
| 534 | 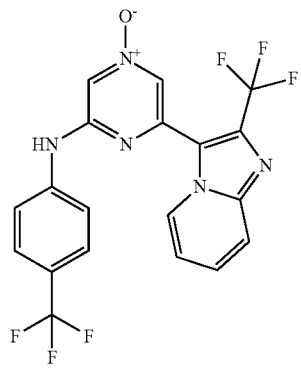 |

535 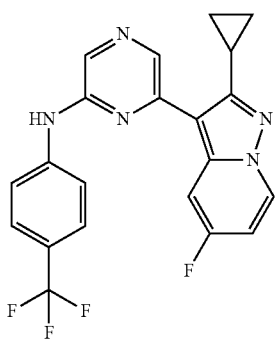
536 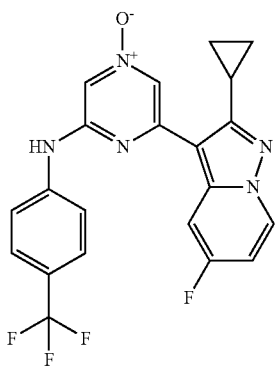
537 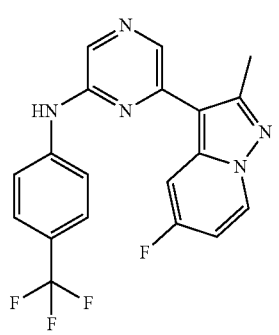
538 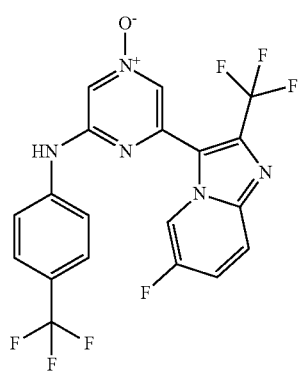
539 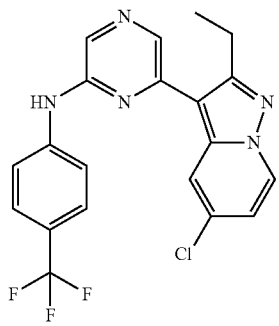
540 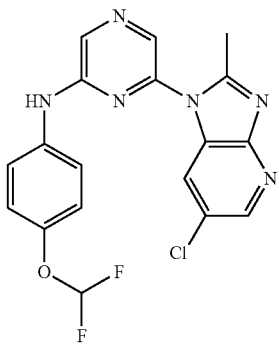
541 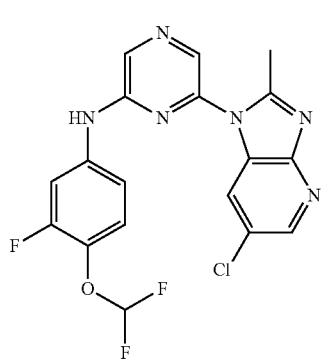
542 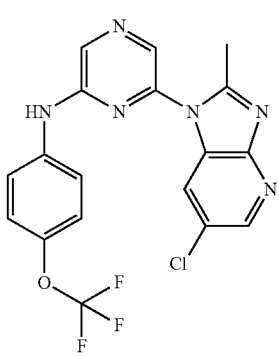
543 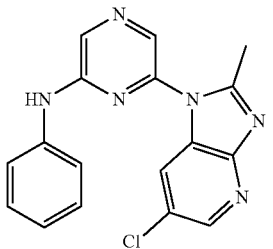

| 544 | 548 |
|---|---|
| 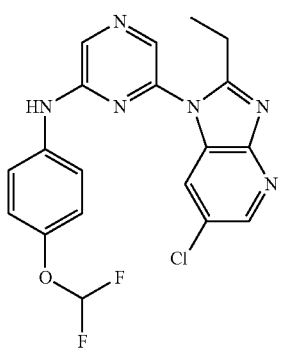 | 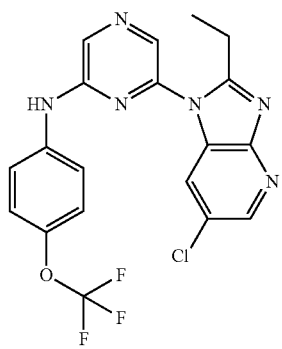 |
| 545 | 549 |
| 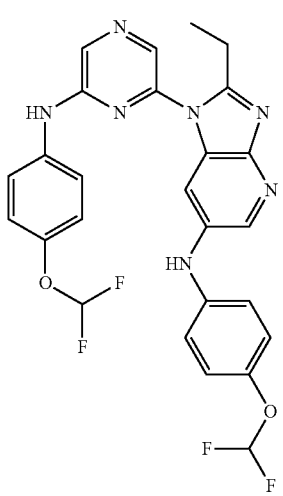 | 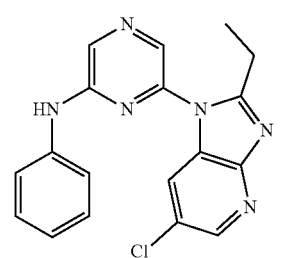 |
| 546 | 550 |
| 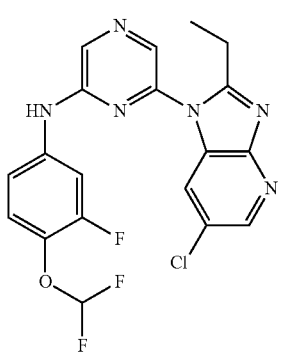 | 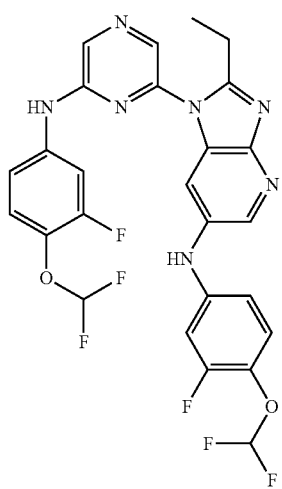 |
| 547 | 551 |
| 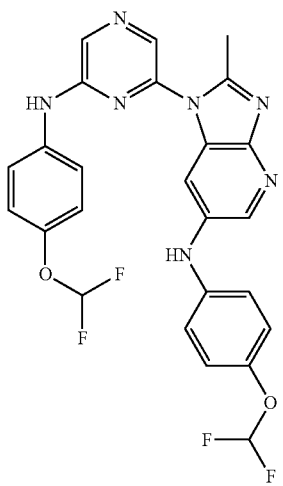 | 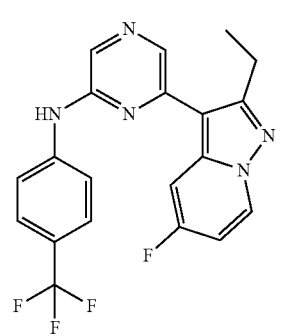 |

552 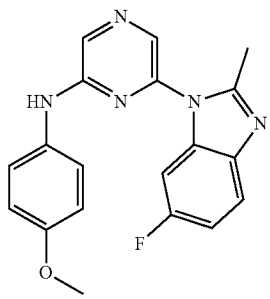
553 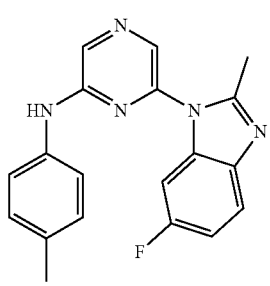
554 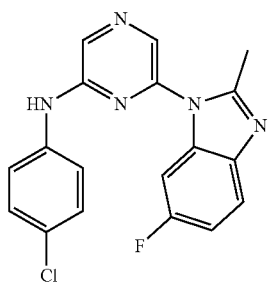
555 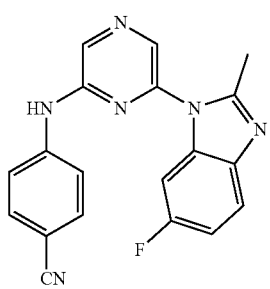
556 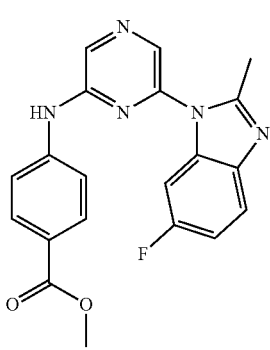
557 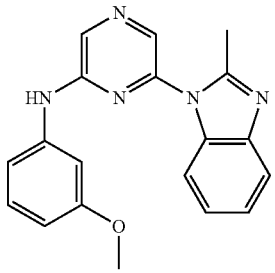
558 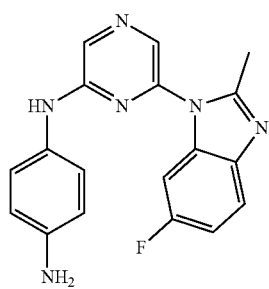
559 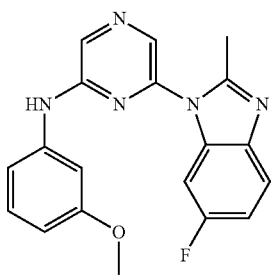
560 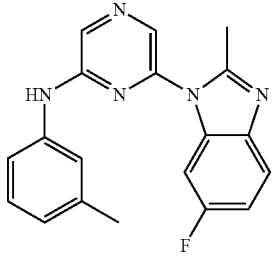
561 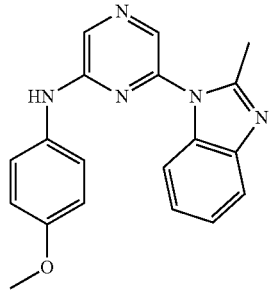

-continued
562
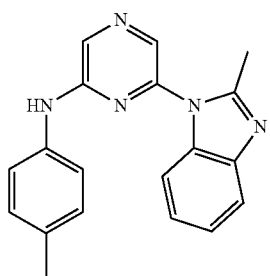
563
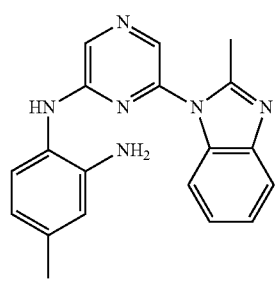
564
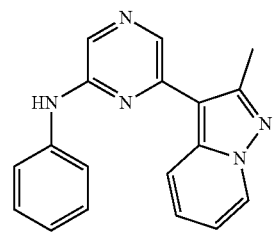
565
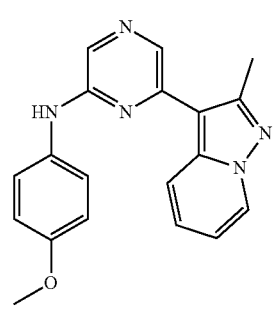
566
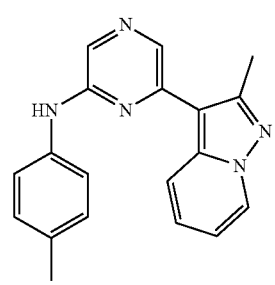
-continued
567
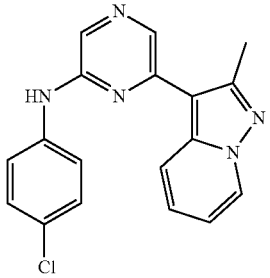
568
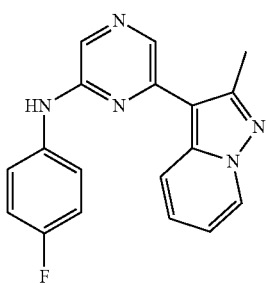
569
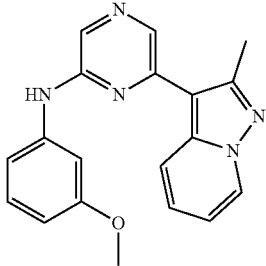
570
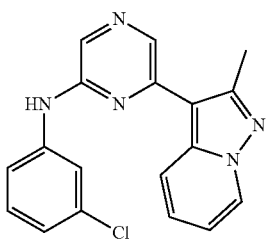
571
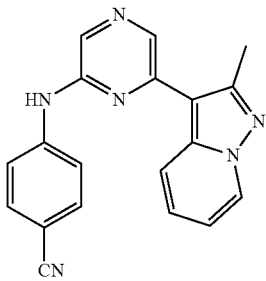

572 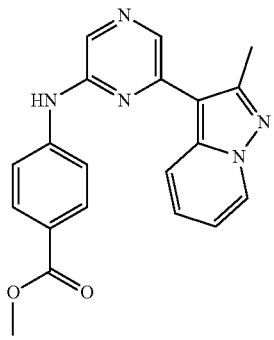
573 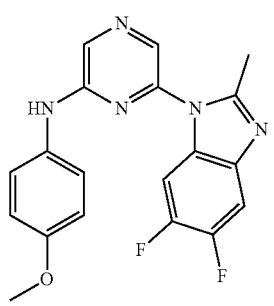
574 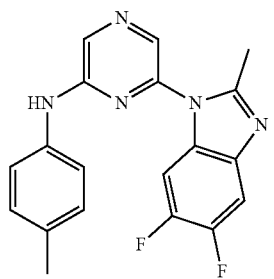
575 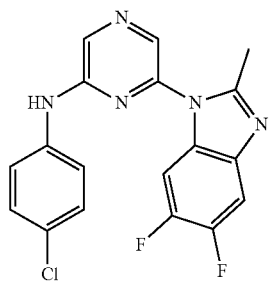
576 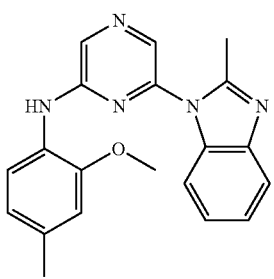
577 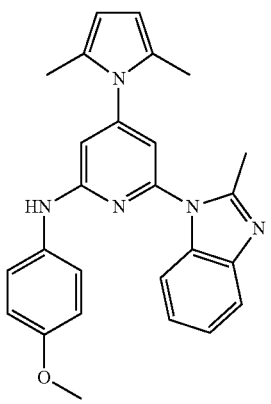
578 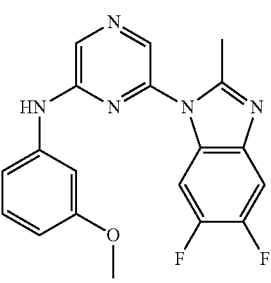
579 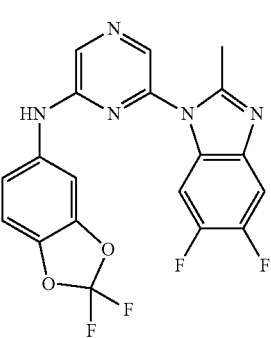
580 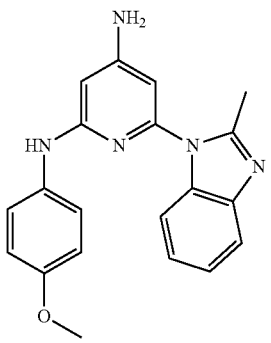
581 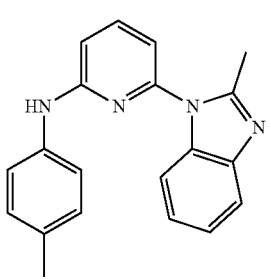

582 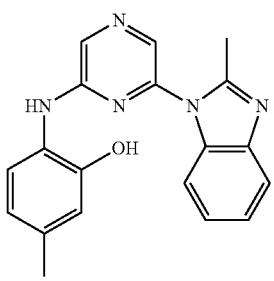
583 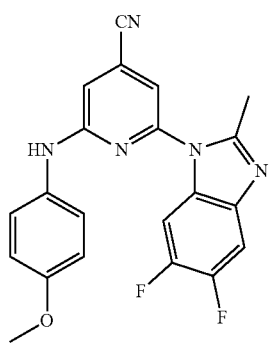
584 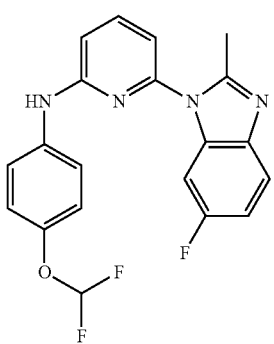
585 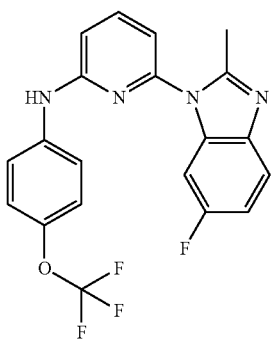
586 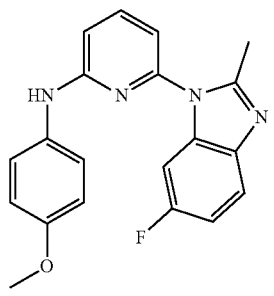
587 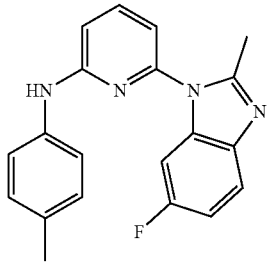
588 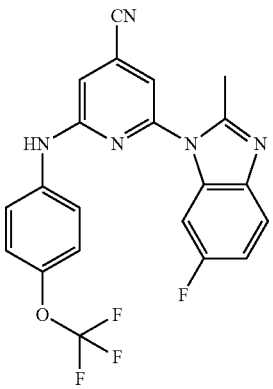
589 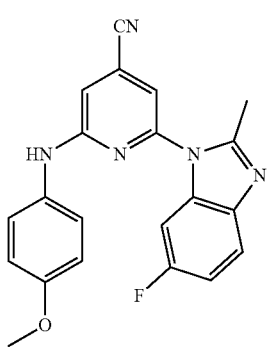
590 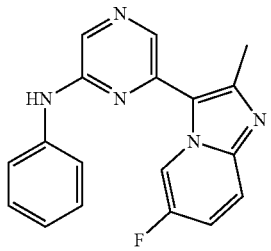
591 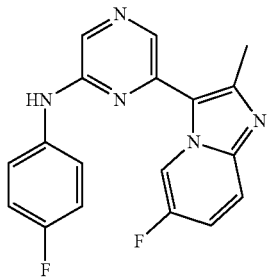

-continued

602 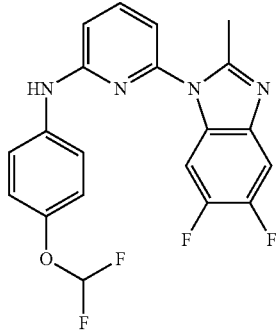
603 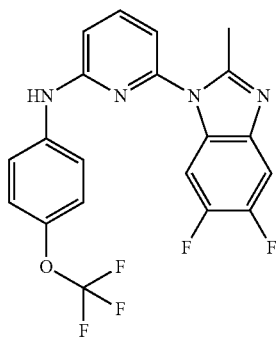
604 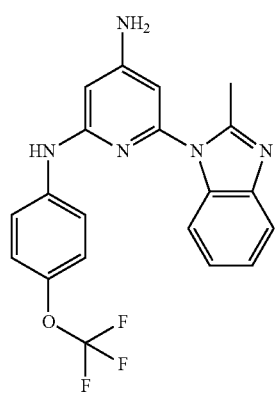
605 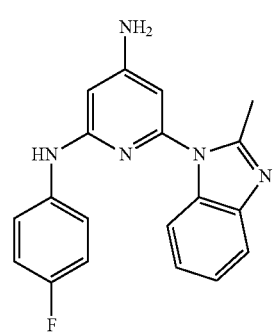
606 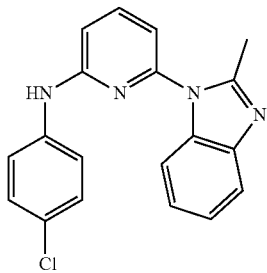
607 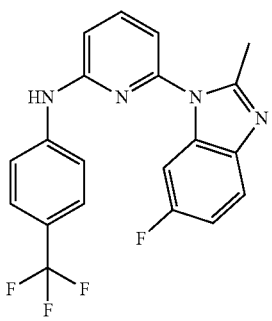
608 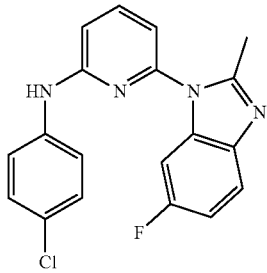
609 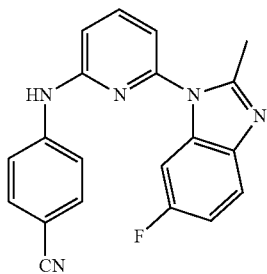
610 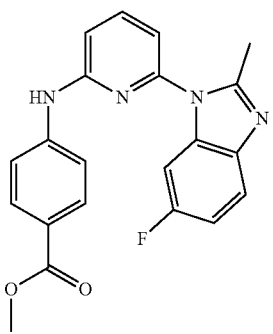

611 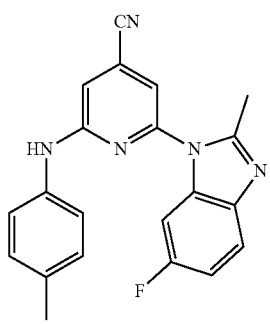
612 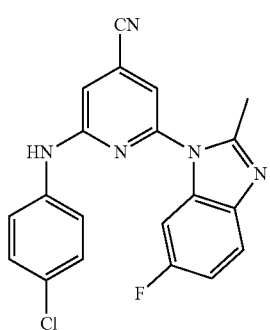
613 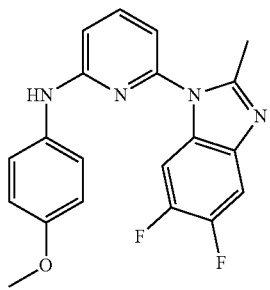
614 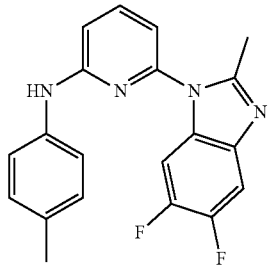
615 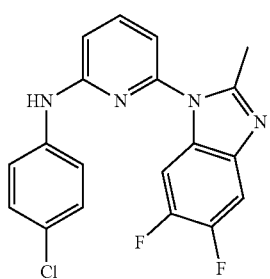
616 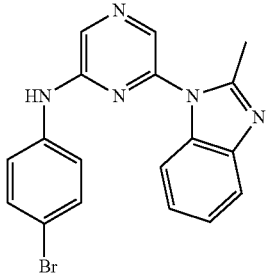
617
618
619
620 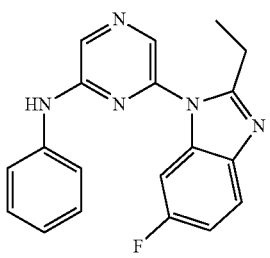

| 621 | 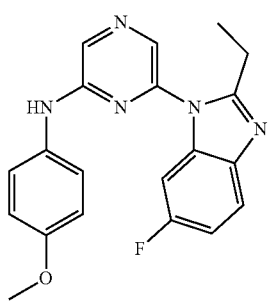 | 626 | 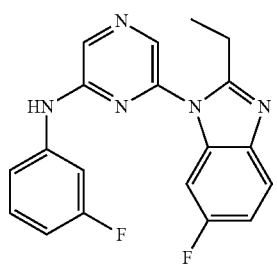 |
| 622 | 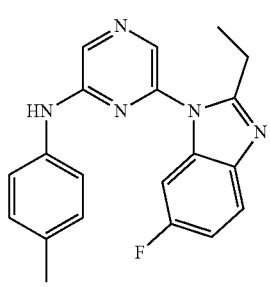 | 627 | 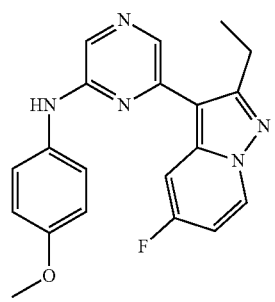 |
| 623 | 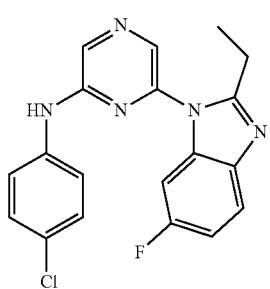 | 628 | 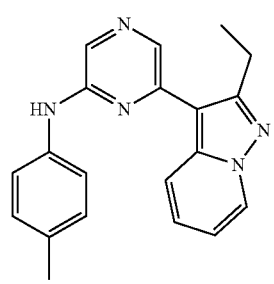 |
| 624 | 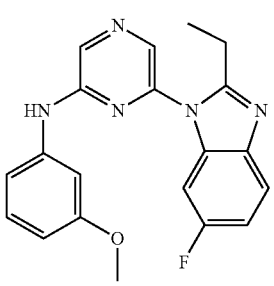 | 629 | 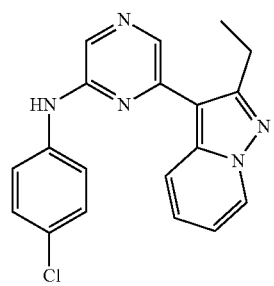 |
| 625 | 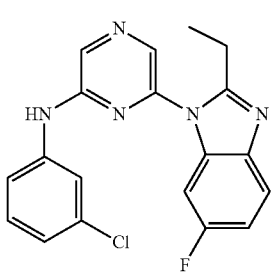 | 630 | 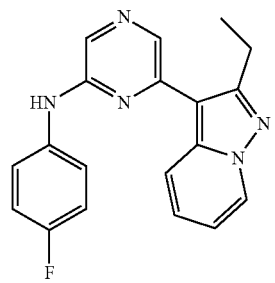 |

-continued
| | |
|---|---|
| 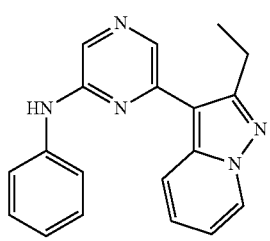 | 631 |
| 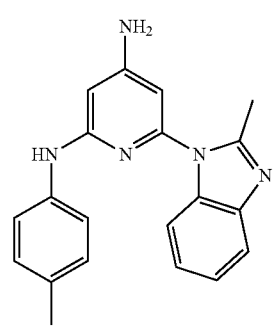 | 632 |
| 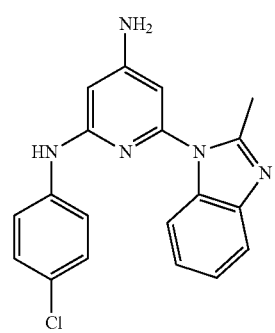 | 633 |
| 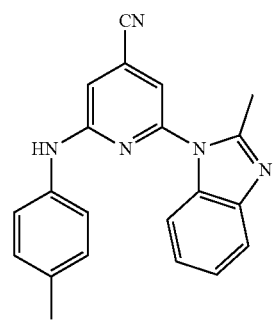 | 634 |
| 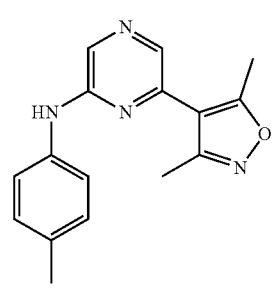 | 635 |
-continued
| | |
|---|---|
| 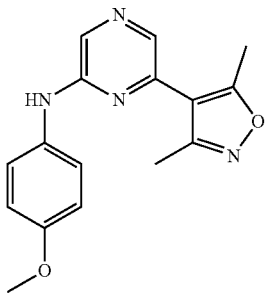 | 636 |
| 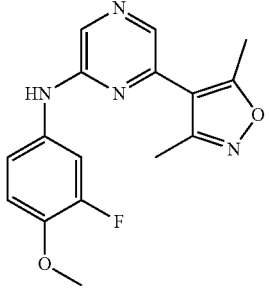 | 637 |
| 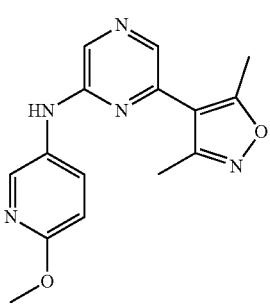 | 638 |
| | 639 |
| 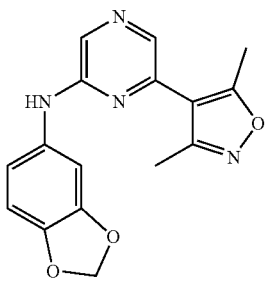 | 640 |

-continued
641 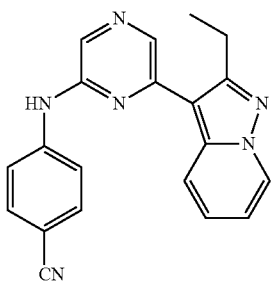
642 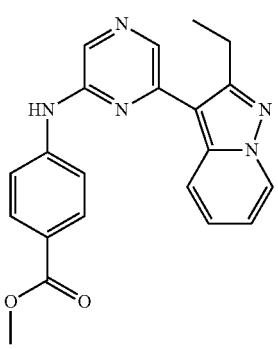
643 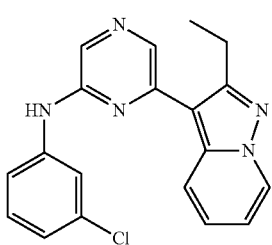
644 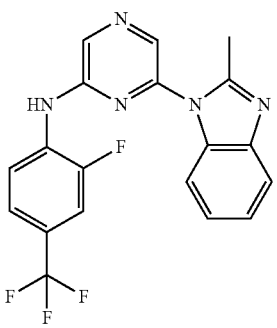
645 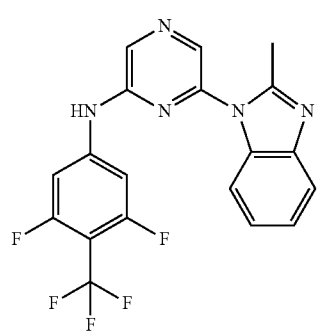
-continued
646 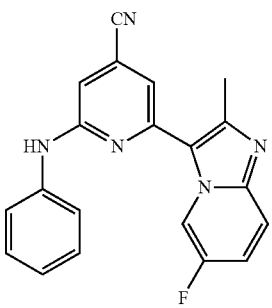
647 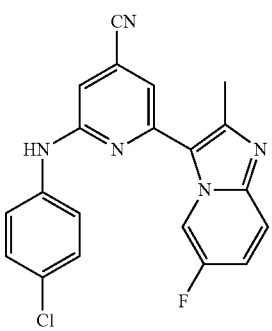
648 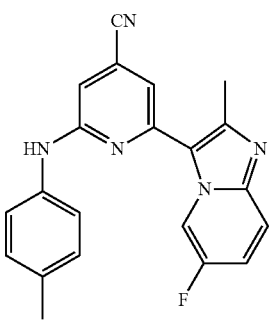
649 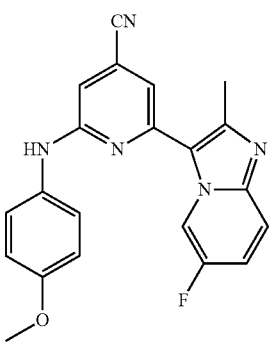
650 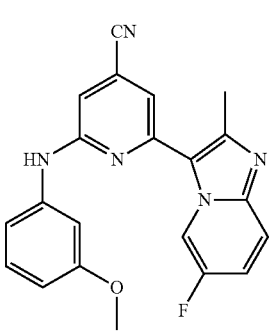

161
-continued
651
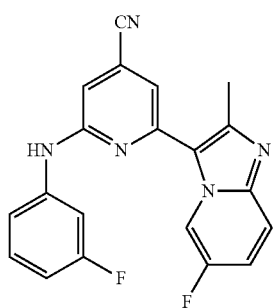
652
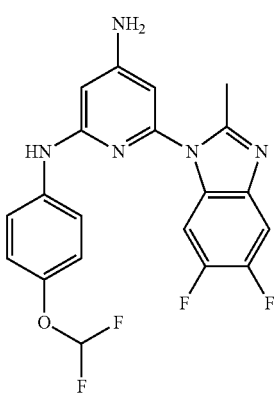
653
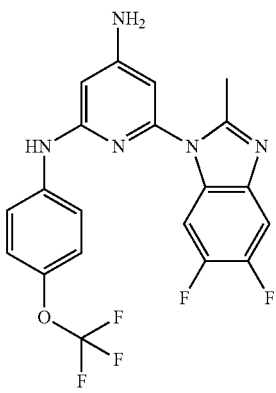
654
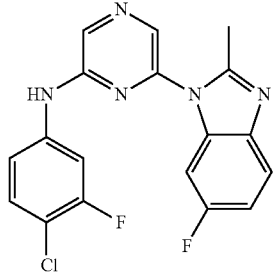
162
-continued
655
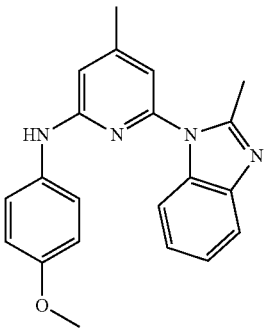
656
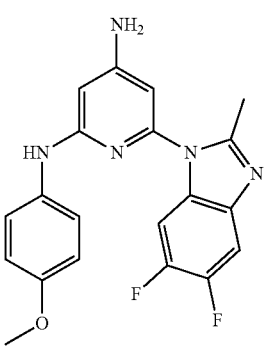
657
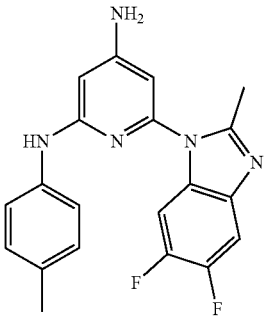
658
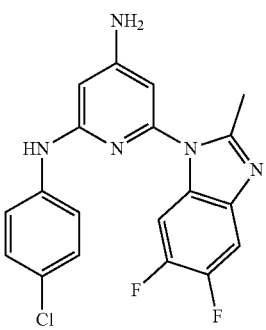
659
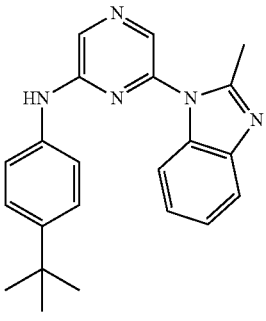

660 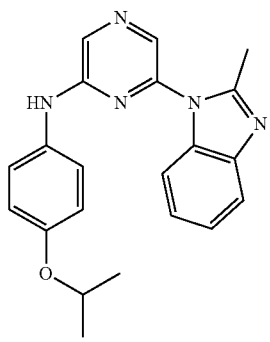
661 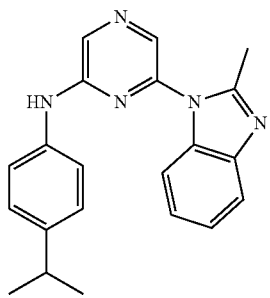
662 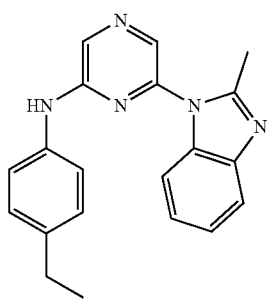
663 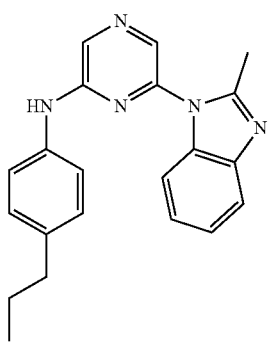
664 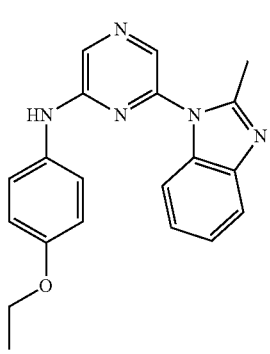
665 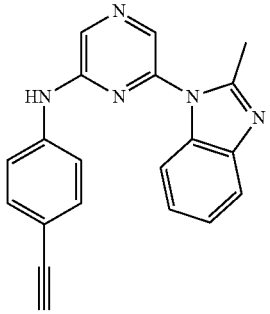
666 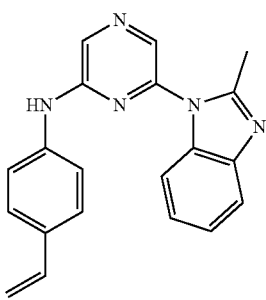
667 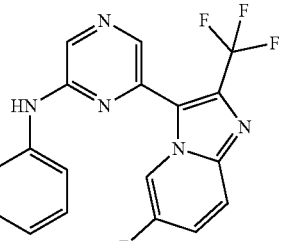
668 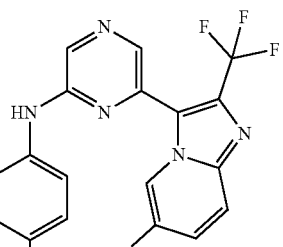
669 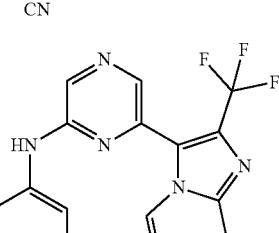

670 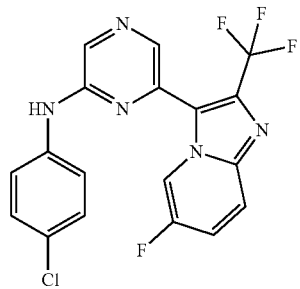
671 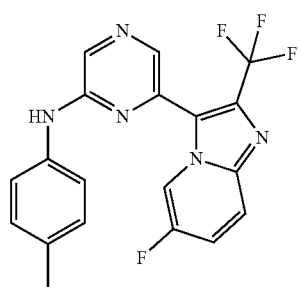
672 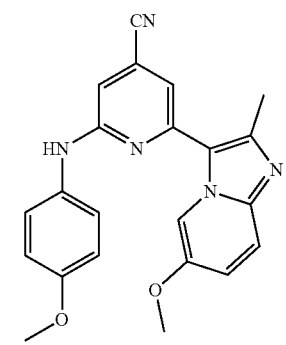
673 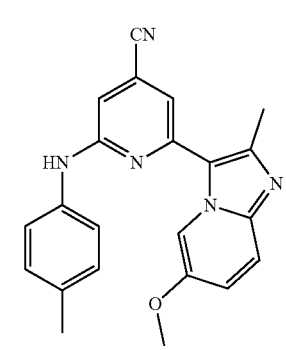
674 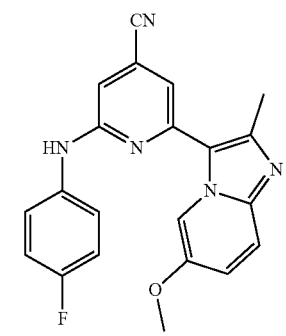
675 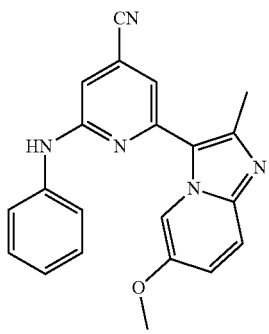
676 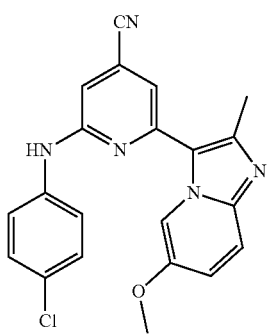
677 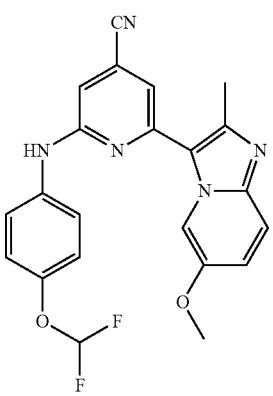
678 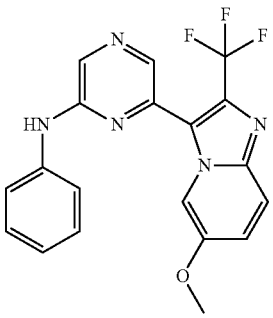

167
-continued

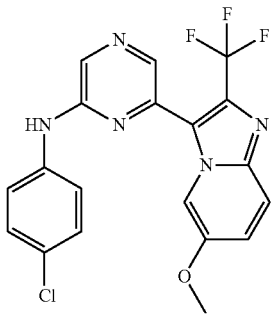
679

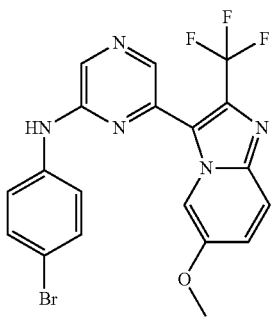
680

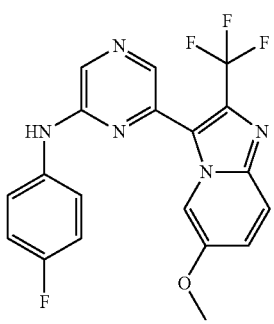
681

168
-continued

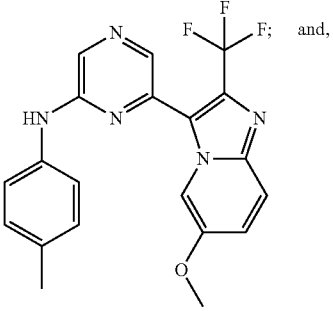
682

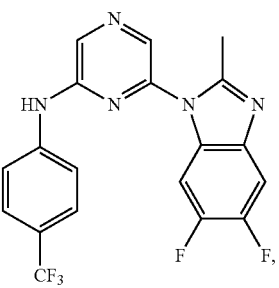
683 wherein the form of the compound is selected from a salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof selected from the group consisting of:

| Cpd | Name |
|---|---|
| 1 | 6-(1H-benzimidazol-1-yl)-N-(4-methoxyphenyl)pyrazin-2-amine |
| 2 | 6-(1H-benzimidazol-1-yl)-N-(4-iodophenyl)pyrazin-2-amine |
| 3 | N-(3-chloro-4-methoxyphenyl)-6-[2-(trifluoromethyl)imidazo[1,2-a]pyridin-3-yl]pyridin-2-amine |
| 4 | N-(4-methoxyphenyl)-6-[2-(trifluoromethyl)imidazo[1,2-a]pyridin-3-yl]pyridin-2-amine |
| 5 | N-(4-methoxyphenyl)-6-[2-(trifluoromethyl)imidazo[1,2-a]pyridin-3-yl]pyrazin-2-amine |
| 6 | 6-[2-(trifluoromethyl)imidazo[1,2-a]pyridin-3-yl]-N-[4-(trifluoromethyl)phenyl]pyrazin-2-amine |
| 7 | N-(3-fluoro-4-methoxyphenyl)-6-[2-(trifluoromethyl)imidazo[1,2-a]pyridin-3-yl]pyrazin-2-amine |
| 8 | N-(3-fluoro-4-methoxyphenyl)-6-[2-(trifluoromethyl)imidazo[1,2-a]pyridin-3-yl]pyridin-2-amine |
| 9 | N-(4-fluorophenyl)-6-[2-(trifluoromethyl)imidazo[1,2-a]pyridin-3-yl]pyrazin-2-amine |
| 10 | N-(4-chlorophenyl)-6-[2-(trifluoromethyl)imidazo[1,2-a]pyridin-3-yl]pyrazin-2-amine |
| 11 | N-[4-(trifluoromethoxy)phenyl]-6-[2-(trifluoromethyl)imidazo[1,2-a]pyridin-3-yl]pyrazin-2-amine |
| 12 | N-(3-fluoro-4-methoxyphenyl)-6-(2-methyl-1H-benzimidazol-1-yl)pyrazin-2-amine |
| 13 | 6-(2-methyl-1H-benzimidazol-1-yl)-N-[4-(trifluoromethyl)phenyl]pyrazin-2-amine |
| 14 | 6-[2-(trifluoromethyl)-1H-benzimidazol-1-yl]-N-[4-(trifluoromethyl)phenyl]pyrazin-2-amine |
| 15 | N-[4-(trifluoromethyl)phenyl]-6-[2-(trifluoromethyl)pyrazolo[1,5-a]pyridin-7-yl]pyrazin-2-amine |
| 16 | N-[4-(trifluoromethoxy)phenyl]-6-[2-(trifluoromethyl)imidazo[1,2-a]pyridin-3-yl]pyridin-2-amine |
| 17 | N-(4-chlorophenyl)-6-[2-(trifluoromethyl)imidazo[1,2-a]pyridin-3-yl]pyridin-2-amine |
| 18 | 6-[2-(trifluoromethyl)imidazo[1,2-a]pyridin-3-yl]-N-[4-(trifluoromethyl)phenyl]pyridin-2-amine |

-continued

| Cpd | Name |
|---|---|
| 19 | 6-(2-methyl-1H-benzimidazol-1-yl)-N-[4-(trifluoromethoxy)phenyl]pyrazin-2-amine |
| 20 | N-(4-chlorophenyl)-6-(2-methyl-1H-benzimidazol-1-yl)pyrazin-2-amine |
| 21 | N-[4-(difluoromethoxy)phenyl]-6-(2-methyl-1H-benzimidazol-1-yl)pyrazin-2-amine |
| 22 | N-(3-chloro-4-methoxyphenyl)-6-[2-(trifluoromethyl)imidazo[1,2-a]pyridin-3-yl]pyrazin-2-amine |
| 23 | 4-({6-[2-(trifluoromethyl)imidazo[1,2-a]pyridin-3-yl]pyrazin-2-yl}amino)benzonitrile |
| 24 | N-[4-(difluoromethoxy)phenyl]-6-[2-(trifluoromethyl)imidazo[1,2-a]pyridin-3-yl]pyrazin-2-amine |
| 25 | N-(4-chloro-3-fluorophenyl)-6-[2-(trifluoromethyl)imidazo[1,2-a]pyridin-3-yl]pyrazin-2-amine |
| 26 | N-(3,4-difluorophenyl)-6-[2-(trifluoromethyl)imidazo[1,2-a]pyridin-3-yl]pyrazin-2-amine |
| 27 | N-[4-(difluoromethoxy)phenyl]-6-[2-(trifluoromethyl)imidazo[1,2-a]pyridin-3-yl]pyridin-2-amine |
| 28 | N-(3-chloro-4-methoxyphenyl)-6-(2-methyl-1H-benzimidazol-1-yl)pyrazin-2-amine |
| 29 | N-(3,4-dichlorophenyl)-6-[2-(trifluoromethyl)imidazo[1,2-a]pyridin-3-yl]pyrazin-2-amine |
| 30 | N-(4-bromo-3-fluorophenyl)-6-[2-(trifluoromethyl)imidazo[1,2-a]pyridin-3-yl]pyrazin-2-amine |
| 31 | N-(4-bromo-3-chlorophenyl)-6-[2-(trifluoromethyl)imidazo[1,2-a]pyridin-3-yl]pyrazin-2-amine |
| 32 | N-(4-methoxyphenyl)-6-(2-methyl-1H-benzimidazol-1-yl)pyridin-2-amine |
| 33 | N-(4-methoxyphenyl)-6-[2-(trifluoromethyl)-1H-benzimidazol-1-yl]pyridin-2-amine |
| 34 | 6-[(4-methoxyphenyl)amino]-2-[2-(trifluoromethyl)imidazo[1,2-a]pyridin-3-yl]pyridine-3-carbonitrile |
| 35 | N-[4-(difluoromethoxy)phenyl]-6-(2-methyl-1H-benzimidazol-1-yl)pyridin-2-amine |
| 36 | 6-(2-methyl-1H-benzimidazol-1-yl)-N-[4-(trifluoromethoxy)phenyl]pyridin-2-amine |
| 37 | 6-(2-methyl-1H-benzimidazol-1-yl)-N-[4-(trifluoromethyl)phenyl]pyridin-2-amine |
| 38 | N-[4-(difluoromethoxy)phenyl]-6-[2-(trifluoromethyl)-1H-benzimidazol-1-yl]pyridin-2-amine |
| 39 | N-[4-(trifluoromethoxy)phenyl]-6-[2-(trifluoromethyl)-1H-benzimidazol-1-yl]pyridin-2-amine |
| 40 | 6-[2-(trifluoromethyl)-1H-benzimidazol-1-yl]-N-[4-(trifluoromethyl)phenyl]pyridin-2-amine |
| 41 | 2-[(4-methoxyphenyl)amino]-6-[2-(trifluoromethyl)imidazo[1,2-a]pyridin-3-yl]pyridine-3-carbonitrile |
| 42 | 2-[(4-methoxyphenyl)amino]-6-[2-(trifluoromethyl)imidazo[1,2-a]pyridin-3-yl]pyridine-4-carbonitrile |
| 43 | N-(4-methoxyphenyl)-6-[2-(trifluoromethyl)-1H-benzimidazol-1-yl]pyrazin-2-amine |
| 44 | N-[4-(difluoromethoxy)phenyl]-6-[2-(trifluoromethyl)-1H-benzimidazol-1-yl]pyrazin-2-amine |
| 45 | 6-[6-methoxy-2-(trifluoromethyl)imidazo[1,2-a]pyridin-3-yl]-N-[4-(trifluoromethoxy)phenyl]pyrazin-2-amine |
| 46 | 6-[6-methoxy-2-(trifluoromethyl)imidazo[1,2-a]pyridin-3-yl]-N-[4-(trifluoromethyl)phenyl]pyrazin-2-amine |
| 47 | N-(4-methoxyphenyl)-6-[6-methoxy-2-(trifluoromethyl)imidazo[1,2-a]pyridin-3-yl]pyrazin-2-amine |
| 48 | N-[4-(difluoromethoxy)phenyl]-6-[6-methoxy-2-(trifluoromethyl)imidazo[1,2-a]pyridin-3-yl]pyrazin-2-amine |
| 49 | 4-({6-[6-methoxy-2-(trifluoromethyl)imidazo[1,2-a]pyridin-3-yl]pyrazin-2-yl}amino)benzonitrile |
| 50 | 4-({6-[2-(trifluoromethyl)imidazo[1,2-a]pyridin-3-yl]pyridin-2-yl}amino)benzonitrile |
| 51 | 6-(2-ethyl-1H-benzimidazol-1-yl)-N-[4-(trifluoromethyl)phenyl]pyrazin-2-amine |
| 52 | 6-[2-(propan-2-yl)-1H-benzimidazol-1-yl]-N-[4-(trifluoromethyl)phenyl]pyrazin-2-amine |
| 53 | 6-(2-propyl-1H-benzimidazol-1-yl)-N-[4-(trifluoromethyl)phenyl]pyrazin-2-amine |
| 54 | 6-[2-(methylsulfanyl)-1H-benzimidazol-1-yl]-N-[4-(trifluoromethyl)phenyl]pyrazin-2-amine |
| 55 | 6-[6-fluoro-2-(trifluoromethyl)imidazo[1,2-a]pyridin-3-yl]-N-[4-(trifluoromethoxy)phenyl]pyrazin-2-amine |
| 56 | N-[4-(difluoromethoxy)phenyl]-6-[6-fluoro-2-(trifluoromethyl)imidazo[1,2-a]pyridin-3-yl]pyrazin-2-amine |
| 57 | 6-[6-fluoro-2-(trifluoromethyl)imidazo[1,2-a]pyridin-3-yl]-N-(4-methoxyphenyl)pyrazin-2-amine |
| 58 | 6-[6-fluoro-2-(trifluoromethyl)imidazo[1,2-a]pyridin-3-yl]-N-[4-(trifluoromethyl)phenyl]pyrazin-2-amine |
| 59 | N-(4-nitrophenyl)-6-[2-(trifluoromethyl)imidazo[1,2-a]pyridin-3-yl]pyrazin-2-amine |
| 60 | N-{6-[2-(trifluoromethyl)imidazo[1,2-a]pyridin-3-yl]pyrazin-2-yl}benzene-1,4-diamine |
| 61 | N-methyl-1-(6-{[4-(trifluoromethyl)phenyl]amino}pyrazin-2-yl)-1H-benzimidazol-2-amine |
| 62 | N-[4-(trifluoromethyl)phenyl]-6-[2-(trifluoromethyl)pyrazolo[1,5-a]pyridin-3-yl]pyrazin-2-amine |
| 63 | N-[4-(trifluoromethoxy)phenyl]-6-[2-(trifluoromethyl)pyrazolo[1,5-a]pyridin-3-yl]pyrazin-2-amine |
| 64 | 6-[2-(trifluoromethyl)imidazo[1,2-a]pyrimidin-3-yl]-N-[4-(trifluoromethyl)phenyl]pyridin-2-amine |
| 65 | 6-[2-(methoxymethyl)-1H-benzimidazol-1-yl]-N-[4-(trifluoromethyl)phenyl]pyrazin-2-amine |
| 66 | [1-(6-{[4-(trifluoromethyl)phenyl]amino}pyrazin-2-yl)-1H-benzimidazol-2-yl]methanol |

-continued

| Cpd | Name |
|---|---|
| 67 | 6-[2-(trifluoromethyl)imidazo[1,2-a]pyrimidin-3-yl]-N-[4-(trifluoromethyl)phenyl]pyrazin-2-amine |
| 68 | N-[4-(methylsulfonyl)phenyl]-6-[2-(trifluoromethyl)imidazo[1,2-a]pyridin-3-yl]pyrazin-2-amine |
| 69 | N-[4-(methylsulfanyl)phenyl]-6-[2-(trifluoromethyl)imidazo[1,2-a]pyridin-3-yl]pyrazin-2-amine |
| 70 | 6-[2-(trifluoromethyl)imidazo[1,2-a]pyridin-3-yl]-N-[6-(trifluoromethyl)pyridin-3-yl]pyrazin-2-amine |
| 71 | 6-[2-(trifluoromethyl)imidazo[1,2-a]pyridin-3-yl]-N-[6-(trifluoromethyl)pyridin-3-yl]pyrazin-2-amine |
| 72 | N-[4-(difluoromethoxy)phenyl]-6-[2-(trifluoromethyl)pyrazolo[1,5-a]pyridin-3-yl]pyrazin-2-amine |
| 73 | 6-(2-methyl-1H-benzimidazol-1-yl)-N-[6-(trifluoromethyl)pyridin-3-yl]pyrazin-2-amine |
| 74 | N-(4-methoxyphenyl)-6-[2-(trifluoromethyl)pyrazolo[1,5-a]pyridin-3-yl]pyrazin-2-amine |
| 75 | N-(4-methylphenyl)-6-[2-(trifluoromethyl)pyrazolo[1,5-a]pyridin-3-yl]pyrazin-2-amine |
| 76 | 1-(6-{[4-(trifluoromethyl)phenyl]amino}pyrazin-2-yl)-1H-benzimidazol-2-amine |
| 77 | 6-(2-methoxy-1H-benzimidazol-1-yl)-N-[4-(trifluoromethyl)phenyl]pyrazin-2-amine |
| 78 | (1S)-1-[1-(6-{[4-(trifluoromethyl)phenyl]amino}pyrazin-2-yl)-1H-benzimidazol-2-yl]ethyl acetate |
| 79 | 6-[2-(ethylsulfanyl)-1H-benzimidazol-1-yl]-N-[4-(trifluoromethyl)phenyl]pyrazin-2-amine |
| 80 | 6-(2-butyl-1H-benzimidazol-1-yl)-N-[4-(trifluoromethyl)phenyl]pyrazin-2-amine |
| 81 | 6-(2-ethoxy-1H-benzimidazol-1-yl)-N-[4-(trifluoromethyl)phenyl]pyrazin-2-amine |
| 82 | 6-(2-methyl-1H-imidazo[4,5-b]pyridin-1-yl)-N-[4-(trifluoromethyl)phenyl]pyrazin-2-amine |
| 83 | 6-(2-ethyl-1H-imidazo[4,5-b]pyridin-1-yl)-N-[4-(trifluoromethyl)phenyl]pyrazin-2-amine |
| 84 | 6-(1-ethyl-3,5-dimethyl-1H-pyrazol-4-yl)-N-[4-(trifluoromethoxy)phenyl]pyrazin-2-amine |
| 85 | N-[4-(difluoromethoxy)phenyl]-6-(2-methyl-1H-imidazo[4,5-b]pyridin-1-yl)pyrazin-2-amine |
| 86 | 6-(2-cyclopropylimidazo[1,2-a]pyridin-5-yl)-N-(4-methoxyphenyl)pyrazin-2-amine |
| 87 | 6-(2-cyclopropylimidazo[1,2-a]pyridin-5-yl)-N-[4-(trifluoromethoxy)phenyl]pyrazin-2-amine |
| 88 | 6-(2-cyclopropylimidazo[1,2-a]pyridin-5-yl)-N-(2,2-difluoro-1,3-benzodioxol-5-yl)pyrazin-2-amine |
| 89 | 6-(2-cyclopropylimidazo[1,2-a]pyridin-5-yl)-N-[4-(trifluoromethyl)phenyl]pyrazin-2-amine |
| 90 | 6-(2-cyclopropylimidazo[1,2-a]pyridin-5-yl)-N-[4-(difluoromethoxy)phenyl]pyrazin-2-amine |
| 91 | N-(2,2-difluoro-1,3-benzodioxol-5-yl)-6-[2-(trifluoromethyl)imidazo[1,2-a]pyridin-3-yl]pyrazin-2-amine |
| 92 | N-(2,2-difluoro-1,3-benzodioxol-5-yl)-6-[2-(trifluoromethyl)pyrazolo[1,5-a]pyridin-3-yl]pyrazin-2-amine |
| 93 | 6-[2-(trifluoromethyl)imidazo[1,2-a]pyrazin-3-yl]-N-[4-(trifluoromethyl)phenyl]pyrazin-2-amine |
| 94 | 6-(8-ethyl-7H-purin-7-yl)-N-[4-(trifluoromethyl)phenyl]pyrazin-2-amine |
| 95 | 6-(2-methyl-1H-imidazo[4,5-b]pyridin-1-yl)-N-[4-(trifluoromethoxy)phenyl]pyrazin-2-amine |
| 96 | N-(4-methyl-1,3-thiazol-2-yl)-6-[2-(trifluoromethyl)imidazo[1,2-a]pyridin-3-yl]pyrazin-2-amine |
| 97 | N-(3-methyl-1,2-oxazol-5-yl)-6-[2-(trifluoromethyl)imidazo[1,2-a]pyridin-3-yl]pyrazin-2-amine |
| 98 | (1S)-1-[1-(6-{[4-(trifluoromethyl)phenyl]amino}pyrazin-2-yl)-1H-benzimidazol-2-yl]ethanol |
| 99 | N-[4-(trifluoromethoxy)phenyl]-6-[2-(trifluoromethyl)imidazo[1,2-a]pyrimidin-3-yl]pyridin-2-amine |
| 100 | N-[4-(trifluoromethoxy)phenyl]-6-[2-(trifluoromethyl)imidazo[1,2-a]pyrimidin-3-yl]pyrazin-2-amine |
| 101 | 6-[6-methoxy-2-(trifluoromethyl)imidazo[1,2-a]pyridin-3-yl]-N-[4-(trifluoromethoxy)phenyl]pyridin-2-amine |
| 102 | 6-[6-methoxy-2-(trifluoromethyl)imidazo[1,2-a]pyridin-3-yl]-N-[4-(trifluoromethyl)phenyl]pyridin-2-amine |
| 103 | N-[4-(difluoromethoxy)phenyl]-6-[6-methoxy-2-(trifluoromethyl)imidazo[1,2-a]pyridin-3-yl]pyridin-2-amine |
| 104 | N-(4-methoxyphenyl)-6-[6-methoxy-2-(trifluoromethyl)imidazo[1,2-a]pyridin-3-yl]pyridin-2-amine |
| 105 | N-[4-(trifluoromethoxy)phenyl]-6-(1,3,5-trimethyl-1H-pyrazol-4-yl)pyrazin-2-amine |
| 106 | N-(4-bromophenyl)-6-(1,3,5-trimethyl-1H-pyrazol-4-yl)pyrazin-2-amine |
| 107 | 4-methoxy-6-[2-(trifluoromethyl)imidazo[1,2-a]pyridin-3-yl]-N-[4-(trifluoromethyl)phenyl]pyridin-2-amine |
| 108 | N-[4-(difluoromethoxy)phenyl]-6-[2-(trifluoromethyl)imidazo[1,2-a]pyrimidin-3-yl]pyridin-2-amine |
| 109 | N-[4-(difluoromethoxy)phenyl]-6-[2-(trifluoromethyl)imidazo[1,2-a]pyrimidin-3-yl]pyrazin-2-amine |
| 110 | 3-(6-{[4-(trifluoromethoxy)phenyl]amino}pyridin-2-yl)-2-(trifluoromethyl)imidazo[1,2-a]pyridin-6-ol |
| 111 | 2-(trifluoromethyl)-3-(6-{[4-(trifluoromethyl)phenyl]amino}pyridin-2-yl)imidazo[1,2-a]pyridin-6-ol |

-continued

| Cpd | Name |
|---|---|
| 112 | 4-({6-[6-methoxy-2-(trifluoromethyl)imidazo[1,2-a]pyridin-3-yl]pyridin-2-yl}amino)phenyl formate |
| 113 | 4-({6-[6-methoxy-2-(trifluoromethyl)imidazo[1,2-a]pyridin-3-yl]pyridin-2-yl}amino)phenol |
| 114 | 6-(2-cyclobutylimidazo[1,2-a]pyridin-5-yl)-N-[4-(trifluoromethyl)phenyl]pyrazin-2-amine |
| 115 | 6-(2-cyclobutylimidazo[1,2-a]pyridin-5-yl)-N-[4-(difluoromethoxy)phenyl]pyrazin-2-amine |
| 116 | 6-(2-cyclobutylimidazo[1,2-a]pyridin-5-yl)-N-(4-methoxyphenyl)pyrazin-2-amine |
| 117 | 6-(2-cyclobutylimidazo[1,2-a]pyridin-5-yl)-N-(2,2-difluoro-1,3-benzodioxol-5-yl)pyrazin-2-amine |
| 118 | 6-[6-(trifluoromethyl)imidazo[2,1-b][1,3]thiazol-5-yl]-N-[4-(trifluoromethyl)phenyl]pyrazin-2-amine |
| 119 | N-(4-methoxyphenyl)-6-[6-(trifluoromethyl)imidazo[2,1-b][1,3]thiazol-5-yl]pyrazin-2-amine |
| 120 | N-[4-(trifluoromethoxy)phenyl]-6-[6-(trifluoromethyl)imidazo[2,1-b][1,3]thiazol-5-yl]pyrazin-2-amine |
| 121 | N-[4-(difluoromethoxy)phenyl]-6-[6-(trifluoromethyl)imidazo[2,1-b][1,3]thiazol-5-yl]pyrazin-2-amine |
| 122 | N-phenyl-6-[6-(trifluoromethyl)imidazo[2,1-b][1,3]thiazol-5-yl]pyrazin-2-amine |
| 123 | 6-[2-(trifluoromethyl)-1H-imidazo[4,5-b]pyridin-1-yl]-N-[4-(trifluoromethyl)phenyl]pyrazin-2-amine |
| 124 | 3-(4-methoxy-6-{[4-(trifluoromethyl)phenyl]amino}pyridin-2-yl)imidazo[1,2-a]pyridine-2-carboxylic acid |
| 125 | N-[4-(difluoromethoxy)phenyl]-4-methoxy-6-[2-(trifluoromethyl)imidazo[1,2-a]pyridin-3-yl]pyridin-2-amine |
| 126 | 6-(1-benzyl-2-ethyl-4-methyl-1H-imidazol-5-yl)-N-[4-(trifluoromethyl)phenyl]pyrazin-2-amine |
| 127 | 6-(3,5-dimethyl-1,2-oxazol-4-yl)-N-[4-(trifluoromethyl)phenyl]pyrazin-2-amine |
| 128 | N-[4-(trifluoromethyl)phenyl]-6-(1,3,5-trimethyl-1H-pyrazol-4-yl)pyrazin-2-amine |
| 129 | 6-(2-cyclopropylimidazo[1,2-a]pyridin-3-yl)-N-[4-(trifluoromethyl)phenyl]pyrazin-2-amine |
| 130 | 6-(2-cyclopropylimidazo[1,2-a]pyridin-3-yl)-N-[4-(difluoromethoxy)phenyl]pyrazin-2-amine |
| 131 | 6-(2-cyclobutylimidazo[1,2-a]pyridin-3-yl)-N-[4-(trifluoromethyl)phenyl]pyrazin-2-amine |
| 132 | 2-(2-methyl-1H-benzimidazol-1-yl)-6-{[4-(trifluoromethyl)phenyl]amino}pyridine-4-carbonitrile |
| 133 | methyl 4-{[6-(2-methyl-1H-benzimidazol-1-yl)pyrazin-2-yl]amino}benzoate |
| 134 | 6-(2-chloro-1H-benzimidazol-1-yl)-N-[4-(trifluoromethyl)phenyl]pyrazin-2-amine |
| 135 | 2-{[4-(difluoromethoxy)phenyl]amino}-6-(2-methyl-1H-benzimidazol-1-yl)pyridine-4-carbonitrile |
| 136 | 2-(2-methyl-1H-benzimidazol-1-yl)-6-{[4-(trifluoromethoxy)phenyl]amino}pyridine-4-carbonitrile |
| 137 | 6-[2-(trifluoromethyl)-1H-imidazo[4,5-b]pyridin-1-yl]-N-[4-(trifluoromethyl)phenyl]pyridin-2-amine |
| 138 | N-ethyl-1-(6-{[4-(trifluoromethyl)phenyl]amino}pyrazin-2-yl)-1H-benzimidazol-2-amine |
| 139 | 6-(2-methyl-1H-imidazo[4,5-b]pyridin-1-yl)-N-[4-(trifluoromethyl)phenyl]pyridin-2-amine |
| 140 | 6-(2-ethyl-1H-imidazo[4,5-b]pyridin-1-yl)-N-[4-(trifluoromethyl)phenyl]pyridin-2-amine |
| 141 | N-[4-(trifluoromethoxy)phenyl]-6-[2-(trifluoromethyl)imidazo[1,2-a]pyrazin-3-yl]pyrazin-2-amine |
| 142 | N-[4-(difluoromethoxy)phenyl]-6-[2-(trifluoromethyl)imidazo[1,2-a]pyrazin-3-yl]pyrazin-2-amine |
| 143 | N-[4-(difluoromethoxy)phenyl]-6-(1,3,5-trimethyl-1H-pyrazol-4-yl)pyrazin-2-amine |
| 144 | N-[4-(trifluoromethoxy)phenyl]-6-(1,3,5-trimethyl-1H-pyrazol-4-yl)pyridin-2-amine |
| 145 | N-[4-(trifluoromethyl)phenyl]-6-(1,3,5-trimethyl-1H-pyrazol-4-yl)pyridin-2-amine |
| 146 | N-[4-(difluoromethoxy)phenyl]-6-(1,3,5-trimethyl-1H-pyrazol-4-yl)pyridin-2-amine |
| 147 | N-(5-methyl-1,3-thiazol-2-yl)-6-[2-(trifluoromethyl)imidazo[1,2-a]pyridin-3-yl]pyridin-2-amine |
| 148 | N-(4-methyl-1,3-thiazol-2-yl)-6-[2-(trifluoromethyl)imidazo[1,2-a]pyridin-3-yl]pyridin-2-amine |
| 149 | N-(4,5-dimethyl-1,3-thiazol-2-yl)-6-[2-(trifluoromethyl)imidazo[1,2-a]pyridin-3-yl]pyridin-2-amine |
| 150 | 1-[1-(6-{[4-(trifluoromethyl)phenyl]amino}pyrazin-2-yl)-1H-benzimidazol-2-yl]ethanol |
| 151 | [3-(6-{[4-(trifluoromethyl)phenyl]amino}pyrazin-2-yl)imidazo[1,2-a]pyridin-2-yl]methanol |
| 152 | (4-{[6-(2-methyl-1H-benzimidazol-1-yl)pyrazin-2-yl]amino}phenyl)methanol |
| 153 | 1-(4-{[6-(2-methyl-1H-benzimidazol-1-yl)pyrazin-2-yl]amino}phenyl)ethanone |
| 154 | N-[4-(aminomethyl)phenyl]-6-(2-methyl-1H-benzimidazol-1-yl)pyrazin-2-amine |
| 155 | 1-(4-{[6-(2-methyl-1H-benzimidazol-1-yl)pyrazin-2-yl]amino}phenyl)ethanol |
| 156 | N-{4-[(1E)-N-hydroxyethanimidoyl]phenyl}-6-(2-methyl-1H-benzimidazol-1-yl)pyrazin-2-amine |
| 157 | 1-(6-{[4-(trifluoromethyl)phenyl]amino}pyrazin-2-yl)-1H-benzimidazole-2-carbonitrile |
| 158 | 4-nitro-6-[2-(trifluoromethyl)imidazo[1,2-a]pyridin-3-yl]-N-[4-(trifluoromethyl)phenyl]pyridin-2-amine |
| 159 | 6-[2-(trifluoromethyl)imidazo[1,2-a]pyridin-3-yl]-$N^2$-[4-(trifluoromethyl)phenyl]pyridine-2,4-diamine |

-continued

| Cpd | Name |
|---|---|
| 160 | 2-[(2-[2-(trifluoromethyl)imidazo[1,2-a]pyridin-3-yl]-6-{[4-(trifluoromethyl)phenyl]amino}pyridin-4-yl)amino]ethanol |
| 161 | $N^4$-(2-methoxyethyl)-6-[2-(trifluoromethyl)imidazo[1,2-a]pyridin-3-yl]-$N^2$-[4-(trifluoromethyl)phenyl]pyridine-2,4-diamine |
| 162 | 6-(2-methyl-1H-indol-1-yl)-N-[4-(trifluoromethyl)phenyl]pyrazin-2-amine |
| 163 | N-[4-(difluoromethoxy)phenyl]-6-(2-methyl-1H-indol-1-yl)pyrazin-2-amine |
| 164 | N-(4-methoxyphenyl)-6-(2-methyl-1H-indol-1-yl)pyrazin-2-amine |
| 165 | N-(4-cyclopropylphenyl)-6-[2-(trifluoromethyl)imidazo[1,2-a]pyridin-3-yl]pyrazin-2-amine |
| 166 | 6-(2-methyl-1H-imidazo[4,5-c]pyridin-1-yl)-N-[4-(trifluoromethyl)phenyl]pyrazin-2-amine |
| 167 | 6-[2-(methylsulfanyl)-1H-benzimidazol-1-yl]-N-[4-(trifluoromethoxy)phenyl]pyrazin-2-amine |
| 168 | N-(4-methylphenyl)-6-[2-(trifluoromethyl)imidazo[1,2-a]pyrazin-3-yl]pyrazin-2-amine |
| 169 | N-[4-(difluoromethoxy)phenyl]-4-nitro-6-[2-(trifluoromethyl)imidazo[1,2-a]pyridin-3-yl]pyridin-2-amine |
| 170 | $N^2$-[4-(difluoromethoxy)phenyl]-6-[2-(trifluoromethyl)imidazo[1,2-a]pyridin-3-yl]pyridine-2,4-diamine |
| 171 | 2-[(2-{[4-(difluoromethoxy)phenyl]amino}-6-[2-(trifluoromethyl)imidazo[1,2-a]pyridin-3-yl]pyridin-4-yl)amino]ethanol |
| 172 | $N^2$-[4-(difluoromethoxy)phenyl]-$N^4$-(2-methoxyethyl)-6-[2-(trifluoromethyl)imidazo[1,2-a]pyridin-3-yl]pyridine-2,4-diamine |
| 173 | 4-(methylsulfanyl)-6-[2-(trifluoromethyl)imidazo[1,2-a]pyridin-3-yl]-N-[4-(trifluoromethyl)phenyl]pyridin-2-amine |
| 174 | N-(4-methoxyphenyl)-6-(2-methyl-1H-indol-1-yl)pyridin-2-amine |
| 175 | 6-(1-ethyl-3,5-dimethyl-1H-pyrazol-4-yl)-N-[4-(trifluoromethyl)phenyl]pyrazin-2-amine |
| 176 | 6-[1-(ethylsulfonyl)-3,5-dimethyl-1H-pyrazol-4-yl]-N-[4-(trifluoromethyl)phenyl]pyrazin-2-amine |
| 177 | 6-(2-ethyl-5,6-difluoro-1H-benzimidazol-1-yl)-N-[4-(trifluoromethyl)phenyl]pyrazin-2-amine |
| 178 | methyl 3-(6-{[4-(difluoromethoxy)phenyl]amino}pyrazin-2-yl)-2-(trifluoromethyl)imidazo[1,2-a]pyridine-6-carboxylate |
| 179 | 6-(2-ethyl-4-methyl-1H-imidazol-1-yl)-N-[4-(trifluoromethyl)phenyl]pyrazin-2-amine |
| 180 | N-[4-(difluoromethoxy)phenyl]-6-(2-ethyl-4-methyl-1H-imidazol-1-yl)pyrazin-2-amine |
| 181 | N-[4-(difluoromethoxy)phenyl]-6-[2-(methylsulfanyl)-1H-benzimidazol-1-yl]pyrazin-2-amine |
| 182 | 6-(2-cyclopropyl-5,6-difluoro-1H-benzimidazol-1-yl)-N-[4-(trifluoromethyl)phenyl]pyrazin-2-amine |
| 183 | N-methyl-1-(6-{[4-(trifluoromethoxy)phenyl]amino}pyrazin-2-yl)-1H-benzimidazol-2-amine |
| 184 | 1-(6-{[4-(trifluoromethoxy)phenyl]amino}pyrazin-2-yl)-1H-benzimidazole-2-carbonitrile |
| 185 | 4-{[6-(2-methyl-1H-benzimidazol-1-yl)pyrazin-2-yl]amino}benzamide |
| 186 | N-methyl-4-{[6-(2-methyl-1H-benzimidazol-1-yl)pyrazin-2-yl]amino}benzamide |
| 187 | 1-(6-{[4-(difluoromethoxy)phenyl]amino}pyrazin-2-yl)-N-methyl-1H-benzimidazol-2-amine |
| 188 | 1-(6-{[4-(difluoromethoxy)phenyl]amino}pyrazin-2-yl)-1H-benzimidazole-2-carbonitrile |
| 189 | 2-[2-(trifluoromethyl)imidazo[1,2-a]pyridin-3-yl]-6-{[4-(trifluoromethyl)phenyl]amino}pyridine-4-carboxamide |
| 190 | 6-[2-(trifluoromethyl)imidazo[1,2-a]pyridin-3-yl]-N-[5-(trifluoromethyl)pyridin-2-yl]pyrazin-2-amine |
| 191 | 6-[2-(methylsulfanyl)imidazo[1,2-a]pyridin-3-yl]-N-[4-(trifluoromethyl)phenyl]pyrazin-2-amine |
| 192 | 6-(5,6-dichloro-2-methyl-1H-benzimidazol-1-yl)-N-[4-(trifluoromethoxy)phenyl]pyrazin-2-amine |
| 193 | 6-(5,6-dichloro-2-methyl-1H-benzimidazol-1-yl)-N-[4-(trifluoromethyl)phenyl]pyrazin-2-amine |
| 194 | 6-[2-(trifluoromethyl)imidazo[1,2-a]pyridin-3-yl]-N-[4-(trifluoromethyl)phenyl]pyridin-2-amine |
| 195 | N-[4-(trifluoromethoxy)phenyl]-6-[2-(trifluoromethyl)imidazo[1,2-a]pyrazin-3-yl]pyridin-2-amine |
| 196 | N-[4-(difluoromethoxy)phenyl]-6-[2-(trifluoromethyl)imidazo[1,2-a]pyrazin-3-yl]pyridin-2-amine |
| 197 | 4-nitro-N-[4-(trifluoromethoxy)phenyl]-6-[2-(trifluoromethyl)imidazo[1,2-a]pyridin-3-yl]pyridin-2-amine |
| 198 | $N^2$-[4-(trifluoromethoxy)phenyl]-6-[2-(trifluoromethyl)imidazo[1,2-a]pyridin-3-yl]pyridine-2,4-diamine |
| 199 | N-[4-(difluoromethoxy)phenyl]-6-(5,6-difluoro-2-methyl-1H-benzimidazol-1-yl)pyrazin-2-amine |
| 200 | 2-chloro-N-{6-[2-(trifluoromethyl)imidazo[1,2-a]pyridin-3-yl]pyrazin-2-yl}pyrimidin-5-amine |
| 201 | 2-methoxy-N-{6-[2-(trifluoromethyl)imidazo[1,2-a]pyridin-3-yl]pyrazin-2-yl}pyrimidin-5-amine |
| 202 | 6-(2-methylimidazo[1,2-a]pyridin-3-yl)-N-[4-(trifluoromethyl)phenyl]pyrazin-2-amine |
| 203 | 2-(2-methyl-1H-benzimidazol-1-yl)-6-{[4-(trifluoromethyl)phenyl]amino}pyridine-4-carboxamide |
| 204 | 6-(5-fluoro-2-methyl-1H-benzimidazol-1-yl)-N-[4-(trifluoromethyl)phenyl]pyrazin-2-amine |

-continued

| Cpd | Name |
|---|---|
| 205 | N-[4-(difluoromethoxy)phenyl]-6-(5-fluoro-2-methyl-1H-benzimidazol-1-yl)pyrazin-2-amine |
| 206 | 6-(5-fluoro-2-methyl-1H-benzimidazol-1-yl)-N-[4-(trifluoromethoxy)phenyl]pyrazin-2-amine |
| 207 | 4-({6-[2-(trifluoromethyl)imidazo[1,2-a]pyridin-3-yl]pyrazin-2-yl}amino)phenol |
| 208 | N-[3-fluoro-4-(trifluoromethyl)phenyl]-6-[2-(trifluoromethyl)imidazo[1,2-a]pyridin-3-yl]pyrazin-2-amine |
| 209 | N-[3-fluoro-4-(trifluoromethyl)phenyl]-6-(2-methyl-1H-benzimidazol-1-yl)pyrazin-2-amine |
| 210 | 2-[2-(trifluoromethyl)imidazo[1,2-a]pyridin-3-yl]-6-{[4-(trifluoromethyl)phenyl]amino}pyridine-4-carbonitrile |
| 211 | 6-[2-(trifluoromethyl)imidazo[1,2-a]pyridin-3-yl]-N-{4-[(trifluoromethyl)sulfanyl]phenyl}pyrazin-2-amine |
| 212 | 2,2,2-trifluoro-1-[4-({6-[2-(trifluoromethyl)imidazo[1,2-a]pyridin-3-yl]pyrazin-2-yl}amino)phenyl]ethanone |
| 213 | [3-(6-{[4-(trifluoromethoxy)phenyl]amino}pyrazin-2-yl)imidazo[1,2-a]pyridin-2-yl]methanol |
| 214 | (3-{6-[(4-methylphenyl)amino]pyrazin-2-yl}imidazo[1,2-a]pyridin-2-yl)methanol |
| 215 | [3-(6-{[4-(difluoromethoxy)phenyl]amino}pyrazin-2-yl)imidazo[1,2-a]pyridin-2-yl]methanol |
| 216 | 2-[2-(1-hydroxyethyl)-1H-benzimidazol-1-yl]-6-{[4-(trifluoromethyl)phenyl]amino}pyridine-4-carbonitrile |
| 217 | 2-{[4-(difluoromethoxy)phenyl]amino}-6-[2-(trifluoromethyl)imidazo[1,2-a]pyridin-3-yl]pyridine-4-carbonitrile |
| 218 | 2-{[4-(trifluoromethoxy)phenyl]amino}-6-[2-(trifluoromethyl)imidazo[1,2-a]pyridin-3-yl]pyridine-4-carbonitrile |
| 219 | (2-[2-(trifluoromethyl)imidazo[1,2-a]pyridin-3-yl]-6-{[4-(trifluoromethyl)phenyl]amino}pyridin-4-yl)methanol |
| 220 | 6-(6-chloro-2-methyl-1H-benzimidazol-1-yl)-N-[4-(trifluoromethoxy)phenyl]pyrazin-2-amine |
| 221 | 6-(6-chloro-2-methyl-1H-benzimidazol-1-yl)-N-[4-(difluoromethoxy)phenyl]pyrazin-2-amine |
| 222 | 2-[6-fluoro-2-(trifluoromethyl)imidazo[1,2-a]pyridin-3-yl]-6-{[4-(trifluoromethoxy)phenyl]amino}pyridine-4-carbonitrile |
| 223 | 6-(5-chloro-2-methyl-1H-benzimidazol-1-yl)-N-[4-(trifluoromethoxy)phenyl]pyrazin-2-amine |
| 224 | 6-(5-chloro-2-methyl-1H-benzimidazol-1-yl)-N-[4-(difluoromethoxy)phenyl]pyrazin-2-amine |
| 225 | N,2-dimethyl-1-(6-{[4-(trifluoromethoxy)phenyl]amino}pyrazin-2-yl)-1H-benzimidazol-5-amine |
| 226 | 6-(3,5-dimethyl-1H-pyrazol-4-yl)-N-[4-(trifluoromethyl)phenyl]pyrazin-2-amine |
| 227 | 6-(2-cyclopropyl-5-fluoro-1H-benzimidazol-1-yl)-N-[4-(difluoromethoxy)phenyl]pyrazin-2-amine |
| 228 | 6-(6-fluoro-2-methyl-1H-benzimidazol-1-yl)-N-[4-(trifluoromethyl)phenyl]pyrazin-2-amine |
| 229 | N-[4-(difluoromethoxy)phenyl]-6-(6-fluoro-2-methyl-1H-benzimidazol-1-yl)pyrazin-2-amine |
| 230 | 6-(6-fluoro-2-methyl-1H-benzimidazol-1-yl)-N-[4-(trifluoromethoxy)phenyl]pyrazin-2-amine |
| 231 | 6-(5,6-difluoro-2-methyl-1H-benzimidazol-1-yl)-$N^2$-[4-(trifluoromethyl)phenyl]pyridine-2,4-diamine |
| 232 | N-[4-(trifluoromethyl)phenyl]-6-[2-(trifluoromethyl)-5,6,7,8-tetrahydroimidazo[1,2-a]pyridin-3-yl]pyrazin-2-amine |
| 233 | N-[4-(difluoromethoxy)phenyl]-6-[2-(trifluoromethyl)-5,6,7,8-tetrahydroimidazo[1,2-a]pyridin-3-yl]pyrazin-2-amine |
| 234 | N-[4-(trifluoromethoxy)phenyl]-6-[2-(trifluoromethyl)-5,6,7,8-tetrahydroimidazo[1,2-a]pyridin-3-yl]pyrazin-2-amine |
| 235 | 6-(imidazo[1,2-a]pyridin-3-yl)-N-[4-(trifluoromethyl)phenyl]pyrazin-2-amine |
| 236 | 2-{[4-(trifluoromethyl)phenyl]amino}-6-[2-(trifluoromethyl)-5,6,7,8-tetrahydroimidazo[1,2-a]pyridin-3-yl]pyridine-4-carbonitrile |
| 237 | 2-{[4-(difluoromethoxy)phenyl]amino}-6-[2-(trifluoromethyl)-5,6,7,8-tetrahydroimidazo[1,2-a]pyridin-3-yl]pyridine-4-carbonitrile |
| 238 | 2-{[4-(trifluoromethoxy)phenyl]amino}-6-[2-(trifluoromethyl)-5,6,7,8-tetrahydroimidazo[1,2-a]pyridin-3-yl]pyridine-4-carbonitrile |
| 239 | 6-(5-chloro-2-methyl-1H-benzimidazol-1-yl)-N-[4-(trifluoromethyl)phenyl]pyrazin-2-amine |
| 240 | 6-(6-chloro-2-methyl-1H-benzimidazol-1-yl)-N-[4-(trifluoromethyl)phenyl]pyrazin-2-amine |
| 241 | 2-(5,6-difluoro-2-methyl-1H-benzimidazol-1-yl)-6-{[4-(trifluoromethyl)phenyl]amino}pyridine-4-carbonitrile |
| 242 | 2-{[4-(difluoromethoxy)phenyl]amino}-6-(5,6-difluoro-2-methyl-1H-benzimidazol-1-yl)pyridine-4-carbonitrile |
| 243 | 2-(5,6-difluoro-2-methyl-1H-benzimidazol-1-yl)-6-{[4-(trifluoromethoxy)phenyl]amino}pyridine-4-carbonitrile |
| 244 | 6-(6-fluoro-2-methylimidazo[1,2-a]pyridin-3-yl)-N-[4-(trifluoromethyl)phenyl]pyrazin-2-amine |

| Cpd | Name |
|---|---|
| 245 | N-[4-(difluoromethoxy)phenyl]-6-(6-fluoro-2-methylimidazo[1,2-a]pyridin-3-yl)pyrazin-2-amine |
| 246 | 6-(6-fluoro-2-methylimidazo[1,2-a]pyridin-3-yl)-N-[4-(trifluoromethoxy)phenyl]pyrazin-2-amine |
| 247 | 2-(6-fluoro-2-methylimidazo[1,2-a]pyridin-3-yl)-6-{[4-(trifluoromethyl)phenyl]amino}pyridine-4-carbonitrile |
| 248 | 2-{[4-(difluoromethoxy)phenyl]amino}-6-(6-fluoro-2-methylimidazo[1,2-a]pyridin-3-yl)pyridine-4-carbonitrile |
| 249 | 2-(6-fluoro-2-methylimidazo[1,2-a]pyridin-3-yl)-6-{[4-(trifluoromethoxy)phenyl]amino}pyridine-4-carbonitrile |
| 250 | 6-[2-cyclopropyl-6-(trifluoromethyl)imidazo[1,2-a]pyridin-3-yl]-N-[4-(trifluoromethyl)phenyl]pyrazin-2-amine |
| 251 | 6-[2-cyclopropyl-6-(trifluoromethyl)imidazo[1,2-a]pyridin-3-yl]-N-[4-(difluoromethoxy)phenyl]pyrazin-2-amine |
| 252 | 6-[2-cyclopropyl-6-(trifluoromethyl)imidazo[1,2-a]pyridin-3-yl]-N-[4-(trifluoromethoxy)phenyl]pyrazin-2-amine |
| 253 | 6-[3,5-dimethyl-1-(2,2,2-trifluoroethyl)-1H-pyrazol-4-yl]-N-[4-(trifluoromethyl)phenyl]pyrazin-2-amine |
| 254 | 6-(6,8-difluoro-2-methylimidazo[1,2-a]pyridin-3-yl)-N-[4-(trifluoromethyl)phenyl]pyrazin-2-amine |
| 255 | N-[4-(difluoromethoxy)phenyl]-6-(6,8-difluoro-2-methylimidazo[1,2-a]pyridin-3-yl)pyrazin-2-amine |
| 256 | N-[4-(1-aminoethyl)phenyl]-6-(2-methyl-1H-benzimidazol-1-yl)pyrazin-2-amine |
| 257 | N-[4-(1-aminoethyl)phenyl]-6-[2-(trifluoromethyl)imidazo[1,2-a]pyridin-3-yl]pyrazin-2-amine |
| 258 | N-[4-(difluoromethoxy)phenyl]-6-(2-methyl-4,5,6,7-tetrahydro-1H-benzimidazol-1-yl)pyrazin-2-amine |
| 259 | 6-(2-ethyl-6-fluoro-1H-benzimidazol-1-yl)-N-[4-(trifluoromethyl)phenyl]pyrazin-2-amine |
| 260 | N-[4-(difluoromethoxy)phenyl]-6-(2-ethyl-6-fluoro-1H-benzimidazol-1-yl)pyrazin-2-amine |
| 261 | 2-(6-fluoro-2-methyl-1H-benzimidazol-1-yl)-6-{[4-(trifluoromethyl)phenyl]amino}pyridine-4-carbonitrile |
| 262 | 2-{[4-(difluoromethoxy)phenyl]amino}-6-(6-fluoro-2-methyl-1H-benzimidazol-1-yl)pyridine-4-carbonitrile |
| 263 | 2-{[4-(trifluoromethyl)phenyl]amino}-6-(1,3,5-trimethyl-1H-pyrazol-4-yl)pyridine-4-carbonitrile |
| 264 | 2-{[4-(difluoromethoxy)phenyl]amino}-6-(1,3,5-trimethyl-1H-pyrazol-4-yl)pyridine-4-carbonitrile |
| 265 | 2-{[4-(trifluoromethoxy)phenyl]amino}-6-(1,3,5-trimethyl-1H-pyrazol-4-yl)pyridine-4-carbonitrile |
| 266 | 6-(5,6-difluoro-2-methyl-1H-benzimidazol-1-yl)-N-[4-(trifluoromethoxy)phenyl]pyrazin-2-amine |
| 267 | 6-(2-methyl-4,5,6,7-tetrahydro-1H-benzimidazol-1-yl)-N-[4-(trifluoromethyl)phenyl]pyrazin-2-amine |
| 268 | 6-(2-methyl-4,5,6,7-tetrahydro-1H-benzimidazol-1-yl)-N-[4-(trifluoromethoxy)phenyl]pyrazin-2-amine |
| 269 | 3-methyl-6-[2-(trifluoromethyl)imidazo[1,2-a]pyridin-3-yl]-N-[4-(trifluoromethyl)phenyl]pyridin-2-amine |
| 270 | 6-(6-fluoro-2-methyl-1H-imidazo[4,5-b]pyridin-1-yl)-N-[4-(trifluoromethyl)phenyl]pyrazin-2-amine |
| 271 | 6-(2-ethyl-6-fluoro-1H-imidazo[4,5-b]pyridin-1-yl)-N-[4-(trifluoromethyl)phenyl]pyrazin-2-amine |
| 272 | 2-[6-fluoro-2-(trifluoromethyl)imidazo[1,2-a]pyridin-3-yl]-6-{[4-(trifluoromethyl)phenyl]amino}pyridine-4-carbonitrile |
| 273 | 2-{[4-(difluoromethoxy)phenyl]amino}-6-[6-fluoro-2-(trifluoromethyl)imidazo[1,2-a]pyridin-3-yl]pyridine-4-carbonitrile |
| 274 | N,2-dimethyl-1-(6-{[4-(trifluoromethyl)phenyl]amino}pyrazin-2-yl)-1H-benzimidazol-6-amine |
| 275 | N-benzyl-2-methyl-1-(6-{[4-(trifluoromethyl)phenyl]amino}pyrazin-2-yl)-1H-benzimidazol-6-amine |
| 276 | 6-[1,5-dimethyl-3-(trifluoromethyl)-1H-pyrazol-4-yl]-N-[4-(trifluoromethyl)phenyl]pyrazin-2-amine |
| 277 | 1-[3,5-dimethyl-4-(6-{[4-(trifluoromethyl)phenyl]amino}pyrazin-2-yl)-1H-pyrazol-1-yl]ethanone |
| 278 | ethyl 3,5-dimethyl-4-(6-{[4-(trifluoromethyl)phenyl]amino}pyrazin-2-yl)-1H-pyrazole-1-carboxylate |
| 279 | ethyl 4-(6-{[4-(difluoromethoxy)phenyl]amino}pyrazin-2-yl)-3,5-dimethyl-1H-pyrazole-1-carboxylate |
| 280 | N-[4-(difluoromethoxy)phenyl]-6-[1,5-dimethyl-3-(trifluoromethyl)-1H-pyrazol-4-yl]pyrazin-2-amine |
| 281 | 6-[1,5-dimethyl-3-(trifluoromethyl)-1H-pyrazol-4-yl]-N-[4-(trifluoromethoxy)phenyl]pyrazin-2-amine |
| 282 | $N^2$-(4-methoxyphenyl)-6-[2-(trifluoromethyl)imidazo[1,2-a]pyridin-3-yl]pyridine-2,5-diamine |
| 283 | 6-(2,4-dimethyl-1H-benzimidazol-1-yl)-N-[4-(trifluoromethyl)phenyl]pyrazin-2-amine |
| 284 | 6-(2-methyl-4-nitro-1H-benzimidazol-1-yl)-N-[4-(trifluoromethyl)phenyl]pyrazin-2-amine |
| 285 | 2-methyl-1-(6-{[4-(trifluoromethyl)phenyl]amino}pyrazin-2-yl)-1H-benzimidazol-6-amine |

-continued

| Cpd | Name |
|---|---|
| 286 | 6-[6-fluoro-2-(trifluoromethyl)imidazo[1,2-a]pyridin-3-yl]-4-nitro-N-[4-(trifluoromethyl)phenyl]pyridin-2-amine |
| 287 | 6-[6-fluoro-2-(trifluoromethyl)imidazo[1,2-a]pyridin-3-yl]-$N^2$-[4-(trifluoromethyl)phenyl]pyridine-2,4-diamine |
| 288 | 2-[2-(hydroxymethyl)imidazo[1,2-a]pyridin-3-yl]-6-{[4-(trifluoromethyl)phenyl]amino}pyridine-4-carbonitrile |
| 289 | [3-(4-amino-6-{[4-(trifluoromethyl)phenyl]amino}pyridin-2-yl)imidazo[1,2-a]pyridin-2-yl]methanol |
| 290 | tert-butyl [2-(2-methyl-1H-imidazo[4,5-b]pyridin-1-yl)-6-{[4-(trifluoromethyl)phenyl]amino}pyridin-4-yl]carbamate |
| 291 | 2-[(2-[6-fluoro-2-(trifluoromethyl)imidazo[1,2-a]pyridin-3-yl]-6-{[4-(trifluoromethyl)phenyl]amino}pyridin-4-yl)amino]ethanol |
| 292 | 6-(2-methyl-1H-imidazo[4,5-b]pyridin-1-yl)-$N^2$-[4-(trifluoromethyl)phenyl]pyridine-2,4-diamine |
| 293 | 6-(2-cyclopropyl-6-fluoro-1H-imidazo[4,5-b]pyridin-1-yl)-N-[4-(trifluoromethyl)phenyl]pyrazin-2-amine |
| 294 | N-(4-chloro-3-fluorophenyl)-6-(5,6-difluoro-2-methyl-1H-benzimidazol-1-yl)pyrazin-2-amine |
| 295 | 6-(5,6-difluoro-2-methyl-1H-benzimidazol-1-yl)-N-[3-fluoro-4-(trifluoromethyl)phenyl]pyrazin-2-amine |
| 296 | 2-methyl-1-(6-{[4-(trifluoromethyl)phenyl]amino}pyrazin-2-yl)-1H-benzimidazol-4-amine |
| 297 | 6-(4,5-dichloro-2-methyl-1H-imidazol-1-yl)-N-[4-(trifluoromethyl)phenyl]pyrazin-2-amine |
| 298 | 6-(4-bromo-2-methyl-1H-imidazol-1-yl)-N-[4-(trifluoromethyl)phenyl]pyrazin-2-amine |
| 299 | 6-(5-chloro-2,4-dimethyl-1H-imidazol-1-yl)-N-[4-(trifluoromethyl)phenyl]pyrazin-2-amine |
| 300 | 6-(2,4-dimethyl-1H-imidazol-1-yl)-N-[4-(trifluoromethyl)phenyl]pyrazin-2-amine |
| 301 | 6-(5,6-difluoro-2-methyl-1H-benzimidazol-1-yl)-N-[3-fluoro-4-(trifluoromethoxy)phenyl]pyrazin-2-amine |
| 302 | 6-{2-[(methylamino)methyl]imidazo[1,2-a]pyridin-3-yl}-N-[4-(trifluoromethyl)phenyl]pyrazin-2-amine |
| 303 | 6-[2-methyl-4-(trifluoromethyl)-1H-imidazol-1-yl]-N-[4-(trifluoromethyl)phenyl]pyrazin-2-amine |
| 304 | 6-(5,6-difluoro-2-methyl-1H-benzimidazol-1-yl)-N-[6-(trifluoromethyl)pyridin-3-yl]pyrazin-2-amine |
| 305 | 6-(5-chloro-2,4-dimethyl-1H-imidazol-1-yl)-N-[4-(difluoromethoxy)phenyl]pyrazin-2-amine |
| 306 | 6-(2-methyl-1H-benzimidazol-1-yl)-N-[4-(2,2,2-trifluoroethoxy)phenyl]pyrazin-2-amine |
| 307 | 6-(2-methyl-1H-benzimidazol-1-yl)-N-[4-(1,1,2,2-tetrafluoroethoxy)phenyl]pyrazin-2-amine |
| 308 | 6-(6-fluoroimidazo[1,2-a]pyridin-3-yl)-N-[4-(trifluoromethyl)phenyl]pyrazin-2-amine |
| 309 | N-[4-(difluoromethoxy)-3-fluorophenyl]-6-(6-fluoro-2-methylimidazo[1,2-a]pyridin-3-yl)pyrazin-2-amine |
| 310 | 6-(6-fluoro-2-methylimidazo[1,2-a]pyridin-3-yl)-N-[3-fluoro-4-(trifluoromethyl)phenyl]pyrazin-2-amine |
| 311 | 2-{[4-(difluoromethoxy)-3-fluorophenyl]amino}-6-(6-fluoro-2-methylimidazo[1,2-a]pyridin-3-yl)pyridine-4-carbonitrile |
| 312 | 2-(6-fluoro-2-methylimidazo[1,2-a]pyridin-3-yl)-6-{[3-fluoro-4-(trifluoromethyl)phenyl]amino}pyridine-4-carbonitrile |
| 313 | 2-[(3,5-difluoro-4-methoxyphenyl)amino]-6-(6-fluoro-2-methylimidazo[1,2-a]pyridin-3-yl)pyridine-4-carbonitrile |
| 314 | 2-[(4-fluoro-3-methoxyphenyl)amino]-6-(6-fluoro-2-methylimidazo[1,2-a]pyridin-3-yl)pyridine-4-carbonitrile |
| 315 | $N^2$-[4-(difluoromethoxy)-3-fluorophenyl]-6-(6-fluoro-2-methylimidazo[1,2-a]pyridin-3-yl)pyridine-2,4-diamine |
| 316 | 6-(6-fluoro-2-methylimidazo[1,2-a]pyridin-3-yl)-$N^2$-[4-(trifluoromethyl)phenyl]pyridine-2,4-diamine |
| 317 | 6-(6-methoxy-2-methyl-1H-benzimidazol-1-yl)-N-[4-(trifluoromethyl)phenyl]pyrazin-2-amine |
| 318 | 6-[2,5-dimethyl-4-(trifluoromethyl)-1H-imidazol-1-yl]-N-[4-(trifluoromethyl)phenyl]pyrazin-2-amine |
| 319 | N-[4-(difluoromethoxy)-3-fluorophenyl]-6-(5,6-difluoro-2-methyl-1H-benzimidazol-1-yl)pyrazin-2-amine |
| 320 | N-[4-(difluoromethoxy)-3-fluorophenyl]-6-(6-fluoro-2-methyl-1H-benzimidazol-1-yl)pyrazin-2-amine |
| 321 | N-[4-(2,2,2-trifluoroethoxy)phenyl]-6-[2-(trifluoromethyl)imidazo[1,2-a]pyridin-3-yl]pyrazin-2-amine |
| 322 | N-[4-(1,1,2,2-tetrafluoroethoxy)phenyl]-6-[2-(trifluoromethyl)imidazo[1,2-a]pyridin-3-yl]pyrazin-2-amine |
| 323 | N-[4-(difluoromethoxy)-3-fluorophenyl]-6-[2-(trifluoromethyl)imidazo[1,2-a]pyridin-3-yl]pyrazin-2-amine |
| 324 | N-[4-(difluoromethoxy)-3-fluorophenyl]-6-(2-methyl-1H-benzimidazol-1-yl)pyrazin-2-amine |
| 325 | N-[4-(difluoromethoxy)-3-fluorophenyl]-6-(2-methyl-1H-imidazo[4,5-b]pyridin-1-yl)pyrazin-2-amine |
| 326 | 2-{[4-(difluoromethoxy)-3-fluorophenyl]amino}-6-(5,6-difluoro-2-methyl-1H-benzimidazol-1-yl)pyridine-4-carbonitrile |

-continued

| Cpd | Name |
|---|---|
| 327 | 6-(6-chloro-2-ethyl-1H-imidazo[4,5-b]pyridin-1-yl)-N-[4-(trifluoromethyl)phenyl]pyrazin-2-amine |
| 328 | [6-fluoro-3-(6-{[4-(trifluoromethyl)phenyl]amino}pyrazin-2-yl)imidazo[1,2-a]pyridin-2-yl]methanol |
| 329 | 6-[1-ethyl-5-methyl-3-(trifluoromethyl)-1H-pyrazol-4-yl]-N-[4-(trifluoromethyl)phenyl]pyrazin-2-amine |
| 330 | N-[4-(difluoromethoxy)phenyl]-6-[1-ethyl-5-methyl-3-(trifluoromethyl)-1H-pyrazol-4-yl]pyrazin-2-amine |
| 331 | 6-[1-ethyl-5-methyl-3-(trifluoromethyl)-1H-pyrazol-4-yl]-N-[4-(trifluoromethoxy)phenyl]pyrazin-2-amine |
| 332 | 6-(3,5-diethyl-1-methyl-1H-pyrazol-4-yl)-N-[4-(trifluoromethyl)phenyl]pyrazin-2-amine |
| 333 | 6-(3,5-diethyl-1-methyl-1H-pyrazol-4-yl)-N-[4-(difluoromethoxy)phenyl]pyrazin-2-amine |
| 334 | 6-(3,5-diethyl-1-methyl-1H-pyrazol-4-yl)-N-[4-(trifluoromethoxy)phenyl]pyrazin-2-amine |
| 335 | 2-[3,5-dimethyl-4-(6-{[4-(trifluoromethyl)phenyl]amino}pyrazin-2-yl)-1H-pyrazol-1-yl]ethanol |
| 336 | 6-(2-cyclopropyl-6-fluoroimidazo[1,2-a]pyridin-3-yl)-N-[4-(trifluoromethyl)phenyl]pyrazin-2-amine |
| 337 | 6-(2-cyclopropyl-6-fluoroimidazo[1,2-a]pyridin-3-yl)-N-[4-(difluoromethoxy)phenyl]pyrazin-2-amine |
| 338 | 6-(2-cyclopropyl-6-fluoroimidazo[1,2-a]pyridin-3-yl)-N-[4-(difluoromethoxy)-3-fluorophenyl]pyrazin-2-amine |
| 339 | 6-(4-fluoro-2-methyl-1H-benzimidazol-1-yl)-N-[4-(trifluoromethyl)phenyl]pyrazin-2-amine |
| 340 | 6-[2-methyl-6-(trifluoromethyl)-1H-benzimidazol-1-yl]-N-[4-(trifluoromethyl)phenyl]pyrazin-2-amine |
| 341 | 6-(4-bromo-2,5-dimethyl-1H-imidazol-1-yl)-N-[4-(trifluoromethyl)phenyl]pyrazin-2-amine |
| 342 | N-[4-(trifluoromethyl)phenyl]-6-(2,4,5-trimethyl-1H-imidazol-1-yl)pyrazin-2-amine |
| 343 | 6-(2,6-dimethyl-1H-benzimidazol-1-yl)-N-[4-(trifluoromethyl)phenyl]pyrazin-2-amine |
| 344 | 2-(5-chloro-2-methyl-1H-benzimidazol-1-yl)-6-{[4-(trifluoromethyl)phenyl]amino}pyridine-4-carbonitrile |
| 345 | 2-(6-chloro-2-methyl-1H-benzimidazol-1-yl)-6-{[4-(trifluoromethyl)phenyl]amino}pyridine-4-carbonitrile |
| 346 | 2-(2-cyclopropyl-6-fluoroimidazo[1,2-a]pyridin-3-yl)-6-{[4-(trifluoromethyl)phenyl]amino}pyridine-4-carbonitrile |
| 347 | 2-(2-cyclopropyl-6-fluoroimidazo[1,2-a]pyridin-3-yl)-6-{[3-fluoro-4-(trifluoromethyl)phenyl]amino}pyridine-4-carbonitrile |
| 348 | 2-(2-cyclopropyl-6-fluoroimidazo[1,2-a]pyridin-3-yl)-6-{[4-(difluoromethoxy)phenyl]amino}pyridine-4-carbonitrile |
| 349 | 2-(2-cyclopropyl-6-fluoroimidazo[1,2-a]pyridin-3-yl)-6-{[4-(difluoromethoxy)-3-fluorophenyl]amino}pyridine-4-carbonitrile |
| 350 | 2-(2-cyclopropyl-6-fluoroimidazo[1,2-a]pyridin-3-yl)-6-{[4-(trifluoromethoxy)phenyl]amino}pyridine-4-carbonitrile |
| 351 | 2-(2-cyclopropyl-6-fluoroimidazo[1,2-a]pyridin-3-yl)-6-[(3,5-difluoro-4-methoxyphenyl)amino]pyridine-4-carbonitrile |
| 352 | 6-{3,5-dimethyl-1-[2-(2H-tetrazol-2-yl)ethyl]-1H-pyrazol-4-yl}-N-[4-(trifluoromethyl)phenyl]pyrazin-2-amine |
| 353 | 6-(2-methylpyridin-4-yl)-N-[4-(trifluoromethyl)phenyl]pyrazin-2-amine |
| 354 | 6-(2'-chloro-2,4'-bipyridin-4-yl)-N-[4-(trifluoromethyl)phenyl]pyrazin-2-amine |
| 355 | 6-(2,5-dimethyl-1H-imidazol-1-yl)-N-[4-(trifluoromethyl)phenyl]pyrazin-2-amine |
| 356 | 6-[2-methyl-5-(trifluoromethoxy)-1H-benzimidazol-1-yl]-N-[4-(trifluoromethyl)phenyl]pyrazin-2-amine |
| 357 | 6-[2-methyl-6-(trifluoromethoxy)-1H-benzimidazol-1-yl]-N-[4-(trifluoromethyl)phenyl]pyrazin-2-amine |
| 358 | 6-(7-fluoro-2-methyl-1H-benzimidazol-1-yl)-N-[4-(trifluoromethyl)phenyl]pyrazin-2-amine |
| 359 | 2-(5,6-difluoro-2-methyl-1H-benzimidazol-1-yl)-6-{[3-fluoro-4-(trifluoromethyl)phenyl]amino}pyridine-4-carbonitrile |
| 360 | N-[3-fluoro-4-(trifluoromethyl)phenyl]-6-(2-methyl-1H-imidazo[4,5-b]pyridin-1-yl)pyrazin-2-amine |
| 361 | 6-(6-chloro-2-methyl-1H-imidazo[4,5-b]pyridin-1-yl)-N-[4-(trifluoromethyl)phenyl]pyrazin-2-amine |
| 362 | 6-(2-cyclopropyl-6-fluoro-1H-benzimidazol-1-yl)-N-[4-(trifluoromethyl)phenyl]pyrazin-2-amine |
| 363 | 6-(2-cyclopropyl-6-fluoroimidazo[1,2-a]pyridin-3-yl)-$N^2$-[4-(trifluoromethyl)phenyl]pyridine-2,4-diamine |
| 364 | 6-(2-cyclopropyl-6-fluoroimidazo[1,2-a]pyridin-3-yl)-$N^2$-[3-fluoro-4-(trifluoromethyl)phenyl]pyridine-2,4-diamine |
| 365 | 6-(2-cyclopropyl-6-fluoroimidazo[1,2-a]pyridin-3-yl)-$N^2$-[4-(difluoromethoxy)phenyl]pyridine-2,4-diamine |
| 366 | 6-(2-cyclopropyl-6-fluoroimidazo[1,2-a]pyridin-3-yl)-$N^2$-[4-(difluoromethoxy)-3-fluorophenyl]pyridine-2,4-diamine |
| 367 | 6-(2-cyclopropyl-6-fluoroimidazo[1,2-a]pyridin-3-yl)-$N^2$-[4-(trifluoromethoxy)phenyl]pyridine-2,4-diamine |
| 368 | N-[2-(2-cyclopropyl-6-fluoroimidazo[1,2-a]pyridin-3-yl)-6-{[4-(trifluoromethyl)phenyl]amino}pyridin-4-yl]sulfuric diamide |

| Cpd | Name |
|---|---|
| 369 | 1-[2-(2-cyclopropyl-6-fluoroimidazo[1,2-a]pyridin-3-yl)-6-{[4-(trifluoromethyl)phenyl]amino}pyridin-4-yl]urea |
| 370 | 6-(2-ethyl-1H-imidazo[4,5-c]pyridin-1-yl)-N-[4-(trifluoromethyl)phenyl]pyrazin-2-amine |
| 371 | 6-(8-methyl-7H-purin-7-yl)-N-[4-(trifluoromethyl)phenyl]pyrazin-2-amine |
| 372 | 6-(5-ethyl-2-methyl-1H-imidazol-1-yl)-N-[4-(trifluoromethyl)phenyl]pyrazin-2-amine |
| 373 | 6-(6-fluoro-2-methyl-1H-imidazo[4,5-b]pyridin-1-yl)-N-[3-fluoro-4-(trifluoromethyl)phenyl]pyrazin-2-amine |
| 374 | 6-(2-ethyl-6-fluoro-1H-imidazo[4,5-b]pyridin-1-yl)-N-[3-fluoro-4-(trifluoromethyl)phenyl]pyrazin-2-amine |
| 375 | 6-[2-methyl-5-(prop-2-en-1-yl)-4,5,6,7-tetrahydro-1H-imidazo[4,5-c]pyridin-1-yl]-N-[4-(trifluoromethyl)phenyl]pyrazin-2-amine |
| 376 | 6-(6-methoxy-2-methylimidazo[1,2-a]pyridin-3-yl)-N-[4-(trifluoromethyl)phenyl]pyrazin-2-amine |
| 377 | 6-(6-methoxy-2-methylimidazo[1,2-a]pyridin-3-yl)-N-[4-(trifluoromethoxy)phenyl]pyrazin-2-amine |
| 378 | 2-methyl-3-(6-{[4-(trifluoromethyl)phenyl]amino}pyrazin-2-yl)imidazo[1,2-a]pyridin-6-ol |
| 379 | 2-(6-methoxy-2-methylimidazo[1,2-a]pyridin-3-yl)-6-{[4-(trifluoromethyl)phenyl]amino}pyridine-4-carbonitrile |
| 380 | 2-(6-methoxy-2-methylimidazo[1,2-a]pyridin-3-yl)-6-{[4-(trifluoromethoxy)phenyl]amino}pyridine-4-carbonitrile |
| 381 | 2-(6-hydroxy-2-methylimidazo[1,2-a]pyridin-3-yl)-6-{[4-(trifluoromethyl)phenyl]amino}pyridine-4-carbonitrile |
| 382 | N-[4-(difluoromethoxy)-3-fluorophenyl]-6-(1-ethyl-3,5-dimethyl-1H-pyrazol-4-yl)pyrazin-2-amine |
| 383 | 2-[6-fluoro-2-(hydroxymethyl)imidazo[1,2-a]pyridin-3-yl]-6-{[4-(trifluoromethyl)phenyl]amino}pyridine-4-carbonitrile |
| 384 | 6-(quinolin-4-yl)-N-[4-(trifluoromethyl)phenyl]pyrazin-2-amine |
| 385 | 6-(7-chloroquinolin-4-yl)-N-[4-(trifluoromethyl)phenyl]pyrazin-2-amine |
| 386 | N-[4-(trifluoromethyl)phenyl]-6-(2,5,6-trimethyl-1H-benzimidazol-1-yl)pyrazin-2-amine |
| 387 | N-[4-(trifluoromethoxy)phenyl]-6-(2,5,6-trimethyl-1H-benzimidazol-1-yl)pyrazin-2-amine |
| 388 | 6-(6-bromo-2-methyl-1H-benzimidazol-1-yl)-N-[4-(trifluoromethyl)phenyl]pyrazin-2-amine |
| 389 | 2-{[4-(trifluoromethyl)phenyl]amino}-6-(2,5,6-trimethyl-1H-benzimidazol-1-yl)pyridine-4-carbonitrile |
| 390 | N-[3-chloro-4-(trifluoromethyl)phenyl]-6-(2-methyl-1H-benzimidazol-1-yl)pyrazin-2-amine |
| 391 | 6-{4-[(Z)-2-ethoxyethenyl]-2-methyl-1H-imidazol-1-yl}-N-[4-(trifluoromethyl)phenyl]pyrazin-2-amine |
| 392 | 6-(6-ethyl-2-methyl-1H-benzimidazol-1-yl)-N-[4-(trifluoromethyl)phenyl]pyrazin-2-amine |
| 393 | 2-{[4-(difluoromethoxy)phenyl]amino}-6-[6-fluoro-2-(hydroxymethyl)imidazo[1,2-a]pyridin-3-yl]pyridine-4-carbonitrile |
| 394 | 2-{[4-(difluoromethoxy)-3-fluorophenyl]amino}-6-[6-fluoro-2-(hydroxymethyl)imidazo[1,2-a]pyridin-3-yl]pyridine-4-carbonitrile |
| 395 | 2-[6-fluoro-2-(hydroxymethyl)imidazo[1,2-a]pyridin-3-yl]-6-{[3-fluoro-4-(trifluoromethyl)phenyl]amino}pyridine-4-carbonitrile |
| 396 | 2-(6-hydroxy-2-methylimidazo[1,2-a]pyridin-3-yl)-6-{[4-(trifluoromethoxy)phenyl]amino}pyridine-4-carbonitrile |
| 397 | 2-{[2-methyl-1-(6-{[4-(trifluoromethyl)phenyl]amino}pyrazin-2-yl)-1H-benzimidazol-6-yl]amino}ethanol |
| 398 | 6-(2-ethyl-5-methyl-4,5,6,7-tetrahydro-3H-imidazo[4,5-c]pyridin-3-yl)-N-[4-(trifluoromethyl)phenyl]pyrazin-2-amine |
| 399 | 6-[1-(2-methoxyethyl)-3,5-dimethyl-1H-pyrazol-4-yl]-N-[4-(trifluoromethyl)phenyl]pyrazin-2-amine |
| 400 | 6-[3,5-dimethyl-1-(pyridin-2-ylmethyl)-1H-pyrazol-4-yl]-N-[4-(trifluoromethyl)phenyl]pyrazin-2-amine |
| 401 | N-[4-(difluoromethoxy)phenyl]-6-[3,5-dimethyl-1-(pyridin-2-ylmethyl)-1H-pyrazol-4-yl]pyrazin-2-amine |
| 402 | 6-[3,5-dimethyl-1-(pyridin-3-ylmethyl)-1H-pyrazol-4-yl]-N-[4-(trifluoromethyl)phenyl]pyrazin-2-amine |
| 403 | 6-[3,5-dimethyl-1-(pyridin-4-ylmethyl)-1H-pyrazol-4-yl]-N-[4-(trifluoromethyl)phenyl]pyrazin-2-amine |
| 404 | (2S)-4-[3,5-dimethyl-4-(6-{[4-(trifluoromethyl)phenyl]amino}pyrazin-2-yl)-1H-pyrazol-1-yl]butane-1,2-diol |
| 405 | N-(6-chloropyridin-3-yl)-6-(5,6-difluoro-2-methyl-1H-benzimidazol-1-yl)pyrazin-2-amine |
| 406 | 6-[6-fluoro-2-(trifluoromethyl)-5,6,7,8-tetrahydroimidazo[1,2-a]pyridin-3-yl]-N-[4-(trifluoromethyl)phenyl]pyrazin-2-amine |
| 407 | 6-(1H-indol-4-yl)-N-[4-(trifluoromethyl)phenyl]pyrazin-2-amine |
| 408 | 6-(2-methyl-1H-benzimidazol-1-yl)-N-[3-methyl-4-(trifluoromethyl)phenyl]pyrazin-2-amine |
| 409 | 6-(6-methoxy-2-methyl-5,6,7,8-tetrahydroimidazo[1,2-a]pyridin-3-yl)-N-[4-(trifluoromethyl)phenyl]pyrazin-2-amine |
| 410 | 2-(2-cyclopropyl-6-fluoro-1H-benzimidazol-1-yl)-6-{[4-(trifluoromethyl)phenyl]amino}pyridine-4-carbonitrile |
| 411 | 6-[6-fluoro-2-(trifluoromethyl)imidazo[1,2-a]pyridin-3-yl]-N-[4-(trifluoromethyl)phenyl]pyridin-2-amine |
| 412 | 6-(5-chloro-1,3-dimethyl-1H-pyrazol-4-yl)-N-[4-(trifluoromethyl)phenyl]pyrazin-2-amine |

-continued

| Cpd | Name |
|---|---|
| 413 | 6-(5-chloro-1,3-dimethyl-1H-pyrazol-4-yl)-N-[4-(difluoromethoxy)phenyl]pyrazin-2-amine |
| 414 | 6-(5-chloro-1,3-dimethyl-1H-pyrazol-4-yl)-N-[4-(trifluoromethoxy)phenyl]pyrazin-2-amine |
| 415 | 6-(5-chloro-1,3-dimethyl-1H-pyrazol-4-yl)-N-[4-(difluoromethoxy)-3-fluorophenyl]pyrazin-2-amine |
| 416 | 6-(5-fluoro-2-methyl-2H-indazol-3-yl)-N-[4-(trifluoromethyl)phenyl]pyrazin-2-amine |
| 417 | 6-(4,6-difluoro-2-methyl-1H-benzimidazol-1-yl)-N-[4-(trifluoromethyl)phenyl]pyrazin-2-amine |
| 418 | 6-[6-fluoro-2-(trifluoromethyl)imidazo[1,2-a]pyridin-3-yl]-$N^4$-hydroxy-$N^2$-[4-(trifluoromethyl)phenyl]pyridine-2,4-diamine |
| 419 | 2-(6-chloro-2-methyl-1H-imidazo[4,5-b]pyridin-1-yl)-6-{[4-(trifluoromethyl)phenyl]amino}pyridine-4-carbonitrile |
| 420 | N-[6-(2-methyl-1H-benzimidazol-1-yl)pyrazin-2-yl]-1,3-benzothiazol-2-amine |
| 421 | N-[4-(trifluoromethyl)phenyl]-6-(2,4,6-trimethyl-1H-benzimidazol-1-yl)pyrazin-2-amine |
| 422 | 6-(2-cyclopropylimidazo[1,2-a]pyrimidin-3-yl)-N-[4-(trifluoromethyl)phenyl]pyrazin-2-amine |
| 423 | 6-(5,6-difluoro-2-methyl-1H-benzimidazol-1-yl)-N-[6-(morpholin-4-yl)pyridin-3-yl]pyrazin-2-amine |
| 424 | N-(2,3-dihydro-1H-inden-2-yl)-6-(2-methyl-1H-benzimidazol-1-yl)pyrazin-2-amine |
| 425 | 2-[(5-{[6-(5,6-difluoro-2-methyl-1H-benzimidazol-1-yl)pyrazin-2-yl]amino}pyridin-2-yl)amino]ethanol |
| 426 | N-(6-chloropyridin-3-yl)-6-(5-fluoro-2-methyl-1H-benzimidazol-1-yl)pyrazin-2-amine |
| 427 | N-(6-chloropyridin-3-yl)-6-(6-fluoro-2-methyl-1H-benzimidazol-1-yl)pyrazin-2-amine |
| 428 | 2-(6-chloro-2-methyl-1H-imidazo[4,5-b]pyridin-1-yl)-6-{[4-(difluoromethoxy)phenyl]amino}pyridine-4-carbonitrile |
| 429 | 2-(6-chloro-2-methyl-1H-imidazo[4,5-b]pyridin-1-yl)-6-{[4-(difluoromethoxy)-3-fluorophenyl]amino}pyridine-4-carbonitrile |
| 430 | $N^5$-[6-(5,6-difluoro-2-methyl-1H-benzimidazol-1-yl)pyrazin-2-yl]-$N^2$-[2-(dimethylamino)ethyl]pyridine-2,5-diamine |
| 431 | 6-(5-fluoro-2-methyl-1H-benzimidazol-1-yl)-N-[6-(trifluoromethyl)pyridin-3-yl]pyrazin-2-amine |
| 432 | 6-(6-fluoro-2-methyl-1H-benzimidazol-1-yl)-N-[6-(trifluoromethyl)pyridin-3-yl]pyrazin-2-amine |
| 433 | 6-(2-methyl-1H-benzimidazol-1-yl)-N-[4-(4,4,5,5-tetramethyl-1,3,2-dioxaborolan-2-yl)phenyl]pyrazin-2-amine |
| 434 | (4-{[6-(2-methyl-1H-benzimidazol-1-yl)pyrazin-2-yl]amino}phenyl)boronic acid |
| 435 | 2-(4-fluoro-2-methyl-1H-benzimidazol-1-yl)-6-{[4-(trifluoromethyl)phenyl]amino}pyridine-4-carbonitrile |
| 436 | 2-{[4-(difluoromethoxy)phenyl]amino}-6-(4-fluoro-2-methyl-1H-benzimidazol-1-yl)pyridine-4-carbonitrile |
| 437 | 2-(6-fluoro-2-methylimidazo[1,2-a]pyrimidin-3-yl)-6-{[4-(trifluoromethyl)phenyl]amino}pyridine-4-carbonitrile |
| 438 | 2-(6-fluoro-2-methylimidazo[1,2-a]pyrimidin-3-yl)-6-{[4-(trifluoromethoxy)phenyl]amino}pyridine-4-carbonitrile |
| 439 | 2-{[4-(difluoromethoxy)-3-fluorophenyl]amino}-6-(6-fluoro-2-methylimidazo[1,2-a]pyrimidin-3-yl)pyridine-4-carbonitrile |
| 440 | N-[6-(2-methyl-1H-benzimidazol-1-yl)pyrazin-2-yl]-6-(trifluoromethyl)-1,3-benzothiazol-2-amine |
| 441 | 2-(6,8-difluoro-2-methylimidazo[1,2-a]pyridin-3-yl)-6-{[4-(trifluoromethyl)phenyl]amino}pyridine-4-carbonitrile |
| 442 | 2-{[4-(difluoromethoxy)phenyl]amino}-6-(6,8-difluoro-2-methylimidazo[1,2-a]pyridin-3-yl)pyridine-4-carbonitrile |
| 443 | 2-(6,8-difluoro-2-methylimidazo[1,2-a]pyridin-3-yl)-6-{[4-(trifluoromethoxy)phenyl]amino}pyridine-4-carbonitrile |
| 444 | 2-{[4-(difluoromethoxy)-3-fluorophenyl]amino}-6-(6,8-difluoro-2-methylimidazo[1,2-a]pyridin-3-yl)pyridine-4-carbonitrile |
| 445 | 2-[6-fluoro-2-(hydroxymethyl)imidazo[1,2-a]pyridin-3-yl]-6-{[6-(trifluoromethyl)pyridin-3-yl]amino}pyridine-4-carbonitrile |
| 446 | 2-[(6-chloropyridin-3-yl)amino]-6-[6-fluoro-2-(hydroxymethyl)imidazo[1,2-a]pyridin-3-yl]pyridine-4-carbonitrile |
| 447 | 2-(4,6-difluoro-2-methyl-1H-benzimidazol-1-yl)-6-{[4-(trifluoromethyl)phenyl]amino}pyridine-4-carbonitrile |
| 448 | 2-{[4-(difluoromethoxy)phenyl]amino}-6-(4,6-difluoro-2-methyl-1H-benzimidazol-1-yl)pyridine-4-carbonitrile |
| 449 | 2-(4,6-difluoro-2-methyl-1H-benzimidazol-1-yl)-6-{[4-(trifluoromethoxy)phenyl]amino}pyridine-4-carbonitrile |
| 450 | 2-(6-chloro-2-ethyl-1H-imidazo[4,5-b]pyridin-1-yl)-6-{[4-(trifluoromethyl)phenyl]amino}pyridine-4-carbonitrile |
| 451 | 2-(6-chloro-2-ethyl-1H-imidazo[4,5-b]pyridin-1-yl)-6-{[4-(difluoromethoxy)phenyl]amino}pyridine-4-carbonitrile |
| 452 | 2-(6-chloro-2-ethyl-1H-imidazo[4,5-b]pyridin-1-yl)-6-{[4-(difluoromethoxy)-3-fluorophenyl]amino}pyridine-4-carbonitrile |
| 453 | 6-(6-fluoro-2-methylimidazo[1,2-a]pyrimidin-3-yl)-N-[4-(trifluoromethyl)phenyl]pyrazin-2-amine |
| 454 | 6-(2-methyl-4,5,6,7-tetrahydro-2H-indazol-3-yl)-N-[4-(trifluoromethyl)phenyl]pyrazin-2-amine |

-continued

| Cpd | Name |
|---|---|
| 455 | 6-(2-cyclopropyl-6-fluoro-1H-imidazo[4,5-b]pyridin-1-yl)-N-[4-(difluoromethoxy)phenyl]pyrazin-2-amine |
| 456 | 6-(2-cyclopropyl-6-fluoro-1H-imidazo[4,5-b]pyridin-1-yl)-N-[4-(trifluoromethoxy)phenyl]pyrazin-2-amine |
| 457 | 6-(2-methyl-1H-benzimidazol-1-yl)-N-[5-(trifluoromethyl)pyridin-2-yl]pyrazin-2-amine |
| 458 | 6-(2-cyclopropyl-6-fluoro-1H-imidazo[4,5-b]pyridin-1-yl)-N-[6-(trifluoromethyl)pyridin-3-yl]pyrazin-2-amine |
| 459 | 6-(2-cyclopropyl-6-fluoro-1H-imidazo[4,5-b]pyridin-1-yl)-N-[4-(difluoromethoxy)-3-fluorophenyl]pyrazin-2-amine |
| 460 | 6-(2-cyclopropyl-5,6-difluoro-1H-benzimidazol-1-yl)-N-[4-(difluoromethoxy)phenyl]pyrazin-2-amine |
| 461 | 6-(2-cyclopropyl-4,6-difluoro-1H-benzimidazol-1-yl)-N-[4-(trifluoromethyl)phenyl]pyrazin-2-amine |
| 462 | 6-(2-cyclopropyl-4,6-difluoro-1H-benzimidazol-1-yl)-N-[4-(difluoromethoxy)phenyl]pyrazin-2-amine |
| 463 | 6-(2-cyclopropyl-4,6-difluoro-1H-benzimidazol-1-yl)-N-[4-(trifluoromethoxy)phenyl]pyrazin-2-amine |
| 464 | 6-(2-cyclopropyl-4,6-difluoro-1H-benzimidazol-1-yl)-N-[6-(trifluoromethyl)pyridin-3-yl]pyrazin-2-amine |
| 465 | 6-(2-methyl-1H-benzimidazol-1-yl)-N$^2$-[4-(trifluoromethyl)phenyl]pyridine-2,3-diamine |
| 466 | 2-[2-(difluoromethyl)-6-fluoroimidazo[1,2-a]pyridin-3-yl]-6-{[4-(trifluoromethyl)phenyl]amino}pyridine-4-carbonitrile |
| 467 | 2-{[4-(difluoromethoxy)phenyl]amino}-6-[2-(difluoromethyl)-6-fluoroimidazo[1,2-a]pyridin-3-yl]pyridine-4-carbonitrile |
| 468 | 2-{[6-(difluoromethoxy)-5-methylpyridin-3-yl]amino}-6-[2-(difluoromethyl)-6-fluoroimidazo[1,2-a]pyridin-3-yl]pyridine-4-carbonitrile |
| 469 | 2-[2-(difluoromethyl)-6-fluoroimidazo[1,2-a]pyridin-3-yl]-6-{[6-(trifluoromethyl)pyridin-3-yl]amino}pyridine-4-carbonitrile |
| 470 | 2-{[6-(difluoromethoxy)-5-methylpyridin-3-yl]amino}-6-(6-fluoro-2-methylimidazo[1,2-a]pyridin-3-yl)pyridine-4-carbonitrile |
| 471 | 2-{[6-(difluoromethoxy)-5-methylpyridin-3-yl]amino}-6-(6,8-difluoro-2-methylimidazo[1,2-a]pyridin-3-yl)pyridine-4-carbonitrile |
| 472 | 6-[2-(difluoromethyl)-6-fluoroimidazo[1,2-a]pyridin-3-yl]-N-[4-(trifluoromethyl)phenyl]pyrazin-2-amine |
| 473 | N-[4-(difluoromethoxy)phenyl]-6-[2-(difluoromethyl)-6-fluoroimidazo[1,2-a]pyridin-3-yl]pyrazin-2-amine |
| 474 | 2-(2-cyclopropyl-4,6-difluoro-1H-benzimidazol-1-yl)-6-{[4-(trifluoromethyl)phenyl]amino}pyridine-4-carbonitrile |
| 475 | 2-(2-cyclopropyl-4,6-difluoro-1H-benzimidazol-1-yl)-6-{[4-(difluoromethoxy)phenyl]amino}pyridine-4-carbonitrile |
| 476 | 2-(2-cyclopropyl-4,6-difluoro-1H-benzimidazol-1-yl)-6-{[4-(difluoromethoxy)-3-fluorophenyl]amino}pyridine-4-carbonitrile |
| 477 | N-[4-(difluoromethoxy)phenyl]-6-(imidazo[1,2-a]pyridin-3-yl)pyrazin-2-amine |
| 478 | 2-(2-cyclopropyl-4,6-difluoro-1H-benzimidazol-1-yl)-6-{[6-(difluoromethoxy)pyridin-3-yl]amino}pyridine-4-carbonitrile |
| 479 | N-[6-(difluoromethoxy)pyridin-3-yl]-6-[2-(difluoromethyl)-6-fluoroimidazo[1,2-a]pyridin-3-yl]pyrazin-2-amine |
| 480 | N-[6-(difluoromethoxy)pyridin-3-yl]-6-(6-fluoro-2-methylimidazo[1,2-a]pyridin-3-yl)pyrazin-2-amine |
| 481 | 6-[2-(difluoromethyl)-1H-benzimidazol-1-yl]-N-[4-(trifluoromethyl)phenyl]pyrazin-2-amine |
| 482 | N-[4-(difluoromethoxy)phenyl]-6-[2-(difluoromethyl)-1H-benzimidazol-1-yl]pyrazin-2-amine |
| 483 | N-[4-(difluoromethoxy)-3-fluorophenyl]-6-[2-(difluoromethyl)-1H-benzimidazol-1-yl]pyrazin-2-amine |
| 484 | 2-[2-(difluoromethyl)-1H-benzimidazol-1-yl]-6-{[4-(trifluoromethyl)phenyl]amino}pyridine-4-carbonitrile |
| 485 | 6-(2-cyclobutyl-6-fluoro-1H-benzimidazol-1-yl)-N-[4-(trifluoromethyl)phenyl]pyrazin-2-amine |
| 486 | 6-[2-(difluoromethyl)-6-fluoro-1H-benzimidazol-1-yl]-N-[4-(trifluoromethyl)phenyl]pyrazin-2-amine |
| 487 | 2-{[4-(trifluoromethyl)phenyl]amino}-6-(2,6,8-trimethylimidazo[1,2-a]pyrazin-3-yl)pyridine-4-carbonitrile |
| 488 | N-[4-(trifluoromethyl)phenyl]-6-(2,6,8-trimethylimidazo[1,2-a]pyrazin-3-yl)pyrazin-2-amine |
| 489 | N-[4-(difluoromethoxy)phenyl]-6-(2,6,8-trimethylimidazo[1,2-a]pyrazin-3-yl)pyrazin-2-amine |
| 490 | 2-(2-cyclopropyl-6-fluoro-1H-imidazo[4,5-b]pyridin-1-yl)-6-{[4-(trifluoromethyl)phenyl]amino}pyridine-4-carbonitrile |
| 491 | 2-(2-cyclopropyl-6,8-dimethylimidazo[1,2-a]pyrazin-3-yl)-6-{[4-(trifluoromethyl)phenyl]amino}pyridine-4-carbonitrile |
| 492 | 6-(2-methyl-1H-benzimidazol-1-yl)-N$^2$-[4-(trifluoromethyl)phenyl]pyridine-2,4-diamine |
| 493 | 4-fluoro-6-(2-methyl-1H-benzimidazol-1-yl)-N-[2-nitro-4-(trifluoromethyl)phenyl]pyridin-2-amine |
| 494 | 4-fluoro-6-(2-methyl-1H-benzimidazol-1-yl)-N-[4-(trifluoromethyl)phenyl]pyridin-2-amine |

-continued

| Cpd | Name |
|---|---|
| 495 | 6-(5,6-difluoro-2-methyl-1H-benzimidazol-1-yl)-N-[4-(trifluoromethyl)phenyl]pyrazin-2-amine 4-oxide |
| 496 | $N^2$-[4-(difluoromethoxy)phenyl]-6-(2-methyl-1H-benzimidazol-1-yl)pyridine-2,4-diamine |
| 497 | 6-(2-methylpyrazolo[1,5-a]pyridin-3-yl)-N-[4-(trifluoromethyl)phenyl]pyrazin-2-amine |
| 498 | N-[4-(difluoromethoxy)phenyl]-6-(2-methylpyrazolo[1,5-a]pyridin-3-yl)pyrazin-2-amine |
| 499 | N-[4-(difluoromethoxy)phenyl]-4-fluoro-6-(2-methyl-1H-benzimidazol-1-yl)pyridin-2-amine |
| 500 | 6-(2-methylpyrazolo[1,5-a]pyridin-3-yl)-N-[4-(trifluoromethoxy)phenyl]pyrazin-2-amine |
| 501 | 6-(5,6-difluoro-2-methyl-1H-benzimidazol-1-yl)-N-[4-(difluoromethyl)phenyl]pyrazin-2-amine |
| 502 | 4-{[6-(5,6-difluoro-2-methyl-1H-benzimidazol-1-yl)pyrazin-2-yl]amino}benzaldehyde |
| 503 | 6-(2-ethyl-5,6-difluoro-1H-benzimidazol-1-yl)-$N^2$-[4-(trifluoromethyl)phenyl]pyridine-2,4-diamine |
| 504 | 6-(2-cyclopropyl-5,6-difluoro-1H-benzimidazol-1-yl)-$N^2$-[4-(trifluoromethyl)phenyl]pyridine-2,4-diamine |
| 505 | 6-(5,6-difluoro-2-methyl-1H-benzimidazol-1-yl)-3-fluoro-$N^2$-[4-(trifluoromethyl)phenyl]pyridine-2,4-diamine |
| 506 | $N^1$-[6-(2-methyl-1H-benzimidazol-1-yl)pyrazin-2-yl]-4-(trifluoromethyl)benzene-1,3-diamine |
| 507 | N-[4-(difluoromethyl)phenyl]-6-(2-methyl-1H-benzimidazol-1-yl)pyrazin-2-amine |
| 508 | N-[4-(difluoromethyl)-3-fluorophenyl]-6-(2-methyl-1H-benzimidazol-1-yl)pyrazin-2-amine |
| 509 | 6-(2-ethyl-5,6-difluoro-1H-benzimidazol-1-yl)-3-fluoro-$N^2$-[4-(trifluoromethyl)phenyl]pyridine-2,4-diamine |
| 510 | 6-(2-ethyl-1H-benzimidazol-1-yl)-$N^2$-[4-(trifluoromethyl)phenyl]pyridine-2,4-diamine |
| 511 | 2-(2-methylpyrazolo[1,5-a]pyridin-3-yl)-6-{[4-(trifluoromethyl)phenyl]amino}pyridine-4-carbonitrile |
| 512 | 2-{[4-(difluoromethoxy)phenyl]amino}-6-(2-methylpyrazolo[1,5-a]pyridin-3-yl)pyridine-4-carbonitrile |
| 513 | 2-{[4-(difluoromethoxy)-3-fluorophenyl]amino}-6-(2-methylpyrazolo[1,5-a]pyridin-3-yl)pyridine-4-carbonitrile |
| 514 | 2-(2-methylpyrazolo[1,5-a]pyridin-3-yl)-6-{[4-(trifluoromethoxy)phenyl]amino}pyridine-4-carbonitrile |
| 515 | 3-fluoro-6-(2-methyl-1H-benzimidazol-1-yl)-$N^2$-[4-(trifluoromethyl)phenyl]pyridine-2,4-diamine |
| 516 | N-[4-(difluoromethoxy)phenyl]-6-(5,6-difluoro-2-methyl-1H-benzimidazol-1-yl)pyrazin-2-amine 4-oxide |
| 517 | 5-{[6-(2-methyl-1H-benzimidazol-1-yl)pyrazin-2-yl]amino}-2-(trifluoromethyl)benzonitrile |
| 518 | $N^2$-(4-methoxyphenyl)-6-(2-methyl-1H-benzimidazol-1-yl)pyridine-2,3-diamine |
| 519 | [5-{[6-(2-methyl-1H-benzimidazol-1-yl)pyrazin-2-yl]amino}-2-(trifluoromethyl)phenyl]methanol |
| 520 | 6-(2-ethylpyrazolo[1,5-a]pyridin-3-yl)-N-[4-(trifluoromethyl)phenyl]pyrazin-2-amine |
| 521 | N-[4-(difluoromethoxy)phenyl]-6-(2-ethylpyrazolo[1,5-a]pyridin-3-yl)pyrazin-2-amine |
| 522 | N-[4-(difluoromethoxy)-3-fluorophenyl]-6-(2-ethylpyrazolo[1,5-a]pyridin-3-yl)pyrazin-2-amine |
| 523 | 6-(2-ethylpyrazolo[1,5-a]pyridin-3-yl)-N-[4-(trifluoromethoxy)phenyl]pyrazin-2-amine |
| 524 | N-[3-(aminomethyl)-4-(trifluoromethyl)phenyl]-6-(2-methyl-1H-benzimidazol-1-yl)pyrazin-2-amine |
| 525 | 6-(2-methyl-1H-benzimidazol-1-yl)-N-[4-(trifluoromethyl)phenyl]pyrazin-2-amine 4-oxide |
| 526 | 2-(2-ethylpyrazolo[1,5-a]pyridin-3-yl)-6-{[4-(trifluoromethyl)phenyl]amino}pyridine-4-carbonitrile |
| 527 | 2-{[4-(difluoromethoxy)phenyl]amino}-6-(2-ethylpyrazolo[1,5-a]pyridin-3-yl)pyridine-4-carbonitrile |
| 528 | 2-{[4-(difluoromethoxy)-3-fluorophenyl]amino}-6-(2-ethylpyrazolo[1,5-a]pyridin-3-yl)pyridine-4-carbonitrile |
| 529 | 2-(2-ethylpyrazolo[1,5-a]pyridin-3-yl)-6-{[4-(trifluoromethoxy)phenyl]amino}pyridine-4-carbonitrile |
| 530 | 6-(2-cyclopropyl-5,6-difluoro-1H-benzimidazol-1-yl)-N-[4-(difluoromethoxy)phenyl]pyrazin-2-amine 4-oxide |
| 531 | N-[4-(difluoromethoxy)phenyl]-6-(2-methyl-1H-benzimidazol-1-yl)pyrazin-2-amine 4-oxide |
| 532 | 6-(6-fluoro-2-methyl-1H-benzimidazol-1-yl)-N-[4-(trifluoromethyl)phenyl]pyrazin-2-amine 4-oxide |
| 533 | 6-(2-cyclopropyl-6-fluoro-1H-imidazo[4,5-b]pyridin-1-yl)-N-[4-(trifluoromethyl)phenyl]pyrazin-2-amine 4-oxide |
| 534 | 6-[2-(trifluoromethyl)imidazo[1,2-a]pyridin-3-yl]-N-[4-(trifluoromethyl)phenyl]pyrazin-2-amine 4-oxide |
| 535 | 6-(2-cyclopropyl-5-fluoropyrazolo[1,5-a]pyridin-3-yl)-N-[4-(trifluoromethyl)phenyl]pyrazin-2-amine |
| 536 | 6-(2-cyclopropyl-5-fluoropyrazolo[1,5-a]pyridin-3-yl)-N-[4-(trifluoromethyl)phenyl]pyrazin-2-amine 4-oxide |
| 537 | 6-(5-fluoro-2-methylpyrazolo[1,5-a]pyridin-3-yl)-N-[4-(trifluoromethyl)phenyl]pyrazin-2-amine |
| 538 | 6-[6-fluoro-2-(trifluoromethyl)imidazo[1,2-a]pyridin-3-yl]-N-[4-(trifluoromethyl)phenyl]pyrazin-2-amine 4-oxide |

-continued

| Cpd | Name |
|---|---|
| 539 | 6-(5-chloro-2-ethylpyrazolo[1,5-a]pyridin-3-yl)-N-[4-(trifluoromethyl)phenyl]pyrazin-2-amine |
| 540 | 6-(6-chloro-2-methyl-1H-imidazo[4,5-b]pyridin-1-yl)-N-[4-(difluoromethoxy)phenyl]pyrazin-2-amine |
| 541 | 6-(6-chloro-2-methyl-1H-imidazo[4,5-b]pyridin-1-yl)-N-[4-(difluoromethoxy)-3-fluorophenyl]pyrazin-2-amine |
| 542 | 6-(6-chloro-2-methyl-1H-imidazo[4,5-b]pyridin-1-yl)-N-[4-(trifluoromethoxy)phenyl]pyrazin-2-amine |
| 543 | 6-(6-chloro-2-methyl-1H-imidazo[4,5-b]pyridin-1-yl)-N-phenylpyrazin-2-amine |
| 544 | 6-(6-chloro-2-ethyl-1H-imidazo[4,5-b]pyridin-1-yl)-N-[4-(difluoromethoxy)phenyl]pyrazin-2-amine |
| 545 | N-[4-(difluoromethoxy)phenyl]-1-(6-{[4-(difluoromethoxy)phenyl]amino}pyrazin-2-yl)-2-ethyl-1H-imidazo[4,5-b]pyridin-6-amine |
| 546 | 6-(6-chloro-2-ethyl-1H-imidazo[4,5-b]pyridin-1-yl)-N-[4-(difluoromethoxy)-3-fluorophenyl]pyrazin-2-amine |
| 547 | N-[4-(difluoromethoxy)phenyl]-1-(6-{[4-(difluoromethoxy)phenyl]amino}pyrazin-2-yl)-2-methyl-1H-imidazo[4,5-b]pyridin-6-amine |
| 548 | 6-(6-chloro-2-ethyl-1H-imidazo[4,5-b]pyridin-1-yl)-N-[4-(trifluoromethoxy)phenyl]pyrazin-2-amine |
| 549 | 6-(6-chloro-2-ethyl-1H-imidazo[4,5-b]pyridin-1-yl)-N-phenylpyrazin-2-amine |
| 550 | N-[4-(difluoromethoxy)-3-fluorophenyl]-1-(6-{[4-(difluoromethoxy)-3-fluorophenyl]amino}pyrazin-2-yl)-2-ethyl-1H-imidazo[4,5-b]pyridin-6-amine |
| 551 | 6-(2-ethyl-5-fluoropyrazolo[1,5-a]pyridin-3-yl)-N-[4-(trifluoromethyl)phenyl]pyrazin-2-amine |
| 552 | 6-(6-fluoro-2-methyl-1H-benzimidazol-1-yl)-N-(4-methoxyphenyl)pyrazin-2-amine |
| 553 | 6-(6-fluoro-2-methyl-1H-benzimidazol-1-yl)-N-(4-methylphenyl)pyrazin-2-amine |
| 554 | N-(4-chlorophenyl)-6-(6-fluoro-2-methyl-1H-benzimidazol-1-yl)pyrazin-2-amine |
| 555 | 4-{[6-(6-fluoro-2-methyl-1H-benzimidazol-1-yl)pyrazin-2-yl]amino}benzonitrile |
| 556 | methyl 4-{[6-(6-fluoro-2-methyl-1H-benzimidazol-1-yl)pyrazin-2-yl]amino}benzoate |
| 557 | N-(3-methoxyphenyl)-6-(2-methyl-1H-benzimidazol-1-yl)pyrazin-2-amine |
| 558 | N-[6-(6-fluoro-2-methyl-1H-benzimidazol-1-yl)pyrazin-2-yl]benzene-1,4-diamine |
| 559 | 6-(6-fluoro-2-methyl-1H-benzimidazol-1-yl)-N-(3-methoxyphenyl)pyrazin-2-amine |
| 560 | 6-(6-fluoro-2-methyl-1H-benzimidazol-1-yl)-N-(3-methylphenyl)pyrazin-2-amine |
| 561 | N-(4-methoxyphenyl)-6-(2-methyl-1H-benzimidazol-1-yl)pyrazin-2-amine |
| 562 | 6-(2-methyl-1H-benzimidazol-1-yl)-N-(4-methylphenyl)pyrazin-2-amine |
| 563 | 4-methyl-N$^1$-[6-(2-methyl-1H-benzimidazol-1-yl)pyrazin-2-yl]benzene-1,2-diamine |
| 564 | 6-(2-methylpyrazolo[1,5-a]pyridin-3-yl)-N-phenylpyrazin-2-amine |
| 565 | N-(4-methoxyphenyl)-6-(2-methylpyrazolo[1,5-a]pyridin-3-yl)pyrazin-2-amine |
| 566 | N-(4-methylphenyl)-6-(2-methylpyrazolo[1,5-a]pyridin-3-yl)pyrazin-2-amine |
| 567 | N-(4-chlorophenyl)-6-(2-methylpyrazolo[1,5-a]pyridin-3-yl)pyrazin-2-amine |
| 568 | N-(4-fluorophenyl)-6-(2-methylpyrazolo[1,5-a]pyridin-3-yl)pyrazin-2-amine |
| 569 | N-(3-methoxyphenyl)-6-(2-methylpyrazolo[1,5-a]pyridin-3-yl)pyrazin-2-amine |
| 570 | N-(3-chlorophenyl)-6-(2-methylpyrazolo[1,5-a]pyridin-3-yl)pyrazin-2-amine |
| 571 | 4-{[6-(2-methylpyrazolo[1,5-a]pyridin-3-yl)pyrazin-2-yl]amino}benzonitrile |
| 572 | methyl 4-{[6-(2-methylpyrazolo[1,5-a]pyridin-3-yl)pyrazin-2-yl]amino}benzoate |
| 573 | 6-(5,6-difluoro-2-methyl-1H-benzimidazol-1-yl)-N-(4-methoxyphenyl)pyrazin-2-amine |
| 574 | 6-(5,6-difluoro-2-methyl-1H-benzimidazol-1-yl)-N-(4-methylphenyl)pyrazin-2-amine |
| 575 | N-(4-chlorophenyl)-6-(5,6-difluoro-2-methyl-1H-benzimidazol-1-yl)pyrazin-2-amine |
| 576 | N-(2-methoxy-4-methylphenyl)-6-(2-methyl-1H-benzimidazol-1-yl)pyrazin-2-amine |
| 577 | 4-(2,5-dimethyl-1H-pyrrol-1-yl)-N-(4-methoxyphenyl)-6-(2-methyl-1H-benzimidazol-1-yl)pyridin-2-amine |
| 578 | 6-(5,6-difluoro-2-methyl-1H-benzimidazol-1-yl)-N-(3-methoxyphenyl)pyrazin-2-amine |
| 579 | N-(2,2-difluoro-1,3-benzodioxol-5-yl)-6-(5,6-difluoro-2-methyl-1H-benzimidazol-1-yl)pyrazin-2-amine |
| 580 | N$^2$-(4-methoxyphenyl)-6-(2-methyl-1H-benzimidazol-1-yl)pyridine-2,4-diamine |
| 581 | 6-(2-methyl-1H-benzimidazol-1-yl)-N-(4-methylphenyl)pyridin-2-amine |
| 582 | 5-methyl-2-{[6-(2-methyl-1H-benzimidazol-1-yl)pyrazin-2-yl]amino}phenol |
| 583 | 2-(5,6-difluoro-2-methyl-1H-benzimidazol-1-yl)-6-[(4-methoxyphenyl)amino]pyridine-4-carbonitrile |
| 584 | N-[-(4-difluoromethoxy)phenyl]-6-(6-fluoro-2-methyl-1H-benzimidazol-1-yl)pyridin-2-amine |
| 585 | 6-(6-fluoro-2-methyl-1H-benzimidazol-1-yl)-N-[4-(trifluoromethoxy)phenyl]pyridin-2-amine |
| 586 | 6-(6-fluoro-2-methyl-1H-benzimidazol-1-yl)-N-(4-methoxyphenyl)pyridin-2-amine |
| 587 | 6-(6-fluoro-2-methyl-1H-benzimidazol-1-yl)-N-(4-methylphenyl)pyridin-2-amine |
| 588 | 2-(6-fluoro-2-methyl-1H-benzimidazol-1-yl)-6-{[4-(trifluoromethoxy)phenyl]amino}pyridine-4-carbonitrile |
| 589 | 2-(6-fluoro-2-methyl-1H-benzimidazol-1-yl)-6-[(4-methoxyphenyl)amino]pyridine-4-carbonitrile |
| 590 | 6-(6-fluoro-2-methylimidazo[1,2-a]pyridin-3-yl)-N-phenylpyrazin-2-amine |
| 591 | 6-(6-fluoro-2-methylimidazo[1,2-a]pyridin-3-yl)-N-(4-fluorophenyl)pyrazin-2-amine |
| 592 | 6-(6-fluoro-2-methylimidazo[1,2-a]pyridin-3-yl)-N-(4-methoxyphenyl)pyrazin-2-amine |
| 593 | N-(4-chlorophenyl)-6-(6-fluoro-2-methylimidazo[1,2-a]pyridin-3-yl)pyrazin-2-amine |
| 594 | 6-(6-fluoro-2-methylimidazo[1,2-a]pyridin-3-yl)-N-[3-(trifluoromethyl)phenyl]pyrazin-2-amine |
| 595 | 6-(6-fluoro-2-methylimidazo[1,2-a]pyridin-3-yl)-N-(3-fluorophenyl)pyrazin-2-amine |
| 596 | 6-(6-fluoro-2-methylimidazo[1,2-a]pyridin-3-yl)-N-(3-methoxyphenyl)pyrazin-2-amine |

-continued

| Cpd | Name |
|---|---|
| 597 | N-(3-chlorophenyl)-6-(6-fluoro-2-methylimidazo[1,2-a]pyridin-3-yl)pyrazin-2-amine |
| 598 | 6-(6-fluoro-2-methylimidazo[1,2-a]pyridin-3-yl)-N-(2-fluorophenyl)pyrazin-2-amine |
| 599 | 2-(5,6-difluoro-2-methyl-1H-benzimidazol-1-yl)-6-[(4-methylphenyl)amino]pyridine-4-carbonitrile |
| 600 | 2-[(4-chlorophenyl)amino]-6-(5,6-difluoro-2-methyl-1H-benzimidazol-1-yl)pyridine-4-carbonitrile |
| 601 | 6-(5,6-difluoro-2-methyl-1H-benzimidazol-1-yl)-N-[4-(trifluoromethyl)phenyl]pyridin-2-amine |
| 602 | N-[4-(difluoromethoxy)phenyl]-6-(5,6-difluoro-2-methyl-1H-benzimidazol-1-yl)pyridin-2-amine |
| 603 | 6-(5,6-difluoro-2-methyl-1H-benzimidazol-1-yl)-N-[4-(trifluoromethoxy)phenyl]pyridin-2-amine |
| 604 | 6-(2-methyl-1H-benzimidazol-1-yl)-$N^2$-[4-(trifluoromethoxy)phenyl]pyridine-2,4-diamine |
| 605 | $N^2$-(4-fluorophenyl)-6-(2-methyl-1H-benzimidazol-1-yl)pyridine-2,4-diamine |
| 606 | N(4-chlorophenyl)-6(2-methyl-1H-benzimidazol-1-yl)pyridin-2-amine |
| 607 | 6-(6-fluoro-2-methyl-1H-benzimidazol-1-yl)-N-[4-(trifluoromethyl)phenyl]pyridin-2-amine |
| 608 | N-(4-chlorophenyl)-6-(6-fluoro-2-methyl-1H-benzimidazol-1-yl)pyridin-2-amine |
| 609 | 4-{[6-(6-fluoro-2-methyl-1H-benzimidazol-1-yl)pyridin-2-yl]amino}benzonitrile |
| 610 | methyl 4-{[6-(6-fluoro-2-methyl-1H-benzimidazol-1-yl)pyridin-2-yl]amino}benzoate |
| 611 | 2-(6-fluoro-2-methyl-1H-benzimidazol-1-yl)-6-[(4-methylphenyl)amino]pyridine-4-carbonitrile |
| 612 | 2-[(4-chlorophenyl)amino]-6-(6-fluoro-2-methyl-1H-benzimidazol-1-yl)pyridine-4-carbonitrile |
| 613 | 6-(5,6-difluoro-2-methyl-1H-benzimidazol-1-yl)-N-(4-methoxyphenyl)pyridin-2-amine |
| 614 | 6-(5,6-difluoro-2-methyl-1H-benzimidazol-1-yl)-N-(4-methylphenyl)pyridin-2-amine |
| 615 | N-(4-chlorophenyl)-6-(5,6-difluoro-2-methyl-1H-benzimidazol-1-yl)pyridin-2-amine |
| 616 | N-(4-bromophenyl)-6-(2-methyl-1H-benzimidazol-1-yl)pyrazin-2-amine |
| 617 | 4-(2,5-dimethyl-1H-pyrrol-1-yl)-6-(2-methyl-1H-benzimidazol-1-yl)-N-(4-methylphenyl)pyridin-2-amine |
| 618 | N-(4-chlorophenyl)-4-(2,5-dimethyl-1H-pyrrol-1-yl)-6-(2-methyl-1H-benzimidazol-1-yl)pyridin-2-amine |
| 619 | N-(4-iodophenyl)-6-(2-methyl-1H-benzimidazol-1-yl)pyrazin-2-amine |
| 620 | 6-(2-ethyl-6-fluoro-1H-benzimidazol-1-yl)-N-phenylpyrazin-2-amine |
| 621 | 6-(2-ethyl-6-fluoro-1H-benzimidazol-1-yl)-N-(4-methoxyphenyl)pyrazin-2-amine |
| 622 | 6-(2-ethyl-6-fluoro-1H-benzimidazol-1-yl)-N-(4-methylphenyl)pyrazin-2-amine |
| 623 | N-(4-chlorophenyl)-6-(2-ethyl-6-fluoro-1H-benzimidazol-1-yl)pyrazin-2-amine |
| 624 | 6-(2-ethyl-6-fluoro-1H-benzimidazol-1-yl)-N-(3-methoxyphenyl)pyrazin-2-amine |
| 625 | N-(3-chlorophenyl)-6-(2-ethyl-6-fluoro-1H-benzimidazol-1-yl)pyrazin-2-amine |
| 626 | 6-(2-ethyl-6-fluoro-1H-benzimidazol-1-yl)-N-(3-fluorophenyl)pyrazin-2-amine |
| 627 | 6-(2-ethylpyrazolo[1,5-a]pyridin-3-yl)-N-(4-methoxyphenyl)pyrazin-2-amine |
| 628 | 6-(2-ethylpyrazolo[1,5-a]pyridin-3-yl)-N-(4-methylphenyl)pyrazin-2-amine |
| 629 | N-(4-chlorophenyl)-6-(2-ethylpyrazolo[1,5-a]pyridin-3-yl)pyrazin-2-amine |
| 630 | 6-(2-ethylpyrazolo[1,5-a]pyridin-3-yl)-N-(4-fluorophenyl)pyrazin-2-amine |
| 631 | 6-(2-ethylpyrazolo[1,5-a]pyridin-3-yl)-N-phenylpyrazin-2-amine |
| 632 | 6-(2-methyl-1H-benzimidazol-1-yl)-$N^2$-(4-methylphenyl)pyridine-2,4-diamine |
| 633 | $N^2$-(4-chlorophenyl)-6-(2-methyl-1H-benzimidazol-1-yl)pyridine-2,4-diamine |
| 634 | 2-(2-methyl-1H-benzimidazol-1-yl)-6-[(4-methylphenyl)amino]pyridine-4-carbonitrile |
| 635 | 6-(3,5-dimethyl-1,2-oxazol-4-yl)-N-(4-methylphenyl)pyrazin-2-amine |
| 636 | 6-(3,5-dimethyl-1,2-oxazol-4-yl)-N-(4-methoxyphenyl)pyrazin-2-amine |
| 637 | 6-(3,5-dimethyl-1,2-oxazol-4-yl)-N-(3-fluoro-4-methoxyphenyl)pyrazin-2-amine |
| 638 | 6-(3,5-dimethyl-1,2-oxazol-4-yl)-N-(6-methoxypyridin-3-yl)pyrazin-2-amine |
| 639 | N-(1,3-benzodioxol-5-yl)-6-(3,5-dimethyl-1,2-oxazol-4-yl)pyrazin-2-amine |
| 640 | 6-(2-ethylpyrazolo[1,5-a]pyridin-3-yl)-N-(3-methoxyphenyl)pyrazin-2-amine |
| 641 | 4-{[6-(2-ethylpyrazolo[1,5-a]pyridin-3-yl)pyrazin-2-yl]amino}benzonitrile |
| 642 | methyl 4-{[6-(2-ethylpyrazolo[1,5-a]pyridin-3-yl)pyrazin-2-yl]amino}benzoate |
| 643 | N-(3-chlorophenyl)-6-(2-ethylpyrazolo[1,5-a]pyridin-3-yl)pyrazin-2-amine |
| 644 | N-[2-fluoro-4-(trifluoromethyl)phenyl]-6-(2-methyl-1H-benzimidazol-1-yl)pyrazin-2-amine |
| 645 | N-[3,5-difluoro-4-(trifluoromethyl)phenyl]-6-(2-methyl-1H-benzimidazol-1-yl)pyrazin-2-amine |
| 646 | 2-(6-fluoro-2-methylimidazo[1,2-a]pyridin-3-yl)-6-(phenylamino)pyridine-4-carbonitrile |
| 647 | 2-[(4-chlorophenyl)amino]-6-(6-fluoro-2-methylimidazo[1,2-a]pyridin-3-yl)pyridine-4-carbonitrile |
| 648 | 2-(6-fluoro-2-methylimidazo[1,2-a]pyridin-3-yl)-6-[(4-methylphenyl)amino]pyridine-4-carbonitrile |
| 649 | 2-(6-fluoro-2-methylimidazo[1,2-a]pyridin-3-yl)-6-[(4-methoxyphenyl)amino]pyridine-4-carbonitrile |
| 650 | 2-(6-fluoro-2-methylimidazo[1,2-a]pyridin-3-yl)-6-[(3-methoxyphenyl)amino]pyridine-4-carbonitrile |
| 651 | 2-(6-fluoro-2-methylimidazo[1,2-a]pyridin-3-yl)-6-[(3-fluorophenyl)amino]pyridine-4-carbonitrile |
| 652 | $N^2$-[4-(difluoromethoxy)phenyl]-6-(5,6-difluoro-2-methyl-1H-benzimidazol-1-yl)pyridine-2,4-diamine |
| 653 | 6-(5,6-difluoro-2-methyl-1H-benzimidazol-1-yl)-$N^2$-[4-(trifluoromethoxy)phenyl]pyridine-2,4-diamine |

-continued

| Cpd | Name |
|---|---|
| 654 | N-(4-chloro-3-fluorophenyl)-6-(6-fluoro-2-methyl-1H-benzimidazol-1-yl)pyrazin-2-amine |
| 655 | N-(4-methoxyphenyl)-4-methyl-6-(2-methyl-1H-benzimidazol-1-yl)pyridin-2-amine |
| 656 | 6-(5,6-difluoro-2-methyl-1H-benzimidazol-1-yl)-$N^2$-(4-methoxyphenyl)pyridine-2,4-diamine |
| 657 | 6-(5,6-difluoro-2-methyl-1H-benzimidazol-1-yl)-$N^2$-(4-methylphenyl)pyridine-2,4-diamine |
| 658 | $N^2$-(4-chlorophenyl)-6-(5,6-difluoro-2-methyl-1H-benzimidazol-1-yl)pyridine-2,4-diamine |
| 659 | N-(4-tert-butylphenyl)-6-(2-methyl-1H-benzimidazol-1-yl)pyrazin-2-amine |
| 660 | 6-(2-methyl-1H-benzimidazol-1-yl)-N-[4-(propan-2-yloxy)phenyl]pyrazin-2-amine |
| 661 | 6-(2-methyl-1H-benzimidazol-1-yl)-N-[4-(propan-2-yl)phenyl]pyrazin-2-amine |
| 662 | N-(4-ethylphenyl)-6-(2-methyl-1H-benzimidazol-1-yl)pyrazin-2-amine |
| 663 | 6-(2-methyl-1H-benzimidazol-1-yl)-N-(4-propylphenyl)pyrazin-2-amine |
| 664 | N-(4-ethoxyphenyl)-6-(2-methyl-1H-benzimidazol-1-yl)pyrazin-2-amine |
| 665 | N-(4-ethynylphenyl)-6-(2-methyl-1H-benzimidazol-1-yl)pyrazin-2-amine |
| 666 | N-(4-ethenylphenyl)-6-(2-methyl-1H-benzimidazol-1-yl)pyrazin-2-amine |
| 667 | 6-[6-fluoro-2-(trifluoromethyl)imidazo[1,2-a]pyridin-3-yl]-N-phenylpyrazin-2-amine |
| 668 | 4-({6-[6-fluoro-2-(trifluoromethyl)imidazo[1,2-a]pyridin-3-yl]pyrazin-2-yl}amino)benzonitrile |
| 669 | N-(4-fluorophenyl)-6-[6-fluoro-2-(trifluoromethyl)imidazo[1,2-a]pyridin-3-yl]pyrazin-2-amine |
| 670 | N-(4-chlorophenyl)-6-[6-fluoro-2-(trifluoromethyl)imidazo[1,2-a]pyridin-3-yl]pyrazin-2-amine |
| 671 | 6-[6-fluoro-2-(trifluoromethyl)imidazo[1,2-a]pyridin-3-yl]-N-(4-methylphenyl)pyrazin-2-amine |
| 672 | 2-(6-methoxy-2-methylimidazo[1,2-a]pyridin-3-yl)-6-[(4-methoxyphenyl)amino]pyridine-4-carbonitrile |
| 673 | 2-(6-methoxy-2-methylimidazo[1,2-a]pyridin-3-yl)-6-[(4-methylphenyl)amino]pyridine-4-carbonitrile |
| 674 | 2-[(4-fluorophenyl)amino]-6-(6-methoxy-2-methylimidazo[1,2-a]pyridin-3-yl)pyridine-4-carbonitrile |
| 675 | 2-(6-methoxy-2-methylimidazo[1,2-a]pyridin-3-yl)-6-(phenylamino)pyridine-4-carbonitrile |
| 676 | 2-[(4-chlorophenyl)amino]-6-(6-methoxy-2-methylimidazo[1,2-a]pyridin-3-yl)pyridine-4-carbonitrile |
| 677 | 2-{[4-(difluoromethoxy)phenyl]amino}-6-(6-methoxy-2-methylimidazo[1,2-a]pyridin-3-yl)pyridine-4-carbonitrile |
| 678 | 6-[6-methoxy-2-(trifluoromethyl)imidazo[1,2-a]pyridin-3-yl]-N-phenylpyrazin-2-amine |
| 679 | N-(4-chlorophenyl)-6-[6-methoxy-2-(trifluoromethyl)imidazo[1,2-a]pyridin-3-yl]pyrazin-2-amine |
| 680 | N-(4-bromophenyl)-6-[6-methoxy-2-(trifluoromethyl)imidazo[1,2-a]pyridin-3-yl]pyrazin-2-amine |
| 681 | N-(4-fluorophenyl)-6-[6-methoxy-2-(trifluoromethyl)imidazo[1,2-a]pyridin-3-yl]pyrazin-2-amine |
| 682 | 6-[6-methoxy-2-(trifluoromethyl)imidazo[1,2-a]pyridin-3-yl]-N-(4-methylphenyl)pyrazin-2-amine; and, |
| 683 | 6-(5,6-difluoro-2-methyl-1H-benzimidazol-1-yl)-N-[4-(trifluoromethyl)phenyl]pyrazin-2-amine, | wherein the form of the compound is selected from a salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof selected from the group consisting of:

| Cpd | Name |
|---|---|
| 154a | N-[4-(aminomethyl)phenyl]-6-(2-methyl-1H-benzimidazol-1-yl)pyrazin-2-amine trifluoroacetate; and, |
| 289a | [3-(4-amino-6-{[4-(trifluoromethyl)phenyl]amino}pyridin-2-yl)imidazo[1,2-a]pyridin-2-yl]methanol hydrochloride (1:2), | wherein the form of the compound is selected from a free acid, free base, ester, hydrate, solvate, chelate, clathrate, polymorph, isotopologue, stereoisomer, racemate, enantiomer, diastereomer or tautomer thereof.

TERMINOLOGY

The chemical terms used above and throughout the description herein, unless specifically defined otherwise, shall be understood by one of ordinary skill in the art to have the following indicated meanings.

As used herein, the term "$C_{1-8}$alkyl" refers to saturated hydrocarbon radicals having from one to eight carbon atoms in a straight or branched chain configuration, including, without limitation, methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-6}$alkyl, $C_{1-4}$alkyl and the like. A $C_{1-8}$alkyl radical may be optionally substituted where allowed by available valences.

As used herein, the term "$C_{2-8}$alkenyl" refers to partially unsaturated hydrocarbon radicals having from two to eight carbon atoms in a straight or branched chain configuration and one or more carbon-carbon double bonds therein, including, without limitation, ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{2-8}$alkynyl" refers to partially unsaturated hydrocarbon radicals having from two to eight carbon atoms in a straight or branched chain configuration and one or more carbon-carbon triple bonds therein, including, without limitation, ethynyl, propynyl and the like. In some embodiments, $C_{2-8}$alkynyl includes $C_{2-6}$alkynyl, $C_{2-4}$alkynyl and the like. A $C_{2-8}$alkynyl radical may be optionally substituted where allowed by available valences.

As used herein, the term "$C_{1-8}$alkoxy" refers to saturated hydrocarbon radicals of from one to eight carbon atoms having a straight or branched chain configuration of the formula: —O—$C_{1-8}$alkyl, including, without limitation, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" refers to a saturated monocyclic, bicyclic or polycyclic hydrocarbon radical, including, without limitation, cyclopropyl, cyclobutyl, cyclopentyl, cyclohexyl, cycloheptyl, cyclooctyl, 1H-indanyl, indenyl, 2,3-dihydro-1H-indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "aryl" refers to a monocyclic, bicyclic or polycyclic aromatic carbon atom ring structure radical, including, without limitation, phenyl, naphthyl (also referred to as naphthalenyl), anthracenyl, fluorenyl, azulenyl, phenanthrenyl and the like. An aryl radical may be optionally substituted where allowed by available valences.

As used herein, the term "heteroaryl" refers to a monocyclic, bicyclic or polycyclic aromatic carbon atom ring structure radical in which one or more carbon atom ring members have been replaced, where allowed by structural stability, with one or more heteroatoms, such as an O, S or N atom, including, without limitation, furanyl, thienyl (also referred to as thiophenyl), pyrrolyl, pyrazolyl (also referred to as 1H-pyrazolyl), imidazolyl (also referred to as 1H-imidazolyl), isoxazolyl (also referred to as 1,2-oxazolyl), isothiazolyl, oxazolyl, thiazolyl, triazolyl, oxadiazolyl, thiadiazolyl, tetrazolyl, pyranyl, thiopyranyl, pyridinyl (also referred to as pyridyl), pyrimidinyl, pyrazinyl, pyridazinyl, triazinyl, indolyl (also referred to as 1H-indolyl), azaindolyl, indazolyl (also referred to as 2H-indazolyl), azaindazolyl, isoindolyl, indolizinyl, benzofuranyl, benzothienyl, benzimidazolyl (also referred to as 1H-benzimidazolyl), benzothiazolyl, benzoxazolyl, imidazo[2,1-b][1,3]thiazolyl, pyrazolo[1,5-a]pyridinyl, pyrazolo[1,5-c]pyrimidinyl, imidazo[1,2-a]pyridinyl, 1H-imidazo[4,5-b]pyridinyl, 1H-imidazo[4,5-c]pyridinyl, imidazo[1,2-a]pyrazinyl, imidazo[1,2-a]pyrimidinyl, 7H-purinyl, 9H-purinyl, quinolinyl, isoquinolinyl, quinazolinyl, quinoxalinyl, acridinyl and the like and associated homologs and regioisomers thereof. A heteroaryl radical may be optionally substituted on a carbon or nitrogen atom ring member where allowed by available valences.

As used herein, the term "heterocyclyl" refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, without limitation, oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, 1,3-dioxolanyl, dihydro-2H-pyranyl, tetrahydro-2H-pyranyl, dihydro-pyridinyl, tetrahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, 1,4-diazepanyl, dihydro-indolyl, indolinyl, tetrahydro-indolyl, dihydro-indazolyl, tetrahydro-indazolyl, dihydro-isoindolyl, dihydro-benzofuranyl, tetrahydro-benzofuranyl, dihydro-benzothienyl, tetrahydro-benzothienyl, dihydro-benzoimidazolyl, tetrahydro-benzoimidazolyl, dihydro-benzooxazolyl, tetrahydro-benzooxazolyl, dihydro-benzooxazinyl, tetrahydro-benzooxazinyl, benzo[1,3]dioxolyl (also referred to as 1,3-benzodioxolyl), benzo[1,4]dioxanyl (also referred to as 1,4-benzodioxanyl or 2,3-dihydro-1,4-benzodioxinyl), benzo[1,4]dioxinyl (also referred to as 1,4-benzodioxinyl), 4,5,6,7-tetrahydro-2H-indazolyl, 5,6,7,8-tetrahydroimidazo[1,2-a]pyridinyl, 4,5,6,7-tetrahydro-3H-imidazo[4,5-c]pyridinyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like and associated homologs thereof. A heterocyclyl radical may be optionally substituted on a carbon or nitrogen atom ring member where allowed by available valences.

As used herein, the term "$B(OR_{10})_2$" refers to a radical of the formula: —B[(—OH)(—OH)] when $R_{10}$ is hydrogen; or, —B[(—OH)(—O—$C_{1-8}$alkyl)] when $R_{10}$ is independently hydrogen or $C_{1-8}$alkyl; or, —B[(—O—$C_{1-8}$alkyl)(—O—$C_{1-8}$ alkyl)] when $R_{10}$ is $C_{1-8}$alkyl; or, a heterocyclyl ring system when $C_{1-8}$alkyl optionally forms a heterocyclyl ring with the oxygen atoms of attachment.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$alkyl.

As used herein, the term "$C_{1-8}$alkoxy-$C_{2-8}$alkenyl" refers to a radical of the formula: —$C_{2-8}$alkenyl-O—$C_{1-8}$alkyl.

As used herein, the term "$C_{1-8}$alkoxy-$C_{2-8}$alkynyl" refers to a radical of the formula: —$C_{2-8}$alkynyl-O—$C_{1-8}$alkyl.

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{1-8}$alkyl" refers to a radical of the formula: —$C_{1-8}$alkyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkoxy-carbonyl-amino-$C_{1-8}$ alkyl" refers to a radical of the formula: —$C_{1-8}$alkyl-NH—C(O)—O—$C_{1-8}$alkyl.

As used herein, the term "$C_{1-8}$alkoxy-imino-$C_{1-8}$alkyl" refers to a radical of the formula: —$C_{1-8}$alkyl(=N—O—$C_{1-8}$alkyl).

As used herein, the term "$C_{1-8}$alkyl-amino" refers to a radical of the formula: —NH—$C_{1-8}$alkyl.

As used herein, the term "$(C_{1-8}$alkyl$)_2$-amino" refers to a radical of the formula: —N($C_{1-8}$alkyl$)_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "$(C_{1-8}$alkyl$)_2$-amino-$C_{1-8}$alkyl" refers to a radical of the formula: —$C_{1-8}$alkyl-N($C_{1-8}$alkyl$)_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "$C_{1-8}$alkyl-amino-carbonyl" refers to a radical of the formula: —C(O)—NH—$C_{1-8}$alkyl.

As used herein, the term "($C_{1-8}$alkyl)$_2$-amino-carbonyl" refers to a radical of the formula: —C(O)—N($C_{1-8}$alkyl)$_2$.

As used herein, the term "$C_{1-8}$alkyl-amino-carbonyl-amino" refers to a radical of the formula: —NH—C(O)—NH—$C_{1-8}$alkyl.

As used herein, the term "($C_{1-8}$alkyl)$_2$-amino-carbonyl-amino" refers to a radical of the formula: —NH—C(O)—N($C_{1-8}$alkyl)$_2$.

As used herein, the term "$C_{1-8}$alkyl-amino-sulfonyl" refers to a radical of the formula: —SO$_2$—NH—$C_{1-8}$alkyl.

As used herein, the term "($C_{1-8}$alkyl)$_2$-amino-sulfonyl" refers to a radical of the formula: —SO$_2$—N($C_{1-8}$alkyl)$_2$.

As used herein, the term "$C_{1-8}$alkyl-amino-sulfonyl-amino" refers to a radical of the formula: —NH—SO$_2$—NH—$C_{1-8}$alkyl.

As used herein, the term "($C_{1-8}$alkyl)$_2$-amino-sulfonyl-amino" refers to a radical of the formula: —NH—SO$_2$—N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "$C_{1-8}$alkyl-carbonyl-amino-$C_{1-8}$alkyl" refers to a radical of the formula: —$C_{1-8}$alkyl-NH—C(O)—$C_{1-8}$alkyl.

As used herein, the term "$C_{1-8}$alkyl-carbonyl-oxy" refers to a radical of the formula: —O—C(O)—$C_{1-8}$alkyl.

As used herein, the term "$C_{1-8}$alkyl-carbonyl-oxy-$C_{1-8}$alkyl" refers to a radical of the formula: —$C_{1-8}$alkyl-O—C(O)—$C_{1-8}$alkyl.

As used herein, the term "$C_{1-8}$alkyl-sulfonyl" refers to a radical of the formula: —SO$_2$—$C_{1-8}$alkyl.

As used herein, the term "$C_{1-8}$alkyl-thio" refers to a radical of the formula: —S—$C_{1-8}$alkyl.

As used herein, the term "amino" refers to a radical of the formula: —NH$_2$.

As used herein, the term "amino-$C_{1-8}$alkyl" refers to a radical of the formula: —$C_{1-8}$ alkyl-NH$_2$.

As used herein, the term "amino-$C_{1-8}$alkyl-amino" refers to a radical of the formula: —NH—$C_{1-8}$alkyl-NH$_2$.

As used herein, the term "amino-carbonyl" refers to a radical of the formula: —C(O)—NH$_2$.

As used herein, the term "amino-carbonyl-amino" refers to a radical of the formula: —NH—C(O)—NH$_2$.

As used herein, the term "amino-sulfonyl" refers to a radical of the formula: —SO$_2$—NH$_2$.

As used herein, the term "amino-sulfonyl-amino" refers to a radical of the formula: —NH—SO$_2$—NH$_2$.

As used herein, the term "aryl-$C_{1-8}$alkyl" refers to a radical of the formula: —$C_{1-8}$alkyl-aryl.

As used herein, the term "aryl-$C_{1-8}$ alkyl-amino" refers to a radical of the formula: —NH—$C_{1-8}$alkyl-aryl.

As used herein, the term "aryl-amino" refers to a radical of the formula: —NH-aryl.

As used herein, the term "carboxyl" refers to a radical of the formula: —COOH, —C(O)OH or —CO$_2$H.

As used herein, the term "formyl" refers to a radical of the formula: —C(O)—H.

As used herein, the term "formyl-oxy" refers to a radical of the formula: —O—C(O)—H.

As used herein, the terms "halo" or "halogen" refer to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms. In some embodiments, halo-$C_{1-8}$alkoxy includes halo-$C_{1-6}$alkoxy, halo-$C_{1-4}$alkoxy and the like.

As used herein, the term "halo-$C_{1-8}$alkoxy-carbonyl" refers to a radical of the formula: —C(O)—O—$C_{1-8}$alkyl-halo.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms. In some embodiments, halo-$C_{1-8}$alkyl includes halo-$C_{1-6}$alkyl, halo-$C_{1-4}$alkyl and the like.

As used herein, the term "halo-$C_{1-8}$ alkyl-carbonyl" refers to a radical of the formula: —C(O)—$C_{1-8}$alkyl-halo.

As used herein, the term "halo-$C_{1-8}$ alkyl-sulfonyl" refers to a radical of the formula: —SO$_2$—$C_{1-8}$alkyl-halo.

As used herein, the term "halo-$C_{1-8}$ alkyl-thio" refers to a radical of the formula: —S—$C_{1-8}$alkyl-halo.

As used herein, the term "heteroaryl-$C_{1-8}$ alkyl" refers to a radical of the formula: —$C_{1-8}$alkyl-heteroaryl.

As used herein, the term "hydroxyl-$C_{1-8}$alkoxy" refers to a radical of the formula: —O—$C_{1-8}$alkyl-OH, wherein $C_{1-8}$alkyl may be partially or completely substituted where allowed by available valences with one or more hydroxyl radicals.

As used herein, the term "hydroxyl-$C_{1-8}$alkyl" refers to a radical of the formula: —$C_{1-8}$alkyl-OH, wherein $C_{1-8}$alkyl may be partially or completely substituted where allowed by available valences with one or more hydroxyl radicals.

As used herein, the term "hydroxyl-amino" refers to a radical of the formula: —NH—OH.

As used herein, the term "hydroxyl-$C_{1-8}$alkyl-amino" refers to a radical of the formula: —NH—$C_{1-8}$alkyl-OH.

As used herein, the term "hydroxyl-$C_{1-8}$alkyl-amino-$C_{1-8}$alkyl" refers to a radical of the formula: —$C_{1-8}$alkyl-NH—$C_{1-8}$alkyl-OH.

As used herein, the term "hydroxyl-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "hydroxyl-imino-$C_{1-8}$alkyl" refers to a radical of the formula: —$C_{1-8}$alkyl(=N—OH).

As used herein, the term "imino" refers to a radical of the formula: =NH.

As used herein, the term "imino-$C_{1-8}$alkyl" refers to a radical of the formula: —$C_{1-8}$alkyl(=NH).

As used herein, the term "N-oxide" refers to a moiety of the formula:

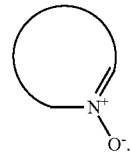

As used herein, the term "oxo" refers to a moiety of the formula:

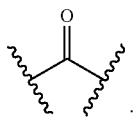

As used herein, the term "P(O)(R$_9$)$_2$-amino" refers to a radical of the formulae: —NH—P(O)(—O—C$_{1-8}$alkyl)(OH) when R$_9$ is independently hydroxyl and (C$_{1-8}$alkoxy)$_n$, where n is 1; or, —NH—P(O)(OH)$_2$ when R$_9$ is hydroxyl; or, —NH—P(O)(—O—C$_{1-8}$alkyl)$_2$ when R$_9$ is (C$_{1-8}$alkoxy)$_n$, where n is 1.

As used herein, the term "substituent" means positional variables on the atoms of a core molecule that are attached at a designated atom position, replacing one or more hydrogen atoms on the designated atom, provided that the atom of attachment does not exceed the available valence or shared valence, such that the substitution results in a stable compound. Accordingly, combinations of substituents and/or variables are permissible only if such combinations result in stable compounds. Any carbon atom as well as heteroatom with a valence level that appears to be unsatisfied as described or shown herein is assumed to have a sufficient number of hydrogen atom(s) to satisfy the valences described or shown.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent variable on a core structure for a compound described herein is understood to include the replacement of the generic substituent with specie substituents that are included within the particular genus, e.g., aryl may be replaced with phenyl or naphthalenyl and the like, such that the resulting compound is to be included within the scope of the compounds described herein.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

Compound names used herein were obtained using the ACD Labs Index Name software provided by ACD Labs and/or ChemDraw Ultra software provided by CambridgeSoft. When the compound name disclosed herein conflicts with the structure depicted, the structure shown will supercede the use of the name to define the compound intended.

Compound Forms

As used herein, the terms a "compound of Formula (Ia)," "compound of Formula (II)," "compound of Formula (IIa)," "compound of Formula (III)," "compound of Formula (IIIa)," "compound of Formula (IV)," "compound of Formula (IVa)," "compound of Formula (V)" or a "compound of Formula (Va)" refer to subgenera of the compound of Formula (I) or a form thereof, as defined herein. Rather than repeat the various subgenera of the compound of Formula (I), in certain embodiments, the term "compound(s) of Formula (I) or a form thereof" is used inclusively to refer to compound(s) of Formula (Ia) or a form thereof, compound(s) of Formula (II) or a form thereof, compound(s) of Formula (IIa) or a form thereof, compound(s) of Formula (III) or a form thereof, compound(s) of Formula (IIIa) or a form thereof, compound(s) of Formula (IV) or a form thereof, compound(s) of Formula (IVa) or a form thereof, compound(s) of Formula (V) or a form thereof or compound(s) of Formula (Va) or a form thereof, either separately or together. Thus, embodiments and references to a "compound of Formula (I)" are intended to be inclusive of compounds of Formula (Ia), compounds of Formula (II), compounds of Formula (IIa), compounds of Formula (III), compounds of Formula (IIIa), compounds of Formula (IV), compounds of Formula (IVa), compounds of Formula (V) and compounds of Formula (Va).

As used herein, the term "form" means a compound of Formula (I) selected from a free acid, free base, salt, ester, hydrate, solvate, chelate, clathrate, polymorph, isotopologue, stereoisomer, racemate, enantiomer, diastereomer, or tautomer thereof.

In certain embodiments described herein, the form of the compound of Formula (I) is selected from a salt, isotopologue, stereoisomer, racemate, enantiomer, diastereomer or tautomer thereof.

In certain embodiments described herein, the form of the compound of Formula (I) is selected from a free acid, isotopologue, stereoisomer, racemate, enantiomer, diastereomer or tautomer thereof.

In certain embodiments described herein, the form of the compound of Formula (I) is selected from a free base, isotopologue, stereoisomer, racemate, enantiomer, diastereomer or tautomer thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or separated and/or purified from a synthetic process (e.g., from a reaction mixture) or natural source or combination thereof according to an isolation, separation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group on a compound of Formula (I) or a form thereof is in a form modified to preclude undesired side reactions of the functional group when the compound is subjected to a reaction. Suitable protecting groups will be recognized by those with ordinary skill in the art as well as by reference to standard textbooks such as, for example, T. W. Greene et al, *Protective Groups in Organic Synthesis* (2007), Wiley, New York.

Prodrugs and solvates of the compounds of Formula (I) or a form thereof described herein are also contemplated.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

Pharmaceutically acceptable prodrugs of compounds of Formula (I) or a form thereof include those compounds substituted with one or more of the following groups: carboxylic acid esters (e.g., via carboxylic acid used to derive a carboxylate ester further substituted with alkyl), sulfonate esters, amino acid esters or phosphonate esters (e.g., via phosphoramidic acid used to derive a phosphoramidate mono-, di- or triphosphate ester further substituted with alkyl). As described herein, it is understood by a person of ordinary skill in the art that one or more of such substituents may be used to provide a compound of Formula (I) or a form thereof as a prodrug.

The compounds of Formula (I) or a form thereof can form salts, which are intended to be included within the scope of this description. Reference to a compound of Formula (I) or a form thereof herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds of Formula (I) or a form thereof described herein that are safe and effective (i.e., non-toxic, physiologically acceptable) for use in mammals and that possess biological activity, although other salts are also useful. Salts of the compounds of the Formula (I) or a form thereof may be formed, for example, by reacting a compound of Formula (I) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds of Formula (I) or a form thereof described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate, trifluoroacetic acid salt and the like. One or more embodiments of acid addition salts include chloride, hydrochloride, dihydrochloride, trihydrochloride, hydrobromide, acetate, diacetate, methanesulfonate, sulfate, trifluoroacetate, trifluoroacetic acid salt and the like. More particular embodiments include a chloride, hydrochloride, dihydrochloride, hydrobromide, methanesulfonate, sulfate, trifluoroacetate, trifluoroacetic acid salt and the like.

In certain embodiments of the compounds of Formula (I) or a form thereof described herein, the compound is isolated as a salt form, wherein the compound is conjugated with the salt in a ratio represented as, in a non-limiting example, "compound:salt (A:B)," wherein "A" and "B" represent the equivalents of compound to salt in the isolated form.

Additionally, acids which are considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium, zinc, and diethanolamine salts. Certain compounds of Formula (I) or a form thereof described herein can also form pharmaceutically acceptable salts with organic bases (for example, organic amines) such as, but not limited to, dicyclohexylamines, tert-butyl amines and the like, and with various amino acids such as, but not limited to, arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be included within the scope of pharmaceutically acceptable salts as described herein. In addition, all such acid and base salts are considered equivalent to the free forms of the corresponding compounds of Formula (I) or a form thereof for purposes of this description.

Compounds of Formula (I), and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, may exist in different stereoisomeric forms. The present description is intended to include all stereoisomeric forms of the compounds of Formula (I) as well as mixtures thereof, including racemic mixtures.

The compounds of Formula (I) or a form thereof described herein may include one or more chiral centers, and as such may exist as racemic mixtures (R/S) or as substantially pure enantiomers and diastereomers. The compounds of Formula (I) or a form thereof may also exist as substantially pure (R) or (S) enantiomers (when one chiral center is present). In one embodiment, the compounds of Formula (I) or a form thereof described herein are (S) isomers and may exist as enantiomerically pure compositions substantially comprising only the (S) isomer. In another embodiment, the compounds of Formula (I) or a form thereof described herein are (R) isomers and may exist as enantiomerically pure compositions substantially comprising only the (R) isomer. As one of skill in the art will recognize, when more than one chiral center is present, the compounds of Formula (I) or a form thereof described herein may also exist as a (R,R), (R,S), (S,R) or (S,S) isomer, as defined by IUPAC Nomenclature Recommendations.

As used herein, the term "substantially pure" refers to compounds of Formula (I) or a form thereof consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, the term "racemate" refers to any mixture of isometric forms that are not "enantiomerically pure", including mixtures such as, without limitation, in a ratio of about 50/50, about 60/40, about 70/30, about 80/20, about 85/15 or about 90/10.

In addition, the compounds of Formula (I) or a form thereof described herein embrace all geometric and positional isomers. For example, if a compound of Formula (I) or a form thereof incorporates a double bond or a fused ring, both the cis- and trans-forms, as well as mixtures thereof, are embraced within the scope of the compounds of Formula (I) or a form thereof described herein.

Diastereomeric mixtures can be separated into their individual diastereomers on the basis of their physical chemical differences by methods well known to those skilled in the art, such as, for example, by chromatography and/or fractional crystallization. Enantiomers can be separated by use of a chiral HPLC column or other chromatographic methods known to those skilled in the art.

Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers.

All stereoisomers (for example, geometric isomers, optical isomers and the like) of the present compounds of Formula (I) or a form thereof described herein (including salts, solvates, esters and prodrugs and transformed prodrugs thereof), which may exist due to asymmetric carbons on various substituents, including enantiomeric forms (which may exist even in the absence of asymmetric carbons), rotameric forms, atropisomers, diastereomeric and regioisomeric forms, are contemplated within the scope of the description herein.

Individual stereoisomers of the compounds of Formula (I) or a form thereof described herein may, for example, be substantially free of other isomers, or may be present in a racemic mixture, as described supra.

The use of the terms "salt," "solvate," "ester," "prodrug" and the like, is intended to apply equally to the salt, solvate, ester and prodrug and the like of enantiomers, stereoisomers, rotamers, tautomers, positional isomers, racemates, isotopologues or prodrugs of the instant compounds.

The term "isotopologue" refers to isotopically-enriched compounds of Formula (I) or a form thereof which are identical to those recited herein, but for the fact that one or more atoms are replaced by an atom having an atomic mass or mass number different from the atomic mass or mass number found in nature. Examples of isotopes that can be incorporated into compounds of Formula (I) or a form thereof described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $O^{31}$, $P^{32}$, $S^{35}$, $F^{18}$, $Cl^{35}$ and $Cl^{36}$, respectively, each of which is also within the scope of this description.

Certain isotopically-enriched forms of compounds of Formula (I) or a form thereof described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with isotopes such as deuterium (i.e., "deuterium enriched") may afford certain therapeutic advantages resulting from greater metabolic stability (e.g., increased in vivo half-life), increased solubility or reduced dosage requirements (e.g., increased bioavailability) or reduced toxicity (e.g., reduced inhibition of metabolic enzymes) and hence may be preferred in some circumstances.

One or more compounds of Formula (I) or a form thereof described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound of Formula (I) or a form thereof described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds of Formula (I) or a form thereof described herein may optionally be converted to a solvate. Preparation of solvates is known. A typical, non-limiting process involves dissolving a compound of Formula (I) or a form thereof in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, differential scanning calorimetry, thermogravimetric analysis, Karl-Fischer and the like, may show the presence of the solvent (or water) in the crystals as a solvate (or hydrate).

As used herein, the term "hydrate" means a solvate wherein the solvent molecule is water.

Polymorphic crystalline and amorphous forms of the compounds of Formula (I) or a form thereof, and of the salts, solvates, esters and prodrugs of the compounds of Formula (I) or a form thereof, are further intended to be included in the scope of the compounds of Formula (I) or a form thereof described herein.

Compound Uses

The Bmi-1 oncogene was first identified as part of a key insertion/activation region of the Moloney murine leukemia virus in the early 1990's (1-6). Bmi-1 is a member of the Polycomb group (PcG) of transcriptional repressors and was identified as a necessary regulator of hematopoietic stem cell (HSC) self-renewal (76, 77). Park found that Bmi-1 is highly expressed in purified mouse and human HSCs and that the absence of Bmi-1, as demonstrated by Bmi-1 knockout mice, results in the progressive loss of all hematopoietic lineages (76). Furthermore, the transplantation of Bmi-1$^{-/-}$ day 14.5 fetal liver cells into lethally irradiated normal mice, demonstrated that the cells were unable to reconstitute myeloid cells, B cells, and T-cells because Bmi-1$^{-/-}$ HSCs were unable to renew (76).

In addition to the role of Bmi-1 in HSC self renewal, it was found that Bmi-1 transgene expression induced lymphoma in mice (2). Bmi-1 was also found to be overexpressed in many tumor types, including acute myeloid leukemia, medulloblastoma, neuroblastoma, colorectal cancer, lung cancer, and prostate cancer, and was found to increase with malignancy (34, 78, 61, 79, 80, 65, 43). Loss of Bmi-1 in various human cancer cell lines via Bmi-1 specific RNA interference (RNAi) was shown to lead to acute cell death and growth inhibition, whereas loss of Bmi-1 in various normal cell lines was shown to lead to only moderate growth inhibition and not significant cell death (69). Thus, Bmi-1 is necessary for the survival of cancer cells but has minimal effect on the survival of normal cells.

Bmi-1 has been subsequently shown to act as an oncogene experimentally and has proven particularly potent in conjunction with c-myc to initiate lymphoma in mice (7, 8). The role of Bmi-1 in lymphomagenesis has been attributed partially to transcriptional repression of the INK4a locus (containing both the p16$^{IK4A}$ and p14$^{ARF}$ genes) leading to maintenance of cancer and tumor cell proliferation and prevention of differentiation (7, 9). Loss of expression of the INK4a locus due to promoter silencing has been extensively studied and is both important for the progression and prognosis of many types of hematologic cancers (10, 11). The INK4a locus is occasionally lost by deletion in leukemia and lymphoma (12, 13).

However, Bmi-1 has been shown to play a role in tumorigenesis in models lacking the INK4a locus, indicating that other loci important in cancer are regulated by this protein (14). Experimental results have demonstrated further that loss of Bmi-1 induces growth arrest and senescence in fibrosarcoma cells known to lack INK4a (15). There is also evidence that Bmi-1 is important for the hedgehog (Hh) pathway in breast cancer. Activation of Hh signaling increases Bmi-1 expression, while down-regulation of Bmi-1 (via siRNA) abrogates the effects of Hh signaling on mammosphere formation in vitro and inhibits ductal/alveolar development in mice (16). Recent work has demonstrated the role of Bmi-1 in the regulation of Hox gene expression. Knockdown of Bmi-1 caused a global and loci-specific loss of H2A ubiquitination, upregulation of the HoxC5 gene, and inhibition of the growth of HeLa cells (17). Another study demonstrated that E2F6 and Bmi-1 cooperate in the regulation of Hox gene expression (particularly Hox C10 and B9), and consequently affect axial skeleton development, but not in the repression of the Ink4a-Arf locus. These findings underscore the significance of the E2F6-Bmi-1 interaction and suggest that the Hox and Ink4a-Arf loci are regulated by somewhat different Bmi-1-dependent mechanisms (18). Current research suggests that Bmi-1 has different roles dependent upon cell types and/or developmental stages. Other genes regulated by Bmi-1 remain to be identified.

Bmi-1 is found to be highly expressed in malignancies, such as diffuse large B cell lymphomas (DLBCL), B cell non-Hodgkin's lymphoma, Hodgkin's lymphoma, acute myeloid leukemia, colorectal carcinoma, liver carcinoma, non-small cell lung cancer, breast carcinoma and medulloblastoma. The study of Bmi-1 knockout mice has revealed that Bmi-1 is required for the self-renewal of both leukemic and normal hematopoietic stem cells.

Additionally, evidence exists linking Bmi-1 levels to blood tumor types, particularly Burkitt's lymphoma, mantle cell lymphoma, Hodgkin's lymphoma (21-23), non-Hodgkin's lymphoma, some T-cell lymphomas (2, 24-31), acute myeloid leukemia and T-ALL (32-35). Raaphorst et al observed that, in Hodgkin's lymphoma, Reed-Sternberg cells (HRS) co-express Bmi-1, EZH2, and Mib-1/Ki-67. Because HRS cells are thought to originate from germinal center lymphocytes that express Bmi-1, such lymphocytes should lose the ability to express Bmi-1 (and gain the ability to express EZH2) as they differentiate. These observations suggest that Hodgkin's lymphoma is associated with aberrant co-expression of Bmi-1 and EZH2 in these cells (22). An assessment of acute myeloid leukemia stem cell populations by van Gosliga et al (36) showed that CD34$^+$/CD38$^-$ cells capable of forming leukemic-cobblestone colonies on a bone marrow substrate through at least two rounds of expansion represented an extreme minority of the cell population. Further analysis showed that this cell population expresses high levels of Bmi-1 mRNA and can establish an aggressive leukemia in mice, while those cells that have lower levels of Bmi-1 mRNA cannot (36). Such studies implicate Bmi-1 in tumor growth and cell survival and suggest a central function in tumor initiation and maintenance of tumor stem cells.

The levels of Bmi-1 have been shown to have prognostic relevance in a number of tumor types. An example of this is found in acute myeloid leukemia based on results from a study assessing the prognostic value of high Bmi-1 levels in 64 patients (32). On the basis of the median value of Bmi-1 (54.58%), patients were divided into two groups and monitored for survival. Patients with lower Bmi-1 positivity (<55%, n=33) had significantly longer overall survival (P=0.0001), relapse-free survival (P=0.0072) and remission duration (P=0.0065) when compared to patients with higher levels of Bmi-1 (>55%, n=31, respectively), regardless of age group (32). Similarly, Van Galen et al (37) have shown that Bmi-1 levels are highly prognostic in diffuse large B cell lymphomas (DLBCL) (37). Neoplastic cells in DLBCL cases originate from germinal centre B (GCB) cells or their descendents (38). Recent microarray analyses have shown that some DLBCL phenotypically resemble non-neoplastic GCB cells, while some show an expression profile similar to that of activated B cells (ABC) (39).

Furthermore, patients with a GCB-like phenotype have a considerably better prognosis than those with an ABC-like phenotype (40). Bmi-1 was identified as one of the genes that distinguish the ABC-like DLBCL (39),(41). Other groups have linked elevated Bmi-1 levels with poor prognosis in mantle cell lymphoma (MCL), non-Hodgkin's lymphoma and other leukemias (22, 26, 27, 29, 42-44), as well as many other tumor types including neuroblastoma, glioblastoma, hepatocellular carcinoma, and breast, colorectal, prostate, lung, gastric and salivary gland cancers (45-57). The loss of expression from the INK4a locus has also been shown to have prognostic value (12, 13). Taken together, these data strongly implicate Bmi-1 in cancer and suggest that inhibiting uncontrolled cell proliferation by inhibiting Bmi-1 function and reducing the level of Bmi-1 in a cancer cell, tumor cell, cancer stem cell or tumor stem cell will have a beneficial therapeutic effect in patients with multiple cancer types, particularly in those afflicted with hematological cancers.

For example, MCL is a rare, aggressive and incurable B cell non-Hodgkin's lymphoma that is refractory (i.e., resistant to conventional chemotherapy) and is associated with a poor prognosis. MCL is characterized by the t(11; 14)(q13; q32) translocation, resulting in amplification and overexpression of the polycomb group gene Bmi-1, which normally functions for self-renewal of hematopoietic stem cells but has the capacity to induce tumors when overexpressed.

Multiple myeloma is another fatal B-cell malignancy characterized by the accumulation of abnormal plasma cells in the bone marrow. Standard therapy for multiple myeloma is similar to the course for MCL and normally consists of combination chemotherapy that often results in a 60-70% response rate. However, most patients will eventually relapse, leaving patients with limited therapeutic options. Recent gene expression profiling of multiple myeloma cells revealed elevated expression of Bmi-1 compared to that in normal plasma cells, as confirmed by immunoblotting.

Bmi-1 has been shown to be regulated transcriptionally by a number of factors including SALL4, FoxM1, c-Myc, E2F-1 and Mel18. Bmi-1 and SALL4 are putative oncogenes that modulate stem cell pluripotency and play a role in leukemigenesis (also referred to as leukemogenesis). Murine Sal14 also has been shown to play an essential role in maintaining the properties of ES (embryonic stem) cells and governing the fate of the primitive inner cell mass. Yang et al demonstrated that transcription from the Bmi-1 promoter is markedly activated by SALL4 in a dose-dependent manner (35). The Forkhead box transcription factor FoxM1 is expressed in proliferating cells and has been shown to upregulate the levels of Bmi-1 in transformed NIH 3T3 cells in response to oxidative stress through c-Myc activation (58). The Bmi-1 homologue, Mel18, acts as a potent repressor on the expression of Bmi-1. The Bmi-1 promoter region contains a functional E-box through which c-Myc and Mel-18 can regulate Bmi-1 expression. Since Mel18 downregulates c-Myc expression and Bmi-1 is a c-Myc target, these data suggest that Mel18 regulates expression of Bmi-1 via repression of c-Myc during cellular senescence and, thus, link c-Myc and polycomb function (59). Similarly, a recent report suggests that E2F-1 may also regulate the levels of Bmi-1 in neuroblastoma (60). The Bmi-1 promoter contains a putative E2F binding site required for the activation of a Bmi-1 promoter-dependent reporter construct by E2F-1. Neither post-transcriptional nor post-translational control of Bmi-1 production has been reported.

Without being limited by theory, the compounds of Formula (I) or a form thereof described herein may play a role in activating the apoptotic pathway as determined by annexin-V expression, as well as cleavage of poly (ADP-ribose) polymerase (PARP) and caspase-9 and caspase-7. Cell cycle analyses of cells treated with these compounds of Formula (I) or a form thereof have further demonstrated a block at the $G_2$/M phase followed by the development of polyploidy. These findings suggest that Bmi-1 may also play a role in DNA repair and/or regulation of mitosis. The compounds of Formula (I) or a form thereof described herein are useful inhibitors of Bmi-1 function, causing a reduction in the level of Bmi-1 protein and are thus potential therapeutics for any cancer cell, tumor cell, cancer stem cell or tumor stem cell that overexpresses Bmi-1. Additionally, the compounds of Formula (I) or a form thereof described herein inhibit the function of Bmi-1 and reduce Bmi-1 levels in cancer stem cell and tumor stem cell environments and are thus useful in targeting cancer cell populations that have been shown to be resistant to current therapies (e.g., such as those using large and small molecule chemotherapeutic agents and/or radiation therapies, as well as targeted therapies that primarily function by indiscriminately damaging mitotic cells).

As used herein, the italicized form of "Bmi-1," unless otherwise specified or clear from the context of the specification, refers to the Bmi-1 gene. The nonitalicized form of "Bmi-1," the capitalized form of "BMI-1" or the term "Bmi-1 protein," unless otherwise specified or clear from the context of the specification, collectively refer to Bmi-1 protein.

As used herein, the term "Bmi-1 inhibitor" or the phrase (or variations thereof) "inhibit Bmi-1 function and reduce the level of Bmi-1" refer to post-translational inhibition of the function of Bmi-1 protein and subsequent degradation, resulting in decreased levels of Bmi-1 protein present in a tumor environment including, but not limited to, in vitro and in vivo environments comprising cancer stem cells or tumor stem cells or cancer stem cells and tumor stem cells.

In accordance with the present description, compounds of Formula (I) or a form thereof that inhibit Bmi-1 function and reduce the level of Bmi-1 also inhibit proliferation of tumor cells in vitro and in vivo and enhance sensitivity of intrinsically resistant populations (e.g., either "cancer stem cells," "tumor stem cells" or both) to chemotherapeutics. Elevated expression of human Bmi-1 has been reported in multiple cancer samples and cancer cell lines (2, 42, 51, 56, 61-68).

Applicants have identified compounds of Formula (I) or a form thereof that inhibit Bmi-1 function and reduce the level of Bmi-1 in vitro and in vivo, with concurrent inhibition of tumor cell growth and xenograft growth in vivo.

One embodiment described herein is directed to a method of inhibiting Bmi-1 function and reducing the level of Bmi-1 to treat a cancer mediated by Bmi-1 in a subject in need thereof comprising contacting a cell having elevated Bmi-1 levels from the subject with an amount of a compound of Formula (I) or a form thereof, wherein the cell is selected from a cancer cell, tumor cell, cancer stem cell or tumor stem cell, determining an effective amount of the compound of Formula (I) or a form thereof that inhibits Bmi-1 function in the cell and subsequently administering the effective amount of the compound of Formula (I) or a form thereof to the subject.

Another embodiment described herein is directed to a method of inhibiting Bmi-1 function and reducing the level of Bmi-1 to treat a cancer mediated by Bmi-1 in a subject in need thereof comprising administering to the subject an effective amount of a compound of Formula (I) or a form thereof.

Another embodiment described herein is directed to a method for treating a cancer mediated by Bmi-1 in a subject in need thereof comprising contacting a cell having elevated Bmi-1 levels from the subject with an amount of a compound of Formula (I) or a form thereof, wherein the cell is selected from a cancer cell, tumor cell, cancer stem cell or tumor stem cell.

Another embodiment described herein is directed to a method further comprising contacting a cell having elevated Bmi-1 levels from the subject with an amount of the compound of Formula (I) or a form thereof, wherein the cell is selected from a cancer cell, tumor cell, cancer stem cell or tumor stem cell, determining an effective amount of the compound of Formula (I) or a form thereof that inhibits Bmi-1 function in the cell and subsequently administering the effective amount of the compound of Formula (I) or a form thereof to the subject.

Another embodiment described herein is directed to a method wherein the effective amount of the compound of Formula (I) or a form thereof determined to inhibit Bmi-1 function in the contacted cell reduces Bmi-1 levels in the contacted cell.

An embodiment of the method described herein comprises administering an effective amount of a compound of Formula (I) or a form thereof to inhibit the function of Bmi-1 in a cancer cell in vivo or in vitro, in a tumor cell in vivo or in vitro, in a cancer stem cell population in vivo or in vitro, or in a tumor stem population in vivo or in vitro.

An embodiment of the method described herein comprises administering an effective amount of a compound of Formula (I) or a form thereof to reduce the level of Bmi-1 in a cancer cell in vivo or in vitro, in a tumor cell in vivo or in vitro, in a cancer stem cell population in vivo or in vitro, or in a tumor stem population in vivo or in vitro.

An embodiment of the method described herein comprises administering an effective amount of a compound of Formula (I) or a form thereof to inhibit cancer cell proliferation, tumor cell proliferation, cancer stem cell proliferation or tumor stem cell proliferation.

An embodiment described herein includes the use of a compound of Formula (I) or a form thereof in the manufacture of a medicament for inhibiting Bmi-1 function and reducing the level of Bmi-1 to treat a cancer mediated by Bmi-1 in a subject in need thereof comprising administering an effective amount of the medicament to the subject.

Without being limited by theory, any type of cancer mediated by or dependent on the presence of overexpressed Bmi-1 can be treated in accordance with the intended use of the compounds of Formula (I) or a form thereof described herein.

As used herein, the term "cancer" refers to cells in which Bmi-1 is aberrantly expressed or overexpressed and the cell depends on Bmi-1 for survival or proliferation.

Without being limited by theory, the cells may be either stem-like or more differentiated, but the cell relies on Bmi-1 to enable uncontrolled cell division and develop resistance to cytotoxic, chemotherapeutic agents.

In another embodiment, the term "a cancer mediated by Bmi-1" refers to a cancer that is characterized by cells or a fraction of cells from a cancer patient that overexpress Bmi-1 compared to cells from a cancer-free patient (i.e., a patient with no detectable cancer as determined by conventional techniques, such as MRI, CAT scan, etc.). Alternatively, the term refers to cells or a fraction of cells from a cancer patient that, relative to the cancer patient's cells from surrounding normal tissues, express a level of Bmi-1 that differs by at least 2%, 4%, 8%, 10%, 15%, 20%, 25%, 30%, 35%, 40%, 45%, 50%, 55%, 60%, 65%, 70%, 75%, 80%, 85%, 90%, or 95% more, as detected by any method routinely used in the art, or described herein, e.g., in an ELISA.

Non-limiting examples of a cancer mediated by Bmi-1 that can be treated with the intended use described herein: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's lymphoma, non-Hodgkin's lymphoma; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; glial brain tumors (i.e., gliomas) such as but not limited to, astrocytoma, ependymoma, oligodendroglioma, brain stem glioma, optic glioma, diffuse intrinsic pontine glioma, mixed glioma (i.e., oligoastrocytoma), glioblastoma, glioblastoma multiforme, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancer-cytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

The compounds of Formula (I) or a form thereof are also useful in the treatment, prevention and/or management of a variety of cancers mediated by Bmi-1 or other abnormal proliferative diseases (where such disease is mediated by overexpressed Bmi-1 or elevated levels of Bmi-1), including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma; tumors of the central and peripheral nervous system, including astrocytoma, neuroblastoma, glioma, and Schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma, or melanoma is treated as described herein.

In a specific embodiment, the cancer mediated by Bmi-1 being treated as described herein is leukemia, lymphoma or myeloma (e.g., multiple myeloma). Non-limiting examples of leukemias and other blood-borne cancers mediated by Bmi-1 that can be treated with the methods described herein include acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), and hairy cell leukemia.

Non-limiting examples of lymphomas mediated by Bmi-1 that can be treated in accordance with the methods described herein include Hodgkin's lymphoma, non-Hodgkin's lymphoma, multiple myeloma, Waldenström's macroglobulinemia, heavy chain disease, and polycythemia vera.

In another embodiment, the cancer mediated by Bmi-1 being treated as described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

In certain embodiments, a cancer mediated by Bmi-1 includes, but is not limited to, brain cancer, gastric cancer, hematologic cancer, lung cancer, non-small cell lung cancer, pancreatic cancer, prostate cancer, salivary gland cancer, colorectal carcinoma, hepatocellular carcinoma, liver carcinoma, breast carcinomas or sarcomas, esophageal carcinomas or sarcomas, stomach carcinomas or sarcomas, fibrosarcoma, glioblastoma, diffuse intrinsic pontine glioma, medulloblastoma, neuroblastoma, diffuse large B cell lymphomas, B cell non-Hodgkin's lymphoma, Hodgkin's lymphoma or chronic or acute myeloid leukemia.

In certain embodiments, a cancer mediated by Bmi-1 includes, but is not limited to, tumors that relapse after therapy despite improved surgical and irradiation techniques. Tumor relapse may occur for a number of reasons, with one plausible explanation being the existence of cancer stem cells (CSC) or tumor stem cells (tumor initiating cells) in the tumor population. CSCs are defined as a population of stem cells relative to any type of blood cancer, solid tumor cancer or metastatic cancer. Tumor stem cells are those specifically found within a tumor. Both have characteristics similar to normal stem cells. Like normal stem cells, CSCs and tumor stem cells have the potential to self renew. Unlike normal stem cells, though, due to the sustained presence of high levels of Bmi-1, the CSCs and tumor stem cells fail to terminally differentiate and proliferate unchecked. Their enhanced DNA repair capacity also enables them to become resistant to cytotoxic, chemotherapeutic drugs designed to kill cancer cells and tumor cells. Therefore, targeting CSCs and tumor stem cells that overexpress Bmi-1 could be an approach for effective cancer treatment. One further approach is to target various transcription factors responsible for maintenance of the self renewal capacity of CSCs and tumor stem cells.

As used herein, the term "treat," "treatment" or "treating" refers to: (i) preventing a disease, disorder and/or condition from occurring in a subject that may be predisposed to the disease, disorder and/or condition but has not yet been diagnosed as having said disease, disorder and/or condition; (ii) inhibiting a disease, disorder and/or condition, i.e., arresting its development; and/or (iii) relieving a disease, disorder and/or condition, i.e., causing regression of the disease, disorder and/or condition.

As used herein, the term "subject" refers to members of the human, equine, porcine, bovine, murine, rattus, canine and feline species. In some embodiments, the subject is a mammal or a warm-blooded vertebrate animal. In other embodiments, the subject is a human. As used herein, the term "patient" may be used interchangeably with "subject" and "human".

In certain embodiments, the subject is a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, the subject is a human infant. In other embodiments, the subject is a human toddler. In other embodiments, the subject is a human child. In other embodiments, the subject is human adult. In yet other embodiments, the subject is an elderly human.

As used herein, the term "elderly human" refers to a human 65 years or older; the term "human adult" refers to a human that is 18 years or older; the term "human child" refers to a human that is 1 year to 18 years old; the term "human infant" refers to a newborn to 1 year old year human; and, the term "human toddler" refers to a human that is 1 year to 3 years old.

In certain embodiments, the subject is in an immunocompromised state or immunosuppressed state or at risk for becoming immunocompromised or immunosuppressed.

In certain embodiments, the subject is receiving or recovering from an immunosuppressive therapy. In certain embodiments, the subject has or is at risk of getting cancer, AIDS, or a bacterial infection. In certain embodiments, the subject is, will or has undergone surgery, chemotherapy and/or radiation therapy. In certain embodiments, the subject has cystic fibrosis, pulmonary fibrosis or another condition affecting the lungs. In certain embodiments, the subject has, will have or had a tissue transplant.

In some embodiments, the subject's cancer, due to the overexpression of Bmi-1 in cancer cells, tumor cells, cancer stem cells or tumor stem cells thereof, has proven refractory to conventional "standard of care" therapies (excluding treatment with a compound of Formula (I) or a form thereof), such that the patient has discontinued the conventional therapy. In one embodiment, without being limited by theory, the term "refractory" means that at least some significant portion of the cancer cells, tumor cells, cancer stem cells or tumor stem cells continue to proliferate due to the overexpression of Bmi-1, despite therapy.

The determination of whether the cancer is refractory to a particular therapy can be made either in vivo or in vitro by any method known in the art for assaying the effect of a therapy on the cancer cells, tumor cells, cancer stem cells or tumor stem cells, using the art-accepted meanings of "refractory" in such a context. In certain embodiments, a patient having a refractory cancer due to the overexpression of Bmi-1 is a patient in which the cancer is non-responsive or resistant to a conventional or "standard of care" therapy. In certain embodiments, a patient with refractory cancer has a cancer mediated by Bmi-1 that progresses. Disease progression, as a lack of clinical response to a therapy, is demonstrated when the tumor or neoplasm has not been significantly eradicated and/or the symptoms have not been significantly alleviated. The determination of whether a patient has a refractory cancer mediated by Bmi-1 can be made either in vivo or in vitro by any method known in the art for assaying the effectiveness of the therapy for the treatment of the cancer, using art-accepted meanings of "refractory" in such a context.

In certain embodiments, the patient to be treated in accordance with the methods described herein is a patient already being treated with antibiotics, anti-virals, anti-fungals, or other biological therapy, immunotherapy or anti-cancer therapy. Among these patients are patients with a refractory cancer mediated by Bmi-1 or patients too young for conventional therapies. In some embodiments, the patient being treated is treatment naive, not having received any prior therapy. In any of the foregoing embodiments, a patient to be treated may receive a small molecule therapy.

In some embodiments, a compound of Formula (I) or a form thereof may be prophylactically administered to a patient to prevent the onset of cancer mediated by Bmi-1 in a patient at risk of developing cancer. In some embodiments, a compound of Formula (I) or a form thereof may be therapeutically administered to a patient that is susceptible to adverse reactions to conventional therapies. In some embodiments, the subject being administered one or more compounds of Formula (I) or a form thereof has not received prior therapy. In other embodiments, one or more compounds of Formula (I) or a form thereof are administered to a subject who has received a prior therapy. In some embodiments, the subject administered a compound of Formula (I) or a form thereof has discontinued a prior therapy due to lack of benefit from the therapy, adverse effects from the therapy or unacceptable levels of toxicity.

In some embodiments, the subject being administered one or more compounds of Formula (I) or a form thereof, will or has undergone surgery, chemotherapy, antibody therapy, hormonal therapy and/or radiation therapy. In certain embodiments, the patient has undergone surgery to remove the tumor or neoplasm. In certain embodiments, the subject will have, or has had, or is undergoing a tissue or organ transplant.

As used herein, the terms "effective amount," "prophylactically effective amount" or "therapeutically effective amount" mean an amount of a compound of Formula (I) or a form thereof that is effective in inhibiting Bmi-1 protein function and reducing the level of Bmi-1 protein, as described herein, and thus producing the desired prophylactic, therapeutic, ameliorative, inhibitory or preventative effect in a cancer mediated by Bmi-1 in a patient in need thereof.

As used herein, the term "effective amount," in the context of administering a compound of Formula (I) or a form thereof to a patient, refers to the amount of a compound of Formula (I) or a form thereof which is sufficient to achieve at least one or more of the following effects, as applicable, in a patient or in patient cell(s): (i) inhibition of Bmi-1 protein function; (ii) reduction in the level or quantity of Bmi-1 protein; (iii) reduction or amelioration in the severity of a cancer mediated by Bmi-1 or a symptom associated therewith; (iv) prevention of the progression of a cancer mediated by Bmi-1 or a symptom associated therewith; (v) regression of a cancer mediated by Bmi-1 or a symptom associated therewith; (vi) prevention of the development or onset of a cancer mediated by Bmi-1 or a symptom associated therewith; (vii) prevention of the recurrence of a cancer mediated by Bmi-1 or a symptom associated with a cancer mediated by Bmi-1; (viii) reduction of the duration of a symptom associated with a cancer mediated by Bmi-1; (ix) reduction or elimination of the cancer stem cell or tumor stem cell population; (x) reduction or elimination of the growth of a tumor or neoplasm overexpressing Bmi-1; (xi) reduction or elimination of the proliferation of cancer cells or tumor cells; (xii) reduction or elimination of the formation of a tumor or neoplasm overexpressing Bmi-1; (xiii) eradication or control of a primary, regional and/or metastatic cancer mediated by Bmi-1; (xiv) reduction in patient mortality; (xv) increased number of patients in remission; (xvi) increased length of remission in patients; (xvii) the size of a tumor or neoplasm overexpressing Bmi-1 is maintained or controlled such that the size does not increase or increases less than the size of the tumor after administration of a standard therapy as measured by conventional methods available to one of skill in the art, such as MRI, X-ray and CAT scan; (xviii) increased delay in disease progression; (xix) increased patient survival; (xx) reduction in incidences of patient hospitalization; (xxi) reduction in the length of patient hospitalization; (xxii) enhancement or improvement in the prophylactic or therapeutic effect(s) of another therapy; (xxiii) reduction in the number of symptoms associated with a cancer mediated by Bmi-1; (xxiv) increased cancer-free survival of patients; and/or (xxv) increased symptom-free survival of cancer patients.

In general, the term "effective amount" also includes that amount of a compound of Formula (I) or a form thereof administered to a patient which is in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 60 to about 100 Kg. The effective amount for the subject will also depend upon various factors, including the body weight, size and health of the subject. An effective amount for a given patient can be determined according to the skill and judgment of the clinician.

In another embodiment, where daily doses are adjusted based upon the weight of the subject or patient, compounds of Formula (I) or a form thereof described herein may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/Kg/day. Daily doses adjusted based upon the weight of the subject or patient may be administered as a single, divided, or continuous dose. In embodiments where a dose of a compound of Formula (I) or a form thereof is given more than once per day, the dose may be administered once, twice, three times, or more per day. In another embodiment, a subject is administered one or more doses of an effective amount of a compound of Formula (I) or a form thereof, wherein the effective amount may not be the same for each dose.

Another embodiment described herein includes an effective amount of the compound of Formula (I) or a form thereof in a range of from about 0.001 mg/Kg/day to about 500 mg/Kg/day.

Within the scope described herein, the "effective amount" of a compound of Formula (I) or a form thereof for use in the manufacture of a medicament or in a method for treating a cancer mediated by Bmi-1 in a subject in need thereof, is intended to include an amount in a range of from about 0.1 ng to about 3500 mg administered daily; from about 0.1 µg to about 3500 mg administered daily; from about 0.1 mg to about 3500 mg administered daily; from about 1 mg to about 3500 mg administered daily; from about 1 mg to about 3000 mg administered daily; from about 0.05 mg to about 1500 mg administered daily; from about 0.5 mg to about 1500 mg administered daily; from about 1 mg to about 1500 mg administered daily; from about 5 mg to about 1500 mg administered daily; from about 10 mg to about 600 mg administered daily; from about 0.5 mg to about 2000 mg administered daily; or, an amount in a range of from about 5.0 mg to about 1500 mg administered daily.

Another embodiment described herein includes an effective amount of the compound of Formula (I) or a form thereof in a range of from about 0.1 ng to about 3500 mg.

For any compound of Formula (I) or a form thereof, the effective amount can be estimated initially by results from cell culture assays or from relevant animal models, such as the mouse, chimpanzee, marmoset or tamarin animal model.

Relevant animal models may also be used to determine the appropriate concentration range and route of administration.

Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between the toxic and therapeutic effect is referred to as the therapeutic index, and can be expressed as the ratio, $LD_{50}/ED_{50}$. In some embodiments, the effective amount is such that a large therapeutic index is achieved. In further embodiments, the dosage is within a range of plasma concentrations that include an $ED_{50}$ with little or no toxicity. The dosage may vary within this range depending upon the dosage form employed, sensitivity of the patient, and the route of administration.

More specifically, the concentration-biological effect (pharmacodynamic) relationship observed with regard to a compound of Formula (I) or a form thereof suggests a target plasma concentration ranging from about 0.001 µg/mL to about 50 µg/mL, from about 0.01 µg/mL to about 20 µg/mL, from about 0.05 µg/mL to about 10 µg/mL, or from about 0.1 µg/mL to about 5 µg/mL. To achieve such plasma concentrations, the compounds of Formula (I) or a form thereof described herein may be administered at doses that vary from 0.001 µg to 100,000 mg, depending upon the route of administration in single, divided, or continuous doses for a patient weighing between about 40 to about 100 kg (which dose may be adjusted for patients above or below this weight range, particularly for children under 40 kg).

The exact dosage will be determined by the practitioner, in light of factors related to the subject. Dosage and administration may be adjusted to provide sufficient levels of the active agent(s) or to maintain the desired effect. Administration factors that may be taken into account include the severity of the disease state, general health of the subject, ethnicity, age, weight, and gender of the subject, diet, time and frequency of administration, drug combination(s), reaction sensitivities, tolerance for toxicity related to drug metabolites, experience with other cancer therapies and regimens, and tolerance/response to such therapies and regimens. Long-acting pharmaceutical compositions may be administered every 2, 3 or 4 days, once every week, or once every two weeks depending on half-life and clearance rate of the particular formulation.

The compounds of Formula (I) or a form thereof described herein may be administered to the subject via any drug delivery route known in the art. Nonlimiting examples include oral, ocular, rectal, buccal, topical, nasal, ophthalmic, subcutaneous, intramuscular, intravenous (bolus and infusion), intracerebral, transdermal, and pulmonary routes of administration.

Compound Metabolites

Also falling within the scope described herein are the in vivo metabolic products of the compounds of Formula (I) or a form thereof. Such products may result, for example, from the oxidation, reduction, hydrolysis, amidation, glucuronidation, esterification and the like of the administered compound of Formula (I) or a form thereof, primarily due to enzymatic processes. Accordingly, the compounds of Formula (I) or a form thereof described herein include those produced by a process comprising contacting a compound of Formula (I) or a form thereof described herein with a mammalian tissue or a mammal for a period of time sufficient to yield a metabolic product thereof.

Such products typically are identified by preparing a radio-labeled (e.g. $C^{14}$ or $H^3$) compound of Formula (I) or a form thereof described herein, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite).

The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of Formula (I) or a form thereof described herein even if they possess no biological activity of their own.

Combination Therapies

The methods of treating a cancer mediated by Bmi-1 in a subject in need thereof, in addition to those previously described herein, further comprise administering to the subject in need thereof an effective amount of one or more of the compounds of Formula (I) or a form thereof alone or in combination with one or more additional agents selected from anti-cancer agents, anti-proliferative agents, chemotherapeutic agents, immunomodulatory agents, anti-angiogenic agents, anti-inflammatory agents, alkylating agents, steroidal and non-steriodal anti-inflammatory agents, pain relievers, leukotriene antagonists, β2-agonists, anticholinergic agents, hormonal agents, biological agents, tubulin binding agents, glucocorticoids, corticosteroid agents, antibacterial agents, antihistamines, anti-malarial agents, antiviral agents, antibiotics and the like; and, optionally with radiation therapy.

In another embodiment, one or more compounds of Formula (I) or a form thereof alone or in combination with one or more additional agents may be administered to the subject in combination with a supportive therapy, a pain relief therapy, or other therapy that does not have an effect on a cancer mediated by Bmi-1.

In some embodiments, one or more compounds of Formula (I) or a form thereof described herein and one or more additional agents described herein are administered as the same pharmaceutical composition. In certain embodiments, one or more compounds of Formula (I) or a form thereof described herein and one or more additional agents described herein are administered in different pharmaceutical compositions. In certain embodiments, one or more compounds of Formula (I) or a form thereof described herein and one or more additional agents described herein are administered by the same route of administration. In certain embodiments, one or more compounds of Formula (I) or a form thereof described herein and one or more additional agents described herein are administered by different routes of administration.

In other embodiments are pharmaceutical compositions wherein one or more compounds of Formula (I) or a form thereof are administered in a combination product with one or more additional agents useful in the treatment of a cancer mediated by Bmi-1. The skilled artisan will recognize that a variety of active ingredients may be administered in a combination with the compounds of Formula (I) or a form thereof described herein whereby the product may act to augment or synergistically enhance the anticancer activity of either or both the additional agent(s) and the compound(s) of Formula (I) or a form thereof described herein.

As used herein, the term "synergistic," refers to the effect of the administration of a combination product as described herein which is more effective than the additive effects of any two or more single agents. In a specific embodiment, a synergistic effect of a combination product permits the use of lower dosages of one or more agents and/or less frequent administration of said agents to a subject with a cancer mediated by Bmi-1. In certain embodiments, the ability to utilize lower dosages of an agent and/or to administer said agents less frequently reduces the toxicity associated with the administration of said agents to a subject without reducing the efficacy of said agents in the prevention or treatment of a cancer mediated by Bmi-1. In some embodiments, a synergistic effect results in improved efficacy of each of the agents in treating a cancer mediated by Bmi-1. In some embodiments, a synergistic effect of a combination of agents avoids or reduces adverse or unwanted side effects associated with the use of any single agent. The combination of agents in such a product can be administered to a subject in the same pharmaceutical composition. Alternatively, the agents can be administered concurrently to a subject in separate pharmaceutical compositions. The agents may also be administered to a subject by the same or different routes of administration. In a specific embodiment, at least one of the agents is a compound of Formula (I) or a form thereof described herein.

It is also possible to combine any compound of Formula (I) or a form thereof described herein with such additional agents useful in the treatment of a cancer mediated by Bmi-1, including compounds of Formula (I) or a form thereof as described herein, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of Formula (I) or a form thereof described herein and one or more additional agents described herein by different routes.

According to the methods described herein, a combination product may include a combination of active ingredients that may be: (1) co-formulated and administered or delivered simultaneously in a combined formulation; (2) delivered sequentially or in parallel as separate formulations; or (3) by any other combination regimen known in the art. When delivered as separate formulations in alternation therapy, the methods described herein may comprise administration or delivery, for example, without limitation, in separate solutions, emulsions, suspensions, tablets, pills or capsules, or by different injections in separate syringes. In general, when administered in alternation, an effective dosage of each active ingredient is administered serially, one dose following another. In contrast, in parallel or simultaneous administration, effective dosages of two or more active ingredients are administered together. Various alternative combinations of intermittent sequential or in parallel combination administration may also be used.

Specific examples of such agents include, but are not limited to, immunomodulatory agents (e.g., interferon, penicillamine and the like), anti-angiogenic agent, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroidal and non-steriodal anti-inflammatory drugs (e.g., aspirin, ibuprofen, diclofenac, and COX-2 inhibitors)), pain relievers, leukotriene antagonists (e.g., montelukast, methyl xanthines, zafirlukast, and zileuton), $\beta$2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), antibacterial agents (e.g., sulphasalazine, dapsone and the like), antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, ribavirin, foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Specific examples of additional agents that may be used in combination with a compound of Formula (I) or a form thereof described herein include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine; azetepa; azotomycin; batimastat; benzodepa; bicalutamide; bisantrene hydrochloride; bisnafide dimesylate; bis-phosphonates (e.g., pamidronate (Aredria®), sodium clondronate (Bonefos®), zoledronic acid (Zometa®), alendronate (Fosamax®), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; demethylation agents; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; 5-fluorouracil; fluorocitabine; fosquidone; fostriecin sodium; gemcitabine; gemcitabine hydrochloride; histone deacetylase inhibitors; hydroxyurea; idarubicin hydrochloride; ifosfamide; ilmofosine; imatinib mesylate; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; volitinib; vorozole; zeniplatin; zinostatin; zorubicin hydrochloride and the like.

Other examples of treating a cancer mediated by Bmi-1 include treatment with an anti-cancer or anti-proliferative agent wherein the anti-cancer or anti-proliferative agent is selected from, but not limited to: 20-Epi-1,25-dihydroxyvitamin D3 (MC1288, MC1301, KH 1060); 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, antiestrogen; antineoplaston; antisense oligonucleotides; aphidicolin glycinate; apoptosis gene modulators; apoptosis regulators; apurinic acid; ara-CDP-DL-PTBA (0-palmitoyl-1-thioglycerol); arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole (CaRest M3); CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate (YNKO 1 or Starasid®); cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide/estrogen/progesterone combinations; leuprorelin; levamisole; LFA-3TIP (see, International Publication No. WO93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF tautomerase inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A/myobacterium cell wall skeleton (CWS/MPL); mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone/pentazocine combinations; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine (BCX-34); pentosan polysulfate sodium; pentostatin; pentrozole; perflubron; perfosfamide; perillyl alcohol dehydrogenase; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; volitinib; vorozole; zanoterone; zeniplatin; zilascorb; zinostatin stimalamer and the like.

In some embodiments, the additional agent that may be used in combination with a compound of Formula (I) or a form thereof described herein is one or more immunomodulatory agent(s). Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), cancer molecules, organic compounds, and inorganic compounds.

In particular, one or more immunomodulatory agents that may be used in combination with a compound of Formula (I) or a form thereof described herein include, but are not limited to, methotrexate, leflunomide, cyclophosphamide, cytoxan, cyclosporine A, minocycline, azathioprine (Imuran®), antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T-cell receptor modulators, cytokine receptor modulators, and modulators mast cell modulators.

In one embodiment, the immunomodulatory agent is a chemotherapeutic agent. In an alternative embodiment, the immunomodulatory agent is an immunomodulatory agent other than a chemotherapeutic agent. In some embodiments, the additional agent used described herein is not an immunomodulatory agent.

In some embodiments, the additional agent that may be used in combination with a compound of Formula (I) or a form thereof described herein is one or more anti-angiogenic agent(s). Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and cancer molecules that reduce or inhibit angiogenesis. In other embodiments, the additional agent described herein is not an anti-angiogenic agent.

In some embodiments, the additional agent that may be used in combination with a compound of Formula (I) or a form thereof described herein is one or more anti-inflammatory agent(s). Non-limiting examples of anti-inflammatory agents include any anti-inflammatory agent useful in treating inflammatory disorders. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT®), β2-agonists (e.g., albuterol (VENTOLIN® and PROVENTIL®), bitolterol (TORNALATE®), levalbuterol (XOPONEX®), metaproterenol (ALUPENT®), pirbuterol (MAXAIR®), terbutlaine (BRETHAIRE® and BRETHINE®), albuterol (PROVENTIL®, REPETABS®, and VOLMAX®), formoterol (FORADIL AEROLIZER®), salmeterol (SEREVENT® and SEREVENT DISKUS®)), methylxanthines (e.g., theophylline (UNIPHYL®, THEO-DUR®, SLO-BID®, AND TEHO-42®)) and the like. Examples of NSAIDs include, but are not limited to, aspirin, ibuprofen, celecoxib (CELEBREX®), diclofenac (VOLTAREN®), etodolac (LODINE®), fenoprofen (NALFON®), indomethacin (INDOCIN®), ketoralac (TORADOL®), oxaprozin (DAYPRO®), nabumentone (RELAFEN®), sulindac (CLINORIL®), tolmentin (TOLECTIN®), rofecoxib (VIOXX®), naproxen (ALEVE®, NAPROSYN®), ketoprofen (ACTRON®), nabumetone (RELAFEN®) and the like. Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON®), corticosteroids (e.g., methylprednisolone (MEDROL®)), cortisone, hydrocortisone, prednisone (PREDNISONE® and DELTASONE®), prednisolone (PRELONE® and PEDIAPRED®), triamcinolone, azulfidine, inhibitors of eicosanoids (e.g., prostaglandins, thromboxanes or leukotrienes) and the like.

In certain embodiments, the additional agent that may be used in combination with a compound of Formula (I) or a form thereof described herein is an alkylating agent, a nitrosourea, an antimetabolite, an anthracyclin, a topoisomerase II inhibitor, a mitotic inhibitor and the like. Alkylating agents include, but are not limited to, busulfan, cisplatin, carboplatin, cholormbucil, cyclophosphamide, ifosfamide, decarbazine, mechlorethamine, mephalen, temozolomide and the like. Nitrosoureas include, but are not limited to, carmustine (BiCNU®), lomustine (CeeNU®) and the like. Antimetabolites include, but are not limited to, 5-fluorouracil, capecitabine, methotrexate, gemcitabine, cytarabine, fludarabine and the like. Anthracyclins include, but are not limited to, daunorubicin, doxorubicin, epirubicin, idarubicin, mitoxantrone and the like. Topoisomerase II inhibitors include, but are not limited to, topotecan, irinotecan, etopiside (VP-16), teniposide and the like. Mitotic inhibitors include, but are not limited to, taxanes (paclitaxel, docetaxel), the vinca alkaloids (vinblastine, vincristine, and vinorelbine) and the like.

In more specific embodiments, the additional anti-cancer agent, anti-proliferative agent or chemotherapeutic agent that may be used in combination with a compound of Formula (I) or a form thereof described herein includes, and is not limited to aflibercept, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin (IV and liposomal), docetaxel, doxorubicin (IV and liposomal), enzastaurin, epirubicin, etoposide, fludarabine, 5-fluorouracil (5-FU), gemcitabine, gliadel implants, hydroxycarbamide, idarubicin, ifosfamide, imatinib mesylate, irinotecan, lanreotide, lenalidomide, leucovorin, lomustine, melphalan, mercaptopurine, mesna, methotrexate, mitomycin, mitoxantrone, octreotide, oxaliplatin, paclitaxel, pemetrexed, pentostatin, procarbazine, raltitrexed, satraplatin, sorafenib, streptozocin, sunitinib, tegafur-uracil, temozolomide, teniposide, thalidomide, thiotepa, tioguanine, topotecan, treosulfan, vatalanib, vinblastine, vincristine, vindesine, vinorelbine, volitinib, ZD6474, monoclonal antibodies (such as bevacizumab, cetuximab, IMC-A12, IMC-1121B, medi-522, rituximab and the like), hormonal agents (such as anastrozole, bicalutamide, buserelin, cyproterone, diethylstilbestrol, exemestane, flutamide, goserelin (breast and prostrate), letrozole, leuprorelin, medroxyprogesterone, megestrol acetate, tamoxifen, toremifene, triptorelin and the like), biological agents (such as interferon, interleukin-12 and the like), angiogenesis receptor tyrosine kinase (RTK) inhibitors (such as AE-941, angiostatin, carboxyamidotriazole, cilengitide, endostatin, halofuginone hydrobromide, 2-methoxyestradiol, squalamine lactate, SU6668 and the like), tubulin binding agents (such as combretastatin A4 phosphate and the like), matrix metalloproteinase inhibitors (such as BMS-275291 and the like) and/or serine/threonine/tyrosine kinase inhibitors and an optional nonsteroidal or COX-2 anti-inflammatory agent (such as celecoxib and the like) or corticosteroid agents (such as prednisone and the like).

In more particular embodiments, one or more additional anti-cancer, anti-proliferative or chemotherapeutic agents that may be used in combination with a compound of Formula (I) or a form thereof described herein is selected from bevacizumab, carboplatin, cisplatin, docetaxel, doxorubicin, exemestane, gemcitabine, 5-fluorouracil, imatinib, irinotecan, sorafenib, sunitinib, temozolomide, volitinib or combinations thereof.

In some embodiments, a compound of Formula (I) or a form thereof described herein and one or more additional anti-cancer, anti-proliferative or chemotherapeutic agents is used in combination with radiation therapy comprising the use of x-rays, gamma rays and other sources of radiation to destroy cancer cells or tumor cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed close to cancer cells, tumor cells and/or a tumor mass.

Currently available anti-cancer, anti-proliferative or chemotherapeutic agents, their dosage regimens, routes of administration and recommended usage alone or in combination are known in the art and have been described in literature such as the *Physician's Desk Reference*.

Any anti-cancer, anti-proliferative or chemotherapeutic agent or anti-cancer therapy which is known to be useful, or which has been used or is currently being used for the treatment of a cancer mediated by Bmi-1, can be used in combination with compounds of Formula (I) or a form thereof described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N J, 1999; Cecil Textbook of Medicine, 20th Ed., Bennett and Plum (eds.), W.B. Saunders, Philadelphia, 1996, and Physician's Desk Reference for information regarding cancer therapies (e.g., using prophylactic or therapeutic agents) which have been or are currently being used for preventing, treating and/or managing a cancer mediated by Bmi-1.

Pharmaceutical Compositions

The present description is also directed to a pharmaceutical composition for use in treating a cancer mediated by Bmi-1 comprising an effective amount of a compound of Formula (I) or a form thereof in admixture with a pharmaceutically acceptable excipient.

An embodiment described herein includes a pharmaceutical composition made by the process of admixing a compound of Formula (I) or a form thereof with a pharmaceutically acceptable excipient. The pharmaceutical composition may also be formulated to achieve a physiologically compatible pH of about pH 7, ranging from about pH 3 to about pH 11.

Another embodiment includes the use of a compound of Formula (I) or a form thereof in a pharmaceutical composition for use in treating a cancer mediated by Bmi-1 comprising an effective amount of a compound of Formula (I) or a form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

In another embodiment, the pharmaceutical composition for use in treating a cancer mediated by Bmi-1 may comprise a combination product of one or more compounds of Formula (I) or a form thereof described herein and one or more additional agents useful in the treatment of a cancer mediated by Bmi-1, such as an anti-cancer, anti-proliferative, chemotherapeutic or biochemotherapeutic agent.

The term "pharmaceutically acceptable excipient" refers to a pharmacologically inactive substance formulated for administration with an active pharmaceutical agent, such as the compounds of Formula (I) or a form thereof described herein. The term refers to any pharmaceutical excipient that may be administered without undue toxicity. Pharmaceutically acceptable excipients may be determined in part by the particular composition being administered, as well as by the particular mode of administration and/or dosage form.

Nonlimiting examples of pharmaceutically acceptable excipients include carriers, solvents, stabilizers, adjuvants, diluents, etc. Accordingly, there exists a wide variety of suitable formulations of pharmaceutical compositions as described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. Suitable formulations for oral administration include solids, liquid solutions, emulsions and suspensions, while suitable inhaleable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert fillers, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions described herein for use in treating a cancer mediated by Bmi-1 may be formulated as suspensions comprising a compound of Formula (I) or a form thereof described herein in admixture with at least one pharmaceutically acceptable excipient suitable for the manufacture of a suspension. In yet other embodiments, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, isotonic sodium chloride solution and the like. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds of Formula (I) or a form thereof described herein may be substantially modified by substitutions or additions of chemical or biochemical moieties which make them more suitable for delivery (e.g., increase solubility, bioactivity, palatability, decrease adverse reactions, etc.), for example by esterification, glycosylation, PEGylation and the like.

In some embodiments, the compound of Formula (I) or a form thereof described herein is formulated for oral administration in formulations that enhance the oral bioavailability of such compounds of Formula (I) or a form thereof. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil and the like.

In other embodiments, the bioavailability of a compound of Formula (I) or a form thereof may be enhanced by using particle size optimization techniques including, but not limited to, the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of $\alpha$-, $\beta$-, and $\gamma$-cyclodextrin, and hydroxypropyl-$\beta$-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the active pharmaceutical ingredient in the composition.

General Synthetic Examples

As disclosed herein, the methods for preparing the compounds of Formula (I) or a form thereof described herein commonly use standard, well-known synthetic methodology. Many of the starting materials are commercially available or can be prepared in the Specific Synthetic Examples that follow using techniques known to those skilled in the art. Functional transformations to modify substituents may also be undertaken where chemically feasible and are considered to be included within the scope of the General Schemes and the knowledge of a person of ordinary skill in the art. Compounds of Formula (I) or a form thereof can be prepared as described in the Schemes below.

General Synthetic Examples

As disclosed herein, the methods for preparing the compounds of Formula (I) or a form thereof described herein commonly use standard, well-known synthetic methodology. Many of the starting materials are commercially available or can be prepared in the Specific Synthetic Examples that follow using techniques known to those skilled in the art. Functional transformations to modify substituents may also be undertaken where chemically feasible and are considered to be included within the scope of the General Schemes and the knowledge of a person of ordinary skill in the art. Compounds of Formula (I) or a form thereof can be prepared as described in the Schemes below.

Scheme A Substituted Pyrazine or Pyridine Compounds

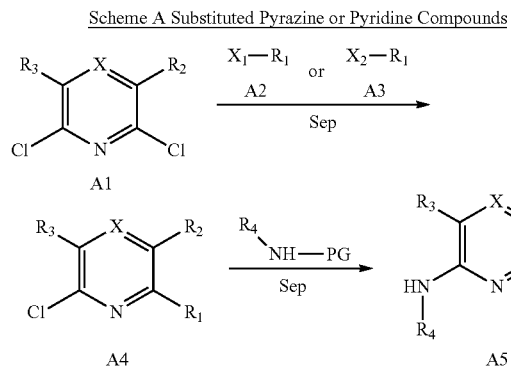

Compound A4 is prepared by reacting a substituted pyrazine or pyridine Compound A1 with a substituted heteroaromatic or heterocyclic Compound A3 (such as an $X_2$ substituted monocyclic or bicyclic ring system selected from $R_1$, as earlier defined, wherein $X_2$ represents a proton group (such as NH and the like) substituted on a nitrogen atom of $R_1$) in the presence of a base (such as KOtBu, NaOtBu, NaOtAm, $K_2CO_3$ and the like) in a solvent (such as THF, DMF and the like) at a suitable temperature.

Alternatively, Compound A4 is prepared by reacting a substituted pyrazine or pyridine Compound A1 with a substituted heteroaromatic or heterocyclic Compound A2 (such as an $X_1$ substituted monocyclic or bicyclic ring system selected from $R_1$, as earlier defined, wherein $X_1$ represents a proton group substituted on a carbon atom) via a palladium catalyzed cross-coupling reaction using a palladium source (wherein the palladium source is selected from $Pd_2(dba)_3$, $PdCl_2(allyl)$, $PdCl_2(ACN)$, $[Pd(OAc)_2]_3$ and the like).

In one embodiment, when $R_2$ and $R_3$ are different or when Compound A1 is pyridine and X is C—$R_5$ and $R_5$ is halogen, the product Compound A4 is a mixture of regioisomers, wherein the term "Sep" refers to isolating the desired Compound A4 isomer to be carried forward from the mixture using separation techniques known to those of ordinary skill in the art. In another embodiment, when X is C—$R_5$ and $R_5$ is a substituted amine, the amine may be protected with a suitable protecting group (using a reagent such as di-tert-butyldicarbonate and the like).

Compound A5, representative of the Compound of Formula (I), may be prepared by reacting Compound A4 with various substituted $C_{3-14}$cycloalkyl, aryl, heteroaryl or heterocyclyl amines (wherein PG represents an optionally present protecting group monosubstituted on the amine) in the presence of a strong base (such as KOtBu, NaOtBu, NaOtAm and the like) in a solvent (such as THF, DMF and the like).

Alternatively, Compound A5 may be prepared by reacting Compound A4 with a substituted $C_{3-14}$cycloalkyl, aryl, heteroaryl or heterocyclyl amines (wherein the protecting group is absent) via a palladium catalyzed cross-coupling reaction using a mixture of a phosphino ligand:palladium source (wherein the palladium source is selected from $Pd_2(dba)_3$, $PdCl_2(allyl)$, $PdCl_2(ACN)$, $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like). Each isomer may be isolated from the mixture using separation techniques known to those of ordinary skill in the art, followed by deprotection also using techniques known to those of skill in the art.

Scheme B Substituted Pyrazine or Pyridine Compounds

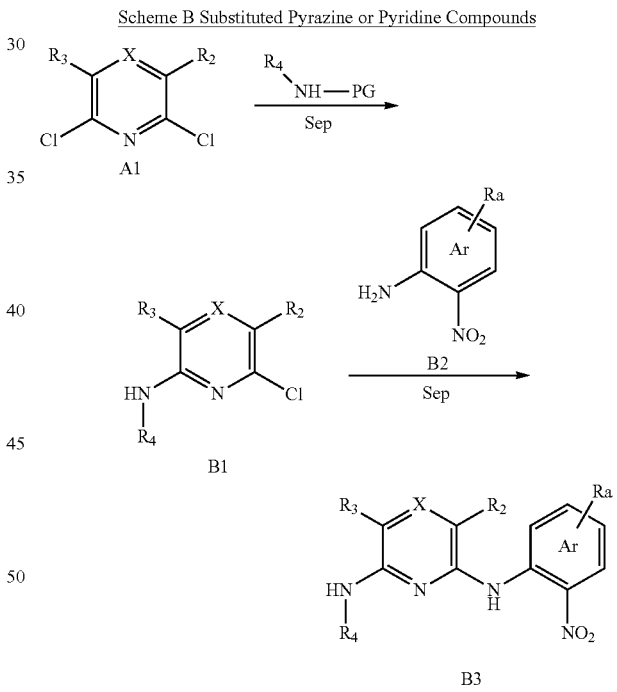

Compound A1 (wherein when X is C—$R_5$ and $R_5$ is a substituted amine, the amine may be protected with a suitable protecting group) is coupled with various substituted $C_{3-14}$cycloalkyl, aryl, heteroaryl or heterocyclyl amines (wherein PG represents an optionally present protecting group monosubstituted on the amine) in the presence of a strong base (such as KOtBu, NaOtBu, NaOtAm and the like) in a solvent (such as THF, DMF and the like), followed by deprotection using techniques known to those of skill in the art to provide a Compound B1.

When $R_2$ and $R_3$ are different or when Compound A1 is pyridine and X is C—$R_5$ and $R_5$ is halogen, the product Compound B1 is obtained as a mixture of regioisomers, wherein the term "Sep" refers to isolating the desired Compound B1 isomer to be carried forward from the mixture using separation techniques known to those of ordinary skill in the art.

Compound B3 is prepared by cross-coupling of Compound B1 with a nitro substituted amine Compound B2 (wherein Ar represents an aromatic or heteroaromatic ring; and, wherein Ra represents one, two or three optional $R_6$ substituents) via a palladium catalyzed cross-coupling reaction using a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like).

When Compound B1 is pyridine and X is C—$R_5$ and $R_5$ is halogen, the product Compound B3 is obtained as a mixture of regioisomers, wherein the term "Sep" refers to isolating the desired Compound B3 isomer to be carried forward from the mixture using separation techniques known to those of ordinary skill in the art.

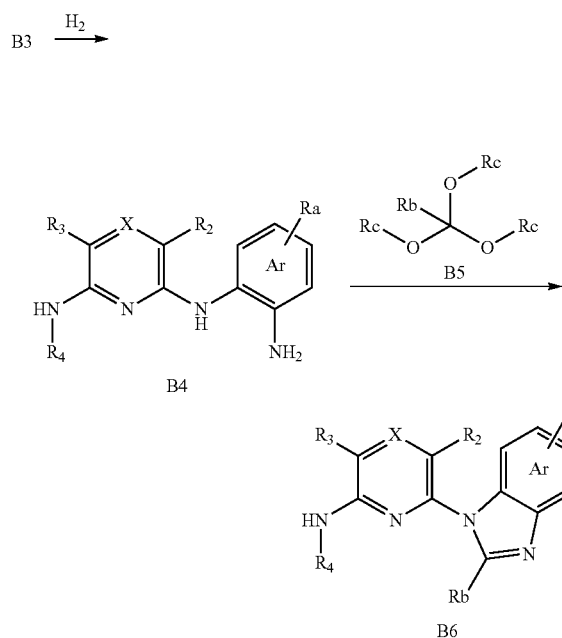

Compound B4 is prepared by reacting Compound B3 in the presence of hydrogen and a catalyst (such as nickel, platinum, palladium on carbon and the like).

Compound B6 is prepared by condensation of Compound B4 with an orthoester Compound B5 (wherein Rb represents an additional optional $R_6$ substituent and Rc represents $C_{1-3}$alkyl). Compound B6 may also be prepared by cyclizing Compound B4 with a variety of reactants to obtain the addition of an optional $R_6$ substituent. For example, the reactant may be TCDI, wherein the additional optional $R_6$ substituent is a thio-carbonyl which may be further substituted.

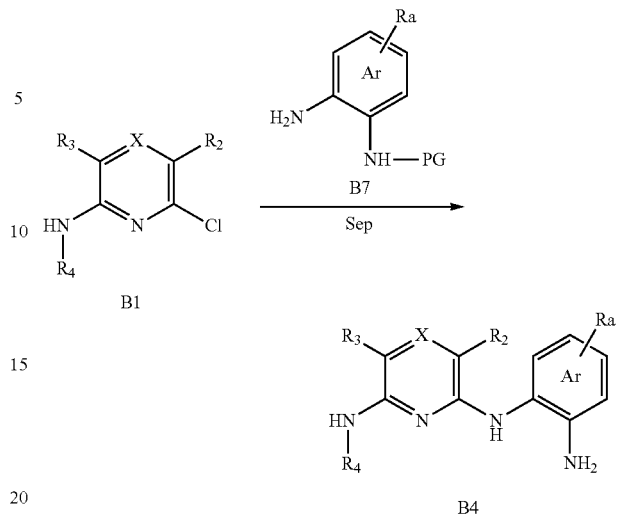

Alternatively, Compound B4 may be prepared by reacting Compound B1 with various substituted diamine Compound B7 (wherein Ar represents an aromatic or heteroaromatic ring; and, wherein Ra represents one, two or three optional $R_5$ substituents and PG represents an optional protecting group) in the presence of a strong base (such as KOtBu, NaOtBu, NaOtAm and the like) in a solvent (such as THF, DMF and the like), followed by deprotection using techniques known to those of skill in the art to provide a Compound B4.

When $R_2$ and $R_3$ are different or when Compound B1 is pyridine and X is C—$R_5$ and $R_5$ is halogen, the product Compound B4 is obtained as a mixture of regioisomers, wherein the term "Sep" refers to isolating the desired Compound B4 isomer to be carried forward from the mixture using separation techniques known to those of ordinary skill in the art.

Alternatively, Compound B4 is prepared by reacting Compound B1 with the substituted diamine Compound B7 via a palladium catalyzed cross-coupling reaction using a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like), followed by deprotection using techniques known to those of skill in the art to provide a Compound B4.

Scheme C Substituted Pyridine Compounds

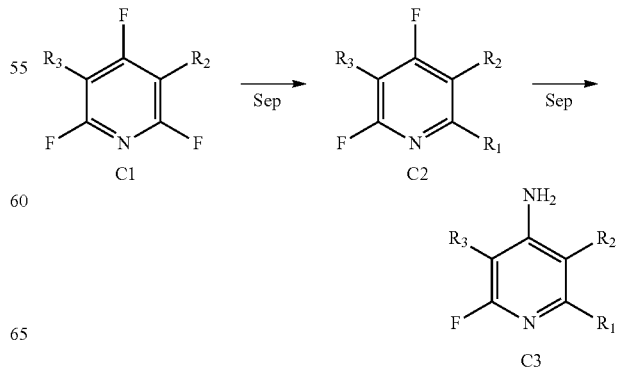

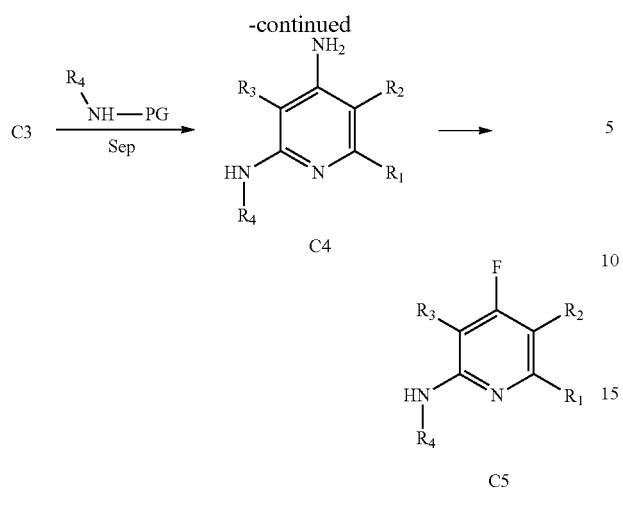

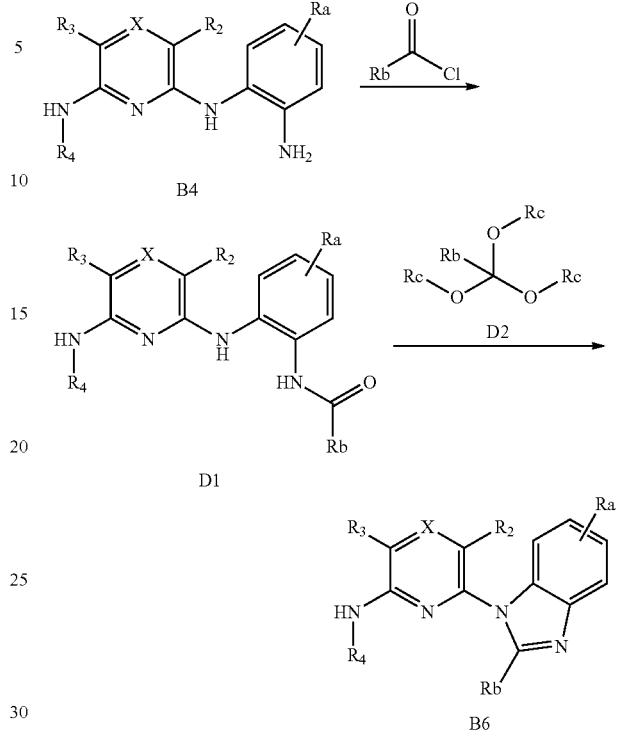

Compound C1 is reacted with a substituted heteroaromatic or heterocyclic compound (such as a substituted monocyclic or bicyclic ring system selected from $R_1$, as earlier defined) to provide an intermediate Compound C2 as a mixture of regioisomers. The desired isomer to be carried forward may be isolated from the mixture using separation techniques known to those of ordinary skill in the art.

Compound C3 is prepared as a mixture of regioisomers by reacting Compound C2 with ammonia. The desired isomer to be carried forward may be isolated from the mixture using separation techniques known to those of ordinary skill in the art. Compound C3 is then coupled with various substituted $C_{3-14}$cycloalkyl, aryl, heteroaryl or heterocyclyl amines (wherein PG represents an optionally present protecting group monosubstituted on the amine) in the presence of a solvent (such as NMP and the like) to provide Compound C4, followed by deprotection using techniques known to those of skill in the art.

In one embodiment, Compound C5 may be obtained by reacting Compound C4 with sodium nitrite in the presence of an acid and a fluoride source (such as HF-Pyridine) at a suitable temperature.

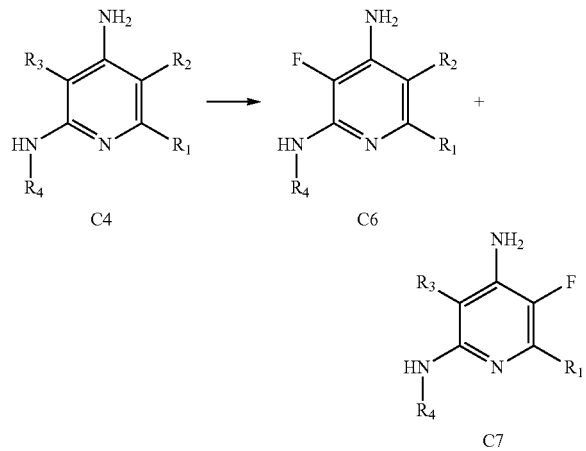

When either or both $R_2$ and $R_3$ are hydrogen, a mixture of Compound C6 and Compound C7 may be obtained via electrophilic fluorination of Compound C4 (such as with 1-(chloromethyl)-4-fluoro-1,4-diazabicyclo[2.2.2]octane-1,4-diium tetrafluoroborate) at a suitable temperature.

Compound D1 is prepared by coupling Compound B4 with a substituted acyl chloride (wherein Rb represents one optional $R_6$ substituent) in an organic solvent (such as acetonitrile and the like) at a suitable temperature.

Compound B6 is prepared by reacting Compound D1 in the presence of an acidic catalyst (such as TFA, acetic acid, formic acid, sulfuric acid and the like) and the optional presence of a dehydrating reagent Compound D2 (such as an orthoester analog of Compound B5, wherein Rc represents $C_{1-3}$alkyl) at a suitable temperature.

239

-continued

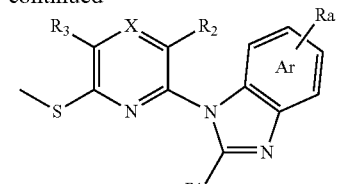

E3 →

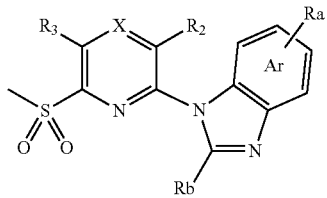

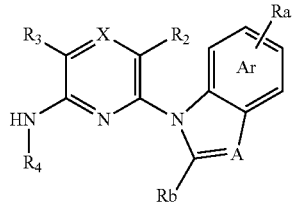

B6

Compound E2 is prepared by reacting a substituted-2-methylthio pyrazine or pyridine Compound E1 with a substituted diamine Compound B7 (wherein Ar represents an aromatic or heteroaromatic ring; and, wherein Ra represents one, two or three optional $R_5$ substituents and PG represents an optional protecting group) in the presence of a base (such as NaH, KOtBu, NaOtBu, NaOtAm, $K_2CO_3$ and the like) in a solvent (such as THF, DMF and the like) at a suitable temperature, followed by deprotection using techniques known to those of skill in the art to provide a Compound E2.

When $R_2$ and $R_3$ are different or when Compound E1 is pyridine and X is C—$R_5$ and $R_5$ is halogen, the product Compound E2 is obtained as a mixture of regioisomers, wherein the term "Sep" refers to isolating the desired Compound E2 isomer to be carried forward from the mixture using separation techniques known to those of ordinary skill in the art.

Compound E2 is reacted with an orthoester Compound B5 (wherein Rb and Rc are as defined above) in the presence of an acid (such as HOAc and the like) to provide a benzimidazole Compound E3.

Compound E4 is prepared by reacting Compound E3 with an oxidizing agent (such as mCPBA, MPS and the like) in a solvent ($CH_2Cl_2$ and the like) at a suitable temperature.

Compound B6 may be prepared by reacting Compound E4 with various substituted $C_{3-14}$cycloalkyl, aryl, heteroaryl or heterocyclyl amines (wherein PG represents an optionally present protecting group monosubstituted on the amine) in the presence of a strong base (such as KOtBu, NaOtBu, NaOtAm and the like) in a solvent (such as THF, DMF and the like), followed by deprotection using techniques known to those of skill in the art to provide a Compound B6.

Alternatively, Compound B6 may be prepared by reacting Compound E4 with a substituted $C_{3-14}$cycloalkyl, aryl, heteroaryl or heterocyclyl amine or amide via a palladium catalyzed cross-coupling reaction using a mixture of a

240 phosphino ligand:palladium source (wherein the palladium source is selected from $Pd_2(dba)_3$, $PdCl_2(allyl)$, $PdCl_2$(ACN), $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like), followed by deprotection using techniques known to those of skill in the art to provide a Compound B6.

Scheme F Substituted Pyrazine or Pyridine Intermediates

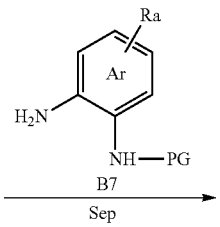

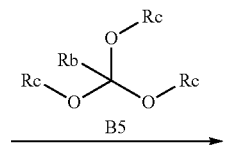

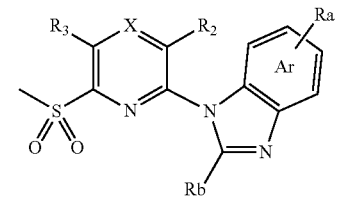

Compound F2 is prepared by reacting a substituted 2-methylsulfonyl Compound F1 with the substituted diamine Compound B7 (wherein Ar represents an aromatic or heteroaromatic ring; and, wherein Ra represents one, two or three optional $R_5$ substituents and PG represents an optional protecting group) in a solvent (such as DMSO and the like) at a suitable temperature, followed by deprotection using techniques known to those of skill in the art to provide a Compound F2.

When Compound F1 is pyridine and X is C—$R_5$ and $R_5$ is halogen, the product Compound F2 is obtained as a mixture of regioisomers, wherein the term "Sep" refers to isolating the desired Compound F2 isomer to be carried forward from the mixture using separation techniques known to those of ordinary skill in the art.

Compound E4 is prepared by reacting Compound F2 with the orthoester Compound B5 in the presence of an acid (such as HOAc and the like).

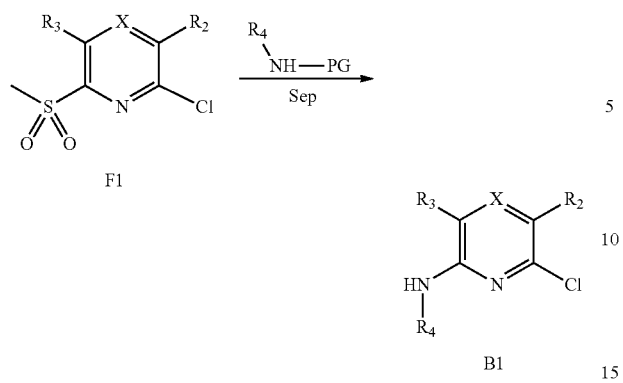

Alternatively, Compound B1 is prepared by reacting methylsulfone Compound F1 with a substituted $C_{3-14}$cycloalkyl, aryl, heteroaryl or heterocyclyl amine or amide (wherein PG represents an optionally present protecting group monosubstituted on the amine) in the presence of a strong base (such as KOtBu, NaOtBu, NaO$^t$Am and the like) in a solvent (such as THF, DMF and the like) at a suitable temperature, followed by deprotection using techniques known to those of skill in the art to provide a Compound B1.

Scheme G Functionalized Pyridine Compounds

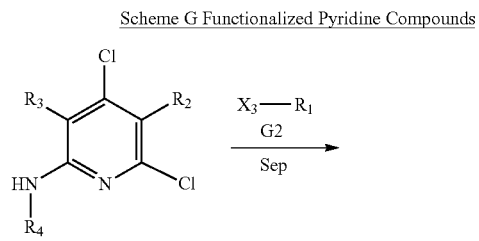

Compound G3 is prepared by reacting Compound G1 with a substituted heteroaromatic or heterocyclic Compound G2 (such as a substituted heteroaromatic or heterocyclic monocyclic or bicyclic ring system selected from $R_1$, as earlier defined; and, wherein $X_3$ represents a functional group selected from boronic acid, boronate ester, trialkyltin, zinc chloride and the like attached to a carbon atom of $R_1$), in the presence of a mixture of a phosphino ligand:palladium source (wherein the palladium source is selected from Pd$_2$(dba)$_3$, PdCl$_2$(allyl), PdCl$_2$(ACN), [Pd(OAc)$_2$]$_3$ and the like and the phosphino ligand is selected from PCy$_3$, Q-Phos, XPhos and the like; alternatively, the palladium:ligand complex may be selected from Pd(dppf)Cl$_2$, Pd(PPh$_3$)$_4$ and the like). The desired isomer to be carried forward may be isolated from the mixture using separation techniques known to those of ordinary skill in the art.

The chlorine atom in Compound G3 may be substituted with another functional group (such as a substituent selected from $R_5$), using conditions known to those of ordinary skill in the art, to provide Compound G4.

Scheme H Halo Substituted Pyridine Compounds

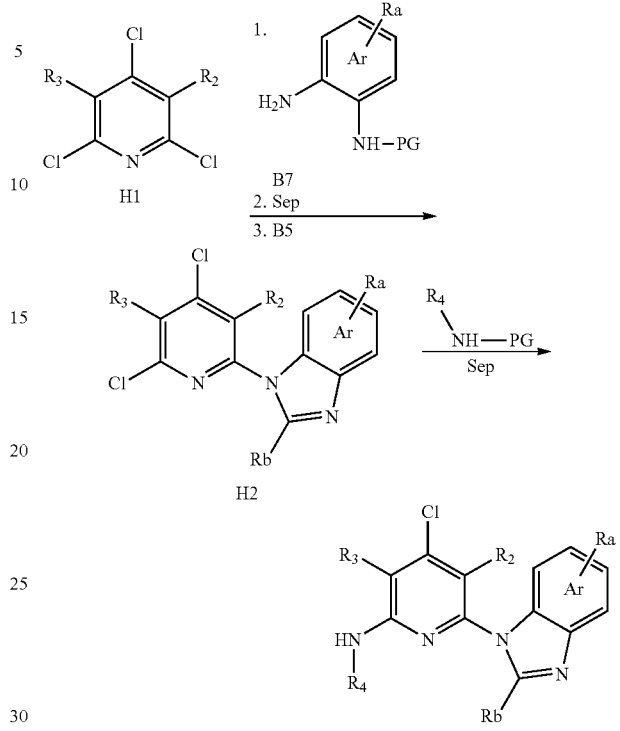

Compound H1 is reacted with diamine Compound B7 (wherein Ar represents an aromatic or heteroaromatic ring; and, wherein Ra represents one, two or three optional $R_5$ substituents and PG represents an optional protecting group) in a solvent (such as ACN, EtOH and the like), followed by separation, wherein the desired isolated intermediate is further reacted with orthoester Compound B5 in the presence of an acidic catalyst (such as AcOH and the like) at a suitable temperature to provide intermediate Compound H2. The intermediate is further reacted with a substituted $C_{3-14}$cycloalkyl, aryl, heteroaryl or heterocyclyl amine or amide (wherein PG represents an optionally present protecting group monosubstituted on the amine) in the presence of a strong base (such as KOtBu, NaOtBu, NaO$^t$Am and the like) in a solvent (such as THF, DMF and the like) at a suitable temperature, followed by separation and deprotection using techniques known to those of skill in the art to provide Compound H3.

Scheme I Substituted Pyrazine or Pyridine Compounds

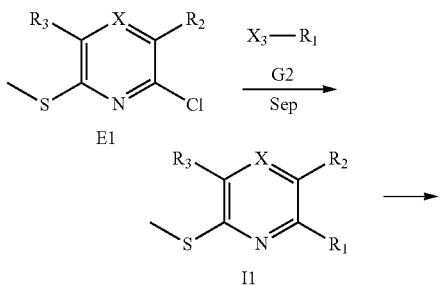

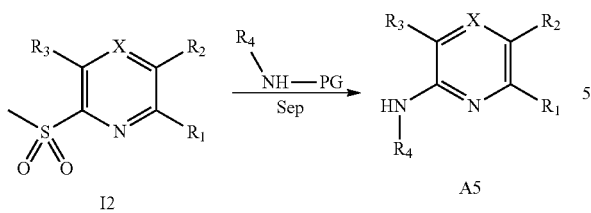
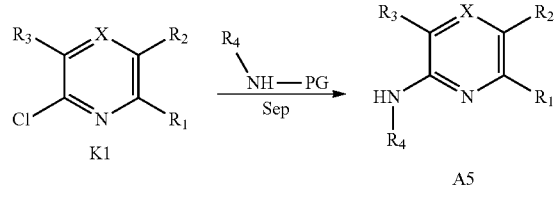

Compound I1 is prepared by reacting Compound E1 with a substituted heteroaromatic Compound G2 (such as a substituted heteroaromatic or heterocyclic monocyclic or bicyclic ring system selected from $R_1$, as earlier defined, wherein $X_3$ represents a functional group selected from boronic acid, boronate ester, trialkyltin, zinc chloride and the like attached to a carbon atom of $R_1$), in the presence of a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like).

Compound I2 is prepared by reacting Compound I1 with an oxidizing agent (such as mCPBA, MPS and the like) in a solvent (such as $CH_2Cl_2$ and the like).

Compound A5 is prepared by reacting either Compound I2 with a substituted $C_{3-14}$cycloalkyl, aryl, heteroaryl or heterocyclyl amine or amide (wherein PG represents an optionally present protecting group monosubstituted on the amine) in the presence of a strong base (such as KOtBu, NaOtBu, NaO$^t$Am and the like) in a solvent (such as THF, DMF and the like) at a suitable temperature, followed by deprotection using techniques known to those of skill in the art to provide a Compound A5.

Scheme J N-Oxide Substituted Pyrazine Compounds

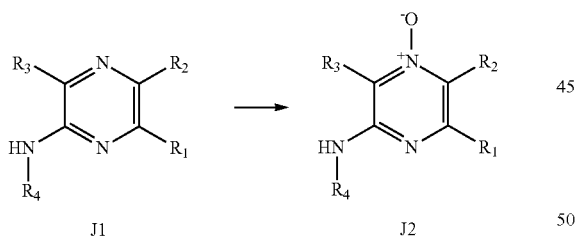

Compound J2 is prepared by reacting Compound J1 with an oxidizing agent (such as mCPBA, MPS and the like) to obtain the N-oxide, representative of a Compound of Formula (V).

Scheme K Substituted Pyrazine or Pyradine Compounds

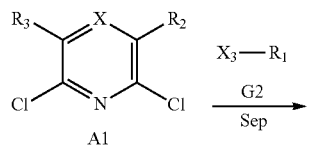

Compound K1 is prepared by reacting Compound A1 with a substituted Compound G2 (wherein $R_1$ is a substituted heteroaromatic or heterocyclic monocyclic or bicyclic ring system; and, wherein $X_3$ represents a functional group such as a boronic acid, boronate ester, trialkyltin, zinc chloride and the like attached to a carbon atom of $R_1$), in the presence of a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like).

When $R_2$ and $R_3$ are different or when Compound A1 is pyridine and X is C—$R_5$ and $R_5$ is halogen, the product Compound K1 is a mixture of regioisomers, wherein the desired Compound K1 isomer to be carried forward is isolated from the mixture using separation techniques known to those of ordinary skill in the art.

Compound A5 is prepared by reacting Compound K1 with various substituted $C_{3-14}$cycloalkyl, aryl, heteroaryl or heterocyclyl amines (wherein PG represents an optionally present protecting group monosubstituted on the amine) in the presence of a strong base (such as KOtBu, NaOtBu, NaO$^t$Am, NaH, NaHMDS and the like) in a solvent (such as THF, DMF and the like) at a suitable temperature, followed by separation and deprotection using techniques known to those of skill in the art to provide a Compound A5.

Alternatively, Compound K1 may be prepared via a Heck reaction of Compound A1 with Compound A2 (wherein $X_1$ represents a proton group on a carbon atom of $R_1$), followed by separation.

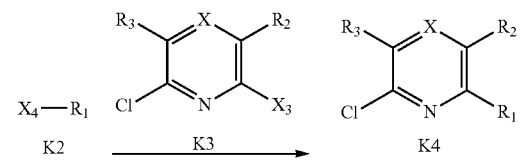

Alternatively, Compound K4 is prepared by reacting a Compound K2 (wherein $R_1$ is a substituted heteroaromatic or heterocyclic monocyclic or bicyclic ring system; and, wherein $X_4$ represents a reactive group such as a halogen atom selected from bromo, chloro or iodo) with a substituted Compound K3 (wherein $X_3$ represents a functional group such as a boronic acid, boronate ester, trialkyltin, zinc chloride and the like).

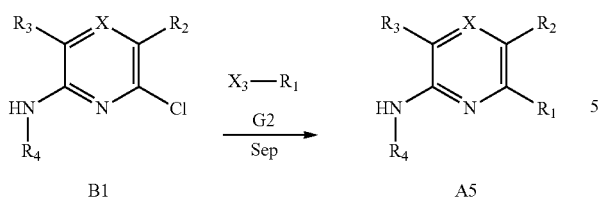

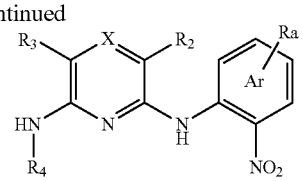

Alternatively, Compound A5 is prepared by reacting Compound B1 with a substituted Compound G2 (wherein $R_1$ is a substituted heteroaromatic or heterocyclic monocyclic or bicyclic ring system; and, wherein $X_3$ represents a functional group such as a boronic acid, boronate ester, trialkyltin, zinc chloride and the like attached to a carbon atom of $R_1$).

Alternatively, Compound A5 may be prepared via a Heck reaction of Compound B1 with Compound A2 (wherein $X_1$ represents a proton group on a carbon atom of $R_1$), followed by separation.

Scheme L Substituted Pyrazine or Pyridine Compounds

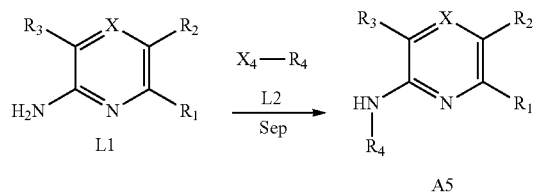

Compound A5 is prepared by reacting a substituted Compound L1 with a monocyclic or bicyclic aromatic ring system Compound L2 (wherein $R_4$ is a $C_{3-14}$cycloalkyl, aryl, heteroaryl or heterocyclyl ring system; and, wherein $X_4$ is a halogen atom selected from bromo, chloro or iodo) in the presence of a transition metal catalyst (such as a catalyst containing a metal selected from copper, palladium and the like).

Scheme M Substituted Pyrazine or Pyridine Intermediates

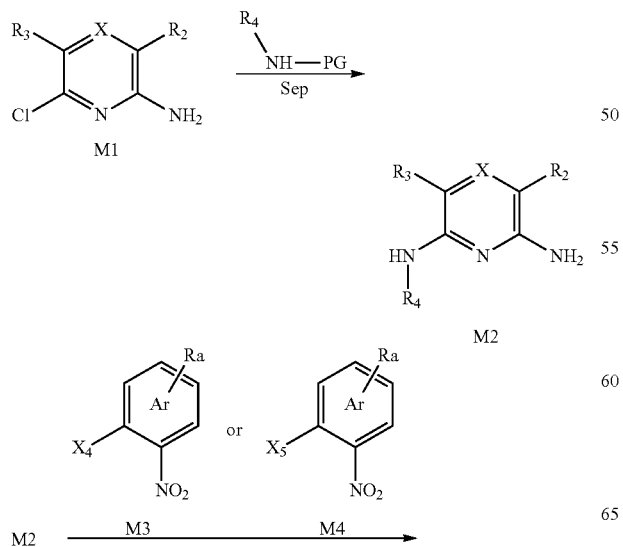

A substituted Compound M1 (wherein when X is C—$R_5$ and $R_5$ is a substituted amine, the amine may be protected with a suitable protecting group) is coupled with various substituted $C_{3-14}$cycloalkyl, aryl, heteroaryl or heterocyclyl amines (wherein PG represents an optionally present protecting group monosubstituted on the amine) in the presence of a strong base (such as KOtBu, NaOtBu, NaOtAm and the like) in a solvent (such as THF, DMF and the like), followed by separation and deprotection using techniques known to those of skill in the art to provide a Compound M2.

When $R_2$ and $R_3$ are different or when Compound M1 is pyridine and X is C—$R_5$ and $R_5$ is halogen, the product Compound M2 is a mixture of regioisomers, wherein the desired Compound M2 isomer to be carried forward is isolated from the mixture using separation techniques known to those of ordinary skill in the art.

Alternatively, Compound M2 may be prepared by reaction of Compound M1 with various substituted $C_{3-14}$cycloalkyl, aryl, heteroaryl or heterocyclyl amines (wherein PG represents an optionally present protecting group monosubstituted on the amine) in the presence of a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, the palladium:ligand complex may be selected from $Pd(dppf)Cl_2$, $Pd(PPh_3)_4$ and the like), followed by separation and deprotection using techniques known to those of skill in the art.

Compound B3 is prepared by reacting Compound M2 with a substituted ortho-halo-nitro benzene Compound M3 (wherein $X_4$ is a halogen atom selected from bromo, chloro or iodo) in the presence of a transition metal catalyst (such as a catalyst containing a metal selected from copper, palladium and the like, when the halogen atom is selected from bromo, chloro or iodo).

Alternatively, Compound B3 is prepared by reacting Compound M2 with a substituted ortho-halo-nitro benzene Compound M4 (wherein $X_5$ is a halogen atom selected from bromo, chloro, fluoro or iodo) in the presence of a strong base (such as KOtBu, NaOtBu, NaOtAm and the like) in a solvent (such as THF, DMF and the like).

Specific Synthetic Examples

To assist in understanding the scope of the compounds of Formula (I) or a form thereof described herein, the following Specific Examples are included. The experiments relating to the compounds of Formula (I) or a form thereof described herein should not, of course, be construed as specifically limiting the scope of the compounds of Formula (I) or a form thereof described herein and such variations of the compounds of Formula (I) or a form thereof as described herein, now known or later developed, which would be within the purview of one skilled in the art are considered to fall within the scope as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the characterization of the compounds of Formula (I) or a form thereof described herein are approximations, the numerical values set forth in the working examples are reported as precisely as possible. Any numerical value, however, inherently contains certain errors necessarily resulting from the standard deviation found in their respective testing measurements.

The compounds of Formula (I) or a form thereof provided herein are described in more detail with reference to the following non-limiting examples, which are offered to more fully illustrate the scope of the compounds of Formula (I) or a form thereof described herein, but are not to be construed as limiting the scope thereof. The examples illustrate the preparation of compounds of Formula (I) or a form thereof described herein, and the testing of these compounds of Formula (I) or a form thereof in vitro and/or in vivo. Those of skill in the art will understand that the synthesis techniques described in these examples represent techniques that fall within the practice of those having ordinary skill in the chemical arts, and as such constitute preferred modes for the practice thereof. However, it should be appreciated that those having skill in the art should, in light of the present disclosure, appreciate that many changes can be made in the specific methods that are disclosed herein while still obtaining a like or similar result without departing from the spirit and scope described herein.

The reagents and solvents were used as purchased (from a variety of vendors), except where noted. Where applicable, the term "Celite" is used as shown in the following examples to represent the tradename CELITE® (brand of diatomaceous earth). Where applicable, chromatographic separations were performed using techniques and equipment commonly available such as, for example, by using an ISCO CombiFlash® Rf system. Where applicable, NMR spectra were obtained using techniques and equipment commonly available such as, for example, by using a Bruker Avance III$^{500}$ spectrometer with deuterated solvents such as, for example, DMSO-d$_6$ or residual solvent as standard. Where applicable, melting points were determined using techniques and equipment commonly available such as, for example, by using a SRS OptiMelt® MPA100 (values as obtained without correction/calibration). Where applicable, TLC analysis was performed using techniques and equipment commonly available such as, for example, by using Aldrich 254 nm glass-backed plates (60 Å, 250 µm), visualized using UV and I$_2$ stains. Where applicable, ESI mass spectra were obtained using techniques and equipment commonly available such as, for example, by using an ACQUITY UPLC® System, with values shown as [M+H]$^+$ or [M−H]$^−$, unless otherwise indicated. Where applicable, the structure of the product was obtained via a 2D NOESY (Nuclear OverhausEr SpectroscopY) experiment.

The following abbreviations are provided to ensure the terms used herein are unambiguous to one skilled in the art:

| Abbreviation | Meaning |
| --- | --- |
| AcOH or HOAc | acetic acid |
| ACN or MeCN | acetonitrile |
| AlMe$_3$ | trimethylaluminum |
| APC | allylpalladium (II) chloride dimer |
| Boc | tert-butoxycarbonyl |
| CsOAc | cesium acetate |
| DCM or CH$_2$Cl$_2$ | dichloromethane |
| DME | dimethyl ether |
| DMF | dimethyl formamide |
| DMA | dimethylacetamide |
| DMAP | 4-dimethylaminopyridine |
| DMSO | dimethylsulfoxide |
| EtOAc | ethyl acetate |
| EtOH | ethanol |
| HPLC | high performance liquid chromatography |
| h, hr, min, s | hour (h or hr), minute (min), second (s) |
| iPrMgCl*LiCl | isopropylmagnesium chloride lithium chloride complex |
| iPrOAc | isopropyl acetate |
| K$_2$CO$_3$ | potassium carbonate |
| K$_3$PO$_4$ | potassium phosphate |
| KOtBu or t-BuOK | potassium tert-butoxide |
| LC/MS, LCMS or LC-MS | liquid chromatographic mass spectroscopy |
| MeOH | methanol |
| MeNH$_2$ × HCl | methanamine hydrochloride |
| MS | mass spectroscopy |
| m.p. | melting point (shown in ° Centigrade) |
| MPS | potassium peroxymonosulfate or OXONE® |
| NaH | sodium hydride |
| NaHCO$_3$ | sodium bicarbonate |
| NaHMDS | sodium hexamethyldisilazide |
| NaIO$_4$ | sodium periodate |
| NaOH | sodium hydroxide |
| NaOtAm | sodium tert-pentoxide |
| NaOMe | sodium methoxide |
| NaOEt | sodium ethoxide |
| NaOtBu | sodium tert-butoxide |
| NCS | N-chlorosuccinimide |
| NH$_4$Cl | ammonium chloride |
| NH$_4$OH | ammonium hydroxide |
| NIS | N-iodosuccinimide |
| NMP | N-methylpyrrolidone |
| NMR | nuclear magnetic resonance |
| PCl$_5$ | phosphorus perchloride or phosphorus pentachloride |
| PCy$_3$ | tricyclohexylphosphine |
| [Pd] | palladium |
| Pd/C. ° | palladium on carbon |
| Pd$_2$(dba)$_3$ or Pd$_2$dba$_3$ | tris(dibenzylideneacetone)dipalladium(0) |
| Pd(dppf)Cl$_2$ | [1,1'-bis(diphenylphosphino)ferrocene]dichloropalladium(II) |
| PdCl$_2$(ACN) | bis(acetonitrile)dichloropalladium(II) |
| PdCl$_2$(allyl) | chloroallylpalladium(II) dimer |
| [Pd(OAc)$_2$]$_3$ | palladium (II) acetate |
| Pd(PPh$_3$)$_4$ | tetrakis(triphenylphosphine)palladium |
| POCl$_3$ | phosphorus oxychloride |
| PPh$_3$ | triphenylphosphine |
| psi | pounds per square inch pressure |
| Pt/C | platinum on carbon |
| PTSA | p-toluenesulfonic acid |
| Q-Phos or QPhos | 1,2,3,4,5-pentaphenyl-1'-(di-tert-butylphosphino)ferrocene |
| RT | room temperature |
| TBSO or OTBS | tert-butyldimethylsilyloxy |
| TCDI | 1,1'-thiocarbonyldiimidazole |
| t-Bu | tert-butyl |
| TEA, NEt$_3$, Et$_3$N | triethylamine |
| TFA | trifluoroacetic acid |
| TFAA | trifluoroacetic anhydride |

-continued

| Abbreviation | Meaning |
|---|---|
| THF | tetrahydrofuran |
| TsOH × H₂O | p-toluenesulfonic acid monohydrate |
| UPLC | ultra performance liquid chromatography |
| Xphos or XPhos | 2-dicyclohexylphosphino-2',4',6'-triisopropylbiphenyl |

Example 1

N-(3-fluoro-4-methoxyphenyl)-6-(2-methyl-1H-benzimidazol-1-yl)pyrazin-2-amine (Cpd 12)

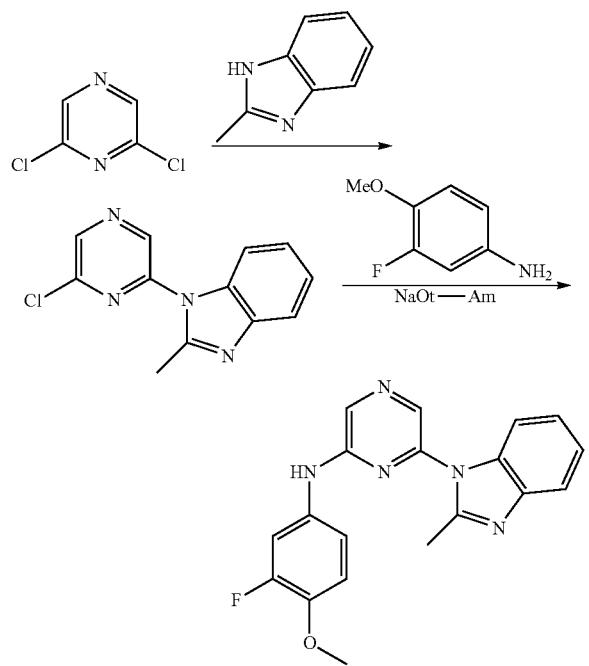

Step 1. To 2,6-dichloropyrazine (20 g, 134 mmol) was added 2-methyl benzimidazole (17.7 g, 134 mmol) and dimethylformamide (100 mL). The mixture was cooled in an ice-bath, then NaOt-Am was added (2.5 M in THF, 54 mL, 134 mmol). The reaction mixture was slowly warmed to 15° C. (external temperature) over 6 hours, then an aqueous saturated solution of NH₄Cl was added. The mixture was extracted with a mixture of ethyl acetate:hexane (1:1). The product was dried, then filtered through a short plug of silica gel and concentrated. The residue was sonicated with ethyl acetate, diluted with an equal volume of hexanes and filtered to provide 1-(6-chloropyrazin-2-yl)-2-methyl-1H-benzo[d]imidazole (5.9 g, 18%) as a white solid. $^1$H NMR (DMSO-d₆) δ 9.10 (s, 1H), 8.97 (d, J=0.6 Hz, 1H), 7.64-7.70 (m, 1H), 7.55-7.61 (m, 1H), 7.26-7.33 (m, 2H), 2.65 (s, 3H); MS m/z 245 (ESI) [M+H]⁺.

Step 2. To a solution of 1-(6-chloropyrazin-2-yl)-2-methyl-1H-benzo[d]imidazole (96 mg, 0.36 mmol) and 3-fluoro-4-methoxyaniline (71 mg, 0.5 mmol) in THF (1 mL) at room temperature was added KOt-Bu (1M in THF, 1 mL, 1 mmol). The mixture was reacted for 5 minutes, then the reaction was quenched with AcOH and the product partitioned between ethyl acetate and aqueous ammonium chloride. The organic layer was dried, concentrated and purified by chromatography on silica gel (gradient from ethyl acetate:hexane 1:2 to ethyl acetate:methanol 5:1). The fractions were concentrated and the residue was washed with an ethyl acetate:ether mixture, then filtered and dried to provide the title compound as a yellow/brown solid (39 mg, 25%). $^1$H NMR (DMSO-d₆) δ 9.93 (s, 1H), 8.31 (s, 1H), 8.25 (s, 1H), 7.61-7.68 (m, 2H), 7.51-7.55 (m, 1H), 7.32-7.36 (m, 1H), 7.26-7.26 (m, 1H), 7.23-7.30 (m, 2H), 7.14 (t, J=9.1 Hz, 1H), 3.79 (s, 3H), 2.63 (s, 3H); MS m/z 350 (ESI) [M+H]⁺.

Additional compounds of Formula (I) or a form thereof described herein may be prepared according to the procedure of Example 1 by substituting the appropriate starting materials, reagents and reaction conditions:

| Cpd | Name and Data |
|---|---|
| 1 | 6-(1H-benzimidazol-1-yl)-N-(4-methoxyphenyl)pyrazin-2-amine<br>$^1$H NMR (DMSO-d₆) δ: 9.65 (br. s, 1H), 8.94 (s, 1H), 8.44 (s, 1H), 8.11-8.19 (m, 2H), 7.78 (s, 1H), 7.55-7.61 (m, 2H), 7.30-7.38 (m, 2H), 6.93-7.00 (m, 2H), 3.77 (s, 3H) MS m/z 318 (theoretical) [M + H]⁺ |
| 2 | 6-(1H-benzimidazol-1-yl)-N-(4-iodophenyl)pyrazin-2-amine<br>$^1$H NMR (500 MHz, DMSO-d₆) δ 9.97 (br. s, 1H), 8.95 (s, 1H), 8.54 (s, 1H), 8.25 (s, 1H), 8.11-8.15 (m, 1H), 7.81 (ddd, J = 0.95, 2.52, 6.94 Hz, 1H), 7.65-7.73 (m, 2H), 7.51-7.57 (m, 2H), 7.37 (dddd, J = 1.58, 7.70, 7.90, 11.50 Hz, 2H); MS m/z 414 (ESI) [M + H]⁺ |
| 13 | 6-(2-methyl-1H-benzimidazol-1-yl)-N-[4-(trifluoromethyl)phenyl]pyrazin-2-amine<br>$^1$H NMR (DMSO-d₆) δ 10.36 (s, 1H), 8.44 (s, 1H), 8.39 (s, 1H), 7.89 (d, J = 8.5 Hz, 2H), 7.64-7.69 (m, 3H), 7.51-7.55 (m, 1H), 7.24-7.31 (m, 2H), 2.65 (s, 3H); MS m/z 370 (ESI) [M + H]⁺ |
| 20 | N-(4-chlorophenyl)-6-(2-methyl-1H-benzimidazol-1-yl)pyrazin-2-amine<br>$^1$H NMR (DMSO-d₆) δ 10.10 (s, 1H), 8.36 (s, 1H), 8.30 (s, 1H), 7.69-7.72 (m, 2H), 7.66 (s, 1H), 7.49-7.52 (m, 1H), 7.34-7.38 (m, 2H), 7.25-7.29 (m, 2H), 2.63 (s, 3H); MS m/z 336 (ESI) [M + H]⁺ |
| 28 | N-(3-chloro-4-methoxyphenyl)-6-(2-methyl-1H-benzimidazol-1-yl)pyrazin-2-amine<br>$^1$H NMR (DMSO-d₆) δ 9.88 (s, 1H), 8.24 (s, 1H), 8.20 (s, 1H), 7.83 (d, J = 2.8 Hz, 1H), 7.57-7.63 (m, 1H), 7.47-7.54 (m, 1H), 7.44 (dd, J = 9.0, 2.7 Hz, 1H), 7.17-7.25 (m, 2H), 7.07 (d, J = 9.1 Hz, 1H), 3.75 (s, 3H), 2.59 (s, 3H); MS m/z 366 (ESI) [M + H]⁺ |

| Cpd | Name and Data |
|---|---|
| 619 | N-(4-iodophenyl)-6-(2-methyl-1H-benzimidazol-1-yl)pyrazin-2-amine<br>$^1$H NMR (DMSO-d$_6$) δ 10.06 (br. s, 1H), 8.34-8.38 (m, 1H), 8.29 (s, 1H), 7.64-7.69 (m, 1H), 7.58-7.64 (m, 2H), 7.48-7.55 (m, 3H), 7.22-7.31 (m, 2H), 2.62 (s, 3H); MS m/z 428 (ESI) [M + H]$^+$ |

Example 2 methyl 4-{[6-(2-methyl-1H-benzimidazol-1-yl)pyrazin-2-yl]amino}benzoate (Cpd 133)

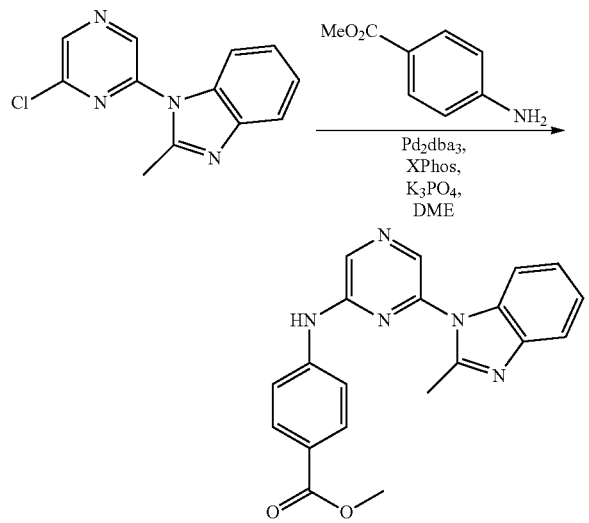

To 1-(6-chloropyrazin-2-yl)-2-methyl-1H-benzo[d]imidazole (150 mg, 0.61 mmol) was added methyl 4-aminobenzoate (181 mg, 1.2 mmol), Pd$_2$dba$_3$ (17 mg, 0.018 mmol), XPhos (17 mg, 0.036 mmol) and K$_3$PO$_4$ (254 mg, 1.2 mmol). The mixture was flushed with nitrogen and 1,2-dimethoxyethane (5 mL) was added. The reaction mixture was heated at 100° C. (heat block temperature) with stirring for 17 hours. UPLC analysis showed only partial conversion (40%), then a mixture Pd$_2$dba$_3$:XPhos (20 mg, 1:1 molar ratio) was added. The reaction mixture was heated with stirring for 3 days at 95° C., then the reaction was quenched with AcOH and the product partitioned between ethyl acetate and water. The organic layer was dried, concentrated and purified by chromatography on silica gel (gradient from ethyl acetate:hexane 1:2 to ethyl acetate:methanol 10:1). The fractions were concentrated and the residue was washed with ether, then filtered and dried to provide the title compound as a light brown solid (130 mg, 59%). $^1$H NMR (500 MHz, DMSO-d$_6$) δ 2.68 (s, 3H) 3.84 (s, 3H) 7.31 (s, 2H) 7.85 (m, J=8.83 Hz, 2H) 7.93 (m, J=8.83 Hz, 2H) 8.42 (s, 1H) 8.47 (s, 1H) 10.41 (s, 1H); MS m/z 360 (ESI) [M+H]$^+$.

Additional compounds of Formula (I) or a form thereof described herein may be prepared according to the procedure of Example 2 by substituting the appropriate starting materials, reagents and reaction conditions:

| Cpd | Name and Data |
|---|---|
| 19 | 6-(2-methyl-1H-benzimidazol-1-yl)-N-[4-(trifluoromethoxy)phenyl]pyrazin-2-amine<br>$^1$H NMR (DMSO-d$_6$) δ 10.28 (br. s., 1H), 8.40 (s, 1H), 8.30 (s, 1H), 7.76-7.82 (m, 2H), 7.64-7.69 (m, 1H), 7.48-7.53 (m, 1H), 7.29-7.34 (m, J = 8.5 Hz, 2H), 7.22-7.29 (m, 2H), 2.63 (s, 3H); MS m/z 386 (ESI) [M + H]$^+$ |
| 21 | N-[4-(difluoromethoxy)phenyl]-6-(2-methyl-1H-benzimidazol-1-yl)pyrazin-2-amine<br>$^1$H NMR (DMSO-d$_6$) δ 10.03 (s, 1H), 8.35 (s, 1H), 8.27 (s, 1H), 7.67-7.73 (m, J = 9.1 Hz, 2H), 7.63-7.67 (m, 1H), 7.48-7.53 (m, 1H), 7.23-7.30 (m, 2H), 7.14 (dist. d, J = 9.8 Hz, 2H), 7.13 (t, J = 74.4 Hz, 1H), 2.62 (s, 3H); MS m/z 368 (ESI) [M + H]$^+$ |
| 44 | N-[4-(difluoromethoxy)phenyl]-6-[2-(trifluoromethyl)-1H-benzimidazol-1-yl]pyrazin-2-amine<br>$^1$H NMR (DMSO-d$_6$) δ 10.15 (s, 1H), 8.47 (s, 1H), 8.32 (s, 1H), 7.96-8.00 (m, 1H), 7.64-7.68 (m, 2H), 7.56-7.61 (m, 1H), 7.48-7.56 (m, 2H), 7.11 (t, J = 1.0 Hz, 1H), 7.11 (m, 2H); MS m/z 422 (ESI) [M + H]$^+$ |
| 73 | 6-(2-methyl-1H-benzimidazol-1-yl)-N-[6-(trifluoromethyl)pyridin-3-yl]pyrazin-2-amine<br>1H NMR (DMSO-d$_6$) δ 10.62 (s, 1H), 8.95 (d, J = 2.5 Hz, 1H), 8.48 (s, 1H), 8.46 (s, 1H), 8.40 (dd, J = 8.7, 2.4 Hz, 1H), 7.84 (d, J = 8.8 Hz, 1H), 7.65-7.70 (m, 1H), 7.54 (m, 1H), 7.24-7.31 (m, 2H), 2.64 (s, 3H); MS m/z 371 (ESI) [M + H]$^+$ |
| 152 | (4-{[6-(2-methyl-1H-benzimidazol-1-yl)pyrazin-2-yl]amino}phenyl)methanol<br>$^1$H NMR (500 MHz, DMSO-d$_6$) δ 2.62 (s, 3 H) 4.42 (d, J = 5.99 Hz, 2 H) 5.07 (t, J = 5.67 Hz, 1 H) 7.20-7.30 (m, 4 H) 7.51-7.55 (m, 1 H) 7.58-7.64 (m, 2 H) 7.66 (s, 1 H) 8.23 (s, 1 H) 8.33 (s, 1 H) 9.90 (s, 1 H); MS m/z 332 (ESI) [M + H]$^+$ |
| 153 | 1-(4-{[6-(2-methyl-1H-benzimidazol-1-yl)pyrazin-2-yl]amino}phenyl)ethanone<br>$^1$H NMR (500 MHz, DMSO-d$_6$) δ 2.50 (s, 3 H) 2.66 (s, 3 H) 7.23-7.32 (m, 2 H) 7.81 (m, J = 8.83 Hz, 2 H) 7.92 (m, J = 9.14 Hz, 2 H) 8.39 (2, 1 H) 8.45 (2, 1 H) 10.38 (2, 1 H); MS m/z 344 (ESI) [M + H]$^+$ |
| 284 | 6-(2-methyl-4-nitro-1H-benzimidazol-1-yl)-N-[4-(trifluoromethyl)phenyl]pyrazin-2-amine<br>$^1$H NMR (DMSO-d$_6$) δ 10.42 (s, 1H), 8.49 (s, 1H), 8.43 (s, 1H), 8.10 (dd, J = 8.0, 0.8 Hz, 1H), 7.95 (dd, J = 8.2, 0.9 Hz, 1H), 7.85 (dist. d, J = 8.5 Hz, 2H), 7.65 (dist. d, J = 8.8 Hz, 2H), 7.46 (t, J = 8.2 Hz, 1H), 2.71 (s, 3H); MS m/z 414 (ESI) [M + H]$^+$ |
| 390 | N-[3-chloro-4-(trifluoromethyl)phenyl]-6-(2-methyl-1H-benzimidazol-1-yl)pyrazin-2-amine |

| Cpd | Name and Data |
|---|---|
| | ¹H NMR (500 MHz, DMSO-d₆) δ 2.67 (s, 3 H) 7.26-7.32 (m, 2 H) 7.56-7.62 (m, 1 H) 7.65-7.70 (m, 2 H) 7.78 (d, J = 8.83 Hz, 1 H) 8.20 (d, J = 1.89 Hz, 1 H) 8.43 (s, 1 H) 8.46 (s, 1 H) 10.54 (s, 1 H); MS m/z 404 (ESI) [M + H]⁺ |
| 408 | 6-(2-methyl-1H-benzimidazol-1-yl)-N-[3-methyl-4-(trifluoromethyl)phenyl]pyrazin-2-amine<br>¹H NMR (500 MHz, DMSO-d₆) δ 2.35 (br. s, 3 H) 2.66 (s, 3 H) 7.25-7.32 (m, 2 H) 7.55-7.61 (m, 2 H) 7.61-7.72 (m, 2 H) 7.79 (br. s, 1 H) 8.39 (s, 1 H) 8.42 (s, 1 H) 10.27 (br. s, 1 H); MS m/z 384 (ESI) [M + H]⁺ |
| 433 | 6-(2-methyl-1H-benzimidazol-1-yl)-N-[4-(4,4,5,5-tetramethyl-1,3,2-dioxaborolan-2-yl)phenyl]pyrazin-2-amine<br>¹H NMR (500 MHz, DMSO-d₆) δ 1.27 (s, 12 H) 2.65 (s, 3 H) 7.22-7.33 (m, 2 H) 7.52-7.57 (m, 1 H) 7.60 (d, J = 8.83 Hz, 2 H) 7.65-7.68 (m, 1 H) 7.68-7.73 (m, 2 H) 8.32 (s, 1 H) 8.39 (s, 1 H) 10.11 (s, 1 H); MS m/z 428 (ESI) [M + H]⁺ |
| 557 | N-(3-methoxyphenyl)-6-(2-methyl-1H-benzimidazol-1-yl)pyrazin-2-amine<br>¹H NMR (DMSO-d₆) δ 9.94 (s, 1H), 8.35 (s, 1H), 8.26 (s, 1H), 7.63-7.67 (m, 1H), 7.51-7.54 (m, 1H), 7.40 (d, J = 1.9 Hz, 1H), 7.25 (dist.quind, J = 7.2, 1.4 Hz, 2H), 7.15-7.21 (m, 2H), 6.56 (dt, J = 7.2, 2.2 Hz, 1H), 3.62 (s, 3H), 2.63 (s, 3H); MS m/z 332 (ESI) [M + H]⁺ |
| 561 | N-(4-methoxyphenyl)-6-(2-methyl-1H-benzimidazol-1-yl)pyrazin-2-amine<br>¹H NMR (DMSO-d₆) δ 9.75 (br. s, 1H), 8.25-8.31 (m, 1H), 8.17 (s, 1H), 7.61-7.68 (m, 1H), 7.53-7.60 (m, 2H), 7.45-7.53 (m, 1H), 7.21-7.30 (m, 2H), 6.86-6.94 (m, 2H), 3.71 (s, 3H), 2.61 (s, 3H); MS m/z 332 (ESI) [M + H]⁺ |
| 562 | 6-(2-methyl-1H-benzimidazol-1-yl)-N-(4-methylphenyl)pyrazin-2-amine<br>¹H NMR (DMSO-d₆) δ 9.84 (br. s, 1H), 8.30-8.34 (m, 1H), 8.21 (s, 1H), 7.62-7.68 (m, 1H), 7.53-7.57 (m, 2H), 7.49-7.53 (m, 1H), 7.22-7.30 (m, 2H), 7.11 (d, J = 1.0 Hz, 2H), 2.62 (s, 3H), 2.24 (s, 3H); MS m/z 316 (ESI) [M + H]⁺ |
| 576 | N-(2-methoxy-4-methylphenyl)-6-(2-methyl-1H-benzimidazol-1-yl)pyrazin-2-amine<br>¹H NMR (DMSO-d₆) δ 9.06 (br. s, 1H), 8.43 (s, 1H), 8.16 (s, 1H), 7.74 (d, J = 7.9 Hz, 1H), 7.58-7.65 (m, 1H), 7.44-7.51 (m, 1H), 7.21-7.27 (m, 2H), 6.91 (d, J = 1.6 Hz, 1H), 6.69 (dd, J = 8.2, 0.9 Hz, 1H), 3.85 (s, 3H), 2.58 (s, 3H), 2.28 (s, 3H); MS m/z 346 (ESI) [M + H]⁺ |
| 644 | N-[2-fluoro-4-(trifluoromethyl)phenyl]-6-(2-methyl-1H-benzimidazol-1-yl)pyrazin-2-amine<br>¹H NMR (DMSO-d₆) δ 10.01 (br. s, 1H), 8.64-8.68 (m, 1H), 8.42-8.45 (m, 1H), 8.36-8.42 (m, 1H), 7.75 (dd, J = 11.5, 1.7 Hz, 1H), 7.63-7.68 (m, 1H), 7.48-7.56 (m, 2H), 7.23-7.30 (m, 2H), 2.61 (s, 3H); MS m/z 388 (ESI) [M + H]⁺ |
| 645 | N-[3,5-difluoro-4-(trifluoromethyl)phenyl]-6-(2-methyl-1H-benzimidazol-1-yl)pyrazin-2-amine<br>¹H NMR (DMSO-d₆) δ 10.76 (br. s, 1H), 8.54 (s, 1H), 8.45 (s, 1H), 7.65-7.71 (m, 1H), 7.55-7.63 (m, 3H), 7.29 (ddd, J = 7.5, 6.4, 1.6 Hz, 2H), 2.66 (s, 3H); MS m/z 406 (ESI) [M + H]⁺ |
| 659 | N-(4-tert-butylphenyl)-6-(2-methyl-1H-benzimidazol-1-yl)pyrazin-2-amine<br>¹H NMR (DMSO-d₆) δ 9.86 (s, 1H), 8.33 (s, 1H), 8.20 (s, 1H), 7.63-7.67 (m, 1H), 7.57 (dist.dt(AB), J = 8.8, 1.9 Hz, 2H), 7.48-7.51 (m, 1H), 7.30 (dist.dt(AB), J = 8.5, 1.9 Hz, 2H), 7.21-7.28 (m, 2H), 2.62 (s, 3H), 1.23 (s, 9H); MS m/z 358 (ESI) [M + H]⁺ |
| 660 | 6-(2-methyl-1H-benzimidazol-1-yl)-N-[4-(propan-2-yloxy)phenyl]pyrazin-2-amine<br>¹H NMR (DMSO-d₆) δ 9.73 (s, 1H), 8.27 (s, 1H), 8.16 (s, 1H), 7.61-7.66 (m, 1H), 7.53 (dist.dt(AB), J = 9.5, 2.2 Hz, 2H), 7.46-7.50 (m, 1H), 7.19-7.30 (m, 2H), 6.86 (dist.dt(AB), J = 8.8, 1.9 Hz, 2H), 4.50 (spt, J = 6.0 Hz, 1H), 2.60 (s, 3H), 1.22 (d, J = 6.3 Hz, 6H); MS m/z 360 (ESI) [M + H]⁺ |
| 661 | 6-(2-methyl-1H-benzimidazol-1-yl)-N-[4-(propan-2-yl)phenyl]pyrazin-2-amine<br>¹H NMR (DMSO-d₆) δ 9.85 (s, 1H), 8.32 (s, 1H), 8.20 (s, 1H), 7.62-7.68 (m, 1H), 7.57 (dist.dt(AB), J = 8.8, 1.9 Hz, 2H), 7.46-7.53 (m, 1H), 7.20-7.29 (m, 2H), 7.16 (dist.dt(AB), J = 8.5, 1.9 Hz, 2H), 2.81 (spt, J = 6.9 Hz, 1H), 2.62 (s, 3H), 1.15 (d, J = 6.9 Hz, 6H); MS m/z 344 (ESI) [M + H]⁺ |
| 662 | N-(4-ethylphenyl)-6-(2-methyl-1H-benzimidazol-1-yl)pyrazin-2-amine<br>¹H NMR (DMSO-d₆) δ 9.85 (s, 1H), 8.32 (s, 1H), 8.21 (s, 1H), 7.61-7.68 (m, 1H), 7.56 (dist.dt(AB), J = 8.5, 1.9 Hz, 2H), 7.47-7.53 (m, 1H), 7.19-7.30 (m, 2H), 7.13 (dist.d(AB), J = 8.5 Hz, 2H), 2.62 (s, 3H), 2.53 (q, J = 7.6 Hz, 2H), 1.13 (t, J = 7.6 Hz, 3H); MS m/z 330 (ESI) [M + H]⁺ |
| 663 | 6-(2-methyl-1H-benzimidazol-1-yl)-N-(4-propylphenyl)pyrazin-2-amine<br>¹H NMR (DMF) δ 9.85 (s, 1H), 8.32 (s, 1H), 8.21 (s, 1H), 7.61-7.68 (m, 1H), 7.55 (dist.dt(AB), J = 8.5, 2.2 Hz, 2H), 7.47-7.53 (m, 1H), 7.21-7.29 (m, 2H), 7.10 (dist.d(AB), J = 8.5 Hz, 2H), 2.61 (s, 3H), 2.47 (t, J = 7.6 Hz, 2H), 1.54 (sxt, J = 7.6 Hz, 2H), 0.86 (t, J = 7.3 Hz, 3H); MS m/z 344 (ESI) [M + H]⁺ |
| 664 | N-(4-ethoxyphenyl)-6-(2-methyl-1H-benzimidazol-1-yl)pyrazin-2-amine<br>¹H NMR (DMSO-d₆) δ 9.74 (s, 1H), 8.27 (s, 1H), 8.16 (s, 1H), 7.61-7.67 (m, 1H), 7.54 (dt, J = 9.5, 2.2 Hz, 2H), 7.46-7.51 (m, 1H), 7.20-7.29 (m, 2H), 6.87 (dt, J = 8.8, 2.2 Hz, 2H), 3.95 (q, J = 6.9 Hz, 2H), 2.60 (s, 3H), 1.28 (t, J = 7.1 Hz, 3H); MS m/z 346 (ESI) [M + H]⁺ |
| 665 | N-(4-ethynylphenyl)-6-(2-methyl-1H-benzimidazol-1-yl)pyrazin-2-amine<br>¹H NMR (DMSO-d₆) δ 10.16 (s, 1H), 8.38 (s, 1H), 8.31 (s, 1H), 7.69 (dist.dt(AB), J = 8.8, 1.9 Hz, 2H), 7.63-7.67 (m, 1H), 7.47-7.54 (m, 1H), 7.40 (dist.dt(AB), J = 8.5, 1.9 Hz, 2H), 7.21-7.30 (m, 2H), 4.04 (s, 1H), 2.62 (s, 3H); MS m/z 326 (ESI) [M + H]⁺ |

| Cpd | Name and Data |
|---|---|
| 666 | N-(4-ethenylphenyl)-6-(2-methyl-1H-benzimidazol-1-yl)pyrazin-2-amine<br>1H NMR (DMSO-d$_6$) δ 10.04 (s, 1H), 8.36 (s, 1H), 8.26 (s, 1H), 7.62-7.71 (m, 3H), 7.47-7.59 (m, 1H), 7.40 (d, J = 8.8 Hz, 2H), 7.21-7.31 (m, 2H), 6.64 (dd, J = 17.7, 11.0 Hz, 1H), 5.69 (dd, J = 17.7, 0.9 Hz, 1H), 5.12 (dd, J = 11.0, 0.9 Hz, 1H), 2.63 (s, 3H); MS m/z 328 (ESI) [M + H]$^+$ |

Example 3

6-(2,4-dimethyl-1H-benzimidazol-1-yl)-N-[4-(trifluoromethyl)phenyl]pyrazin-2-amine (Cpd 283)

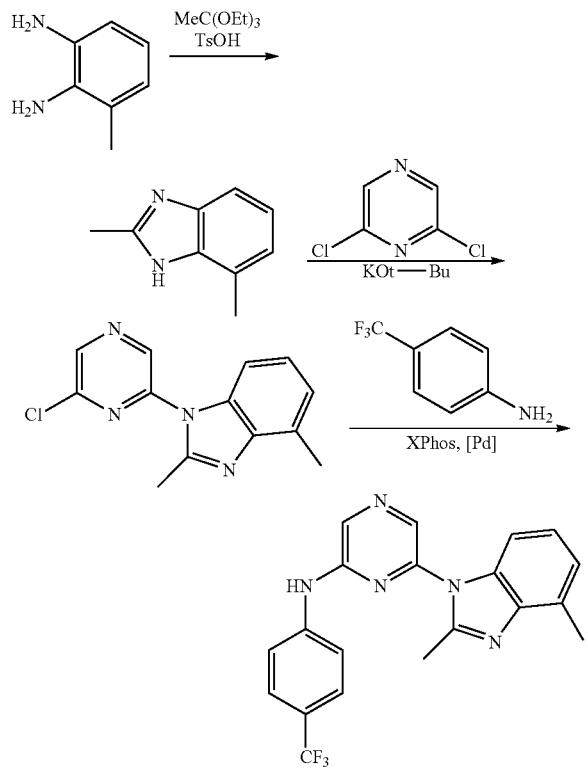

Step 1. To 3-methylbenzene-1,2-diamine (920 mg, 7.5 mmol) was added triethyl orthoacetate (5 mL) and a pinch of TsOH X H$_2$O (excess). The reaction mixture was heated at 110° C. (heating block temperature) for 15 minutes, then cooled to room temperature and hexane and a mixture of water:K$_2$CO$_3$ were added. The organic layer was filtered through a short plug of silica gel, then concentrated and the solid was washed with hexane to provide 2,7-dimethyl-1H-benzo[d]imidazole (600 mg, 55%) as a pink solid. $^1$H NMR (CHLOROFORM-d) δ 7.38 (dist. d (AB), J=7.9 Hz, 1H), 7.15 (dist. t (AB), J=7.7 Hz, 1H), 7.06 (dist. d(AB), J=7.3 Hz, 1H), 6.18 (br. s., 1H), 2.68 (s, 3H), 2.60 (s, 3H).

Step 2. To 2,7-dimethyl-1H-benzo[d]imidazole (528 mg, 3.61 mmol), was added 2,6-dichloropyrazine (957 mg, 6.5 mmol), DMF (5 mL) and KOtBu (1M solution in THF, 4 mL, 4 mmol) at room temperature. The mixture was reacted for 30 minutes at room temperature, heated at 60° C. (heating block temperature) for 1.5 hours, then cooled to room temperature and the product partitioned between water and a mixture of EtOAc/hexane (1:1). The organic layer was concentrated and purified by chromatography on silica gel (gradient ethyl acetate:hexane 1:2 to 1:0). The product was washed with ether/hexane (1:1) to provide 1-(6-chloropyrazin-2-yl)-2,4-dimethyl-1H-benzo[d]imidazole as a brown solid (355 mg, 38%). $^1$H NMR (DMSO-d$_6$) δ 9.07 (s, 1H), 8.96 (d, J=0.6 Hz, OH), 7.37 (dist. d (AB), J=7.6 Hz, 1H), 7.16 (dist. t(AB), J=7.3 Hz, 1H), 7.11 (dist. dt (AB), J=7.3, 0.9 Hz, 1H), 2.65 (s, 3H), 2.56 (s, 3H); MS m/z 259 (ESI) [M+H]$^+$.

Step 3. The obtained product was carried forward (using the procedure described in Example 2 and appropriate starting materials, reagents and reaction conditions) to provide the title compound. $^1$H NMR (DMSO-d$_6$) δ 10.35 (br. s, 1H), 8.42 (br. s, 1H), 8.35 (br. s, 1H), 7.87 (dist. d, J=8.5 Hz, 2H), 7.64 (dist. d, J=8.8 Hz, 2H), 7.31 (dist. d (AB), J=7.9 Hz, 1H), 7.14 (dist. t (AB), J=7.7 Hz, 1H), 7.08 (dist. d (AB), J=7.3 Hz, 1H), 2.63 (s, 3H), 2.56 (s, 3H); MS m/z 384 (ESI) [M+H]$^+$.

Additional compounds of Formula (I) or a form thereof described herein may be prepared according to the procedure of Example 3 by substituting the appropriate starting materials, reagents and reaction conditions:

| Cpd | Name and Data |
|---|---|
| 339 | 6-(4-fluoro-2-methyl-1H-benzimidazol-1-yl)-N-[4-(trifluoromethyl)phenyl]pyrazin-2-amine<br>$^1$H NMR (DMSO-d$_6$) δ 10.37 (s, 1H), 8.45 (s, 1H), 8.38 (s, 1H), 7.86 (dist.d(AB), J = 8.5 Hz, 2H), 7.65 (dist.d(AB), J = 8.8 Hz, 2H), 7.35 (dd, J = 8.2, 0.6 Hz, 1H), 7.24 (td, J = 8.1, 4.9 Hz, 1H), 7.10 (ddd, J = 11.0, 8.2, 0.6 Hz, 1H), 2.64 (s, 3H); MS m/z 388 (ESI) [M + H]$^+$ |
| 386 | N-[4-(trifluoromethyl)phenyl]-6-(2,5,6-trimethyl-1H-benzimidazol-1-yl)pyrazin-2-amine<br>$^1$H NMR (DMSO-d$_6$) δ 10.34 (s, 1H), 8.41 (s, 1H), 8.34 (s, 1H), 7.88 (dist.d(AB), J = 8.5 Hz, 2H), 7.65 (dist.d(AB), J = 8.5 Hz, 2H), 7.42 (s, 1H), 7.33 (s, 1H), 2.60 (s, 3H), 2.32 (s, 3H), 2.27 (s, 3H); MS m/z 398 (ESI) [M + H]$^+$ |
| 387 | N-[4-(trifluoromethoxy)phenyl]-6-(2,5,6-trimethyl-1H-benzimidazol-1-yl)pyrazin-2-amine<br>$^1$H NMR (DMSO-d$_6$) δ 10.11 (s, 1H), 8.34 (s, 1H), 8.27 (s, 1H), 7.78 (dist. dt(AB), J = 9.1, 2.2 Hz, 2H), 7.41 (s, 1H), 7.29-7.33 (m, 3H), 2.58 (s, 3H), 2.32 (s, 3H), 2.27 (s, 3H); MS m/z 414 (ESI) [M + H]$^+$ |

| Cpd | Name and Data |
|---|---|
| 417 | 6-(4,6-difluoro-2-methyl-1H-benzimidazol-1-yl)-N-[4-(trifluoromethyl)phenyl]pyrazin-2-amine<br>$^1$H NMR (DMSO-$d_6$) δ 10.38 (s, 1H), 8.45 (s, 1H), 8.39 (s, 1H), 7.85 (dist.d(AB), J = 8.5 Hz, 2H), 7.65 (dist.d(AB), J = 8.8 Hz, 2H), 7.28 (dd, J = 8.8, 2.2 Hz, 1H), 7.17 (td, J = 10.4, 2.2 Hz, 1H), 2.62 (s, 3H); MS m/z 398 (ESI) [M + H]$^+$ |

Example 4

2-methyl-1-(6-{[4-(trifluoromethyl)phenyl]amino}pyrazin-2-yl)-1H-benzimidazol-4-amine (Cpd 296)

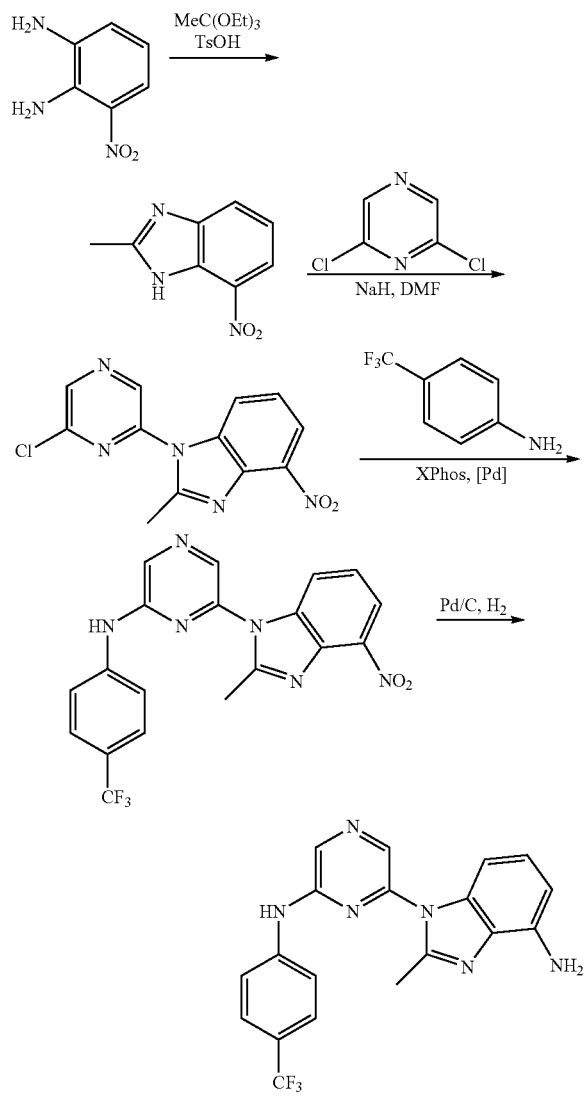

Step 1. 1-(6-chloropyrazin-2-yl)-2-methyl-4-nitro-1H-benzo[d]imidazole (prepared using the procedure described in Example 3 and appropriate starting materials, reagents and reaction conditions) was obtained as a white solid. $^1$H NMR (DMSO-$d_6$) δ 9.16 (d, J=0.6 Hz, 1H), 9.06 (d, J=0.6 Hz, 1H), 8.12 (dd, J=7.9, 0.9 Hz, 1H), 7.99 (dd, J=8.0, 0.8 Hz, 1H), 7.49 (t, J=8.0 Hz, 1H), 2.73 (s, 3H); MS m/z 290 (ESI) [M+H]$^+$.

Step 2. The title compound (prepared using the procedure described in Example 24 and appropriate starting materials, reagents and reaction conditions) was obtained as an off white solid. $^1$H NMR (DMSO-$d_6$) δ 10.43 (br. s, 1H), 8.41 (s, 1H), 8.30 (s, 1H), 7.89 (dist. d, J=8.5 Hz, 2H), 7.65 (dist. d, J=8.8 Hz, 2H), 6.92 (t, J=7.9 Hz, 1H), 6.65 (dd, J=8.2, 0.9 Hz, 1H), 6.44 (dd, J=7.7, 0.8 Hz, 1H), 5.35 (s, 2H), 2.58 (s, 3H); MS m/z 385 (ESI) [M+H]$^+$.

Example 5

6-[2-methyl-5-(trifluoromethoxy)-1H-benzimidazol-1-yl]-N-[4-(trifluoromethyl)phenyl]pyrazin-2-amine (Cpd 356)

6-[2-methyl-6-(trifluoromethoxy)-1H-benzimidazol-1-yl]-N-[4-(trifluoromethyl)phenyl]pyrazin-2-amine (Cpd 357)

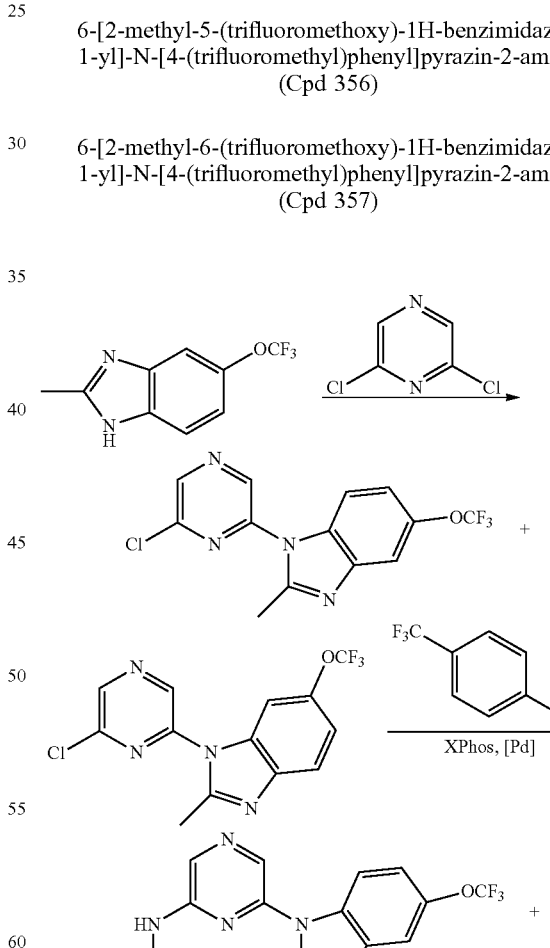

-continued

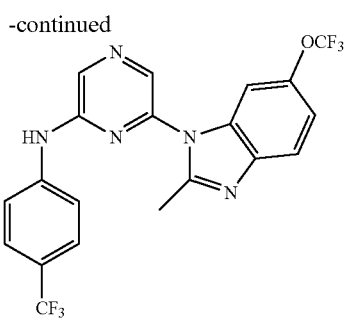

Intermediate 1-(6-chloropyrazin-2-yl)-2-methyl-5-(trifluoromethoxy)-1H-benzo[d]imidazole (prepared using the procedure described in Example 3 and appropriate starting materials, reagents and reaction conditions) (less polar on TLC) in a mixture of EtOAc:hexane (1:1) was eluted before intermediate isomer 1-(6-chloropyrazin-2-yl)-2-methyl-6-(trifluoromethoxy)-1H-benzo[d]imidazole (more polar on TLC) Each intermediate was carried forward (using the procedure described in Example 3 and appropriate materials, reagents and reaction conditions) to provide the title Compound 356 and Compound 357.

Cpd 356: $^1$H NMR (DMSO-d$_6$) δ 10.37 (s, 1H), 8.45 (s, 1H), 8.40 (s, 1H), 7.86 (d, J=8.5 Hz, 2H), 7.63-7.69 (m, 3H), 7.61 (d, J=8.8 Hz, 1H), 7.27 (dd, J=8.8, 1.3 Hz, 1H), 2.65 (s, 3H)); MS m/z 454 (ESI) [M+H]$^+$.

Cpd 357: $^1$H NMR (DMSO-d$_6$) δ 8.37 (s, 1H), 8.23 (s, 1H), 7.82 (dist. d(AB), J=8.5 Hz, 2H), 7.74 (d, J=8.8 Hz, 1H), 7.55-7.57 (m, 1H), 7.54 (dist. d(AB), J=8.8 Hz, 2H), 7.26 (ddd, J=8.8, 2.2, 0.9 Hz, 1H), 2.65 (s, 3H). NH signal was not observed.

Example 6

6-[2-methyl-4-(trifluoromethyl)-1H-imidazol-1-yl]-N-[4-(trifluoromethyl)phenyl]pyrazin-2-amine (Cpd 303)

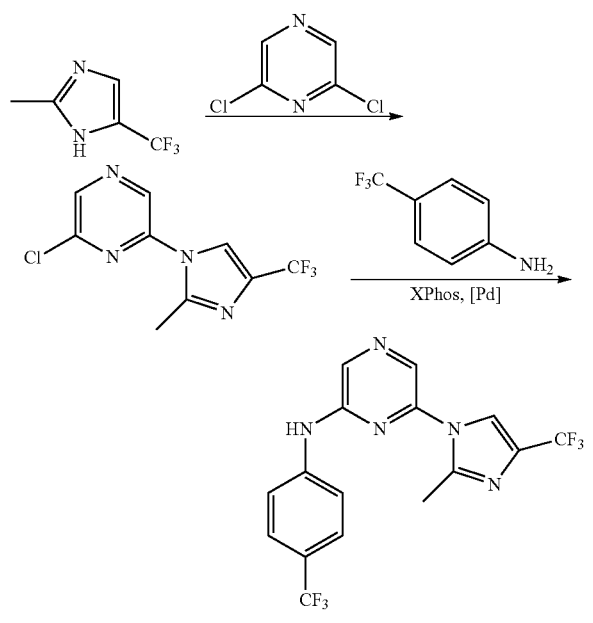

Step 1. To 2-methyl-5-(trifluoromethyl)-1H-imidazole (555 mg, 3.7 mmol) was added 2,6-dichloropyrazine (1.88 g, 12.6 mmol), Cs$_2$CO$_3$ (1,630 mg, 5 mmol) and ACN (6 mL). The reaction mixture was heated at 50° C. for 2.5 hours, then at room temperature for 16 hours and the product was partitioned between water and DCM. The organic layer was concentrated and purified by chromatography on silica gel (gradient ethyl acetate:hexane 1:4 to 1:0) to provide 2-chloro-6-(2-methyl-4-(trifluoromethyl)-1H-imidazol-1-yl)pyrazine as a yellow oil (742 mg, 77%). $^1$H NMR (DMSO-d$_6$) δ 9.09-9.12 (m, 1H), 8.94 (d, J=0.6 Hz, 1H), 8.38 (dist. q, J=1.6 Hz, 1H), 2.57 (s, 3H); MS m/z 263 (ESI) [M+H]$^+$.

Step 2. The product of Step 1 was carried forward (using the procedure described in Example 2 and appropriate materials, reagents and reaction conditions) to provide the title compound. $^1$H NMR (DMSO-d$_6$) δ 10.32 (s, 1H), 8.38 (s, 1H), 8.34 (s, 1H), 8.26 (dist. q, J=1.6 Hz, 1H), 7.85 (dist. d (AB), J=8.5 Hz, 2H), 7.71 (dist. d(AB), J=8.5 Hz, 2H), 2.53 (s, 3H); MS m/z 388 (ESI) [M+H]$^+$.

Example 7

6-(4-bromo-2,5-dimethyl-1H-imidazol-1-yl)-N-[4-(trifluoromethyl)phenyl]pyrazin-2-amine (Cpd 341)

N-[4-(trifluoromethyl)phenyl]-6-(2,4,5-trimethyl-1H-imidazol-1-yl)pyrazin-2-amine (Cpd 342)

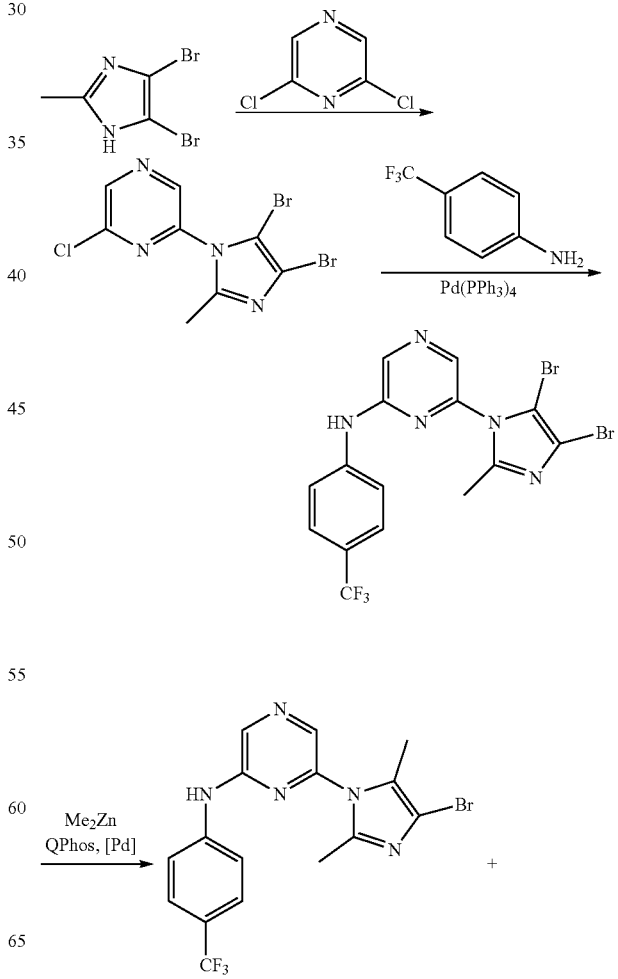

-continued

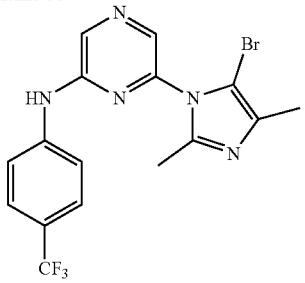

| Cpd | Name and Data |
|---|---|
| 388 | 6-(6-bromo-2-methyl-1H-benzimidazol-1-yl)-N-[4-(trifluoromethyl)phenyl]pyrazin-2-amine<br>$^1$H NMR (DMSO-d$_6$) δ 11.39 (br. s., 1H), 8.61 (s, 1H), 8.35 (s, 1H), 7.94 (d, J = 8.5 Hz, 2H), 7.76 (d, J = 1.6 Hz, 1H), 7.60-7.64 (m, 3H), 7.42 (dd, J = 8.5, 1.9 Hz, 1H), 2.63 (s, 3H); MS m/z 448 (ESI) [M + H]$^+$ |

Example 8

N-[4-(difluoromethyl)phenyl]-6-(2-methyl-1H-benzimidazol-1-yl)pyrazin-2-amine (Cpd 507)

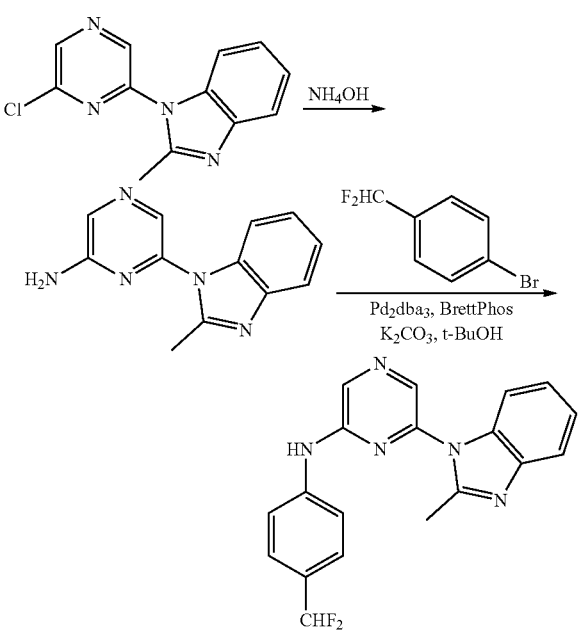

Step 1. To 4,5-dibromo-2-methyl-1H-imidazole (5.3 g, 22 mmol) was added Cs$_2$CO$_3$ (10 g, 30 mmol), 2,6-dichloropyrazine (9.9 g, 66 mmol) and DMF (30 mL). The mixture was stirred at room temperature for 15 hours, then at 60° C. for 24 hours. The reaction mixture was diluted with water. The resulting precipitate was filtered, dissolved in EtOAc, then dried and filtered through a short plug of silica gel. The product was purified by chromatography on silica gel (gradient ethyl acetate:hexane 1:4 to 1:1) to provide 2-chloro-6-(4,5-dibromo-2-methyl-1H-imidazol-1-yl)pyrazine as a heterogeneous yellow/white solid (3.95 g, 51%). $^1$H NMR (DMSO-d$_6$) δ 9.09 (s, 1H), 9.04 (d, J=0.6 Hz, 1H), 2.33 (s, 3H).

Step 2. A solution of the product prepared in Step 1 (3.95 g, 11.2 mmol) and 4-(trifluoromethyl)aniline (2.7 mL, 22 mmol) in DME (50 mL) was added to a mixture of tetrakis(triphenylphosphine)palladium (385 mg, 6%) and K$_3$PO$_4$ (6.4 g, 30 mmol). The mixture was reacted at 100° C. for 7 hours, then at 70° C. for 14 hours, then at 100° C. for 3 hours. The reaction mixture was cooled, diluted with DME/MeOH, then filtered and concentrated. The product was dissolved in EtOAc (10 mL). The mixture was heated at reflux, then cooled in ice bath. The product was filtered and washed with ether to provide 6-(4,5-dibromo-2-methyl-1H-imidazol-1-yl)-N-(4-(trifluoromethyl)phenyl)pyrazin-2-amine as a light brown solid (4.19 g, 78%). $^1$H NMR (DMSO-d$_6$) δ 10.42 (s, 1H), 8.46 (s, 1H), 8.27 (s, 1H), 7.85 (dist. d(AB), J=8.5 Hz, 2H), 7.70 (dist. d(AB), J=8.8 Hz, 2H), 2.33 (s, 3H).

Step 3. To 6-(4,5-dibromo-2-methyl-1H-imidazol-1-yl)-N-(4-(trifluoromethyl)phenyl)pyrazin-2-amine (152 mg, 0.32 mmol) was added Pd$_2$dba$_3$ (9 mg, 3%), QPhos (14 mg, 6%), dioxane (3 mL), DMF (2 mL) and Me$_2$Zn (1.2 M solution in toluene, 0.8 mL, 1 mmol). The mixture was reacted at 60° C. for 1 hour, the product was partitioned between EtOAc and NH$_4$Cl (aqueous) and the organic layer was purified by chromatography on silica gel (gradient from ethyl acetate:hexane 1:2 to EtOAc:MeOH 5:1).

The less polar fractions were dissolved in ether and precipitated with hexane to provide the title Compound 341 as a pink solid (35 mg, 27%). $^1$H NMR (DMSO-d$_6$) δ 10.34 (s, 1H), 8.41 (s, 1H), 8.23 (s, 1H), 7.84 (d, J=8.5 Hz, 2H), 7.71 (d, J=8.8 Hz, 2H), 2.28 (s, 3H), 2.10 (s, 3H); MS m/z 412 (ESI) [M+H]$^+$.

The more polar fractions were dissolved in DCM, then precipitated with hexane and washed with ether to provide the title compound 342 as a gray solid (40 mg, 37%). $^1$H NMR (DMSO-d$_6$) δ 10.30 (s, 1H), 8.39 (s, 1H), 8.16 (s, 1H), 7.84 (dist. d(AB), J=8.5 Hz, 2H), 7.69 (dist. d(AB), J=8.8 Hz, 2H), 2.30 (s, 3H), 2.11 (s, 3H), 2.05 (s, 3H); MS m/z 348 (ESI) [M+H]$^+$.

Additional compounds of Formula (I) or a form thereof described herein may be prepared according to the procedure of Example 7 by substituting the appropriate starting materials, reagents and reaction conditions:

Step 1. To 1-(6-chloropyrazin-2-yl)-2-methyl-1H-benzo[d]imidazole (1.11 g, 4.55 mmol) was added MeCN (3 mL), NH$_4$OH (2 mL, 30% in water) and DMSO (2 mL). The mixture was sealed in a high-pressure tube and heated at 100° C. (heating block temperature) for 47 hours, then DMSO (2 mL) and NH$_4$OH (2 mL) were added. The mixture was reacted at 100° C. for 3 additional days, then diluted with water and the resulting precipitate was filtered to provide 6-(2-methyl-1H-benzo[d]imidazol-1-yl)pyrazin-2-amine (909 mg, 89%) as a light yellow solid. $^1$H NMR (500 MHz, DMSO-d$_6$) δ 2.58 (s, 3H) 6.95 (br. s, 2H) 7.18-7.27 (m, 2H) 7.41-7.46 (m, 1H) 7.60-7.64 (m, 1H) 7.99 (s, 1H) 8.00 (s, 1H); MS m/z 226 (ESI) [M+H]$^+$.

Step 2. To the product of Step 1 (70 mg, 0.31 mmol) was added Brettphos (17 mg, 0.1 equiv), Pd$_2$dba$_3$ (9 mg, 0.03 equiv) and K$_2$CO$_3$ (138 mg, 3 equiv). The mixture was flushed with nitrogen, then 1-bromo-4-(difluoromethyl)benzene (0.12 mL, 3 equiv) and a mixture of tert-butanol:1,2-dimethoxyethane (9:1)(1.5 mL) was added. The reaction mixture was heated at 110° C. (heat block temperature) with stirring for 4 hours. The product was diluted with a mixture of DCM, DME and MeOH, filtered through a short plug of silica gel, concentrated and purified by chromatography on silica gel (gradient from ethyl acetate:hexane 1:2 to ethyl acetate:methanol 10:1). The fractions were concentrated, the resulting product was washed with ether, then filtered and dried to provide the title compound (23 mg, 21%) as a light yellow solid. $^1$H NMR (500 MHz, DMSO-d$_6$) δ 2.65 (s, 3H) 6.94 (t, J=55 Hz, 1H) 7.25-7.32 (m, 2H) 7.50 (m, 2H)

7.53-7.56 (m, 1H) 7.67 (s, 1H) 7.81 (m, 2H) 8.34 (s, 1H) 8.41 (s, 1H) 10.23 (br. s, 1H); MS m/z 352 (ESI) [M+H]⁺.

Additional compounds of Formula (I) or a form thereof described herein may be prepared according to the procedure of Example 8 by substituting the appropriate starting materials, reagents and reaction conditions:

| Cpd | Name and Data |
|---|---|
| 508 | N-[4-(difluoromethyl)-3-fluorophenyl]-6-(2-methyl-1H-benzimidazol-1-yl)pyrazin-2-amine<br>¹H NMR (DMSO-d₆) δ 10.52 (br. s, 1H), 8.47 (s, 1H), 8.44 (s, 1H), 7.85 (br. d, J = 13.9 Hz, 1H), 7.75 (dd, J = 5.7, 1.3 Hz, 1H), 7.62-7.68 (m, 1H), 7.53-7.59 (m, 1H), 7.47 (dd, J = 8.5, 1.9 Hz, 1H), 7.37 (dtd, J = 15.8, 8.0, 1.4 Hz, 2H), 7.10 (t, J = 54.9 Hz, 1H), 2.72 (s, 3H); MS m/z 370 (ESI) [M + H]⁺ |
| 517 | 5-{[6-(2-methyl-1H-benzimidazol-1-yl)pyrazin-2-yl]amino}-2-(trifluoromethyl)benzonitrile<br>¹H NMR (DMSO-d₆) δ 10.70 (s, 1H), 8.50 (s, 1H), 8.43-8.47 (m, 2H), 8.02 (dist.dd(AB), J = 9.1, 1.9 Hz, 1H), 7.93 (dist.d(AB), J = 8.8 Hz, 1H), 7.64-7.70 (m, 1H), 7.57-7.62 (m, 1H), 7.26-7.31 (m, 2H), 2.66 (s, 3H); MS m/z 395 (ESI) [M + H]⁺ |
| 519 | [5-{[6-2-methyl-1H-benzimidazol-1-yl)pyrazin-2-yl]amino]2-(trifluoromethyl)phenyl]methanol<br>1H NMR (DMSO-d₆) δ 10.40 (br. s, 1H), 8.45 (s, 1H), 8.37 (s, 1H), 8.02 (br. s, 1H), 7.59 (d, J = 8.5 Hz, 1H), 7.53-7.57 (m, 1H), 7.26-7.32 (m, 2H), 4.64 (br. s, 2H), 2.68 (s, 3H); MS m/z 400 (ESI) [M + H]⁺ |

Example 9

N-[3-(aminomethyl)-4-(trifluoromethyl)phenyl]-6-(2-methyl-1H-benzimidazol-1-yl)pyrazin-2-amine (Cpd 524)

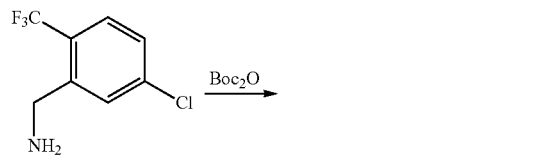

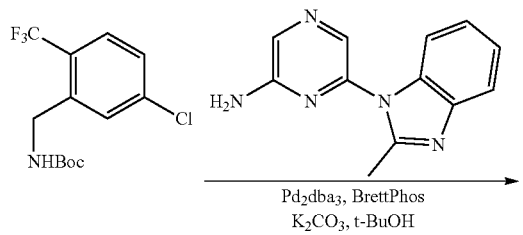

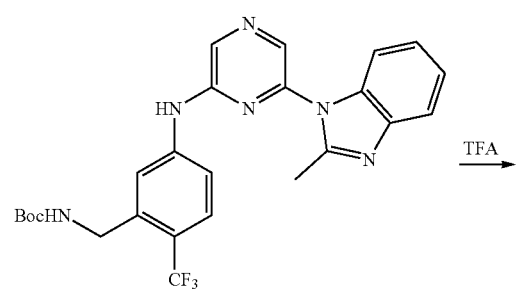

-continued

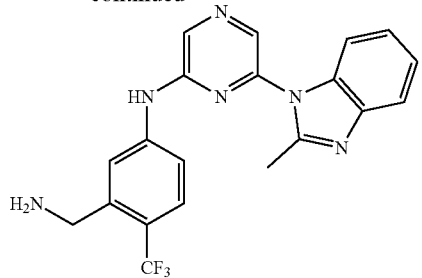

Step 1. To (5-chloro-2-(trifluoromethyl)phenyl)methanamine (300 mg, 1.4 mmol) was added DCM (3 mL) and Boc₂O (0.5 mL, 2 mmol). The mixture was heated at 60° C. for 15 minutes, then cooled, and a grain of DMAP, then water and a few drops of ammonium hydroxide were added. The organic layer was dried, then filtered through a plug of silica gel, and concentrated to provide tert-butyl 5-chloro-2-(trifluoromethyl)benzylcarbamate.

Step 2. Intermediate tert-butyl 5-chloro-2-(trifluoromethyl)benzylcarbamate was carried forward (using the procedure described in Example 8 and appropriate materials, reagents and reaction conditions) to provide intermediate tert-butyl 5-(6-(2-methyl-1H-benzo[d]imidazol-1-yl)pyrazin-2-ylamino)-2-(trifluoromethyl)benzylcarbamate which was used in the next step without further purification.

Step 3. Intermediate tert-butyl 5-(6-(2-methyl-1H-benzo[d]imidazol-1-yl)pyrazin-2-ylamino)-2-(trifluoromethyl)benzylcarbamate was dissolved in DCM (3 mL) and TFA (1 mL) was added. The mixture was reacted for 30 minutes at room temperature, then diluted with ammonium hydroxide and partially concentrated in a flow of nitrogen. The precipitate was filtered, then washed with water and an EtOAc:Hexane mixture to provide the title compound as a gray solid (35 mg). ¹H NMR (DMSO-d₆) δ 10.35 (s, 1H), 8.44 (s, 1H), 8.37 (s, 1H), 8.02 (br. s, 1H), 7.82 (d, J=8.2 Hz, 1H), 7.63-7.68 (m, 1H), 7.57 (d, J=8.8 Hz, 1H), 7.54-7.56 (m, 1H), 7.24-7.29 (m, 2H), 3.84 (s, 2H), 2.66 (s, 3H). The NH₂ signals were not seen.

Example 10

N-(4-bromophenyl)-6-(2-methyl-1H-benzimidazol-1-yl)pyrazin-2-amine (Cpd 616)

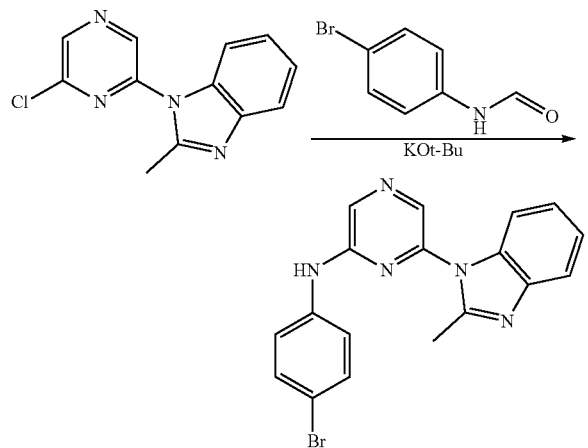

To 1-(6-chloropyrazin-2-yl)-2-methyl-1H-benzo[d]imidazole (103 mg, 0.42 mmol) was added N-(4-bromophenyl)formamide (119 mg, 0.6 mmol), NaH (excess, 60% in oil) and DMF (1 mL) at room temperature. The reaction mixture was stirred at room temperature for 22 hours, quenched with AcOH, then diluted with EtOAc/hexane and aqueous HCl and filtered to provide the title compound as a brown solid (46 mg, 29%). $^1$H NMR (DMSO-$d_6$) δ 10.08 (br. s, 1H), 8.33-8.39 (m, 1H), 8.30 (s, 1H), 7.61-7.71 (m, 3H), 7.42-7.54 (m, 3H), 7.23-7.35 (m, 2H), 2.63 (s, 3H); MS m/z 380 (ESI) [M+H]$^+$.

Example 11

6-[2-(trifluoromethyl)-1H-benzimidazol-1-yl]-N-[4-(trifluoromethyl)phenyl]pyrazin-2-amine (Cpd 14)

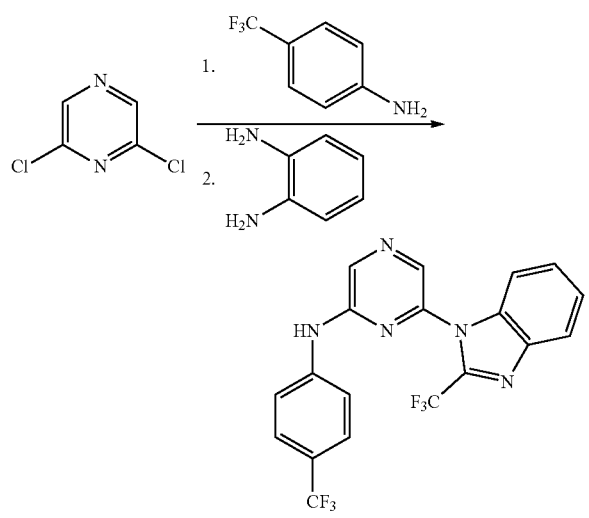

Step 1. To 2,6-dichloropyrazine (984 mg, 6.6 mmol) was added 4-(trifluoromethyl)aniline (1.07 g, 6.6 mmol), QPhos (6 mg, 0.017 mmol), allylpalladium (II) chloride dimer (APC) (47 mg, 0.06 mmol), $K_3PO_4$ (2.8 g, 13.2 mmol) and 1,2-dimethoxyethane (10 mL). The mixture was heated at 110° C. (heating block temperature) for 1 hour. The reaction mixture was partitioned between aqueous acetic acid and EtOAc. The organic layer was dried over $Na_2SO_4$, then filtered, concentrated and purified by chromatography on silica gel (gradient ethyl acetate:hexane 1:10 to 1:1). The fractions were concentrated and the residue was dissolved in ether, then precipitated with hexanes, filtered and dried to provide 6-chloro-N-(4-(trifluoromethyl)phenyl)pyrazin-2-amine (480 mg, 63%) and $N^2,N^6$-bis(4-(trifluoromethyl)phenyl)pyrazine-2,6-diamine (28%) as a pink solid.

Step 2. To the crude 6-chloro-N-(4-(trifluoromethyl)phenyl)pyrazin-2-amine (200 mg, 0.44 mmol) was added benzene-1,2-diamine (216 mg, 2 mmol) and isopropyl alcohol (4 mL). The mixture was heated in a microwave oven at 160° C. for 10 minutes, then partly concentrated and diluted with EtOAc. The suspension was treated with trifluoroacetic anhydride (1.5 mL). The reaction mixture was washed with aqueous $NaHCO_3$, then concentrated and purified by chromatography on silica gel (gradient ethyl acetate:hexane 1:4 to 1:1) to provide 2,2,2-trifluoro-N-(2-(6-(4-(trifluoromethyl)phenylamino)pyrazin-2-ylamino)phenyl)acetamide (72%) and $N^2,N^6$-bis(4-(trifluoromethyl)phenyl)pyrazine-2,6-diamine (21%).

Step 3. The crude 2,2,2-trifluoro-N-(2-(6-(4-(trifluoromethyl)phenylamino)pyrazin-2-ylamino)phenyl)acetamide was dissolved in acetonitrile (4 mL) and trifluoroacetic acid (0.5 mL) was added. The mixture was heated in a microwave oven at 180° C. for 1.5 hours. Purification by chromatography on silica gel (gradient ethyl acetate:hexane 1:4 to 1:1) and recrystallization from a mixture of ethyl ether in hexanes provided the title compound as a white solid (142 mg). $^1$H NMR (DMSO-$d_6$) δ 10.55 (br. s, 1H), 8.58 (d, J=6.0 Hz, 1H), 7.94-8.02 (m, 2H), 7.96 (d, J=7.3 Hz, 1H), 7.84-7.92 (m, J=8.5 Hz, 2H), 7.64-7.72 (m, J=8.8 Hz, 2H), 7.48-7.57 (m, 2H), 7.04 (d, J=6.0 Hz, 1H); MS m/z 424 (ESI) [M+H]$^+$.

Example 12

N-(4-methoxyphenyl)-6-[2-(trifluoromethyl)-1H-benzimidazol-1-yl]pyrazin-2-amine (Cpd 43)

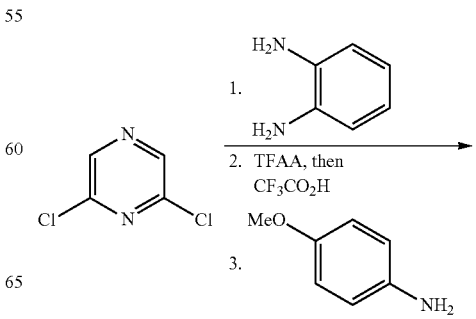

-continued

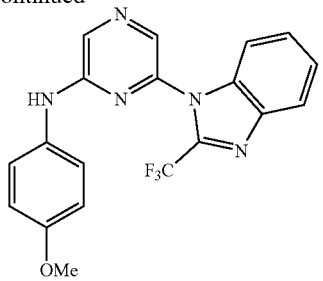

Step 1. To 2,6-dichloropyrazine (1.27 g, 8.5 mmol) was added benzene-1,2-diamine (2.8 g, 25 mmol), triethylamine (1.25 mL, 9 mmol) and acetonitrile. The mixture was heated in a microwave oven at 180° C. for 30 min, then at 160° C. for 60 minutes. The reaction mixture was concentrated, then triturated with water and filtered. The product was isolated by chromatography on silica gel (gradient ethyl acetate: hexane 1:10 to 1:0) to provide $N^1$-(6-chloropyrazin-2-yl)benzene-1,2-diamine (158 mg, 8%).

Step 2. $N^1$-(6-chloropyrazin-2-yl)benzene-1,2-diamine was dissolved in acetonitrile (10 mL), then treated with TFAA (0.1 mL, 1 equiv) and TFA (1 mL). The mixture was heated in a microwave oven at 160° C. for 1 hour. The reaction mixture was concentrated to provide 1-(6-chloropyrazin-2-yl)-2-(trifluoromethyl)-1H-benzo[d]imidazole (190 mg) as an orange oil.

Step 3. To 1-(6-chloropyrazin-2-yl)-2-(trifluoromethyl)-1H-benzo[d]imidazole (63 mg, 0.21 mmol) was added 4-methoxyaniline (37 mg, 0.3 mmol), QPhos (3 mg, 0.004 mmol), $Pd_2dba_3$ (3.7 mg, 0.004 mmol), $K_3PO_4$ (85 mg, 0.4 mmol) and 1,2-DME (3 mL). The mixture was flushed with nitrogen and heated at 110° C. (heating block temperature) for 4 hours. The reaction mixture was partitioned between toluene and water. The organic layer was concentrated and purified by chromatography on silica gel (gradient ethyl acetate:hexane 1:10 to 1:1) to provide the title compound as a yellow solid (28 mg, 34%). $^1$H NMR (DMSO-$d_6$) δ 9.90 (s, 1H), 8.40 (s, 1H), 8.22 (s, 1H), 7.97 (s, 1H), 7.46-7.59 (m, 5H), 6.87 (d, J=8.8 Hz, 2H), 3.69 (s, 3H); MS m/z 386 (ESI) [M+H]$^+$.

Example 13

6-(2-ethyl-1H-benzimidazol-1-yl)-N-[4-(trifluoromethyl)phenyl]pyrazin-2-amine (Cpd 51)

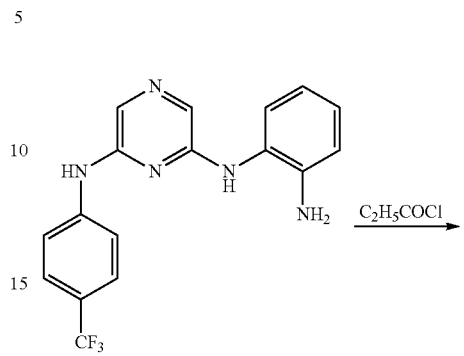

To $N^2$-(2-aminophenyl)-$N^6$-(4-(trifluoromethyl)phenyl)pyrazine-2,6-diamine (88 mg, 0.26 mmol) was added acetonitrile (1 mL) and propionyl chloride (40 µL, 0.4 mmol) at room temperature. The resulting unstirrable gel was heated in a microwave oven at 160° C. for 10 minutes, then was partitioned between EtOAc/toluene and water. The organic layer was concentrated and purified by chromatography on silica gel (gradient from ethyl acetate:hexane 1:4 to 1:0) to provide the title compound as a brownish green solid (37 mg, 37%). $^1$H NMR (DMSO-$d_6$) δ 10.38 (br. s, 1H), 8.45 (s, 1H), 8.37 (s, 1H), 7.85-7.91 (m, J=8.5 Hz, 2H), 7.68-7.74 (m, 1H), 7.62-7.67 (m, J=8.5 Hz, 2H), 7.43-7.54 (m, 1H), 7.23-7.32 (m, 2H), 2.99 (q, J=7.4 Hz, 2H), 1.30 (t, J=7.6 Hz, 3H); MS m/z 384 (ESI) [M+H]$^+$.

Additional compounds of Formula (I) or a form thereof described herein may be prepared according to the procedure of Example 13 by substituting the appropriate starting materials, reagents and reaction conditions:

| Cpd | Name and Data |
|---|---|
| 52 | 6-[2-(propan-2-yl)-1H-benzimidazol-1-yl]-N-[4-(trifluoromethyl)phenyl]pyrazin-2-amine<br>$^1$H NMR (DMSO-$d_6$) δ 10.40 (s, 1H), 8.48 (s, 1H), 8.36 (s, 1H), 7.83-7.89 (m, J = 8.5 Hz, 2H), 7.69-7.73 (m, 1H), 7.62-7.67 (m, J = 8.8 Hz, 2H), 7.41 (s, 1H), 7.23-7.31 (m, 2H), 3.36-3.41 (m, 1H), 1.30 (d, J = 6.6 Hz, 6H); MS m/z 398 (ESI) [M + H]$^+$ |
| 53 | 6-(2-propyl-1H-benzimidazol-1-yl)-N-[4-(trifluoromethyl)phenyl]pyrazin-2-amine<br>$^1$H NMR (DMSO-$d_6$) δ 10.38 (s, 1H), 8.45 (s, 1H), 8.36 (s, 1H), 7.85-7.89 (m, J = 8.5 Hz, 2H), 7.69-7.73 (m, 1H), 7.63-7.68 (m, J = 8.5 Hz, 2H), 7.45-7.50 (m, 1H), 7.24-7.31 (m, J = 7.4, 5.5, 1.6 Hz, 2H), 2.95 (t, J = 7.6 Hz, 2H), 1.77 (sxt, J = 7.4 Hz, 1H), 0.89 (t, J = 7.4 Hz, 3H); MS m/z 398 (ESI) [M + H]$^+$ |
| 65 | 6-[2-(methoxymethyl)-1H-benzimidazol-1-yl]-N-[4-(trifluoromethyl)phenyl]pyrazin-2-amine<br>$^1$H NMR (DMSO-$d_6$) δ 10.36 (br. s, 1H), 8.44 (s, 1H), 8.42 (s, 1H), 7.85-7.92 (m, J = 8.5 Hz, 2H), 7.76-7.81 (m, 1H), 7.63-7.68 (m, J = 8.8 Hz, 2H), 7.59-7.63 (m, 1H), 7.35 (m, 1H), 4.81 (s, 2H), 3.21 (s, 3H); MS m/z 400 (ESI) [M + H]$^+$ |
| 78 | (1S)-1-[1-(6-{[4-(trifluoromethyl)phenyl]amino}pyrazin-2-yl)-1H-benzimidazol-2-yl]ethyl acetate<br>$^1$H NMR (DMSO-$d_6$) δ 10.37 (s, 1H), 8.45 (s, 1H), 8.34 (s, 1H), 7.85 (dist.d(AB), J = 8.5 Hz, 2H), 7.77-7.81 (m, 1H), 7.64 (dist.d(AB), J = 8.8 Hz, 2H), 7.48-7.52 (m, 1H), 7.32-7.37 (m, 2H), 6.20 (q, J = 6.6 Hz, 1H), 1.76 (s, 3H), 1.67 (d, J = 6.6 Hz, 3H); MS m/z 442 (ESI) [M + H]$^+$ |

| Cpd | Name and Data |
|---|---|
| 80 | 6-(2-butyl-1H-benzimidazol-1-yl)-N-[4-(trifluoromethyl)phenyl]pyrazin-2-amine<br>$^1$H NMR (DMSO-$d_6$) δ 10.36 (s, 1H), 8.44 (s, 1H), 8.35 (s, 1H), 7.85 (dist.d(AB), J = 8.5 Hz, 2H), 7.67-7.70 (m, 1H), 7.64 (dist.d(AB), J = 8.5 Hz, 2H), 7.45-7.48 (m, 1H), 7.23-7.29 (m, 2H), 2.95 (t, J = 7.9 Hz, 2H), 1.71 (dist. quin, J = 7.6 Hz, 2H), 1.28 (dist. sxt, J = 7.4 Hz, 2H), 0.78 (t, J = 7.4 Hz, 3H); MS m/z 412 (ESI) [M + H]$^+$ |

Example 14

[1-(6-{[4-(trifluoromethyl)phenyl]amino}pyrazin-2-yl)-1H-benzimidazol-2-yl]methanol (Cpd 66)

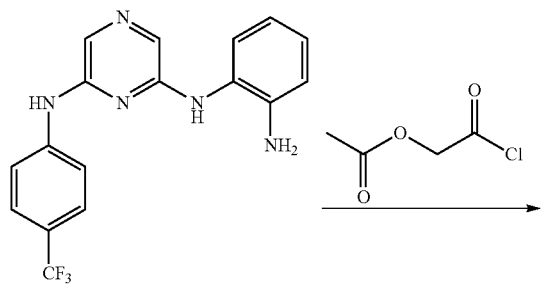

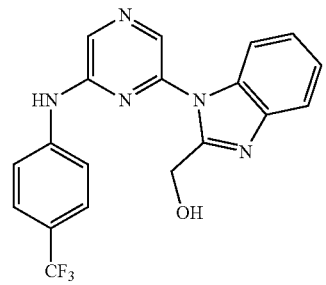

Intermediate (1-(6-(4-(trifluoromethyl)phenylamino)pyrazin-2-yl)-1H-benzo[d]imidazol-2-yl)methyl acetate (prepared using the procedure described in Example 13 and appropriate starting materials, reagents and reaction conditions) was dissolved in isopropanol and treated with aqueous NaOH (5N solution in water) at room temperature for 15 minutes. The product was purified by chromatography on silica gel (gradient from ethyl acetate:hexane 1:2 to EtOAc:MeOH 10:0), then recrystallized from ether/hexanes to provide the title compound as a gray solid (232 mg). $^1$H NMR (DMSO-$d_6$) δ 8.45 (s, 1H), 8.42 (s, 1H), 7.87-7.92 (m, J=8.5 Hz, 2H), 7.72-7.78 (m, 1H), 7.62-7.67 (m, J=8.8 Hz, 2H), 7.59-7.62 (m, 1H), 7.31-7.36 (m, 1H), 5.59 (t, J=5.8 Hz, 1H), 4.83-4.86 (m, 2H); MS m/z 386 (ESI) [M+H]$^+$.

Additional compounds of Formula (I) or a form thereof described herein may be prepared according to the procedure of Example 14 by substituting the appropriate starting materials, reagents and reaction conditions:

| Cpd | Name and Data |
|---|---|
| 98 | (1S)-1-[1-(6-{[4-(trifluoromethyl)phenyl]amino}pyrazin-2-yl)-1H-benzimidazol-2-yl]ethanol<br>$^1$H NMR (DMSO-$d_6$) δ 10.33 (s, 1H), 8.43 (s, 1H), 8.41 (s, 1H), 7.85-7.90 (m, J = 8.5 Hz, 2H), 7.75 (s, 1H), 7.60-7.65 (m, J = 8.8 Hz, 2H), 7.49-7.53 (m, 1H), 7.28-7.35 (m, 2H), 5.51 (d, J = 6.6 Hz, 1H), 5.16 (quin, J = 6.5 Hz, 1H), 1.60 (d, J = 6.3 Hz, 3H); MS m/z 401 (ESI) [M + H]$^+$ |

Example 15

6-(2-methoxy-1H-benzimidazol-1-yl)-N-[4-(trifluoromethyl)phenyl]pyrazin-2-amine (Cpd 77)

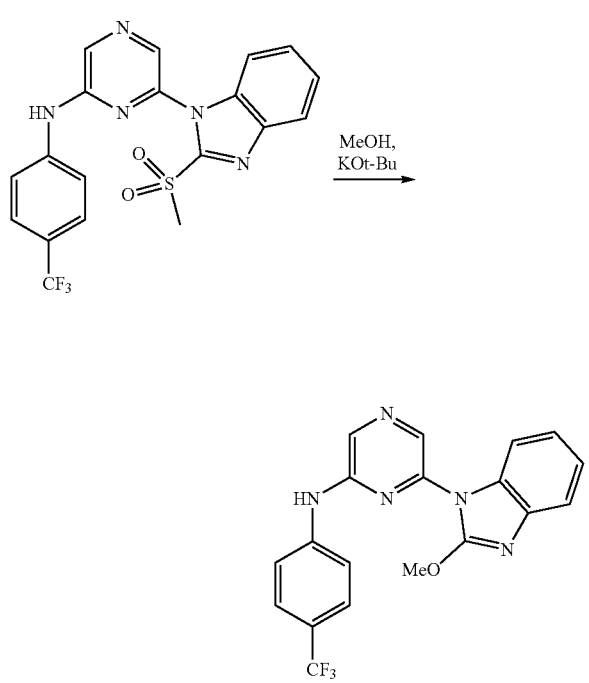

To 6-(2-(methylsulfonyl)-1H-benzo[d]imidazol-1-yl)-N-(4-(trifluoromethyl)phenyl)pyrazin-2-amine (48 mg, 0.11 mmol) was added MeOH (1 mL) followed by KOtBu (0.5 mL, 1M solution in THF). The mixture was reacted for 2 hours, then quenched with AcOH. The product was purified by chromatography on silica gel (gradient ethyl acetate:hexane 1:2 to 1:0), then washed with hexanes to provide the title compound (16 mg, 38%). $^1$H NMR (DMSO-$d_6$) δ 10.30 (br. s, 1H), 8.40 (s, 1H), 8.34 (s, 1H), 7.89 (d, J=8.8 Hz, 2H), 7.62-7.68 (m, 3H), 7.55 (d, J=7.3 Hz, 1H), 7.24 (td, J=7.6, 0.9 Hz, 1H), 7.17 (dd, J=7.9, 0.9 Hz, 1H), 4.22 (s, 3H)); MS m/z 386 (ESI) [M+H]$^+$.

Additional compounds of Formula (I) or a form thereof described herein may be prepared according to the procedure of Example 15 by substituting the appropriate starting materials, reagents and reaction conditions:

| Cpd | Name and Data |
|---|---|
| 81 | 6-(2-ethoxy-1H-benzimidazol-1-yl)-N-[4-(trifluoromethyl)phenyl]pyrazin-2-amine<br>$^1$H NMR (DMSO-$d_6$) δ 10.30 (s, 1H), 8.41 (s, 1H), 8.34 (s, 1H), 7.90 (d, J = 8.5 Hz, 2H), 7.62-7.67 (m, 3H), 7.53 (d, J = 7.3 Hz, 1H), 4.65 (q, J = 6.9 Hz, 2H), 1.45 (t, J = 7.1 Hz, 3H); MS m/z 400 (ESI) [M + H]$^+$ |

Example 16

6-(2-chloro-1H-benzimidazol-1-yl)-N-[4-(trifluoromethyl)phenyl]pyrazin-2-amine (Cpd 134)

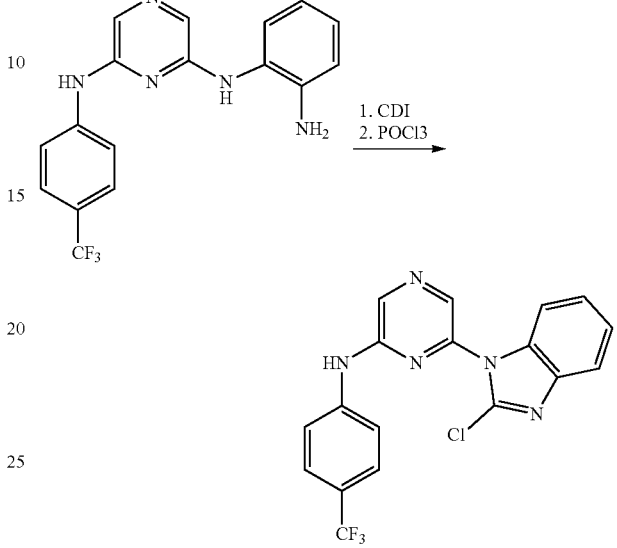

Step 1. To $N^2$-(2-aminophenyl)-$N^6$-(4-(trifluoromethyl)phenyl)pyrazine-2,6-diamine (230 mg, 0.67 mmol) was added acetonitrile (3 mL) and an excess of 1,1'-carbonyldiimidazole. The reaction mixture was stirred at room temperature for 30 minutes, then CDI (catalytic) was added. The mixture was reacted for an additional 30 minutes at room temperature, then treated with water and aqueous NaOH (1 mL, 5N) m and stirred at room temperature for 20 minutes. The resulting product was filtered and dried to provide the intermediate 1-(6-(4-(trifluoromethyl)phenylamino)pyrazin-2-yl)-1H-benzo[d]imidazol-2(3H)-one as a gray solid (274 mg).

Step 2. To 1-(6-(4-(trifluoromethyl)phenylamino)pyrazin-2-yl)-1H-benzo[d]imidazol-2(3H)-one (100 mg, 0.27 mmol) was added acetonitrile (1 mL) and POCl$_3$ (1.2 mL, 12 mmol). The reaction mixture was heated in a microwave oven at 160° C. for 40 minutes, then at 180° C. for 40 minutes. The reaction was quenched with aqueous NaHCO$_3$, then extracted with DCM and EtOAc. The combined organic product was purified by chromatography on silica gel (gradient ethyl acetate:hexane 1:4 to 1:0) and then washed with hexanes to provide the title compound (13 mg, 12%). $^1$H NMR (DMSO-$d_6$) δ 10.46 (br. s, 1H), 8.51 (s, 1H), 8.44 (s, 1H), 7.88 (d, J=8.5 Hz, 2H), 7.74-7.80 (m, 1H), 7.66 (d, J=8.8 Hz, 2H), 7.53-7.58 (m, 1H), 7.36-7.42 (m, 2H); MS m/z 390 (ESI) [M+H]$^+$.

Example 17

1-[1-(6-{[4-(trifluoromethyl)phenyl]amino}pyrazin-2-yl)-1H-benzimidazol-2-yl]ethanol (Cpd 150)

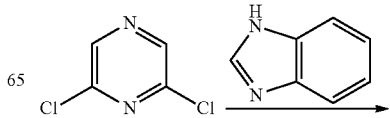

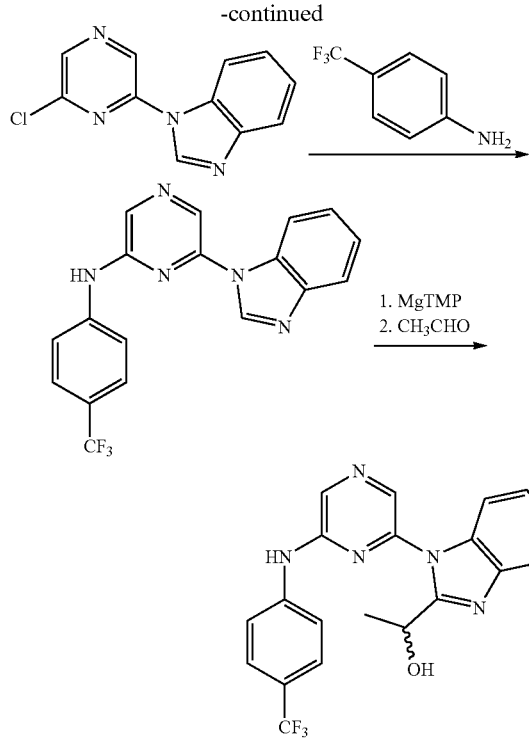

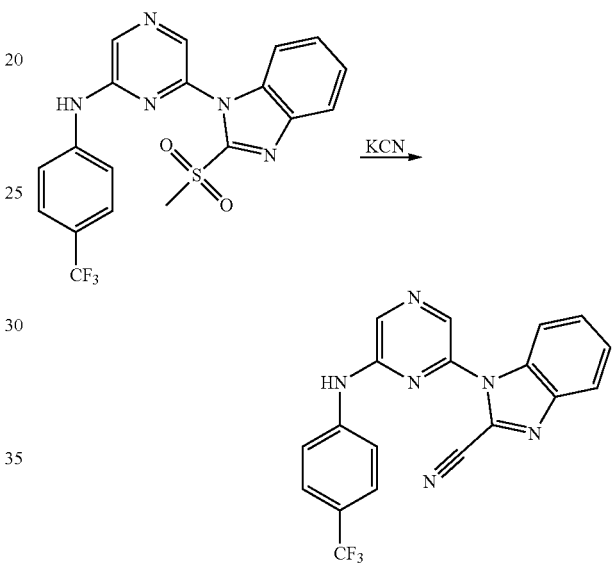

over K$_2$CO$_3$, filtered through a short plug of silica gel, then concentrated, dissolved in ether and precipitated with hexane to provide the title compound as an off-white solid (111 mg, 84%). $^1$H NMR (DMSO-d$_6$) δ 10.33 (br. s, 1H), 8.43 (s, 1H), 8.41 (s, 1H), 7.85-7.90 (m, J=8.5 Hz, 2H), 7.61-7.65 (m, J=8.5 Hz, 2H), 7.31 (dtd, J=7.3, 3.6, 1.9 Hz, 1H), 5.52 (d, J=6.6 Hz, 1H), 5.16 (quin, J=6.5 Hz, 1H), 1.60 (d, J=6.3 Hz, 3H); MS m/z 400 (ESI) [M+H]$^+$.

Example 18

1-(6-{[4-(trifluoromethyl)phenyl]amino}pyrazin-2-yl)-1H-benzimidazole-2-carbonitrile (Cpd 157)

Step 1. To 2,6-dichloropyrazine (2.3 g, 15.4 mmol) was added 1H-benzo[d]imidazole (1.9 g, 16 mmol), acetonitrile (15 mL) and DIEA (2.5 mL, 15 mmol). The mixture was heated in a microwave oven at 160° C. for 50 minutes and then at 180° C. for 90 minutes. The mixture was filtered and the resulting product was washed on the filter with acetonitrile, then water and EtOAc. The filtrate was diluted with water and filtered again. The two solid fractions were combined and washed with hot EtOAc to provide 1-(6-chloropyrazin-2-yl)-1H-benzo[d]imidazole as a yellow solid (1.35 g, 39%). $^1$H NMR (DMSO-d$_6$) δ 9.38 (d, J=0.6 Hz, 1H), 9.15 (s, 1H), 8.80 (d, J=0.6 Hz, 1H), 8.31 (dt, J=8.2, 0.9 Hz, 1H), 7.83 (ddd, J=7.9, 1.9, 0.6 Hz, 1H), 7.47 (td, J=7.7, 1.3 Hz, 1H), 7.41 (dd, J=7.3, 1.3 Hz, 1H).

Step 2. To 1-(6-chloropyrazin-2-yl)-1H-benzo[d]imidazole (1.35 g, 5.9 mmol) was added 4-(trifluoromethyl)aniline (1.3 g, 8 mmol), DMF (5 mL) and THF (6 mL). The mixture was cooled in ice bath, then KOt-Bu was slowly added (1M in THF, 12 mL, 12 mmol). The mixture was reacted for 15 minutes in an ice bath, then the reaction was quenched with AcOH, followed by water and hexane. The precipitate was filtered, then washed with water and ether. The organic layer was concentrated to provide 6-(1H-benzo[d]imidazol-1-yl)-N-(4-(trifluoromethyl)phenyl)pyrazin-2-amine (1.0 g).

Step 3. To 2,2,6,6-tetramethylpiperidine (0.17 mL, 1 mmol) was added THF (3 mL). The solution was cooled to −60° C. and n-BuLi was added (2.2 M in c-Hex, 0.45 mL, 1 mmol). The mixture was reacted for 1 minute at −60° C., then cannulated into a suspension of 6-(1H-benzo[d]imidazol-1-yl)-N-(4-(trifluoromethyl)phenyl)pyrazin-2-amine (117 mg, 0.33 mmol) in THF (3 mL) at −70° C. The mixture was reacted for 6 minutes, then acetaldehyde was added dropwise (0.1 mL, 1.8 mmol). The mixture was reacted for another 3 minutes at −70° C., then the reaction was quenched with AcOH. The solution was partitioned between EtOAc and aqueous NH$_4$Cl. The organic portion was dried To 6-(2-(methylsulfonyl)-1H-benzo[d]imidazol-1-yl)-N-(4-(trifluoromethyl)phenyl)pyrazin-2-amine (75 mg, 0.17 mmol) was added KCN (33 mg, 0.5 mmol) and DMSO (1 mL). The mixture was heated at 80° C. and reacted for 10 minutes, then diluted with water and filtered. The precipitate was washed with aqueous methanol to provide the title compound as an off-white solid (52 mg, 80%). $^1$H NMR shows a mixture of rotamers 10:1, (DMSO-d$_6$) δ 10.47-10.53 (m, 1H), 8.57 (s, 1H), 8.53 (s, 1H), 7.99 (d, J=8.2 Hz, 1H), 7.96 (d, J=8.5 Hz, 2H), 7.89 (d, J=0.6 Hz, 1H), 7.67 (d, J=8.8 Hz, 2H), 7.64 (ddd, J=8.4, 7.3, 1.1 Hz, 1H), 7.56 (ddd, J=8.2, 7.3, 0.9 Hz, 1H); MS m/z 381 (ESI) [M+H]$^+$.

Additional compounds of Formula (I) or a form thereof described herein may be prepared according to the procedure of Example 18 by substituting the appropriate starting materials, reagents and reaction conditions:

| Cpd | Name and Data |
|---|---|
| 184 | 1-(6-{[4-(trifluoromethoxy)phenyl]amino}pyrazin-2-yl)-1H-benzimidazole-2-carbonitrile HNMR showed a mixture of rotamers 4:6; MS m/z 397 (ESI) [M + H]$^+$ |
| 188 | 1-(6-{[4-(difluoromethoxy)phenyl]amino}pyrazin-2-yl)-1H-benzimidazole-2-carbonitrile HNMR showed a mixture of rotamers 4:6; MS m/z 379 (ESI) [M + H]$^+$ |

Example 19

6-[2-(methylsulfanyl)-1H-benzimidazol-1-yl]-N-[4-(trifluoromethoxy)phenyl]pyrazin-2-amine (Cpd 167)

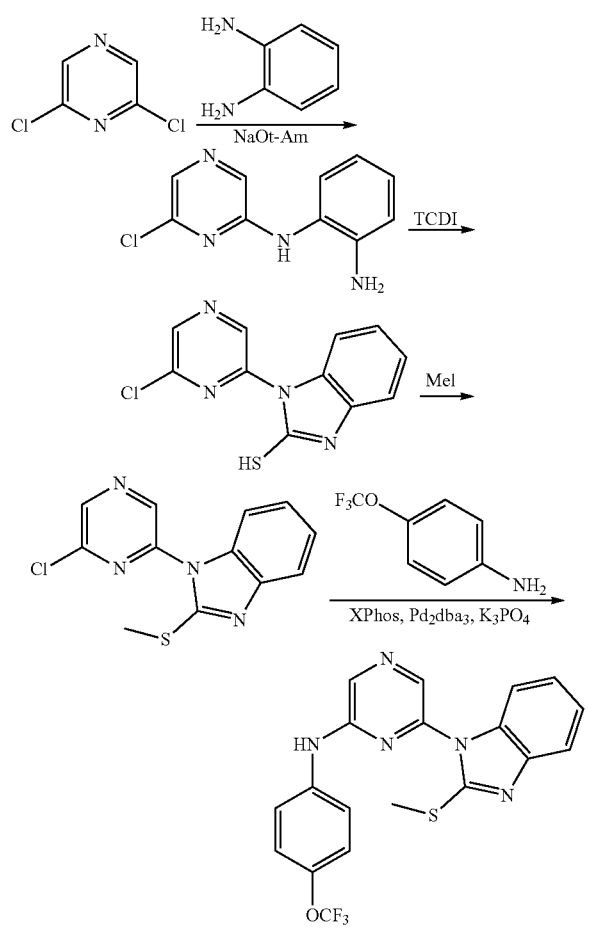

Step 1. To 2,6-dichloropyrazine (3.74 g, 25 mmol) was added 2-Me-THF (30 mL). The mixture was cooled in ice-bath, then benzene-1,2-diamine (13.5 g, 125 mmol), and NaOt-Am (2.5 M in THF, 24 mL, 60 mmol) were added. The mixture was reacted for 40 minutes, then the reaction was quenched with AcOH and partitioned between water and EtOAc. The organic layer was dried, filtered through a short plug of silica gel and concentrated to provide a red solid.

Step 2. The product obtained above was dissolved in acetonitrile, heated at 90° C., then TCDI was added portionwise until the starting material was consumed (as shown by UPLC). The reaction mixture was cooled in an ice bath, then the precipitate was filtered and washed with acetonitrile to provide 1-(6-chloropyrazin-2-yl)-1H-benzo[d]imidazole-2-thiol, which was taken forward directly in the next step.

Step 3. The obtained product (still wet with acetonitrile) was suspended in acetonitrile (100 mL) then cooled in ice bath and treated with iodomethane (1.6 mL, 25 mmol) and NaOH (5N solution in water, 5 mL, 25 mmol). The mixture was reacted for 5 minutes, then the reaction was quenched with AcOH and water and hexane were added. The resulting precipitate was filtered and dried to provide 1-(6-chloropyrazin-2-yl)-2-(methylthio)-1H-benzo[d]imidazole as a pink solid (2.06 g, 7.5 mmol, 30% for the 3 steps). $^1$H NMR (DMSO-$d_6$) δ 9.15 (d, J=0.6 Hz, 1H), 8.99 (s, 1H), 7.68-7.71 (m, 1H), 7.63-7.66 (m, 1H), 7.27-7.35 (m, OH), 2.74 (s, 3H); MS m/z 277 (ESI) [M+H]$^+$.

Step 4. To 1-(6-chloropyrazin-2-yl)-2-(methylthio)-1H-benzo[d]imidazole (630 mg, 2.28 mmol) was added XPhos (65 mg, 0.13 mmol), Pd$_2$dba$_3$ (63 mg, 0.07 mmol), K$_3$PO$_4$ (975 mg, 4.6 mmol), 4-(trifluoromethoxy)aniline (814 mg, 4.6 mmol) and DME (10 mL). The mixture was heated under nitrogen at 110° C. (heating block) for 3 hours, then QPhos (excess) and Pd$_2$dba$_3$ (excess) were added. The mixture was then heated for 21 hours, then the product was partitioned between aqueous NH$_4$Cl and EtOAc and purified by chromatography on silica gel (gradient ethyl acetate:hexane 1:4 to 1:1). The product was dissolved in ether and precipitated with hexanes to provide the title compound (340 mg, 36%). $^1$H NMR (DMSO-$d_6$) δ 10.19 (s, 1H), 8.39 (s, 1H), 8.30 (s, 1H), 7.84 (d, J=9.1 Hz, 2H), 7.66-7.70 (m, 1H), 7.51-7.55 (m, 1H), 7.32 (d, J=8.5 Hz, 2H), 7.22-7.30 (m, 2H), 2.73 (s, 3H); MS m/z 418 (ESI) [M+H]$^+$.

Additional compounds of Formula (I) or a form thereof described herein may be prepared according to the procedure of Example 19 by substituting the appropriate starting materials, reagents and reaction conditions:

| Cpd | Name and Data |
|---|---|
| 181 | N-[4-(difluoromethoxy)phenyl]-6-[2-(methylsulfanyl)-1H-benzimidazol-1-yl]pyrazin-2-amine<br>$^1$H NMR (DMSO-$d_6$) δ 10.08 (s, 1H), 8.34 (s, 1H), 8.25 (s, 1H), 7.76 (dist. d, J = 9.1 Hz, 2H), 7.65-7.69 (m, 1H), 7.49-7.54 (m, 1H), 7.21-7.32 (m, 2H), 7.13 (dist. d, J = 8.8 Hz, 2H), 7.13 (t, J = 75.0 Hz, 1H), 2.71 (s, 3H); MS m/z 400 (ESI) [M + H]$^+$ |

Example 20

N-[4-(aminomethyl)phenyl]-6-(2-methyl-1H-benzimidazol-1-yl)pyrazin-2-amine trifluoroacetate (Cpd 154a)

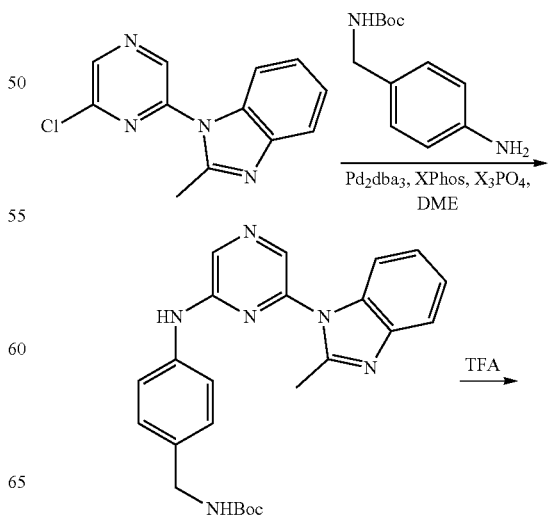

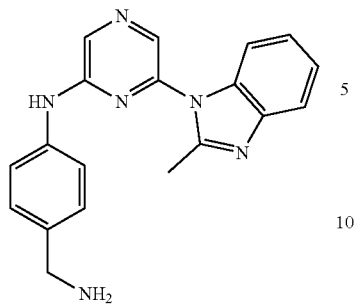

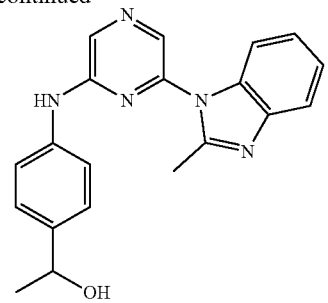

Intermediate tert-butyl 4-(6-(2-methyl-1H-benzo[d]imidazol-1-yl)pyrazin-2-ylamino)benzylcarbamate (130 mg, 0.30 mmol) (prepared using the procedure described in Example 2 and appropriate starting materials, reagents and reaction conditions) was dissolved in dichloromethane (5 mL) and TFA (0.25 mL) was added. The mixture was heated at 50° C. (heat block temperature) for 2 hours then concentrated and recrystallized from a mixture of ethyl acetate and ether to provide the title compound as an off-white solid (133 mg, 100%). $^1$H NMR (500 MHz, DMSO-d$_6$) δ 2.64 (s, 3H) 3.96 (q, J=5.40 Hz, 2H) 7.24-7.31 (m, 2H) 7.37 (m, J=8.83 Hz, 2H) 7.52-7.56 (m, 1H) 7.65-7.69 (m, 1H) 7.69-7.74 (m, 2H) 8.31 (s, 1H) 8.38 (s, 1H) 10.08 (s, 1H); MS m/z 331 (ESI) [M+H]$^+$.

To Compound 153 (60 mg, 0.17 mmol) (prepared using the procedure described in Example 2 and appropriate starting materials, reagents and reaction conditions) was added ethanol (3 mL) and sodium borohydride (catalytic) at room temperature. The mixture was reacted for 30 minutes at room temperature, then the reaction was quenched with AcOH, diluted with water, and partially concentrated in vacuo. The residue was filtered, then washed with aqueous methanol and ether to provide the title compound as a light green solid (33 mg, 56%). $^1$H NMR (500 MHz, DMSO-d$_6$) δ 1.29 (d, J=6.31 Hz, 3H) 2.63 (s, 3H) 4.66 (m, J=6.30, 4.40 Hz, 1H) 5.04 (d, J=4.10 Hz, 1H) 7.23-7.30 (m, 4H) 7.48-7.55 (m, 1H) 7.57-7.63 (m, 2H) 7.64-7.69 (m, 1H) 8.23 (s, 1H) 8.34 (s, 1H) 9.89 (s, 1H); MS m/z 346 (ESI) [M+H]$^+$.

Additional compounds of Formula (I) or a form thereof described herein may be prepared according to the procedure of Example 20 by substituting the appropriate starting materials, reagents and reaction conditions:

| Cpd | Name and Data |
|---|---|
| 256 | N-[4-(1-aminoethyl)phenyl]-6-(2-methyl-1H-benzimidazol-1-yl)pyrazin-2-amine<br>$^1$H NMR (DMSO-d$_6$) δ 9.88 (s, 1H), 8.33 (s, 1H), 8.21 (s, 1H), 7.62-7.68 (m, 1H), 7.54-7.61 (m, 2H), 7.48-7.53 (m, 1H), 7.21-7.31 (m, 4H), 3.93 (q, J = 6.5 Hz, 1H), 2.62 (s, 3H), 2.23 (br. s., 2H), 1.21 (d, J = 6.6 Hz, 3H); MS m/z 345 (ESI) [M + H]$^+$ |

Example 21

1-(4-{[6-(2-methyl-1H-benzimidazol-1-yl)pyrazin-2-yl]amino}phenyl)ethanol (Cpd 155)

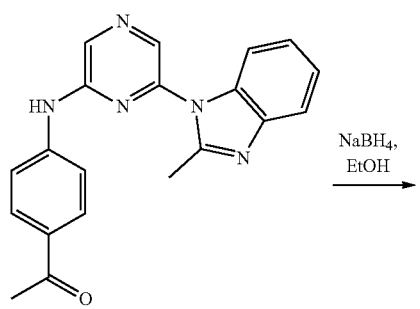

Example 22

N-{4-[(1E)-N-hydroxyethanimidoyl]phenyl}-6-(2-methyl-1H-benzimidazol-1-yl)pyrazin-2-amine (Cpd 156)

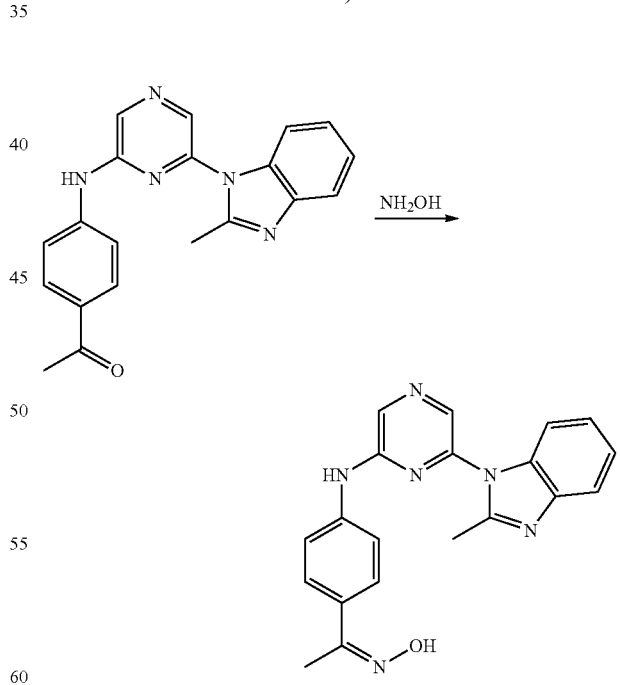

A mixture of Compound 153 (94 mg, 0.27 mmol) (prepared (prepared using the procedure described in Example 2 and appropriate starting materials, reagents and reaction conditions), methanol (5 mL) and NH$_2$OH×HCl (catalytic) was heated at 40° C. and reacted for 30 minutes. The resulting suspension was filtered and washed with water and ether, then dried to provide the title compound as a yellow solid (101 mg, 95%). $^1$H NMR (500 MHz, DMSO-d$_6$) δ 2.11 (s, 3H) 2.80 (s, 3H) 7.48 (m, 2H) 7.57-7.61 (m, 2H) 7.69-7.74 (m, 3H) 7.80-7.84 (m, 1H) 8.35 (s, 1H) 8.50 (s, 1H) 10.31 (s, 1H); MS m/z 359 (ESI) [M+H]$^+$.

Example 23

N$^1$-[6-(2-methyl-1H-benzimidazol-1-yl)pyrazin-2-yl]-4-(trifluoromethyl)benzene-1,3-diamine (Cpd 506)

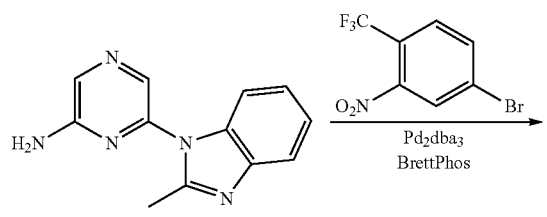

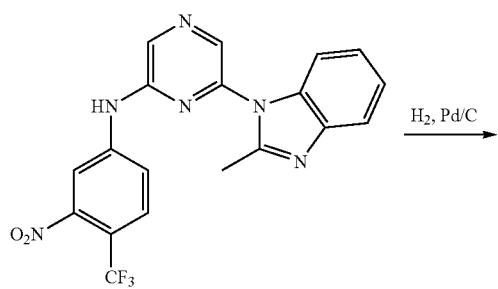

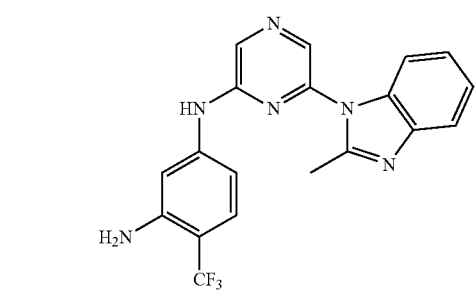

Intermediate 6-(2-methyl-1H-benzo[d]imidazol-1-yl)-N-(3-nitro-4-(trifluoromethyl)phenyl)pyrazin-2-amine (prepared using the procedure described in Example 8 and appropriate starting materials, reagents and reaction conditions) was dissolved in methanol (10 mL) and Pd/C (10%) (catalytic) was added. The reaction mixture was shaken under hydrogen (50 psi) for 3 days. The reaction mixture was filtered through a short plug of silica gel, then concentrated, washed with ether and filtered to provide the title compound (471 mg, 52%). $^1$H NMR (500 MHz, DMSO-d$_6$) δ 2.64 (s, 3H) 5.48-5.57 (m, 2H) 7.03 (d, J=8.51 Hz, 1H) 7.09 (d, J=1.58 Hz, 1H) 7.22-7.33 (m, 3H) 7.47-7.56 (m, 1H) 7.64-7.73 (m, 1H) 8.30 (s, 1H) 8.39 (s, 1H) 10.00 (br. s, 1H); MS m/z 384 (ESI) [M+H]$^+$.

Example 24

(4-{[6-(2-methyl-1H-benzimidazol-1-yl)pyrazin-2-yl]amino}phenyl)boronic acid (Cpd 434)

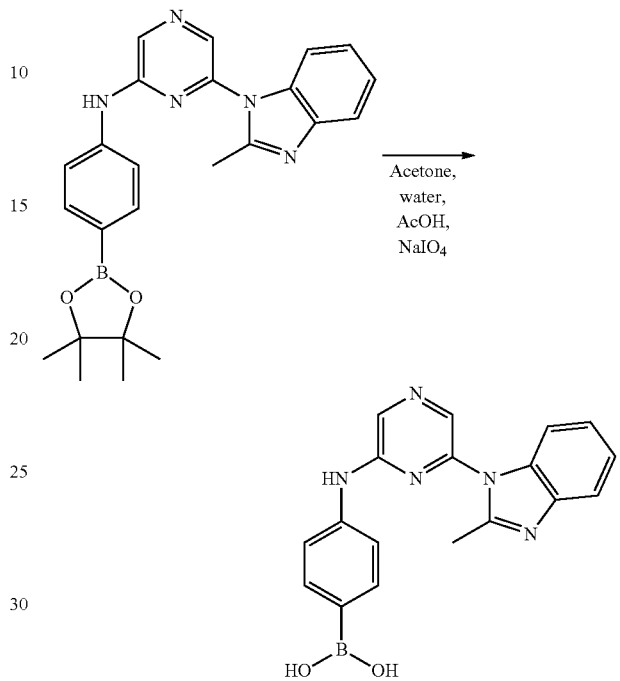

A mixture of the concentrated mother liquor of Compound 433 (prepared using the procedure described in Example 2 and appropriate starting materials, reagents and reaction conditions), aqueous acetone and acetic acid was stirred at room temperature for 2 days (UPLC analysis showed only partial conversion), then NaIO$_4$ (214 mg, 1 mmol) was added. The reaction mixture was stirred for an additional 24 hours, diluted with water and the resulting precipitate was filtered and dried to provide the title compound as a brown solid. $^1$H NMR (500 MHz, DMSO-d$_6$) δ 2.65 (s, 3H) 7.20-7.32 (m, 2H) 7.51-7.59 (m, 1H) 7.64 (d, J=8.51 Hz, 2H) 7.66-7.69 (m, 1H) 7.72 (d, J=8.51 Hz, 2H) 7.86 (br. s., 2H) 8.29 (s, 1H) 8.38 (s, 1H) 10.01 (s, 1H); MS m/z 346 (ESI) [M+H]$^+$.

Example 25

4-methyl-N$^1$-[6-(2-methyl-1H-benzimidazol-1-yl)pyrazin-2-yl]benzene-1,2-diamine (Cpd 563)

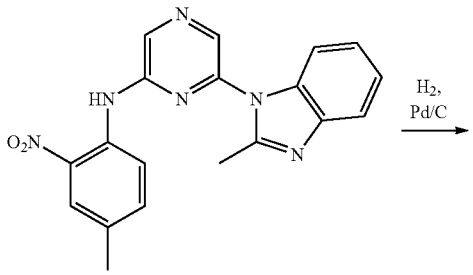

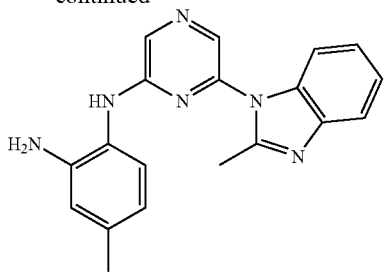

Intermediate 6-(2-methyl-1H-benzo[d]imidazol-1-yl)-N-(4-methyl-2-nitrophenyl)pyrazin-2-amine (prepared using the procedure described in Example 2 and appropriate starting materials, reagents and reaction conditions). $^1$H NMR (DMSO-d$_6$) δ 10.04 (br. s, 1H), 8.53 (s, 1H), 8.36 (s, 1H), 7.84-7.88 (m, 2H), 7.60-7.65 (m, 1H), 7.52 (dd, J=8.5, 1.6 Hz, 1H), 7.39-7.43 (m, 1H), 7.19-7.27 (m, 1H), 2.34 (s, 3H) (having one or more Me peaks likely hidden below the DMSO signal); $^{13}$C NMR (DMSO-d$_6$) δ 151.1, 151.0, 142.4, 142.3, 140.8, 135.1, 134.7, 134.4, 134.0, 130.9, 130.4, 125.1, 124.9, 122.8, 122.5, 118.6, 110.7, 19.9, 14.7; MS m/z 361 (ESI) [M+H]$^+$.

To the obtained intermediate was added platinum on carbon (Pt/C), and a mixture of EtOAc and MeOH. The reaction mixture was stirred under hydrogen (1 atm) for 2 hours, filtered through a plug of silica gel, then concentrated and washed with a mixture of ethyl acetate:ether:hexane to provide the title compound as a yellow solid (31 mg, 24% over two steps). $^1$H NMR (DMSO-d$_6$) δ 8.74 (br. s, 1H), 8.09 (s, 1H), 8.07 (s, 1H), 7.57-7.64 (m, 1H), 7.47-7.56 (m, 1H), 7.17-7.26 (m, 2H), 7.08 (d, J=7.9 Hz, 1H), 6.57 (d, J=1.3 Hz, 1H), 6.36 (dd, J=8.0, 1.4 Hz, 1H), 4.95 (br. s, 2H), 2.57 (s, 3H), 2.17 (s, 3H); MS m/z 331 (ESI) [M+H]$^+$.

Example 26

5-methyl-2-{[6-(2-methyl-1H-benzimidazol-1-yl)pyrazin-2-yl]amino}phenol (Cpd 582)

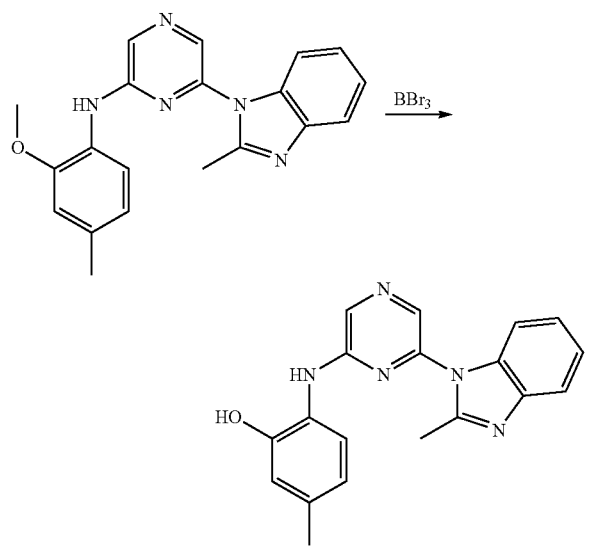

A mixture of Compound 576 (50 mg, 0.14 mmol) (prepared using the procedure described in Example 2 and appropriate starting materials, reagents and reaction conditions), dichloromethane (1 mL) and a BBr$_3$ solution (1 mL, 1M in dichloromethane) was reacted for 1 hour at room temperature, then quenched with ice and ammonium hydroxide. The product was extracted with dichloromethane, then dried over K$_2$CO$_3$ and filtered through a short plug of silica gel. The residue was concentrated and purified by chromatography on silica gel (gradient from ethyl acetate:hexane 1:2 to ethyl acetate:methanol 10:1) to provide the title compound as a yellow solid (46 mg, 97%). $^1$H NMR (DMSO-d$_6$) δ 9.72 (br. s., 1H), 8.97 (br. s, 1H), 8.40 (s, 1H), 8.13 (s, 1H), 7.60-7.68 (m, 2H), 7.47-7.53 (m, 1H), 7.20-7.29 (m, 2H), 6.73 (d, J=1.3 Hz, 1H), 6.55 (dd, J=8.2, 1.3 Hz, 1H), 2.59 (s, 3H), 2.19 (s, 3H); MS m/z 332 (ESI) [M+H]$^+$.

Example 27

6-[2-(methylsulfanyl)-1H-benzimidazol-1-yl]-N-[4-(trifluoromethyl)phenyl]pyrazin-2-amine (Cpd 54)

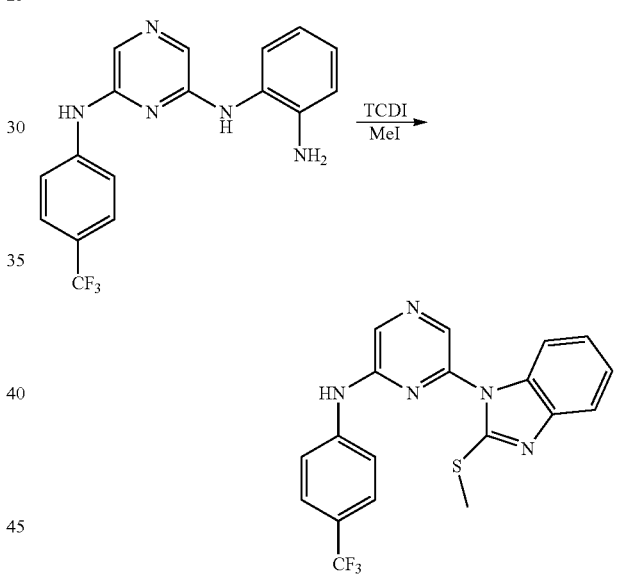

To N$^2$-(2-aminophenyl)-N$^6$-(4-(trifluoromethyl)phenyl)pyrazine-2,6-diamine (228 mg, 0.63 mmol) was added isopropanol (2 mL) and 1,1'-thiocarbonyldiimidazole (190 mg, 1 mmol). The mixture was heated in a microwave oven to 160° C. for 35 minutes. The reaction mixture was cooled to room temperature, DIEA (0.33 mL, 2 mmol) was added, followed by MeI (0.13 mL, 2 mmol). The mixture was reacted for 5 minutes at room temperature, then diluted with water and extracted with dichloromethane. The organic layer was purified by chromatography on silica gel (gradient ethyl acetate:hexane 1:4 to 1:0), then recrystallized from ether/hexanes to provide the title compound as an off-white solid (164 mg, 65%). $^1$H NMR (DMSO-d$_6$) δ 10.42 (s, 1H), 8.44 (s, 1H), 8.38 (s, 1H), 7.96 (d, J=8.5 Hz, 2H), 7.68-7.71 (m, 1H), 7.67 (d, J=8.5 Hz, 2H), 7.52-7.57 (m, 1H), 7.24-7.32 (m, J=8.9, 7.5, 1.3 Hz, 2H), 2.74 (s, 3H); MS m/z 402 (ESI) [M+H]$^+$.

Additional compounds of Formula (I) or a form thereof described herein may be prepared according to the procedure of Example 27 by substituting the appropriate starting materials, reagents and reaction conditions:

| Cpd | Name and Data |
|---|---|
| 79 | 6-[2-(ethylsulfanyl)-1H-benzimidazol-1-yl]-N-[4-(trifluoromethyl)phenyl]pyrazin-2-amine<br>$^1$H NMR (DMSO-$d_6$) δ 10.41 (s, 1H), 8.44 (s, 1H), 8.37 (s, 1H), 7.90-8.00 (m, J = 8.5 Hz, 2H), 7.69 (d, J = 7.6 Hz, 1H), 7.62-7.68 (m, J = 8.5 Hz, 2H), 7.53 (d, J = 7.6 Hz, 1H), 7.21-7.33 (m, 2H), 3.31-3.39 (m, 2H), 1.38 (t, J = 7.3 Hz, 3H); MS m/z 416 (ESI) [M + H]$^+$ |

Example 28

N-methyl-1-(6-{[4-(trifluoromethyl)phenyl] amino}pyrazin-2-yl)-1H-benzimidazol-2-amine (Cpd 61)

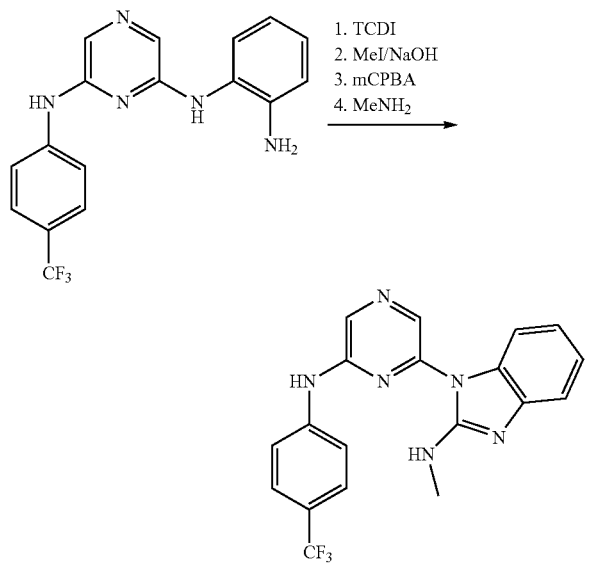

Step 1. To $N^2$-(2-aminophenyl)-$N^6$-(4-(trifluoromethyl) phenyl)pyrazine-2,6-diamine (2.58 g, 7.5 mmol) was added 1,1'-thiocarbonyldiimidazole (1.8 g, 10 mmol) and acetonitrile (20 mL). The mixture was heated at reflux for 45 min, then cooled, diluted with water and filtered.

Step 2. To the still wet product was added acetonitrile (100 mL), methanol (50 mL), NaOH (3 mL, 5N solution in water) and methyl iodide (0.62 mL, 10 mmol). The mixture was left at room temperature for 10 min, diluted with water, hexane and AcOH, then stirred and filtered to provide Compound 54 (alternate synthesis, compare Example 27).

Step 3. To the still wet Compound 54 was added dichloromethane (50 mL) and EtOAc (50 mL). The mixture was cooled in an ice bath, then mCPBA (70% pure, 3.7 g, 15 mmol) was added. The mixture was stirred for 1.5 hours, then NaHCO$_3$ (excess), water, hexane and NaHSO$_3$ were added. The mixture was filtered, then washed with a ether/hexane mixture and dried in vacuo. UPLC analysis (UV, 254 nM) showed the solid product (2.3 g) to consist of 6-(2-(methylsulfonyl)-1H-benzo[d]imidazol-1-yl)-N-(4-(trifluoromethyl)phenyl)pyrazin-2-amine (94%) and 6-(2-(methylsulfinyl)-1H-benzo[d]imidazol-1-yl)-N-(4-(trifluoromethyl) phenyl)pyrazin-2-amine (3%).

Step 4. To a portion of the obtained intermediate was added acetonitrile (20 mL), a pinch of MeNH$_2$×HCl (excess) and triethylamine (2 mL). The mixture was heated in a sealed tube at 100° C. for 18 hours. The reaction mixture was partly concentrated, diluted with water, filtered, then washed with hexanes and dried to provide the title compound as a light yellow solid (249 mg). $^1$H NMR (DMSO-$d_6$) δ 10.28 (s, 1H), 8.36 (s, 1H), 8.31 (s, 1H), 7.86-7.91 (m, J=8.5 Hz, 2H), 7.64-7.70 (m, J=8.8 Hz, 2H), 7.33 (d, J=7.9 Hz, 1H), 7.28 (d, J=7.6 Hz, 1H), 7.08 (td, J=7.7, 0.9 Hz, 1H), 6.96 (td, J=7.7, 0.9 Hz, 1H), 6.85 (q, J=4.4 Hz, 1H), 2.96 (d, J=4.7 Hz, 3H); MS m/z 385 (ESI) [M+H]$^+$.

Additional compounds of Formula (I) or a form thereof described herein may be prepared according to the procedure of Example 28 by substituting the appropriate starting materials, reagents and reaction conditions:

| Cpd | Name and Data |
|---|---|
| 76 | 1-(6-{[4-(trifluoromethyl)phenyl]amino}pyrazin-2-yl)-1H-benzimidazol-2-amine<br>$^1$H NMR (DMSO-$d_6$) δ 10.29 (s, 1H), 8.35 (s, 1H), 8.31 (s, 1H), 7.88 (dist.d(AB), J = 8.5 Hz, 2H), 7.65 (dist.d(AB), J = 8.8 Hz, 2H), 7.27 (dist.t, J = 8.5 Hz, 2H), 7.08 (td, J = 7.6, 1.3 Hz, 1H), 6.96 (td, J = 7.5, 0.9 Hz, 1H), 6.80 (br. s., 1H, should by NH$_2$); MS m/z 371 (ESI) [M + H]$^+$ |
| 138 | N-ethyl-1-(6-{[4-(trifluoromethyl)phenyl]amino}pyrazin-2-yl)-1H-benzimidazol-2-amine<br>1H NMR (DMSO-$d_6$) δ 10.29 (br. s, 1H), 8.35 (s, 1H), 8.32 (s, 1H), 7.87-7.92 (m, J = 8.8 Hz, 2H), 7.64-7.68 (m, J = 8.8 Hz, 2H), 7.32 (d, J = 7.9 Hz, 1H), 7.29 (d, J = 7.6 Hz, 1H), 7.08 (td, J = 7.6, 1.1 Hz, 1H), 6.96 (td, J = 7.6, 1.1 Hz, 1H), 6.90 (t, J = 5.7 Hz, 1H), 3.43 (qd, J = 6.9, 5.7 Hz, 1H), 1.17 (t, J = 7.1 Hz, 3H); MS m/z 399 (ESI) [M + H]$^+$ |
| 183 | N-methyl-1-(6-{[4-(trifluoromethoxy)phenyl]amino}pyrazin-2-yl)-1H-benzimidazol-2-amine<br>1H NMR (DMSO-$d_6$) δ 10.06 (s, 1H), 8.29 (s, 1H), 8.24 (s, 1H), 7.73-7.79 (m, 2H), 7.33 (d, J = 8.5 Hz, 2H), 7.29 (dd, J = 18.6, 7.6 Hz, 2H), 7.07 (td, J = 7.9, 0.9 Hz, 1H), 6.94 (td, J = 7.9, 0.9 Hz, 1H), 6.85 (q, J = 4.4 Hz, 1H), 2.93 (d, J = 4.7 Hz, 3H); MS m/z 383 (ESI) [M + H]$^+$ |
| 187 | 1-(6-{[4-(difluoromethoxy)phenyl]amino}pyrazin-2-yl)-N-methyl-1H-benzimidazol-2-amine<br>1H NMR (DMSO-$d_6$) δ 9.93 (s, 1H), 8.25 (s, 1H), 8.21 (s, 1H), 7.65-7.71 (m, 2H), 7.25-7.33 (m, 2H), 7.13-7.18 (m, 2H), 7.07 (td, J = 7.6, 1.1 Hz, 1H), 7.14 (t, J = 74.4 Hz, 1H), 6.94 (td, J = 7.6, 1.3 Hz, 1H), 6.87 (q, J = 4.5 Hz, 1H), 2.93 (d, J = 4.7 Hz, 3H); MS m/z 383 (ESI) [M + H]$^+$ |

Example 29

4-{[6-(2-methyl-1H-benzimidazol-1-yl)pyrazin-2-yl] amino}benzamide (Cpd 185)

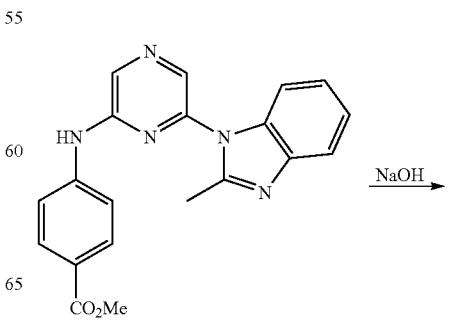

-continued

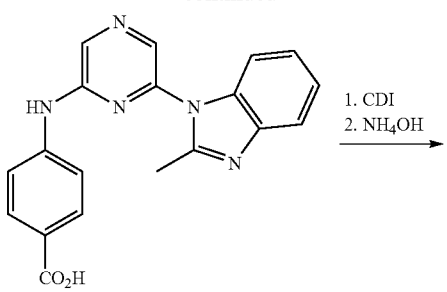

Step 1. To methyl 4-(6-(2-methyl-1H-benzo[d]imidazol-1-yl)pyrazin-2-ylamino)benzoate (100 mg, 0.28 mmol) was added methanol (10 mL) and NaOH (5 M solution in water, 1.5 mL, 7.5 mmol). The reaction mixture was heated at 70° C. for 2 hours, then quenched with AcOH, partially concentrated and diluted with water. The residue was filtered to provide 4-(6-(2-methyl-1H-benzo[d]imidazol-1-yl)pyrazin-2-ylamino)benzoic acid as an off-white solid (110 mg). $^1$H NMR (DMSO-d$_6$) δ 10.05 (s, 1H), 8.37 (s, 1H), 8.23 (s, 1H), 7.75 (d, J=8.5 Hz, 2H), 7.64-7.67 (m, 1H), 7.52-7.57 (m, 3H), 7.23-7.29 (m, 2H), 2.64 (s, 3H); MS m/z 346 (ESI) [M+H]$^+$.

Step 2. To 4-(6-(2-methyl-1H-benzo[d]imidazol-1-yl)pyrazin-2-ylamino)benzoic acid (63 mg, 0.18 mmol) was added CDI (58 mg, 0.36 mmol) then DMF (1 mL) at room temperature. The mixture was stirred for 15 minutes, then CDI (excess) was added. The mixture was stirred for 5 minutes, then NH$_4$OH (0.5 mL, excess) was added. The mixture was reacted for 45 minutes at room temperature, then diluted with water and the product filtered to provide the title compound as a light yellow solid (54 mg, 86%). $^1$H NMR (DMSO-d$_6$) δ 10.22 (s, 1H), 8.40 (s, 1H), 8.34 (s, 1H), 7.81 (d, J=8.8 Hz, 2H), 7.79 (br. s, 1H), 7.73 (d, J=8.8 Hz, 2H), 7.64-7.69 (m, 1H), 7.51-7.57 (m, 1H), 7.22-7.31 (m, 2H), 7.18 (br. s., 1H), 2.64 (s, 3H); MS m/z 345 (ESI) [M+H]$^+$.

Additional compounds of Formula (I) or a form thereof described herein may be prepared according to the procedure of Example 29 by substituting the appropriate starting materials, reagents and reaction conditions:

| Cpd | Name and Data |
|---|---|
| 186 | N-methyl-4-{[6-(2-methyl-1H-benzimidazol-1-yl)pyrazin-2-yl]amino}benzamide<br>$^1$H NMR (DMSO-d$_6$) δ 10.21 (s, 1H), 8.40 (s, 1H), 8.34 (s, 1H), 8.26 (q, J = 3.8 Hz, 1H), 7.70-7.80 (m, 4H), 7.63-7.70 (m, 1H), 7.51-7.58 (m, 1H), 7.21-7.32 (m, 2H), 2.74 (d, J = 4.4 Hz, 3H), 2.64 (s, 3H); MS m/z 359 (ESI) [M + H]$^+$ |

Example 30

N-[4-(difluoromethoxy)phenyl]-6-(2-methyl-4,5,6,7-tetrahydro-1H-benzimidazol-1-yl)pyrazin-2-amine
(Cpd 258)

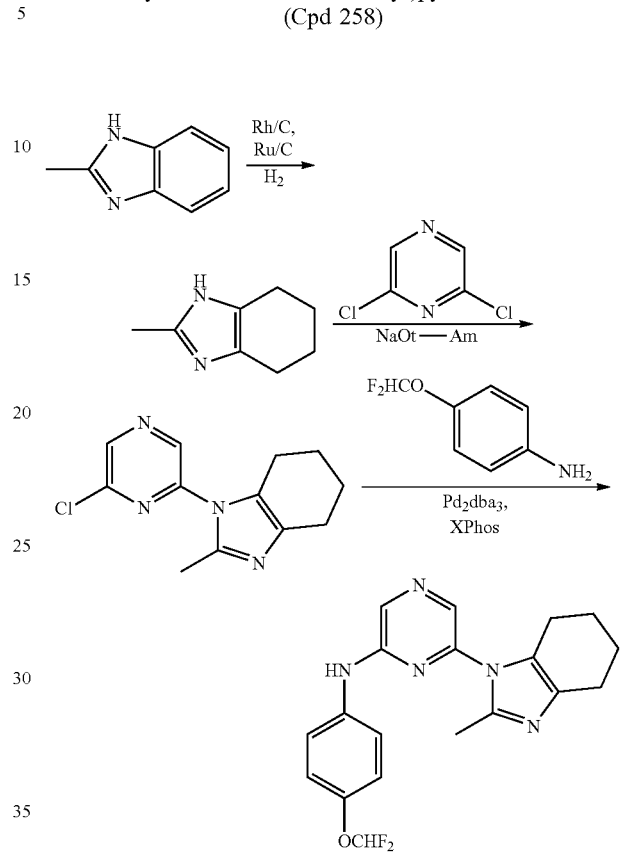

Step 1. To 2-methyl-1H-benzo[d]imidazole (1.09 g, 8.2 mmol) was added methanol (20 mL), HCl (aqueous, conc., 1 mL) and Rh/C (5%, 108 mg). The reaction mixture was shaken at room temperature under hydrogen (60 psi) for two days. LC-MS analysis showed that the reaction stalled at 50% conversion. Ru/C (50%) (catalytic) was added and the mixture was shaken under hydrogen (60 psi) for an additional three days. LC-MS analysis showed that the reaction had not progressed. The reaction mixture was filtered, then concentrated and partitioned between EtOAc and water and NH$_4$OH and K$_2$CO$_3$ were added. The organic layer was filtered through a short plug of silica gel, which was washed with a mixture of EtOAc:MeOH (10:1). The combined solutions were concentrated to provide 2-methyl-1H-benzo[d]imidazole and 2-methyl-4,5,6,7-tetrahydro-1H-benzo[d]imidazole as a mixture of isomers.

Step 2. To the mixture was added 2,6-dichloropyrazine (2.23 g, 15 mmol) and DMF (10 mL). The solution was cooled in ice bath and NaOt-Am was added (2.5 M solution in THF, 4 mL, 10 mmol). The reaction mixture was stirred in the ice bath for 40 minutes, then at room temperature for 40 minutes. The reaction was quenched with an aqueous solution of NaHCO$_3$ (conc.), extracted with a mixture of EtOAc:hexane (1:1) then extracted with EtOAc alone. The organic layers were concentrated and purified by chromatography on silica gel (gradient from ethyl acetate:hexane 1:1 to EtOAc:MeOH 10:0) to provide 1-(6-chloropyrazin-2-yl)-2-methyl-4,5,6,7-tetrahydro-1H-benzo[d]imidazole as a gray solid (475 mg, 23% for two steps).

Step 3. To 1-(6-chloropyrazin-2-yl)-2-methyl-4,5,6,7-tetrahydro-1H-benzo[d]imidazole (158 mg, 0.63 mmol) was added XPhos (7 mg, 0.014 mmol), Pd$_2$dba$_3$ (4 mg, 0.047 mmol), K$_3$PO$_4$ (254 mg, 1.2 mmol), DME (1 mL) and 4-difluoromethoxy)aniline (0.15 mL, 1.2 mmol). The reaction mixture was heated at 115° C. (heating block temperature) for 5 hours. LC-MS analysis showed that the reaction stalled at 25% conversion. A catalytic amount of chloro(2-dicyclohexylphosphino-2',4',6'-tri-i-propyl-1,1'-biphenyl)[2-(2-aminoethyl)phenyl]palladium(II) methyl-t-butylether adduct (XPhos Palladacycle) was added. The reaction mixture was heated for additional 15 hours, then partitioned between EtOAc and water. The organic layer was dried and filtered through a short plug of silica gel, which was washed with a mixture of DME:MeOH (10:1). The combined solution was concentrated and purified by chromatography on silica gel (gradient ethyl acetate:hexane 1:1 to DME:MeOH 10:0) to provide the title compound as a yellow solid (101 mg, 43%). $^1$H NMR (DMSO-d$_6$) δ 9.89 (s, 1H), 8.24 (s, 1H), 8.02 (s, 1H), 7.67 (dist. d, J=9.1 Hz, 2H), 7.17 (dist. d, J=9.1 Hz, 2H), 7.13 (t, J=74.4 Hz, 1H), 2.45 (dist. t, J=5.4 Hz, 4H), 2.30 (s, 3H), 1.64-1.81 (m, 4H); MS m/z 372 (ESI) [M+H]$^+$.

Additional compounds of Formula (I) or a form thereof described herein may be prepared according to the procedure of Example 30 by substituting the appropriate starting materials, reagents and reaction conditions:

| Cpd | Name and Data |
|---|---|
| 267 | 6-(2-methyl-4,5,6,7-tetrahydro-1H-benzimidazol-1-yl)-N-[4-(trifluoromethyl)phenyl]pyrazin-2-amine<br>$^1$H NMR (DMSO-d$_6$) δ 10.24 (s, 1H), 8.33 (s, 1H), 8.13 (s, 1H), 7.86 (d, J = 8.5 Hz, 2H), 7.70 (d, J = 8.5 Hz, 2H), 2.47 (q, J = 5.7 Hz, 4H), 2.32 (s, 3H), 1.65-1.81 (m, 4H); MS m/z 374 (ESI) [M + H]$^+$ |
| 268 | 6-(2-methyl-4,5,6,7-tetrahydro-1H-benzimidazol-1-yl)-N-[4-(trifluoromethoxy)phenyl]pyrazin-2-amine<br>$^1$H NMR (DMSO-d$_6$) δ 10.02 (s, 1H), 8.27 (s, 1H), 8.06 (s, 1H), 7.73-7.78 (m, 2H), 7.33-7.39 (dist. d, J = 8.5 Hz, 2H), 2.45 (dist. t, J = 5.7 Hz, 4H), 2.30 (s, 3H), 1.65-1.81 (m, J = 11.2, 5.2 Hz, 4H); MS m/z 390 (ESI) [M + H]$^+$ |
| 375 | 6-[(2-methyl-5-(prop-2-en-1-yl)-4,5,6,7-tetrahydro-1H-imidazo[4,5-c]pyridin-1-yl]-N-[4-(trifluoromethyl)phenyl]pyrazin-2-amine MS m/z 415 (ESI) [M + H]$^+$ |
| 398 | 6-(2-ethyl-5-methyl-4,5,6,7-tetrahydro-3H-imidazo[4,5-c]pyridin-3-yl)-N-[4-(trifluoromethyl)phenyl]pyrazin-2-amine MS m/z 403 (ESI) [M + H]$^+$ |

Example 31

6-(6-methoxy-2-methyl-1H-benzimidazol-1-yl)-N-[4-(trifluoromethyl)phenyl]pyrazin-2-amine (Cpd 317)

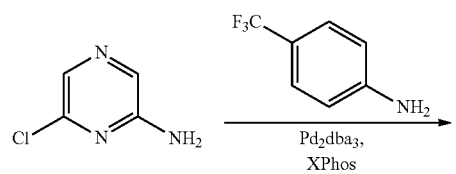

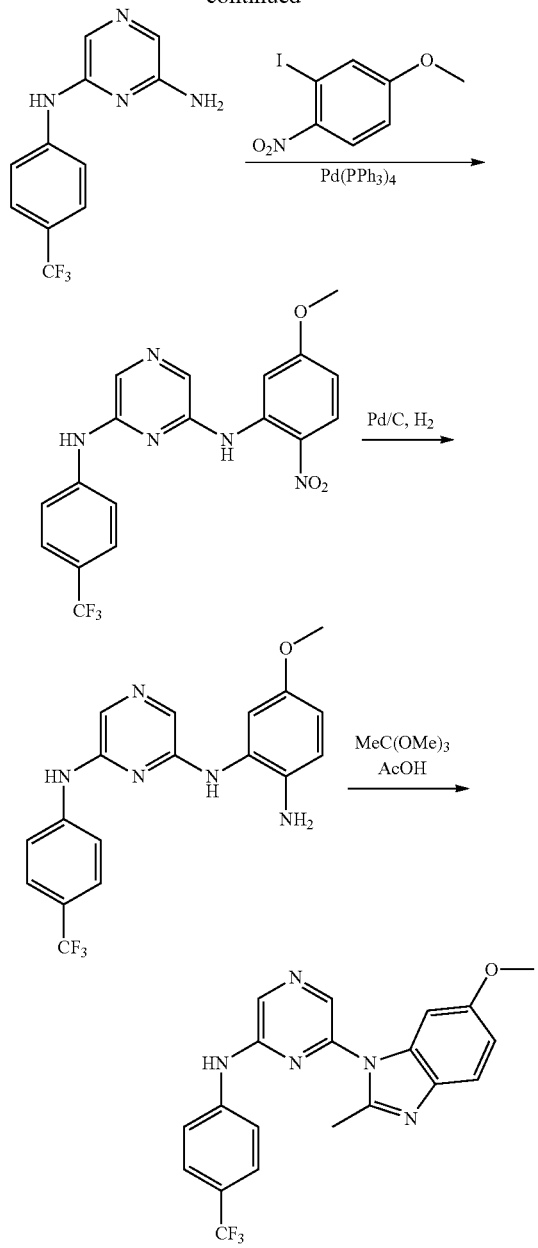

Step 1. To 6-chloropyrazin-2-amine (1.05 g, 8 mmol) was added K$_3$PO$_4$ (3.4 g, 16 mmol), XPhos (191 mg, 0.4 mmol), Pd$_2$dba$_3$ (183 mg, 0.2 mmol), 4-(trifluoromethyl) aniline (1.99 mL, 16 mmol) and DME (20 mL). The reaction mixture was heated at 110° C. for 30 minutes, then partitioned between EtOAc and NH$_4$Cl (aqueous solution). The organic layer was purified by chromatography on silica gel (gradient from ethyl acetate:hexane 1:2 to EtOAc:MeOH 4:0) and washed with hexane to provide N$^2$-(4-(trifluoromethyl)phenyl)pyrazine-2,6-diamine as a brown solid (530 mg, 26%). $^1$H NMR (DMSO-d$_6$) δ 9.39 (s, 1H), 7.87 (dist. d, J=8.5 Hz, 2H), 7.54 (dist. d, J=8.8 Hz, 2H), 7.39 (s, 1H), 7.31 (s, 1H), 6.24 (s, 2H); MS m/z 255 (ESI) [M+H]$^+$.

Step 2. To the obtained product (94 mg, 0.37 mmol) was added 2-iodo-4-methoxy-1-nitrobenzene (140 mg, 0.5 mmol), K$_3$PO$_4$ (170 mg, 0.8 mmol), tetrakis(triphenylphosphine)palladium (26 mg, 6%) and DME (1 mL). The reaction mixture was heated at 120° C. for 1 hour 50 minutes, then a pinch of XPhos (catalytic) and a pinch of Pd$_2$dba$_3$ (catalytic) were added. The mixture was heated at 120° C. for an additional 50 minutes, then cooled, diluted with EtOAc and filtered. Purification by chromatography on silica gel (gradient ethyl acetate:hexane 1:2 to 1:0) provided N$^2$-(5-methoxy-2-nitrophenyl)-N$^6$-(4-(trifluoromethyl)phenyl)pyrazine-2,6-diamine as a brown solid (98 mg, 87% pure according to LC analysis).

Step 3. The obtained product was dissolved in a mixture of MeOH:EtOAc (50 mL: 10 mL). The reaction mixture was hydrogenated in a H-Cube hydrogenator using Pd/C under H$_2$ (20 bar) at room temperature until complete consumption of the starting material. The solution was concentrated to provide a crude N$^2$-(2-amino-5-methoxyphenyl)-N$^6$-(4-(trifluoromethyl)phenyl)pyrazine-2,6-diamine.

Step 4. To a solution of the obtained product in EtOAc (5 mL) was added MeC(OMe)$_3$ (1 mL, excess) and a pinch of TsOH (catalytic). The mixture was reacted at room temperature for 70 minutes, then MeOH (2 mL) and AcOH (3 mL) were added. The mixture was reacted at room temperature for an additional 2 hours, then partitioned between water and EtOAc. The organic layer was purified by chromatography on silica gel (gradient from ethyl acetate:hexane 1:2 to EtOAc:MeOH 10:1) to provide the title compound as a light brown solid (16 mg). $^1$H NMR (DMSO-d$_6$) δ 10.34 (s, 1H), 8.41 (s, 1H), 8.37 (s, 1H), 7.89 (dist. d(AB), J=8.5 Hz, 2H), 7.66 (dist. d (AB), J=8.8 Hz, 2H), 7.53 (d, J=8.8 Hz, 1H), 7.06 (d, J=2.5 Hz, 1H), 6.88 (dd, J=8.7, 2.4 Hz, 1H), 3.68 (s, 3H), 2.59 (s, 3H); MS m/z 400 (ESI) [M+H]$^+$.

Example 32

6-[2,5-dimethyl-4-(trifluoromethyl)-1H-imidazol-1-yl]-N-[4-(trifluoromethyl)phenyl]pyrazin-2-amine (Cpd 318)

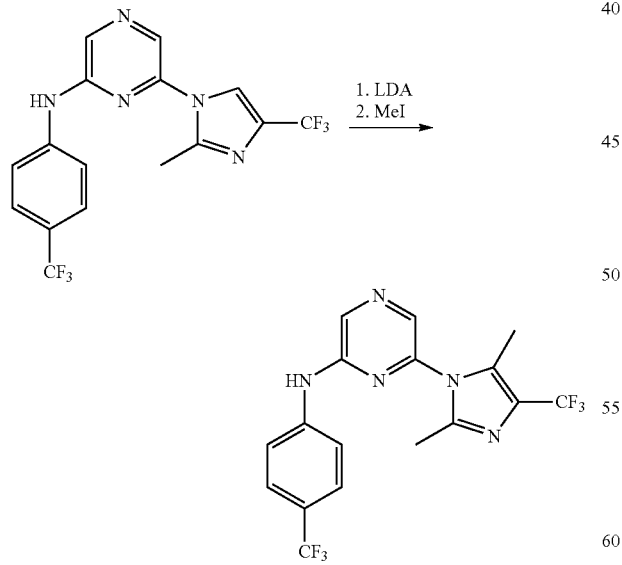

To 6-(2-methyl-4-(trifluoromethyl)-1H-imidazol-1-yl)-N-(4-(trifluoromethyl)phenyl)pyrazin-2-amine (105 mg, 0.27 mmol) was added THF (2 mL). The mixture was cooled to −60° C. and a solution of LDA freshly prepared from diisopropylamine (0.11 mL, 0.81 mmol) and n-BuLi (2.2 M solution in c-hexane, 0.27 mL, 0.6 mmol) in THF (1 mL) was added via cannula. The dark red suspension was reacted at −60° C. for 1.75 hours, then iodomethane (0.06 mL, 1 mmol) was added. The mixture was reacted at −60° C. for an additional hour, then quenched with AcOH and partitioned between EtOAc and water. The organic layer was purified by chromatography on silica gel (gradient from ethyl acetate:hexane 1:2 to EtOAc:MeOH 10:1) to provide the title compound as a light yellow solid (16 mg). $^1$H NMR (DMSO-d$_6$) δ 10.38 (s, 1H), 8.46 (s, 1H), 8.27 (s, 1H), 7.83 (dist. d(AB), J=8.5 Hz, 2H), 7.71 (dist. d(AB), J=8.8 Hz, 2H), 2.29 (s, 3H), 2.23 (dist. q, J=1.6 Hz, 3H); MS m/z 402 (ESI) [M+H]$^+$.

Example 33

6-[2-methyl-6-(trifluoromethyl)-1H-benzimidazol-1-yl]-N-[4-(trifluoromethyl)phenyl]pyrazin-2-amine (Cpd 340)

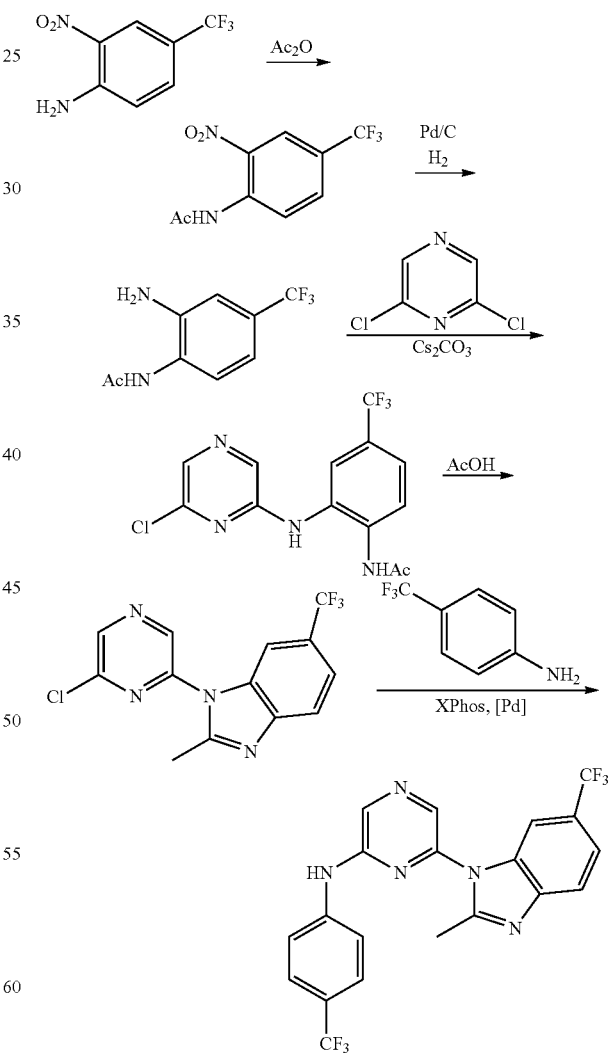

Step 1. To 2-nitro-4-(trifluoromethyl)aniline (800 mg, 3.94 mmol) was added AcOH (2 mL). The mixture was heated at 120° C. for 22 hours, then cooled and diluted with water. The product was filtered and washed with hexane to provide crude N-(2-nitro-4-(trifluoromethyl)phenyl)acetamide.

Step 2. The crude product from the previous step was dissolved in MeOH (20 mL) and Pd/C (catalytic) was added. The reaction mixture was shaken at room temperature under hydrogen (50 psi) for 20 minutes, then filtered through Celite. The product was concentrated and made into the azeotrope using toluene to provide crude N-(2-amino-4-(trifluoromethyl)phenyl)acetamide.

Step 3. To the crude product from the previous step was added 2,6-dichloropyrazine (745 mg, 5 mmol), $Cs_2CO_3$ (1.6 g, 5 mmol) and ACN (10 mL). The mixture was heated at 80° C. for 2 hours, then at 90° C. for 1 hour. A pinch of $Cs_2CO_3$ (excess) was added and the mixture was heated for an additional 1.5 hours. The mixture was cooled, then partitioned between EtOAc and water and dried. The product was filtered through a short plug of silica gel and concentrated to provide crude N-(2-(6-chloropyrazin-2-ylamino)-4-(trifluoromethyl)phenyl)acetamide.

Step 4. To the crude product from the previous step was added AcOH (10 mL) and TFA (1 mL). The mixture was reacted at 100° C. for 14 hours, then at 120° C. for 23 hours. The reaction mixture was concentrated and purified by chromatography on silica gel (gradient ethyl acetate:hexane 1:3 to 1:1) to provide 1-(6-chloropyrazin-2-yl)-2-methyl-6-(trifluoromethyl)-1H-benzo[d]imidazole (more polar fractions). $^1$H NMR (DMSO-$d_6$) δ 9.15 (d, J=0.6 Hz, 1H), 9.02 (s, 1H), 7.96-7.98 (m, 1H), 7.87 (d, J=8.2 Hz, 1H), 7.63 (dd, J=8.5, 1.3 Hz, 1H), 2.69 (s, 3H). The less polar fractions contain the isomer (1-(6-chloropyrazin-2-yl)-2-methyl-5-(trifluoromethyl)-1H-benzo[d]imidazole). $^1$H NMR (DMSO-$d_6$) δ 9.15 (s, 1H), 9.03 (d, J=0.6 Hz, 1H), 8.03-8.06 (m, 1H), 7.78 (d, J=8.5 Hz, 1H), 7.63 (dd, J=8.7, 1.4 Hz, 1H), 2.70 (s, 3H).

Step 5. The more polar product obtained was carried forward (using the procedure described in Example 2 and appropriate starting materials, reagents and reaction conditions) to provide the title compound. $^1$H NMR (DMSO-$d_6$) δ 10.38 (s, 1H), 8.44 (s, 2H), 7.94-7.98 (m, 1H), 7.84-7.88 (m, 3H), 7.61 (dd, J=8.8, 1.3 Hz, 1H), 7.60 (d, J=8.8 Hz, 2H), 2.70 (s, 3H); MS m/z 438 (ESI) [M+H]$^+$.

Example 34

6-(2,6-dimethyl-1H-benzimidazol-1-yl)-N-[4-(trifluoromethyl)phenyl]pyrazine-2-amine (Cpd 343)

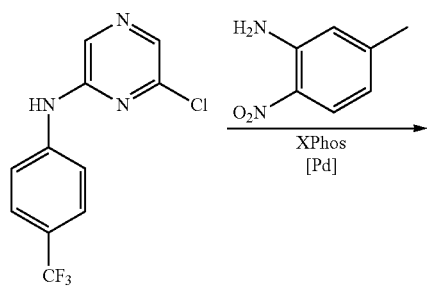

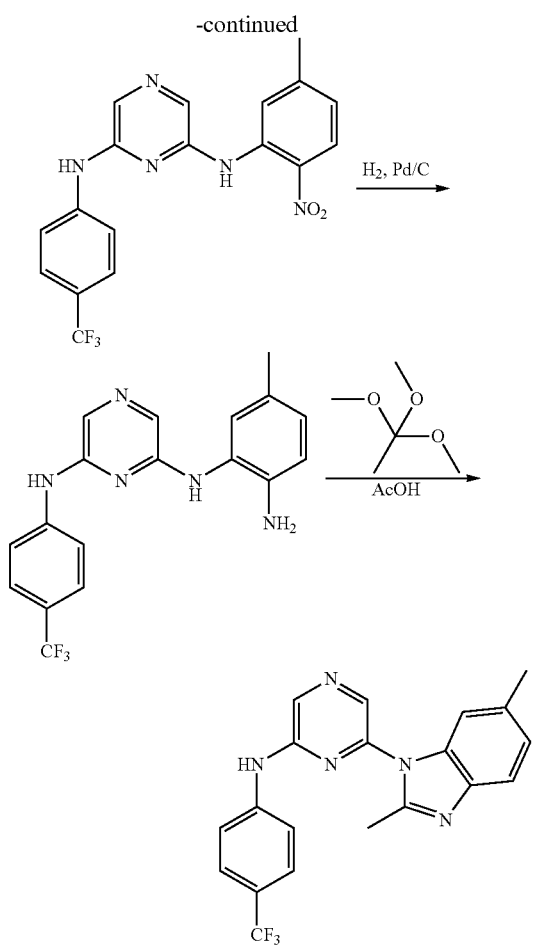

Step 1. To 6-chloro-N-(4-(trifluoromethyl)phenyl)pyrazin-2-amine (100 mg, 0.37 mmol) was added 5-methyl-2-nitroaniline (112 mg, 0.74 mmol), XPhos (10.5 mg, 6%), $Pd_2dba_3$ (10 mg, 3%), $K_3PO_4$ (212 mg, 1 mmol) and DME (3 mL). The mixture was heated at 100° C. for 1.5 hours, then cooled and filtered through a short plug of silica gel. The product was washed with EtOAc, then concentrated and purified by chromatography on silica gel (gradient from DCM:hexane 1:2 to DCM:MeOH 10:1) to provide $N^2$-(5-methyl-2-nitrophenyl)-$N^6$-(4-(trifluoromethyl)phenyl)pyrazine-2,6-diamine as a red solid.

Step 2. The obtained product was dissolved in EtOH (10 mL), then a pinch of Pd/C (catalytic) was added. The mixture was shaken at room temperature under hydrogen (50 psi) for 15 hours, then filtered and concentrated to provide crude $N^2$-(2-amino-5-methylphenyl)-$N^6$-(4-(trifluoromethyl)phenyl)pyrazine-2,6-diamine.

Step 3. The obtained product was dissolved in AcOH (3 mL) and MeC(OMe)$_3$ (0.5 mL). The mixture was heated at reflux for 30 minutes, then concentrated and purified by chromatography on silica gel (gradient from DCM:hexane 1:1 to DCM:MeOH 10:1). The product was washed with ether to provide the title compound as a light brown solid (23 mg). $^1$H NMR (DMSO-$d_6$) δ 10.34 (s, 1H), 8.41 (s, 1H), 8.36 (s, 1H), 7.88 (dist. d(AB), J=8.5 Hz, 2H), 7.66 (dist. d(AB), J=8.8 Hz, 2H), 7.53 (d, J=8.2 Hz, 1H), 7.33 (s, 1H), 7.09 (dd, J=8.2, 0.9 Hz, 1H), 2.60 (s, 3H), 2.38 (s, 3H); MS m/z 384 (ESI) [M+H]$^+$.

Example 35

6-(7-fluoro-2-methyl-1H-benzimidazol-1-yl)-N-[4-(trifluoromethyl)phenyl]pyrazin-2-amine (Cpd 358)

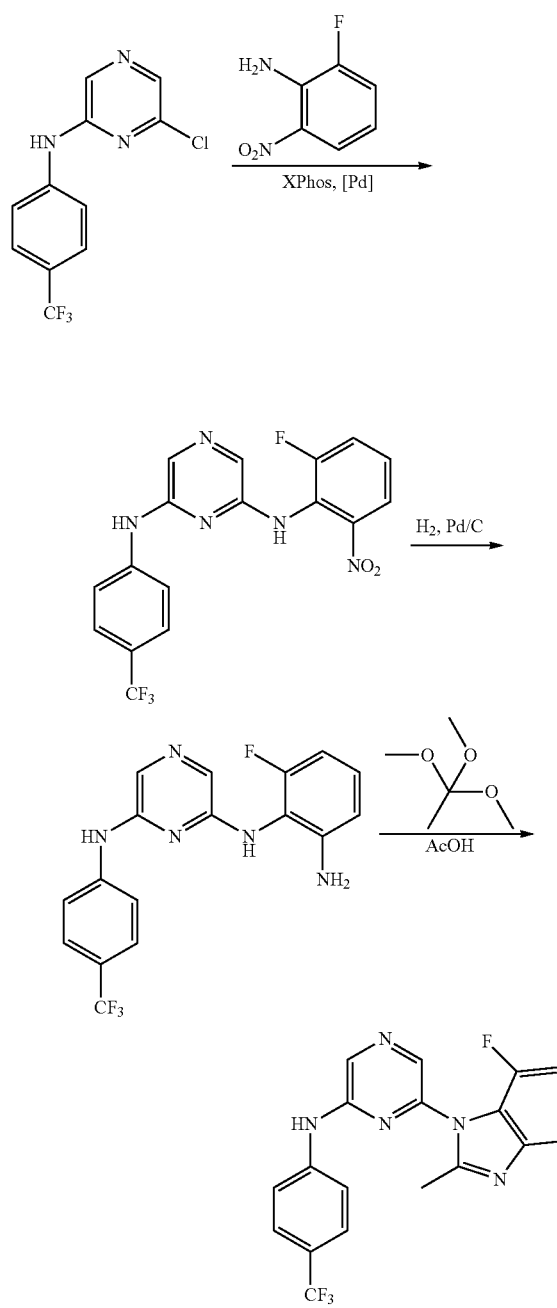

The title compound (prepared using the procedure described in Example 34 and appropriate starting materials, reagents and reaction conditions) was obtained. $^1$H NMR (DMSO-d$_6$) δ 10.35 (s, 1H), 8.45 (s, 1H), 8.38 (d, J=1.6 Hz, 1H), 7.84 (dist. d(AB), J=8.5 Hz, 2H), 7.64 (dist. d(AB), J=8.5 Hz, 2H), 7.52 (d, J=7.9 Hz, 1H), 7.26 (td, J=8.1, 4.9 Hz, 1H), 7.11 (dd, J=11.5, 8.0 Hz, 1H), 2.54 (s, 3H); MS m/z 388 (ESI) [M+H]$^+$.

Example 36

6-(4-bromo-2-methyl-1H-imidazol-1-yl)-N-[4-(trifluoromethyl)phenyl]pyrazin-2-amine (Cpd 298)

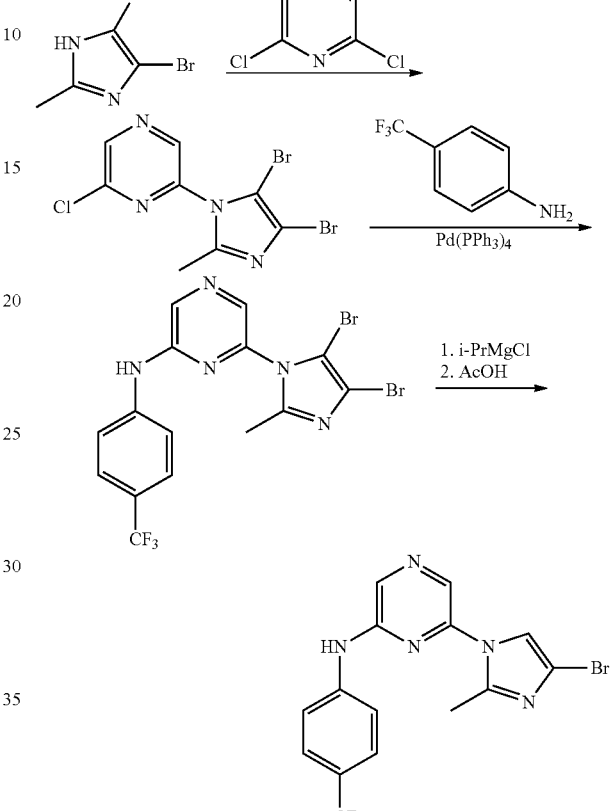

Step 1. To 4,5-dibromo-2-methyl-1H-imidazole (2.56 g, 10.7 mmol) was added 2,6-dichloropyrazine (3.39 g, 22 mmol), K$_2$CO$_3$ (3.04 g, 22 mmol) and acetonitrile (30 mL). The mixture was stirred at 90° C. for 3 days, cooled, diluted with water, then partially concentrated and filtered. The product was purified by chromatography on silica gel (gradient ethyl acetate:hexane 1:4 to 1:1) and washed with hexanes to provide 2-chloro-6-(4,5-dibromo-2-methyl-1H-imidazol-1-yl)pyrazine as a white solid (1.83 g, 49%). $^1$H NMR (DMSO-d$_6$) δ 9.09 (d, J=0.6 Hz, 1H), 9.04 (d, J=0.6 Hz, 1H), 2.33 (s, 3H).

Step 2. To a portion of 2-chloro-6-(4,5-dibromo-2-methyl-1H-imidazol-1-yl)pyrazine prepared above (678 mg, 1.93 mmol) was added K$_3$PO$_4$ (1.06 g, 5 mmol), tetrakis(triphenylphosphine)palladium (54 mg, 0.047 mmol), 4-(trifluoromethyl)aniline (0.37 mL, 3 mmol) and DME (5 mL). The mixture was heated at 110° C. for 2.5 hours, then at room temperature for 4 days. The mixture was partitioned between EtOAc and water, the organic layer was purified by chromatography on silica gel (gradient from ethyl acetate:hexane 1:2 to EtOAc:MeOH 10:1), then washed with EtOAc to provide 6-(4,5-dibromo-2-methyl-1H-imidazol-1-yl)-N-(4-(trifluoromethyl)phenyl)pyrazin-2-amine as a pink solid (310 mg, 34%). $^1$H NMR (DMSO-d$_6$) δ 10.42 (s, 1H), 8.46 (s, 1H), 8.27 (s, 1H), 7.85 (dist. d(AB), J=8.5 Hz, 2H), 7.70 (dist. d(AB), J=8.8 Hz, 2H), 2.33 (s, 3H).

Step 3. To 6-(4,5-dibromo-2-methyl-1H-imidazol-1-yl)-N-(4-(trifluoromethyl)phenyl)pyrazin-2-amine (87 mg, 0.18 mmol) was added THF (3 mL). The mixture was cooled to −65° C., and a solution of i-PrMgCl×2 LiCl (1M solution in THF, 0.4 mL, 0.4 mmol) was added dropwise. A red solution was formed upon addition, and the mixture was allowed to warm up to −30° C. over 2.5 hours. The reaction was quenched with AcOH, then partitioned between EtOAc and water and purified by chromatography on silica gel (gradient ethyl acetate:hexane 1:2 to 1:0) to provide the title compound as a yellow solid (19 mg, 27%). $^1$H NMR (DMSO-$d_6$) δ 10.28 (s, 1H), 8.33 (s, 1H), 8.28 (s, 1H), 7.85 (dist. d(AB), J=8.5 Hz, 2H), 7.78 (s, 1H), 7.71 (dist. d(AB), J=8.5 Hz, 2H), 2.49 (br. s., 3H); MS m/z 398 (ESI) [M+H]$^+$.

Example 37

6-(5-ethyl-2-methyl-1H-imidazol-1-yl)-N-[4-(trifluoromethyl)phenyl]pyrazin-2-amine (Cpd 372)

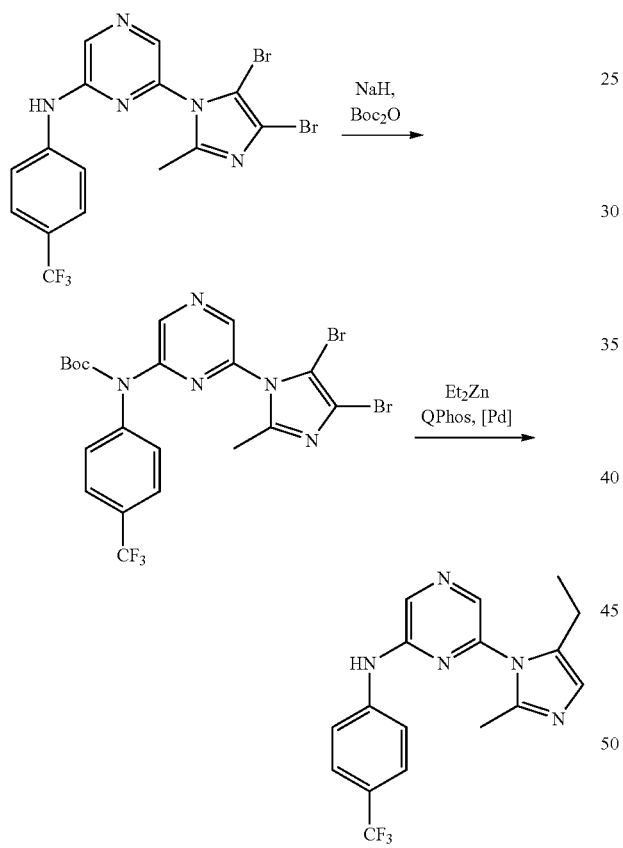

Step 1. To 6-(4,5-dibromo-2-methyl-1H-imidazol-1-yl)-N-(4-(trifluoromethyl)phenyl)pyrazin-2-amine (593 mg, 1.24 mmol) was sequentially added NaH (60% in oil, 200 mg, 5 mmol), THF (6 mL, with gas evolution), then Boc$_2$O (0.33 mL, 1.5 mmol). A thick suspension formed and the mixture was reacted for 25 minutes at room temperature, then quenched with AcOH and partitioned between EtOAc and water. The product was filtered through a short plug of silica gel and concentrated to provide tert-butyl 6-(4,5-dibromo-2-methyl-1H-imidazol-1-yl)pyrazin-2-yl(4-(trifluoromethyl)phenyl)carbamate (752 mg) as a yellow oil that partly solidified upon drying in vacuum.

Step 2. To the obtained product was added QPhos (35 mg, 4%), Pd$_2$dba$_3$ (23 mg, 2%), THF (6 mL) and Et$_2$Zn (1M solution in hexane, 2.5 mL, 2.5 mmol). The reaction mixture was stirred at room temperature for 20 min, diluted with brine and EtOAc, then filtered through Celite and the organic layer was purified by chromatography on silica gel (gradient from ethyl acetate:hexane 1:2 to EtOAc:MeOH 10:1). The minor by-product was isolated and treated with a mixture of TFA and DCM at room temperature overnight. The reaction mixture was concentrated, triturated with a mixture of DCM, ether and hexane then filtered to provide the title compound as a light brown solid (12 mg). $^1$H NMR (DMSO-$d_6$) δ 10.36 (s, 1H), 8.45 (s, 1H), 8.26 (s, 1H), 7.83 (dist. d(AB), J=8.8 Hz, 2H), 7.69 (dist. d(AB), J=8.8 Hz, 2H), 6.88 (s, 1H), 2.52-2.57 (m, 2H), 2.37 (s, 3H), 1.04 (t, J=7.1 Hz, 3H); MS m/z 348 (ESI) [M+H]$^+$.

Example 38

6-(4,5-dichloro-2-methyl-1H-imidazol-1-yl)-N-[4-(trifluoromethyl)phenyl]pyrazin-2-amine (Cpd 297)

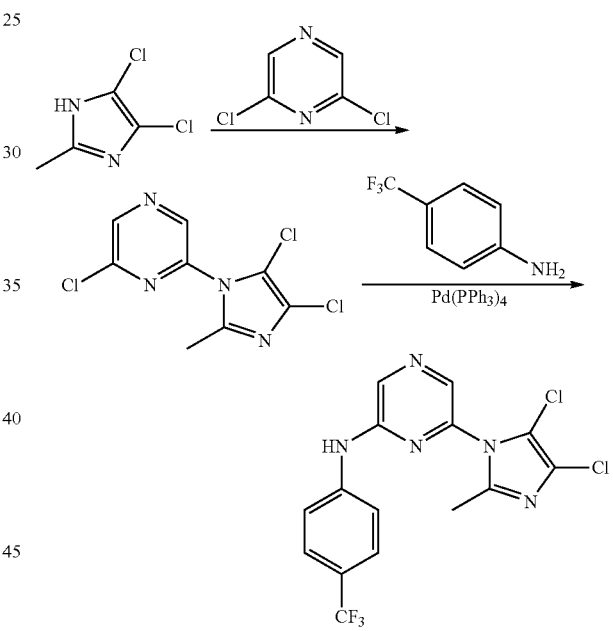

Step 1. To 4,5-dichloro-2-methyl-1H-imidazole (1.69 g, 11.3 mmol) was added 2,6-dichloropyrazine (0.91 g, 6 mmol), K$_2$CO$_3$ (1.38 g, 10 mmol) and acetonitrile (20 mL). The mixture was stirred at 110° C. for 5 days, cooled, then partitioned between water and EtOAc and purified by chromatography on silica gel (gradient ethyl acetate:hexane 1:4 to 1:1). The product was washed with ether:hexane to provide 2-chloro-6-(4,5-dichloro-2-methyl-1H-imidazol-1-yl)pyrazine (0.51 g, 33%) as a yellow solid. $^1$H NMR (DMSO-$d_6$) δ 9.09 (d, J=0.6 Hz, 1H), 9.05 (d, J=0.6 Hz, 1H), 2.33 (s, 3H).

Step 2. To the obtained product (135 mg, 0.51 mmol) was added tetrakis(triphenylphosphine)palladium (29 mg, 5%), K$_3$PO$_4$ (210 mg, 1 mmol), DME (3 mL) and 4-(trifluoromethyl)aniline (0.13 mL, 1 mmol). The reaction mixture was heated at 110° C. for 18 hours, then partitioned between NH$_4$Cl (aqueous) and a mixture of EtOAc and MeOH. The product was purified by chromatography on silica gel (gradient ethyl acetate:hexane 1:2 to 1:0) and washed with EtOAc:hexane to provide the title compound as a light brown solid (137 mg, 69%). $^1$H NMR (DMSO-$d_6$) δ 10.42 (s, 1H), 8.47 (s, 1H), 8.29 (s, 1H), 7.85 (dist. d(AB), J=8.8 Hz, 2H), 7.70 (dist. d(AB), J=8.5 Hz, 2H), 2.32 (s, 3H); MS m/z 388 (ESI) [M+H]$^+$.

Example 39

6-{4-[(Z)-2-ethoxyethenyl]-2-methyl-1H-imidazol-1-yl}-N-[4-(trifluoromethyl)phenyl]pyrazin-2-amine (Cpd 391)

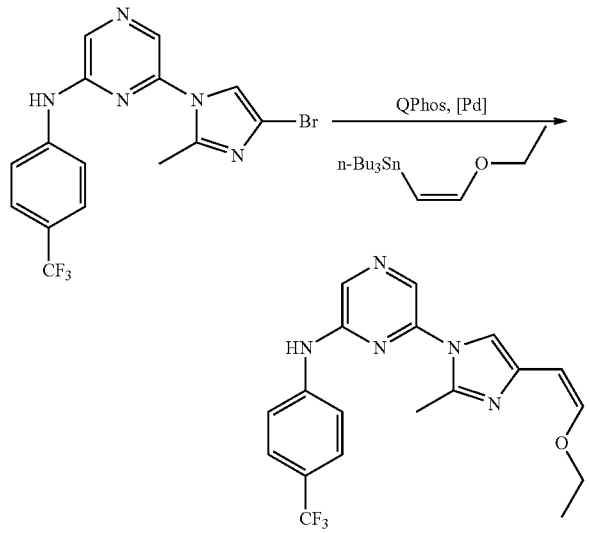

A mixture of Cpd 298 (prepared using the procedure described in Example 36 and appropriate starting materials, reagents and reaction conditions) (53 mg, 0.13 mmol), QPhos (6 mg, 6%), Pd$_2$dba$_3$ (4 mg, 3%), (Z)-tributyl(2-ethoxyvinyl)stannane (0.07 mL, 0.2 mmol) and dioxane (2 mL) was heated at 110° C. for 6 hours, then cooled and diluted with DME. The solution was filtered through a short plug of silica gel, then concentrated and purified by chromatography on silica gel (gradient from ethyl acetate:hexane 1:1 to EtOAc:MeOH 10:1) to provide the title compound as a light yellow solid (25 mg, 49%). MS m/z 348 (ESI) [M+H]$^+$. H NMR (DMSO-$d_6$) δ 10.23 (s, 1H), 8.28 (s, 1H), 8.26 (s, 1H), 7.87 (d, J=8.5 Hz, 2H), 7.68 (d, J=8.5 Hz, 2H), 7.57 (s, 1H), 6.35 (d, J=6.6 Hz, 1H), 5.25 (d, J=6.3 Hz, 1H), 3.98 (q, J=7.0 Hz, 2H), 1.25 (t, J=6.9 Hz, 3H). MS m/z 390 (ESI) [M+H]$^+$.

Example 40

6-(6-ethyl-2-methyl-1H-benzimidazol-1-yl)-N-[4-(trifluoromethyl)phenyl]pyrazin-2-amine (Cpd 392)

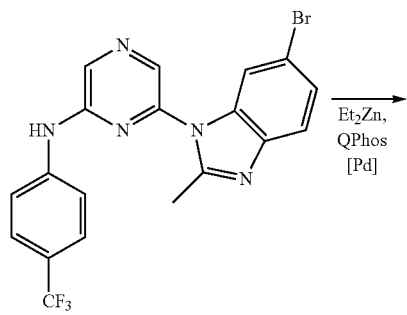

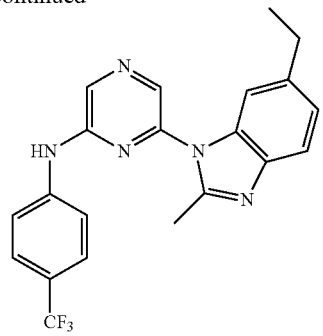

To Cpd 388 (prepared using the procedure described in Example 7 and appropriate starting materials, reagents and reaction conditions) (47 mg, 0.1 mmol) was added QPhos (4.5 mg, 6%), Pd$_2$dba$_3$ (2.7 mg, 3%), THF (1 mL) and Et$_2$Zn (1.5 M solution in toluene, 0.13 mL, 0.2 mmol) at room temperature. The mixture was reacted for 2 hours at room temperature, then partitioned between EtOAc and NH$_4$Cl (aqueous). The organic layer was purified by chromatography on silica gel (gradient from ethyl acetate:hexane 1:2 to EtOAc:MeOH 10:1). The product was washed with DCM:hexane to provide the title compound as a white solid (13 mg, 33%). $^1$H NMR (DMSO-$d_6$) δ 10.34 (br. s, 1H), 8.41 (s, 1H), 8.37 (s, 1H), 7.89 (dist. d(AB), J=8.2 Hz, 2H), 7.64 (dist. d(AB), J=8.5 Hz, 2H), 7.55 (d, J=8.2 Hz, 1H), 7.37 (s, 1H), 7.13 (d, J=8.2 Hz, 1H), 2.67 (q, J=7.7 Hz, 2H), 2.62 (s, 3H), 1.16 (t, J=7.6 Hz, 3H); MS m/z 398 (ESI) [M+H]$^+$.

Example 41

N-[4-(trifluoromethyl)phenyl]-6-(2,4,6-trimethyl-1H-benzimidazol-1-yl)pyrazin-2-amine (Cpd 421)

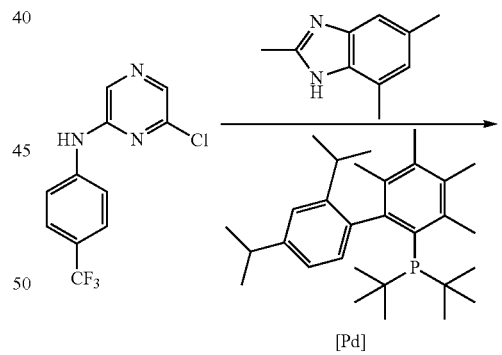

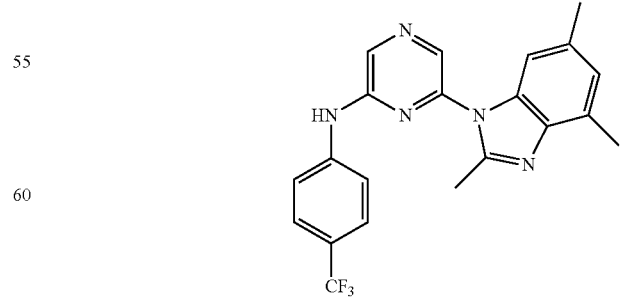

To 6-chloro-N-(4-(trifluoromethyl)phenyl)pyrazin-2-amine (112 mg, 0.41 mmol) was added 2,5,7-trimethyl-1H- benzo[d]imidazole (139 mg, 1 mmol), di-tert-butyl(2',4',6'-triisopropyl-3,4,5,6-tetramethylbiphenyl-2-yl)phosphine (12 mg, 6%), $Pd_2dba_3$ (11 mg, 3%), $K_3PO_4$ (212 mg, 1 mmol) and DME (2 mL). The mixture was heated at 110° C. for 16 hours, then cooled and filtered through a short plug of silica gel, which was additionally eluted with a mixture of DME:MeOH. The combined eluent was purified by chromatography on silica gel (gradient from ethyl acetate:hexane 1:2 to EtOAc:MeOH 10:1). The product was dissolved in MeOH, then precipitated with diluted aqueous AcOH and filtered to provide the title compound (32 mg, 20%). $^1$H NMR (DMSO-$d_6$) δ 10.38 (s, 1H), 8.46 (s, 1H), 8.38 (s, 1H), 7.91-7.99 (dist. d(AB), J=8.8 Hz, 2H), 7.70 (dist. d(AB), J=8.5 Hz, 2H), 7.18 (s, 1H), 6.96 (s, 1H), 2.65 (s, 3H), 2.57 (s., 3H), 2.39 (s, 3H); MS m/z 397 (ESI) [M+H]$^+$.

Example 42

N-(4-methoxyphenyl)-6-[2-(trifluoromethyl)imidazo[1,2-a]pyridin-3-yl]pyrazin-2-amine (Cpd 5)

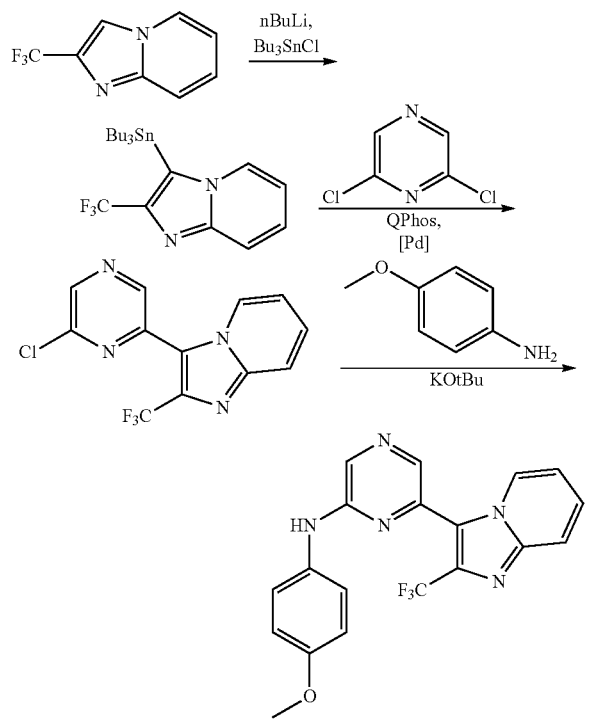

Step 1. To 2-(trifluoromethyl)imidazo[1,2-a]pyridine (1.02 g, 5.5 mmol) was added THF (20 mL). The mixture was cooled to −70° C., then n-BuLi was added (2.2 M solution in c-Hexane, 2.73 mL, 6 mmol). The reaction mixture was kept at −70° C. for one hour, then $Bu_3SnCl$ was added (1.63 mL, 6 mmol). The mixture was slowly warmed to −20° C. over 3 hours, then additional $Bu_3SnCl$ (0.2 mL) was added and the mixture was allowed to warm to room temperature over 14 hours. The mixture was partitioned between hexane and aqueous ammonium chloride and the organic layer was purified by chromatography on silica gel (gradient from ethyl acetate:hexane 0:1 to 1:4) to provide 3-(tributylstannyl)-2-(trifluoromethyl)imidazo[1,2-a]pyridine as a yellow oil (1.99 g, 77%). $^1$H NMR (DMSO-$d_6$) δ 8.33 (dt, J=6.9, 0.9 Hz, 1H), 7.70 (dt, J=8.8, 0.9 Hz, 1H), 7.41 (ddd, J=9.1, 6.7, 0.9 Hz, 1H), 7.07 (td, J=6.8, 1.3 Hz, 1H), 1.41-1.53 (m, 6H), 1.22-1.34 (m, 12H), 0.82 (t, J=7.3 Hz, 9H).

Step 2. To 2,6-dichloropyrazine (1.67 g, 11.2 mmol) was added 3-(tributylstannyl)-2-(trifluoromethyl)imidazo[1,2-a]pyridine (1.28 g, 2.69 mmol), allylpalladium chloride (5 mg, 0.013 mmol), QPhos (38 mg, 0.054 mmol) and dioxane (10 mL). The mixture was heated at 50° C. for 30 min, then at 90° C. for 1 hour. The reaction mixture was concentrated and purified by chromatography on silica gel (gradient ethyl acetate:hexane 1:10 to 1:1), to provide 3-(6-chloropyrazin-2-yl)-2-(trifluoromethyl)imidazo[1,2-a]pyridine as a pink solid (0.63 g, 79%). $^1$H NMR (DMSO-$d_6$) δ 8.96 (s, 1H), 8.94 (s, 1H), 8.73 (dt, J=6.9, 1.1 Hz, 1H), 7.87 (dt, J=9.1, 1.1 Hz, 1H), 7.62 (ddd, J=9.1, 6.9, 1.3 Hz, 1H), 7.22 (td, J=6.9, 1.1 Hz, 1H); MS m/z 299 (ESI) [M+H]$^+$.

Step 3. To 3-(6-chloropyrazin-2-yl)-2-(trifluoromethyl)imidazo[1,2-a]pyridine (70 mg, 0.24 mmol) was added 4-methoxyaniline (37 mg, 0.3 mmol) and THF (2 mL). The mixture was cooled in an ice-bath and KOt-Bu was added (1M solution in THF, 1 mL, 1 mmol). The mixture was reacted for 10 minutes, then quenched with AcOH and partitioned between water and EtOAc. The organic layer was purified by chromatography on silica gel (gradient ethyl acetate:hexane 1:4 to 2:1) and the product recrystallized from a mixture of ether:hexane to provide the title compound as a yellow solid (27 mg, 29%). $^1$H NMR (DMSO-$d_6$) δ 9.65 (s, 1H), 8.72 (dt, J=7.3, 1.3 Hz, 1H), 8.26 (s, 1H), 8.10 (s, 1H), 7.82 (dt, J=9.1, 1.3 Hz, 1H), 7.53-7.58 (m, 3H), 7.14 (td, J=6.9, 1.3 Hz, 1H), 6.87 (dist. dt(AB), J=8.8, 1.9 Hz, 2H), 3.70 (s, 3H); MS m/z 386 (ESI) [M+H]$^+$.

Additional compounds of Formula (I) or a form thereof described herein may be prepared according to the procedure of Example 42 by substituting the appropriate starting materials, reagents and reaction conditions:

| Cpd | Name and Data |
|---|---|
| 6 | 6-[2-(trifluoromethyl)imidazo[1,2-a]pyridin-3-yl]-N-[4-(trifluoromethyl)phenyl]pyrazin-2-amine<br>$^1$H NMR (DMSO-$d_6$) δ 10.27 (s, 1H), 8.72 (dt, J = 6.9, 0.9 Hz, 1H), 8.42 (s, 1H), 8.30 (s, 1H), 7.87 (d, J = 9.1 Hz, 2H), 7.85 (dt, J = 9.1, 0.9 Hz, 1H), 7.61 (d, J = 8.5 Hz, 2H), 7.58 (ddd, J = 9.1, 6.9, 1.3 Hz, 1H), 7.16 (td, J = 6.9, 1.1 Hz, 1H); MS m/z 424 (ESI) [M + H]$^+$ |
| 7 | N-(3-fluoro-4-methoxyphenyl)-6-[2-(trifluoromethyl)imidazo[1,2-a]pyridin-3-yl]pyrazin-2-amine<br>$^1$H NMR (DMSO-$d_6$) δ 9.84 (s, 1H), 8.74 (dt, J = 6.9, 1.1 Hz, 1H), 8.29 (s, 1H), 8.18 (s, 1H), 7.84 (dt, J = 9.3, 1.0 Hz, 1H), 7.68 (dd, J = 13.9, 2.5 Hz, 1H), 7.57 (ddd, J = 9.1, 6.9, 1.1 Hz, 1H), 7.29 (ddd, J = 8.8, 2.5, 1.3 Hz, 1H), 7.14 (td, J = 6.9, 1.3 Hz, 1H), 7.10 (t, J = 9.5 Hz, 1H), 3.77 (s, 3H); MS m/z 404 (ESI) [M + H]$^+$ |
| 9 | N-(4-fluorophenyl)-6-[2-(trifluoromethyl)imidazo[1,2-a]pyridin-3-yl]pyrazin-2-amine<br>$^1$H NMR (DMSO-$d_6$) δ 9.87 (s, 1H), 8.71 (dt, J = 7.0, 1.1 Hz, 1H), 8.31 (s, 1H), 8.18 (s, 1H), 7.83 (dt, J = 9.1, 0.9 Hz, 1H), 7.63-7.69 (m, 2H), 7.56 (ddd, J = 9.1, 6.9, 1.1 Hz, 1H), 7.08-7.18 (m, 3H); MS m/z 374 (ESI) [M + H]$^+$ |
| 10 | N-(4-chlorophenyl)-6-[2-(trifluoromethyl)imidazo[1,2-a]pyridin-3-yl]pyrazin-2-amine<br>$^1$H NMR (DMSO-$d_6$) δ 10.00 (s, 1H), 8.71 (dt, J = 7.1, 1.2 Hz, 1H), 8.34 (s, 1H), 8.21 (s, 1H), 7.84 (dt, J = 9.1, 0.9 Hz, 1H), 7.69 (dist.dt(AB), J = 9.1, 2.2 Hz, 2H), 7.57 (ddd, J = 9.1, 6.6, 1.3 Hz, 1H), 7.31 (dist.dt(AB), J = 9.5, 2.2 Hz, 2H), 7.15 (td, J = 6.9, 1.3 Hz, 1H); MS m/z 390 (ESI) [M + H]$^+$ |
| 11 | N-[4-(trifluoromethoxy)phenyl]-6-[2-(trifluoromethyl)imidazo[1,2-a]pyridin-3-yl]pyrazin-2-amine<br>$^1$H NMR (DMSO-$d_6$) δ 10.06 (s, 1H), 8.71 (dt, J = 6.9, 1.1 Hz, 1H), 8.36 (s, 1H), 8.23 (s, 1H), 7.84 (dt, J = 9.1, 1.1 Hz, 1H), |

| Cpd | Name and Data |
|---|---|
| | 7.76 (dist.dt(AB), J = 9.1, 2.2 Hz, 2H), 7.57 (ddd, J = 9.1, 6.9, 1.3 Hz, 1H), 7.28 (d, J = 8.2 Hz, 2H), 7.14 (td, J = 6.9, 1.1 Hz, 1H); MS m/z 440 (ESI) [M + H]⁺ |
| 22 | N-(3-chloro-4-methoxyphenyl)-6-[2-(trifluoromethyl)imidazo[1,2-a]pyridin-3-yl]pyrazin-2-amine<br>¹H NMR (DMSO-d₆) δ 9.82 (br. s, 1H), 8.79 (dt, J = 6.9, 1.2 Hz, 1H), 8.29 (s, 1H), 8.18 (s, 1H), 7.92 (d, J = 2.5 Hz, 1H), 7.85 (dt, J = 9.1, 1.2 Hz, 1H), 7.59 (ddd, J = 9.1, 6.9, 1.3 Hz, 1H), 7.46 (dd, J = 8.8, 2.5 Hz, 1H), 7.16 (td, J = 6.9, 1.2 Hz, 1H), 7.11 (d, J = 8.8 Hz, 1H), 3.80 (s, 3H); MS m/z 420 (ESI) [M + H]⁺ |
| 23 | 4-({6-[2-(trifluoromethyl)imidazo[1,2-a]pyridin-3-yl]pyrazin-2-y]}amino)benzonitrile<br>¹H NMR (DMSO-d₆) δ 10.39 (br. s, 1H), 8.73 (dt, J = 6.9, 1.2 Hz, 1H), 8.44 (s, 1H), 8.35 (s, 1H), 7.81-7.92 (m, 3H), 7.72 (d, J = 9.1 Hz, 2H), 7.60 (ddd, J = 9.1, 6.9, 1.3 Hz, 1H), 7.18 (td, J = 6.9, 1.1 Hz, 1H); MS m/z 381 (ESI) [M + H]⁺ |
| 24 | N-[4-(difluoromethoxy)phenyl]-6-[2-(trifluoromethyl)imidazo[1,2-a]pyridin-3-yl]pyrazin-2-amine<br>¹H NMR (DMSO-d₆) δ 9.91 (br. s, 1H), 8.73 (dt, J = 6.9, 0.9 Hz, 1H), 8.34 (s, 1H), 8.20 (s, 1H), 7.85 (dt, J = 9.1, 0.9 Hz, 1H), 7.68-7.74 (m, 2H), 7.58 (ddd, J = 9.1, 6.8, 1.1 Hz, 1H), 7.16 (td, J = 6.9, 1.3 Hz, 1H), 7.09-7.14 (m, 2H), 7.12 (t, J = 74.4 Hz, 1H); MS m/z 422 (ESI) [M + H]⁺ |
| 25 | N-(4-chloro-3-fluorophenyl)-6-[2-(trifluoromethyl)imidazo[1,2-a]pyridin-3-yl]pyrazin-2-amine<br>¹H NMR (DMSO-d₆) δ 10.23 (br. s, 1H), 8.76 (dt, J = 7.3, 0.9 Hz, 1H), 8.38 (s, 1H), 8.31 (s, 1H), 7.96 (dd, J = 12.6, 2.5 Hz, 1H), 7.86 (dt, J = 9.1, 0.9 Hz, 1H), 7.59 (ddd, J = 9.1, 6.6, 1.3 Hz, 1H), 7.48 (t, J = 9.1 Hz, 1H), 7.37 (ddd, J = 8.5, 2.2, 0.9 Hz, 1H), 7.17 (td, J = 6.9, 1.3 Hz, 1H); MS m/z 408 (ESI) [M + H]⁺ |
| 26 | N-(3,4-difluorophenyl)-6-[2-(trifluoromethyl)imidazo[1,2-a]pyridin-3-yl]pyrazin-2-amine<br>¹H NMR (DMSO-d₆) δ 10.08 (br. s, 1H), 8.76 (dt, J = 6.9, 1.2 Hz, 1H), 8.35 (s, 1H), 8.27 (s, 1H), 7.93 (ddd, J = 13.6, 7.3, 2.7 Hz, 1H), 7.86 (dt, J = 9.1, 1.2 Hz, 1H), 7.59 (ddd, J = 9.1, 6.6, 1.3 Hz, 1H), 7.29-7.41 (m, 2H), 7.16 (td, J = 6.9, 1.3 Hz, 1H); MS m/z 392 (ESI) [M + H]⁺ |
| 29 | N-(3,4-dichlorophenyl)-6-[2-(trifluoromethyl)imidazo[1,2-a]pyridin-3-yl]pyrazin-2-amine<br>¹H NMR (DMSO-d₆) δ 10.17 (s, 1H), 8.78 (dt, J = 6.9, 0.9 Hz, 1H), 8.35 (s, 1H), 8.29 (s, 1H), 8.18 (d, J = 2.2 Hz, 1H), 7.85 (dt, J = 9.1, 1.1 Hz, 1H), 7.58 (ddd, J = 9.1, 6.9, 1.3 Hz, 1H), 7.52 (dist.d(AB), J = 8.8 Hz, 1H), 7.48 (dist.dd(AB) J = 8.8, 2.5 Hz, 1H), 7.16 (td, J = 6.9, 1.3 Hz, 1H); MS m/z 424 (ESI) [M + H]⁺ |
| 30 | N-(4-bromo-3-fluorophenyl)-6-[2-(trifluoromethyl)imidazo[1,2-a]pyridin-3-yl]pyrazin-2-amine<br>¹H NMR (DMSO-d₆) δ 10.22 (s, 1H), 8.75 (dt, J = 7.1, 1.0 Hz, 1H), 8.37 (s, 1H), 8.29 (s, 1H), 7.92 (dd, J = 12.0, 2.2 Hz, 1H), 7.85 (dt, J = 9.1, 1.1 Hz, 1H), 7.56-7.61 (m, 2H), 7.30 (ddd, J = 8.8, 2.5, 0.6 Hz, 1H), 7.16 (td, J = 6.9, 1.3 Hz, 1H); MS m/z 452 (ESI) [M + H]⁺ |
| 31 | N-(4-bromo-3-chlorophenyl)-6-[2-(trifluoromethyl)imidazo[1,2-a]pyridin-3-yl]pyrazin-2-amine<br>¹H NMR (DMSO-d₆) δ 10.17 (s, 1H), 8.78 (dt, J = 6.9, 0.9 Hz, 1H), 8.35 (s, 1H), 8.29 (s, 1H), 8.18 (d, J = 2.5 Hz, 1H), 7.85 (dt, J = 9.1, 0.9 Hz, 1H), 7.63 (d, J = 8.8 Hz, 1H), 7.58 (ddd, J = 9.1, 6.9, 1.3 Hz, 1H), 7.41 (dd, J = 8.8, 2.8 Hz, 1H), 7.16 (td, J = 6.9, 1.3 Hz, 1H); MS m/z 470 (ESI) [M + H]⁺ |
| 45 | 6-[6-methoxy-2-(trifluoromethyl)imidazo[1,2-a]pyridin-3-yl]-N-[4-(trifluoromethoxy)phenyl]pyrazin-2-amine<br>¹H NMR (DMSO-d₆) δ 10.09 (br. s, 1H), 8.36 (s, 1H), 8.33 (dd, J = 2.2, 0.9 Hz, 1H), 8.23 (s, 1H), 7.79-7.82 (m, 2H), 7.78 (dd, J = 9.8, 0.9 Hz, 1H), 7.37 (dd, J = 9.8, 2.5 Hz, 1H), 7.32 (d, J = 8.2 Hz, 2H), 3.56 (s, 3H); MS m/z 470 (ESI) [M + H]⁺ |
| 46 | 6-[6-methoxy-2-(trifluoromethyl)imidazo[1,2-a]pyridin-3-yl]-N-[4-(trifluoromethyl)phenyl]pyrazin-2-amine<br>¹H NMR (DMSO-d₆) δ 10.07 (br. s, 1H), 8.19 (s, 1H), 8.10 (s, 1H), 8.05 (s, 1H), 7.68 (d, J = 8.2 Hz, 2H), 7.56 (d, J = 9.8 Hz, 1H), 7.42 (d, J = 8.2 Hz, 2H), 7.15 (dd, J = 9.8, 2.2 Hz, 1H), 3.35 (s, 3H); MS m/z 454 (ESI) [M + H]⁺ |
| 47 | N-(4-methoxyphenyl)-6-[6-methoxy-2-(trifluoromethyl)imidazo[1,2-a]pyridin-3-yl]pyrazin-2-amine<br>¹H NMR (DMSO-d₆) δ 9.69 (br. s, 1H), 8.35 (s, 1H), 8.27 (s, 1H), 8.06-8.16 (m, 1H), 7.77 (d, J = 9.8 Hz, 1H), 7.60 (d, J = 8.5 Hz, 2H), 7.36 (dd, J = 11.3, 2.2 Hz, 1H), 6.90 (d, J = 8.8 Hz, 2H), 3.72 (s, 3H), 3.59 (s, 3H); MS m/z 416 (ESI) [M + H]⁺ |
| 48 | N-[4-(difluoromethoxy)phenyl]-6-[6-methoxy-2-(trifluoromethyl)imidazo[1,2-a]pyridin-3-yl]pyrazin-2-amine<br>¹H NMR (DMSO-d₆) δ 9.95 (br. s, 1H), 8.32-8.34 (m, 2H), 8.19 (s, 1H), 7.77 (dd, J = 9.8, 0.9 Hz, 1H), 7.71-7.75 (m, 2H), 7.37(dd, J = 9.8, 2.5 Hz, 1H), 7.12-7.16 (m, 2H), 7.13 (t, J = 74.7 Hz, 1H), 3.59 (s, 3H); MS m/z 452 (ESI) [M + H]⁺ |
| 49 | 4-({6-[6-methoxy-2-(trifluoromethyl)imidazo[1,2-a]pyridin-3-yl]pyrazin-2-yl}amino)benzonitrile<br>¹H NMR (DMSO-d₆) δ 10.41 (br. s, 1H), 8.44 (s, 1H), 8.33 (s, 1H), 8.31 (dd, J = 1.9, 0.9 Hz, 1H), 7.87-7.92 (m, 2H), 7.79 (d, J = 9.8 Hz, 1H), 7.73-7.77 (m, 2H), 7.39 (dd, J = 9.8, 2.5 Hz, 1H), 3.62 (s, 3H); MS m/z 411 (ESI) [M + H]⁺ |
| 55 | 6-[6-fluoro-2-(trifluoromethyl)imidazo[1,2-a]pyridin-3-yl]-N-[4-(trifluoromethoxy)phenyl]pyrazin-2-amine<br>¹H NMR (DMSO-d₆) δ 10.05 (br. s, 1H), 8.94 (ddd, J = 5.0, 2.4, 0.8 Hz, 1H), 8.37 (s,1H), 8.24 (s, 1H), 7.94 (ddd, J = 9.9, 5.2, 0.9 Hz, 1H), 7.76-7.81 (m, 2H), 7.70 (dd, J = 10.0, 8.0, 2.5 Hz, 1H), 7.29 (d, J = 8.5 Hz, 2H); MS m/z 458 (ESI) [M + H]⁺ |
| 56 | N-[4-(difluoromethoxy)phenyl]-6-[6-fluoro-2-(trifluoromethyl)imidazo[1,2-a]pyridin-3-yl]pyrazin-2-amine<br>¹H NMR (DMSO-d₆) δ 9.91 (br. s, 1H), 8.94 (ddd, J = 5.0, 2.5, 0.8 Hz, 1H), 8.34 (s, 1H), 8.20 (s, 1H), 7.94 (ddd, J = 9.9, 5.2, 0.9 Hz, 1H), 7.67-7.72 (m, 3H), 7.10-7.14 (m, 2H), 7.12 (t, J = 74.7 Hz, 1H); MS m/z 440 (ESI) [M + H]⁺ |
| 57 | 6-[6-fluoro-2-(trifluoromethyl)imidazo[1,2-a]pyridin-3-yl]-N-(4-methoxyphenyl)pyrazin-2-amine<br>¹H NMR (DMSO-d₆) δ 9.64 (s, 1H), 8.95 (ddd, J = 5.0, 2.2, 0.9 Hz, 1H), 8.26 (s, 1H), 8.12 (s, 1H), 7.93 (ddd, J = 9.9, 5.2, 0.9 Hz, 1H), 7.69 (ddd, J = 10.2, 8.0, 2.4 Hz, 1H), 7.51-7.59 (m, 2H), 6.84-6.92 (m, 2H), 3.72 (s, 3H); MS m/z 404 (ESI) [M + H]⁺ |
| 58 | 6-[6-fluoro-2-(trifluoromethyl)imidazo[1,2-a]pyridin-3-yl]-N-[4-(trifluoromethyl)phenyl]pyrazin-2-amine<br>¹H NMR (DMSO-d₆) δ 10.27 (s, 1H), 8.95 (dd, J = 5.0, 1.9 Hz, 1H), 8.43 (s, 1H), 8.31 (s, 1H), 7.96 (dd, J = 9.9, 5.2 Hz, 1H), 7.86-7.91 (m, 2H), 7.71 (dd, J = 10.0, 8.0, 2.2 Hz, 1H), 7.60-7.66 (m, 2H); MS m/z 442 (ESI) [M + H]⁺ |
| 59 | N-(4-nitrophenyl)-6-[2-(trifluoromethyl)imidazo[1,2-a]pyridin-3-yl]pyrazin-2-amine<br>MS m/z 401 (ESI) [M + H]⁺ |
| 201 | 2-methoxy-N-{6-[2-(trifluoromethyl)imidazo[1,2-a]pyridin-3-yl]pyrazin-2-yl}pyrimidin-5-amine<br>¹H NMR (500 MHz, CHLOROFORM-d) δ 7.92-8.00 (s, 1H), 7.78-7.83 (m, 2H), 7.71 (d, J = 6.94 Hz, 1H), 7.18-7.22 (m, 1H), 6.66 (d, J = 9.14 Hz, 1H), 6.42-6.50 (m, 1H), 5.99-6.06 (m, 1H), 2.79 (s, 3H); MS m/z 392 (ESI) [M + H]⁺ |
| 208 | N-[3-fluoro-4-(trifluoromethyl)phenyl]-6-[2-(trifluoromethyl)imidazo[1,2-a]pyridin-3-yl]pyrazin-2-amine<br>¹H NMR (DMSO-d₆) δ 10.51 (s, 1H), 8.77 (dt, J = 7.1, 1.2 Hz, 1H), 8.45 (s, 1H), 8.39 (s, 1H), 7.99 (dd, J = 14.2, 1.6 Hz, 1H), 7.87 (dt, J = 9.1, 0.9 Hz, 1H), 7.67 (t, J = 8.7 Hz, 1H), 7.60 (ddd, J = 9.1, 6.9, 1.3 Hz, 1H), 7.48 (dd, J = 8.7, 1.4 Hz, 1H), 7.18 (td, J = 6.9, 1.1 Hz, 1H); MS m/z 442 (ESI) [M + H]⁺ |
| 678 | 6-[6-methoxy-2-(trifluoromethyl)imidazo[1,2-a]pyridin-3-yl]-N-phenylpyrazin-2-amine<br>¹H NMR (DMSO-d₆) δ 9.88 (br. s, 1H), 8.36 (d, J = 1.9 Hz, 1H), 8.32-8.35 (m, 1H), 8.17 (s, 1H), 7.77 (d, J = 9.8 Hz, 1H), 7.71 (dd, J = 8.5, 0.9 Hz, 2H), 7.36 (dd, J = 9.8, 2.5 Hz, 1H), 7.30 (dd, J = 8.5, 7.3 Hz, 2H), 6.99 (tt, J = 7.3, 0.9 Hz, 1H), 3.58 (s, 3H); MS m/z 386 (ESI) [M + H]⁺ |
| 679 | N-(4-chlorophenyl)-6-[6-methoxy-2-(trifluoromethyl)imidazo[1,2-a]pyridin-3-yl]pyrazin-2-amine<br>¹H NMR (DMSO-d₆) δ 10.02 (s, 1H), 8.34 (s, 1H), 8.31 (dd, J = 1.9, 0.6 Hz, 1H), 8.21 (s, 1H), 7.78 (dd, J = 9.8, 0.9 Hz, 1H), 7.73 (s, 2H), 7.28-7.40 (m, 3H), 3.59 (s, 3H); MS m/z 420 (ESI) [M + H]⁺ |
| 680 | N-(4-bromophenyl)-6-[6-methoxy-2-(trifluoromethyl)imidazo[1,2-a]pyridin-3-yl]pyrazin-2-amine<br>¹H NMR (DMSO-d₆) δ 10.02 (br. s., 1H), 8.31 (s, 1H), 8.34 (s, 1H), 8.21 (s, 1H), 7.77 (d, J = 9.8 Hz, 1H), 7.68 (d, J = 8.5 Hz, 2H), 7.47 (d, J = 8.5 Hz, 2H), 7.37 (dd, J = 9.8, 1.2 Hz, 1H), 3.59 (s, 3H); MS m/z 465 (ESI) [M + H]⁺ |

| Cpd | Name and Data |
|---|---|
| 681 | N-(4-fluorophenyl)-6-[6-methoxy-2-(trifluoromethyl)imidazo[1,2-a]pyridin-3-yl]pyrazin-2-amine<br>$^1$H NMR (DMSO-$d_6$) δ 9.90 (s, 1H), 8.30-8.32 (m, 2H), 8.17 (s, 1H), 7.77 (dd, J = 9.8, 0.6 Hz, 1H), 7.67-7.73 (m, 2H), 7.36 (dd, J = 9.8, 2.5 Hz, 1H), 7.11-7.19 (m, 2H), 3.58 (s, 3H); MS m/z 404 (ESI) [M + H]$^+$ |
| 682 | 6-[6-methoxy-2-(trifluoromethyl)imidazo[1,2-a]pyridin-3-yl]-N-(4-methylphenyl)pyrazin-2-amine<br>$^1$H NMR (DMSO-$d_6$) δ 8.24 (br. s, 1H), 7.77 (s, 1H), 7.75 (s, 1H), 7.39 (d, J = 2.5 Hz, 1H), 7.37 (d, J = 2.5 Hz, 1H), 7.16-7.19 (m, 2H), 7.12-7.16 (m, 1H), 7.06-7.10 (m, 2H), 3.81 (s, 3H), 2.28 (s, 3H); MS m/z 400 (ESI) [M + H]$^+$ |

Example 43

N-{6-[2-(trifluoromethyl)imidazo[1,2-a]pyridin-3-yl]pyrazin-2-yl}benzene-1,4-diamine (Cpd 60)

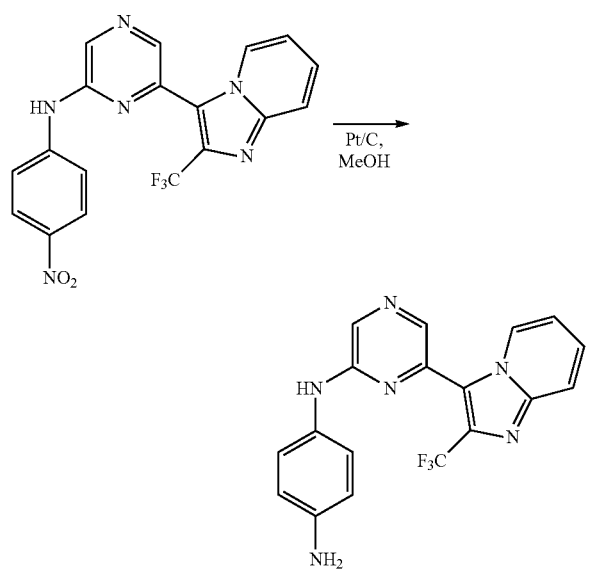

A mixture of Cpd 59 (prepared using the procedure described in Example 42 and appropriate starting materials, reagents and reaction conditions), MeOH (10 mL) and Pt/C (catalytic amount) was shaken at room temperature under hydrogen (50 psi) for one hour. The solution was filtered through Celite, then concentrated and dissolved in EtOAc. This obtained solution was filtered through a short plug of silica gel, then concentrated and dissolved in EtOAc. This obtained solution was diluted with hexane, then concentrated and filtered. The obtained product was washed with ether to provide the title compound as a yellow-green solid (30 mg). $^1$H NMR (DMSO-$d_6$) δ 9.30 (s, 1H), 8.74 (dt, J=7.1, 1.0 Hz, 1H), 8.16 (s, 1H), 8.01 (s, 1H), 7.81 (dt, J=9.1, 1.1 Hz, 1H), 7.54 (ddd, J=9.1, 6.6, 1.3 Hz, 1H), 7.25 (dist. dt(AB), J=8.5, 1.9 Hz, 2H), 7.11 (td, J=6.9, 1.1 Hz, 1H), 6.51 (dist. dt(AB), J=8.5, 1.9 Hz, 2H), 4.86 (s, 2H); MS m/z 371 (ESI) [M+H]$^+$.

Additional compounds of Formula (I) or a form thereof described herein may be prepared according to the procedure of Example 43 by substituting the appropriate starting materials, reagents and reaction conditions:

| Cpd | Name and Data |
|---|---|
| 200 | 2-chloro-N-{6-[2-(trifluoromethyl)imidazo[1,2-a]pyridin-3-yl]pyrazin-2-yl}pyrimidin-5-amine<br>MS m/z 392 (ESI) [M + H]$^+$ |

Example 44

6-[2-(trifluoromethyl)imidazo[1,2-a]pyridin-3-yl]-N-[5-(trifluoromethyl)pyridin-2-yl]pyrazin-2-amine (Cpd 190)

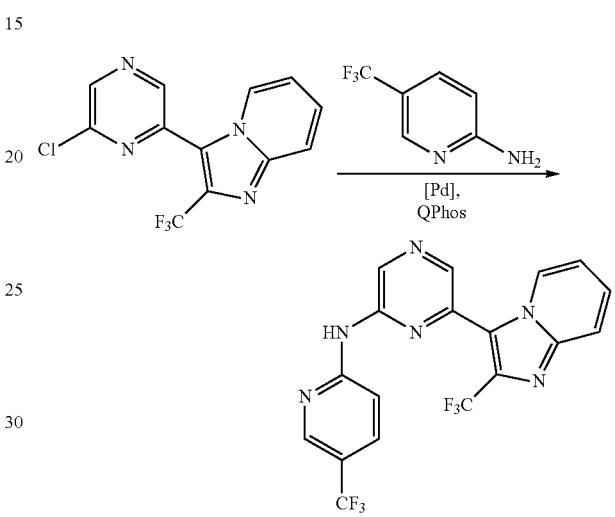

To 3-(6-chloropyrazin-2-yl)-2-(trifluoromethyl)imidazo[1,2-a]pyridine (63 mg, 0.2 mmol) was added 5-(trifluoromethyl)pyridin-2-amine (81 mg, 0.5 mmol), Pd$_2$dba$_3$ (3 mg, 0.004 mmol), QPhos (3 mg), K$_3$PO$_4$ (100 mg, 0.47 mmol) and DME (1 mL). The reaction mixture was heated at 100° C. for 2 hours, then cooled and partitioned between EtOAc and aqueous AcOH. The organic layer was filtered through a plug of silica gel and concentrated. The residue was dissolved in ether, precipitated with hexanes, then partially concentrated and filtered. The crude product was further purified by chromatography on silica gel (gradient ethyl acetate:hexane 1:4 to 1:0), then washed with a mixture of ether and hexane to provide the title compound as an off-white solid (36 mg, 42%). $^1$H NMR (DMSO-$d_6$) δ 10.86 (s, 1H), 9.20-9.22 (m, 1H), 8.81 (dt, J=6.9, 1.3 Hz, 1H), 8.70-8.72 (m, 1H), 8.45 (s, 1H), 8.06 (dd, J=8.8, 2.5 Hz, 1H), 7.85 (dt, J=9.1, 1.1 Hz, 1H), 7.77 (d, J=8.8 Hz, 1H), 7.59 (ddd, J=9.1, 6.9, 1.3 Hz, 1H), 7.18 (td, J=6.9, 1.1 Hz, 1H); MS m/z 425 (ESI) [M+H]$^+$.

Additional compounds of Formula (I) or a form thereof described herein may be prepared according to the procedure of Example 44 by substituting the appropriate starting materials, reagents and reaction conditions:

| Cpd | Name and Data |
|---|---|
| 70 | 6-[2-(trifluoromethyl)imidazo[1,2-a]pyridin-3-yl]-N-[6-(trifluoromethyl)pyridin-3-yl]pyrazin-2-amine<br>$^1$H NMR (DMSO-$d_6$) δ 10.52 (s, 1H), 8.96 (d, J = 2.5 Hz, 1H), 8.73 (dt, J = 6.9, 1.3 Hz, 1H), 8.46 (s, 1H), 8.35-8.39 (m, J = 2.5 Hz, 2H), 7.85 (dt, J = 9.1, 1.1 Hz, 1H), 7.78 (d, J = 8.8 Hz, |

| Cpd | Name and Data |
|---|---|
|  | 1H), 7.58 (ddd, J = 9.1, 6.9, 1.3 Hz, 1H), 7.16 (td, J = 6.9, 1.3 Hz, 1H); MS m/z 425 (ESI) [M + H]+ |
| 100 | N-[4-(trifluoromethoxy)phenyl]-6-[2-(trifluoromethyl)imidazo[1,2-a]pyrimidin-3-yl]pyrazin-2-amine<br>$^1$H NMR (DMSO-d$_6$) δ 10.06 (s, 1H), 9.14 (dd, J = 7.3, 1.9 Hz, 1H), 8.85 (dd, J = 3.9, 2.0 Hz, 1H), 8.37 (s, 1H), 8.25 (s, 1H), 7.76 (dist.dt(AB), J = 9.1, 2.2 Hz, 2H), 7.30 (dd, J = 6.9, 4.1 Hz, 1H), 7.27 (d, J = 8.5 Hz, 2H); MS m/z 441 (ESI) [M + H]+ |
| 109 | N-[4-(difluoromethoxy)phenyl]-6-[2-(trifluoromethyl)imidazo[1,2-a]pyrimidin-3-yl]pyrazin-2-amine<br>$^1$H NMR (DMSO-d$_6$) δ 9.93 (s, 1H), 9.14 (dd, J = 6.9, 1.9 Hz, 1H), 8.84 (dd, J = 4.1, 1.9 Hz, 1H), 8.34 (s, 1H), 8.21 (s, 1H), 7.69 (dist.dt(AB), J = 8.8, 2.2 Hz, 2H), 7.30 (dd, J = 7.1, 3.9 Hz, 1H), 7.10 (dist.d(AB), J = 9.1 Hz, 2H), 7.11 (t, J = 74.4 Hz, 1H); MS m/z 423 (ESI) [M + H]+ |

Example 45

6-[2-(trifluoromethyl)imidazo[1,2-a]pyrimidin-3-yl]-N-[4-(trifluoromethyl)phenyl]pyrazin-2-amine (Cpd 67)

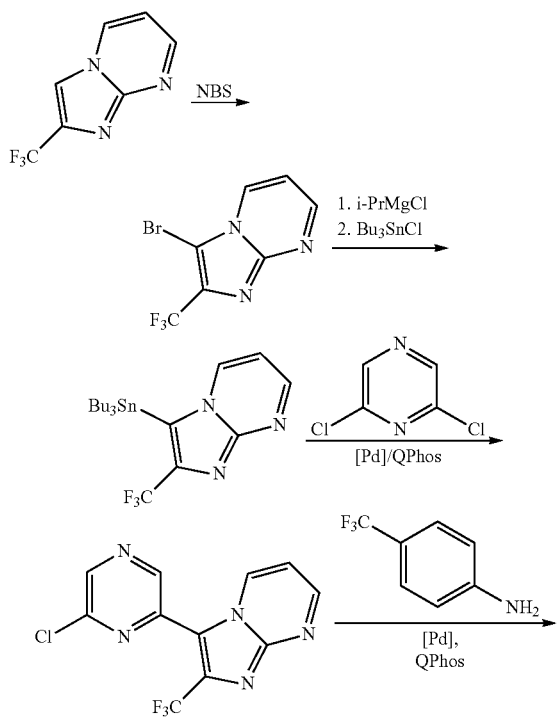

Step 1. To 2-(trifluoromethyl)-imidazo[1,2-a]pyrimidine (1.1 g, 5 mmol, commercially available) was added chloroform (20 mL), then NBS (0.9 g, 5 mmol) at room temperature. The mixture was reacted for 30 minutes at room temperature, then NBS (catalytic) was added. The mixture was reacted for 30 minutes, dried (Na$_2$SO$_4$), then filtered, concentrated and purified by chromatography on silica gel (gradient ethyl acetate:hexane 1:2 to 1:0) to provide crude 3-bromo-2-(trifluoromethyl)imidazo[1,2-a]pyrimidine (1.86 g, 140%, by $^1$H-NMR contains 40% of pyrrolidine-2,5-dione). $^1$H NMR (DMSO-d$_6$) δ 8.93 (dd, J=6.9, 1.9 Hz, 1H), 8.80 (dd, J=4.1, 1.9 Hz, 1H), 7.36 (dd, J=6.9, 4.1 Hz, 1H).

Step 2. To the obtained product (1.57 g, 5.9 mmol, 60% pure) was added THF (30 mL). The resulting solution was cannulated into a mixture of i-PrMgCl×LiCl (1M solution in THF, 10 mL, 10 mmol) cooled to −60° C. The mixture was reacted for 50 minutes at −60° C. The cooling bath was removed and the mixture was reacted for 20 minutes at room temperature then cooled to −60° C. and Bu$_3$SnCl was added (2.7 mL, 10 mmol). The mixture was reacted for 5 minutes at −60° C., the cooling bath was removed, then the mixture was stirred at room temperature for 1 hour and partitioned between NH$_4$Cl (aqueous) and hexane. The organic layer was filtered through a short plug of silica gel, then concentrated and purified by chromatography on silica gel (gradient ethyl acetate:hexane 1:10 to 1:1), to provide 3-(tributylstannyl)-2-(trifluoromethyl)imidazo[1,2-a]pyrimidine as a yellow oil (0.51 g, 1.1 mmol).

Step 3. To the obtained product was added 2,6-dichloropyrazine (745 mg, 5 mmol), QPhos (14 mg), Pd$_2$dba$_3$ (17 mg) and dioxane (10 mL). The reaction mixture was heated at 120° C. for 2 hours, then concentrated and purified by chromatography on silica gel (gradient ethyl acetate:hexane 1:2 to 1:0), to provide 3-(6-chloropyrazin-2-yl)-2-(trifluoromethyl)imidazo[1,2-a]pyrimidine as a tan-colored solid (164 mg, 50%). $^1$H NMR (DMSO-d$_6$) δ 9.16 (dd, J=7.1, 2.0 Hz, 1H), 8.98 (s, 1H), 8.95 (s, 1H), 8.89 (dd, J=4.1, 1.9 Hz, 1H), 7.38 (dd, J=7.3, 4.1 Hz, 1H); MS m/z 300 (ESI) [M+H]+.

Step 4. To 3-(6-chloropyrazin-2-yl)-2-(trifluoromethyl)imidazo[1,2-a]pyrimidine (80 mg, 0.27 mmol) was added 4-(trifluoromethyl)aniline (86 mg, 0.54 mmol), QPhos (3 mg), Pd$_2$dba$_3$ (3 mg), K$_3$PO$_4$ (100 mg, 0.47 mmol) and DME (1 mL). The reaction mixture was stirred at 110° C. for 2 hours, then partitioned between water and EtOAc and the organic layer was purified by chromatography on silica gel (gradient from ethyl acetate:hexane 1:4 to EtOAc:MeOH 10:1). The product was washed with a mixture of EtOAc and hexane to provide the title compound as a light orange solid (47 mg, 41%). $^1$H NMR (DMSO-d$_6$) δ 10.29 (s, 1H), 9.15 (dd, J=6.9, 1.9 Hz, 1H), 8.86 (dd, J=4.1, 1.9 Hz, 1H), 8.43 (s, 1H), 8.32 (s, 1H), 7.87 (dist. d(AB), J=8.5 Hz, 2H), 7.61 (dist. d(AB), J=8.5 Hz, 2H), 7.32 (dd, J=6.9, 4.1 Hz, 1H); MS m/z 425 (ESI) [M+H]+.

Example 46

N-[4-(trifluoromethyl)phenyl]-6-[2-(trifluoromethyl)-5,6,7,8-tetrahydroimidazo[1,2-a]pyridin-3-yl]pyrazin-2-amine (Cpd 232)

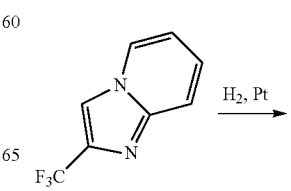

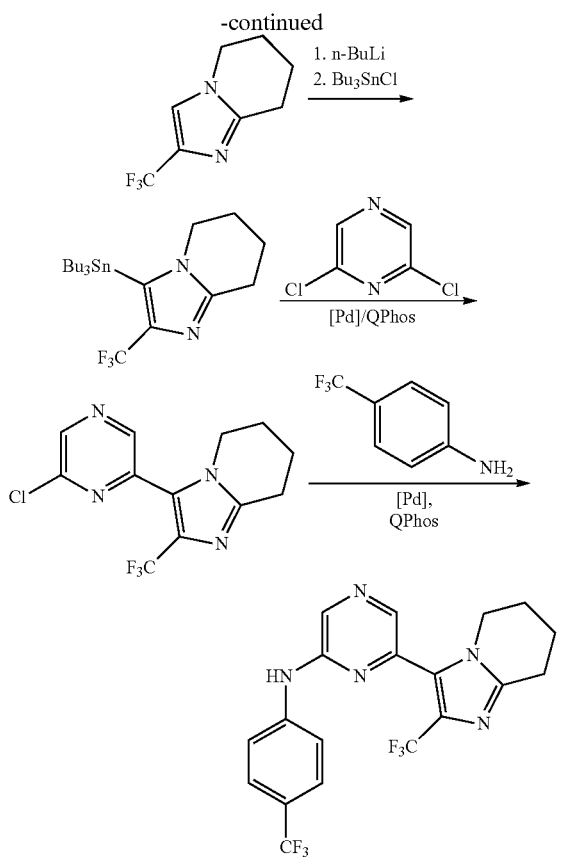

Step 1. To 2-(trifluoromethyl)imidazo[1,2-a]pyridine (615 mg, 3.3 mmol) was added a pinch of PtO$_2$ (catalytic) and MeOH (10 mL). The mixture was shaken at room temperature under hydrogen (50 psi) for 50 minutes, then HCl was added (aqueous, concentrated, 0.5 mL) and another pinch of PtO$_2$ (catalytic). The mixture was shaken at room temperature under hydrogen (50 psi) for 17 hours then diluted with EtOAc. The reaction mixture was washed with NaHCO$_3$ (aqueous saturated), then dried, filtered through a short plug of silica gel and concentrated to provide 2-(trifluoromethyl)-5,6,7,8-tetrahydroimidazo[1,2-a]pyridine as a white solid (576 mg, 92%). $^1$H NMR (DMSO-d$_6$) δ 7.62 (q, J=1.6 Hz, 1H), 3.98 (t, J=6.0 Hz, 2H), 2.74 (t, J=6.5 Hz, 2H), 1.80-1.95 (m, 4H); MS m/z 191 (ESI) [M+H]$^+$.

Step 2. To THF (2 mL, cooled to −70° C.) was added diisopropylamine (0.28 mL, 2 mmol) and a solution of n-BuLi in c-Hexane (2.2M, 0.82 mL, 1.8 mmol). The mixture was added via a cannula into a solution of a portion of the obtained product (265 mg, 1.39 mmol) in THF (2 mL). The mixture was cooled to −70° C. and reacted for 1 hour and 15 minutes, then Bu$_3$SnCl (0.54 mL, 2 mmol) was added. The mixture was reacted for an additional hour at −70° C. then diluted with hexane. The reaction mixture was washed with aqueous NH$_4$Cl, then filtered through a plug of silica gel and purified by chromatography on silica gel (gradient ethyl acetate:hexane 1:10 to 1:1), to provide 3-(tributylstannyl)-2-(trifluoromethyl)-5,6,7,8-tetrahydroimidazo[1,2-a]pyridine as a colorless oil (620 mg, 92%). $^1$H NMR (DMSO-d$_6$) δ 3.91 (t, J=6.0 Hz, 2H), 2.76 (t, J=6.5 Hz, 2H), 1.88-1.98 (m, 2H), 1.77-1.88 (m, 2H), 1.39-1.53 (m, 6H), 1.28 (sxt, J=7.3 Hz, 6H), 1.12 (m, 6H), 0.85 (t, J=7.4 Hz, 9H).

Step 3. To the obtained product (620 mg, 1.3 mmol), was added 2,6-dichloropyrazine (387 mg, 2.6 mmol), Pd$_2$dba$_3$ (55 mg, 0.06 mmol), QPhos (43 mg, 0.06 mmol) and dioxane (5 mL). The mixture was heated at 110° C. for 2 hours and 20 minutes, then concentrated and purified by chromatography on silica gel (gradient ethyl acetate:hexane 1:4 to 1:1), to provide 3-(6-chloropyrazin-2-yl)-2-(trifluoromethyl)-5,6,7,8-tetrahydroimidazo[1,2-a]pyridine as a brown oil (210 mg, 53%). $^1$H NMR (DMSO-d$_6$) δ 8.90 (s, 1H), 8.81 (s, 1H), 3.96 (t, J=5.4 Hz, 2H), 2.87 (t, J=6.0 Hz, 2H), 1.83-1.97 (m, 4H).

Step 4. To the obtained product (70 mg, 0.23 mmol) was added 4-(trifluoromethyl)aniline (80 mg, 0.5 mmol), XPhos (7 mg, 0.014 mmol), Pd$_2$dba$_3$ (7 mg, 0.007 mmol), K$_3$PO$_4$ (106 mg, 0.5 mmol) and DME (2 mL). The mixture was heated at 110° C. for 4 hours and partitioned between EtOAc and water. The organic layer was purified by chromatography on silica gel (gradient from ethyl acetate:hexane 1:2 to EtOAc:MeOH 10:1), to provide the title compound as a pink solid (67 mg, 68%). $^1$H NMR (DMSO-d$_6$) δ 10.16 (s, 1H), 8.35 (s, 1H), 8.14 (s, 1H), 7.90 (dist. d(AB), J=8.5 Hz, 2H), 7.66 (dist. d(AB), J=8.5 Hz, 2H), 3.95 (br. s., 2H), 2.87 (br. s., 2H), 1.91 (br. s., 4H); MS m/z 428 (ESI) [M+H]$^+$.

Additional compounds of Formula (I) or a form thereof described herein may be prepared according to the procedure of Example 46 by substituting the appropriate starting materials, reagents and reaction conditions:

| Cpd | Name and Data |
|-----|---------------|
| 233 | N-[4-(difluoromethoxy)phenyl]-6-[2-(trifluoromethyl)-5,6,7,8-tetrahydroimidazo[1,2-a]pyridin-3-yl]pyrazin-2-amine<br>$^1$H NMR (DMSO-d$_6$) δ 9.81 (s, 1H), 8.26 (s, 1H), 8.04 (s, 1H), 7.70 (dist.dt(AB), J = 9.1, 1.9 Hz, 2H), 7.14 (dist.dt(AB), J = 9.1, 1.9 Hz, 2H), 7.12 (t, J = 74.4 Hz, 1H), 3.93 (br. s., 2H), 2.86 (br. s., 2H), 1.85-1.94 (m, 4H); MS m/z 426 (ESI) [M + H]$^+$ |
| 234 | N-[4-(trifluoromethoxy)phenyl]-6-[2-(trifluoromethyl)-5,6,7,8-tetrahydroimidazo[1,2-a]pyridin-3-yl]pyrazin-2-amine<br>$^1$H NMR (DMSO-d$_6$) δ 9.94 (s, 1H), 8.29 (s, 1H), 8.08 (s, 1H), 7.78 (dist.dt(AB), J = 9.1, 2.2 Hz, 2H), 7.32 (dist.d(AB), J = 8.5 Hz, 2H), 3.93 (br. s., 2H), 2.86 (br. s., 2H), 1.90 (br. s., 4H); MS m/z 444 (ESI) [M + H]$^+$ |

Example 47

6-(2,5-dimethyl-1H-imidazol-1-yl)-N-[4-(trifluoromethyl)phenyl]pyrazin-2-amine (Cpd 355)

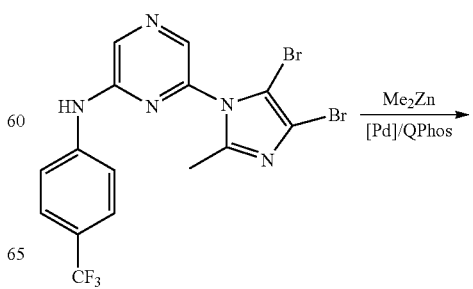

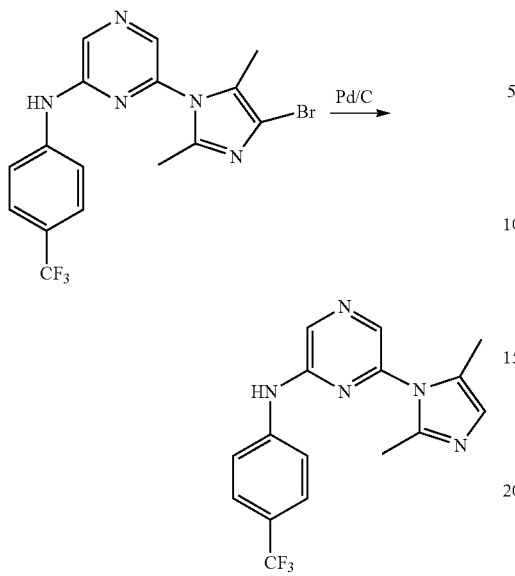

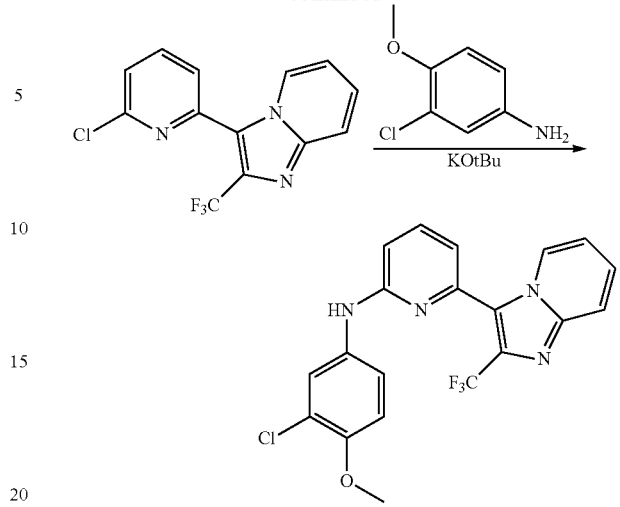

Step 1. To 6-(4,5-dibromo-2-methyl-1H-imidazol-1-yl)-N-(4-(trifluoromethyl)phenyl)pyrazin-2-amine (527 mg, 1.10 mmol) was added QPhos (79 mg, 10%), Pd$_2$dba$_3$ (30 mg, 3%), DME (6 mL) and Me$_2$Zn (1.2 M solution in toluene, 2.75 mL, 3 equiv). The mixture was heated at 50° C. for 4 hours, then partitioned between aqueous ammonium chloride and EtOAc, and the organic layer was purified by chromatography on silica gel (gradient from ethyl acetate: hexane 1:2 to EtOAc:MeOH 5:1), to provide the minor product Cpd 341 (100 mg) (also prepared as shown in Example 7). The major product Cpd 342 (also prepared as shown in Example 7), could not be purified by chromatography.

Step 2. Cpd 341 was dissolved in methanol (200 mL) and hydrogenated in a H-Cube apparatus using a Pd/C cartridge at 30° C. under hydrogen (30 bar). The starting material was almost completely consumed, then the reaction mixture was concentrated and the product was sequentially washed with a mixture of DME and ether, then EtOAc followed by a mixture of EtOAc and methanol to provide the title compound (27 mg). $^1$H NMR (DMSO-d$_6$) δ 10.60 (s, 1H), 8.58 (s, 1H), 8.36 (s, 1H), 7.85 (dist. d(AB), J=8.5 Hz, 2H), 7.70 (dist. d(AB), J=8.5 Hz, 2H), 7.53 (s, 1H), 2.57 (s, 3H), 2.23 (s, 3H); MS m/z 334 (ESI) [M+H]$^+$.

Example 48

N-(3-chloro-4-methoxyphenyl)-6-[2-(trifluoromethyl)imidazo[1,2-a]pyridin-3-yl]pyridin-2-amine
(Cpd 3)

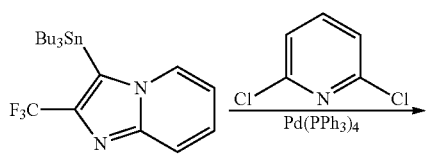

To 3-(tributylstannyl)-2-(trifluoromethyl)imidazo[1,2-a]pyridine (155 mg, 0.32 mmol) was added 2,6-dichloropyridine (59 mg, 0.4 mmol), a pinch of tetrakis(triphenylphosphine)palladium (catalytic) and THF (2.5 mL). The mixture was heated at 80° C. for 14 hours, then cooled in ice bath and 3-chloro-4-methoxyaniline (126 mg, 0.8 mmol) and KOtBu (1M solution in THF, 0.8 mL, 0.8 mmol) were added. The mixture was reacted for 2 hours and additional 3-chloro-4-methoxyaniline and KOtBu were added until the starting material was consumed. The mixture was partitioned between aqueous acetic acid and hexane, then the organic layer was purified by chromatography on silica gel (gradient ethyl acetate:hexane 1:10 to 1:1) to provide the title compound as a brown solid (15 mg). $^1$H NMR (DMSO-d$_6$) δ 9.31 (s, 1H), 8.74 (dt, J=6.9, 0.9 Hz, 1H), 7.89 (d, J=2.5 Hz, 1H), 7.78 (dd, J=8.5, 7.3 Hz, 1H), 7.80 (dt, J=9.1, 0.9 Hz, 1H), 7.53 (ddd, J=9.1, 6.6, 1.3 Hz, 1H), 7.41 (dd, J=9.0, 2.7 Hz, 1H), 7.11 (td, J=6.9, 0.9 Hz, 1H), 7.02-7.06 (m, 2H), 6.90 (d, J=8.2 Hz, 1H), 3.77 (s, 3H); MS m/z 419 (ESI) [M+H]$^+$.

Additional compounds of Formula (I) or a form thereof described herein may be prepared according to the procedure of Example 48 by substituting the appropriate starting materials, reagents and reaction conditions:

| Cpd | Name and Data |
|---|---|
| 4 | N-(4-methoxyphenyl)-6-[2-(trifluoromethyl)imidazo[1,2-a]pyridin-3-yl]pyridin-2-amine<br>$^1$H NMR (DMSO-d$_6$) δ 9.11 (s, 1H), 8.73 (d, J = 7.3 Hz, 1H), 7.79 (d, J = 9.1 Hz, 1H), 7.73 (dd, J = 8.5, 7.6 Hz, 1H), 7.47-7.55 (m, 1H), 7.50 (dist.d, J = 9.1 Hz, 2H), 7.09 (td, J = 6.9, 0.9 Hz, 1H), 6.98 (d, J = 7.3 Hz, 1H), 6.87 (d, J = 8.5 Hz, 1H), 6.82 (dist.dt(AB), J = 9.1, 1.9 Hz, 2H), 3.69 (s, 3H); MS m/z 385 (ESI) [M + H]$^+$ |
| 8 | N-(3-fluoro-4-methoxyphenyl)-6-[2-(trifluoromethyl)imidazo[1,2-a]pyridin-3-yl]pyridin-2-amine<br>$^1$H NMR (DMSO-d$_6$) δ 9.34 (s, 1H), 8.72 (dt, J = 6.9, 0.9 Hz, 1H), 7.80 (dt, J = 9.1, 1.3 Hz, 1H), 7.78 (dd, J = 8.5, 7.6 Hz, 1H), 7.69 (dd, J = 14.2, 2.5 Hz, 1H), 7.53 (ddd, J = 9.1, 6.9, 1.3 Hz, 1H), 7.23 (ddd, J = 9.0, 2.5, 1.6 Hz, 1H), 7.10 (td, J = 6.9, 1.3 Hz, 1H), 7.02-7.07 (m, 2H), 6.91 (d, J = 8.2 Hz, 1H), 3.76 (s, 3H); MS m/z 403 (ESI) [M + H]$^+$ |
| 16 | N-[4-(trifluoromethoxy)phenyl]-6-[2-(trifluoromethyl)imidazo[1,2-a]pyridin-3-yl]pyridin-2-amine<br>$^1$H NMR (DMSO-d$_6$) δ 9.57 (s, 1H), 8.69 (dt, J = 7.1, 1.2 Hz, 1H), 7.80 (dt, J = 8.8, 1.3 Hz, 1H), 7.83 (dd, J = 8.5, 7.6 Hz, 1H), 7.74 (dist.dt(AB), J = 9.1, 2.2 Hz, 2H), 7.53 (ddd, J = 9.1, |

| Cpd | Name and Data |
|---|---|
| | 6.8, 1.1 Hz, 1H), 7.21 (d, J = 8.2 Hz, 2H), 7.07-7.13 (m, 2H), 6.99 (d, J = 7.9 Hz, 1H); MS m/z 439 (ESI) [M + H]$^+$ |
| 17 | N-(4-chlorophenyl)-6-[2-(trifluoromethyl)imidazo[1,2-a]pyridin-3-yl]pyridin-2-amine<br>$^1$H NMR (DMSO-d$_6$) δ 9.51 (s, 1H), 8.70 (dt, J = 6.9, 1.3 Hz, 1H), 7.79-7.84 (m, 2H), 7.67 (dist.dt(AB), J = 8.8, 1.9 Hz, 2H), 7.53 (ddd, J = 9.1, 6.8, 1.1 Hz, 1H), 7.24 (dist.dt(AB), J = 9.1, 1.9 Hz, 2H), 7.07-7.14 (m, 2H), 6.97 (d, J = 8.2 Hz, 1H); MS m/z 389 (ESI) [M + H]$^+$ |

Example 49

6-[2-(trifluoromethyl)imidazo[1,2-a]pyridin-3-yl]-N-[4-(trifluoromethyl)phenyl]pyridin-2-amine (Cpd 18)

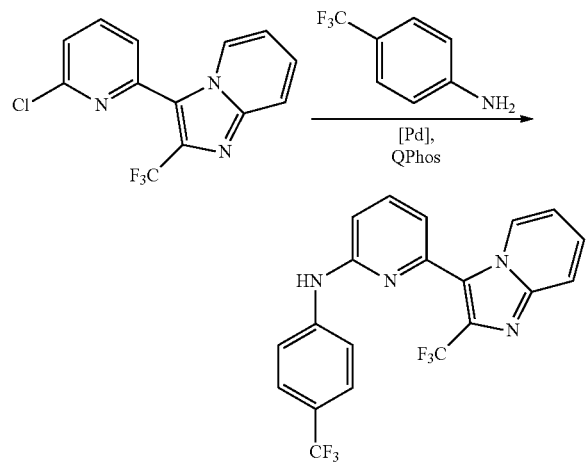

To 3-(6-chloropyridin-2-yl)-2-(trifluoromethyl)imidazo[1,2-a]pyridine (71 mg, 0.24 mmol) was added 4-(trifluoromethyl)aniline (78 mg, 0.48 mmol), QPhos (1.7 mg, 0.002 mmol), Pd$_2$dba$_3$ (1.8 mg, 0.002 mmol), K$_3$PO$_4$ (106 mg, 0.5 mmol) and DME (2 mL). The mixture was heated at 110° C. for 29 hours, then partitioned between toluene and aqueous ammonium chloride and the organic layer was purified by chromatography on silica gel (gradient ethyl acetate:hexane 1:4 to 1:1). The product was sonicated in a mixture of ether and hexane to provide the title compound as a white solid (74 mg, 73%). $^1$H NMR (DMSO-d$_6$) δ 9.82 (s, 1H), 8.70 (dt, J=7.1, 1.0 Hz, 1H), 7.88 (dd, J=8.5, 7.6 Hz, 1H), 7.85 (d, J=8.5 Hz, 2H), 7.82 (dt, J=9.1, 1.1 Hz, 1H), 7.51-7.58 (m, 3H), 7.17 (d, J=7.3 Hz, 1H), 7.12 (td, J=6.9, 1.3 Hz, 1H), 7.06 (d, J=8.2 Hz, 1H); MS m/z 423 (ESI) [M+H]$^+$.

Additional compounds of Formula (I) or a form thereof described herein may be prepared according to the procedure of Example 49 by substituting the appropriate starting materials, reagents and reaction conditions:

| Cpd | Name and Data |
|---|---|
| 27 | N-[4-(difluoromethoxy)phenyl]-6-[2-(trifluoromethyl)imidazo[1,2-a]pyridin-3-yl]pyridin-2-amine<br>$^1$H NMR (DMSO-d$_6$) δ 9.42 (s, 1H), 8.70 (dt, J = 6.9, 0.9 Hz, 1H), 7.78-7.82 (m, 2H), 7.66 (dist.dt(AB), J = 8.8, 2.2 Hz, 2H), 7.53 (ddd, J = 9.1, 6.6, 1.3 Hz, 1H), 7.10 (td, J = 6.9, 1.1 Hz, 1H), 7.02-7.08 (m, 3H), 6.95 (d, J = 8.2 Hz, 1H), 7.08 (t, J = 74.4 Hz, 1H); MS m/z 421 (ESI) [M + H]$^+$ |
| 50 | 4-({6-[2-(trifluoromethyl)imidazo[1,2-a]pyridin-3-yl]pyridin-2-yl}amino)benzonitrile<br>$^1$H NMR (DMSO-d$_6$) δ 9.95 (s, 1H), 8.68 (dt, J = 7.1, 1.2 Hz, 1H), 7.90 (dd, J = 8.4, 7.4 Hz, 1H), 7.80-7.86 (m, 3H), 7.63 (dist.dt(AB), J = 8.8, 1.9 Hz, 2H), 7.54 (ddd, J = 9.1, 6.8, 1.1 Hz, 1H), 7.21 (d, J = 7.3 Hz, 1H), 7.12 (dist.td(AB), J = 6.9, 1.3 Hz, 1H), 7.08 (d, J = 7.9 Hz, 1H); MS m/z 380 (ESI) [M + H]$^+$ |

Example 50

N-(4-methoxyphenyl)-6-(2-methyl-1H-benzimidazol-1-yl)pyridin-2-amine (Cpd 32)

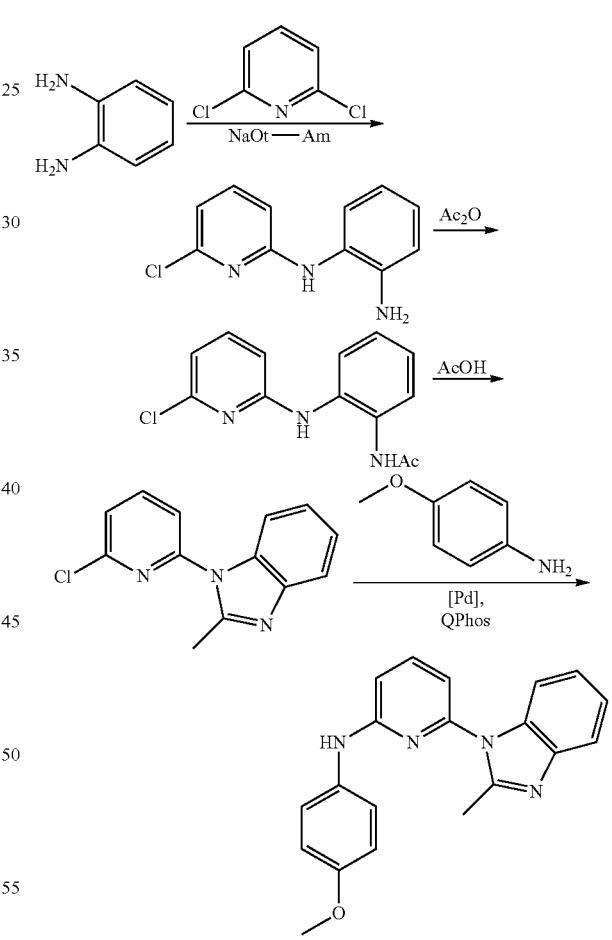

Step 1. To 2,6-dichloropyridine (1.46 g, 9.9 mmol) was added benzene-1,2-diamine (3.2 g, 30 mmol) and THF (20 mL). The mixture was cooled in ice bath and NaOt-Am was added (2.5 M solution in THF, 8 mL, 20 mmol). The mixture was reacted at room temperature for 1 hour, then a pinch of QPhos (catalytic) and Pd$_2$dba$_3$ (catalytic) were added. The mixture was heated at 60° C. for 1 hour, then at 110° C. for 25 minutes. The mixture was cooled and partitioned between aqueous acetic acid and a mixture of EtOAc and hexane. The organic layer was dried, filtered and concentrated to provide crude N$^1$-(6-chloropyridin-2-yl)benzene-1,2-diamine (2.58 g, 120%).

Step 2. To the obtained product (1.3 g, 5 mmol) was added DCM (10 mL) and acetic anhydride (2 mL). The mixture was washed with aqueous sodium bicarbonate and purified by chromatography on silica gel (gradient ethyl acetate: hexane 1:4 to 1:0) to provide N-(2-(6-chloropyridin-2-ylamino)phenyl)acetamide as a pink solid (828 mg, 3.2 mmol). $^1$H NMR (DMSO-d$_6$) δ 9.45 (s, 1H), 8.43 (s, 1H), 7.52-7.58 (m, 3H), 7.15 (td, J=7.9, 1.3 Hz, 1H), 7.08 (td, J=7.9, 1.6 Hz, 1H), 6.76 (d, J=7.6 Hz, 1H), 6.64 (d, J=8.2 Hz, 1H), 2.04 (s, 3H).

Step 3. The obtained product was heated in mixture of ACN (6 mL) and AcOH (5.5 mL) in a microwave oven at 180° C. for 2 hours. The mixture was cooled, partitioned between toluene.EtOAc and aqueous sodium bicarbonate. The organic layer was filtered through a plug of silica gel and concentrated to provide 1-(6-chloropyridin-2-yl)-2-methyl-1H-benzo[d]imidazole as an orange oil (710 mg, 91%). $^1$H NMR (DMSO-d$_6$) δ 8.19 (t, J=7.9 Hz, 1H), 7.79 (d, J=7.6 Hz, 1H), 7.71 (d, J=7.9 Hz, 1H), 7.63-7.67 (m, 1H), 7.45-7.49 (m, 1H), 7.23-7.29 (m, 2H), 2.60 (s, 3H).

Step 4. To 1-(6-chloropyridin-2-yl)-2-methyl-1H-benzo[d]imidazole (100 mg, 0.41 mmol) was added QPhos (5.8 mg, 0.0082 mmol), Pd$_2$dba$_3$ (7.5 mg, 0.0082 mmol), K$_3$PO$_4$ (174 mg, 0.82 mmol) and DME (1.5 mL). The mixture was heated at 100° C. for 18 hours, then cooled and partitioned between a mixture of toluene:EtOAc and aqueous ammonium chloride. The organic layer was purified by chromatography on silica gel (gradient ethyl acetate:hexane 1:4 to 1:0) and crystallized from a mixture of ether and hexane to provide the title compound as a light pink solid (100 mg). $^1$H NMR (DMSO-d$_6$) δ 9.20 (s, 1H), 7.79 (dd, J=8.2, 7.6 Hz, 1H), 7.60-7.64 (m, 1H), 7.50 (dist. dt(AB), J=8.8, 2.2 Hz, 2H), 7.41-7.45 (m, 1H), 7.19-7.25 (m, 2H), 6.91 (d, J=7.6 Hz, 1H), 6.81-6.88 (m, 3H), 3.69 (s, 3H), 2.58 (s, 3H); MS m/z 331 (ESI) [M+H]$^+$.

Additional compounds of Formula (I) or a form thereof described herein may be prepared according to the procedure of Example 50 by substituting the appropriate starting materials, reagents and reaction conditions:

| Cpd | Name and Data |
|---|---|
| 35 | N-[4-(difluoromethoxy)phenyl]-6-(2-methyl-1H-benzimidazol-1-yl)pyridin-2-amine<br>$^1$H NMR (DMSO-d$_6$) δ 9.50 (s, 1H), 7.86 (dd, J = 8.2, 7.6 Hz, 1H), 7.66 (dist.dt(AB), J = 9.1, 2.2 Hz, 2H), 7.61-7.64 (m, 1H), 7.42-7.46 (m, 1H), 7.16-7.27 (m, 2H), 7.07 (dist.dt(AB), J = 9.1, 2.2 Hz, 2H), 7.00 (d, J = 6.9 Hz, 1H), 6.93-6.96 (m, 1H), 7.08 (t, J = 74.7 Hz, 1H), 2.59 (s, 3H); MS m/z 367 (ESI) [M + H]$^+$ |
| 36 | 6-(2-methyl-1H-benzimidazol-1-yl)-N-[4-(trifluoromethoxy)phenyl]pyridin-2-amine<br>$^1$H NMR (DMSO-d$_6$) δ 9.64 (s, 1H), 7.89 (dd, J = 8.2, 7.6 Hz, 1H), 7.72-7.76 (m, 2H), 7.61-7.65 (m, 1H), 7.41-7.45 (m, 1H), 7.19-7.26 (m, 4H), 7.04 (d, J = 7.6 Hz, 1H), 6.98 (d, J = 8.2 Hz, 1H), 2.59 (s, 3H); MS m/z 385 (ESI) [M + H]$^+$ |
| 37 | 6-(2-methyl-1H-benzimidazol-1-yl)-N-[4-(trifluoromethyl)phenyl]pyridin-2-amine<br>1H NMR (DMSO-d$_6$) δ 9.89 (s, 1H), 7.94 (dd, J = 8.2, 7.6 Hz, 1H), 7.85 (dist.d(AB), J = 8.8 Hz, 2H), 7.62-7.66 (m, 1H), 7.58 (dist.d(AB), J = 8.5 Hz, 2H), 7.42-7.47 (m, 1H), 7.20-7.27 (m, 2H), 7.12 (d, J = 7.6 Hz, 1H), 7.05 (d, J = 7.9 Hz, 1H), 2.61 (s, 3H); MS m/z 369 (ESI) [M + H]$^+$ |
| 71 | 6-[2-(trifluoromethyl)imidazo[1,2-a]pyridin-3-yl]-N-[6-(trifluoromethyl)pyridin-3-yl]pyridin-2-amine<br>$^1$H NMR (DMSO-d$_6$) δ 10.07 (s, 1H), 8.92 (d, J = 2.5 Hz, 1H), 8.67 (dt, J = 6.9, 0.9 Hz, 1H), 8.37 (dd, J = 8.5, 2.2 Hz, 1H), 7.93 (dd, J = 8.4, 7.4 Hz, 1H), 7.82 (dt, J = 9.1, 1.1 Hz, 1H), 7.70 (d, J = 8.8 Hz, 1H), 7.54 (ddd, J = 9.1, 6.6, 1.3 Hz, 1H), 7.23 (d, J = 7.6 Hz, 1H), 7.09-7.13 (m, 2H); MS m/z 424 (ESI) [M + H]$^+$ |
| 581 | 6-(2-methyl-1H-benzimidazol-1-yl)-N-(4-methylphenyl)pyridin-2-amine<br>1H NMR (DMSO-d$_6$) δ 9.30 (s, 1H), 7.81 (dd, J = 8.2, 7.6 Hz, 1H), 7.61-7.65 (m, 1H), 7.50 (dist.d, J = 8.5 Hz, 2H), 7.43-7.47 (m, 1H), 7.19-7.26 (m, 2H), 7.04 (dist.d, J = 8.2 Hz, 2H), 6.94 (d, J = 7.6 Hz, 1H), 6.92 (d, J = 8.2 Hz, 1H), 2.59 (s, 3H), 2.21 (s, 3H); MS m/z 315 (ESI) [M + H]$^+$ |
| 584 | N-[4-(difluoromethoxy)phenyl]-6-(6-fluoro-2-methyl-1H-benzimidazol-1-yl)pyridin-2-amine<br>$^1$H NMR (Acetone-d$_6$) δ 8.77 (br. s, 1H), 7.90 (dd, J = 8.4, 7.4 Hz, 1H), 7.71-7.80 (m, 2H), 7.62 (dd, J = 8.8, 4.7 Hz, 1H), 7.26 (dd, J = 9.5, 2.5 Hz, 1H), 7.12-7.16 (m, 2H), 7.03-7.08 (m, 2H), 7.01 (dd, J = 8.5, 0.9 Hz, 1H), 6.90 (t, J = 74.4 Hz, 1H), 2.64 (s, 3H); MS m/z 385 (ESI) [M + H]$^+$ |
| 585 | 6-(6-fluoro-2-methyl-1H-benzimidazol-1-yl)-N-[4-(trifluoromethoxy)phenyl]pyridin-2-amine<br>$^1$H NMR (Acetone-d$_6$) δ 8.91 (br. s, 1H), 7.92 (dd, J = 8.2, 7.6 Hz, 1H), 7.81-7.87 (m, 2H), 7.62 (dd, J = 8.8, 5.0 Hz, 1H), 7.20-7.30 (m, 3H), 7.09 (dd, J = 7.3, 0.9 Hz, 1H), 7.02-7.07 (m, 2H), 2.64 (s, 3H); MS m/z 403 (ESI) [M + H]$^+$ |
| 586 | 6-(6-fluoro-2-methyl-1H-benzimidazol-1-yl)-N-(4-methoxyphenyl)pyridin-2-amine<br>$^1$H NMR (Acetone-d$_6$) δ 8.43 (br. s, 1H), 7.83 (dd, J = 8.4, 7.4 Hz, 1H), 7.60 (dd, J = 8.7, 4.9 Hz, 1H), 7.51-7.58 (m, 2H), 7.26 (dd, J = 9.3, 2.4 Hz, 1H), 7.04 (ddd, J = 9.8, 8.8, 2.5 Hz, 1H), 6.95 (dd, J = 7.3, 0.6 Hz, 1H), 6.83-6.93 (m, 3H), 3.78 (s, 3H), 2.63 (s, 3H); MS m/z 349 (ESI) [M + H]$^+$ |
| 587 | 6-(6-fluoro-2-methyl-1H-benzimidazol-1-yl)-N-(4-methylphenyl)pyridin-2-amine<br>$^1$H NMR (Acetone-d$_6$) δ 8.54 (br. s., 1H), 7.85 (dd, J = 8.2, 7.6 Hz, 1H), 7.61 (dd, J = 8.8, 4.7 Hz, 1H), 7.52-7.58 (m, 2H), 7.27 (dd, J = 9.1, 2.5 Hz, 1H), 7.11 (d, J = 8.2 Hz, 2H), 7.05 (ddd, J = 9.8, 8.8, 2.5 Hz, 1H), 6.98 (dd, J = 7.9, 4.7 Hz, 2H), 2.64 (s, 3H), 2.28 (s, 3H); MS m/z 333 (ESI) [M + H]$^+$ |
| 606 | N-(4-chlorophenyl)-6-(2-methyl-1H-benzimidazol-1-yl)pyridin-2-amine<br>$^1$H NMR (DMSO-d$_6$) δ 9.58 (s, 1H), 7.87 (dd, J = 8.5, 7.6 Hz, 1H), 7.67 (dist.dt, J = 8.8, 2.2 Hz, 2H), 7.62-7.65 (m, 1H), 7.41-7.46 (m, 1H), 7.28 (dist.dt, J = 8.8, 1.9 Hz, 2H), 7.18-7.26 (m, 2H), 7.02 (d, J = 7.3 Hz, 1H), 6.96 (d, J = 8.2 Hz, 1H), 2.59 (s, 3H); MS m/z 335 (ESI) [M + H]$^+$ |
| 607 | 6-(6-fluoro-2-methyl-1H-benzimidazol-1-yl)-N-[4-(trifluoromethyl)phenyl]pyridin-2-amine<br>$^1$H NMR (Acetone-d$_6$) δ 9.49 (br. s., 1H), 8.35 (dd, J = 8.2, 7.8 Hz, 1H), 8.26-8.34 (m, 2H), 8.01 (dd, J = 8.8, 4.7 Hz, 1H), 7.95-8.00 (m, 2H), 7.65 (dd, J = 9.3, 2.4 Hz, 1H), 7.53 (dd, J = 7.6, 0.6 Hz, 1H), 7.48 (d, J = 8.2 Hz, 1H), 7.44 (ddd, J = 9.8, 8.8, 2.5 Hz, 1H), 3.03 (s, 3H); MS m/z 387 (ESI) [M + H]$^+$ |
| 608 | N-(4-chlorophenyl)-6-(6-fluoro-2-methyl-1H-benzimidazol-1-yl)pyridin-2-amine<br>$^1$H NMR (DMSO-d$_6$) δ 9.59 (br. s, 1H), 7.88 (dd, J = 8.2, 7.6 Hz, 1H), 7.66-7.69 (m, 2H), 7.64 (dd, J = 8.7, 4.9 Hz, 1H), 7.28-7.34 (m, 2H), 7.26 (dd, J = 9.1, 2.5 Hz, 1H), 7.10 (ddd, J = 9.8, 8.8, 2.5 Hz, 1H), 7.05 (d, J = 7.3 Hz, 1H), 6.98 (d, J = 8.2 Hz, 1H), 2.59 (s, 3H); MS m/z 353 (ESI) [M + H]$^+$ |
| 609 | 4-{[6-(6-fluoro-2-methyl-1H-benzimidazol-1-yl)pyridin-2-yl]amino}benzonitrile<br>$^1$H NMR (DMSO-d$_6$) δ 10.02 (s, 1H), 7.97 (t, J = 8.2 Hz, 1H), 7.81-7.86 (m, 2H), 7.67-7.71 (m, 2H), 7.66 (dd, J = 8.8, 5.0 Hz, 1H), 7.27 (dd, J = 9.5, 2.5 Hz, 1H), 7.18 (d, J = 7.6 Hz, 1H), 7.12 (ddd, J = 9.8, 8.8, 2.8 Hz, 1H), 7.08 (d, J = 8.5 Hz, 1H), 2.60 (s, 3H); MS m/z 344 (ESI) [M + H]$^+$ |
| 610 | methyl 4-{[6-(6-fluoro-2-methyl-1H-benzimidazol-1-yl)pyridin-2-yl]amino}benzoate<br>$^1$H NMR (DMSO-d$_6$) δ 9.92 (s, 1H), 7.94 (dd, J = 8.2, 7.3 Hz, 1H), 7.82-7.89 (m, 2H), 7.73-7.82 (m, 2H), 7.66 (dd, J = 8.2, 4.7 Hz, 1H), 7.30 (dd, J = 9.1, 2.5 Hz, 1H), 7.16 (d, J = 7.3 Hz, 1H), 7.12 (ddd, J = 9.8, 8.8, 2.5 Hz, 1H), 7.07 (d, J = 8.5 Hz, 1H), 3.80 (s, 3H), 2.61 (s, 3H); MS m/z 377 (ESI) [M + H]$^+$ |

Example 51

N-(4-methoxyphenyl)-6-[2-(trifluoromethyl)-1H-benzimidazol-1-yl]pyridin-2-amine (Cpd 33)

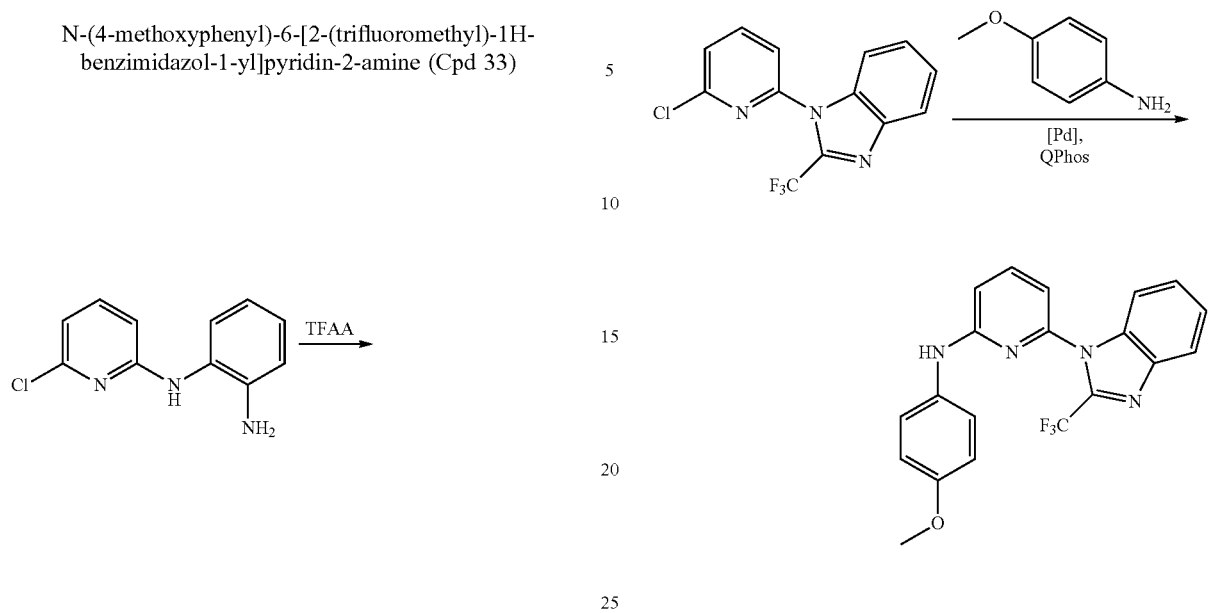

The title compound (prepared using the procedure described in Example 50 and appropriate starting materials, reagents and reaction conditions) was obtained. $^1$H NMR (DMSO-d$_6$) δ 9.29 (s, 1H), 7.92-7.95 (m, 1H), 7.83 (dd, J=8.4, 7.4 Hz, 1H), 7.44-7.51 (m, 5H), 6.97 (t, J=7.3 Hz, 2H), 6.80 (dist. dt(AB), J=9.1, 2.2 Hz, 2H), 3.67 (s, 3H); MS m/z 385 (ESI) [M+H]$^+$.

Additional compounds of Formula (I) or a form thereof described herein may be prepared according to the procedure of Example 51 by substituting the appropriate starting materials, reagents and reaction conditions:

| Cpd | Name and Data |
|---|---|
| 38 | N-[4-(difluoromethoxy)phenyl]-6-[2-(trifluoromethyl)-1H-benzimidazol-1-yl]pyridin-2-amine <br> $^1$H NMR (DMSO-d$_6$) δ 9.59 (s, 1H), 7.93-7.97 (m, 1H), 7.90 (dd, J = 8.4, 7.4 Hz, 1H), <br> 7.61 (dist. dt(AB), J = 8.8, 1.9 Hz, 2H), 7.45-7.52 (m, 3H), 7.01-7.09 (m, 4H), 7.07 (t, J = <br> 74.7 Hz, 1H); MS m/z 421 (ESI) [M + H]$^+$ |
| 39 | N-[4-(trifluoromethoxy)phenyl]-6-[2-(trifluoromethyl)-1H-benzimidazol-1-yl]pyridin-2-amine <br> $^1$H NMR (DMSO-d$_6$) δ: 9.73 (s, 1H), 7.91-7.97 (m, 2H), 7.69 (dt, J = 9.1, 2.2 Hz, 2H), <br> 7.44-7.54 (m, 3H), 7.21 (d, J = 8.8 Hz, 2H), 7.12 (d, J = 7.3 Hz, 1H), 7.08 (d, J = 8.5 Hz, <br> 1H); MS m/z 439 (ESI) [M + H]$^+$ |
| 40 | 6-[2-(trifluoromethyl)-1H-benzimidazol-1-yl]-N-[4-(trifluoromethyl)phenyl]pyridin-2-amine <br> $^1$H NMR (DMSO-d$_6$) δ 9.96 (s, 1H), 7.99 (dd, J = 8.5, 7.6 Hz, 1H), 7.94-7.97 (m, 1H), <br> 7.80 (dist. d, J = 8.5 Hz, 2H), 7.55 (dist. d, J = 8.5 Hz, 2H), 7.45-7.52 (m, 3H), 7.19 (d, J = 7.3 Hz, 1H), 7.15 (d, J = 8.2 Hz, 1H); MS m/z 423 (ESI) [M + H]$^+$ |

Example 52

6-[(4-methoxyphenyl)amino]-2-[2-(trifluoromethyl) imidazo[1,2-a]pyridin-3-yl]pyridine-3-carbonitrile (Cpd 34)

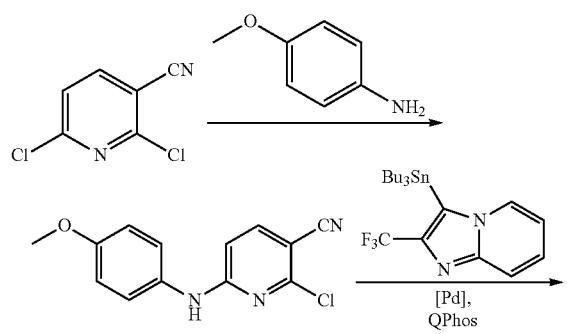

Step 1. To 2,6-dichloronicotinonitrile (100 mg, 0.57 mmol) was added 4-methoxyaniline (285 mg, 2.32 mmol) and ACN (2 mL). The mixture was heated at 100° C. for 23 hours, then cooled and partitioned between EtOAc and aqueous sodium bicarbonate. The product was purified by chromatography on silica gel (gradient ethyl acetate:hexane 1:10 to 1:2), and crystallization from a mixture of ether: hexane to provide 2-chloro-6-(4-methoxyphenylamino) nicotinonitrile as an off-white solid (108 mg, 73%). $^1$H NMR (DMSO-$d_6$) δ 9.96 (s, 1H), 7.91 (d, J=8.8 Hz, 1H), 7.46 (br. d, J=8.5 Hz, 2H), 6.96 (dist. dt(AB), J=9.1, 2.2 Hz, 2H), 6.72 (d, J=8.5 Hz, 1H), 3.74 (s, 3H).

The less polar (eluted earlier) fraction contained the isomer 6-chloro-2-(4-methoxyphenylamino)nicotinonitrile (23 mg). $^1$H NMR (DMSO-$d_6$) δ 9.33 (s, 1H), 8.07 (d, J=7.9 Hz, 1H), 7.37 (dist. dt(AB), J=9.1, 2.2 Hz, 2H), 6.92 (dist. dt(AB), J=8.8, 1.9 Hz, 2H), 6.89 (d, J=8.2 Hz, 1H), 3.75 (s, 3H).

Step 2. To 2-chloro-6-(4-methoxyphenylamino)nicotinonitrile (51 mg, 0.20 mmol) was added 3-(tributylstannyl)-2-(trifluoromethyl)imidazo[1,2-a]pyridine (105 mg, 0.22 mmol), QPhos (7.1 mg, 0.01 mmol), Pd$_2$dba$_3$ (9.2 mg, 0.01 mmol) and dioxane (2 mL). The mixture was heated at 115° C. for one hour, then concentrated and purified by chromatography on silica gel (gradient ethyl acetate:hexane 1:4 to 1:1). The product was washed from ether to provide the title compound as a pink solid (30 mg, 37%). $^1$H NMR (DMSO-$d_6$) δ 9.89 (s, 1H), 8.43 (dt, J=6.9, 1.3 Hz, 1H), 8.06 (d, J=8.8 Hz, 1H), 7.84 (dt, J=9.1, 1.3 Hz, 1H), 7.59 (ddd, J=9.1, 6.9, 1.3 Hz, 1H), 7.46 (dist. d, J=8.8 Hz, 2H), 7.17 (td, J=6.9, 0.9 Hz, 1H), 6.95 (d, J=8.8 Hz, 1H), 6.84 (dist. d, J=8.8 Hz, 2H), 3.68 (s, 3H); MS m/z 410 (ESI) [M+H]$^+$.

Additional compounds of Formula (I) or a form thereof described herein may be prepared according to the procedure of Example 52 by substituting the appropriate starting materials, reagents and reaction conditions:

| Cpd | Name and Data |
|---|---|
| 41 | 2-[(4-methoxyphenyl)amino]-6-[2-(trifluoromethyl)imidazo[1,2-a]pyridin-3-yl]pyridine-3-carbonitrile<br>$^1$H NMR (DMSO-$d_6$) δ: 9.24 (s, 1H), 8.78 (dt, J = 7.1, 1.2 Hz, 1H), 8.25 (d, J = 7.9 Hz, 1H), 7.78 (dt, J = 9.1, 1.1 Hz, 1H), 7.53 (ddd, J = 9.1, 6.6, 1.3 Hz, 1H), 7.40 (d, J = 8.8 Hz, 2H), 7.09 (d, J = 8.2 Hz, 1H), 7.03 (td, J = 6.9, 1.4 Hz, 1H), 6.90 (dt, J = 8.8, 2.2 Hz, 2H), 3.72 (s, 3H); MS m/z 410 (ESI) [M + H]$^+$ |

-continued

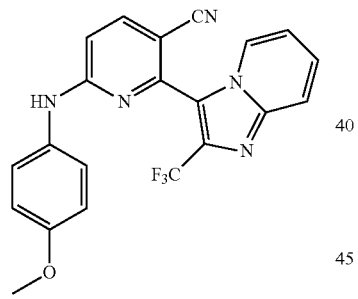

Example 53

2-[(4-methoxyphenyl)amino]-6-[2-(trifluoromethyl) imidazo[1,2-a]pyridin-3-yl]pyridine-4-carbonitrile (Cpd 42)

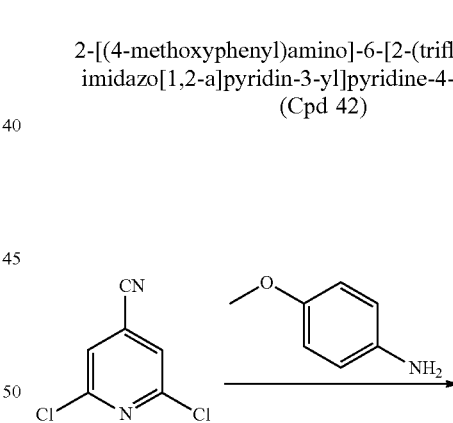

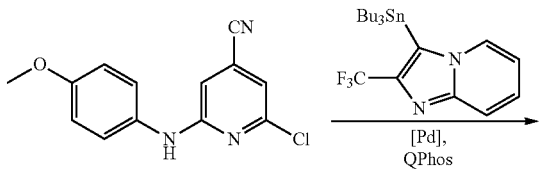

-continued

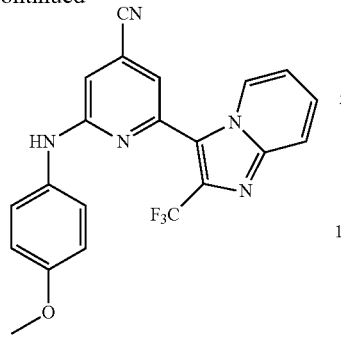

Step 1. To 2,6-dichloroisonicotinonitrile (100 mg, 0.57 mmol) was added 4-methoxyaniline (285 mg, 2.32 mmol) and ACN (2 mL). The mixture was heated at 100° C. for 2 days, then concentrated and purified by chromatography on silica gel (gradient ethyl acetate:hexane 1:10 to 1:1) to provide 2-chloro-6-(4-methoxyphenylamino)isonicotinonitrile as a yellow solid (40 mg, 27%).

Step 2. To 2-chloro-6-(4-methoxyphenylamino)isonicotinonitrile (40 mg, 0.15 mmol) was added 3-(tributylstannyl)-2-(trifluoromethyl)imidazo[1,2-a]pyridine (95 mg, 0.2 mmol), QPhos (2.1 mg, 0.003 mmol), Pd$_2$dba$_3$ (2.7 mg, 0.003 mmol) and dioxane (2 mL). The mixture was heated at 110° C. for 5 hours, then concentrated and purified by chromatography on silica gel (gradient ethyl acetate:hexane 1:4 to 1:1). The product was washed with ether to provide the title compound as a yellow solid (23 mg). $^1$H NMR (DMSO-d$_6$) δ 9.57 (s, 1H), 8.70 (dt, J=6.9, 0.9 Hz, 1H), 7.81 (dt, J=9.1, 1.3 Hz, 1H), 7.55 (ddd, J=9.1, 6.6, 0.9 Hz, 1H), 7.48 (dist. dt, J=9.1, 2.2 Hz, 2H), 7.28 (s, 1H), 7.17 (d, J=0.9 Hz, 1H), 7.12 (td, J=6.9, 0.9 Hz, 1H), 6.86 (dist. dt, J=8.8, 2.2 Hz, 2H), 3.70 (s, 3H); MS m/z 410 (ESI) [M+H]$^+$.

Additional compounds of Formula (I) or a form thereof described herein may be prepared according to the procedure of Example 53 by substituting the appropriate starting materials, reagents and reaction conditions:

Example 54

6-[2-(trifluoromethyl)imidazo[1,2-a]pyrimidin-3-yl]-N-[4-(trifluoromethyl)phenyl]pyridin-2-amine (Cpd 64)

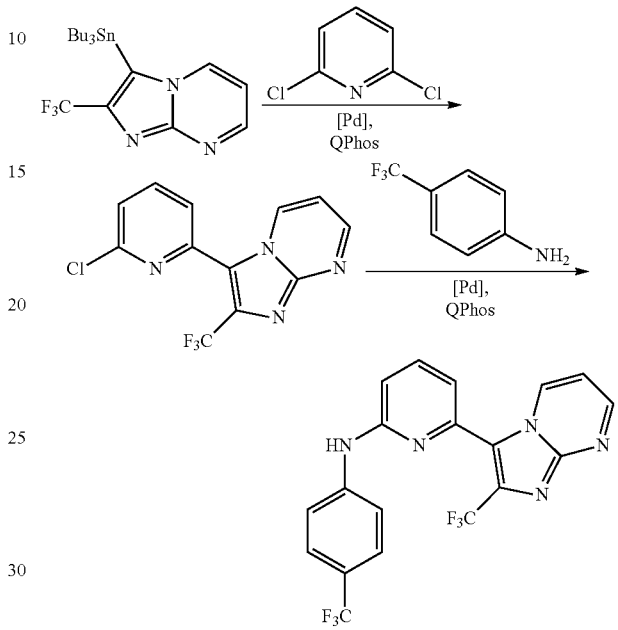

Step 1. To 3-(tributylstannyl)-2-(trifluoromethyl)imidazo[1,2-a]pyrimidine (236 mg, 0.5 mmol) was added 2,6-dichloropyridine (450 mg, 3 mmol), QPhos (7 mg, 0.01 mmol), Pd$_2$dba$_3$ (9 mg, 0.01 mmol) and dioxane (10 mL). The mixture was heated at 110° C. for 15 minutes, then concentrated and purified by chromatography on silica gel (gradient ethyl acetate:hexane 1:2 to 1:0). The product was washed with hexane to provide 3-(6-chloropyridin-2-yl)-2-(trifluoromethyl)imidazo[1,2-a]pyrimidine as an off-white

| Cpd | Name and Data |
|---|---|
| 107 | 4-methoxy-6-[2-(trifluoromethyl)imidazo[1,2-a]pyridin-3-yl]-N-[4-(trifluoromethyl)phenyl]pyridin-2-amine<br>$^1$H NMR (500 MHz, CHLOROFORM-d) δ: 8.79 (d, J = 7.3 Hz, 1H), 7.76 (d, J = 9.1 Hz, 1H), 7.55 (q, J = 8.8 Hz, 4H), 7.39 (dd, J = 8.7, 7.1 Hz, 1H), 7.25 (br. s., 1H), 6.93 (t, J = 6.9 Hz, 1H), 6.84 (s, 1H), 6.43 (d, J = 1.9 Hz, 1H), 3.91 (s, 3H); MS m/z 385 (ESI) [M + H]$^+$ |
| 124 | 3-(4-methoxy-6-{[4-(trifluoromethyl)phenyl]amino}pyridin-2-yl)imidazo[1,2-a]pyridine-2-carboxylic acid<br>$^1$H NMR (500 MHz, Acetone-d6) δ 8.90-8.94 (m, 1H), 8.84 (s, 1H), 7.85 (d, J = 9.14 Hz, 2H), 7.80 (d, J = 9.14 Hz, 2H), 7.73 (d, J = 9.14 Hz, 1H), 7.08-7.12 (m, 1H), 6.83 (dd, J = 0.79, 1.73 Hz, 1H), 6.55 (d, J = 2.21 Hz, 1H), 5.63 (s, 1H), 3.81 (s, 3H); MS m/z 429 (ESI) [M + H]$^+$ |
| 125 | N-[4-(difluoromethoxy)phenyl]-4-methoxy-6-[2-(trifluoromethyl)imidazo[1,2-a]pyridin-3-yl]pyridin-2-amine<br>$^1$H NMR (500 MHz, CHLOROFORM-d) δ 8.81 (d, J = 6.94 Hz, 1H), 7.76 (d, J = 9.14 Hz, 1H), 7.36-7.42 (m, 3H), 7.14 (d, J = 8.83 Hz, 2H), 6.94 (d, J = 1.26 Hz, 1H), 6.76-6.81 (m, 1H), 6.52 (t, J = 148.80 Hz, 1H), 6.33 (d, J = 1.89 Hz, 1H), 3.89 (s, 3H); MS m/z 451 (ESI) [M + H]$^+$ | solid (88 mg, 0.29 mmol, 58%). $^1$H NMR (DMSO-d$_6$) δ 9.14 (dd, J=7.1, 2.0 Hz, 1H), 8.85 (dd, J=4.1, 1.9 Hz, 1H), 8.14 (t, J=7.9 Hz, 1H), 7.76 (d, J=7.6 Hz, 1H), 7.72 (dd, J=8.2, 0.6 Hz, 1H), 7.34 (dd, J=6.9, 4.1 Hz, 1H).

Step 2. To the obtained product was added 4-(trifluoromethyl)aniline (81 mg, 0.5 mmol), QPhos (3 mg), Pd$_2$dba$_3$ (3 mg), K$_3$PO$_4$ (106 mg, 0.5 mmol) and DME (1 mL). The mixture was heated at reflux for one hour and additional QPhos (catalytic) and Pd$_2$dba$_3$ (catalytic) were added. The mixture was heated for 3 hours, then cooled and partitioned between EtOAc and water. The organic layer was concentrated and purified by chromatography on silica gel (gradient ethyl acetate:hexane 1:4 to 1:1). The product was washed with ether and hexane to provide the title compound (51 mg, 42%). $^1$H NMR (DMSO-d$_6$) δ 9.83 (s, 1H), 9.14 (dd, J=6.9, 1.9 Hz, 1H), 8.82 (dd, J=3.9, 2.0 Hz, 1H), 7.89 (dd, J=8.5, 7.6 Hz, 1H), 7.84 (dist. d(AB), J=8.5 Hz, 2H), 7.54 (dist. d(AB), J=8.8 Hz, 2H), 7.27 (dd, J=7.3, 4.1 Hz, 1H), 7.20 (d, J=7.3 Hz, 1H), 7.07 (d, J=7.9 Hz, 1H); MS m/z 424 (ESI) [M+H]$^+$.

Additional compounds of Formula (I) or a form thereof described herein may be prepared according to the procedure of Example 54 by substituting the appropriate starting materials, reagents and reaction conditions:

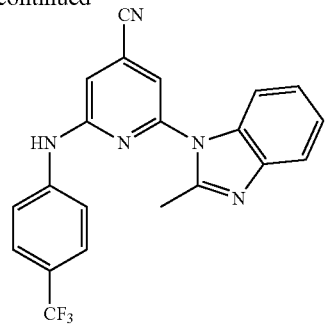

Step 1. To 2,6-dichloroisonicotinonitrile (567 mg, 3.33. mmol) was added 2-methyl-1H-benzo[d]imidazole (660 mg, 5 mmol), DMF (3 mL) and KOt-Bu (1M solution in THF, 3.3 mL, 3.3 mmol) at room temperature. The mixture was reacted at room temperature for 20 hours. The reaction was quenched with AcOH, then partitioned between water and a mixture of EtOAc:hexane. The organic layer was purified by chromatography on silica gel (gradient ethyl acetate:hexane 1:2 to 1:0) to provide 2-chloro-6-(2-methyl-1H-benzo[d]

| Cpd | Name and Data |
|---|---|
| 99 | N-(4-(trifluoromethoxy)phenyl)-6-(2-(trifluoromethyl)imidazo[1,2-a]pyrimidin-3-yl)pyridin-2-amine<br>$^1$H NMR (DMSO-d$_6$) δ 9.59 (s, 1H), 9.13 (dd, J = 6.9, 1.9 Hz, 1H), 8.82 (dd, J = 4.1, 1.9 Hz, 1H), 7.84 (dd, J = 8.5, 7.3 Hz, 1H), 7.73 (dist. dt(AB), J = 9.1, 2.2 Hz, 2H), 7.25 (dd, J = 6.9, 4.1 Hz, 1H), 7.21 (dist. d(AB), J = 8.5 Hz, 2H), 7.13 (d, J = 7.3 Hz, 1H), 7.00 (d, J = 7.9 Hz, 1H); MS m/z 439 (ESI) [M + H]$^+$ |
| 108 | N-[4-(difluoromethoxy)phenyl]-6-[2-(trifluoromethyl)imidazo[1,2-a]pyrimidin-3-yl]pyridin-2-amine<br>$^1$H NMR (DMSO-d$_6$) δ 9.44 (s, 1H), 9.15 (dd, J = 6.9, 1.9 Hz, 1H), 8.82 (dd, J = 3.9, 2.0 Hz, 1H), 7.81 (dd, J = 8.5, 7.3 Hz, 1H), 7.65 (dist. dt(AB), J = 9.1, 2.2 Hz, 2H), 7.25 (dd, J = 6.9, 4.1 Hz, 1H), 7.10 (d, J = 7.3 Hz, 1H), 7.05 (dist. dt(AB), J = 8.8, 1.9 Hz, 2H), 6.96 (dd, J = 8.5, 0.6 Hz, 1H), 7.08 (t, J = 74.7 Hz, 1H); MS m/z 422 (ESI) [M + H]$^+$ |

Example 55

2-(2-methyl-1H-benzimidazol-1-yl)-6-{[4-(trifluoromethyl)phenyl]amino}pyridine-4-carbonitrile (Cpd 132)

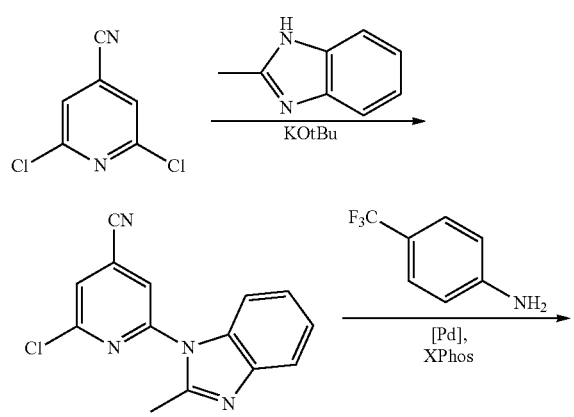

imidazol-1-yl)isonicotinonitrile as a pink solid (402 mg, 45%). $^1$H NMR (DMSO-d$_6$) δ 8.34 (dist. d(AB), J=0.9 Hz, 1H), 8.33 (dist. d(AB), J=0.9 Hz, 1H), 7.64-7.67 (m, 1H), 7.57-7.60 (m, 1H), 7.26-7.31 (m, 2H), 2.64 (s, 3H).

Step 2. To the obtained product (201 mg, 0.75 mmol) was added 4-(trifluoromethyl)aniline (0.19 mL, 1.5 mmol), XPhos (21 mg, 0.05 mmol), Pd$_2$dba$_3$ (21 mg, 0.023 mmol), K$_3$PO$_4$ (318 mg, 1.5 mmol) and DME (5 mL). The mixture was heated at 110° C. for 16 hours, then diluted with EtOAc and a few drops of water and AcOH were added. The mixture was filtered, then concentrated and recrystallized from EtOAc:ether. The product was washed with ether to provide the title compound as a gray solid (194 mg, 64%). $^1$H NMR (DMSO-d$_6$) δ 10.46 (s, 1H), 7.85 (dist. d(AB), J=8.5 Hz, 2H), 7.64-7.66 (m, 1H), 7.62 (dist. d(AB), J=8.5 Hz, 2H), 7.53-7.57 (m, 2H), 7.41 (d, J=0.9 Hz, 1H), 7.23-7.30 (m, 2H), 2.63 (s, 3H); MS m/z 394 (ESI) [M+H]$^+$.

Additional compounds of Formula (I) or a form thereof described herein may be prepared according to the procedure of Example 55 by substituting the appropriate starting materials, reagents and reaction conditions:

| Cpd | Name and Data |
|---|---|
| 135 | 2-{[4-(difluoromethoxy)phenyl]amino}-6-(2-methyl-1H-benzimidazol-1-yl)pyridine-4-carbonitrile<br>$^1$H NMR (DMSO-d$_6$) δ 9.91 (s, 1H), 7.61-7.67 (m, 3H), 7.51-7.54 (m, 1H), 7.44 (d, J = 0.9 Hz, 1H), 7.22-7.28 (m, 3H), 7.09-7.14 (m, 2H), 7.12 (t, J = 74.4 Hz, 1H), 2.60 (s, 3H);<br>MS m/z 392 (ESI) [M + H]$^+$ |
| 136 | 2-(2-methyl-1H-benzimidazol-1-yl)-6-{[4-(trifluoromethoxy)phenyl]amino}pyridine-4-carbonitrile<br>$^1$H NMR (DMSO-d$_6$) δ 10.05 (s, 1H), 7.71 (dist. dt(AB), J = 9.1, 1.9 Hz, 2H), 7.63-7.65 (m, 1H), 7.52-7.54 (m, 1H), 7.49 (d, J = 0.9 Hz, 1H), 7.21-7.32 (m, 5H), 2.61 (s, 3H);<br>MS m/z 410 (ESI) [M + H]$^+$ |
| 389 | 2-{[4-(trifluoromethyl)phenyl]amino}-6-(2,5,6-trimethyl-1H-benzimidazol-1-yl)pyridine-4-carbonitrile<br>$^1$H NMR (DMSO-d$_6$) δ 10.22 (s, 1H), 7.84 (dist. d(AB), J = 8.5 Hz, 2H), 7.63 (dist. d(AB), J = 8.8 Hz, 2H), 7.51 (d, J = 0.9 Hz, 1H), 7.41 (s, 1H), 7.36 (s, 1H), 7.32 (d, J = 0.9 Hz, 1H), 2.59 (s, 3H), 2.32 (s, 3H), 2.27 (s, 3H); MS m/z 422 (ESI) [M + H]$^+$ |
| 435 | 2-(4-fluoro-2-methyl-1H-benzimidazol-1-yl)-6-{[4-(trifluoromethyl)phenyl]amino}pyridine-4-carbonitrile<br>$^1$H NMR (DMSO-d$_6$) δ 10.28 (s, 1H), 7.82 (dist. d(AB), J = 8.5 Hz, 2H), 7.63 (dist. d(AB), J = 8.8 Hz, 2H), 7.59 (s, 1H), 7.35-7.40 (m, 2H), 7.24 (td, J = 8.1, 4.9 Hz, 1H), 7.10 (dd, J = 10.7, 8.2 Hz, 1H), 2.63 (s, 3H); MS m/z 412 (ESI) [M + H]$^+$ |
| 436 | 2-{[4-(difluoromethoxy)phenyl]amino}-6-(4-fluoro-2-methyl-1H-benzimidazol-1-yl)pyridine-4-carbonitrile<br>$^1$H NMR (DMSO-d$_6$) δ 9.94 (s, 1H), 7.62 (dist.d, J = 8.8 Hz, 2H), 7.46 (s, 1H), 7.36 (d, J = 8.2 Hz, 1H), 7.27 (s, 1H), 7.19-7.25 (m, 1H), 6.95-7.16 (m, 4H), 2.61 (s, 3H);<br>MS m/z 410 (ESI) [M + H]$^+$ |
| 447 | 2-(4,6-difluoro-2-methyl-1H-benzimidazol-1-yl)-6-{[4-(trifluoromethyl)phenyl]amino}pyridine-4-carbonitrile<br>$^1$H NMR (DMSO-d$_6$) δ 10.27 (s, 1H), 7.81 (dist. d(AB), J = 8.5 Hz, 2H), 7.64 (dist. d (AB), J = 8.8 Hz, 2H), 7.59 (d, J = 0.9 Hz, 1H), 7.38 (d, J = 0.9 Hz, 1H), 7.33 (dd, J = 9.1, 2.2 Hz, 1H), 7.17 (td, J = 10.4, 2.2 Hz, 1H), 2.61 (s, 3H); MS m/z 430 (ESI) [M + H]$^+$ |
| 448 | 2-{[4-(difluoromethoxy)phenyl]amino}-6-(4,6-difluoro-2-methyl-1H-benzimidazol-1-yl)pyridine-4-carbonitrile<br>$^1$H NMR (DMSO-d$_6$) δ 9.93 (s, 1H), 7.61 (dist. dt(AB), J = 9.1, 2.2 Hz, 2H), 7.46 (d, J = 0.9 Hz, 1H), 7.30 (dd, J = 9.0, 2.0 Hz, 1H), 7.26-7.28 (m, 1.25H), 7.10-7.19 (m, 3.5H), 6.97 (s, 0.25H), 2.59 (s, 3H); MS m/z 428 (ESI) [M + H]$^+$ |
| 449 | 2-(4,6-difluoro-2-methyl-1H-benzimidazol-1-yl)-6-{[4-(trifluoromethoxy)phenyl]amino}pyridine-4-carbonitrile<br>$^1$H NMR (DMSO-d$_6$) δ 10.06 (s, 1H), 7.70 (dist. dt(AB), J = 9.1, 2.2 Hz, 2H), 7.51 (d, J = 0.9 Hz, 1H), 7.28-7.33 (m, 4H), 7.16 (td, J = 10.4, 2.2 Hz, 1H), 2.60 (s, 3H); MS m/z 446 (ESI) [M + H]$^+$ |
| 634 | 2-(2-methyl-1H-benzimidazol-1-yl)-6-[(4-methylphenyl)amino]pyridine-4-carbonitrile<br>$^1$H NMR (DMSO-d$_6$) δ 9.74 (s, 1H), 7.61-7.66 (m, 1H), 7.52-7.56 (m, 1H), 7.48 (dist. d, J = 8.2 Hz, 2H), 7.38 (d, J = 0.9 Hz, 1H), 7.21-7.28 (m, 2H), 7.21 (d, J = 0.9 Hz, 1H), 7.09 (dist. d, J = 8.2 Hz, 2H), 2.60 (s, 3H), 2.23 (s, 3H); MS m/z 340 (ESI) [M + H]$^+$ |

Example 56

2-[2-(trifluoromethyl)imidazo[1,2-a]pyridin-3-yl]-6-{[4-(trifluoromethyl)phenyl]amino}pyridine-4-carboxamide (Cpd 189)

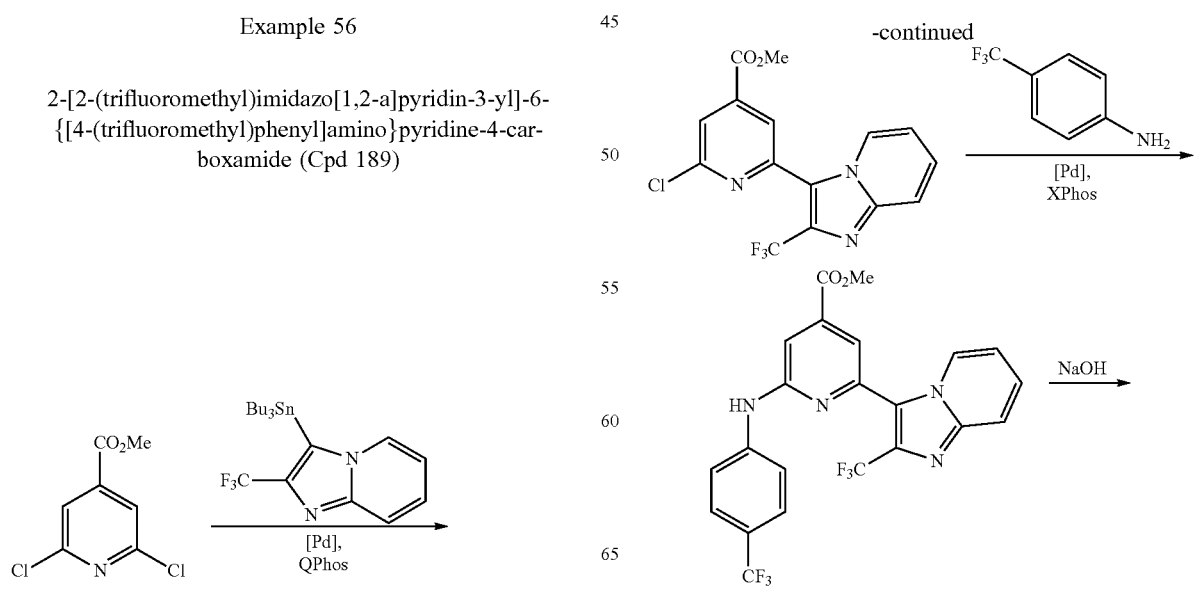

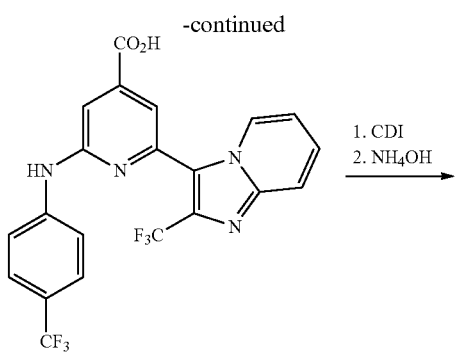

10.00 (s, 1H), 8.67 (dt, J=6.9, 1.3 Hz, 1H), 8.26 (s, 1H), 7.86 (d, J=8.5 Hz, 2H), 7.83 (dt, J=9.2, 1.1 Hz, 1H), 7.78 (s, 1H), 7.54-7.58 (m, 3H), 7.53 (s, 1H), 7.45 (d, J=1.3 Hz, 1H), 7.14 (td, J=6.9, 1.1 Hz, 1H); MS m/z 466 (ESI) [M+H]+.

Example 57

2-(2-methyl-1H-benzimidazol-1-yl)-6-{[4-(trifluoromethyl)phenyl]amino}pyridine-4-carboxamide
(Cpd 203)

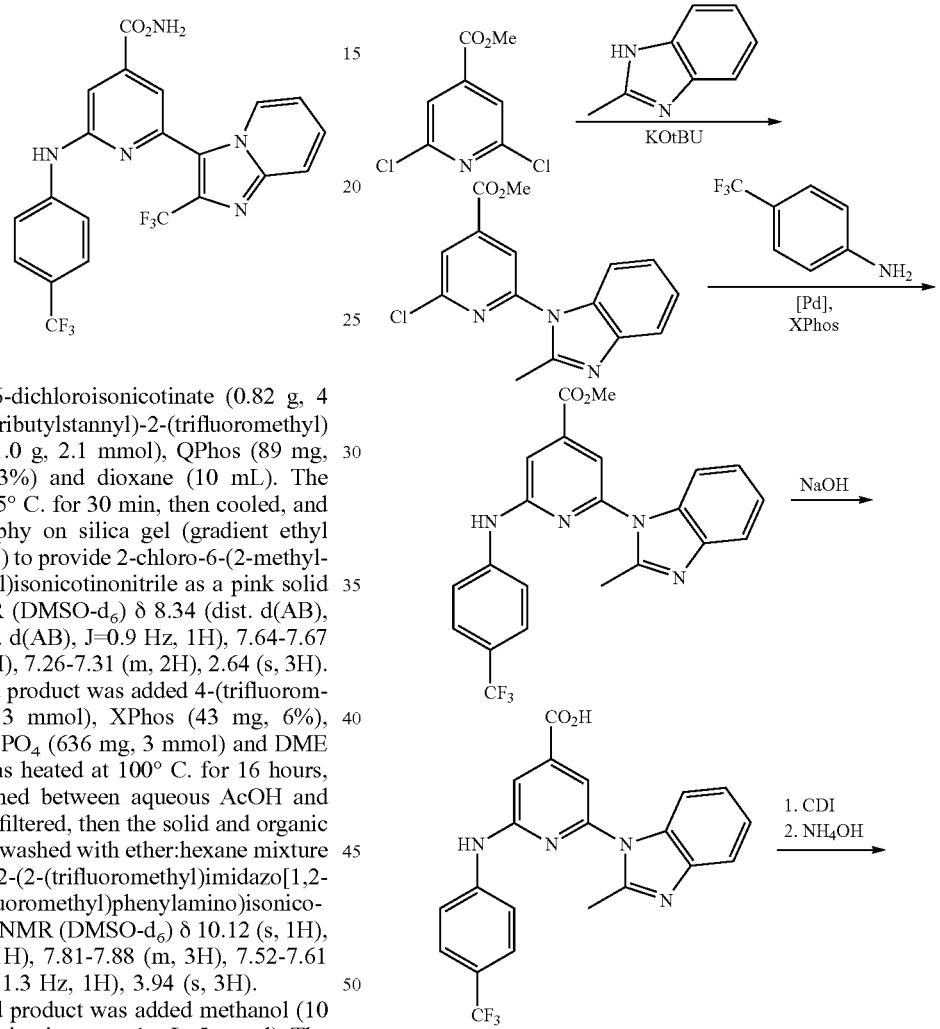

Step 1. To methyl 2,6-dichloroisonicotinate (0.82 g, 4 mmol) was added 3-(tributylstannyl)-2-(trifluoromethyl)imidazo[1,2-a]pyridine (1.0 g, 2.1 mmol), QPhos (89 mg, 6%), Pd$_2$dba$_3$ (60 mg, 3%) and dioxane (10 mL). The mixture was heated at 115° C. for 30 min, then cooled, and purified by chromatography on silica gel (gradient ethyl acetate:hexane 1:10 to 1:1) to provide 2-chloro-6-(2-methyl-1H-benzo[d]imidazol-1-yl)isonicotinonitrile as a pink solid (402 mg, 45%). $^1$H NMR (DMSO-d$_6$) δ 8.34 (dist. d(AB), J=0.9 Hz, 1H), 8.33 (dist. d(AB), J=0.9 Hz, 1H), 7.64-7.67 (m, 1H), 7.57-7.60 (m, 1H), 7.26-7.31 (m, 2H), 2.64 (s, 3H).

Step 2. To the obtained product was added 4-(trifluoromethyl)aniline (0.37 mL, 3 mmol), XPhos (43 mg, 6%), Pd$_2$dba$_3$ (41 mg, 6%), K$_3$PO$_4$ (636 mg, 3 mmol) and DME (10 mL). The mixture was heated at 100° C. for 16 hours, then cooled and partitioned between aqueous AcOH and EtOAc. The product was filtered, then the solid and organic layer were combined and washed with ether:hexane mixture to provide crude methyl 2-(2-(trifluoromethyl)imidazo[1,2-a]pyridin-3-yl)-6-(4-(trifluoromethyl)phenylamino)isonicotinate (690 mg, 95%). $^1$H NMR (DMSO-d$_6$) δ 10.12 (s, 1H), 8.73 (dt, J=6.9, 0.9 Hz, 1H), 7.81-7.88 (m, 3H), 7.52-7.61 (m, 5H), 7.14 (td, J=6.9, 1.3 Hz, 1H), 3.94 (s, 3H).

Step 3. To the obtained product was added methanol (10 mL) and NaOH (5 M solution in water, 1 mL, 5 mmol). The mixture was heated at reflux for 10 minutes, then cooled and diluted with aqueous diluted AcOH. The product was filtered to provide 2-(2-(trifluoromethyl)imidazo[1,2-a]pyridin-3-yl)-6-(4-(trifluoromethyl)phenylamino)isonicotinic acid as an off-white solid (470 mg, 72%). $^1$H NMR (DMSO-d$_6$) δ 13.88 (br. s., 1H), 10.07 (s, 1H), 8.74 (dt, J=7.3, 0.9 Hz, 1H), 7.86 (d, J=8.8 Hz, 2H), 7.83 (dt, J=9.1, 0.9 Hz, 1H), 7.51-7.60 (m, 5H), 7.13 (td, J=6.9, 1.1 Hz, 1H).

Step 4. To the obtained product (240 mg, 0.5 mmol) was added CDI (320 mg, 2 mmol) and then DMF (3 mL). The mixture was stirred at room temperature for 30 minutes, then 1/3 of the reaction mixture was added to ammonium hydroxide (3 mL). The mixture was reacted for 5 minutes, then diluted with water and filtered to provide the title compound as an off-white solid (60 mg, 77%). $^1$H NMR (DMSO-d$_6$) δ

Step 1. To methyl 2,6-dichloroisonicotinate (1.54 g, 7.5 mmol) was added 2-methyl-1H-benzo[d]imidazole (0.66 g, 5 mmol), DMF (10 mL) and KOt-Bu (1M solution on THF, 5 mL, 5 mmol). The mixture was reacted at room temperature for 3 days, diluted with aqueous ammonium chloride, then filtered and purified by chromatography on silica gel (gradient ethyl acetate:hexane 1:4 to 1:0) to provide crude methyl 2-chloro-6-(2-methyl-1H-benzo[d]imidazol-1-yl)isonicotinate (96 mg).

Step 2. To the obtained product was added 4-(trifluoromethyl)aniline (0.06 mL, 0.6 mmol), XPhos (14 mg, 0.003), Pd$_2$dba$_3$ (14 mg, 0.015), K$_3$PO$_4$ (127 mg, 0.6 mmol) and DME (2 mL). The mixture was heated at 100° C. for 4 hours, then cooled and water and EtOAc were added. The solution was filtered through Celite, then washed with mixture of DMSO and MeOH. The combined filtrate (organic layers) were partially concentrated, then diluted with water and filtered. The product was washed with water, then ether, to provide methyl 2-(2-methyl-1H-benzo[d]imidazol-1-yl)-6-(4-(trifluoromethyl)phenylamino)isonicotinate (96 mg). $^1$H NMR (DMSO-d$_6$) δ 10.19 (s, 1H), 7.86 (dist. d(AB), J=8.5 Hz, 2H), 7.64-7.68 (m, 1H), 7.62 (dist. d(AB), J=8.8 Hz, 2H), 7.58 (d, J=0.9 Hz, 1H), 7.45-7.50 (m, 1H), 7.40 (d, J=0.9 Hz, 1H), 7.23-7.29 (m, 2H), 3.92-3.95 (m, 3H), 2.62 (s, 3H).

Step 3. To methyl 2-(2-methyl-1H-benzo[d]imidazol-1-yl)-6-(4-(trifluoromethyl)phenylamino)isonicotinate (80 mg, 0.19 mmol) was added MeOH (10 mL) and NaOH (5 M solution in water, 0.5 mL). The mixture was heated at reflux for 20 minutes, then cooled and diluted with diluted aqueous AcOH. The product was filtered to provide 2-(2-methyl-1H-benzo[d]imidazol-1-yl)-6-(4-(trifluoromethyl)phenylamino)isonicotinic acid as a light yellow solid (60 mg, 77%). $^1$H NMR (DMSO-d$_6$) δ 13.91 (br. s., 1H), 10.15 (s, 1H), 7.86 (dist. d(AB), J=8.5 Hz, 2H), 7.64-7.67 (m, 1H), 7.62 (dist. d(AB), J=8.8 Hz, 2H), 7.56 (d, J=0.9 Hz, 1H), 7.45-7.49 (m, 1H), 7.38 (d, J=0.9 Hz, 1H), 7.22-7.30 (m, 2H), 2.62 (s, 3H).

Step 4. To the obtained product (32 mg, 0.078 mmol) was added a pinch of CDI (excess) and DMF (1 mL). The mixture was stirred at room temperature for 1.5 hours, then quenched with ammonium hydroxide (2 mL) and diluted with water. The product was filtered to provide the title compound as an off white solid (32 mg) in a mixture with DMF (1:1 molar ratio). $^1$H NMR (DMSO-d$_6$) δ 10.07 (s, 1H), 8.26 (s, 1H), 7.95 (s, 1H, DMF), 7.85 (dist. d(AB), J=8.8 Hz, 2H), 7.80 (s, 1H), 7.63-7.67 (m, 1H), 7.61 (dist. d(AB), J=8.5 Hz, 2H), 7.49-7.52 (m, 1H), 7.45 (d, J=0.9 Hz, 1H), 7.48 (d, J=0.9 Hz, 1H), 7.21-7.30 (m, 2H), 2.89 (s, 3H, DMF), 2.73 (s, 3H, DMF), 2.63 (s, 3H); MS m/z 412 (ESI) [M+H]$^+$.

Example 58

2-{[4-(difluoromethoxy)phenyl]amino}-6-[2-(trifluoromethyl)imidazo[1,2-a]pyridin-3-yl]pyridine-4-carbonitrile (Cpd 216)

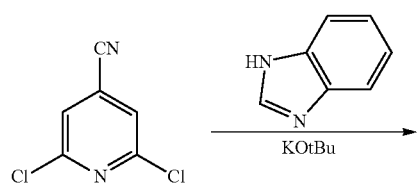

KOtBu

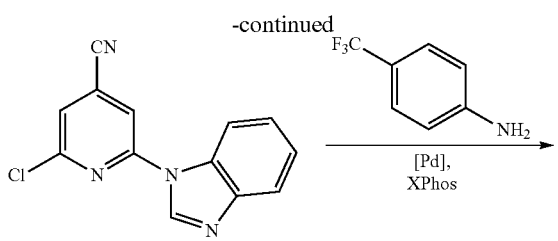

[Pd], XPhos

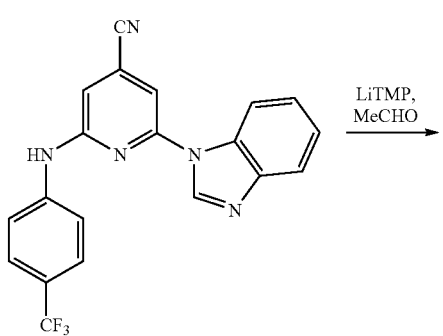

LiTMP, MeCHO

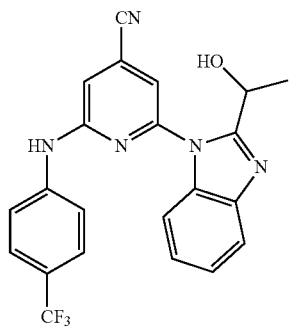

Step 1. Intermediate 2-(1H-benzo[d]imidazol-1-yl)-6-(4-(trifluoromethyl)phenylamino)isonicotinonitrile (prepared using the procedure described in Example 55 and appropriate starting materials, reagents and reaction conditions) was obtained.

Step 2. To THF (3 mL) cooled to −70° C. was added 2,2,6,6-tetramethylpiperidine (0.084 mL, 0.5 mmol) and n-BuLi (2.2 M solution in hexane, 0.22 mL, 0.48 mmol). The mixture was transferred via a cannula into a solution of the obtained product (83 mg, 0.22 mmol) in THF (9 mL) cooled to −60° C. The resulting reddish mixture was reacted for 20 minutes, then quenched with acetaldehyde (0.26 mL, 4.3 mmol). The resulting mixture was reacted for 5 minutes, then quenched with AcOH and aqueous ammonium chloride. The product was extracted with EtOAc, and purified by chromatography on silica gel (gradient ethyl acetate:hexane 1:4 to 1:0) to provide the title compound as a light yellow solid (67 mg, 72%). $^1$H NMR (DMSO-d$_6$) δ 10.23 (s, 1H), 7.82 (d, J=8.5 Hz, 2H), 7.72-7.76 (m, 1H), 7.61 (d, J=0.9 Hz, 1H), 7.60 (d, J=8.8 Hz, 2H), 7.52-7.57 (m, 1H), 7.36 (d, J=0.9 Hz, 1H), 7.25-7.33 (m, 2H), 5.51 (d, J=6.6 Hz, 1H), 5.17 (quin, J=6.5 Hz, 1H), 1.59 (d, J=6.3 Hz, 3H); MS m/z 424 (ESI) [M+H]$^+$.

Example 59

2-{[4-(difluoromethoxy)phenyl]amino}-6-[2-(trifluoromethyl)imidazo[1,2-a]pyridin-3-yl]pyridine-4-carbonitrile (Cpd 217)

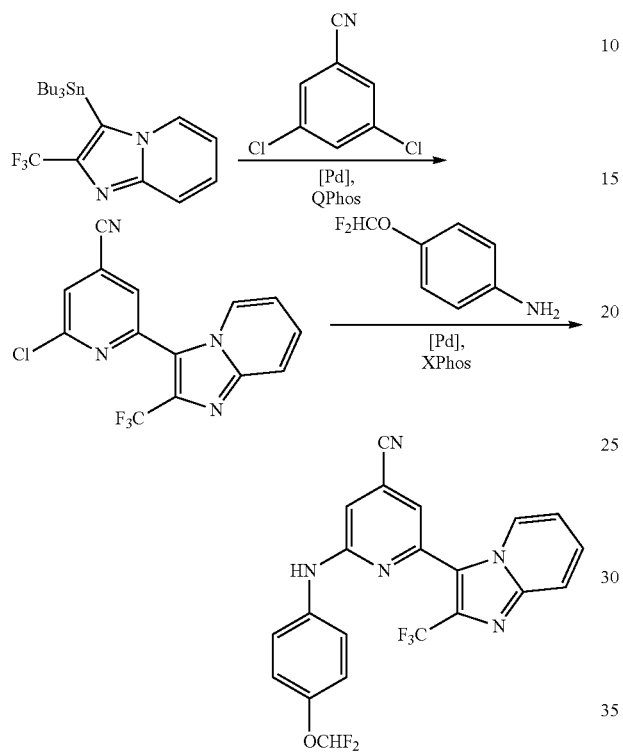

| Cpd | Name and Data |
|---|---|
| 218 | 2-{[4-(trifluoromethoxy)phenyl]amino}-6-[2[(trifluoromethyl)imidazo[1,2-a]pyridin-3-yl]pyridine-4-carbonitrile MS m/z 464 (ESI) [M + H]+ |

Example 60

2-(4-(1-aminoethyl)phenylamino)-6-(2-(trifluoromethyl)imidazo[1,2-a]pyridin-3-yl)isonicotinonitrile (Cpd 257)

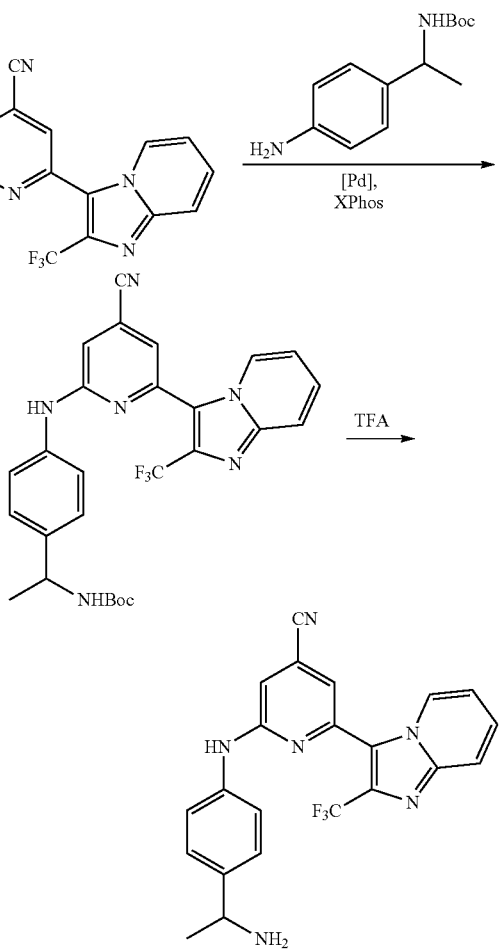

Step 1. To 3-(tributylstannyl)-2-(trifluoromethyl)imidazo[1,2-a]pyridine (1.04 g, 2.18 mmol) was added 2,6-dichloroisonicotinonitrile (378 mg, 2.18 mmol), a pinch of QPhos (catalytic) and Pd$_2$dba$_3$ (catalytic) and dioxane (3 mL). The mixture was heated at 115° C. for 30 minutes, then concentrated and purified by chromatography on silica gel (gradient ethyl acetate:hexane 1:4 to 1:0) to provide crude 2-chloro-6-(2-(trifluoromethyl)imidazo[1,2-a]pyridin-3-yl)isonicotinonitrile (392 mg, 56%) as a yellow solid. $^1$H NMR (DMSO-d$_6$) δ 8.69 (dt, J=7.1, 1.0 Hz, 1H), 8.34 (d, J=0.9 Hz, 1H), 8.25 (s, 1H), 7.86 (dt, J=9.1, 1.1 Hz, 1H), 7.61 (ddd, J=9.1, 6.9, 1.3 Hz, 1H), 7.21 (td, J=6.9, 1.3 Hz, 1H).

Step 2. To the obtained product (80 mg, 0.25 mmol) was added 4-(difluoromethoxy)aniline (0.1 mL, 1 mmol), XPhos (7 mg, 0.015 mmol), Pd$_2$dba$_3$ (7 mg), K$_3$PO$_4$ (106 mg, 0.5 mmol) and DME (2 mL). The mixture was heated at 110° C. for 23 hours, then partitioned between water and EtOAc and purified by chromatography on silica gel (gradient ethyl acetate:hexane 1:4 to 1:0) to provide the title compound (65 mg, 58%) as a yellow solid. $^1$H NMR (DMSO-d$_6$) δ 9.82 (s, 1H), 8.68 (dt, J=7.1, 1.0 Hz, 1H), 7.82 (dt, J=9.1, 0.9 Hz, 1H), 7.64 (dist. dt(AB), J=9.1, 2.2 Hz, 2H), 7.56 (ddd, J=9.1, 6.6, 1.3 Hz, 1H), 7.39 (s, 1H), 7.26 (d, J=1.3 Hz, 1H), 7.13 (td, J=6.9, 1.1 Hz, 1H), 7.08 (dist. dt(AB), J=8.8, 1.9 Hz, 2H), 7.11 (t, J=74.4 Hz, 1H); MS m/z 446 (ESI) [M+H]+.

Additional compounds of Formula (I) or a form thereof described herein may be prepared according to the procedure of Example 59 by substituting the appropriate starting materials, reagents and reaction conditions:

Step 1. Intermediate tert-butyl 1-(4-(4-cyano-6-(2-(trifluoromethyl)imidazo[1,2-a]pyridin-3-yl)pyridin-2-ylamino)phenyl)ethylcarbamate (prepared using the procedure described in Example 59 and appropriate starting materials, reagents and reaction conditions) was obtained.

Step 2. To the obtained intermediate (133 mg, 0.25 mmol) was added DCM (5 mL) and TFA (1 mL) at room temperature (with gas evolution). The mixture was reacted for 30 minutes at room temperature, then concentrated and sonicated with aqueous ammonium hydroxide. The product was filtered to provide the title compound as a yellow solid (86 mg, 82%). $^1$H NMR (DMSO-d$_6$) δ 9.75 (s, 1H), 8.70 (d, J=6.9 Hz, 1H), 7.83 (d, J=9.1 Hz, 1H), 7.53-7.60 (m, 3H), 7.36 (s, 1H), 7.24-7.31 (m, 3H), 7.13 (td, J=6.9, 0.9 Hz, 1H), 4.04 (q, J=6.4 Hz, 1H), 1.27 (d, J=6.6 Hz, 3H); MS m/z 421 (ESI) [M−H]⁻.

Example 61

(2-[2-(trifluoromethyl)imidazo[1,2-a]pyridin-3-yl]-6-{[4-(trifluoromethyl)phenyl]amino}pyridin-4-yl)methanol (Cpd 219)

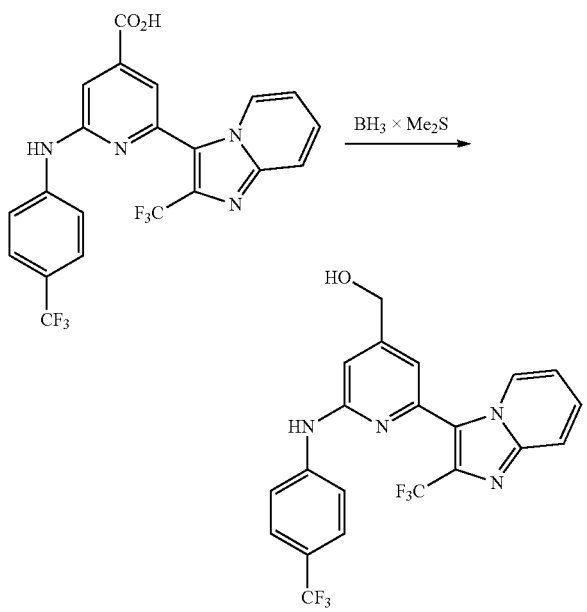

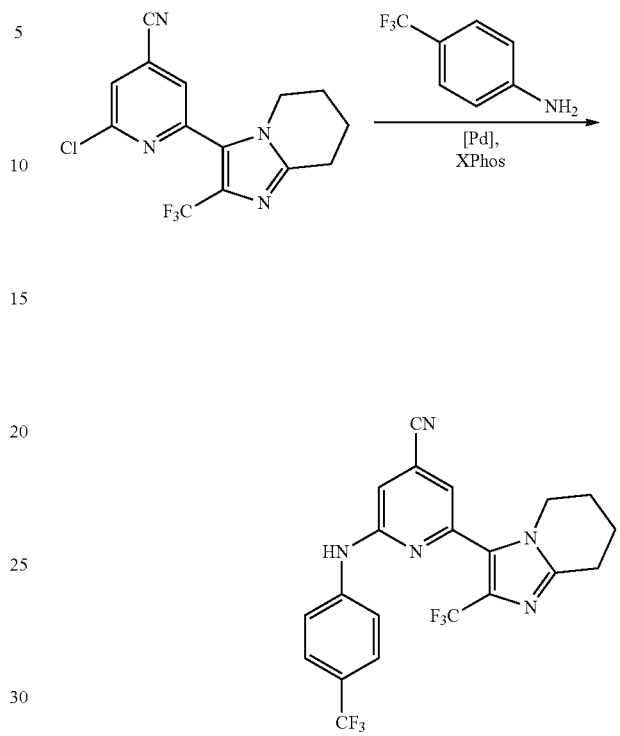

To 2-(2-(trifluoromethyl)imidazo[1,2-a]pyridin-3-yl)-6-(4-(trifluoromethyl)phenylamino)isonicotinic acid (65 mg, 0.2 mmol) was added THF (2 mL). The mixture was heated at 40° C. to dissolve the material, then BH₃×Me₂S was added (2 mmol). The mixture was heated at reflux for 20 minutes, then cooled in an ice bath and HCl (conc. aqueous, 1 mL) was added. The mixture was heated at reflux for 5 minutes, then cooled and partitioned between aqueous sodium bicarbonate and hexane. The organic layer was partly concentrated to remove THF and the precipitate was isolated by filtration to provide the title compound as a white solid (51 mg, 86%). ¹H NMR (DMSO-d₆) δ 9.79 (s, 1H), 8.67 (dt, J=7.1, 1.2 Hz, 1H), 7.85 (d, J=8.5 Hz, 2H), 7.81 (dt, J=9.1, 0.9 Hz, 1H), 7.50-7.56 (m, 3H), 7.12 (td, J=6.9, 1.1 Hz, 1H), 7.07-7.10 (m, 2H), 5.55 (br. s., 1H), 4.60 (s, 2H); MS m/z 452 (ESI) [M+H]⁺.

Example 62

2-{[4-(trifluoromethyl)phenyl]amino}-6-[2-(trifluoromethyl)-5,6,7,8-tetrahydroimidazo[1,2-a]pyridin-3-yl]pyridine-4-carbonitrile (Cpd 236)

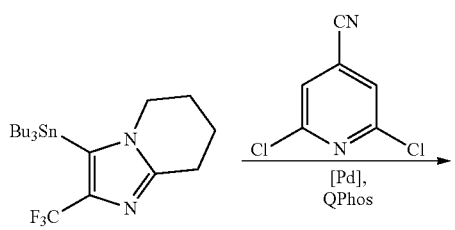

Step 1. To 3-(tributylstannyl)-2-(trifluoromethyl)-5,6,7,8-tetrahydroimidazo[1,2-a]pyridine (758 mg, 1.58 mmol) was added 2,6-dichloroisonicotinonitrile (430 mg, 2.5 mmol), QPhos (64 mg, 0.09 mmol), Pd₂dba₃ (55 mg, 0.06 mmol) and dioxane (6 mL). The mixture was heated at 120° C. for 19 hours, then concentrated and purified by chromatography on silica gel (gradient ethyl acetate:hexane 1:4 to 1:0) to provide 2-chloro-6-(2-(trifluoromethyl)-5,6,7,8-tetrahydroimidazo[1,2-a]pyridin-3-yl)isonicotinonitrile (290 mg, 56%) as a yellow solid. ¹H NMR (DMSO-d₆) δ 8.26 (d, J=0.9 Hz, 1H), 8.10 (br. s, 1H), 3.92 (t, J=5.5 Hz, 2H), 2.86 (t, J=6.0 Hz, 2H), 1.79-1.97 (m, 4H).

Step 2. To the obtained product (90 mg, 0.28 mmol) was added 4-(trifluoromethyl)aniline (0.05 mL, 0.5 mmol), XPhos (8 mg, 0.017 mmol), Pd₂dba₃ (8 mg), K₃PO₄ (106 mg, 0.5 mmol) and DME (2 mL). The mixture was heated at 115° C. for 20 hours, then partitioned between EtOAc and aqueous acetic acid. The organic layer was filtered through a short plug of silica gel, then concentrated and washed with ether to provide the title compound as a green solid (85 mg, 67%). ¹H NMR (DMSO-d₆) δ 10.09 (s, 1H), 7.86 (dist. d(AB), J=8.5 Hz, 2H), 7.64 (dist. d(AB), J=8.8 Hz, 2H), 7.37 (s, 1H), 7.30 (d, J=0.9 Hz, 1H), 3.92 (br. s., 2H), 2.86 (br. s., 2H), 1.89 (br. s., 4H); MS m/z 452 (ESI) [M+H]⁺.

Additional compounds of Formula (I) or a form thereof described herein may be prepared according to the procedure of Example 62 by substituting the appropriate starting materials, reagents and reaction conditions:

| Cpd | Name and Data |
|---|---|
| 237 | 2-{[4-(difluoromethoxy)phenyl]amino}-6-[2-(trifluoromethyl)-5,6,7,8-tetrahydroimidazo[1,2-a]pyridin-3-yl]pyridine-4-carbonitrile<br>$^1$H NMR (DMSO-d$_6$) δ 9.73 (s, 1H), 7.65 (dist. dt(AB), J = 9.1, 2.2 Hz, 2H), 7.24 (s, 1H), 7.19 (d, J = 1.3 Hz, 1H), 7.13 (dist. dt(AB), J = 9.1, 2.2 Hz, 2H), 7.12 (t, J = 74.4 Hz, 1H), 3.89 (br. s., 2H), 2.85 (br. s., 2H), 1.88 (dist. quin, J = 2.8 Hz, 4H); MS m/z 450 (ESI) [M + H]$^+$ |
| 238 | 2-{[4-(trifluoromethoxy)phenyl]amino}-6-[2-(trifluoromethyl)-5,6,7,8-tetrahydroimidazo[1,2-a]pyridin-3-yl]pyridine-4-carbonitrile<br>$^1$H NMR (DMSO-d$_6$) δ 9.86 (s, 1H), 7.73 (dist. dt(AB), J = 9.1, 2.2 Hz, 2H), 7.27-7.32 (m, 3H), 7.23 (d, J = 1.3 Hz, 1H), 3.89 (br. s., 2H), 2.85 (br. s., 2H), 1.88 (br. s., 4H); MS m/z 468 (ESI) [M + H]$^+$ |

Example 63

3-methyl-6-[2-(trifluoromethyl)imidazo[1,2-a]pyridin-3-yl]-N-[4-(trifluoromethyl)phenyl]pyridin-2-amine (Cpd 269)

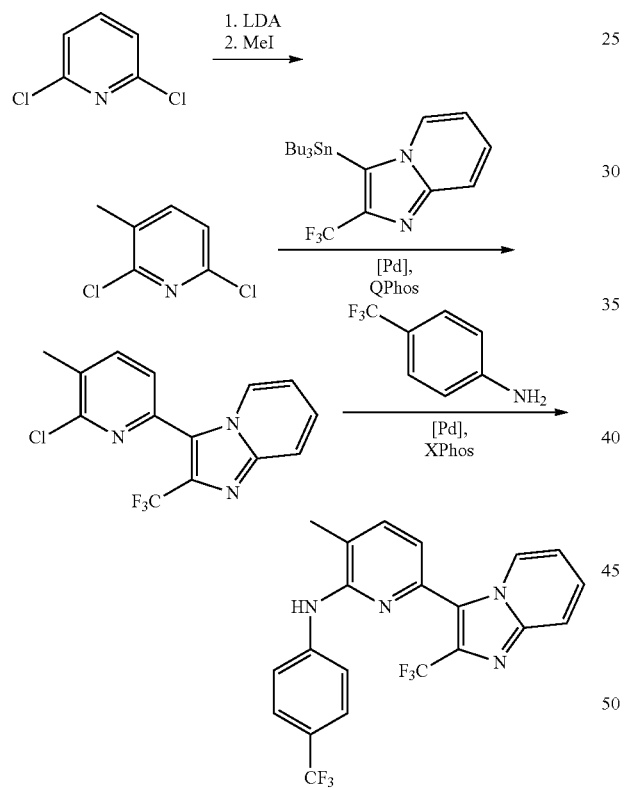

Step 1. To diisopropylamine (0.71 mL, 5 mmol) was added THF (6 mL) cooled to −70° C. and n-BuLi (2.2 M solution in c-Hex, 2.2 mL, 5 mmol). The mixture was reacted for 2 minutes at −70° C., then a solution of 2,6-dichloropyridine (656 mg, 4.4 mmol) in THF (3 mL) was added dropwise via a cannula. The mixture was reacted for 1.5 hours at −70° C., then MeI was added (0.28 mL, 4.5 mmol). The mixture was reacted for 25 minutes at −70° C. with stirring, then quenched with aqueous ammonium chloride. The product was extracted with ether, then concentrated and purified by chromatography on silica gel (gradient ethyl acetate:hexane 1:10 to 1:2), to provide crude 2,6-dichloro-3-methylpyridine as a waxy low-melting solid (758 mg, 80% pure by $^1$H-NMR+20% of 2,6-dichloropyridine). $^1$H NMR (DMSO-d$_6$) δ 7.90 (dd, J=7.9, 0.6 Hz, 1H), 7.51 (d, J=7.9 Hz, 1H), 2.33 (s, 3H).

Step 2. To 3-(tributylstannyl)-2-(trifluoromethyl)imidazo[1,2-a]pyridine (1.1 g, 2.31 mmol) was added the obtained product, dioxane (6 mL), QPhos (49 mg, 0.07 mmol) and Pd$_2$dba$_3$ (21 mg, 0.023 mmol). The mixture was heated at 110° C. for one hour, then at 90° C. for 15 hours. The product was concentrated and purified by chromatography on silica gel (gradient ethyl acetate:hexane 1:10 to 1:1) to provide a mixture of crude isomers: 3-(6-chloro-5-methylpyridin-2-yl)-2-(trifluoromethyl)imidazo[1,2-a]pyridine as a pink solid (58 mg, 8%) and 3-(6-chloro-3-methylpyridin-2-yl)-2-(trifluoromethyl)imidazo[1,2-a]pyridine (more polar) (130 mg).

Step 3. The title compound (prepared using the procedure described in Example 59 and appropriate starting materials, reagents and reaction conditions) was obtained. $^1$H NMR (DMSO-d$_6$) δ 8.63 (d, J=6.9 Hz, 1H), 8.52 (s, 1H), 7.87 (d, J=8.5 Hz, 2H), 7.75 (d, J=7.6 Hz, 1H), 7.78 (d, J=9.1 Hz, 1H), 7.53 (dist. d, J=7.9 Hz, 2H), 7.48-7.51 (m, 1H), 7.15 (d, J=7.6 Hz, 1H), 7.07 (t, J=6.9 Hz, 1H), 2.41 (s, 3H); MS m/z 437 (ESI) [M+H]$^+$.

Example 64

N$^2$-(4-methoxyphenyl)-6-[2-(trifluoromethyl)imidazo[1,2-a]pyridin-3-yl]pyridine-2,5-diamine (Cpd 282)

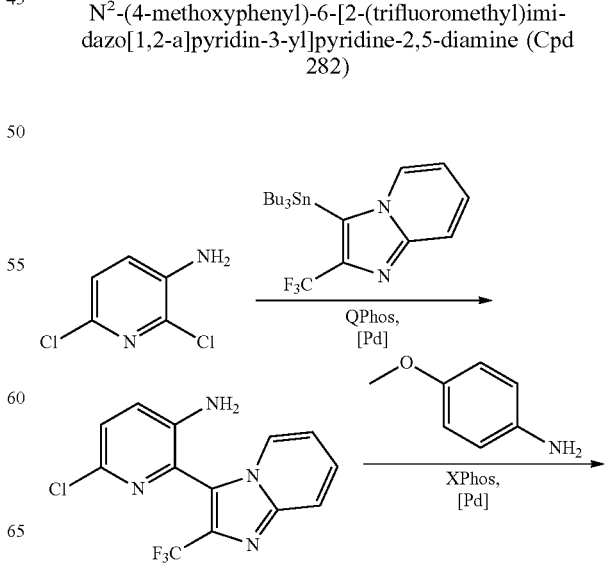

335
-continued

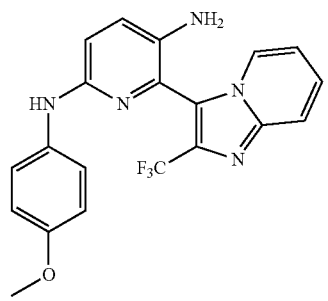

336
-continued

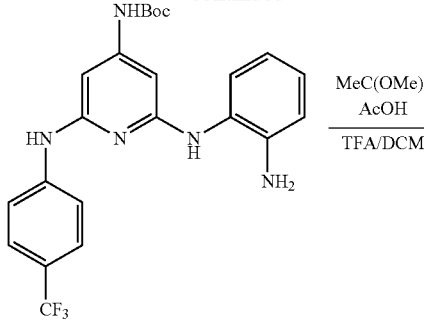

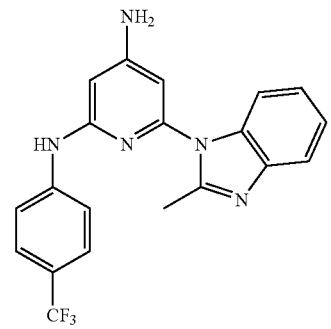

Step 1. To 3-(tributylstannyl)-2-(trifluoromethyl)imidazo[1,2-a]pyridine (640 mg, 1.35 mmol) was added 2,6-dichloropyridin-3-amine (440 mg, 2.7 mmol), QPhos (92 mg, 0.13 mmol), $Pd_2dba_3$ (40 mg, 0.04 mmol) and dioxane (6 mL). The mixture was heated at 120° C. for 1.5 hours, then concentrated and purified by chromatography on silica gel (gradient ethyl acetate:hexane 1:10 to 1:0) to provide 6-chloro-2-(2-(trifluoromethyl)imidazo[1,2-a]pyridin-3-yl)pyridin-3-amine as a gray solid (80 mg, 19%). $^1$H NMR (DMSO-$d_6$) δ 7.88 (dt, J=6.9, 1.1 Hz, 1H), 7.78 (dt, J=9.1, 1.1 Hz, 1H), 7.49 (ddd, J=9.1, 6.6, 1.3 Hz, 1H), 7.33 (dist. d(AB), J=8.5 Hz, 1H), 7.28 (dist. d(AB), J=8.8 Hz, 1H), 7.06 (td, J=6.9, 1.1 Hz, 1H), 5.57 (br. s, 2H).

Step 2. To the obtained product was added 4-methoxyaniline (62 mg, 0.5 mmol), XPhos (10 mg, 0.02 mmol), $Pd_2dba_3$ (9 mg, 0.01 mmol), $K_3PO_4$ (110 mg, 0.5 mmol) and DME (3 mL). The mixture was heated at 115° C. for 21 hours, then filtered, concentrated and purified by chromatography on silica gel (gradient from ethyl acetate:hexane 1:2 to ethyl acetate:methanol 10:1). The product was washed with ether to provide the title compound as a pinkish solid (63 mg, 61%). $^1$H NMR (DMSO-$d_6$) δ 8.46 (s, 1H), 7.86 (dt, J=7.3, 0.9 Hz, 1H), 7.76 (dt, J=9.1, 0.9 Hz, 1H), 7.46 (ddd, J=9.1, 6.9, 1.1 Hz, 1H), 7.43 (dist. dt(AB), J=9.1, 2.2 Hz, 2H), 7.20 (d, J=8.8 Hz, 1H), 7.05 (td, J=6.9, 1.1 Hz, 1H), 6.80 (d, J=8.8 Hz, 1H), 6.71 (dist. dt(AB), J=9.1, 2.2 Hz, 2H), 4.62 (s, 2H), 3.32 (s, 3H); MS m/z 400 (ESI) [M+H]$^+$.

Example 65

6-(2-methyl-1H-benzimidazol-1-yl)-$N^2$-[4-(trifluoromethyl)phenyl]pyridine-2,4-diamine (Cpd 492)

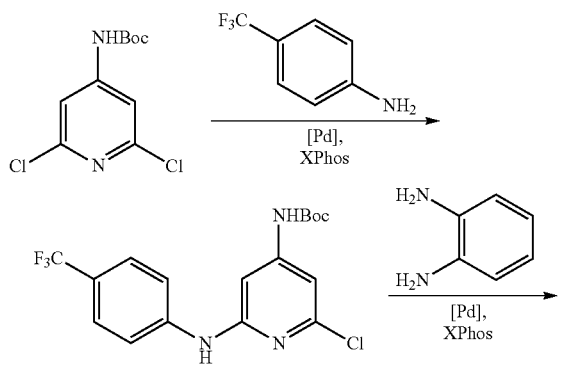

Step 1. To tert-butyl 2,6-dichloropyridin-4-ylcarbamate (679 mg, 2.6 mmol) was added XPhos (37 mg, 3%), $Pd_2dba_3$ (24 mg, 1%), $K_3PO_4$ (1,060 mg, 5 mmol), 4-(trifluoromethyl)aniline (0.25 mL, 2 mmol) and DME (3 mL). The mixture was heated at 100° C. for 2 hours, then cooled and diluted with EtOAc. The product was filtered and purified by chromatography on silica gel (gradient ethyl acetate:hexane 1:10 to 1:1) to provide tert-butyl 2-chloro-6-(4-(trifluoromethyl)phenylamino)pyridin-4-ylcarbamate (351 mg, 45%).

Step 2. To the obtained product was added benzene-1,2-diamine (216 mg, 2 mmol), XPhos (21 mg, 5%), $Pd_2dba_3$ (16 mg, 2%), $K_3PO_4$ (424 mg, 2 mmol) and DME (3 mL). The mixture was heated at 110° C. for 14 hours, then cooled and diluted with DCM. The product was filtered and concentrated to provide crude tert-butyl 2-(2-aminophenylamino)-6-(4-(trifluoromethyl)phenylamino)pyridin-4-ylcarbamate.

Step 3. To the obtained product was added MeOH (5 mL), AcOH (2 mL) and $MeC(OMe)_3$ (1 mL). The mixture was reacted for 10 minutes at room temperature, then diluted with water and left at room temperature for 3 hours. The product was concentrated and purified by chromatography on silica gel (gradient ethyl acetate:hexane 1:4 to 1:0) to provide a dark orange oil (568 mg). To the oil was added DCM (1 mL) and TFA (1 mL). The resulting mixture was heated at 50° C. for 16 hours, then concentrated and stirred with aqueous ammonium hydroxide and hexane. The product was filtered to provide the title compound as a light brown solid (291 mg, 84% from steps B, C). H NMR (DMSO-$d_6$) δ 9.34 (s, 1H), 7.76 (dist. d(AB), J=8.5 Hz, 2H), 7.58-7.64 (m, 1H), 7.51 (dist. d(AB), J=8.8 Hz, 2H), 7.40-7.45 (m, 1H), 7.19-7.24 (m, 2H), 6.35-6.39 (m, 2H), 6.29 (d, J=1.6 Hz, 1H), 6.14 (d, J=1.9 Hz, 1H), 2.59 (s, 3H); MS m/z 384 (ESI) [M+H]$^+$.

Additional compounds of Formula (I) or a form thereof described herein may be prepared according to the procedure of Example 65 by substituting the appropriate starting materials, reagents and reaction conditions:

| Cpd | Name and Data |
|---|---|
| 496 | $N^2$-[4-(difluoromethoxy)phenyl]-6-(2-methyl-1H-benzimidazol-1-yl) pyridine-2,4-diamine<br>$^1$H NMR (DMSO-$d_6$) δ 8.91 (s, 1H), 7.58-7.62 (m, 1H), 7.54-7.58 (m, 2H), 7.39-7.43 (m, 1H), 7.18-7.24 (m, 2H), 6.99-7.04 (m, 2H), 7.05 (t, J = 75.0 Hz, 1H), 6.23-6.27 (m, 2H), 6.21 (d, J = 1.6 Hz, 1H), 6.04 (d, J = 1.6 Hz, 1H), 2.57 (s, 3H); MS m/z 382 (ESI) [M + H]$^+$ |

Example 66

4-fluoro-6-(2-methyl-1H-benzimidazol-1-yl)-N-[2-nitro-4-(trifluoromethyl)phenyl]pyridin-2-amine (Cpd 493)

4-fluoro-6-(2-methyl-1H-benzimidazol-1-yl)-N-[4-(trifluoromethyl)phenyl]pyridin-2-amine (Cpd 494)

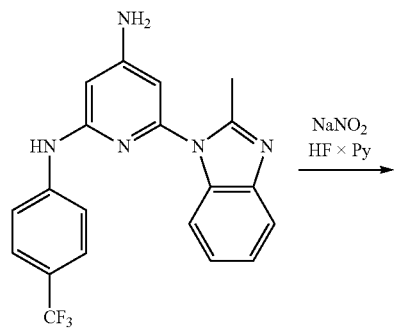

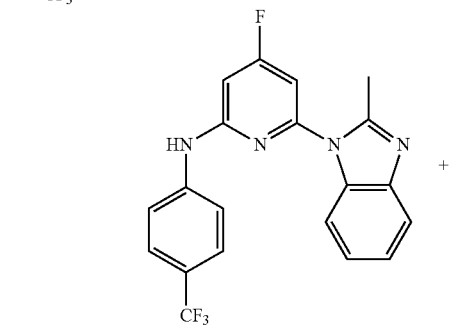

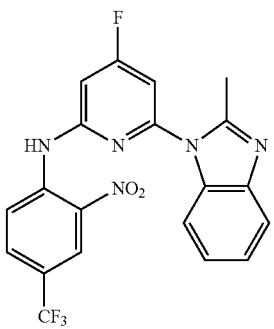

Step 1. To 6-(2-methyl-1H-benzo[d]imidazol-1-yl)-$N^2$-(4-(trifluoromethyl)phenyl)pyridine-2,4-diamine (77 mg, 0.20 mmol) in a plastic tube with a magnetic stir bar was added a (HF)$_x$ pyridine/H$_2$O system (HF×Py) (0.5 mL). The mixture was stirred until the starting materials were completely dissolved, then NaNO$_2$ was added (28 mg, 0.4 mmol). The mixture was reacted for 30 minutes at room temperature, then turned a deep red color and was heated at 80° C. for one hour and cooled to provide a crude mixture of polar isomers. The mixture was diluted with water, then purified by chromatography on silica gel and triturated with ether to provide the more polar title Compound 494 as a yellow solid (22 mg, 28%). $^1$H NMR (DMSO-$d_6$) δ 10.12 (s, 1H), 7.81 (dist. d, J=8.5 Hz, 2H), 7.73-7.78 (m, 1H), 7.63-7.67 (m, 1H), 7.60 (dist. d, J=8.8 Hz, 2H), 7.36-7.45 (m, 2H), 7.24 (dd, J=8.8, 1.6 Hz, 1H), 6.88 (dd, J=10.4, 1.9 Hz, 1H), 2.73 (s, 3H); MS m/z 387 (ESI) [M+H]$^+$.

Step 2. The less polar fractions were combined to provide the title Compound 493 as a yellow solid (13 mg). $^1$H NMR (DMSO-$d_6$) δ: 10.36 (s, 1H), 8.29-8.33 (m, 1H), 8.25 (d, J=9.1 Hz, 1H), 7.98 (dd, J=9.0, 2.4 Hz, 1H), 7.73 (dd, J=7.3, 1.6 Hz, 1H), 7.52-7.58 (m, 1H), 7.33-7.44 (m, 3H), 7.27 (dd, J=10.1, 1.9 Hz, 1H), 2.63 (s, 3H); MS m/z 432 (ESI) [M+H]$^+$.

Additional compounds of Formula (I) or a form thereof described herein may be prepared according to the procedure of Example 66 by substituting the appropriate starting materials, reagents and reaction conditions:

| Cpd | Name and Data |
|---|---|
| 499 | N-[4-(difluoromethoxy)phenyl]-4-fluoro-6-(2-methyl-1H-benzimidazol-1-yl) pyridin-2-amine<br>$^1$H NMR (DMSO-$d_6$) δ 9.67 (s, 1H), 7.59-7.65 (m, 3H), 7.49-7.53 (m, 1H), 7.21-7.27 (m, 2H), 7.07-7.10 (m, 2H), 7.05 (dd, J = 9.1, 1.9 Hz, 1H), 7.11 (t, J = 74.4 Hz, 1H), 6.69 (dd, J = 10.7, 1.6 Hz, 1H), 2.61 (s, 3H); MS m/z 385 (ESI) [M + H]$^+$ |

Example 67

$N^2$-(4-methoxyphenyl)-6-(2-methyl-1H-benzimidazol-1-yl)pyridine-2,3-diamine (Cpd 518)

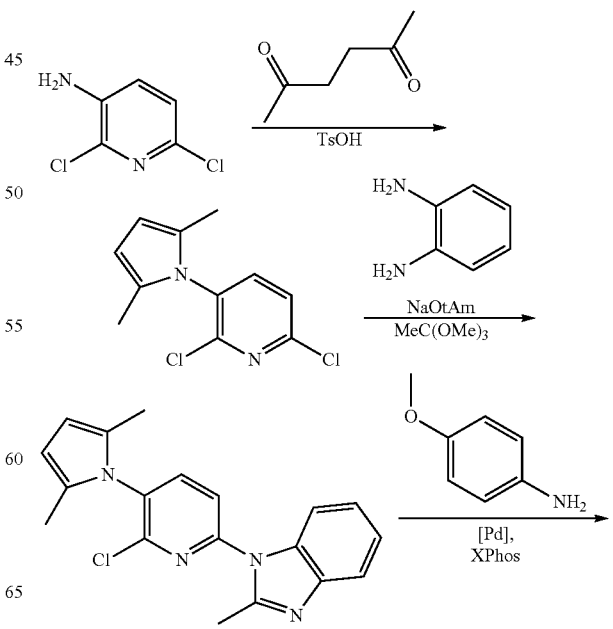

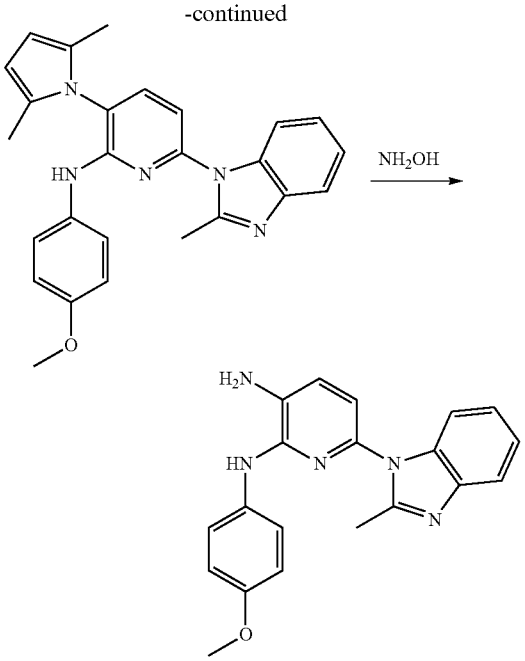

Step 1. To 2,6-dichloropyridin-3-amine (3.66 g, 22.5 mmol) was added hexane-2,5-dione (3.1 g, 27 mmol), TsOH (0.43 g, 10%) and toluene (50 mL). The mixture was refluxed with a Dean-Stark trap for 1.5 hours, then cooled to room temperature and washed with aqueous sodium bicarbonate. The product was filtered through a plug of silica gel and concentrated to provide 2,6-dichloro-3-(2,5-dimethyl-1H-pyrrol-1-yl)pyridine as a dark brownish red oil (4.40 g, 81%). $^1$H NMR (DMSO-$d_6$) δ 8.07 (d, J=8.2 Hz, 1H), 7.78 (d, J=7.9 Hz, 1H), 5.86 (s, 2H), 1.89 (s, 6H).

Step 2. To the obtained product (2 g, 8.3 mmol) was added benzene-1,2-diamine (1.6 g, 15 mmol), THF (7 mL) and NaOtAm (2.5 M solution in THF, 7 mL, 17.5 mmol). The mixture was heated at 75° C. for one hour, then cooled in ice bath and AcOH (6 mL) and MeC(OMe)$_3$ (6 mL) were added. The mixture was reacted at room temperature for 3 days and TFA (2 mL) was added. The mixture was reacted for one hour at room temperature, partially concentrated, then diluted with water and extracted with DCM. The product was purified by chromatography on silica gel (gradient ethyl acetate:hexane 1:4 to 1:0) to provide 1-(6-chloro-5-(2,5-dimethyl-1H-pyrrol-1-yl)pyridin-2-yl)-2-methyl-1H-benzo[d]imidazole as a pink solid (1 g, 36%). $^1$H NMR (DMSO-$d_6$) δ 8.29 (d, J=8.2 Hz, 1H), 7.96 (d, J=8.2 Hz, 1H), 7.64-7.69 (m, 1H), 7.59-7.64 (m, 1H), 7.26-7.33 (m, 2H), 5.90 (s, 2H), 2.69 (s, 3H), 1.99 (s, 6H).

Step 3. To the obtained product (597 mg, 1.8 mmol) was added 4-methoxyaniline (370 mg, 3 mmol), XPhos (43 mg, 5%), Pd$_2$dba$_3$ (33 mg, 2%), K$_3$PO$_4$ (848 mg, 4 mmol) and DME (6 mL). The reaction mixture was heated at 110° C. for 8 hours, then cooled and diluted with EtOAc. The product was filtered and purified by chromatography on silica gel (gradient ethyl acetate:hexane 1:4 to 1:0) to provide 3-(2,5-dimethyl-1H-pyrrol-1-yl)-N-(4-methoxyphenyl)-6-(2-methyl-1H-benzo[d]imidazol-1-yl)pyridin-2-amine as a light brown solid (644 mg, 85%).

Step 4. To the obtained product (600 mg, 1.41 mmol) was added NH$_2$OH×HCl (1.4 g, 20 mmol), EtOH (20 mL), water (2 mL) and triethylamine (0.75 mL, 5 mmol). The mixture was heated at reflux for 3 days, then concentrated and partitioned between DCM and aqueous ammonium hydroxide. The solid was filtered, then dried and washed with a mixture of DCM:toluene. The product was washed with ether to provide the title compound (282 mg, 58%). $^1$H NMR (DMSO-$d_6$) δ 7.87 (s, 1H), 7.55-7.60 (m, 1H), 7.50 (dist. dt, J=9.1, 2.2 Hz, 2H), 7.25-7.29 (m, 1H), 7.13-7.20 (m, 2H), 7.07 (dist. d, J=7.6 Hz, 1H), 6.80 (dist. dt, J=9.1, 2.2 Hz, 2H), 6.76 (d, J=7.9 Hz, 1H), 5.35-5.42 (m, 2H), 3.67 (s, 3H), 2.47 (s, 3H); MS m/z 346 (ESI) [M+H]$^+$.

Additional compounds of Formula (I) or a form thereof described herein may be prepared according to the procedure of Example 67 by substituting the appropriate starting materials, reagents and reaction conditions:

| Cpd | Name and Data |
|---|---|
| 577 | 4-(2,5-dimethyl-1H-pyrrol-1-yl)-N-(4-methoxyphenyl)-6-(2-methyl-1H-benzimidazol-1-yl)pyridin-2-amine<br>MS m/z 424 (ESI) [M + H]$^+$ |
| 580 | N$^2$-(4-methoxyphenyl)-6-(2-methyl-1H-benzimidazol-1-yl)pyridine-2,4-diamine<br>$^1$H NMR (DMSO-$d_6$) δ 8.54 (s, 1H), 7.56-7.61 (m, 1H), 7.37-7.44 (m, 3H), 7.17-7.23 (m, 2H), 6.80 (dist. dt, J =8.8, 2.2 Hz, 2H), 6.12-6.17 (m, 3H), 5.97 (d, J = 1.6 Hz, 1H),<br>3.68 (s, 3H), 2.57 (s, 3H); MS m/z 346 (ESI) [M + H]$^+$ |
| 604 | 6-(2-methyl-1H-benzimidazol-1-yl)-N$^2$-[4-(trifluoromethoxy)phenyl]pyridine-2,4-diamine<br>$^1$H NMR (DMSO-$d_6$) δ 9.10 (s, 1H), 7.66 (app. dt, J = 9.1, 2.2 Hz, 2H), 7.60-7.64 (m, 1H), 7.41-7.46 (m, 1H), 7.21-7.27 (m, 2H), 7.18 (app. d, J = 8.5 Hz, 2H), 6.32 (br. s., 2H), 6.26 (d, J = 1.6 Hz, 1H), 6.10 (d, J = 1.6 Hz, 1H), 2.59 (s, 3H); MS m/z 400 (ESI) [M + H]$^+$ |
| 605 | N$^2$-(4-fluorophenyl)-6-(2-methyl-1H-benzimidazol-1-yl)pyridine-2,4-diamine<br>$^1$H NMR (DMSO-$d_6$) δ 8.83 (s, 1H), 7.57-7.62 (m, 1H), 7.51-7.56 (m, 2H), 7.39-7.43 (m, 1H), 7.17-7.23 (m, 2H), 6.99-7.07 (m, 2H), 6.23 (br. s, 2H), 6.20 (d, J = 1.6 Hz, 1H), 6.03 (d, J = 1.6 Hz, 1H), 2.57 (s, 3H); MS m/z 334 (ESI) [M + H]$^+$ |
| 617 | 4-(2,5-dimethyl-1H-pyrrol-1-yl)-6-(2-methyl-1H-benzimidazol-1-yl)-N-(4-methylphenyl)pyridin-2-amine<br>MS m/z 408 (ESI) [M + H]$^+$ |
| 618 | N-(4-chlorophenyl)-4-(2,5-dimethyl-1H-pyrrol-1-yl)-6-(2-methyl-1H-benzimidazol-1-yl)pyridin-2-amine<br>MS m/z 428 (ESI) [M + H]$^+$ |
| 632 | 6-(2-methyl-1H-benzimidazol-1-yl)-N$^2$-(4-methylphenyl)pyridine-2,4-diamine<br>1H NMR (DMSO-$d_6$) δ 8.68 (s, 1H), 7.57-7.61 (m, 1H), 7.41-7.45 (m, 1H), 7.37-7.41 |

| Cpd | Name and Data |
|---|---|
| | (m, 2H), 7.17-7.22 (m, 2H), 7.00 (dist.d, J = 8.2 Hz, 2H), 6.18 (s, 2H), 6.17 (d, J = 1.6 Hz, 1H), 6.04 (d, J = 1.6 Hz, 1H), 2.58 (s, 3H), 2.20 (s, 3H); MS m/z 330 (ESI) [M + H]$^+$ |
| 633 | N$^2$-(4-chlorophenyl)-6-(2-methyl-1H-benzimidazol-1-yl)pyridine-2,4-diamine<br>$^1$H NMR (DMSO-d$_6$) δ 8.99 (s, 1H), 7.55-7.64 (m, 3H), 7.38-7.44 (m, 1H), 7.17-7.24 (m, 4H), 6.27 (s, 2H), 6.23 (d, J = 1.6 Hz, 1H), 6.06 (d, J = 1.6 Hz, 1H), 2.57 (s, 3H); MS m/z 350 (ESI) [M + H]$^+$ |

Example 68

N-(4-methoxyphenyl)-4-methyl-6-(2-methyl-1H-benzimidazol-1-yl)pyridin-2-amine (Cpd 655)

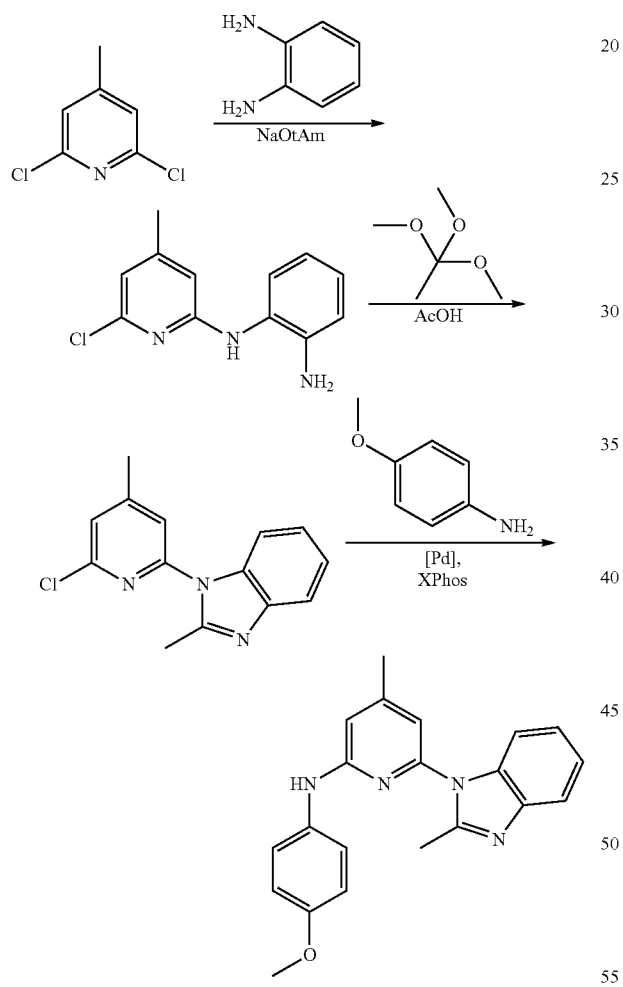

Step 1. To 2,6-dichloro-4-methylpyridine (250 mg, 1.54 mmol) was added benzene-1,2-diamine (324 mg, 3 mmol), THF (3 mL) and NaOtAm (2.5 M solution in THF, 1.2 mL, 3 mmol). The mixture was heated at 60° C. for 2 hours, then 70° C. for 3 hours and then cooled in ice bath. To the mixture was added AcOH (5 drops) and aqueous ammonium chloride. The mixture was extracted with toluene, followed by EtOAc, then the product was dried and concentrated to provide N$^2$-(6-chloro-4-methylpyridin-2-yl)benzene-1,2-diamine as a crude product used in the next step without further purification.

Step 2. To the obtained product was added AcOH (2 mL) and 1,1,1-trimethoxyethane (2 mL). The mixture was reacted at room temperature for 16 hours, then concentrated and purified by chromatography on silica gel to provide 1-(6-chloro-4-methylpyridin-2-yl)-2-methyl-1H-benzo[d]imidazole as an off-white solid (114 mg, 29% for two steps).

Step 3. The obtained product was carried forward (using the procedure described in Example 67 and appropriate starting materials, reagents and reaction conditions) to provide the title compound as a white solid. $^1$H NMR (DMSO-d$_6$) δ 9.06 (s, 1H), 7.59-7.63 (m, 1H), 7.48 (dist. dt, J=8.8, 2.2 Hz, 2H), 7.42-7.45 (m, 1H), 7.18-7.24 (m, 2H), 6.84 (dist. dt, J=9.1, 1.9 Hz, 2H), 6.77 (s, 1H), 6.67 (s, 1H), 3.68 (s, 3H), 2.57 (s, 3H), 2.34 (s, 3H); MS m/z 345 (ESI) [M+H]$^+$.

Example 69

6-(5,6-difluoro-2-methyl-1H-benzimidazol-1-yl)-N-[4-(trifluoromethyl)phenyl]pyrazin-2-amine (Cpd 683)

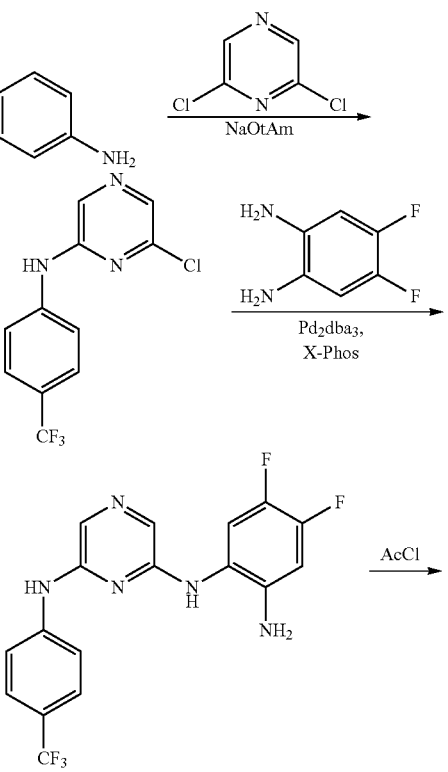

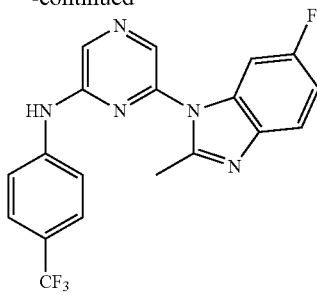

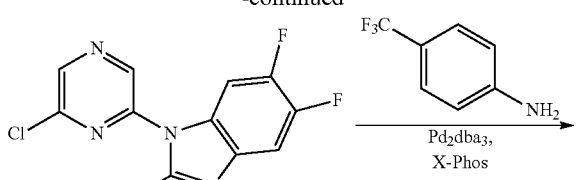

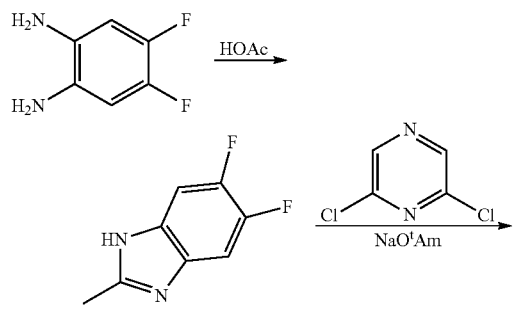

Step 1. 4-trifluoromethylaniline (4.83 g, 30 mmol) and 2,6-dichloropyrazine (4.5 g, 30 mmol) were dissolved in DMF (50 mL). The mixture was cooled to −78° C., then a solution of sodium tert-pentoxide in THF (2.5M, 40 mL, 100 mmol) was added. The reaction mixture was gradually warmed to room temperature, until LC-MS showed that the reaction was complete, followed by aqueous work up and chromatography to provide 6-chloro-N-(4-(trifluoromethyl)phenyl)pyrazin-2-amine as a dark solid (7.08 g, 86%).

Step 2. To a microwave tube was added the obtained product (546 mg, 2 mmol), 1,2-difluoro-4,5-diaminobenzene (560 mg, 4 mmol), Pd$_2$dba$_3$ (100 mg, 0.1 mmol), X-Phos (100 mg, 0.2 mmol), K$_3$PO$_4$ (1.27 g, 6 mmol) and DME (10 mL). The reaction mixture was heated under microwave at 120° C. for one hour, until LC-MS showed that the reaction was complete, followed by aqueous work up and chromatography (eluted from a gradient of 30% to 100% EtOAc:hexane followed by a gradient of 0% to 10% MeOH:EtOAc) to provide N$^2$-(2-amino-4,5-difluorophenyl)-N$^6$-(4-(trifluoromethyl)phenyl)pyrazine-2,6-diamine as a dark solid (627 mg, 83%).

Step 3. To a solution of the obtained product (76 mg, 0.2 mmol) in MeCN (2 mL) was added acetyl chloride (21 µL, 0.3 mmol). The reaction mixture was stirred at room temperature for 10 minutes, then heated by microwave at 180° C. for 10 minutes. The mixture was diluted with EtOAc and washed with NaHCO$_3$, followed by brine. The ester layer was concentrated and purified by chromatography to give the title compound (32 mg, 35%). $^1$H NMR (CDCl$_3$, 500 MHz) δ 8.31 (1H, s), 8.13 (1H, s), 7.73 (2H, d, J=8.6), 7.56 (2H, d, J=8.6 Hz), 7.52 (1H, m), 7.31 (1H, m), 3.03 (2H, q, J=7.5 Hz), 2.68 (3H, s); MS m/z 406.3 (ESI) [M+H]$^+$ Example 70

6-(5,6-difluoro-2-methyl-1H-benzimidazol-1-yl)-N-[4-(trifluoromethyl)phenyl]pyrazin-2-amine (Cpd 683) (Alternative Synthesis)

Step 1. 1,2-difluoro-4,5-diaminobenzene (2.88 g, 20 mmol) was dissolved in HOAc (20 mL). The mixture was heated under microwave at 150° C. for 2 hours, then carefully poured into saturated aqueous NaHCO$_3$ and extracted with EtOAc. The ester layer was washed with brine, then dried and filtered through Celite. The solvent was removed under reduced pressure to give 5,6-difluoro-2-methyl-1H-benzo[d]imidazole as a purple solid (3.18 g, 95%).

Step 2. 5,6-difluoro-2-methyl-1H-benzo[d]imidazole (1.68 g, 10 mmol) and 2,6-dichloropyrazine (2.25 g, 15 mmol) were dissolved in DMF. The reaction mixture was cooled to 0° C., then a solution of sodium t-pentoxide in THF (1.4M, 8.5 mL, 12 mmol) was added. The reaction mixture was stirred at room temperature overnight, followed by aqueous work up and chromatography to provide 1-(6-chloropyrazin-2-yl)-5,6-difluoro-2-methyl-1H-benzo[d]imidazole (1.76 g, 63%).

Step 3. To a round bottom flask was added 4-trifluoromethylaniline (1.92 g, 12 mmol), 1-(6-chloropyrazin-2-yl)-5,6-difluoro-2-methyl-1H-benzo[d]imidazole (1.76 g, 6.3 mmol), Pd$_2$dba$_3$ (300 mg, 0.3 mmol), X-Phos (300 mg, 0.6 mmol), K$_3$PO$_4$ (4.2 g, 20 mmol) and DME (30 mL). The reaction mixture was heated at 110° C. overnight, then diluted with EtOAc and filtered through Celite. The filtrate was concentrated and purified by chromatography (30%-100% EtOAc:Hexane, then 0%-10% MeOH:EtOAc) to give a crude product as a brown solid (1.26 g, 49%). The brown solid was dissolved in minimum amount of DME (about 10 mL), then hexane was added to the solution. The resulting precipitate was collected by filtration to give the title compound as pale brown powder. $^1$H NMR (CDCl$_3$, 500 MHz) δ 8.31 (1H, s), 8.13 (1H, s), 7.73 (2H, d, J=8.6), 7.56 (2H, d, J=8.6 Hz), 7.52 (1H, m), 7.31 (1H, m), 3.03 (2H, q, J=7.5 Hz), 2.68 (3H, s); MS m/z 406.3 (ESI) [M+H]$^+$ Additional compounds of Formula (I) or a form thereof described herein may be prepared according to the procedure of either Example 69 or 70 by substituting the appropriate starting materials, reagents and reaction conditions:

| Cpd | Name and Data |
|---|---|
| 82 | 6-(2-methyl-1H-imidazo[4,5-b]pyridin-1-yl)-N-[4-(trifluoromethyl)phenyl]pyrazin-2-amine<br>MS m/z 371 (ESI) [M + H]+ |
| 83 | 6-(2-ethyl-1H-imidazo[4,5-b]pyridin-1-yl)-N-[4-(trifluoromethyl)phenyl]pyrazin-2-amine<br>$^1$H NMR (CDCl$_3$, 500 MHz) δ 8.50 (1H, d, J = 4.9 Hz), 8.40 (1H, s), 8.09(1H, s), 7.78 (1H, s), 7.78 (2H, d, J = 8.6 Hz), 7.50 (2H, d, J =8.6 Hz), 7.23 (1H, dd, J = 6.6, 4.9 Hz), 3.08 (2H, q, J = 7.5 Hz), 1.40 (3H, t, J = 7.5 Hz). 8.05 (1H, dd, J = 8.1, 1.4 Hz), 7.90 (2H, d, J = 8.7 Hz), 7.61 (2H, d, J = 8.7 Hz), 7.40 (1H, dd, J = 4.9, 8.1 Hz), 2.81 (3H, s); MS m/z 385.3 (ESI) [M + H]+ |
| 85 | N-[4-(difluoromethoxy)phenyl]-6-(2-methyl-1H-imidazo[4,5-b]pyridin-1-yl)pyrazin-2-amine<br>$^1$H NMR (CDCl$_3$, 500 MHz) δ 8.49 (1H, dd, J = 4.8, 1.5 Hz), 8.36 (1H, s), 8.23 (1H, s), 8.03 (1H, dd, J = 8.1, 1.4 Hz), 7.72 (2H, d, J = 9.1 Hz), 7.39 (1H, dd, J = 8.1, 4.8 Hz), 7.13 (2H, d, J = 9.1 Hz), 6.77 (1H, t, J = 74.4 Hz), 2.79 (3H, s); MS m/z 369.3 (ESI) [M + H]+ |
| 94 | 6-(8-ethyl-7H-purin-7-yl)-N-[4-(trifluoromethyl)phenyl]pyrazin-2-amine<br>MS m/z 386.1 (ESI) [M + H]+ |
| 95 | 6-(2-methyl-1H-imidazo[4,5-b]pyridin-1-yl)-N-[4-(trifluoromethoxy)phenyl]pyrazin-2-amine<br>$^1$H NMR (MeOD-d$_4$, 500 MHz) δ 8.36 (1H, dd, J = 5, 1.4 Hz), 8.24 (1H, s), 8.14 (1H, s), 7.90 (1H, dd, J = 8, 1.5 Hz), 7.65 (sH, d, J = 9 Hz), 7.25 (1H, dd, J = 8, 4.8 Hz), 7.11, 2H, d, J = 8 Hz), 2.66 (3H, s); MS m/z 387.2 (ESI) [M + H]+ |
| 123 | 6-[2-(trifluoromethyl)-1H-imidazo[4,5-b]pyridin-1-yl]-N-[4-(trifluoromethyl)phenyl]pyrazin-2-amine<br>$^1$H NMR (MeOD-d$_4$, 500 MHz) δ 8.73 (1H, dd, J = 4.7, 1.5 Hz), 8.50 (1H, s), 8.33 (1H, s), 8.12 (1H, dd, J = 8.3, 1.5 Hz), 7.86 (2H, d, J = 8.5 Hz), 7.60 (1H, dd, J = 8.3, 4.7 Hz), 7.57 (2H, d, J = 8.5 Hz); MS m/z 425.1 (ESI) [M + H]+ |
| 177 | 6-(2-ethyl-5,6-difluoro-1H-benzimidazol-1-yl)-N-[4-(trifluoromethyl)phenyl]pyrazin-2-amine<br>$^1$H NMR (MeOD-d$_4$, 500 MHz) δ 8.41 (1H, s), 8.25 (1H, s), 7.86 (2H, d, J = 8.5), 7.57 (3H, m), 7.45 (1H, dd, J = 10, 7 Hz), 3.03 (2H, q, J = 7.5 Hz), 1.36 (3H, t, J = 7.5 Hz); MS m/z 420.8 (ESI) [M + H]+ |
| 182 | 6-(2-cyclopropyl-5,6-difluoro-1H-benzimidazol-1-yl)-N-[4-(trifluoromethyl)phenyl]pyrazin-2-amine<br>$^1$H NMR (MeOD-d$_4$, 500 MHz) δ 8.41 (1H, s), 8.35 (1H, s), 7.93 (2H, d, J = 8.6), 7.61 (2H, d, J = 8.6 Hz), 7.49 (2H, dd, J = 7.5, 7.2 Hz), 2.27 (1H, m), 1.29 (2H, m), 1.17 (2H, m); MS m/z 432.3 (ESI) [M + H]+ |
| 199 | N-[4-(difluoromethoxy)phenyl]-6-(5,6-difluoro-2-methyl-1H-benzimidazol-1-yl)pyrazin-2-amine<br>$^1$H NMR (MeOD-d$_4$, 500 MHz) δ 8.31 (1H, s), 8.18 (1H, s), 7.70 (2H, d, J = 9 Hz), 7.52 (2H, m), 7.12 (2H, d, J = 9 Hz), 6.75 (1H, t, J = 75 Hz), 2.68 (3H, s); MS m/z 404.0 (ESI) [M + H]+ |
| 266 | 6-(5,6-difluoro-2-methyl-1H-benzimidazol-1-yl)-N-[4-(trifluoromethoxy)phenyl]pyrazin-2-amine<br>$^1$H NMR (MeOD-d$_4$, 500 MHz) δ 8.34 (1H, s), 8.21 (1H, s), 7.75 (2H, d, J = 9.2 Hz), 7.52 (2H, m), 7.23 (2H, d, J = 9 Hz), 2.68 (3H, s); MS m/z 422.0 (ESI) [M + H]+ |
| 270 | 6-(6-fluoro-2-methyl-1H-imidazo[4,5-b]pyridin-1-yl)-N-[4-(trifluoromethyl)phenyl]pyrazin-2-amine<br>$^1$H NMR (Acetone-d$_6$, 500 MHz) δ 8.50 (1H, s), 8.46 (1H, s), 8.42 (1H, dd, J = 2.7, 1.8 Hz), 8.00 (2H, d, J = 8.7 Hz), 7.89 (1H, dd, J = 8.5, 2.7 Hz), 7.70 (2H, d = 8.7 Hz), 2.79 (3H, s); MS m/z 389.3 (ESI) [M + H]+ |
| 271 | 6-(2-ethyl-6-fluoro-1H-imidazo[4,5-b]pyridin-1-yl)-N-[4-(trifluoromethyl)phenyl]pyrazin-2-amine<br>$^1$H NMR (DMSO-d$_6$, 500 MHz) δ 10.39 (1H, s), 8.47 (1H, s), 8.46 (1H, m), 7.94 (1H, dd, J = 2.8, 2.8 Hz), 7.85 (2H, d, J = 8.6 Hz), 7.66 (2H, d, J = 8.7 Hz), 3.03 (2H, q, J = 7.4 Hz), 1.32 (3H, t, J = 7.4 Hz); MS m/z 403.1 (ESI) [M + H]+ |
| 293 | 6-(2-cyclopropyl-6-fluoro-1H-imidazo[4,5-b]pyridin-1-yl)-N-[4-(trifluoromethyl)phenyl]pyrazin-2-amine<br>$^1$H NMR (MeOD-d$_4$, 500 MHz) δ 8.42 (1H, s), 8.39 (1H, s), 8.37 (1H, m), 7.93 (2H, d, 8.6 Hz), 7.83 (1H, dd, J = 8.5, 2.7 Hz), 7.60 (2H, d, J = 8.7 Hz), 4.65 (1H, s), 2.34 (1H, m), 1.39 (2H, m), 1.24 (2H, m); MS m/z 415.1 (ESI) [M + H]+ |
| 294 | N-(4-chloro-3-fluorophenyl)-6-(5,6-difluoro-2-methyl-1H-benzimidazol-1-yl)pyrazin-2-amine<br>$^1$H NMR (Acetone-d$_6$, 500 MHz) δ 9.51 (1H, br s), 8.42 (1H, s), 8.39 (1H, s), 7.93 (1H, dd, J = 7.1, 2.4 Hz), 7.64-7.58 (2H, m), 7.53-7.45 (2H, m), 2.72 (3H, s); MS m/z 390.3 (ESI) [M + H]+ |
| 295 | 6-(5,6-difluoro-2-methyl-1H-benzimidazol-1-yl)-N-[3-fluoro-4-(trifluoromethyl)phenyl]pyrazin-2-amine<br>$^1$H NMR (MeOD-d$_4$, 500 MHz) δ 8.30 (1H, S), 8.24 (1H, s), 7.75 (1H, d, J = 13.5 Hz), 7.44 (4H, m), 2.60 (3H, s); MS m/z 424.0 (ESI) [M + H]+ |
| 299 | 6-(5-chloro-2,4-dimethyl-1H-imidazol-1-yl)-N-[4-(trifluoromethyl)phenyl]pyrazin-2-amine<br>$^1$H NMR (CDCl$_3$, 500 MHz) δ 8.31 (1H, s), 8.04 (1H, s), 7.71 (2H, d, J = 8.5 Hz), 7.58 (2H, d, J = 8.5 Hz), 2.37 (3H, s), 2.22 (3H, s); MS m/z 368.0 (ESI) [M + H]+ |
| 300 | 6-(2,4-dimethyl-1H-imidazol-1-yl)-N-P-(trifluoromethyl)phenyl]pyrazin-2-amine<br>$^1$H NMR (CDCl$_3$, 500 MHz) δ 8.13 (1H, s), 7.99 (1H, s), 7.64 (2H, d, J = 8.6 Hz), 7.52 (2H, d, J = 8.6 Hz), 6.96 (1H, d, J = 1 Hz), 2.51 (3H, s), 2.18 (3 H, d, J = 1 Hz); MS m/z 334.0 (ESI) [M + H]+ |

| Cpd | Name and Data |
|---|---|
| 304 | ¹H NMR (MeOD-d₄, 500 MHz) δ 8.83 (1H, d, J = 2.5 Hz), 8.34 (1H, s), 8.33 (1H, m), 8.25 91H, s), 7.64 (1H, d, J = 8.7 Hz), 7.44 (1H, dd, J = 10.3, 7.3 Hz), 7.38 (1H, dd, J = 10.3, 7.3 Hz), 2.57 (3H, s); MS m/z 407.1 (ESI) [M + H]⁺ |
| 305 | ¹H NMR (Acetone-d₆, 500 MHz) δ 9.22 (1H, br s), 8.37 (1H, s,), 8.09 (1H, s), 7.81 (2H, J = 9.1 Hz), 7.21 (2H, d, J = 9.1 Hz), 6.95 (1H, t, J = 74.5 Hz), 2.34 (3H, s), 2.17 (3H, s); MS m/z 366.4 (ESI) [M + H]⁺ |
| 319 | N-[4-(difluoromethoxy)-3-fluorophenyl]-6-(5,6-difluoro-2-methyl-1H-benzimidazol-1-yl)pyrazin-2-amine<br>¹H NMR (CDCl₃, 500 MHz) δ 8.23 (1H, s), 8.04 (1H, s), 7.59 (1H, d, J = 12.4 Hz), 7.47 (1H, t, J = 10.9 Hz), 7.29-7.24 (3H, m), 7.13 (1H, t, J = 8.5 Hz), 6.46 (1H, t, J = 73.7 Hz), 2.64 (3H, s); MS m/z 422.0 (ESI) [M + H]⁺ |
| 325 | N-4-(difluoromethoxy)-3-fluorophenyl]-6-(2-methyl-1H-imidazo[4,5-b]pyridin-1-yl)pyrazin-2-amine<br>¹H NMR (Acetone-d₆, 500 MHz) δ 8.50 (1H, dd, J = 4.7, 1.5 Hz0, 8.46 (1H, s), 8.40 (1H, s), 8.01 (1H, dd, J = 8.1, 1.5 Hz), 7.92 (1H, dd, J = 13.2, 2.6 Hz), 7.54 (1H, m), 7.33 (1H, t, J = 8.9 Hz), 7.30 (1H, dd, J = 8.1, 4.8 Hz), 6.95 (1H, t, J = 73.8 Hz), 2.79 (3H, s); MS m/z 387.0 (ESI) [M + H]⁺ |
| 360 | N-[4-fluoro-4-(trifluoromethyl)phenyl]-6-(2-methyl-1H-imidazo[4,5-b]pyridin-1-yl)pyrazin-2-amine<br>¹H NMR (CDCl₃, 500 MHz) δ 8.45 (1H, d, J = 3.8 Hz), 8.30 (1H, s), 8.12 (1H, s), 7.79 (1H, 8.2 Hz), 7.63 (1H, d, J = 13.2 Hz0), 7.43 (3H, m), 7.21 (1H, m), 2.74 (3H, s); MS m/z 389.0 (ESI) [M + H]⁺ |
| 371 | 6-(8-methyl-7H-purin-7-yl)-N-[4-(trifluoromethyl)phenyl]pyrazin-2-amine<br>¹H NMR of the acetate (DMSO-d₆) δ: 11.97 (br. s., 1H), 10.41 (s, 1H), 9.08 (s, 1H), 9.02 (s, 1H), 8.49 (s, 1H), 8.46 (s, 1H), 7.83-7.88 (m, J = 8.8 Hz, 2H), 7.63-7368 (m, J = 8.8 Hz, 2H), 2.80 (s, 3H), 1.91 (s, 3H) |
| 373 | 6-(6-fluoro-2-methyl-1H-imidazo[4,5-b]pyridin-1-yl)-N-[3-fluoro-4-(trifluoromethyl)phenyl]pyrazin-2-amine<br>¹H NMR (Acetone-d₆, 500 MHz) δ 9.84 (1H, br s), 8.53 (2H, m), 8.44 (1H, dd, J = 2.7, 1.8 Hz), 7.98 (1H, d, J = 14 Hz), 7.92 (1H, dd, J = 8.7, 2.8 Hz), 7.72-7.66 (3H, m), 2.72 (3H, s); MS m/z 407.0 (ESI) [M + H]⁺ |
| 374 | 6-(2-ethyl-6-fluoro-1H-imidazo[4,5-b]pyridin-1-yl)-N-[3-fluoro-4-(trifluoromethyl)phenyl]pyrazin-2-amine<br>¹H NMR (CDCl₃, 500 MHz) δ 8.39 (1H, dd, J = 2.6, 1.7 Hz), 8.34 (1H, s), 8.11 (1H, s), 7.62 (1H, m), 7.49-7.41 (4H, m), 3.03 (2H, q, J = 7.5 Hz), 1.40 (3H, t, J = 7.5 Hz); MS m/z 421.0 (ESI) [M + H]⁺ |
| 431 | 6-(5-fluoro-2-methyl-1H-benzimidazol-1-yl)-N-[6-(trifluoromethyl)pyridin-3-yl]pyrazin-2-amine<br>¹H NMR (Acetone-d⁶, 500 MHz) δ 9.93 (1H, br s), 8.96 (1H, d, J = 2.3 Hz), 8.62 (1, dd, J = 8.7, 2.2 Hz), 8.54 (1H, s), 8.46 (1H, s), 7.81 (1H, d, J = 8.7 Hz), 7.60 (1H, dd, J = 8.9, 4.2 Hz), 7.43 (1H, dd, J = 9.4, 2.5 Hz), 7.11 (1H, td, J = 9.4, 2.5 Hz), 2.72 (3H, s); MS m/z 389.0 (ESI) [M + H]⁺ |
| 432 | 6-(6-fluoro-2-methyl-1H-benzimidazol-1-yl)-N-[6-(trifluoromethyl)pyridin-3-yl]pyrazin-2-amine<br>¹H NMR (Acetone-d₆, 500 MHz) δ 8.66 (1H, s), 8.47 (1H, m), 8.33 (1H, d, J = 3.6 hz), 8.13 (1H, d, J = 3.6 Hz), 7.60 (1H, m), 7.54 (1H, dd, J = 8.8, 3.6 Hz), 7.07 (1H, m), 6.99 (1H, m), 2.59 (3H, d, J = 3.7 Hz); MS m/z 389.0 (ESI) [M + H]⁺ |
| 455 | 6-(2-cyclopropyl-6-fluoro-1H-imidazo[4,5-b]pyridin-1-yl)-N-[4-(difluoromethoxy)phenyl]pyrazin-2-amine<br>¹H NMR (Acetone-d₆, 500 MHz) δ 9.29 (1H, br s), 8.420 (1H, s), 8.416 (1H, s), 8.38 (1H, dd, J = 2.5, 1.8 Hz), 7.87-7.82 (3H, m), 7.20 (2H, d, J = 9.1 Hz), 6.95 (1H, t, J = 74.6 Hz), 2.39 (1H, m), 1.38 (2H, m), 1.22 (2H, m); MS m/z 413.0 (ESI) [M + H]⁺ |
| 456 | 6-(2-cyclopropyl-6-fluoro-1H-imidazo[4,5-b]pyridin-1-yl)-N-[4-(trifluoromethoxy)phenyl]pyrazin-2-amine<br>¹H NMR (Acetone-d₆, 500 MHz) δ 9.41 (1H, br s), 8.45 (1H, d, J = 3.4 Hz), 8.38 (1H, s), 7.93 (2H, 9.1 Hz), 7.84 (1H, dd, J = 8.7, 2.7 Hz), 7.34 (2H, d, J = 8.6 Hz), 2.39 (1H, m), 1.29 (2H, m), 1.22 (2H, m); MS m/z 431.0 (ESI) [M + H]⁺ |
| 458 | 6-(2-cyclopropyl-6-fluoro-1H-imidazo[4,5-b]pyridin-1-yl)-N-[6-(trifluoromethyl)pyridin-3-yl]pyrazin-2-amine<br>¹H NMR (Acetone-d₆, 500 MHz) δ 9.80 (1H, br s), 8.90 (1H, d, J = 2.6 Hz), 8.67 (1H, dd, J = 7.8, 2.3 Hz), 8.60 (1H, s), 8.56 (1H, s), 8.39 (1, dd, J = 2.7, 1.8 Hz), 7.86 (1H, dd, J = 8.6, 2.7 Hz), 7.83 (1H, d, J = 8.7 Hz), 2.38 (1H, m), 1.39 (2H, m), 1.23 (2H, m); MS m/z 416.0 (ESI) [M + H]⁺ |
| 459 | 6-(2-cyclopropyl-6-fluoro-1H-imidazo[4,5-b]pyridin-1-yl)-N-[4-(difluoromethoxy)-3-fluorophenyl]pyrazin-2-amine<br>¹H NMR (Acetone-d₆, 500 MHz) δ 9.48 (1H, br s), 8.49 (1H, s), 8.45 (1H, s), 8.39 (1H, dd, J = 2.6, 1.7 Hz), 8.01 (1H, dd, J = 13.1, 2.6 Hz), 7.86 (1H, dd, J = 8.6, 2.7 Hz), 7.51 (1H, ddd, J = 8.9, 2.6, 1.5 Hz), 7.35 (1H, t, J = 8.9 Hz), 6.96 (1H, t, J = 72.5 Hz), 2.40 (1H, m), 1.39 (2H, m), 1.24 (2H, m); MS m/z 431.0 (ESI) [M + H]⁺ |
| 460 | 6-(2-cyclopropyl-5,6-difluoro-1H-benzimidazol-1-yl)-N-[4-(difluoromethoxy)phenyl]pyrazin-2-amine<br>¹H NMR (CDCl₃, 500 MHz) δ 8.30 (1H, s), 8.25 (1H, s), 7.54 (2H, d, J = 8.9 Hz), 7.46 (1H, dd, J = 10.4, 7.3 Hz), 7.33 (1H, dd, J = 10.1, 7.1 Hz), 7.16 (2H, d, J = 8.9 Hz), 6.82 |

| Cpd | Name and Data |
|---|---|
|  | (1H, s), 6.50 (1H, t, J = 73.7 Hz), 2.1 3 (1H, m), 1.36 (2H, m), 1.13 (2H, m); MS m/z 412.0 (ESI) [M + H]$^+$ |
| 579 | N-(2,2-difluoro-1,3-benzodioxol-5-yl)-6-(5,6-difluoro-2-methyl-1H-benzimidazol-1-yl)pyrazin-2-amine<br>$^1$H NMR (CDCl$_3$, 500 MHz) δ 8.19 (1H, s), 8.00 (1H, s), 7.47-7.43 (2H, m), 7.21 (1H, m), 6.95 (2H, d, J = 8.7 Hz), 2.62 (3H, s); MS m/z 418.0 (ESI) [M + H]$^+$ |

Example 71

N-(6-chloropyridin-3-yl)-6-(5,6-difluoro-2-methyl-1H-benzimidazol-1-yl)pyrazin-2-amine (Cpd 405)

6-(5,6-difluoro-2-methyl-1H-benzimidazol-1-yl)-N-[6-(morpholin-4-yl)pyridin-3-yl]pyrazin-2-amine (Cpd 423)

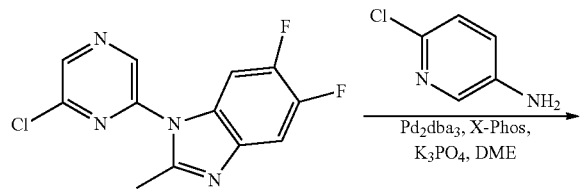

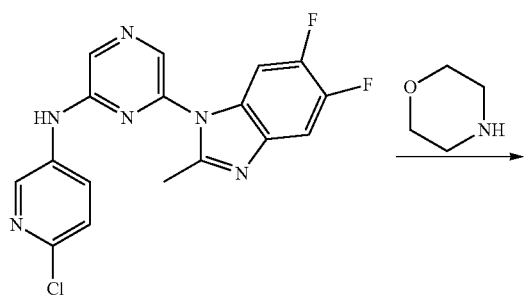

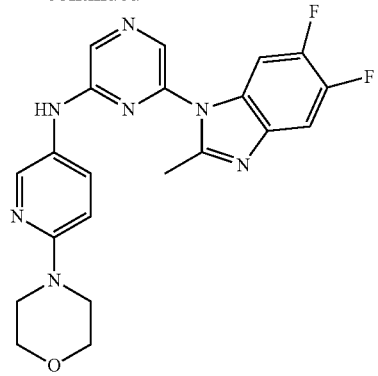

Step 1. In a microwave tube 1-(6-chloropyrazin-2-yl)-5,6-difluoro-2-methyl-1H-benzo[d]imidazole (1.4 g, 5 mmol) and 2-chloro-5-aminopyridine (635 mg, 5 mmol) were mixed with Pd$_2$dba$_3$ (250 mg, 0.25 mmol), X-phos (250 mg), K$_3$PO$_4$ (2.2 g, 10 mmol) and DME (5 mL). The mixture was microwaved at 120° C. for one hour, loaded onto a silica gel column, followed by flash chromatography (30%:100% EtOAc:Hexane, then 0%:10% MeOH:EtOAc) to provide the title Compound 405 (1.45 g, 78%). $^1$H NMR (Acetone-d$_6$, 500 MHz) δ 9.48 (1H, br s), 8.71 (1H, d, J=2.9 Hz), 8.47 (1H, s), 8.40 (1H, s), 8.34 (1H, dd, J=8.7, 2.9 Hz), 7.59 (3H, m), 7.43 (1H, d, J=8.7 Hz), 2.69 (3H, s); LCMS m/z 373.0 [M+H]$^+$ Step 2. Compound 405 (85 mg, 0.22 mmol) was suspended in morpholine (1 mL). The mixture was heated at 130° C. for 2 days, then poured into water. The product was extracted with EtOAc, then concentrated under reduced pressure. The crude residue was purified by flash chromatography (0%:10% MeOH:CH$_2$Cl$_2$, 1% Et$_3$N) to provide the title Compound 423 (66 mg, 69%). $^1$H NMR (Acetone-d$_6$, 500 MHz) δ 9.01 (1H, br s), 8.44 (1H, d, J=2.6 Hz), 8.34 (1H, s), 8.21 91h, S), 7.97 (1H, dd, J=9.1, 2.8 Hz), 7.56 (2H, m), 6.83 (1H, d, J=9.1 Hz), 3.76 (4H, m), 3.45 (4H, m), 2.67 (3H, s); LCMS m/z 424.0 [M+H]$^+$ Additional compounds of Formula (I) or a form thereof described herein may be prepared according to the procedure of Example 71 by substituting the appropriate starting materials, reagents and reaction conditions:

| Cpd | Name and Data |
|---|---|
| 425 | 2-[(5-{[6-(5,6-difluoro-2-methyl-1H-benzimidazol-1-yl)pyrazin-2-yl]amino}pyridin-2-yl)amino]ethanol<br>$^1$H NMR (Acetone-d$_6$, 500 MHz) δ 9.59 (1H, br s), 8.25 (1H, s), 8.18 (1H, d, J = 2.6 Hz), 8.15 (1H, s), 7.73 (1H, dd, J = 10.9, 7.5 Hz), 7.63 (1H, dd, J = 9.0, 2.5 Hz), 6.52 (1H, d, J = 8.9 Hz), 6.37 (1H, t, J = 5.7 Hz), 3.42 (2H, m), 3.29 (2H, m), 2.60, 3H, s); LCMS m/z 398.1 [M + H]$^+$ |

-continued

| Cpd | Name and Data |
|---|---|
| 426 | N-(6-chloropyridin-3-yl)-6-(5-fluoro-2-methyl-1H-benzimidazol-1-yl)pyrazin-2-amine<br>$^1$H NMR (CDCl$_3$, 500 MHz) δ 8.40 (1H, m), 8.26 (1H, m), 8.24 (1H, s), 8.09 (1H, s), 7.35<br>(1H, dd, J = 9.0, 2.1 Hz), 7.31 (1H, dd, J = 6.0, 4.5 Hz), 7.20 (1H, d, J = 8.8 Hz), 6.97 (1H,<br>M), 2.62 (3H, s); LCMS m/z 355.0 [M + H]$^+$ |
| 427 | N-(6-chloropyridin-3-yl)-6-(6-fluoro-2-methyl-1H-benzimidazol-1-yl)pyrazin-2-amine<br>1H NMR (CDCl$_3$, 500 MHz) δ 8.40 (1H, d, J = 2.7 Hz), 8.28 (1H, d, J = 8.8, 2.9 Hz), 8.26<br>(1H, s), 8.10 (1H, s), 7.62 (1H, d, J = 8.8, 4.8 Hz), 7.22 (1H, d, J = 8.8 Hz), 7.09 (1H, dd,<br>J = 8.8, 2.4 Hz), 7.02 (1H, td, J = 9.1, 2.5 Hz), 2.62 (3H, s); LCMS m/z 355.0 [M + H]$^+$ |
| 430 | $N^5$-[6-(5,6-difluoro-2-methyl-1H-benzimidazol-1-yl)pyrazin-2-yl]-$N^2$-[2-(dimethylamino)ethyl]pyridine-2,5-diamine<br>$^1$H NMR (Acetone-d$_6$, 500 MHz) δ 8.25 91H, d, J = 2.5 Hz), 8.24 (1H, s), 7.95 (1H, s),<br>7.73 (1H, dd, J = 8.5, 2.6 Hz), 7.37 (2H, m), 6.48 (1H, d, J = 9.1 Hz), 3.59 (2H, t, J = 6.4<br>Hz), 2.89 (3H, s), 2.48 (3H, s), 2.36 (3H, s); LCMS m/z 425.2 [M + H]$^+$ |

Example 72

6-(5,6-difluoro-2-methyl-1H-benzimidazol-1-yl)-N-[4-(trifluoromethyl)phenyl]pyrazin-2-amine 4-oxide (Cpd 495)

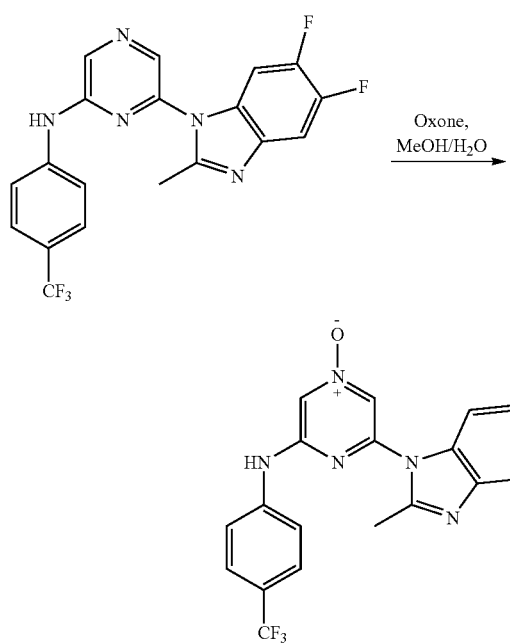

In a round bottom flask, to a solution of Cpd 318 (prepared using the procedure described in Example 69 or 70 and appropriate starting materials, reagents and reaction conditions) (810 mg, 2 mmol) in MeOH (75 mL) was added a solution of oxone (6.15 g, 10 mmol) in water (75 mL) with stirring. A white precipitate formed instantly and the mixture was stirred at room temperature for 4 days until Cpd 318 was consumed. LCMS showed a clean formation of the N-oxide product. MeOH was removed under reduced pressure, then the suspension was neutralized with saturated NaHCO$_3$ and extracted with EtOAc. The ester layer was washed with water then brine. The solvent was removed under reduced pressure to give a yellow residue. The product was purified by chromatography (30%-100% EtOAc:Hexane, then 0-10% MeOH:EtOAc) to give the title compound as pale yellow powder (0.7 g, 83%). $^1$H NMR (CDCl$_3$, 500 MHz) δ 7.93 (1H, d, J=1 Hz), 7.85 (1H, d, J=1 Hz), 7.66 (2H, d, J=8.5 Hz), 7.55 (2H, d, J=8.5 Hz), 7.52 (1H, dd, J=10, 7.2 Hz), 7.36 (1H, dd, J=9.9, 7.4 Hz), 7.32 (1H, br s), 2.72 (3H, s); LCMS m/z 422.0 [M+H]$^+$ Additional compounds of Formula (I) or a form thereof described herein may be prepared according to the procedure of Example 72 by substituting the appropriate starting materials, reagents and reaction conditions:

| Cpd | Name and Data |
|---|---|
| 137 | 6-[2-(trifluoromethyl)-1H-imidazo[4,5-b]pyridin-1-yl]-N-[4-(trifluoromethyl)phenyl]pyridin-2-amine<br>$^1$H NMR (MeOD-d$_4$, 500 MHz) δ 8.71 (1H, dd, J = 4.7, 1.4 Hz), 8.05 (1H, dd, J = 8.4, 1.5<br>Hz), 7.94 (1H, dd, J = 8.4, 7.5 Hz), 7.81 (2H, d, J = 8.5 Hz), 7.57 (1H, dd, J = 8.4, 5.7<br>Hz), 7.49 (2H, d, J = 8.7 Hz), 7.13 (1H, dd, J = 7.4, 5.5 Hz); LCMS m/z 424.2 [M + H]$^+$ |
| 139 | 6-(2-methyl-1H-imidazo[4,5-b]pyridin-1-yl)-N-[4-(trifluoromethyl)phenyl]pyridin-2-amine<br>$^1$H NMR (DMSO-d$_6$, 500 MHz) δ 8.47 (1H, dd, J = 4.8, 1.2 Hz), 8.00 (1H, dd, J = 8.1, 1.4<br>Hz), 7.93 (1H, t, J = 8.0 Hz), 7.84 (2H, d, J = 8.6 Hz), 7.53 (2H, d, J = 8.7 Hz), 7.36 (1H, |

-continued

| Cpd | Name and Data |
|---|---|
| | dd, J = 8.0, 4.9 Hz), 7.10 (1H, d, J = 7.5 Hz), 7.07 (1H, d, J = 8.4 Hz), 2.78 (3H, s); LCMS m/z 370.1 [M + H]$^+$ |
| 140 | 6-(2-ethyl-1H-imidazo[4,5-b]pyridin-1-yl)-N-[4-(trifluoromethyl)phenyl]pyridin-2-amine<br>$^1$H NMR (Acetone-d$_6$, 500 MHz) δ 8.49 (1H, dd, J = 4.8, 1.6 Hz), 8.01-7.95 (3H, m), 7.89<br>(1H, dd, J = 8.1, 1.6 Hz), 7.61 (2H, d, J = 8.7 Hz), 7.26 (1H, dd, J = 8.0, 4.8 Hz0, 7.17<br>(1H, dd, J = 5.2, 4.5 Hz), 3.14 (2H, q, J = 7.5 Hz), 1.40 (3H, t, J = 7.5 Hz); LCMS m/z 384.4 [M + H]$^+$ |
| 516 | N-[4-(difluoromethoxy)phenyl]-6-(5,6-difluoro-2-methyl-1H-benzimidazol-1-yl)pyrazin-2-amine 4-oxide<br>$^1$H NMR (CDCl$_3$, 500 MHz) δ 7.76 (1H, dd, J = 10.1, 1 Hz), 7.51 (1H, dd, J = 10.1, 7.2 Hz), 7,39-7.34 (3H, m), 7.20 (2H, d, J = 8.9 Hz), 6.68 (1H, br s), 6.53 (1H, t, J = 73 Hz),<br>2.70 (3H, s); LCMS m/z 420.0 [M + H]$^+$ |
| 525 | 6-(2-methyl-1H-benzimidazol-1-yl)-N-[4-(trifluoromethyl)phenyl]pyrazin-2-amine 4-oxide<br>$^1$H NMR (CDCl$_3$, 500 MHz) δ 7.92 (1H, s), 7.76 (1H, d, J = 7.5 Hz), 7.64 (2H, d, J = 8.6<br>Hz), 7.56 (2H, d, J = 8.6 Hz), 7.51 (1H, d, J = 7.5 Hz), 7.33 (1H, m), 2.73 (3H, s); LCMS<br>m/z 386.1 [M + H]$^+$ |
| 530 | 6-(2-cyclopropyl-5,6-difluoro-1H-benzimidazol-1-yl)-N-[4-(difluoromethoxy)phenyl]pyrazin-2-amine 4-oxide<br>$^1$H NMR (CDCl$_3$, 500 MHz) δ 7.96 (1H, d, J = 1.1 Hz), 7.77 (1H, d, J = 1.1 Hz), 7.46-7.40 (4H, m), 7.19 (2H, d, J = 8.9 Hz), 7.02 (1H, br s), 6.52 (1H, t, J = 73.3 Hz), 2.14 (1H, m), 1.36 (2H, m), 1.18 (2H, m); LCMS m/z 446.0 [M + H]$^+$ |
| 531 | N-[4-(difluoromethoxy)phenyl]-6-(2-methyl-1H-benzimidazol-1-yl)pyrazin-2-amine 4-oxide<br>$^1$H NMR (Acetone-d$_6$, 500 MHz) δ 9.13 (1H, br s), 8.03 (1H, s), 7.94 (1H, s), 7.73 92H, d, J = 8 Hz), 7.67 (1H, m), 7.63 (1H, m), 7.31 (1H, m), 7.18 (2H, d, J = 8 Hz), 7.17 (1H,<br>dd, J = 7.8, 3.1, Hz), 2.72 (3H, s); LCMS m/z 398.3 [M + H]$^+$ |
| 532 | 6-(6-fluoro-2-methyl-1H-benzimidazol-1-yl)-N-[4-(trifluoromethyl)phenyl]pyrazin-2-amine 4-oxide<br>$^1$H NMR (CDCl$_3$, 500 MHz) δ 7.90 (1H, s), 7.87 (1H, s), 7.69-7.65 (3H, m), 7.55-7.53 (2H, d, J = 8.5 Hz), 7.23 (1H, dd, J = 8.8, 2.3 Hz), 7.06 (1H, td, J = 9.2, 2.3 Hz), 6.99 (1H,<br>s), 2.68 (3H, s); LCMS m/z 404.0 [M + H]$^+$ |
| 533 | 6-(2-cyclopropyl-6-fluoro-1H-imidazo[4,5-b]pyridin-1-yl)-N-[4-(trifluoromethyl)phenyl]pyrazin-2-amine 4-oxide<br>$^1$H NMR (DMSO-d$_6$, 500 MHz) δ 10.29 (1H, br s), 8.45 (1H, dd, J = 2.7, 1.8 Hz),, 8.38 (1H, d, J = 1.2 Hz), 8.05 (1H, d, J = 1.2 Hz), 8.02 (1H, dd, J = 8.8, 2.7 Hz), 7.84 (2H, d, J =<br>8.6 Hz), 7.70 (2H, d, J = 8.6 Hz), 2.38 (1H, m), 1.28 (2H, m), 1.19 (2H, m); LCMS m/z 431.1 [M + H]$^+$ |
| 534 | 6-[2-(trifluoromethyl)imidazo[1,2-a]pyridin-3-yl]-N-[4-(trifluoromethyl)phenyl]pyrazin-2-amine 4-oxide<br>$^1$H NMR (Acetone-d$_6$) δ 9.21 (br. s., 1H), 8.78 (dt, J = 7.6, 1.2 Hz, 1H), 7.90 (s, 1H), 7.86<br>(d, J = 0.9 Hz, 1H), 7.77 (d, J = 8.5 Hz, 2H), 7.66 (dt, J = 9.1, 1.2 Hz, 1H), 7.44-7.52 (m,<br>3H), 7.05 (td, J = 6.8, 1.2 Hz, 1H); MS m/z 440 (ESI) [M + H]$^+$ |
| 538 | 6-[6-fluoro-2-(trifluoromethyl)imidazo[1,2-a]pyridin-3-yl]-N-[4-(trifluoromethyl)phenyl]pyrazin-2-amine 4-oxide<br>$^1$H NMR (Acetone-d$_6$) δ 9.23 (br. s, 1H), 8.90 (ddd, J = 5.0, 2.5, 0.9 Hz, 1H), 7.90 (s, 1H), 7.87 (d, J = 1.3 Hz, 1H), 7.78 (d, J = 8.5 Hz, 2H), 7.72 (ddd, J = 9.8, 5.0, 0.9 Hz, 1H), 7.44-7.53 (m, 3H); MS m/z 458 (ESI) [M + H]$^+$ |

Example 73

4-nitro-6-[2-(trifluoromethyl)imidazo[1,2-a]pyridin-3-yl]-N-[4-(trifluoromethyl)phenyl]pyridin-2-amine (Cpd 158)

6-[2-(trifluoromethyl)imidazo[1,2-a]pyridin-3-yl]-N²-[4-(trifluoromethyl)phenyl]pyridine-2,4-diamine (Cpd 159)

2-[(2-[2-(trifluoromethyl)imidazo[1,2-a]pyridin-3-yl]-6-{[4-(trifluoromethyl)phenyl]amino}pyridin-4-yl)amino]ethanol (Cpd 160)

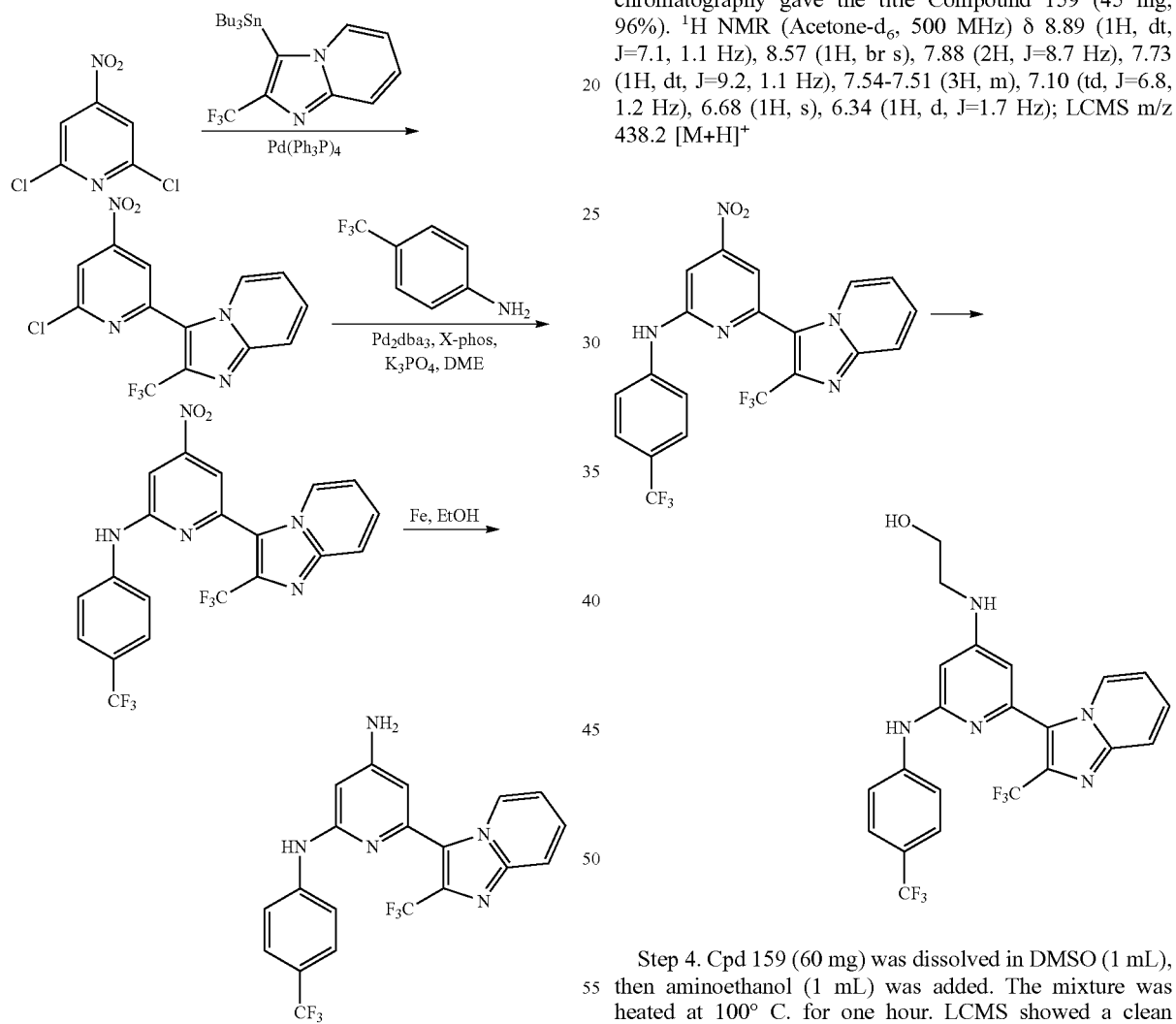

Step 1. A mixture of 2,6-dichloro-4-nitropyridine (1.92 g, 10 mmol), 3-(tributylstannyl)-2-(trifluoromethyl)imidazo[1,2-a]pyridine (2 g, 4 mmol) and Pd(Ph₃P)₄ (230 mg, 0.02 mmol) was dissolved in dioxane (10 mL). The mixture was irradiated by microwave at 100° C. for 30 minutes. The solvent was evaporated under reduced pressure and the residue was purified by flash chromatography to give 3-(6-chloro-4-nitropyridin-2-yl)-2-(trifluoromethyl)imidazo[1,2-a]pyridine (0.8 g, 69%).

Step 2. The obtained product (342 mg, 1 mmol), 4-trifluoromethylaniline (240 mg, 1.5 mmol), Pd₂dba₃ (45 mg, 0.05 mmol), X-phos (45 mg) and K₃PO₄ (425 mg, 2 mmol) were suspended in dioxane (5 mL). The mixture was heated by microwave at 100° C. for 30 minutes, then concentrated and purified by flash chromatography to give the title Compound 158 (355 mg, 76%). ¹H NMR (Acetone-$d_6$, 500 MHz) δ 9.64 (1H, br, s), 8.95 (1H, dt, J=7, 1.2 Hz), 7.98 (2H, d, J=8.6 Hz), 7.90 (1H, s), 7.84-7.81 (3H, m), 7.65 (2H, d, J=8.7 Hz), 7.62 (1H, m), 7.17 (1H, td, J=6.5, 1.2 Hz); LCMS m/z 468.3 [M+H]⁺

Step 3. To EtOH (2 mL) was added Cpd 158 (50 mg) and iron (50 mg) followed by water (2 mL) and one drop of HCl. The mixture was heated at 60° C. for 3 hours. LCMS showed completion and an aqueous work up followed by flash chromatography gave the title Compound 159 (45 mg, 96%). ¹H NMR (Acetone-$d_6$, 500 MHz) δ 8.89 (1H, dt, J=7.1, 1.1 Hz), 8.57 (1H, br s), 7.88 (2H, J=8.7 Hz), 7.73 (1H, dt, J=9.2, 1.1 Hz), 7.54-7.51 (3H, m), 7.10 (td, J=6.8, 1.2 Hz), 6.68 (1H, s), 6.34 (1H, d, J=1.7 Hz); LCMS m/z 438.2 [M+H]⁺

Step 4. Cpd 159 (60 mg) was dissolved in DMSO (1 mL), then aminoethanol (1 mL) was added. The mixture was heated at 100° C. for one hour. LCMS showed a clean conversion. Aqueous work up followed by flash chromatography gave the title Compound 160 (55 mg, 92%). ¹H NMR (Acetone-$d_6$, 500 MHz) δ 8.89 (1H, dt, J=7.1, 1.2 Hz), 8.61 (1H, br s), 7.91 (2H, J=8.7 Hz), 7.73 (1H, dt, J=9.2, 1.2 Hz), 7.54-7.51 (3H, m), 7.10 (td, J=6.8, 1.2 Hz), 6.70 (1H, d, J=0.9 Hz), 6.27 (1H, d, J=1.8 Hz), 3.82 (2H, m), 3.38 (2H, m); LCMS m/z 482.2 [M+H]⁺

Additional compounds of Formula (I) or a form thereof described herein may be prepared according to the procedure of Example 73 by substituting the appropriate starting materials, reagents and reaction conditions:

| Cpd | Name and Data |
|---|---|
| 161 | $N^4$-(2-methoxyethyl)-6-[2-(trifluoromethyl)imidazo[1,2-a]pyridin-3-yl]-$N^2$-[4-(trifluoromethyl)phenyl]pyridine-2,4-diamine<br>$^1$H NMR (MeOD-$d_4$, 500 MHz) δ 8.75 (1H, d, J = 7 hz), 7.73-7.69 (3H, m), 7.52 (1H, m), 7.44 (2H, d, J = 8.5 Hz), 7.05 (1H, td, J = 7, 1 Hz), 6.57 (1H, s), 6.18 (1H, d, J = 1 Hz), 3.63 (2H, t, J = 5.5 Hz), 3.38 (2H, t, J = 5.5 Hz); LCMS m/z 497.1 [M + H]$^+$ |
| 169 | N-[4-(difluoromethoxy)phenyl]-4-nitro-6-[2-(trifluoromethyl)imidazo[1,2-a]pyridin-3-yl]pyridin-2-amine<br>$^1$H NMR (Acetone-$d_6$, 500 MHz) δ 9.27 (1H, br s), 8.96 (1H, dt, J = 7.1, 1.2 Hz), 7.82-7.79 (4H, m), 7.73 (1H, d, J = 3.2 Hz), 7.60 (1H, ddd, J = 9.2, 6.7, 1.2 Hz), 7.18 (2H, d, J = 9 Hz), 7.15 (1H, td, J = 6.7, 1.2 Hz), 6.95 (1H, t, J = 74.5 Hz); LCMS m/z 466.1 [M + H]$^+$ |
| 170 | $N^2$-[4-(difluoromethoxy)phenyl]-6-[2-(trifluoromethyl)imidazo[1,2-a]pyridin-3-yl]pyridine-2,4-diamine<br>LCMS m/z 436.5 [M + H]$^+$ |
| 171 | 2-[(2-{[4-(difluoromethoxy)phenyl]amino}-6-[2-(trifluoromethyl)imidazo[1,2-a]pyridin-3-yl]pyridin-4-yl)amino]ethanol<br>$^1$H NMR (MeOD-$d_4$, 500 MHz) δ 8.73 91H, dt, J = 7.1, 1.1 Hz), 7.68 (1H, dt, J = 9.2,<br>1 Hz), 7.53-7.50 (3H, m), 7.06-7.01 (3H, m), 6.69 (1H, t, J = 74.7 Hz), 6.50 (1H, d, J = 1 Hz), 6.10 (1H, d, J = 1.9 Hz), 3.76 (2H, t, J = 5.8 Hz), 3.32 (2H, t, J = 5.8 Hz);<br>LCMS m/z 480.3 [M + H]$^+$ |
| 172 | $N^2$-[4-(difluoromethoxy)phenyl]-$N^4$-(2-methoxyethyl)-6-[2-(trifluoromethyl)imidazo[1,2-a]pyridin-3-yl]pyridine-2,4-diamine<br>$^1$H NMR (MeOD-$d_4$, 500 MHz) δ 8.72 (1H, dt, J = 12.5, 1.1 Hz), 7.67 (1H, td, J = 12.5, 1.1 Hz), 7.51 (3H, m), 7.03 (3H, m), 6.69 (1H, t, J = 75 Hz), 6.49 (1H, d, J = 1.1 Hz), 6.08 (1H, d, J = 1.1 Hz), 3.61 (2H, t, J = 5.5 Hz), 3.41 (3H, s), 3.33 (2H, m);<br>LCMS m/z 494.1 [M + H]$^+$ |
| 197 | 4-nitro-N-[4-(trifluoromethoxy)phenyl]-6-[2-(trifluoromethyl)imidazo[1,2-a]pyridin-3-yl]pyridin-2-amine<br>$^1$H NMR (Acetone-$d_6$, 500 MHz) δ 9.39 (1H, br s), 8.95 (1H, dt, J = 6.7, 1.1 Hz), 7.88 (2H, d, J = 9.1 Hz), 7.84 (1H, d, J = 0.8 Hz), 7.80 (1H, dt, J = 8.7, 1 hz), 7.76 (1H, d, J = 1.7 Hz), 7.60 (1H, m), 7.30 (2H, d, J = 9 Hz), 7.14 (1H, td, J = 6.9, 1.1 Hz); LCMS m/z 484.3 [M + H]$^+$ |
| 198 | $N^2$-[4-(trifluoromethoxy)phenyl]-6-[2-(trifluoromethyl)imidazo[1,2-a]pyridin-3-yl]pyridine-2,4-diamine<br>$^1$H NMR (MeOD-$d_4$, 500 MHz) δ 8.71 (1H, d, J = 7 Hz), 7.66 (1H, d, J = 9.2 Hz), 7.55 (2H, d, J = 9.1 Hz), 7.48 (1H, m), 7.10 (2H, d, J = 8.5 Hz), 7.01 (1H, td, J = 7, 1 Hz);<br>LCMS m/z 454.0 [M + H]$^+$ |

Example 74

4-(methylsulfanyl)-6-[2-(trifluoromethyl)imidazo[1,2-a]pyridin-3-yl]-N-[4-(trifluoromethyl)phenyl]pyridin-2-amine (Cpd 173)

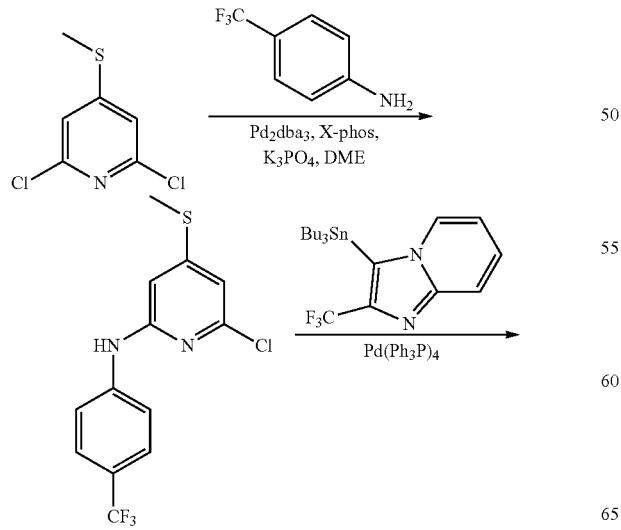

-continued

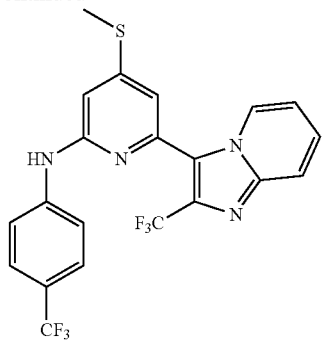

Step 1. 2,6-Dichloro-4-methylthiopyridine (1.37 g, 7 mmol), 4-trifluoromethylaniline (640 mg, 4 mmol), Pd$_2$dba$_3$ (180 mg, 0.2 mmol), X-phos (180 mg) and K$_3$PO$_4$ (1.4 g, 7 mmol) were suspended in dioxane (20 mL). The mixture was heated at 100° C. overnight. The reaction mixture was concentrated and purified by flash chromatography to give 6-chloro-4-(methylthio)-N-(4-(trifluoromethyl)phenyl)pyridin-2-amine (814 mg, 64%).

Step 2. The obtained product (177 mg, 0.55 mmol), 2-methyl-3-(tributylstannyl)imidazolopyridine (300 mg, 0.6 mmol) and tetrakistriphenylphospine palladium (35 mg) were dissolved in dioxane (5 mL). The mixture was heated by microwave at 100° C. for 1.5 hours. The reaction mixture was concentrated and purified by flash chromatography to give the title compound (215 mg, 81%). LCMS m/z 469.2 [M+H]$^+$ Additional compounds of Formula (I) or a form thereof described herein may be prepared according to the procedure of Example 74 by substituting the appropriate starting materials, reagents and reaction conditions:

| Cpd | Name and Data |
|---|---|
| 210 | 2-[2-(trifluoromethyl)imidazo[1,2-a]pyridin-3-yl]-6-{[4-(trifluoromethyl)phenyl]amino}pyridine-4-carbonitrile<br>LCMS intz 448.0 [M + H]$^+$ |
| 241 | 2-(5,6-difluoro-2-methyl-1H-benzimidazol-1-yl)-6-{[4-(trifluoromethyl)phenyl]amino}pyridine-4-carbonitrile<br>$^1$H NMR (MeOD-d$_4$, 500 MHz) δ 7.71 (1H, d, J = 8.5 Hz), 7.46 (1H, J = 8.5 Hz), 7.42 (1H, m), 7.40 (1H, m), 7.24 (1H, d, J = 0.9 Hz), 7.18 (1H, d, J = 0.9 Hz), 2.57 (3H, s); LCMS intz 430.1 [M + H]$^+$ |
| 242 | 2-{[4-(difluoromethoxy)phenyl]amino}-6-(5,6-difluoro-2-methyl-1H-benzimidazol-1-yl)pyridine-4-carbonitrile<br>$^1$H NMR (Acetone-d$_6$, 500 MHz) δ 9.22 (1H, br s), 7.75 (2H, d, J = 9 Hz), 7.65 (1H, dd, J = 10.7, 7.3 Hz), 7.57 (1H, dd, J = 10.7, 7.3 Hz), 7.40 (1H, d, J = 1 Hz), 7.32 (1H, d, J = 1 Hz), 7.20 (2H, d, J = 9 Hz), 6.95 (1H, t, J = 74.5 Hz), 2.70 (3H, s); LCMS m/z 428.4 [M + H]$^+$ |
| 243 | 2-(5,6-difluoro-2-methyl-1H-benzimidazol-1-yl)-6-{[4-(trifluoromethoxy)phenyl]amino}pyridine-4-carbonitrile<br>$^1$H NMR (MeOD-d$_4$, 500 MHz) δ 7.71 (2H, d, J = 9.1 Hz), 7.52 (2H, m), 7.30 (1H, d, J = 0.8 Hz), 7.24 (1H, d, J = 0.8 Hz), 7.22 (1H, br s), 2.67 (3H, s); LCMS m/z 446.0 [M + H]$^+$ |
| 290 | tert-butyl[2-(2-methyl-1H-imidazo[4,5-b]pyridin-1-yl)-6-{[4-(trifluoromethyl)phenyl]amino}pyridin-4-yl]carbamate<br>$^1$H NMR (MeOD-d$_4$, 500 MHz) δ 8.46 (1H, dd, J = 5, 1.5 Hz), 8.02 (1H, d,d J = 8.1, 1.5 Hz), 7.79 (2H, d, J = 8.6 Hz), 7.51 (2H, d, J = 8.6 Hz), 7.36 (1H, dd, J = 8.1, 4.9 Hz), 7.33 (1H, d, J = 1.5 Hz), 7.06 (1H, d, J = 1.5 Hz), 2.78 (3H, s); LCMS m/z 485.1 [M + H]$^+$ |
| 292 | 6-(2-methyl-1H-imidazo[4,5-b]pyridin-1-yl)-N$^2$-[4-(trifluoromethyl)phenyl]pyridine-2,4-diamine<br>$^1$H NMR (MeOD-d$_4$, 500 MHz) δ 8.32 (1H, br d, J = 4.1 Hz), 7.86 (1H, dd, J = 8.1, 1.4 Hz), 7.59 (2H, d, J = 8.6 Hz), 7.35 (2H, d, J = 8.6 H7.23 (1H, dd, J = 8.1, 4.9 Hz), 6.26 (1H, d, J = 1.7 Hz), 6.13 (1H, d, J = 1.7 Hz), 2.65 (3H, s); LCMS m/z 385.1 [M + H]$^+$ |
| 326 | 2-{[4-(difluoromethoxy)-3-fluorophenyl]amino}-6-(5,6-difluoro-2-methyl-1H-benzimidazol-1-yl)pyridine-4-carbonitrile<br>$^1$H NMR (Acetone-d$_6$, 500 MHz) δ 9.40 (1H, br s), 7.85 (1H, dd, J = 13.1, 2.6 Hz), 7.68 (1H, d,d, J = 10.7, 7.3 Hz), 7.59 (1H, dd, J = 10.7, 7.3 Hz), 7.50 (1H, d, J = 0.9 Hz), 7.46 (1H, m), 7.38 (1H, d, J = 0.9 Hz), 7.34 (1H, t, J = 8.9 Hz), 2.72 (3H, s); LCMS m/z 446.0 [M + H]$^+$ |
| 359 | 2-(5,6-difluoro-2-methyl-1H-benzimidazol-1-yl)-6-{[3-fluoro-4-(trifluoromethyl)phenyl]amino}pyridine-4-carbonitrile<br>$^1$H NMR (CDCl$_3$, 500 MHz) δ 7.58 (1H, d, J = 13 Hz), 7.49-7.43 (2H, m), 7.38 (1H, d, J = 8.6 Hz), 7.24 (1H, m), 7.15 (1H, d, J = 0.9 Hz), 7.00 (1H, d, J = 0.9 Hz), 2.64 (3H, s); LCMS m/z 448 [M + H]$^+$ |
| 490 | 2-(2-cyclopropyl-6-fluoro-1H-imidazo[4,5-b]pyridin-1-yl)-6-{[4-(trifluoromethyl)phenyl]amino}pyridine-4-carbonitrile<br>$^1$H NMR (CDCl$_3$, 500 MHz) δ 8.33 (1H, s), 7.70 (2H, d, J = 8.5 Hz), 7.54-7.51 (3H, m), 7.14 (1H, s), 7.11 (1H, s), 2.15 (1H, m), 1.45 (2H, m), 1.17 (2H, m); LCMS m/z 439.1 [M + H]$^+$ |

Example 75

6-(5,6-difluoro-2-methyl-1H-benzimidazol-1-yl)-N²-[4-(trifluoromethyl)phenyl]pyridine-2,4-diamine (Cpd 231)

6-(5,6-difluoro-2-methyl-1H-benzimidazol-1-yl)-3-fluoro-N²-[4-(trifluoromethyl)phenyl]pyridine-2,4-diamine (Cpd 505)

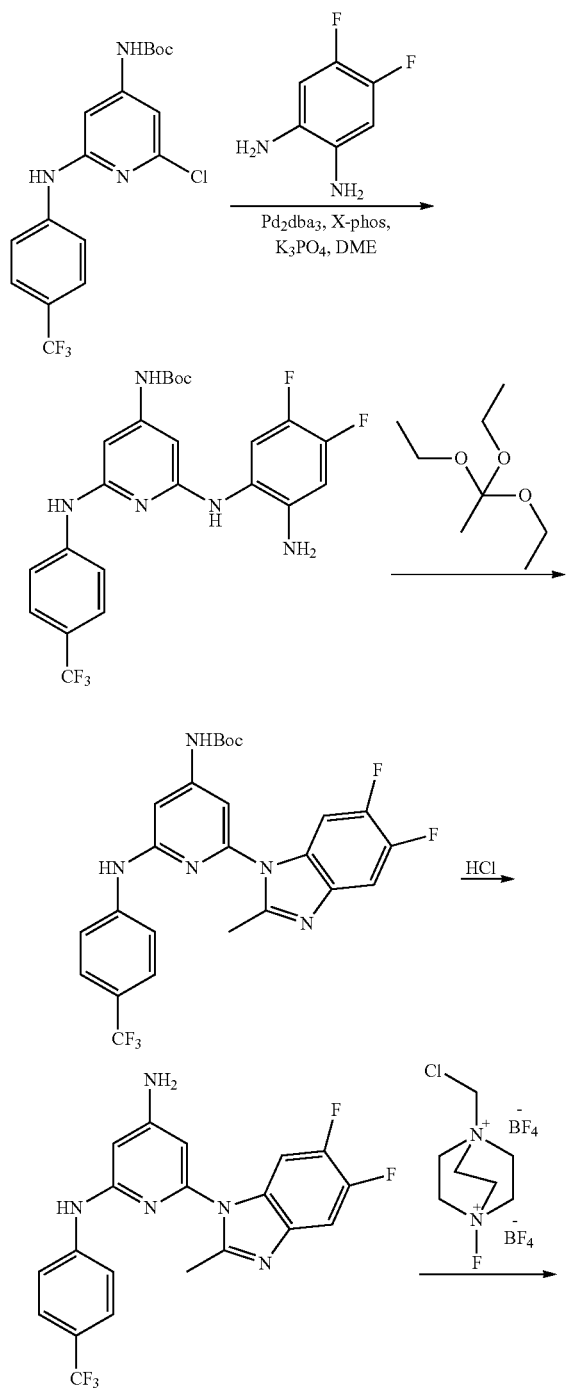

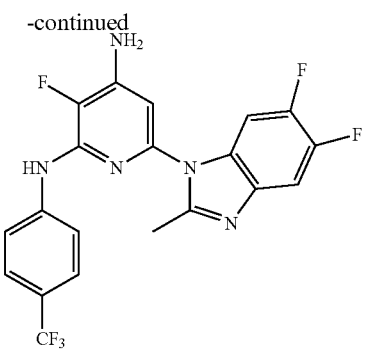

Step 1. To a microwave tube was added tert-butyl (2-chloro-6-((4-(trifluoromethyl)phenyl)amino)pyridin-4-yl)carbamate (387 mg, 1 mmol), 4,5-difluorobenzene-1,2-diamine (430 mg, 3 mmol), Pd₂dba₃ (50 mg, 0.05 mmol), X-Phos (50 mg), K₃PO₄ (636 mg, 3 mmol) and DME (5 mL). The mixture was heated by microwave at 120° C. for one hour. LCMS showed completion. The reaction mixture was concentrated and purified by flash chromatography to give tert-butyl (2-((2-amino-4,5-difluorophenyl)amino)-6-((4-(trifluoromethyl)phenyl)amino)pyridin-4-yl)carbamate (431 mg, 87%).

Step 2. The obtained product (150 mg, 0.3 mmol) was dissolved in acetic acid (1 mL) and 1,1,1-triethoxyethane (0.1 mL) was added. The reaction was stirred at room temperature overnight. LCMS showed a clean formation of the desired product. The reaction mixture was diluted with hexane and the precipitate was collected by filtration to give the desired product tert-butyl (2-(5,6-difluoro-2-methyl-1H-benzo[d]imidazol-1-yl)-6-((4-(trifluoromethyl)phenyl)amino)pyridin-4-yl)carbamate (142 mg, 91%).

Step 3. The obtained product (140 mg, 0.2 mmol) was treated with 4N HCl in dioxane (5 mL). The reaction mixture was stirred at room temperature for 3 hours. The reaction mixture was diluted with EtOAc and washed with aqueous NaHCO₃. The ester layer was collected, dried and evaporated to give the title Compound 231 (80 mg, 95%). ¹H NMR (MeOD-d₄, 500 MHz) δ 7.57 (1H, d, J=8.5 Hz), 7.37 (3H, m), 7.29 (1H, dd, J=10, 7 Hz), 6.21 (1H, d, J=1.7 Hz), 6.11 (1H, d, J=1.7 Hz), 2.54 (3H, s); LCMS m/z 420 [M+H]⁺

Step 4. To a solution of the obtained Compound 231 (70 mg, 0.17 mmol) in MeCN (2 mL) was added SELECTFLUOR® (brand of 1-(chloromethyl)-4-fluoro-1,4-diazabicyclo[2.2.2]octane-1,4-diium tetrafluoroborate) (70 mg, 0.2 mmol) at 0° C. The reaction mixture was stirred at 0° C. for one hour. Aqueous work up followed by flash chromatography gave the title Compound 505 (40 mg, 55%). ¹H NMR (CDCl₃, 500 MHz) δ 7.69 (2H, d, J=8.6 Hz), 7.52 (2H, d, J=8.6 Hz), 7.48 (1H, dd, J=10.2, 7.3 Hz), 7.20 (1H, dd, J=10.1, 7.1 Hz), 6.81 (1H, br d, J=3.2 Hz), 6.35 (1H, d, J=5.2 Hz), 2.63 (3H, s); LCMS m/z 438.1 [M+H]⁺

Additional compounds of Formula (I) or a form thereof described herein may be prepared according to the procedure of Example 75 by substituting the appropriate starting materials, reagents and reaction conditions:

| Cpd | Name and Data |
|---|---|
| 503 | 6-(2-ethyl-5,6-difluoro-1H-benzimidazol-1-yl)-N²-[4-(trifluoromethyl)phenyl]pyridine-2,4-diamine<br>¹H NMR (CDCl₃, 500 MHz) δ 7.56-7.51 (3H, m), 7.44 (2H, d, J = 8.5 Hz), 7.23 (1, dd, J = 10.1, 7 Hz), 6.74 (1H, br s), 6.20 |

-continued

| Cpd | Name and Data |
|---|---|
|  | (2H, m), 3.02 (2H, q, J = 7.5 Hz), 1.39 (3H, t, J = 7.5 Hz); LCMS m/z 434.1 [M + H]+ |
| 504 | 6-(2-cyclopropyl-5,6-difluoro-1H-benzimidazol-1-yl)-N2-[4-(trifluoromethyl)phenyl]pyridine-2,4-diamine LCMS m/z 446.1 [M + H]+ |
| 509 | 6-(2-ethyl-5,6-difluoro-1H-benzimidazol-1-yl)-3-fluoro-N2-[4-(trifluoromethyl)phenyl]pyridine-2,4-diamine 1H NMR (CDCl3, 500 MHz) δ 7.68 (2H, d, J = 8.5 Hz), 7.54-7.50 (3H, m), 7.15 (1H, dd, J = 10, 7 Hz), 6.81 (1H, br d, J = 3.2 Hz), 6.32 (1H, d, J = 3.2 Hz), 2.96 (2H, q, J = 7.5 Hz), 1.35 (3H, t, J = 7.5 Hz); LCMS m/z 452 [M + H]+ |
| 510 | 6-(2-ethyl-1H-benzimidazol-1-yl)-N2-[4-(trifluoromethyl)phenyl]pyridine-2,4-diamine LCMS m/z 398.2 [M + H]+ |
| 515 | 3-fluoro-6-(2-methyl-1H-benzimidazol-1-yl)-N2-[4-(trifluoromethyl)phenyl]pyridine-2,4-diamine 1H NMR (CDCl3, 500 MHz) δ 7.74 (1H, d, J = 7.7 Hz), 7.71 (2H, d, J = 8.5 Hz), 7.51 (2H, d, J = 8.5 Hz), 7.40 (1H, d, J = 7.5 Hz), 7.41-7.21 (3H, m), 6.78 (1H, br d, J = 1.6 Hz), 6.40 (1H, d, J = 5.3 Hz), 2.66 (3H, s); LCMS m/z 402.1 [M + H]+ |
| 424 | N-(2,3-dihydro-1H-inden-2-yl)-6-(2-methyl-1H-benzimidazol-1-yl)pyrazin-2-amine 1H NMR (500 MHz, Acetone-d6) δ 8.08 (1H, s) 8.02 (1H, d, J = 0.63 Hz) 7.62-7.67 (1H, m) 7.53-7.58 (1H, m) 7.22-7.29 (4H, m) 7.13-7.19 (3H, m) 4.74-4.82 (1H, m) 3.41 (2H, dd, J = 15.92, 7.09 Hz) 2.99 (2H, dd, J = 15.92, 5.20 Hz) 2.70 (3H, s); MS m/z 342.1 (ESI) [M + H]+ |
| 440 | N-[6-(2-methyl-1H-benzimidazol-1-yl)pyrazin-2-yl]-6-(trifluoromethyl)-1,3-benzothiazol-2-amine 1H NMR (500 MHz, Acetone-d6) δ 11.32 (1H, br. s.) 8.77 (1H, s) 8.41-8.48 (1H, m) 8.04 (1H, s) 7.61-7.74 (2H, m) 7.50-7.58 (1H, m) 7.40-7.49 (1H, m) 7.16-7.28 (2 H, m) 2.72 (3H, s); MS m/z 427.2 (ESI) [M + H]+ |
| 457 | 6-(2-methyl-1H-benzimidazol-1-yl)-N-[5-(trifluoromethyl)pyridin-2-yl]pyrazin-2-amine 1H NMR (500 MHz, Acetone-d6) δ 9.91 (1H, br. s.) 9.36 (1H, d, J = 0.63 Hz) 8.70 (1H, dt, J = 1.65, 0.91 Hz) 8.56 (1H, d, J = 0.63 Hz) 8.08 (1H, dd, J = 8.83, 2.21 Hz) 7.96 (1H, d, J = 8.83 Hz) 7.65-7.70 (1H, m) 7.56-7.60 (1H, m) 7.24-7.33 (2H, m) 2.70 (3H, s); MS m/z 371.1 (ESI) [M + H]+ |

Example 76

N-[6-(2-methyl-1H-benzimidazol-1-yl)pyrazin-2-yl]-1,3-benzothiazol-2-amine (Cpd 420)

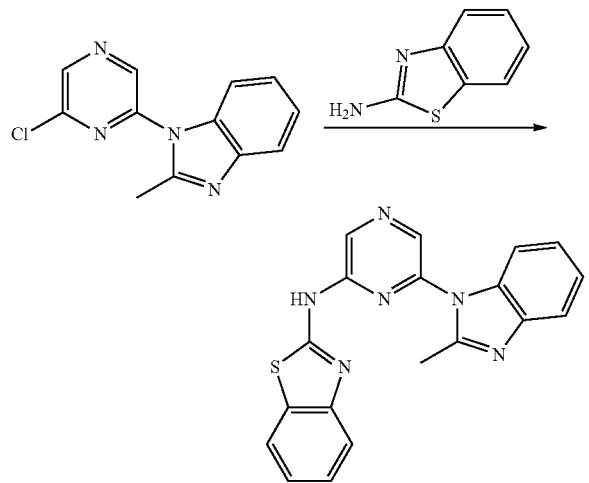

A mixture of 1-(6-chloropyrazin-2-yl)-2-methyl-1H-benzo[d]imidazole (49 mg, 0.20 mmol), 2-aminobenzothiazole (30 mg, 0.40 mmol), Pd2dba3 (6 mg, 3 mol %), 2-dicyclohexylphosphino-2',4',6'-triisopropylbiphenyl (6 mg, 6 mol %) and K3PO4 (127 mg, 0.60 mmol) in DME (1 mL) was heated for 20 hours at 110° C. The crude mixture was purified by column chromatography to provide the title compound as an off-white solid (34 mg, 48%). 1H NMR (500 MHz, Acetone-d6) δ 8.85 (1H, s) 8.56 (1H, d, J=0.63 Hz) 7.87-7.90 (1H, m) 7.69-7.73 (2H, m) 7.58-7.61 (1H, m) 7.44 (1H, ddd, J=8.04, 7.09, 1.26 Hz) 7.25-7.35 (3H, m) 2.77 (3H, s); MS m/z 359.0 [M+H]+.

Additional compounds of Formula (I) or a form thereof described herein may be prepared according to the procedure of Example 76 by substituting the appropriate starting materials, reagents and reaction conditions:

Example 77

6-(quinolin-4-yl)-N-[4-(trifluoromethyl)phenyl]pyrazin-2-amine (Cpd 384)

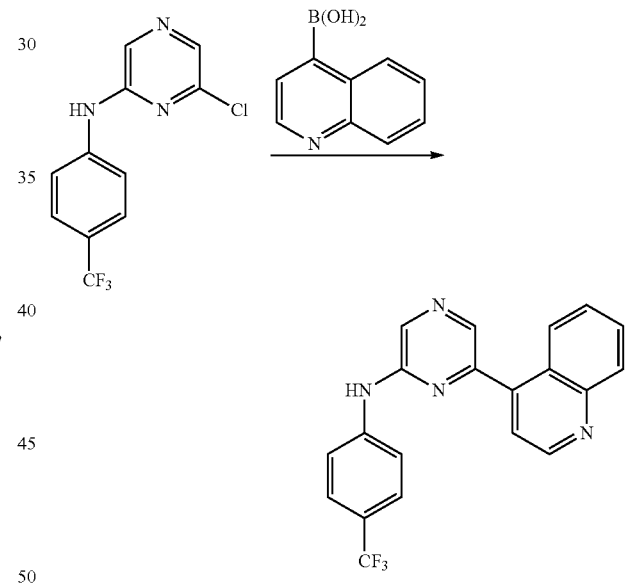

A mixture of 6-chloro-N-(4-(trifluoromethyl)phenyl)pyrazin-2-amine (55 mg, 0.20 mmol), quinolin-4-ylboronic acid (52 mmol, 0.30 mmol), K2CO3 (55 mg, 0.40 mmol) and tetrakis(triphenylphosphine)palladium(0) in dioxane (1 mL) and water (0.2 mL) was heated for 6 hours at 100° C. The resulting crude product was directly loaded onto a short pad of silica gel and purified by column chromatography to provide the title compound as an off white solid (82 mg). 1H NMR (500 MHz, Acetone-d6) δ 9.41 (1H, br. s.) 9.07 (1H, d, J=4.41 Hz) 8.47 (1H, d, J=0.63 Hz) 8.45 (1H, d, J=0.63 Hz) 8.40 (1H, dd, J=8.51, 0.95 Hz) 8.21 (1H, d, J=7.88 Hz) 8.05 (2H, d, J=8.51 Hz) 7.86 (1H, ddd, J=8.43, 6.86, 1.42 Hz) 7.77 (1H, d, J=4.41 Hz) 7.66-7.71 (1H, m) 7.58-7.62 (2H, m); MS m/z 367.1 [M+H]+.

Additional compounds of Formula (I) or a form thereof described herein may be prepared according to the procedure of Example 77 by substituting the appropriate starting materials, reagents and reaction conditions:

| Cpd | Name and Data |
|---|---|
| 353 | 6-(2-methylpyridin-4-yl)-N-[4-(trifluoromethyl)phenyl]pyrazin-2-amine<br>$^1$H NMR (500 MHz, CHLOROFORM-d) δ 8.58-8.61 (1H, m) 8.52 (1H, d, J = 0.63 Hz) 8.22-8.23 (1H, m) 7.63-7.70 (4H, m) 7.56-7.60 (2H, m) 6.82 (1H, s) 2.63 (3H, s); MS m/z 331.0 (ESI) [M + H]$^+$ |
| 354 | 6-(2'-chloro-2,4'-bipyridin-4-yl)-N-[4-(trifluoromethyl)phenyl]pyrazin-2-amine<br>$^1$H NMR (500 MHz, CHLOROFORM-d) δ 8.92 (1H, dd, J = 5.04, 0.95 Hz) 8.70 (1H, s) 8.57 (1H, dd, J = 5.04, 0.63 Hz) 8.46 (1H, dd, J = 1.58, 0.95 Hz) 8.39 (1H, s) 8.08 (1H, dd, J = 1.58, 0.63 Hz) 7.97 (2H, ddd, J = 11.82, 5.20, 1.58 Hz) 7.75-7.80 (2H, m) 7.69-7.72 (2H, m) 7.09 (1H, s); MS m/z 428.0 (ESI) [M + H]$^+$ |
| 385 | 6-(7-chloroquinolin-4-yl)-N-[4-(trifluoromethyl)phenyl]pyrazin-2-amine<br>$^1$H NMR (500 MHz, Acetone-d$_6$) δ 9.41-9.47 (1H, m) 9.09-9.12 (1H, m) 8.48 (1H, s) 8.46 (1H, s) 8.19-8.23 (1H, m) 8.01-8.06 (2H, m) 7.79-7.83 (1H, m) 7.67-7.71 (1H, m) 7.59-7.64 (2H, m) 7.53-7.59 (1H, m); MS m/z 401.1 (ESI) [M + H]$^+$ |
| 407 | 6-(1H-indol-4-yl)-N-[4-(trifluoromethyl)phenyl]pyrazin-2-amine<br>$^1$H NMR (500 MHz, CHLOROFORM-d) δ 8.47 (1H, s) 8.36 (2H, br. s.) 7.78 (2H, d, J = 8.51 Hz) 7.57 (1H, dd, J = 7.57, 0.95 Hz) 7.47-7.55 (3H, m) 7.25-7.31 (2H, m) 6.96-6.99 (1H, m); MS m/z 355.1 (ESI) [M + H]$^+$ |

Example 78

6-[2-(trifluoromethyl)imidazo[1,2-a]pyrazin-3-yl]-N-[4-(trifluoromethyl)phenyl]pyrazin-2-amine (Cpd 93)

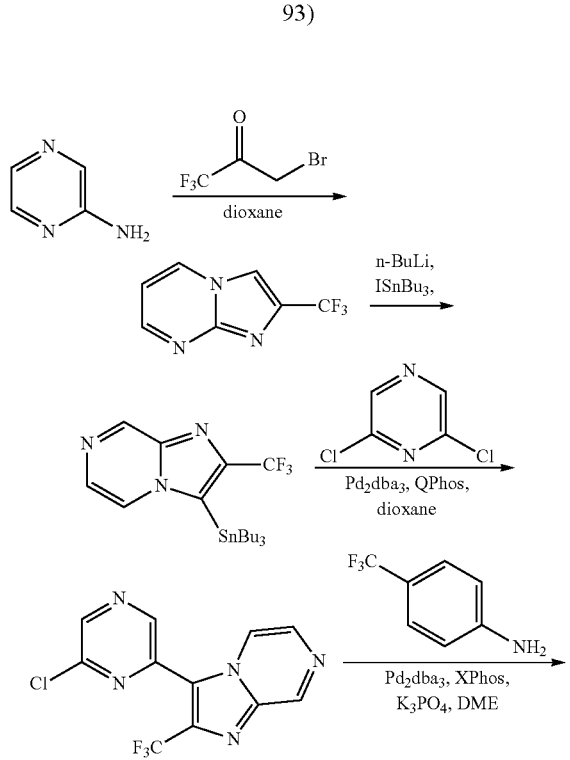

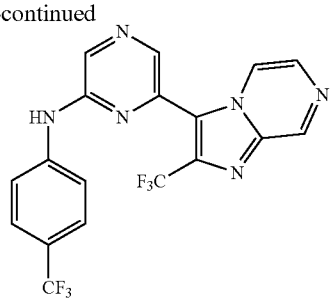

Step 1. To 2-aminopyrazine (4.45 g, 46.3 mmol) in dioxane (50 mL) was added 3-bromo-1,1,1-trifluoropropan-2-one (9.14 g, 47.9 mmol). The mixture was heated overnight at 50° C. The resulting precipitate was collected on a filter, washed with EtOAc (2×50 mL) and dried under vacuum. The residue (12.33 g) was suspended in isopropanol (50 mL) and heated for one hour at reflux. The mixture was cooled to room temperature, then EtOAc (100 mL) and a saturated aqueous solution of NaHCO$_3$ (100 mL) were added. The aqueous layer was extracted with EtOAc (100 mL). The combined organics were washed with brine (100 mL), then dried over Na$_2$SO$_4$ and concentrated to provide 7-(trifluoromethyl)pyrrolo[1,2-a]pyrazine as a light brown crystalline solid (6.06 g, 70%).

Step 2. To 7-(trifluoromethyl)pyrrolo[1,2-a]pyrazine (1.02 g, 5.50 mmol) in THF (20 mL) at −78° C. was slowly added n-butyl lithium (2.64 mL, 2.5 M in hexanes). The mixture was stirred for 20 minutes, then tri-n-butyltin iodide (2.27 mL) was added all at once. The mixture warmed to room temperature, then DCM (20 mL) was added. The solution was passed through a plug of silica, washed with 40% EtOAc:hexane and concentrated. Chromatography on silica (0 to 20% EtOAc:hexane as eluent) provided 6-(tributylstannyl)-7-(trifluoromethyl)pyrrolo[1,2-a]pyrazine as a clear oil (1.87 g, 78%).

Step 3. A mixture of the obtained product (0.37 g, 0.78 mmol), 2,6-dichloropyrazine (0.35 g, 2.28 mmol), Pd$_2$dba$_3$ (22 mg, 0.024 mmol) and Q-Phos (18 mg, 0.024 mmol) was flushed with argon for 20 minutes, then dioxane (5 mL) was added. The mixture was heated at 100° C. for 2 hours and a second portion of 2,6-dichloropyrazine (0.11 g, 0.72 mmol) was added. The mixture was heated for additional 2 hours, then concentrated and chromatographed on silica (20 to 50% EtOAc:hexane as eluent) to provide 6-(6-chloropyrazin-2-yl)-7-(trifluoromethyl)pyrrolo[1,2-a]pyrazine as a tan crystalline solid (101 mg, 44%).

Step 4. A mixture of the obtained product (40.9 mg, 0.136 mmol), Pd$_2$dba$_3$ (7.5 mg, 0.008 mmol), X-Phos (8.2 mg, 0.017 mmol) and tripotassium phosphate (90 mg, 0.411 mmol) were flushed with argon for 20 minutes, then dimethoxyethane (1 mL) and 4-trifluoromethylaniline (34 µL, 0.271 mmol) were added. The resulting mixture was heated at 105° C. for 2 hours, then cooled and concentrated under a stream of nitrogen. The product was chromatographed on silica (gradient from 50% EtOAc:hexane to 10% MeOH:DCM) to provide the title compound as a tan solid (49.4 mg, 85%). $^1$H NMR (500 MHz, Acetone-d$_6$) δ 7.62 (d, J=8.83 Hz, 3H) 7.98 (d, J=8.20 Hz, 3H) 8.12 (d, J=4.73 Hz, 2H) 8.38-8.53 (m, 3H) 8.84-8.94 (m, 2H) 9.26 (s, 1H) 9.47 (br. s., 1H); MS m/z 425 (ESI) [M+H]$^+$.

Additional compounds of Formula (I) or a form thereof described herein may be prepared according to the procedure of Example 78 by substituting the appropriate starting materials, reagents and reaction conditions:

| Cpd | Name and Data |
|---|---|
| 141 | N-[4-(trifluoromethoxy)phenyl]-6-[2-(trifluoromethyl)imidazo[1,2-a]pyrazin-3-yl]pyrazin-2-amine<br>$^1$H NMR (500 MHz, Acetone-$d_6$) δ 9.11 (d, J = 1.58 Hz, 1H) 8.71 (dd, J = 4.73, 1.58 Hz, 1H)) 8.25 (s, 1H) 8.20 (s, 1H 9.12 (br. s., 1H) 7.95 (d, J = 4.73 Hz, 1H) 7.69-7.78 (m, 2H) 7.10-7.17 (m, 2H); MS m/z 441.2 (ESI) [M + H]$^+$ |
| 142 | N-[4-(difluoromethoxy)phenyl]-6-[2-(trifluoromethyl)imidazo[1,2-a]pyrazin-3-yl]pyrazin-2-amine<br>$^1$H NMR (500 MHz, Acetone-$d_6$) δ 9.24 (d, J = 1.26 Hz, 1H) 9.10-9.17 (m, 1H) 8.85 (dd, J = 4.73, 1.58 Hz, 1H) 8.37 (s, 1H) 8.31 (s, 1H) 8.09 (d, J = 4.73 Hz, 1H) 7.74-7.82 (m, 2H) 7.10-7.18 (m, 2H) 6.90 (t, J = 74.70 Hz, 1H); MS m/z 423.2 (ESI) [M + H]$^+$ |
| 168 | N-(4-methylphenyl)-6-[2-(trifluoromethyl)imidazo[1,2-a]pyrazin-3-yl]pyrazin-2-amine<br>$^1$H NMR (500 MHz, Acetone-$d_6$) δ 9.24 (d, J = 1.58 Hz, 1H) 8.91-8.98 (m, 1H) 8.85-8.89 (m, 1H) 8.26 (s, 1H) 8.34 (s, 1H) 8.08 (d, J = 4.73 Hz, 1H) 7.60 (d, J = 8.51 Hz, 2H) 7.13 (d, J = 8.20 Hz, 2H) 2.28 (s, 3H); MS m/z 371.2 (ESI) [M + H]$^+$ |
| 194 | 6-[2-(trifluoromethyl)imidazo[1,2-a]pyrazin-3-yl]-N-[4-(trifluoromethyl)phenyl]pyridin-2-amine<br>$^1$H NMR (500 MHz, Acetone-$d_6$) δ 9.22 (d, J = 1.58 Hz, 1H) 9.07 (s, 1H) 8.86 (dd, J = 4.73, 1.58 Hz, 1H) 8.07 (d, J = 4.73 Hz, 1H) 7.87-7.97 (m, 3H) 7.56 (d, J = 8.51 Hz, 2H) 7.30 (d, J = 7.25 Hz, 1H) 7.10-7.17 (m, 1H); MS m/z 424.2 (ESI) [M + H]$^+$ |
| 195 | N-[4-(trifluoromethoxy)phenyl]-6-[2-(trifluoromethyl)imidazo[1,2-a]pyrazin-3-yl]pyridin-2-amine<br>$^1$H NMR (500 MHz, Acetone-$d_6$) δ 9.21 (d, J = 1.58 Hz, 1H) 8.87 (dd, J = 4.89, 1.42 Hz, 1H) 8.83 (s, 1H) 8.04 (d, J = 4.73 Hz, 1H) 7.23 (m, 3H) 7.06 (d, J = 8.20 Hz, 1H); MS m/z 440.2 (ESI) [M + H]$^+$ |
| 196 | N-[4-(difluoromethoxy)phenyl]-6-[2-(trifluoromethyl)imidazo[1,2-a]pyrazin-3-yl]pyridin-2-amine<br>$^1$H NMR (500 MHz, Acetone-$d_6$) δ 9.20 (d, J = 1.58 Hz, 1H) 8.88 (dd, J = 4.89, 1.42 Hz, 1H) 8.69 (s, 1H) 8.04 (d, J = 4.73 Hz, 1H) 7.83 (dd, J = 8.35, 7.41 Hz, 1H) 7.70-7.76 (m, 2H) 7.18-7.23 (m, 1H) 7.10 (dd, J = 1.00, 1.00 Hz, 2H) 7.00-7.05 (m, 1H) 6.88 (t, J = 74.70 Hz, 1H); MS m/z 422.2 (ESI) [M + H]$^+$ |
| 211 | 6-[2-(trifluoromethyl)imidazo[1,2-a]pyridin-3-yl]-N-{4-[(trifluoromethyl)sulfanyl]phenyl}pyrazin-2-amine<br>$^1$H NMR (500 MHz, Acetone-$d_6$) δ 9.39 (s, 1H) 8.86 (dt, J = 7.09, 1.18 Hz, 1H) 8.40 (s, 1H) 8.36 (s, 1H) 7.89-7.98 (m, 2H) 7.78 (dt, J = 9.14, 1.10 Hz, 1H) 7.60-7.63 (m, 2H) 7.57 (ddd, J = 9.14, 6.62, 1.26 Hz, 1H) 7.14 (td, J = 6.94, 1.26 Hz, 1H); MS m/z 456.2 (ESI) [M + H]$^+$ |
| 212 | 2,2,2-trifluoro-1-[4-({6-[2-(trifluoromethyl)imidazo[1,2-a]pyridin-3-yl]pyrazin-2-yl}amino)phenyl]ethanone<br>$^1$H NMR (500 MHz, Acetone-$d_6$) δ 9.75 (br. s., 1H) 8.88 (dt, J = 7.02, 1.22 Hz, 1H) 8.48 (s, 1H) 8.45 (s, 1H) 7.99-8.09 (m, 4H) 7.79 (dt, J = 9.14, 1.10 Hz, 1H) 7.59 (ddd, J = 9.22, 6.70, 1.10 Hz, 1H) 7.16 (td, J = 6.86, 1.10 Hz, 1H); MS m/z 452.2 (ESI) [M + H]$^+$ |

Example 79

[3-(6-{[4-(trifluoromethyl)phenyl]amino}pyrazin-2-yl)imidazo[1,2-a]pyridin-2-yl]methanol (Cpd 151)

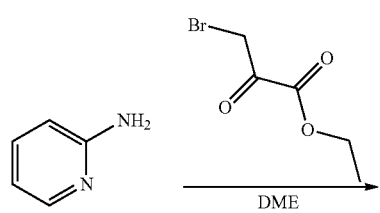

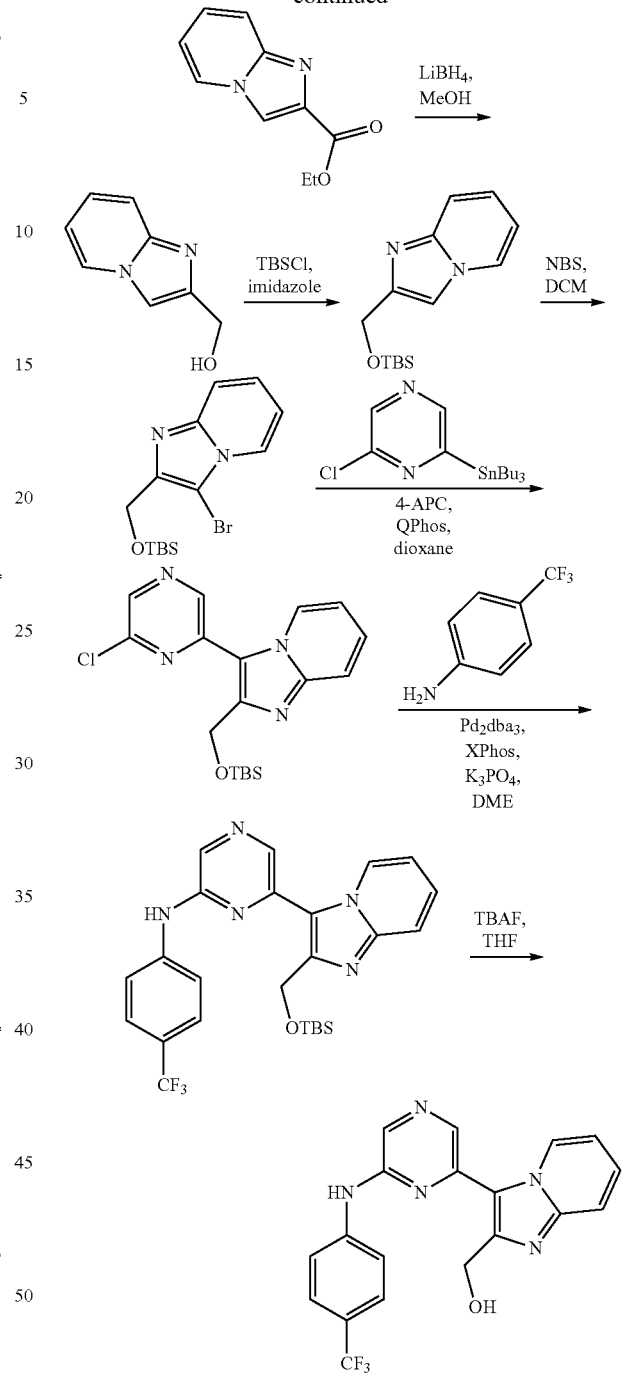

Step 1. To 2-aminopyridine (12.03 g, 127.8 mmol) in dimethoxyethane (100 mL) was added ethyl 3-bromo-2-oxopropanoate ethyl bromopyruvate (17.9 mL, 128.0 mmol). The mixture was stirred at room temperature for 3 hours. The resulting precipitate was collected on a filter, washed with diethyl ether and dried under vacuum. The residue (33.75 g) was suspended in ethanol (100 mL) and heated for 2 hours at reflux, then cooled to room temperature and the solvent removed on a rotovap to provide ethyl indolizine-2-carboxylate (34.74 g, 100%) as an HBr salt. A portion of the salt (3.02 g) was taken up in DCM (50 mL) and neutralized to about pH 7 with a saturated aqueous solution of NaHCO$_3$ (100 mL). The product was then extracted with DCM (3×20 mL) and the combined organics were dried over Na$_2$SO$_4$, then concentrated and chromatographed on silica (1 to 5% MeOH:DCM as eluent) to provide ethyl indolizine-2-carboxylate as a light brown crystalline solid (1.83 g, 86%).

Step 2. To ethyl indolizine-2-carboxylate (7.12 g, 37.4 mmol) in THF (100 mL) at 0° C. was added methanol (1 mL) and then LiBH$_4$ (57 mL, 2.0 M in THF) via slow addition. The mixture was heated at 60° C. for 3 hours, then cooled to room temperature overnight. The mixture was further cooled to 0° C. and water (100 mL) was added. The pH was adjusted to about pH 7 with 1 N HCl and the resulting precipitate was collected on a filter. The product was washed with diethyl ether and dried under vacuum to provide indolizin-2-ylmethanol BH$_3$ adduct as a white solid (5.19 g).

Step 3. To the obtained product (5.19 g, 35.0 mmol) was added DMF (60 mL), imidazole (4.81 g, 70.6 mmol) and t-butyldimethylsilyl chloride (7.94 g, 50.0 mmol). The mixture was stirred at room temperature for 4 hours, then poured into water (150 mL) and extracted with EtOAc (6×25 mL). The product was dried over Na$_2$SO$_4$ and concentrated to provide a clear oil (12.58 g). The oil was taken up in methanol (100 mL), then palladium on carbon (0.5 g, 10%) was added. The mixture was stirred overnight, filtered through Celite, then washed with methanol and concentrated to provide the product as a clear, light yellow oil (10.54 g).

Step 4. To a solution of the obtained product (1.79 g, 6.82 mmol) in DCM (40 mL) at 0° C. was added N-bromosuccinamide (1.24 g, 69.7 mmol) in several portions. The mixture was allowed to warm to room temperature over 2 hours and was then poured into a saturated aqueous solution of NaHCO$_3$ (10 mL). The product was extracted with DCM (5×20 mL), dried over Na$_2$SO$_4$, then concentrated and chromatographed on silica (20 to 50% EtOAc:hexane as eluent) to provide 1.69 g (72%) of 3-bromo-2-((tert-butyldimethylsilyloxy)methyl)indolizine as a white crystalline solid.

Step 5. A mixture of 2-((tert-butyldimethylsilyloxy)methyl)indolizine (143 mg, 0.418 mmol), APC (9.6 mg, 0.026 mmol) and Q-Phos (37.7 mg, 0.053 mmol) was flushed with nitrogen for 30 minutes, then dioxane (4 mL) and 2-chloro-6-(tributylstannyl)pyrazine (286 mg, 0.708 mmol) (prepared as described in Buron, F. et al *Journal of Organic Chemistry* 70(7), 2616-2621; 2005) were added. The mixture was heated at 105° C. for 30 minutes, cooled, then concentrated under a stream of nitrogen and chromatographed on silica (40 to 100% EtOAc:hexane as eluent) to provide 2-((tert-butyldimethylsilyloxy)methyl)-3-(6-chloropyrazin-2-yl)indolizine as a cream colored crystalline solid (64.8 mg, 41%).

Step 6. A mixture of 2-((tert-butyldimethylsilyloxy)methyl)-3-(6-chloropyrazin-2-yl)indolizine (57.4 mg, 0.153 mmol), Pd$_2$dba$_3$ (8.8 mg, 0.010 mmol), X-Phos (9.5 mg, 0.019 mmol) and tripotassium phosphate (101 mg, 0.461 mmol) was flushed with nitrogen for 30 minutes, then dimethoxyethane (2 mL) and 4-trifluoromethylaniline (40 μL, 0.318 mmol) were added. The resulting mixture was heated at 105° C. for 2 hours, cooled, then concentrated under a stream of nitrogen and chromatographed on silica (1 to 10% MeOH:DCM as eluent) to provide 6-(2-((tert-butyldimethylsilyloxy)methyl)indolizin-3-yl)-N-(4-(trifluoromethyl)phenyl)pyrazin-2-amine as a tan solid (40.9 mg, 53%).

Step 7. To the obtained product (36.7 mg, 0.073 mmol) in THF at 0° C. was added tetrabutylammonium fluoride (74 μL, 1.0 M in THF). The mixture was allowed to warm to room temperature over 4 hours, was concentrated under a stream of nitrogen and chromatographed on silica (5 to 10% MeOH:DCM as eluent) to provide the title compound as a light green solid (18.4 mg, 65%). MS m/z 386.2 M+H$^+$; $^1$H NMR (500 MHz, Acetone-d$_6$) δ 9.64 (s, 1H) 9.29 (dt, J=7.09, 1.18 Hz, 1H) 8.66 (s, 1H) 8.30 (s, 1H) 7.97 (d, J=8.51 Hz, 2H) 7.58-7.73 (m, 3H) 7.41 (ddd, J=8.99, 6.78, 1.26 Hz, 1H) 6.93-7.06 (m, 1H) 4.86 (d, J=5.67 Hz, 2H) 4.70 (s, 1H)

Additional compounds of Formula (I) or a form thereof described herein may be prepared according to the procedure of Example 79 by substituting the appropriate starting materials, reagents and reaction conditions:

| Cpd | Name and Data |
|---|---|
| 213 | [3-(6-{[4-(trifluoromethoxy)phenyl]amino}pyrazin-2-yl)imidazo[1,2-a]pyridin-2-yl]methanol<br>$^1$H NMR (500 MHz, Acetone-d$_6$) δ 9.59-9.76 (m, 1H) 8.38-8.51 (m, 3H) 7.87-7.99 (m, 2H) 7.61 (d, J = 8.83 Hz, 1H) 7.23-7.42 (m, 4H) 4.73 (br. s., 2H) 4.35-4.48 (m, 1H); MS m/z 402.2 (ESI) [M + H]$^+$ |
| 214 | (3-{6-[(4-methylphenyl)amino]pyrazin-2-yl}imidazo[1,2-a]pyridin-2-yl)methanol<br>$^1$H NMR (500 MHz, Acetone-d$_6$) δ 9.34-9.39 (m, 1H) 9.06 (s, 1H) 8.54 (s, 1H) 8.19 (s, 1H) 7.57-7.66 (m, 3H) 7.38 (d, J = 1.26 Hz, 1H) 7.15 (d, J = 8.20 Hz, 2H) 6.94 (d, J = 1.26 Hz, 1H) 4.84 (d, J = 5.67 Hz, 2H) 4.71-4.75 (m, 1H) 2.30 (s, 3H); MS m/z 332.2 (ESI) [M + H]$^+$ |
| 215 | [3-(6-{[4-(difluoromethoxy)phenyl]amino}pyrazin-2-yl)imidazo[1,2-a]pyridin-2-yl]methanol<br>$^1$H NMR (500 MHz, Acetone-d$_6$) δ 9.32 (dt, J = 7.09, 1.18 Hz, 1H) 8.89 (s, 1H) 8.57 (s, 1H) 8.19 (s, 1H) 7.71-7.82 (m, 2H) 7.63 (dt, J = 8.98, 1.02 Hz, 1H) 7.34-7.45 (m, 1H) 7.15-7.23 (m, 2H) 6.96 (d, J = 1.26 Hz, 1H) 6.93 (t, J = 74.70 Hz, 1H) 4.88 (d, J = 5.67 Hz, 2H) 4.36 (s, 1H); MS m/z 384.2 (ESI) [M + H]$^+$ |
| 328 | [6-fluoro-3-(6-{[4-(trifluoromethyl)phenyl]amino}pyrazin-2-yl)imidazo[1,2-a]pyridin-2-yl]methanol<br>$^1$H NMR (500 MHz, Acetone-d$_6$) δ 9.38-9.46 (m, 1H) 9.24-9.32 (m, 1H) 8.72 (s, 1H) 8.29 (s, 1H) 7.91-7.99 (m, 2H) 7.68 (s, 3H) 7.35-7.48 (m, 1H) 4.90 (d, J = 5.67 Hz, 2H) 4.47 (t, J = 6.00 Hz, 1H); MS m/z 404.1 (ESI) [M + H]$^+$ |

Example 80

2-[2-(hydroxymethyl)imidazo[1,2-a]pyridin-3-yl]-6-{[4-(trifluoromethyl)phenyl]amino}pyridine-4-carbonitrile (Cpd 288)

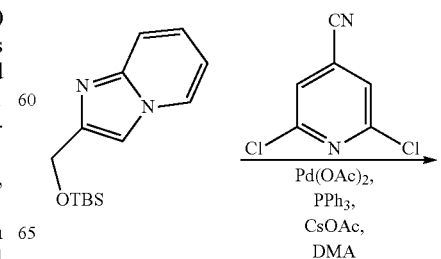

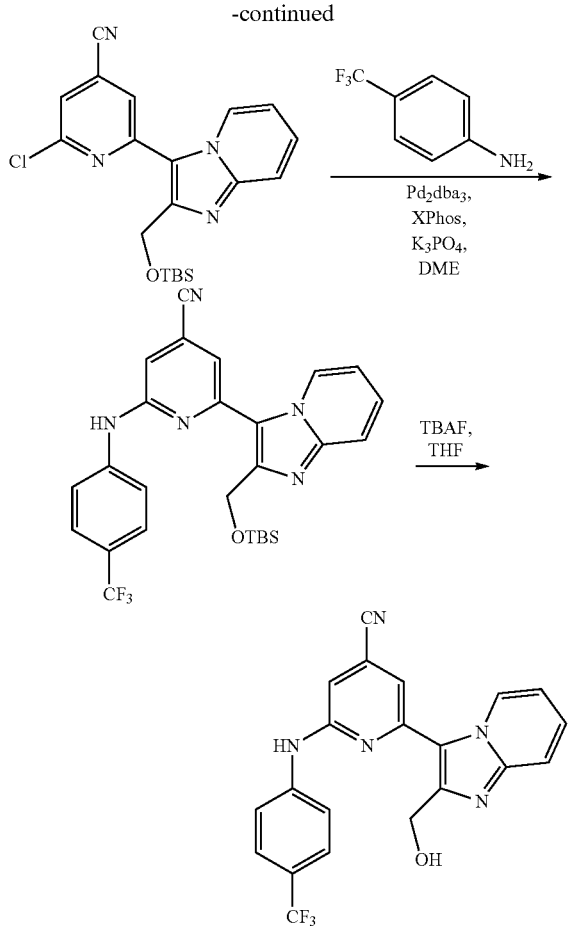

Step 1. A mixture of 2-((tert-butyldimethylsilyloxy) methyl)indolizine (0.28 g, 1.1 mmol) (prepared using the procedure described in Example 79 and appropriate starting materials, reagents and reaction conditions), Pd(OAc)$_2$ (12 mg, 0.052 mmol), triphenylphosphine (17 mg, 0.066 mmol), cesium acetate (0.41 g, 2.1 mmol) and 2,6-dichloroisonicotinonitrile (0.35 mg, 2.0 mmol) was flushed with nitrogen for 30 minutes, then dimethylacetamide (2 mL) was added. The reaction mixture was heated at 100° C. for 40 minutes and a second portion of Pd(OAc)$_2$ (12 mg, 0.052 mmol), triphenylphosphine (18 mg, 0.069 mmol) and cesium acetate (0.42 g, 2.2 mmol) was added. The obtained mixture was heated for an additional 20 minutes, then cooled to room temperature and EtOAc (20 mL) was added. The obtained solution was washed with brine (4×5 mL), dried over Na$_2$SO$_4$, then concentrated and chromatographed on silica (gradient from EtOAc:hexane 20:50 to 10% MeOH:DCM) to provide 2-(2-((tert-butyldimethylsilyloxy)methyl)indolizin-3-yl)-6-chloroisonicotinonitrile as a white, crystalline solid (47.8 mg, 11%).

Step 2. A mixture of 2-(2-((tert-butyldimethylsilyloxy) methyl)indolizin-3-yl)-6-chloroisonicotinonitrile (47.8 mg, 0.120 mmol), Pd$_2$dba$_3$ (6.6 mg, 0.007 mmol), XPhos (7.2 mg, 0.015 mmol) and tripotassium phosphate (80 mg, 0.36 mmol) was flushed with nitrogen for 30 minutes, then dimethoxyethane (2 mL) and 4-trifluoromethylaniline (30 µL, 0.24 mmol) were added. The resulting mixture was heated at 105° C. for 2 hours, cooled, then concentrated under a stream of nitrogen and chromatographed on silica (1 to 10% MeOH:DCM as eluent) to provide 2-(2-((tert-butyldimethylsilyloxy)methyl)indolizin-3-yl)-6-(4-(trifluoromethyl)phenylamino)isonicotinonitrile as a light yellow solid (84.6 mg) used in the next step without further purification.

Step 3. To a solution of the obtained product (84.6 mg, 0.12 mmol) in THF at room temperature was added tetrabutylammonium fluoride (0.14 mL, 1.0 M in THF). The mixture was stirred overnight, then concentrated under a stream of nitrogen and chromatographed on silica (5 to 10% MeOH:DCM as eluent) to provide the title compound as a light yellow solid (59.2 mg, 90% for two steps). $^1$H NMR (500 MHz, Acetone-d$_6$) δ 9.60-9.75 (m, 1H) 9.37 (d, J=6.94 Hz, 1H) 7.91 (d, J=8.51 Hz, 2H) 7.83 (d, J=1.26 Hz, 1H) 7.58-7.69 (m, 3H) 7.37-7.47 (m, 1H) 7.22 (d, J=0.95 Hz, 1H) 6.96 (d, J=1.26 Hz, 1H) 4.81-4.94 (m, 3H)

Additional compounds of Formula (I) or a form thereof described herein may be prepared according to the procedure of Example 80 by substituting the appropriate starting materials, reagents and reaction conditions:

| Cpd | Name and Data |
|---|---|
| 289a | [3-(4-amino-6-{[4-(trifluoromethyl)phenyl]amino}pyridin-2-yl)imidazo[1,2-a]pyridin-2-yl)methanol hydrochloride (1:2) <br> $^1$H NMR (500 MHz, DMSO-d$_6$) δ 9.90-10.12 (m, 1H) 9.13 (d, J = 5.04 Hz, 1H) 7.93-8.08 (m, 3H) 7.64 (s, 4H) 7.45-7.57 (m, 2H) 6.67 (s, 1H) 6.36 (s, 1H) 4.81-5.02 (m, 3H) |
| 383 | 2-[6-fluoro-2-(hydroxymethyl)imidazo[1,2-a]pyridin-3-yl]-6-{[4-(trifluoromethyl)phenyl]amino}pyridine-4-carbonitrile <br> $^1$H NMR (500 MHz, CHLOROFORM-d) δ 9.46-9.51 (m, 1H) 9.30 (br. s, 1H) 7.84-7.91 (m, 3H) 7.63-7.73 (m, 3H) 7.39-7.46 (m, 1H) 7.23 (d, J = 0.95 Hz, 1H) 4.91 (d, J = 5.36 Hz, 2H) 4.54-4.62 (m, 1H); MS m/z 428.1 (ESI) [M + H]$^+$ |
| 393 | 2-{[4-(difluoromethoxy)phenyl]amino}-6-[6-fluoro-2-(hydroxymethyl)imidazo[1,2-a]pyridin-3-yl]pyridine-4-carbonitrile <br> $^1$H NMR (500 MHz, Acetone-d$_6$) δ 9.42-9.58 (m, 1H) 8.94 (s, 1H) 7.77 (d, J = 1.26 Hz, 1H) 7.61-7.71 (m, 3H) 7.40 (ddd, J = 9.93, 7.72, 2.52 Hz, 1H) 7.17-7.24 (m, 2H) 7.06-7.12 (m, 1H) 6.93 (t, J = 74.70 Hz, 1H) 4.89 (d, J = 5.36 Hz, 2H) 4.60 (t, J = 5.52 Hz, 1H); MS m/z 426.1 (ESI) [M + H]$^+$ |
| 394 | 2-{[4-(difluoromethoxy)-3-fluorophenyl]amino}-6-[6-fluoro-2-(hydroxymethyl)imidazo[1,2-a]pyridin-3-yl]pyridine-4-carbonitrile <br> $^1$H NMR (500 MHz, Acetone-d$_6$) δ 9.41-9.52 (m, 1H) 9.15 (s, 1H) 7.83 (d, J = 0.95 Hz, 1H) 7.75 (dd, J = 12.61, 2.52 Hz, 1H) 7.65-7.72 (m, 1H) 7.39-7.45 (m, 2H) 7.33 (t, J = 8.50 Hz, 1H) 7.16 (d, J = 1.26 Hz, 1H) 6.93 (t, J = 73.80 Hz, 1H) 4.90 (d, J = 5.36 Hz, 2H) 4.59 (t, J = 5.40 Hz, 1H); MS m/z 444.0 (ESI) [M + H]$^+$ |
| 395 | 2-[6-fluoro-2-(hydroxymethyl)imidazo[1,2-a]pyridin-3-yl]-6-{[3-fluoro-4-(trifluoromethyl)phenyl]amino}pyridine-4-carbonitrile <br> $^1$H NMR (500 MHz, Acetone-d$_6$) δ 9.52 (br. s, 1H) 9.42-9.47 (m, 1H) 7.92 (d, J = 1.26 Hz, 1H) 7.85-7.91 (m, 1H) 7.69-7.74 (m, 1H) 7.66 (t, J = 8.50 Hz, 1H) 7.52-7.57 (m, 1H) 7.41-7.48 (m, 1H) 7.26 (d, J = 0.95 Hz, 1H) 4.91 (d, J = 5.36 Hz, 2H) 4.61 (t, J = 5.70 Hz, 1H); MS m/z 446.0 (ESI) [M + H]$^+$ |
| 445 | 2-[6-fluoro-2-(hydroxymethyl)imidazo[1,2-a]pyridin-3-yl]-6-{[6-(trifluoromethyl)pyridin-3-yl]amino}pyridine-4-carbonitrile <br> $^1$H NMR (500 MHz, DMSO-d$_6$) δ 10.27 (s, 1H) 9.20-9.31 (m, 1H) 8.87 (d, J = 2.52 Hz, 1H) 8.30-8.37 (m, 1H) 7.79-7.82 (m, 2H) 7.78 (s, 1H) 7.48-7.54 (m, 1H) 7.24 (d, J = 0.95 Hz, 1H) 5.58 (t, J = 5.70 Hz, 1H) 4.71 (d, J = 5.36 Hz, 2H); MS m/z 429.1 (ESI) [M + H]$^+$ |
| 446 | 2-[(6-chloropyridin-3-yl)amino]-6-[6-fluoro-2-(hydroxymethyl)imidazo[1,2-a]pyridin-3-yl]pyridine-4-carbonitrile <br> $^1$H NMR (500 MHz, DMSO-d$_6$) δ 9.86-10.18 (m, 1H) 9.18-9.29 (m, 1H) 8.58 (d, J = 2.52 Hz, 1H) 8.09 (dd, J = 8.83, 2.84 Hz, 1H) 7.72 (d, J = 0.95 Hz, 2H) 7.47-7.54 (m, 1H) 7.42 (d, J = 8.51 Hz, 1H) 7.15 (d, J = 0.95 Hz, 1H) 5.46-5.67 (m, 1H) 4.70 (s, 2H); MS m/z 395.1 (ESI) [M + H]$^+$ |

Example 81

6-{2-[(methylamino)methyl]imidazo[1,2-a]pyridin-3-yl}-N-[4-(trifluoromethyl)phenyl]pyrazin-2-amine (Cpd 302)

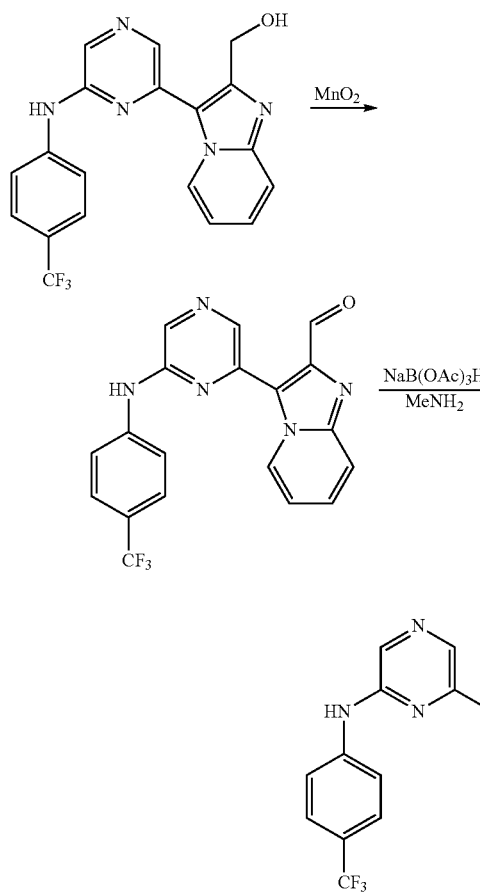

Step 1. To a mixture of Compound 151 (0.12 g, 0.31 mmol) (prepared using the procedure described in Example 79 and appropriate starting materials, reagents and reaction conditions) in DCM (10 mL) at room temperature was added manganese dioxide (0.62 g, 6.4 mmol) in three portions over 48 hours. The reaction mixture was filtered through a plug of Celite, rinsing with DCM, followed by 10% MeOH: DCM. The product was eluted and concentrated to give a dark solid (80 mg, 68%), used in the next step without further purification.

Step 2. To a mixture of the obtained product (27.6 mg, 0.072 mmol) in dichloroethane (3 mL) at room temperature was added acetic acid (8.5 µL, 0.15 mmol), dimethylamine (72 µL, 2 M in THF) and NaB(OAc)$_3$H (23 mg, 0.11 mmol). The mixture was reacted for 3 hours, then water was added. The remaining starting material precipitated (8.9 mg) and was removed by filtration. To the aqueous layer was added a saturated aqueous solution of NaHCO$_3$, then the resulting precipitate was collected by filtration and dried under a stream of nitrogen to provide the title compound as a brown powder (7.3 mg, 38%). MS m/z 399.5 M+H$^+$; $^1$H NMR (500 MHz, DMSO-d$_6$) δ 10.16 (br. s, 1H) 9.03-9.15 (m, 1H) 8.50-8.59 (m, 1H) 8.20-8.32 (m, 1H) 7.80-7.95 (m, 2H) 7.57-7.71 (m, 3H) 7.35-7.45 (m, 1H) 6.95-7.06 (m, 1H) 3.84-3.93 (m, 2H) 2.35 (s, 3H) 2.19-2.26 (m, 1H)

Example 82

2-(6-chloro-2-methyl-1H-imidazo[4,5-b]pyridin-1-yl)-6-{[4-(trifluoromethyl)phenyl]amino}pyridine-4-carbonitrile (Cpd 419)

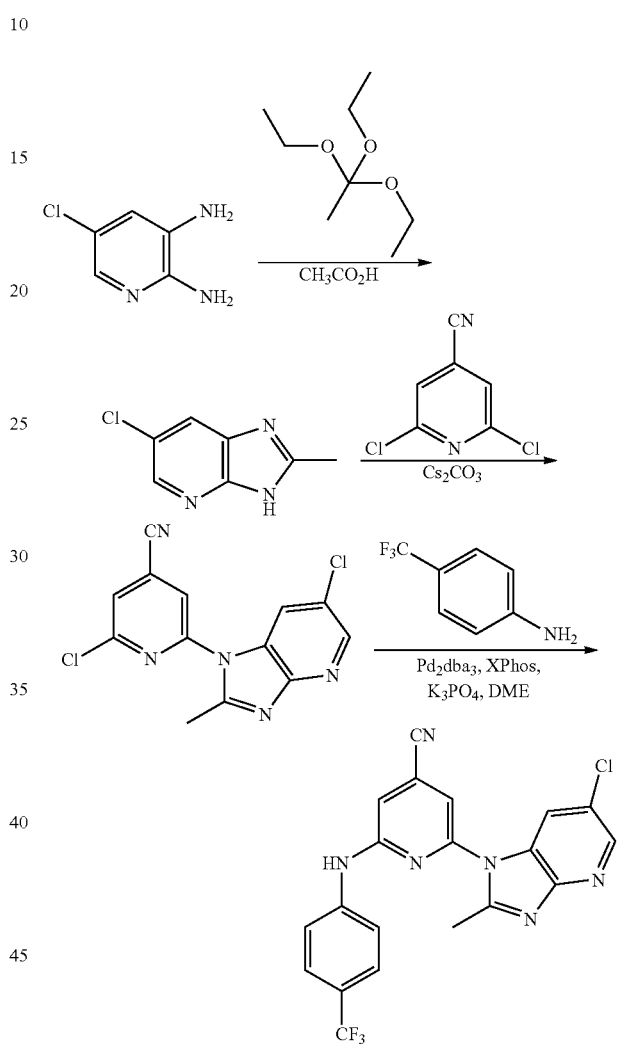

Step 1. To 5-chloro-2, 3-diaminopyridine (2.98 g, 20.1 mmol) in acetic acid (35 mL) at room temperature was added triethyl orthoacetate (12 mL, 63 mmol). The mixture was reacted for three days, diluted with water (30 mL), then the pH adjusted to about pH 6 with addition of solid Na$_2$CO$_3$. The resulting precipitate was collected on a filter, washed with water and dried at 50° C. in a vacuum oven to provide 6-chloro-2-methyl-3H-imidazo[4,5-b]pyridine as a tan solid (2.60 g, 77%).

Step 2. To 6-chloro-2-methyl-3H-imidazo[4,5-b]pyridine (0.28 g, 1.67 mmol) in DMF (4 mL) at room temperature was added cesium carbonate (0.60 g, 1.83 mmol). The mixture was reacted for 20 minutes, then 2,6-dichloroisonicotinonitrile (0.58 g, 3.35 mmol) was added. The mixture was reacted for 3 days, poured into water (10 mL) and the resulting precipitate was collected on a filter and dried under a stream of nitrogen. The mixture was chromatographed on silica (gradient from 20 to 50% EtOAc:hexane, then 10% MeOH:DCM) to provide a chromatographically faster regioisomer, 2-chloro-6-(6-chloro-2-methyl-3H-imidazo[4,5-b]pyridin-3-yl)isonicotinonitrile (27.8 mg, 5%), and a chromatographically slower regioisomer, 2-chloro-6-(6-chloro-2-methyl-1H-imidazo[4,5-b]pyridin-1-yl)isonicotinonitrile (0.16 g, 31%).

Step 3. A mixture of 2-chloro-6-(6-chloro-2-methyl-1H-imidazo[4,5-b]pyridin-1-yl)isonicotinonitrile (0.64 g, 0.120 mmol), Pd$_2$dba$_3$ (0.12 g, 0.12 mmol), X-Phos (0.13 mg, 0.27 mmol) and tripotassium phosphate (1.37 g, 6.27 mmol) was flushed with nitrogen for one hour, then dimethoxyethane (2 mL) and 4-trifluoromethylaniline (0.35 mL, 2.79 mmol) were added. The resulting mixture was evacuated three times via vacuum and argon refill and then heated at 80° C. for 2 hours. The mixture was cooled, then concentrated under a stream of nitrogen and chromatographed on silica (gradient from 50% EtOAc:hexane to 10% MeOH:DCM) to provide the title compound as a light tan solid (0.31 g, 34%). MS m/z 429.1 M+H$^+$; $^1$H NMR (500 MHz, Acetone-d$_6$) δ 9.52 (s, 1H) 8.43 (d, J=2.21 Hz, 1H) 8.14 (d, J=2.52 Hz, 1H) 7.92 (d, J=8.51 Hz, 2H) 7.66 (d, J=8.51 Hz, 2H) 7.57 (d, J=0.95 Hz, 1H) 7.43 (d, J=0.95 Hz, 1H) 2.83 (s, 3H)

Additional compounds of Formula (I) or a form thereof described herein may be prepared according to the procedure of Example 82 by substituting the appropriate starting materials, reagents and reaction conditions:

| Cpd | Name and Data |
|---|---|
| 344 | 2-(5-chloro-2-methyl-1H-benzimidazol-1-yl)-6-{[4-(trifluoromethyl)phenyl]amino}pyridine-4-carbonitrile<br>$^1$H NMR (DMSO-d$_6$) δ 10.28 (br. s, 1H), 7.82 (d, J = 8.5 Hz, 2H), 7.73 (d, J = 1.9 Hz, 1H), 7.65 (d, J = 8.5 Hz, 2H), 7.55-7.61 (m, 2H), 7.38 (d, J = 0.9 Hz, 1H), 7.30 (dd, J = 8.7, 2.0 Hz, 1H), 2.64 (s, 3H); MS m/z 428 (ESI) [M + H]$^+$ |
| 345 | 2-(6-chloro-2-methyl-1H-benzimidazol-1-yl)-6-{[4-(trifluoromethyl)phenyl]amino}pyridine-4-carbonitrile<br>$^1$H NMR (DMSO-d$_6$) δ 10.27 (br. s, 1H), 7.83 (d, J = 8.8 Hz, 2H), 7.56-7.70 (m, 5H), 7.37 (s, 1H), 7.31 (dd, J = 8.5, 1.9 Hz, 1H), 2.64 (s, 3H); MS m/z 428 (ESI) [M + H]$^+$ |
| 428 | 2-(6-chloro-2-methyl-1H-imidazo[4,5-b]pyridin-1-yl)-6-{[4-(difluoromethoxy)phenyl]amino}pyridine-4-carbonitrile<br>$^1$H NMR (500 MHz, Acetone-d$_6$) δ 9.74 (s, 1H) 8.41 (d, J = 2.52 Hz, 1H) 8.11 (d, J = 2.21 Hz, 1H) 7.69-7.80 (m, 2H) 7.43 (d, J = 0.95 Hz, 1H) 7.35 (d, J = 0.95 Hz, 1H) 7.12-7.20 (m, 2H) 6.93 (t, J = 75.00 Hz, 1H) 2.75 (s, 3H) |
| 429 | 2-(6-chloro-2-methyl-1H-imidazo[4,5-b]pyridin-1-yl)-6-{[4-(difluoromethoxy)-3-fluorophenyl]amino}pyridine-4-carbonitrile<br>$^1$H NMR (500 MHz, Acetone-d$_6$) δ 9.46 (s, 1H) 8.42 (d, J = 2.21 Hz, 1H) 8.13 (d, J = 2.21 Hz, 1H) 7.80 (dd, J = 12.93, 2.52, 1H) 7.52 (d, J = 0.63 Hz, 1H) 7.42-7.47 (m, 1H) 7.38 (d, J = 0.95 Hz, 1H) 7.31 (t, J = 8.98 Hz, 1H) 6.92 (t, J = 72.20 Hz, 1H) 2.71-2.80 (m, 3H) |
| 450 | 2-(6-chloro-2-ethyl-1H-imidazo[4,5-b]pyridin-1-yl)-6-{[4-(trifluoromethyl)phenyl]amino}pyridine-4-carbonitrile<br>$^1$H NMR (500 MHz, Acetone-d$_6$) δ 9.51 (s, 1H) 8.43 (d, J = 2.52 Hz, 1H) 8.10 (d, J = 2.21 Hz, 1H) 7.91 (d, J = 8.51 Hz, 2H) 7.65 (d, J = 8.51 Hz, 2H) 7.56 (d, J = 0.95 Hz, 1H) 7.44 (d, J = 0.95 Hz, 1H) 3.14 (q, J = 7.57 Hz, 2H) 1.38 (t, J = 7.41 Hz, 3H); MS m/z 443.1 (ESI) [M + H]$^+$ |
| 451 | 2-(6-chloro-2-ethyl-1H-imidazo[4,5-b]pyridin-1-yl)-6-{[4-(difluoromethoxy)phenyl]amino}pyridine-4-carbonitrile<br>$^1$H NMR (500 MHz, Acetone-d$_6$) δ 9.06-9.32 (m, 1H) 8.42 (d, J = 2.21 Hz, 1H) 8.08 (d, J = 2.52 Hz, 1H) 7.65-7.76 (m, 2H) 7.43 (d, J = 0.95 Hz, 1H) 7.32 (d, J = 1.26 Hz, 1H) 7.16 (d, J = 8.83 Hz, 2H) 6.91 (t, J = 72.80 Hz, 1H) 3.12 (q, J = 7.57 Hz, 2H) 1.37 (t, J = 7.41 Hz, 3H); MS m/z 441.2 (ESI) [M + H]$^+$ |
| 452 | 2-(6-chloro-2-ethyl-1H-imidazo[4,5-b]pyridin-1-yl)-6-{[4-(difluoromethoxy)phenyl]amino}pyridine-4-carbonitrile<br>$^1$H NMR (500 MHz, Acetone-d$_6$) δ 9.38 (s, 1H) 8.43 (d, J = 2.21 Hz, 1H) 8.10 (d, J = 2.21 Hz, 1H) 7.79 (dd, J = 12.93, 2.52, 1H) 7.52 (d, J = 0.95 Hz, 1H) 7.39-7.45 (m, 1H) 7.38 (d, J = 0.95 Hz, 1H) 7.27-7.33 (m, 1H) 6.92 (t, J = 74.40 Hz, 1H) 3.13 (q, J = 7.57 Hz, 2H) 1.38 (t, J = 7.41 Hz, 3H); MS m/z 459.1 (ESI) [M + H]$^+$ |
| 588 | 2-(6-fluoro-2-methyl-1H-benzimidazol-1-yl)-6-{[4-(trifluoromethoxy)phenyl]amino}pyridine-4-carbonitrile<br>$^1$H NMR (Acetone-d$_6$) δ 9.28 (br. s, 1H), 7.79-7.86 (m, 2H), 7.63 (dd, J = 8.8, 4.7 Hz, 1H), 7.43 (d, J = 0.9 Hz, 1H), 7.41 (dd, J = 9.3, 2.4 Hz, 1H), 7.34 (d, J = 0.9 Hz, 1H), 7.31 (dd, J = 9.1, 0.9 Hz, 2H), 7.08 (ddd, J = 9.8, 8.8, 2.5 Hz, 1H), 2.68 (s, 3H); MS m/z 428 (ESI) [M + H]$^+$ |
| 589 | 2-(6-fluoro-2-methyl-1H-benzimidazol-1-yl)-6-[(4-methoxyphenyl)amino]pyridine-4-carbonitrile<br>$^1$H NMR (Acetone-d$_6$) δ 8.86 (br. s, 1H), 7.61 (dd, J = 8.8, 4.7 Hz, 1H), 7.50-7.57 (m, 2H), 7.40 (dd, J = 9.3, 2.4 Hz, 1H), 7.28 (d, J = 0.9 Hz, 1H), 7.18 (d, J = 1.3 Hz, 1H), 7.07 (ddd, J = 9.6, 8.7, 2.5 Hz, 1H), 6.88-6.97 (m, 2H), 3.80 (s, 3H), 2.67 (s, 3H); MS m/z 374 (ESI) [M + H]$^+$ |
| 611 | 2-(6-fluoro-2-methyl-1H-benzimidazol-1-yl)-6-[(4-methylphenyl)amino]pyridine-4-carbonitrile<br>$^1$H NMR (DMSO-d$_6$) δ 9.76 (br. s, 1H), 7.64 (dd, J = 8.8, 5.0 Hz, 1H), 7.45-7.51 (m, 2H), 7.38-7.44 (m, 2H), 7.20-7.23 (m, 1H), 7.08-7.15 (m, 3H), 2.60 (s, 3H), 2.25 (s, 3H); MS m/z 358 (ESI) [M + H]$^+$ |
| 612 | 2-[(4-chlorophenyl)amino]-6-(6-fluoro-2-methyl-1H-benzimidazol-1-yl)pyridine-4-carbonitrile<br>$^1$H NMR (DMSO-d$_6$) δ 9.99 (s, 1H), 7.62-7.67 (m, 3H), 7.47-7.51 (m, 1H), 7.42 (dd, J = 9.1, 2.5 Hz, 1H), 7.33-7.36 (m, 2H), 7.27-7.29 (m, 1H), 7.13 (ddd, J = 9.8, 8.8, 2.5 Hz, 1H), 2.60 (s, 3H); MS m/z 378 (ESI) [M + H]$^+$ |

Example 83

6-(6-chloro-2-methyl-1H-imidazo[4,5-b]pyridin-1-yl)-N-[4-(trifluoromethyl)phenyl]pyrazin-2-amine (Cpd 361)

-continued

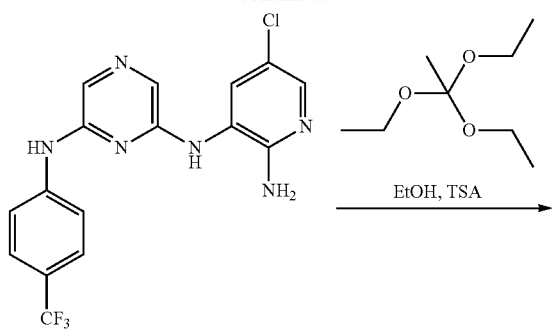

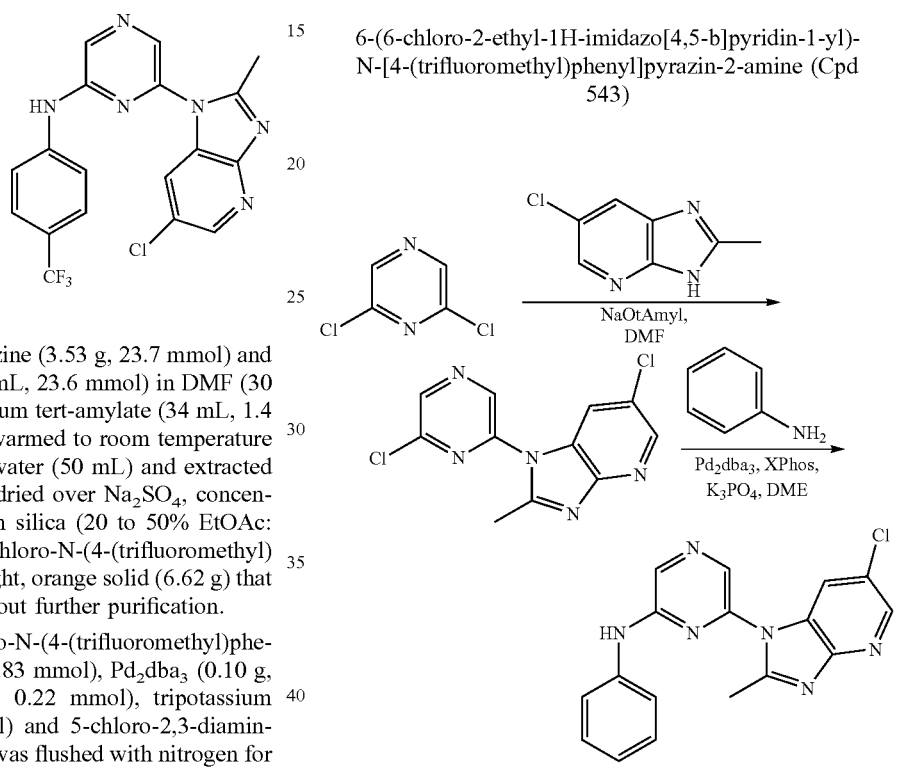

| Cpd | Name and Data |
|---|---|
| 327 | 6-(6-chloro-2-ethyl-1H-imidazo[4,5-b]pyridin-1-yl)-N-[4-(trifluoromethyl)phenyl]pyrazin-2-amine<br>$^1$H NMR (500 MHz, DMSO-$d_6$) δ 10.32-10.47 (br. s., 1H) 8.45-8.51 (m, 2H) 8.38-8.42 (m, 1H) 8.08-8.14 (m, 1H) 7.80-7.88 (m, 2H) 7.59-7.69 (m, 2H) 3.03 (q, J = 7.60 Hz, 2H) 1.31 (t, J = 6.90 Hz, 3H); MS m/z 419.1 (ESI) [M + H]$^+$ |
| 370 | 6-(2-ethyl-1H-imidazo[4,5-c]pyridin-1-yl)-N-[4-(trifluoromethyl)phenyl]pyrazin-2-amine<br>MS m/z 385 (ESI) [M + H]$^+$ |

Example 84

6-(6-chloro-2-ethyl-1H-imidazo[4,5-b]pyridin-1-yl)-N-[4-(trifluoromethyl)phenyl]pyrazin-2-amine (Cpd 543)

Step 1. To 2, 6-dichloropyrazine (3.53 g, 23.7 mmol) and 4-trifluoromethylaniline (2.97 mL, 23.6 mmol) in DMF (30 mL) at −78° C. was added sodium tert-amylate (34 mL, 1.4 M in THF). The mixture was warmed to room temperature over 30 minutes, poured into water (50 mL) and extracted with EtOAc (4×30 mL), then dried over Na$_2$SO$_4$, concentrated and chromatographed on silica (20 to 50% EtOAc:hexane as eluent) to provide 6-chloro-N-(4-(trifluoromethyl) phenyl)pyrazin-2-amine as a light, orange solid (6.62 g) that was used in the next step without further purification.

Step 2. A mixture of 6-chloro-N-(4-(trifluoromethyl)phenyl)pyrazin-2-amine (0.50 g, 1.83 mmol), Pd$_2$dba$_3$ (0.10 g, 0.11 mmol), X-Phos (0.11 g, 0.22 mmol), tripotassium phosphate (1.20 g, 5.48 mmol) and 5-chloro-2,3-diaminopyridine (0.41 g, 2.77 mmol) was flushed with nitrogen for 30 minutes, then dimethoxyethane (16 mL) was added. The resulting mixture was heated at 107° C. for 2 hours, cooled, then concentrated under a stream of nitrogen and chromatographed on silica (gradient from 50% EtOAc:hexane, then 10% MeOH:DCM) to provide a mixture of isomers as a dark solid (0.43 g, 62%), used in the next step without further purification.

Step 3. To a solution of the obtained product (86.1 mg, 0.23 mmol) in ethanol (3 mL) at room temperature was added triethyl orthoacetate (0.13 mL, 0.69 mmol) and p-toluenesulfonic acid (tip of spatula, catalytic). The resulting mixture was heated at reflux overnight, cooled and concentrated under a stream of nitrogen, then chromatographed on silica (5 to 10% MeOH:DCM as eluent) to provide the title compound (36.1 mg, 39%) as a white solid. MS m/z 405.4 M+H$^+$; H NMR (500 MHz, DMSO-$d_6$) δ 10.33-10.44 (br.s., 1H) 8.45-8.48 (m, 1H) 8.44 (s, 1H) 8.42 (s, 1H) 8.10-8.16 (m, 1H) 7.82-7.89 (m, 2H) 7.61-7.68 (m, 2H) 2.71 (s, 3H)

Additional compounds of Formula (I) or a form thereof described herein may be prepared according to the procedure of Example 83 by substituting the appropriate starting materials, reagents and reaction conditions:

Step 1. To 6-chloro-2-methyl-3H-imidazo[4,5-b]pyridine (3.00 g, 17.9 mmol) in DMF (40 mL) at 0° C. was added sodium hydride (0.79 g, 19.8 mmol), The mixture was stirred at 0° C. for 15 minutes, then at room temperature for 30 minutes and 2,6-dichloropyrazine (8.01 g, 53.8 mmol) was added. The mixture was heated at 50° C. for 4 hours and cooled into water (150 mL). The product was extracted with EtOAc (5×50 mL) and the organics were washed with water (100 mL), then brine (3×30 mL) and dried over Na$_2$SO$_4$ and concentrated. Approximately half the crude product obtained (3.3 g from 6.4 g) was chromatographed on silica gel (eluted from 2 to 5% MeOH:DCM as eluent) to provide the chromatographically faster isomer, 6-chloro-3-(6-chloropyrazin-2-yl)-2-methyl-3H-imidazo[4,5-b]pyridine (0.32 g, 13%), and the chromatographically slower isomer, 6-chloro-1-(6-chloropyrazin-2-yl)-2-methyl-1H-imidazo[4, 5-b]pyridine (1.10 g, 44%) as a light, pink solid.

Step 2. A mixture of the slower isomer (0.10 g, 0.36 mmol), Pd$_2$dba$_3$ (20 mg, 0.022 mmol), X-Phos (21 mg, 0.043 mmol) and tripotassium phosphate (0.23 g, 0.10 mmol) was flushed with nitrogen for 30 minutes, then dimethoxyethane (16 mL) and aniline (0.11 mL, 1.21 mmol) were added. The resulting mixture was heated via microwave at 120° C. for 30 minutes, then cooled to room temperature and filtered into ice-water (10 mL). The resulting precipitate was collected on a filter, then dried on a vacuum oven at 50° C. and chromatographed on silica (5 to 10% MeOH:DCM as eluent) to provide the title compound as a brown solid (42.2 mg, 35%). MS m/z 337.1 M+H$^+$; $^1$H NMR (500 MHz, Acetone-d$_6$) δ 9.62-9.82 (m, 1H) 8.38-8.49 (m, 2H) 8.29 (s, 1H) 8.08 (d, J=1.89 Hz, 1H) 7.73 (d, J=7.57 Hz, 2H) 7.31 (dd, J=8.51, 7.25 Hz, 2H) 7.02 (s, 1H) 2.75 (s, 3H)

Additional compounds of Formula (I) or a form thereof described herein may be prepared according to the procedure of Example 84 by substituting the appropriate starting materials, reagents and reaction conditions:

| Cpd | Name and Data |
|---|---|
| 540 | 6-(6-chloro-2-methyl-1H-imidazo[4,5-b]pyridin-1-yl)-N-[4-(difluoromethoxy)phenyl]pyrazin-2-amine<br>$^1$H NMR (500 MHz, Acetone-d$_6$) δ 9.47 (br. s., 1H) 8.42 (d, J = 2.48 Hz, 1H) 8.39 (s, 1H) 8.32 (s, 1H) 8.06 (d, J = 2.48 Hz, 1H) 7.72-7.82 (m, 2H) 7.11-7.20 (m, 2H) 6.91 (t, J = 74.60 Hz, 1H) 2.75 (s, 3H); MS m/z 403.2 (ESI) [M + H]$^+$ |
| 541 | 6-(6-chloro-2-methyl-1H-imidazo[4,5-b]pyridin-1-yl)-N-[4-(difluoromethoxy)-3-fluorophenyl]pyrazin-2-amine<br>$^1$H NMR (500 MHz, Acetone-d$_6$) δ 9.81-10.03 (m, 1H) 8.43 (m, 2H) 8.38 (s, 1H) 8.08 (d, J = 2.21 Hz, 1H) 7.80-7.92 (m, 1H) 7.42-7.54 (m, 1H) 7.30 (s, 1H) 6.93 (t, J = 73.80 Hz, 1H) 2.75 (s, 3H); MS m/z 421.2 (ESI) [M + H]$^+$ |
| 542 | 6-(6-chloro-2-methyl-1H-imidazo[4,5-b]pyridin-1-yl)-N-[4-(trifluoromethoxy)phenyl]pyrazin-2-amine<br>$^1$H NMR (500 MHz, Acetone-d$_6$) δ 9.77-9.94 (m, 1H) 8.39-8.48 (m, 2H) 8.34 (d, J = 0.63 Hz, 1H) 8.07 (d, J = 2.21 Hz, 1H) 7.86 (d, J = 9.14 Hz, 2H) 7.29 (d, J = 8.20 Hz, 2H) 2.75 (s, 3H); MS m/z 421.2 (ESI) [M + H]$^+$ |
| 544 | 6-(6-chloro-2-ethyl-1H-imidazo[4,5-b]pyridin-1-yl)-N-[4-(difluoromethoxy)phenyl]pyrazin-2-amine<br>$^1$H NMR (500 MHz, Acetone-d$_6$) δ 9.24 (s, 1H) 8.42 (d, J = 2.21 Hz, 1H) 8.39 (s, 1H) 8.31 (s, 1H) 8.02 (d, J = 2.52 Hz, 1H) 7.72-7.81 (m, 2H) 7.12-7.20 (m, 2H) 6.90 (t, J = 74.40 Hz, 1H) 3.09 (q, J = 7.25 Hz, 2H) 1.38 (t, J = 7.41 Hz, 3H); MS m/z 417.2 (ESI) [M + H]$^+$ |
| 545 | N-[4-(difluoromethoxy)phenyl]-1-(6-{[4-(difluoromethoxy)phenyl]amino}pyrazin-2-yl)-2-ethyl-1H-imidazo[4,5-b]pyridin-6-amine<br>$^1$H NMR (500 MHz, CHLOROFORM-d) δ ppm 9.22 (s, 1H) 8.34 (s, 1H) 8.28 (d, J = 2.21 Hz, 1H) 8.25 (s, 1H) 7.72-7.82 (m, 1H) 7.67 (s, 1H) 7.60 (s, 1H) 7.05-7.18 (m, 5H) 6.90-7.00 (m, 1H) 6.87 (t, J = 74.70 Hz, 1H) 6.77 (t, J = 74.40 Hz, 1H) 3.05 (q, J = 7.57 Hz, 2H) 1.36 (t, J = 7.57 Hz, 3H); MS m/z 540.3 (ESI) [M + H]$^+$ |
| 546 | 6-(6-chloro-2-ethyl-1H-imidazo[4,5-b]pyridin-1-yl)-N-[4-(difluoromethoxy)-3-fluorophenyl]pyrazin-2-amine<br>$^1$H NMR (500 MHz, Acetone-d$_6$) δ 9.42 (s, 1H) 8.44 (d, J = 2.21 Hz, 1H) 8.41 (s, 1H) 8.38 (s, 1H) 8.04 (d, J = 2.21 Hz, 1H) 7.84 (dd, J = 13.08, 2.68 Hz, 1H) 7.44-7.49 (m, 1H) 7.27-7.34 (m, 1H) 6.91 (t, J = 73.10 Hz, 1H) 3.10 (q, J = 7.46 Hz, 2H) 1.40 (t, J = 7.41 Hz, 3H); MS m/z 435.2 (ESI) [M + H]$^+$ |
| 547 | N-[4-(difluoromethoxy)phenyl]-1-(6-{[4-(difluoromethoxy)phenyl]amino}pyrazin-2-yl)-2-methyl-1H-imidazo[4,5-b]pyridin-6-amine<br>$^1$H NMR (500 MHz, Acetone-d$_6$) δ ppm 9.28 (s, 1H) 8.34 (s, 1H) 8.22-8.29 (m, 2H) 7.74-7.83 (m, 2H) 7.71 (d, J = 2.20 Hz, 1H) 7.63 (s, 1H) 7.06-7.17 (m, 4H) 6.89-6.98 (m, 2H) 6.87 (t, J = 74.60 Hz, 1H) 6.77 (t, J = 74.30 Hz, 1H) 2.69 (s, 3H); MS m/z 526.3 (ESI) [M + H]$^+$ |
| 548 | 6-(6-chloro-2-ethyl-1H-imidazo[4,5-b]pyridin-1-yl)-N-[4-(trifluoromethoxy)phenyl]pyrazin-2-amine<br>$^1$H NMR (500 MHz, Acetone-d$_6$) δ 9.91 (s, 1H) 8.40-8.50 (m, 2H) 8.32 (s, 1H) 8.03 (d, J = 2.20 Hz, 1H) 7.82-7.89 (m, 2H) 7.29 (q, J = 7.52 Hz, 2H) 1.38 (t, J = 7.43 Hz, 3H); MS m/z 435.2 (ESI) [M + H]$^+$ |
| 549 | 6-(6-chloro-2-ethyl-1H-imidazo[4,5-b]pyridin-1-yl)-N-[4-phenylpyrazin-2-amine<br>$^1$H NMR (500 MHz, Acetone-d$_6$) δ 9.43-9.55 (m, 1H) 8.40-8.46 (m, 2H) 8.27 (s, 1H) 8.04 (d, J = 2.20 Hz, 1H) 7.67-7.77 (m, 2H) 7.26-7.36 (m, 2H) 6.98-7.08 (m, 1H) 3.10 (q, J = 7.52 Hz, 2H) 1.38 (t, J = 7.43 Hz, 3H); MS m/z 351.2 (ESI) [M + H]$^+$ |
| 550 | N-[4-(difluoromethoxy)-3-fluorophenyl]-1-(6-{[4-(difluoromethoxy)-3-fluorophenyl]amino}pyrazin-2-yl)-2-ethyl-1H-imidazo[4,5-b]pyridin-6-amine<br>$^1$H NMR (500 MHz, Acetone-d$_6$) δ ppm 9.44 (s, 1H) 8.38 (s, 1H) 8.34 (s, 1H) 8.32 (d, J = 2.20 Hz, 1H) 7.83-7.89 (m, 1H) 7.75-7.82 (m, 2H) 7.43-7.52 (m, 1H) 7.28 (t, J = 8.94 Hz, 1H) 7.06 (t, J = 8.80 Hz, 1H) 6.82-6.92 (m, 2H) 6.88 (t, J = 74.00 Hz, 1H) 6.80 (t, J = 74.80 Hz, 1H) 3.08 (q, J = 7.43 Hz, 2H) 1.38 (t, J = 7.43 Hz, 3H); MS m/z 576.3 (ESI) [M + H]$^+$ |
| 573 | 6-(5,6-difluoro-2-methyl-1H-benzimidazol-1-yl)-N-(4-methoxyphenyl)pyrazin-2-amine<br>$^1$H NMR (500 MHz, Acetone-d$_6$) δ 8.90 (s, 1H) 8.28 (d, J = 0.63 Hz, 1H) 8.17 (s, 1H) 7.57-7.63 (m, 2H) 7.54 (ddd, J = 10.64, 7.33, 1.58 Hz, 2H) 6.85-6.95 (m, 2H) 3.77 (s, 4H) 2.65 (s, 3H); MS m/z 367.8 (ESI) [M + H]$^+$ |
| 574 | 6-(5,6-difluoro-2-methyl-1H-benzimidazol-1-yl)-N-(4-methylphenyl)pyrazin-2-amine<br>$^1$H NMR (500 MHz, Acetone-d$_6$) δ 9.00 (br. s., 1H) 8.32 (s, 1H) 8.21 (s, 1H) 7.49-7.62 (m, 4H) 7.14 (d, J = 8.20 Hz, 2H) 2.66 (s, 3H) 2.28 (s, 3H); MS m/z 352.6 (ESI) [M + H]$^+$ |
| 575 | N-(4-chlorophenyl)-6-(5,6-difluoro-2-methyl-1H-benzimidazol-1-yl)pyrazin-2-amine<br>$^1$H NMR (500 MHz, Acetone-d$_6$) δ 9.25 (br. s., 1H) 8.37 (s, 1H) 8.29 (s, 1H) 7.72-7.81 (m, 2H) 7.55 (ddd, J = 10.56, 7.57, 2.68 Hz, 2H) 7.29-7.37 (m, 2H) 2.66 (s, 3H); MS m/z 374.1 (ESI) [M + H]$^+$ |
| 578 | 6-(5,6-difluoro-2-methyl-1H-benzimidazol-1-yl)-N-(3-methoxyphenyl)pyrazin-2-amine<br>$^1$H NMR (500 MHz, Acetone-d$_6$) δ 9.13 (br. s., 1H) 8.36 (d, J = 0.63 Hz, 1H) 8.26 (s, 1H) 7.51-7.69 (m, 2H) 7.43 (d, J = 1.58 Hz, 1H) 7.15-7.26 (m, 2H) 6.56-6.69 (m, 1H) 3.70 (s, 3H) 2.67 (s, 3H); MS m/z 367.9 (ESI) [M + H]$^+$ |
| 583 | 2-(5,6-difluoro-2-methyl-1H-benzimidazol-1-yl)-6-[(4-methoxyphenyl)amino]pyridine-4-carbonitrile<br>$^1$H NMR (500 MHz, Acetone-d$_6$) δ 9.11 (s, 1H) 7.61 (dd, J = 10.88, 7.41 Hz, 1H) 7.48-7.56 (m, 3H) 7.26 (d, J = 0.95 Hz, 1H) 7.17-7.21 (m, 1H) 6.87-6.96 (m, 2H) 3.77 (s, 3H) 2.66 (s, 3H); MS m/z 392.3 (ESI) [M + H]$^+$ |
| 599 | 2-(5,6-difluoro-2-methyl-1H-benzimidazol-1-yl)-6-[(4-methylphenyl)amino]pyridine-4-carbonitrile<br>$^1$H NMR (500 MHz, Acetone-d$_6$) δ 9.26-9.43 (m, 1H) 7.59-7.68 (m, 1H) 7.53 (d, J = 8.51 Hz, 3H) 7.30 (d, J = 0.95 Hz, 1H) 7.27 (d, J = 0.95 Hz, 1H) 7.14 (s, 2H) 2.67 (s, 3H) 2.28 (s, 3H); MS m/z 376.2 (ESI) [M + H]$^+$ |
| 600 | 2-[(4-chlorophenyl)amino]-6-(5,6-difluoro-2-methyl-1H-benzimidazol-1-yl)pyridine-4-carbonitrile<br>$^1$H NMR (500 MHz, DMSO-d$_6$) δ 9.90-10.06 (m, 1H) 7.64-7.76 (m, 2H) 7.58-7.64 (m, 2H) 7.44-7.50 (m, 1H) 7.31-7.38 (m, 2H) 7.24-7.30 (m, 1H) 2.58-2.62 (m, 3H); MS m/z 396.2 (ESI) [M + H]$^+$ |

Example 85

6-(5,6-difluoro-2-methyl-1H-benzimidazol-1-yl)-N$^2$-[4-(trifluoromethoxy)phenyl]pyridine-2,4-diamine (Cpd 653)

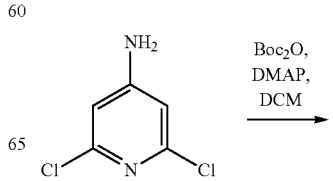

381

-continued

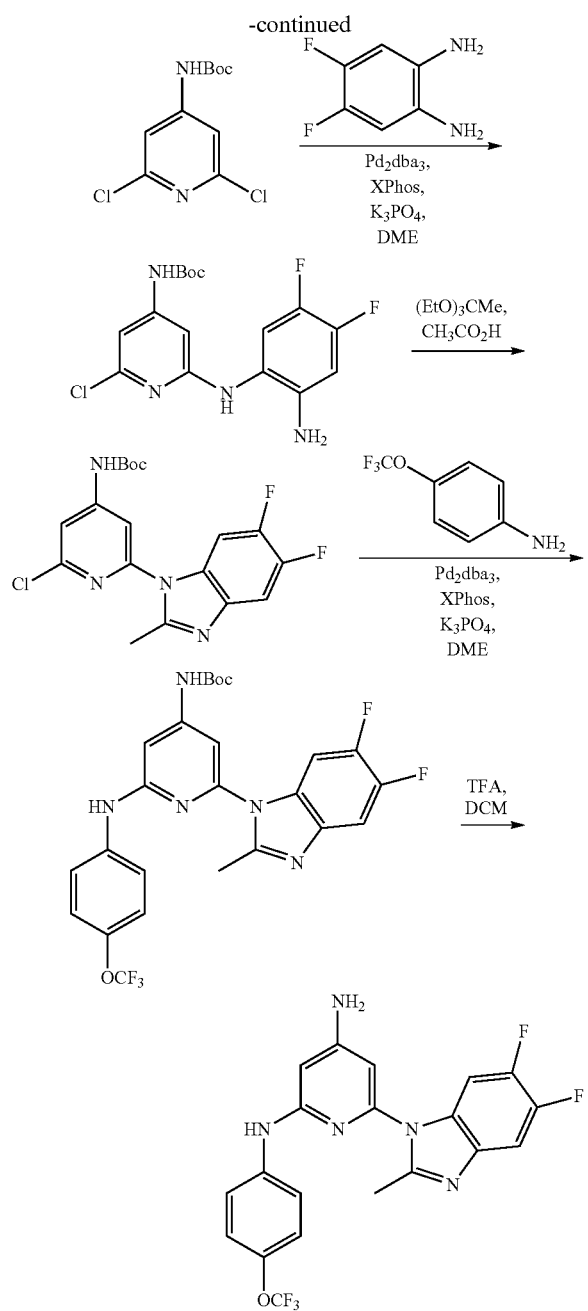

Step 1. To 4-amino-2, 6-dichloropyridine (5.04 g, 30.3 mmol) in DCM (100 mL) at room temperature was added dimethylaminopyridine (0.61 g, 4.99 mmol) and di-tert-butyl dicarbonate (13.71 g, 60.9 mmol). The mixture was stirred overnight, washed with a saturated aqueous solution of $NH_4Cl$ (5 mL) (3×30 mL) and brine (40 mL), then dried over $Na_2SO_4$ and concentrated. The mixture was taken up in THF (30 mL) and water (30 mL) and sodium hydroxide (4.5 g, 112 mmol) added. The mixture was heated at 65° C. for 4 hours, cooled to room temperature and extracted with EtOAc (5×30 mL). The organics were washed with 1 N HCl (2×30 mL) and water (40 mL), then dried over $Na_2SO_4$ and concentrated to a solid. The solid was collected on a filter, washed with 1 N HCl (4×10 mL) and water (20 mL), then dried in a vacuum oven at 50° C. to provide 7.44 g (93%) of tert-butyl 2,6-dichloropyridin-4-ylcarbamate as a white solid.

382

Step 2. A mixture of tert-butyl 2,6-dichloropyridin-4-ylcarbamate (1.11 g, 4.22 mmol), $Pd_2dba_3$ (0.23 g, 0.25 mmol), X-Phos (0.25 g, 0.51 mmol), tripotassium phosphate (2.77 g, 12.6 mmol) and 4, 5-difluoro-1, 2-diaminobenzene (1.24 g, 8.60 mmol) was flushed with nitrogen for 30 minutes, then dimethoxyethane (16 mL) was added. The mixture was heated at 80° C. for 3 hours, cooled, then passed through a filter and poured into water. The resulting precipitate was collected on a filter and dried under a stream of nitrogen to provide a mixture of product and starting material as a tan solid (1.60 g) that was used in the next step without further purification.

Step 3. To a solution of the obtained product (1.60 g) in acetic acid (12 mL) at room temperature was added triethyl orthoacetate (2.4 mL, 13 mmol). The mixture was heated at 45° C. overnight, then ice water (100 mL) was added. The resulting precipitate was collected on a filter, washed with a saturated aqueous solution of $NaHCO_3$ (2×30 mL) and water (30 mL), then dried under a stream of nitrogen to provide tert-butyl 2-chloro-6-(5,6-difluoro-2-methyl-1H-benzo[d]imidazol-1-yl)pyridin-4-ylcarbamate as a tan solid (1.21, 73% in two steps).

Step 4. A mixture of tert-butyl 2-chloro-6-(5,6-difluoro-2-methyl-1H-benzo[d]imidazol-1-yl)pyridin-4-ylcarbamate (67.6 mg, 0.171 mmol), $Pd_2dba_3$ (10 mg, 0.016 mmol), X-Phos (11 mg, 0.034 mmol) and tripotassium phosphate (0.11 mg, 0.78 mmol) was flushed with nitrogen for 30 minutes, then dimethoxyethane (2 mL) and 4-trifluoromethoxyaniline (0.05 mL, 0.37 mmol) were added. The resulting mixture was heated at 80° C. for one hour, cooled, then poured into water and extracted with EtOAc (4×5 mL). The product was dried over $Na_2SO_4$, then concentrated and chromatographed on silica (1 to 5% MeOH:DCM as eluent) to provide tert-butyl 2-(5,6-difluoro-2-methyl-1H-benzo[d]imidazol-1-yl)-6-(4-(trifluoromethoxy)phenylamino)pyridin-4-ylcarbamate as an off-white solid (74.0 mg, 81%).

Step 5. To (tert-butyl 2-(5,6-difluoro-2-methyl-1H-benzo[d]imidazol-1-yl)-6-(4-(trifluoromethoxy)phenylamino) pyridin-4-ylcarbamate (74.0 mg, 0.138 mmol) in DCM (2 mL) at room temperature was added trifluoroacetic acid (0.5 mL). The mixture was stirred for 4 hours, then DCM (2 mL) and a saturated aqueous solution of $NaHCO_3$ (5 mL) was added. The resulting precipitate was collected on a filter and dried under a stream of nitrogen to provide the title compound as an off-white solid (52.2 mg, 87%). MS m/z 435.9 $M+H^+$; $^1H$ NMR (500 MHz, Acetone-$d_6$) δ 8.36 (s, 1H) 7.62-7.82 (m, 2H) 7.49 (dd, J=10.88, 7.41 Hz, 1H) 7.44 (dd, J=10.72, 7.57 Hz, 1H) 7.16-7.23 (m, 2H) 6.41 (d, J=1.58 Hz, 1H) 6.25 (d, J=1.58 Hz, 1H) 5.84 (br. s., 2H) 2.62 (s, 3H)

Additional compounds of Formula (I) or a form thereof described herein may be prepared according to the procedure of Example 85 by substituting the appropriate starting materials, reagents and reaction conditions:

| Cpd | Name and Data |
|---|---|
| 601 | 6-(5,6-difluoro-2-methyl-1H-benzimidazol-1-yl)-N-[4-(trifluoromethyl)phenyl]pyridin-2-amine<br>$^1H$ NMR (500 MHz, Acetone-$d_6$) δ 9.13 (s, 1H) 7.86-7.99 (m, 3H) 7.60 (d, J = 8.51 Hz, 2H) 7.42-7.57 (m, 2H) 7.15 (d, J = 7.57 Hz, 1H) 7.10 (d, J = 8.20 Hz, 1H) 2.65 (s, 3H); MS m/z 404.9 (ESI) $[M + H]^+$ |
| 602 | N-[4-(difluoromethoxy)phenyl]-6-(5,6-difluoro-2-methyl-1H-benzimidazol-1-yl)pyridin-2-amine<br>$^1H$ NMR (500 MHz, Acetone-$d_6$) δ 8.77 (s, 1H) 7.88 (dd, J = 8.20, 7.57 Hz, 1H) 7.69-7.75 (m, 2H) 7.53 (dd, J = 10.88, 7.41 Hz, 1H) 7.46 (dd, J = 10.72, 7.25 Hz, 1H) 7.08-7.14 (m, |

-continued

| Cpd | Name and Data |
|---|---|
| | 2H) 7.03 (d, J = 6.94 Hz, 1H) 6.99 (d, J = 8.20 Hz, 1H) 6.88 (t, J = 74.40 Hz, 1H) 2.63 (s, 3H); MS m/z 403.0 (ESI) [M + H]$^+$ |
| 603 | 6-(5,6-difluoro-2-methyl-1H-benzimidazol-1-yl)-N-[4-(trifluoromethoxy)phenyl]pyridin-2-amine<br>$^1$H NMR (500 MHz, Acetone-d$_6$) δ 8.91 (s, 1H) 7.90 (dd, J = 8.51, 7.57 Hz, 1H) 7.76-7.85 (m, 2H) 7.53 (dd, J = 10.88, 7.41 Hz, 1H) 7.47 (dd, J = 10.72, 7.25 Hz, 1H) 7.21-7.30 (m, 2H) 7.05-7.10 (m, 1H) 7.03 (dd, J = 8.20, 0.63 Hz, 1H) 2.63 (s, 3H); MS m/z 420.9 (ESI) [M + H]$^+$ |
| 613 | 6-(5,6-difluoro-2-methyl-1H-benzimidazol-1-yl)-N-(4-methoxyphenyl)pyridin-2-amine<br>$^1$H NMR (500 MHz, Acetone-d$_6$) δ 8.41 (s, 1H) 7.80 (dd, J = 8.51, 7.57 Hz, 1H) 7.48-7.57 (m, 3H) 7.46 (dd, J = 10.72, 7.25 Hz, 1H) 6.91-6.96 (m, 1H) 6.86-6.91 (m, 3H) 3.76 (s, 3H) 2.62 (s, 3H); MS m/z 367.6 (ESI) [M + H]$^+$ |
| 614 | 6-(5,6-difluoro-2-methyl-1H-benzimidazol-1-yl)-N-(4-methylphenyl)pyridin-2-amine<br>$^1$H NMR (500 MHz, Acetone-d$_6$) δ 8.54 (s, 1H) 7.82 (dd, J = 8.20, 7.57 Hz, 1H) 7.43-7.57 (m, 4H) 7.10 (d, J = 8.20 Hz, 2H) 6.96 (dd, J = 7.72, 5.20 Hz, 2H) 2.63 (s, 3H) 2.26 (s, 3H); MS m/z 351.7 (ESI) [M + H]$^+$ |
| 615 | N-(4-chlorophenyl)-6-(5,6-difluoro-2-methyl-1H-benzimidazol-1-yl)pyridin-2-amine<br>$^1$H NMR (500 MHz, Acetone-d$_6$) δ 8.83 (s, 1H) 7.88 (dd, J = 8.20, 7.57 Hz, 1H) 7.67-7.77 (m, 2H) 7.53 (dd, J = 10.72, 7.57 Hz, 1H) 7.46 (dd, J = 10.72, 7.25 Hz, 1H) 7.25-7.31 (m, 1H) 7.05 (d, J = 7.25 Hz, 1H) 7.00 (d, J = 7.88 Hz, 1H) 2.60-2.66 (m, 3H); MS m/z 370.9 (ESI) [M + H]$^+$ |
| 652 | 6-(5,6-difluoro-2-methyl-1H-benzimidazol-1-yl)-N$^2$-[4-(trifluoromethoxy)phenyl]pyridine-2,4-diamine<br>$^1$H NMR (500 MHz, DMSO-d$_6$) δ 10.32-10.47 (br. s., 1H) 8.45-8.51 (m, 2H) 8.38-8.42 (m, 1H) 8.08-8.14 (m, 1H) 7.80-7.88 (m, 2H) 7.59-7.69 (m, 2H) 3.03 (q, J = 7.60 Hz, 2H) 1.31 (t, J = 6.90 Hz, 3H); MS m/z 419.1 (ESI) [M + H]$^+$ |
| 656 | 6-(5,6-difluoro-2-methyl-1H-benzimidazol-1-yl)-N$^2$-(4-methoxyphenyl)pyridine-2,4-diamine<br>$^1$H NMR (500 MHz, Acetone-d$_6$) δ 7.92-8.20 (m, 1H) 7.49 (ddd, J = 19.23, 10.88, 7.41 Hz, 2H) 7.37-7.43 (m, 2H) 6.83-6.91 (m, 2H) 6.32 (d, J = 1.58 Hz, 1H) 6.11 (d, J = 1.58 Hz, 1H) 3.76 (s, 3H) 2.60-2.65 (m, 3H); MS m/z 381.9 (ESI) [M + H]$^+$ |
| 657 | 6-(5,6-difluoro-2-methyl-1H-benzimidazol-1-yl)-N$^2$-(4-methylphenyl)pyridine-2,4-diamine<br>$^1$H NMR (500 MHz, Acetone-d$_6$) δ 7.98 (s, 1H) 7.48 (dd, J = 13.87, 7.57 Hz, 1H) 7.46 (dd, J = 10.72, 7.25 Hz, 1H) 7.39-7.43 (m, 2H) 7.06 (d, J = 7.88 Hz, 2H) 6.33 (d, J = 1.58 Hz, 1H) 6.20 (d, J = 1.58 Hz, 1H) 5.79 (br. s, 2H) 2.62 (s, 3H) 1.58 (s, 3H); MS m/z 365.9 (ESI) [M + H]$^+$ |
| 658 | N$^2$-(4-chlorophenyl)-6-(5,6-difluoro-2-methyl-1H-benzimidazol-1-yl)pyridine-2,4-diamine<br>$^1$H NMR (500 MHz, Acetone-d$_6$) δ 8.28 (br. s, 1H) 7.60-7.65 (m, 2H) 7.49 (dd, J = 10.88, 7.41 Hz, 1H) 7.44 (dd, J = 10.72, 7.25 Hz, 1H) 7.20-7.26 (m, 2H) 6.40 (d, J = 1.58 Hz, 1H) 6.22 (d, J = 1.58 Hz, 1H) 5.82 (br. s., 2H) 2.83 (s, 3H); MS m/z 386.5 (ESI) [M + H]$^+$ |

Example 86

6-(2-methyl-4,5,6,7-tetrahydro-2H-indazol-3-yl)-N-[4-(trifluoromethyl)phenyl]pyrazin-2-amine (Cpd 454)

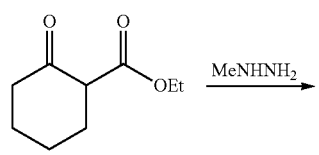

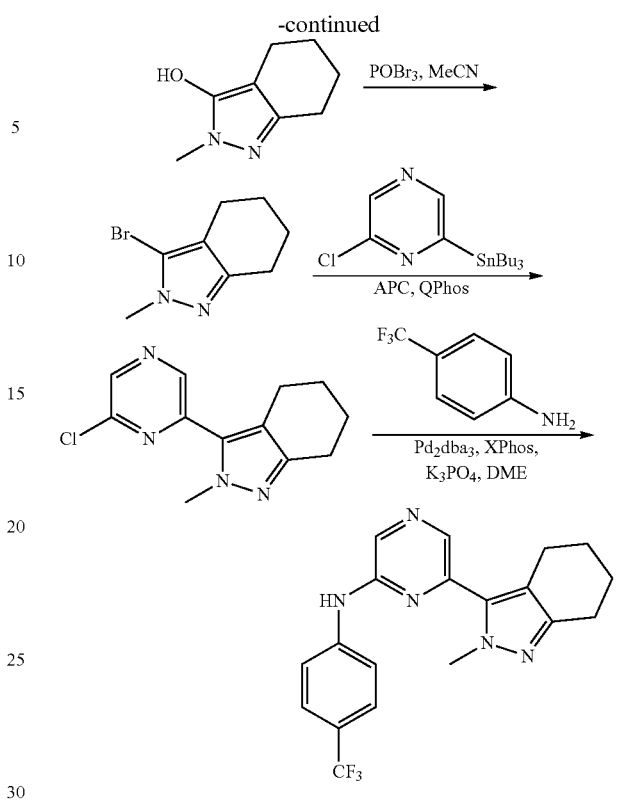

Step 1. To ethyl 2-oxocyclohexanecarboxylate (4.29 g, 23.9 mmol) at room temperature was added methyl hydrazine (1.29 mL, 2.4 mmol). The mixture was stirred for two days at room temperature and the product was chromatographed on silica (5 to 10% MeOH:DCM as eluent) to provide 3.43 g (94%) of 2-methyl-4,5,6,7-tetrahydro-2H-indazol-3-ol as an off-white solid.

Step 2. To a solution of the obtained product (0.22 g, 1.42 mmol) in acetonitrile (5 mL) was added phosphorous oxytribromide (1.00 g, 3.42 mmol). The mixture was heated at reflux overnight, cooled to room temperature, then diluted with EtOAc (15 mL) and taken to about pH 6 with a saturated aqueous solution of NaHCO$_3$. The product was extracted with EtOAc (5×10 mL), dried over Na$_2$SO$_4$, then concentrated and chromatographed on silica (20 to 50% EtOAc:hexane as eluent to provide 3-bromo-2-methyl-4,5,6,7-tetrahydro-2H-indazole as a clear, colorless oil (0.13 g, 43%).

Step 3. A mixture of the obtained product (0.10 g, 0.46 mmol), APC (8.9 mg, 0.024 mmol), Q-Phos (33.6 mg, 0.047 mmol) and 2-chloro-6-(tributylstannyl)pyrazine (0.29 g, 0.72 mmol) [prepared as described in Buron, F. et al *Journal of Organic Chemistry* 70(7), 2616-2621; 2005] was flushed with nitrogen for 30 minutes, then dioxane (2 mL) was added and the mixture was heated at 100° C. for four hours. The reaction mixture was cooled and concentrated under a stream of nitrogen, then chromatographed on silica (40 to 100% EtOAc:hexane as eluent) to provide 35.1 mg (24%) of 3-(6-chloropyrazin-2-yl)-2-methyl-4,5,6,7-tetrahydro-2H-indazole as a solid.

Step 4. A mixture of the obtained product (35.1 mg, 0.141 mmol), Pd$_2$dba$_3$ (8 mg, 0.009 mmol), XPhos (9 mg, 0.018 mmol) and tripotassium phosphate (93 mg, 0.44 mmol) was flushed with nitrogen for one hour, then dimethoxyethane (2 mL) and 4-trifluoromethylaniline (0.36 μL, 0.28 mmol) were added. The mixture was heated at 100° C. for 2 hours, cooled, then concentrated under a stream of nitrogen and chromatographed on silica (gradient from 50% EtOAc:hexane to 10% MeOH:DCM) to provide the title compound as a tan solid (17.5 mg, 33%). MS m/z 374.2 M+H+; 1H NMR (500 MHz, Acetone-d6) δ 9.23 (br. s., 1H) 8.24 (s, 1H) 8.18 (s, 1H) 7.99 (d, J=8.51 Hz, 2H) 7.69 (d, J=8.51 Hz, 2H) 4.01 (s, 3H) 2.65 (dt, J=18.05, 6.27 Hz, 4H) 1.80-1.89 (m, 2H) 1.70-1.80 (m, 2H)

Example 87

6-(2-methylpyrazolo[1,5-a]pyridin-3-yl)-N-[4-(trifluoromethyl)phenyl]pyrazin-2-amine (Cpd 497)

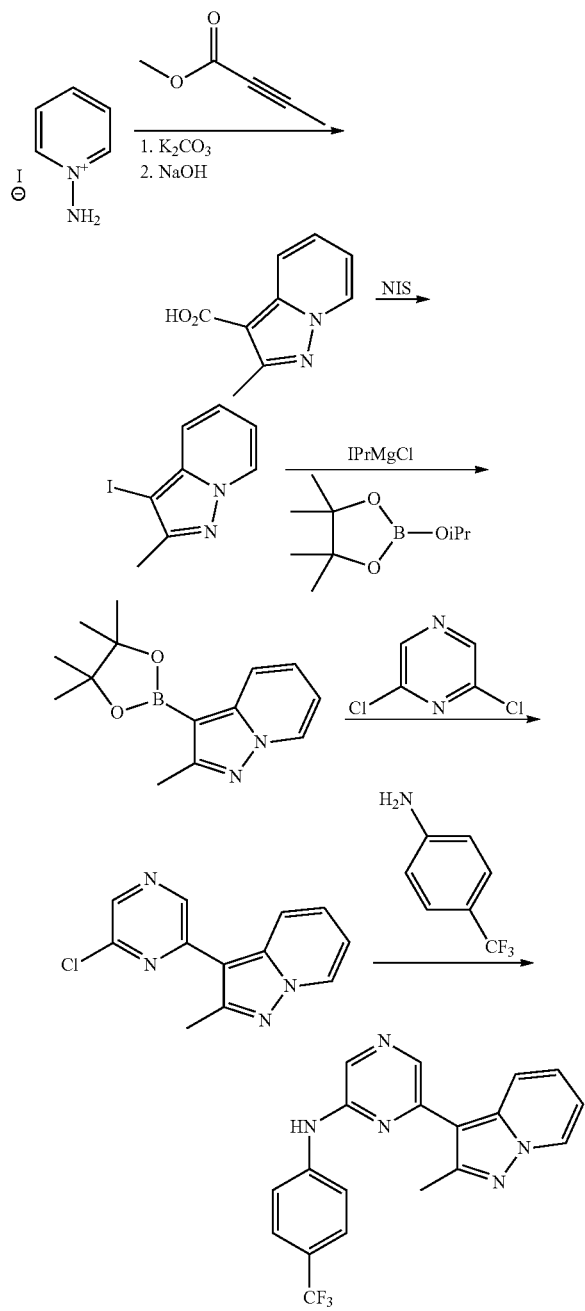

Intermediates synthesized according to Steps 1-3 were prepared analogously to a procedure described in Bethel, P A., et al, Tetrahedron, 2012, Vol. 68, No. 27-28, pp. 5434-5444.

Step 1. A mixture of 1-aminopyridinium iodide (9.59 g, 43.2 mmol) and ethyl but-2-ynoate (5.2 mL, 51.83 mmol) in DMF (50 mL) was cooled to 0° C., then K2CO3 (11.94 g, 86.4 mmol) was added. The reaction mixture was warmed to room temperature and stirred for 3 days until UPLC showed complete conversion. The solution was portioned between water and EtOAc. The organic portion was concentrated, then MeOH (50 mL) and NaOH (6 mL, 50% in H2O) were added. The reaction mixture was heated at 70° C. for one hour, the MeOH was removed by evaporation and the remaining mixture was acidified with 1N HCl to about pH 4. The product 2-methylpyrazolo[1,5-a]pyridine-3-carboxylic acid was isolated on a filter, dried under vacuum and directly used in the next step.

Step 2. The obtained product was dissolved in MeOH (50 mL) and CHCl3 (100 mL) and N-iodosuccinimide (7.3 g, 32.4 mmol) were added in one portion. The reaction mixture was stirred for 20 minutes at room temperature, then the MeOH was removed by evaporation and the reminder washed with an aqueous solution of NaHCO3 (×3). The organic portion was dried over Na2SO4, then the solvent was removed under reduced pressure and the crude product was purified by silica gel chromatography to give 3-iodo-2-methylpyrazolo[1,5-a]pyridine (4.2 g, 38% over 3 steps) as off-white solid. 1H NMR (Acetone-d6) δ 8.51 (dt, J=6.8, 1.3 Hz, 1H), 7.41 (dt, J=8.8, 1.3 Hz, 1H), 7.31 (ddd, J=8.8, 6.8, 1.3 Hz, 1H), 6.90 (td, J=6.8, 1.3 Hz, 1H), 2.42 (s, 3H); MS m/z 298.1 [M+H].

Step 3. To a mixture of the obtained product (780 mg, 3.02 mmol) in THF (5 mL) was added a solution of isopropylmagnesium chloride lithium chloride complex (1.3 M in THF, 3.5 mL, 4.5 mmol) at 0° C. The reaction mixture was stirred at 0° C. for 20 min, then 2-isopropoxy-4,4,5,5-tetramethyl-1,3,2-dioxaborolane (1.68 g, 9.07 mmol) was added in one portion with stirring at 0° C. for 20 minutes until UPLC showed complete consumption of the starting material. The mixture was partitioned between ethyl acetate and water and the organic phase was washed with brine, then dried over Na2SO4 and concentrated. The residue was purified by silica gel chromatography to afford 2-methyl-3-(4,4,5,5-tetramethyl-1,3,2-dioxaborolan-2-yl)pyrazolo[1,5-a]pyridine (587 mg, 75%) as clear solid. 1H NMR (Acetone-d6) δ 8.52 (dt, J=6.9, 1.1 Hz, 1H), 7.85 (dt, J=8.8, 1.1 Hz, 1H), 7.28 (ddd, J=8.8, 6.8, 1.1 Hz, 1H), 6.88 (td, J=6.9, 1.4 Hz, 1H), 2.52 (s, 3H), 1.37 (s, 12H); MS m/z 259.1 [M+H].

Step 4. To a mixture of the obtained product (130 mg, 0.5 mmol), 2,6-dichloropyrazine (375 mg, 2.5 mmol), tris(dibenzylideneacetone) dipalladium(0) (46 mg, 0.05 mmol) and tricyclohexylphosphine (35 mg, 0.125 mmol) was added a solution of tripotassium phosphate (212 mg, 1.0 mmol) in dioxane (3 mL) and water (0.15 mL). The reaction mixture was degassed by purging with Ar, then heated at 85° C. for 16 hours. The mixture was cooled and filtered via plug of Celite, then concentrated and purified by silica gel column chromatography to give 3-(6-chloropyrazin-2-yl)-2-methylpyrazolo[1,5-a]pyridine (98 mg, 82%) as a white solid. 1H NMR (Acetone-d6) δ 8.92 (s, 1H), 8.64 (dt, J=6.9, 1.3 Hz, 1H), 8.46 (s, 1H), 8.34 (dt, J=8.8, 1.3 Hz, 1H), 7.50 (ddd, J=9.0, 6.8, 1.3 Hz, 1H), 7.07 (td, J=6.9, 1.4 Hz, 1H), 2.76 (s, 3H); MS m/z 245.2.

Step 5. To a mixture of the obtained product (37 mg, 0.151 mmol), 4-trifluoromethylaniline (49 mg, 0.303 mmol), 2-dicyclohexylphosphino-2',4',6'-triisopropylbiphenyl (X-phos, 7 mg, 0.015 mmol) and tris(dibenzylideneacetone) dipalladium(0) (14 mg, 0.015 mmol) was added a solution of tripotassium phosphate (64 mg, 0.303 mmol) in dioxane (2.5 mL). The reaction mixture was degassed by three cycles of vacuum pumping and N$_2$ purging and then heated at 85° C. for 30 minutes. The mixture was cooled to room temperature, filtered via a plug of Celite and washed with EtOAc. The filtrate was concentrated and purified by silica gel column chromatography to give the title compound (42 mg, 75%) as an yellow solid. $^1$H NMR (Acetone-d$_6$) δ 8.98 (br. s, 1H), 8.46 (dt, J=6.9, 1.1 Hz, 1H), 8.24 (s, 1H), 8.04 (dt, J=9.0, 1.2 Hz, 1H), 8.01 (s, 1H), 7.87 (d, J=8.5 Hz, 2H), 7.53 (d, J=8.5 Hz, 2H), 7.22 (ddd, J=8.9, 6.7, 1.1 Hz, 1H), 6.84 (td, J=6.9, 1.4 Hz, 1H), 2.58 (s, 3H); MS m/z 370.

Additional compounds of Formula (I) or a form thereof described herein may be prepared according to the procedure of Example 87 by substituting the appropriate starting materials, reagents and reaction conditions:

| Cpd | Name and Data |
|-----|---------------|
| 498 | N-[4-(difluoromethoxy)phenyl]-6-(2-methylpyrazolo[1,5-a]pyridin-3-yl)pyrazin-2-amine<br>$^1$H NMR (Acetone-d$_6$) δ 8.77 (br. s, 1H), 8.58 (dt, J = 6.9, 1.1 Hz, 1H), 8.30 (s, 1H), 8.19 (dt, J = 9.1, 1.1 Hz, 1H), 8.08 (s, 1H), 7.81-7.85 (m, 2H), 7.33 (ddd, J = 9.0, 6.8, 1.3 Hz, 1H), 7.20 (d, J = 9.5 Hz, 2H), 6.97 (td, J = 6.9, 1.4 Hz, 1H), 6.95 (t, J = 74.7 Hz, 1H), 2.71 (s, 3H); MS m/z 368 (ESI) [M + H]$^+$ |
| 500 | 6-(2-methylpyrazolo[1,5-a]pyridin-3-yl)-N-[4-(trifluoromethoxy)phenyl]pyrazin-2-amine<br>$^1$H NMR (Acetone-d$_6$) δ 8.90 (br. s, 1H), 8.58 (dt, J = 6.9, 0.9 Hz, 1H), 8.33 (s, 1H), 8.18 (dt, J = 8.8, 0.9 Hz, 1H), 8.10 (s, 1H), 7.82-7.94 (m, 2H), 7.26-7.37 (m, 3H), 6.97 (td, J = 6.8, 1.3 Hz, 1H), 2.71 (s, 3H); MS m/z 386 (ESI) [M + H]$^+$ |
| 520 | 6-(2-ethylpyrazolo[1,5-a]pyridin-3-yl)-N-[4-(trifluoromethyl)phenyl]pyrazin-2-amine<br>$^1$H NMR (Acetone-d$_6$) δ 9.14 (br. s, 1H), 8.62 (dt, J = 6.9, 1.2 Hz, 1H), 8.35 (s, 1H), 8.17 (s, 1H), 8.14 (dt, J = 8.9, 1.2 Hz, 1H), 8.02 (d, J = 8.2 Hz, 2H), 7.66 (d, J = 8.5 Hz, 2H), 7.37 (ddd, J = 9.0, 6.6, 1.1 Hz, 1H), 6.99 (td, J = 6.9, 1.4 Hz, 1H), 3.18 (q, J = 7.6 Hz, 2H), 1.39 (t, J = 7.6 Hz, 3H); MS m/z 384 (ESI) [M + H]$^+$ |
| 521 | N-[4-(difluoromethoxy)phenyl]-6-(2-ethylpyrazolo[1,5-a]pyridin-3-yl)pyrazin-2-amine<br>$^1$H NMR (Acetone-d$_6$) δ 8.62 (br. s, 1H), 8.45 (dt, J = 6.9, 0.9 Hz, 1H), 8.12 (s, 1H), 7.99 (dt, J = 9.1, 0.9 Hz, 1H), 7.94 (s, 1H), 7.63-7.71 (m, 2H), 7.18 (ddd, J = 9.0, 6.8, 1.3 Hz, 1H), 7.04 (d, J = 9.1 Hz, 2H), 6.82 (dd, J = 13.6, 1.3 Hz, 1H), 6.79 (t, J = 75.0 Hz, 1H), 3.01 (q, J = 7.6 Hz, 2H), 1.23 (t, J = 7.6 Hz, 3H); MS m/z 382 (ESI) [M + H]$^+$ |
| 522 | N-[4-(difluoromethoxy)-3-fluorophenyl]-6-(2-ethylpyrazolo[1,5-a]pyridin-3-yl)pyrazin-2-amine<br>$^1$H NMR (Acetone-d$_6$) δ 8.99 (br. s, 1H), 8.62 (dt, J = 6.9, 1.2 Hz, 1H), 8.32 (s, 1H), 8.14 (dt, J = 8.8, 1.2 Hz, 1H), 8.11 (s, 1H), 8.05 (dd, J = 13.4, 2.7 Hz, 1H), 7.45 (ddd, J = 8.9, 2.6, 1.4 Hz, 1H), 7.36 (ddd, J = 9.0, 6.8, 1.3 Hz, 1H), 7.32 (t, J = 9.1 Hz, 1H), 6.99 (td, J = 6.9, 1.4 Hz, 1H), 6.95 (t, J = 74.1 Hz, 1H), 3.17 (q, J = 7.4 Hz, 3H), 1.39 (t, J = 7.4 Hz, 3H); MS m/z 400 (ESI) [M + H]$^+$ |
| 523 | 6-(2-ethylpyrazolo[1,5-a]pyridin-3-yl)-N-[4-(trifluoromethoxy)phenyl]pyrazin-2-amine<br>$^1$H NMR (Acetone-d$_6$) δ 8.91 (br. s, 1H), 8.61 (dt, J = 6.9, 1.1 Hz, 1H), 8.30 (s, 1H), 8.11-8.14 (m, 2H), 7.82-7.95 (m, 2H), 7.30-7.35 (m, 3H), 6.98 (td, J = 6.8, 1.3 Hz, 1H), 3.16 (q, J = 7.6 Hz, 2H), 1.38 (t, J = 7.6 Hz, 3H); MS m/z 400 (ESI) [M + H]$^+$ |
| 537 | 6-(5-fluoro-2-methylpyrazolo[1,5-a]pyridin-3-yl)-N-[4-(trifluoromethyl)phenyl]pyrazin-2-amine<br>$^1$H NMR (Acetone-d$_6$) δ 8.89 (br. s, 1H), 8.42 (ddd, J = 7.6, 5.4, 0.9 Hz, 1H), 8.16 (s,1H), 7.94 (s, 1H), 7.74 (d, J = 8.5 Hz, 2H), 7.69 (ddd, J = 9.8, 2.8, 0.9 Hz, 1H), 7.46 (d, J = 8.5 Hz, 2H), 6.69 (td, J = 7.4, 2.8 Hz, 1H), 2.49 (s, 3H); MS m/z 388 (ESI) [M + H]$^+$ |
| 539 | 6-(5-chloro-2-ethylpyrazolo[1,5-a]pyridin-3-yl)-N-[4-(trifluoromethyl)phenyl]pyrazin-2-amine<br>$^1$H NMR (Acetone-d$_6$) δ 8.98 (br. s., 1H), 8.48 (d, J = 7.3 Hz, 1H), 8.22 (s, 1H), 8.12 (d, J = 1.9 Hz, 1H), 8.03 (s, 1H), 7.83 (d, J = 8.5 Hz, 2H), 7.55 (d, J = 8.5 Hz, 2H), 6.84 (dd, J = 7.3, 2.2 Hz, 1H), 3.02 (q, J = 7.6 Hz, 2H), 1.26 (t, J = 7.6 Hz, 3H); MS m/z 418 (ESI) [M + H]$^+$ |
| 564 | 6-(2-methylpyrazolo[1,5-a]pyridin-3-yl)-N-phenylpyrazin-2-amine<br>$^1$H NMR (DMSO-d$_6$) δ 9.49 (br. s, 1H), 8.69 (dt, J = 6.9, 0.9 Hz, 1H), 8.24 (s, 1H), 8.13 (dt, J = 8.8, 1.3 Hz, 1H), 8.08 (s, 1H), 7.71 (dd, J = 8.5, 0.9 Hz, 2H), 7.29-7.38 (m, 3H), 6.99 (tt, J = 7.3, 0.9 Hz, 1H), 6.96 (td, J = 6.9, 1.6 Hz, 1H), 2.65 (s, 3H); MS m/z 302 (ESI) [M + H]$^+$ |
| 565 | N-(4-methoxyphenyl)-6-(2-methylpyrazolo[1,5-a]pyridin-3-yl)pyrazin-2-amine<br>$^1$H NMR (DMSO-d$_6$) δ 9.27 (br. s, 1H), 8.68 (dt, J = 6.9, 1.2 Hz, 1H), 8.17 (s, 1H), 8.11 (dt, J = 9.1, 1.2 Hz, 1H), 7.99 (s, 1H), 7.54-7.66 (m, 2H), 7.31 (ddd, J = 9.0, 6.6, 1.1 Hz, 1H), 6.96 (dd, J = 6.9, 1.3 Hz, 1H), 6.91-6.95 (m, 2H), 3.75 (s, 3H), 2.64 (s, 3H); MS m/z 332 (ESI) [M + H]$^+$ |
| 566 | N-(4-methylphenyl)-6-(2-methylpyrazolo[1,5-a]pyridin-3-yl)pyrazin-2-amine<br>$^1$H NMR (DMSO-d$_6$) δ 9.38 (br. s, 1H), 8.69 (dt, J = 6.9, 1.2 Hz, 1H), 8.20 (s, 1H), 8.13 (dt, J = 8.8, 1.2 Hz, 1H), 8.04 (s, 1H), 7.59 (d, J = 8.5 Hz, 2H), 7.32 (ddd, J = 9.0, 6.8, 0.9 Hz, 1H), 7.14 (d, J = 8.2 Hz, 2H), 6.96 (td, J = 6.8, 1.3 Hz, 1H), 2.64 (s, 3H), 2.28 (s, 3H); MS m/z 316 (ESI) [M + H]$^+$ |
| 567 | N-(4-chlorophenyl)-6-(2-methylpyrazolo[1,5-a]pyridin-3-yl)pyrazin-2-amine<br>$^1$H NMR (DMSO-d$_6$) δ 9.65 (br. s, 1H), 8.70 (dt, J = 7.3, 0.9 Hz, 1H), 8.26 (s, 1H), 8.08 (s, 2H), 7.75 (s, 2H), 7.37 (s, 3H), 6.97 (td, J = 6.9, 1.4 Hz, 1H), 2.64 (s, 3H); MS m/z 336 (ESI) [M + H]$^+$ |
| 568 | N-(4-fluorophenyl)-6-(2-methylpyrazolo[1,5-a]pyridin-3-yl)pyrazin-2-amine<br>$^1$H NMR (DMSO-d$_6$) δ 9.51 (s, 1H), 8.69 (dt, J = 6.9, 0.9 Hz, 1H), 8.22-8.24 (m, 1H), 8.08 (dt, J = 9.1, 0.9 Hz, 1H), 8.05 (s, 1H), 7.68-7.73 (m, 2H), 7.34 (ddd, J = 8.9, 6.9, 1.2 Hz, 1H), 7.15-7.21 (m, 2H), 6.96 (td, J = 6.8, 1.3 Hz, 1H), 2.64 (s, 3H); MS m/z 320 (ESI) [M + H]$^+$ |
| 569 | N-(3-methoxyphenyl)-6-(2-methylpyrazolo[1,5-a]pyridin-3-yl)pyrazin-2-amine<br>$^1$H NMR (DMSO-d$_6$) δ 9.51 (br. s, 1H), 8.69 (dt, J = 6.9, 1.2 Hz, 1H), 8.24 (s, 1H), 8.15 (dt, J = 9.1, 1.2 Hz, 1H), 8.08 (s, 1H), 7.43-7.45 (m, 1H), 7.32 (ddd, J = 9.0, 6.8, 1.3 Hz, 1H), 7.22-7.24 (m, 2H), 6.97 (td, J = 6.9, 1.4 Hz, 1H), 6.55-6.60 (m, 1H), 3.70 (s, 3H), 2.65 (s, 3H); MS m/z 332 (ESI) [M + H]$^+$ |
| 570 | N-(3-chlorophenyl)-6-(2-methylpyrazolo[1,5-a]pyridin-3-yl)pyrazin-2-amine<br>$^1$H NMR (Acetone-d$_6$) δ 8.90 (br. s., 1H), 8.59 (dt, J = 6.9, 0.9 Hz, 1H), 8.35 (s, 1H), 8.24 (dt, J = 8.8, 0.9 Hz, 1H), 8.21 (t, J = 2.0 Hz, 1H), 8.10 (s, 1H), 7.52 (ddd, J = 8.2, 2.2, 0.9 Hz, 1H), 7.31-7.41 (m, 2H), 7.04 (ddd, J = 8.2, 2.2, 0.9 Hz, 1H), 6.98 (td, J = 6.9, 1.3 Hz, 1H), 2.73 (s, 3H); MS m/z 336 (ESI) [M + H]$^+$ |
| 571 | 4-{[6-(2-methylpyrazolo[1,5-a]pyridin-3-yl)pyrazin-2-yl]amino}benzonitrile<br>$^1$H NMR (DMSO-d$_6$) δ 10.05 (br. s, 1H), 8.72 (dt, J = 6.9, 0.9 Hz, 1H), 8.38 (s, 1H), 8.17 (s, 1H), 8.07 (dt, J = 8.8, 0.9 Hz, 1H), 7.85-7.95 (m, 2H), 7.76 (s, 2H), 7.40 (ddd, J = 8.9, 6.9, 0.9 Hz, 1H), 6.99 (td, J = 6.9, 1.4 Hz, 1H), 2.66 (s, 3H); MS m/z 327 (ESI) [M + H]$^+$ |
| 572 | methyl 4-{[6-(2-methylpyrazolo[1,5-a]pyridin-3-yl)pyrazin-2-yl]amino}benzoate<br>$^1$H NMR (DMSO-d$_6$) δ 9.99 (br. s, 1H), 8.72 (dt, J = 6.9, 0.9 Hz, 1H), 8.35 (s, 1H), 8.17 (s, 1H), 8.10 (dt, J = 9.5, 0.9 Hz, 1H), 7.89-7.98 (m, 2H), 7.82-7.89 (m, 2H), 7.38 (ddd, J = 9.0, 6.8, 0.9 Hz, 1H), 6.99 (td, J = 6.8, 1.3 Hz, 1H), 3.82 (s, 3H), 2.66 (s, 3H); MS m/z 360 (ESI) [M + H]$^+$ |
| 627 | 6-(2-ethylpyrazolo[1,5-a]pyridin-3-yl)-N-(4-methoxyphenyl)pyrazin-2-amine<br>$^1$H NMR (DMSO-d$_6$) δ 9.33 (br. s, 1H), 8.75 (dt, J = 6.9, 0.9 Hz, 1H), 8.18 (s, 1H), 8.11 (dt, J = 8.8, 0.9 Hz, 1H), 8.06 (s, 1H), 7.64 (s, 2H), 7.36 (ddd, J = 8.8, 6.6, 0.9 Hz, 1H), 7.00 |

| Cpd | Name and Data |
|---|---|
| | (td, J = 6.9, 1.6 Hz, 1H), 6.95-6.98 (m, 2H), 3.80 (s, 3H), 3.12 (q, J = 7.6 Hz, 2H), 1.35 (t, J = 7.6 Hz, 3H); MS m/z 346 (ESI) [M + H]$^+$ |
| 628 | 6-(2-ethylpyrazolo[1,5-a]pyridin-3-yl)-N-(4-methylphenyl)pyrazin-2-amine<br>$^1$H NMR (DMSO-d$_6$) δ 9.39 (br. s, 1H), 8.71 (dt, J = 6.9, 0.9 Hz, 1H), 8.16 (s, 1H), 8.06 (dt, J = 8.8, 0.9 Hz, 1H), 8.05-8.05 (m, 1H), 7.59 (d, J = 8.5 Hz, 2H), 7.32 (ddd, J = 8.8, 6.6, 0.9 Hz, 1H), 7.13 (d, J = 8.2 Hz, 2H), 6.96 (td, J = 6.9, 1.6 Hz, 1H), 3.09 (q, J = 7.6 Hz, 2H), 2.28 (s, 3H), 1.31 (t, J = 7.6 Hz, 3H); MS m/z 330 (ESI) [M + H]$^+$ |
| 629 | N-(4-chlorophenyl)-6-(2-ethylpyrazolo[1,5-a]pyridin-3-yl)pyrazin-2-amine<br>$^1$H NMR (DMSO-d$_6$) δ 9.65 (br. s, 1H), 8.73 (dt, J = 6.9, 0.9 Hz, 1H), 8.23 (s, 1H), 8.09 (s, 1H), 8.02 (dt, J = 8.8, 0.9 Hz, 1H), 7.70-7.79 (m, 2H), 7.32-7.39 (m, 3H), 6.97 (td, J = 6.9, 1.6 Hz, 1H), 3.08 (q, J = 7.6 Hz, 2H), 1.30 (t, J = 7.6 Hz, 3H); MS m/z 350 (ESI) [M + H]$^+$ |
| 630 | 6-(2-ethylpyrazolo[1,5-a]pyridin-3-yl)-N-(4-fluorophenyl)pyrazin-2-amine<br>$^1$H NMR (DMSO-d$_6$) δ 9.49 (br. s, 1H), 8.71 (dt, J = 6.9, 0.9 Hz, 1H), 8.19 (s, 1H), 8.05 (s, 1H), 8.03 (dt, J = 8.8, 0.9 Hz, 1H), 7.67-7.74 (m, 2H), 7.33 (ddd, J = 8.8, 6.6, 0.9 Hz, 1H), 7.16 (s, 2H), 6.96 (td, J = 7.2, 1.3 Hz, 1H), 3.07 (q, J = 7.6 Hz, 2H), 1.30 (t, J = 7.6 Hz, 3H); MS m/z 334 (ESI) [M + H]$^+$ |
| 631 | 6-(2-ethylpyrazolo[1,5-a]pyridin-3-yl)-N-phenylpyrazin-2-amine<br>$^1$H NMR (DMSO-d$_6$) δ 9.50 (br. s, 1H), 8.72 (dt, J = 6.9, 0.9 Hz, 1H), 8.20 (s, 1H), 8.09 (s, 1H), 8.07 (dt, J = 8.9, 0.9 Hz, 1H), 7.67-7.75 (m, 2H), 7.28-7.36 (m, 3H), 6.93-7.03 (m, 2H), 3.09 (q, J = 7.3 Hz, 2H), 1.31 (t, J = 7.3 Hz, 1H); MS m/z 316 (ESI) [M + H]$^+$ |
| 640 | 6-(2-ethylpyrazolo[1,5-a]pyridin-3-yl)-N-(3-methoxyphenyl)pyrazin-2-amine<br>$^1$H NMR (DMSO-d$_6$) δ 9.50 (br. s, 1H), 8.72 (dt, J = 6.9, 1.2 Hz, 1H), 8.19 (s, 1H), 8.09 (s, 1H), 8.09 (dt, J = 9.1, 1.2 Hz, 1H), 7.42 (dd, J = 2.0, 1.9 Hz, 1H), 7.32 (ddd, J = 9.0, 6.8, 1.3 Hz, 1H), 7.18-7.27 (m, 2H), 6.97 (td, J = 6.9, 1.4 Hz, 1H), 6.57 (ddd, J = 7.6, 2.5, 1.6 Hz, 1H), 3.70 (s, 3H), 3.10 (q, J = 7.9 Hz, 2H), 1.31 (t, J = 7.9 Hz, 3H); MS m/z 346 (ESI) [M + H]$^+$ |
| 641 | 4-{[6-(2-ethylpyrazolo[1,5-a]pyridin-3-yl)pyrazin-2-yl]amino}benzonitrile<br>$^1$H NMR (DMSO-d$_6$) δ 10.09 (br. s, 1H), 8.75 (dt, J = 6.9, 1.1 Hz, 1H), 8.34 (s, 1H), 8.18 (s, 1H), 8.02 (dt, J = 9.1, 1.1 Hz, 1H), 7.88-7.93 (m, 2H), 7.73-7.77 (m, 2H), 7.39 (ddd, J = 8.9, 6.9, 1.1 Hz, 1H), 6.99 (td, J = 6.9, 1.3 Hz, 1H), 3.10 (q, J = 7.6 Hz, 2H), 1.32 (t, J = 7.6 Hz, 3H); MS m/z 341 (ESI) [M + H]$^+$ |
| 642 | methyl 4-{[6-(2-ethylpyrazolo[1,5-a]pyridin-3-yl)pyrazin-2-yl]amino}benzoate<br>$^1$H NMR (DMSO-d$_6$) δ 9.99 (br. s, 1H), 8.74 (dt, J = 6.9, 0.9 Hz, 1H), 8.31 (s, 1H), 8.18 (s, 1H), 8.05 (dt, J = 8.8, 1.2 Hz, 1H), 7.89-7.93 (m, 2H), 7.84-7.89 (m, 2H), 7.37 (ddd, J = 9.1, 6.9, 1.3 Hz, 1H), 6.99 (td, J = 6.9, 1.3 Hz, 1H), 3.82 (s, 3H), 3.11 (q, J = 7.6 Hz, 1H), 1.32 (t, J = 7.6 Hz, 2H); MS m/z 374 (ESI) [M + H]$^+$ |
| 643 | N-(3-chlorophenyl)-6-(2-ethylpyrazolo[1,5-a]pyridin-3-yl)pyrazin-2-amine<br>$^1$H NMR (Acetone-d$_6$) δ 8.76 (br. s., 1H), 8.45 (dt, J = 6.9, 0.9 Hz, 1H), 8.16 (s, 1H), 7.99-8.06 (m, 2H), 7.96 (s, 1H), 7.38 (ddd, J = 8.2, 1.9, 0.9 Hz, 1H), 7.14-7.24 (m, 2H), 6.88 (ddd, J = 7.9, 2.0, 0.8 Hz, 1H), 6.82 (td, J = 6.9, 1.4 Hz, 1H), 3.03 (q, J = 7.6 Hz, 2H), 1.24 (t, J = 7.6 Hz, 9H); MS m/z 350 (ESI) [M + H]$^+$ |

Example 88

2-(2-methylpyrazolo[1,5-a]pyridin-3-yl)-6-{[4-(trifluoromethyl)phenyl]amino}pyridine-4-carbonitrile (Cpd 511)

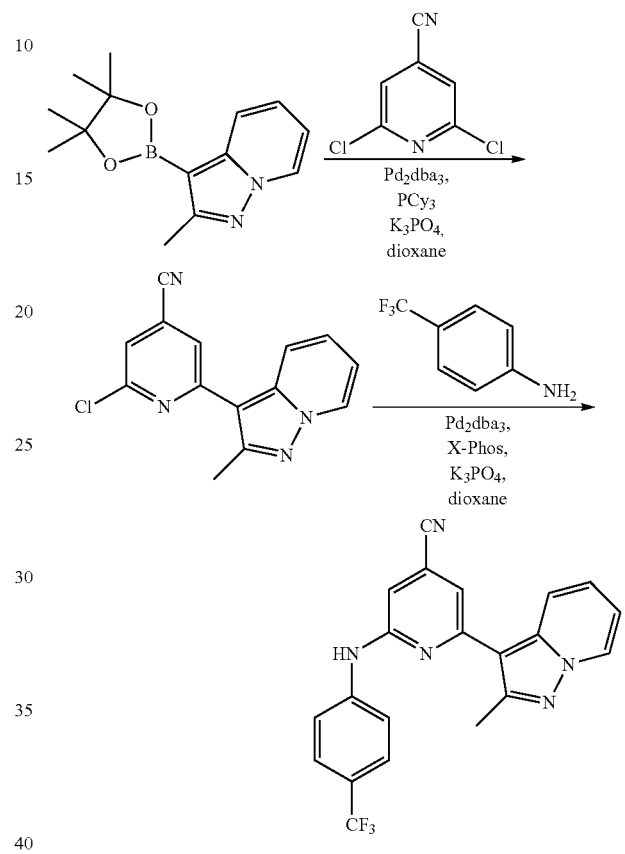

Step 1. To a mixture of 2-methyl-3-(4,4,5,5-tetramethyl-1,3,2-dioxaborolan-2-yl)pyrazolo[1,5-a]pyridine (189 mg, 0.732 mmol), 2,6-dichloroisonicotinonitrile (380 mg, 2.19 mmol), tris(dibenzylideneacetone) dipalladium(0) (64 mg, 0.07 mmol) and tricyclohexylphosphine (50 mg, 0.18 mmol) was added a solution of tripotassium phosphate (151 mg, 1.46 mmol) in dioxane (3 mL) and water (0.1 mL). The mixture was degassed by purging with Ar, and then heated at 85° C. for 2 hours. The reaction mixture was cooled, filtered via plug of Celite, then concentrated and purified by silica gel column chromatography to give 2-chloro-6-(2-methylpyrazolo[1,5-a]pyridin-3-yl)isonicotinonitrile (98 mg, 82%) as a white solid. $^1$H NMR (Acetone-d$_6$) δ 8.68 (dt, J=6.9, 1.3 Hz, 1H), 8.45 (dt, J=9.1, 1.3 Hz, 1H), 8.07 (d, J=0.9 Hz, 1H), 7.71 (d, J=1.3 Hz, 1H), 7.55 (ddd, J=9.1, 6.9, 1.1 Hz, 1H), 7.11 (td, J=6.8, 1.3 Hz, 1H), 2.81 (s, 3H); MS m/z 269.3.

Step 2. To a mixture of the obtained product (40 mg, 0.149 mmol), 4-trifluoromethylaniline (48 mg, 0.291 mmol), 2-dicyclohexylphosphino-2',4',6'-triisopropylbiphenyl (X-phos, 7 mg, 0.015 mmol) and tris(dibenzylideneacetone) dipalladium(0) (14 mg, 0.015 mmol) was added a solution of tripotassium phosphate (64 mg, 0.303 mmol) in dioxane (2.5 mL). The mixture was degassed by three cycles of vacuum pumping and N$_2$ purging, then heated at 160° C. in a microwave oven for 25 minutes. The reaction mixture was cooled to room temperature, then filtered via a plug of Celite and washed with EtOAc. The filtrate was concentrated and purified by silica gel column chromatography to give the title compound (56 mg, 93%) as a yellow solid. $^1$H NMR (Acetone-d$_6$) δ 8.99 (br. s, 1H), 8.45 (dt, J=6.9, 0.9 Hz, 1H), 8.08 (dt, J=9.1, 0.9 Hz, 1H), 7.80 (d, J=8.5 Hz, 2H), 7.52 (d, J=8.5 Hz, 2H), 7.28 (d, J=0.9 Hz, 1H), 7.19 (ddd, J=9.1, 6.9, 0.9 Hz, 1H), 6.94 (d, J=0.9 Hz, 1H), 6.84 (td, J=6.8, 1.3 Hz, 1H), 2.58 (s, 3H); MS m/z 269.3.

Additional compounds of Formula (I) or a form thereof described herein may be prepared according to the procedure of Example 88 by substituting the appropriate starting materials, reagents and reaction conditions:

| Cpd | Name and Data |
|---|---|
| 222 | 2-[6-fluoro-2-(trifluoromethyl)imidazo[1,2-a]pyridin-3-yl]-6-{[4-(trifluoromethoxy)phenyl]amino}pyridine-4-carbonitrile<br>$^1$H NMR (DMSO-d$_6$) δ 9.96 (s, 1H), 8.93 (ddd, J = 5.0, 2.5, 0.9 Hz, 1H), 7.93 (ddd, J = 9.9, 5.2, 0.9 Hz, 1H), 7.73 (dd, J = 9.1, 0.9 Hz, 2H), 7.69 (ddd, J = 10.0, 8.0, 2.5 Hz, 1H), 7.44 (s, 1H), 7.31 (s, 1H), 7.27 (d, J = 8.5 Hz, 2H); MS m/z 482 (ESI) [M + H]$^+$ |
| 272 | 2-[6-fluoro-2-(trifluoromethyl)imidazo[1,2-a]pyridin-3-yl]-6-{[4-(trifluoromethyl)phenyl]amino}pyridine-4-carbonitrile<br>$^1$H NMR (DMSO-d$_6$) δ 10.19 (s, 1H), 8.94 (ddd, J = 4.9, 2.4, 0.9 Hz, 1H), 7.95 (ddd, J = 9.9, 5.2, 0.9 Hz, 1H), 7.85 (d, J = 8.8 Hz, 2H), 7.70 (ddd, J = 10.2, 8.0, 2.4 Hz, 1H), 7.61 (d, J = 8.8 Hz, 2H), 7.53 (s, 1H), 7.38 (d, J = 1.3 Hz, 1H); MS m/z 466 (ESI) [M + H]$^+$ |
| 273 | 2-{[4-(difluoromethoxy)phenyl]amino}-6-[6-fluoro-2-(trifluoromethyl)imidazo[1,2-a]pyridin-3-yl]pyridine-4-carbonitrile<br>$^1$H NMR (DMSO-d$_6$) δ 9.83 (s, 1H), 8.92 (ddd, J = 4.7, 2.2, 0.9 Hz, 1H), 7.93 (ddd, J = 9.8, 5.2, 0.9 Hz, 1H), 7.69 (ddd, J = 10.0, 8.0, 2.5 Hz, 1H), 7.63-7.67 (m, 2H), 7.40 (s, 1H), 7.27 (d, J = 0.9 Hz, 1H), 7.08-7.12 (m, 2H), 7.12 (t, J = 74.4 Hz, 1H); MS m/z 464 (ESI) [M + H]$^+$ |
| 379 | 2-(6-methoxy-2-methylimidazo[1,2-a]pyridin-3-yl)-6-{[4-(trifluoromethyl)phenyl]amino}pyridine-4-carbonitrile<br>$^1$H NMR (DMSO-d$_6$) δ 10.06 (s, 1H), 8.71-8.74 (m, 1H), 7.82 (dd, J = 8.5, 2.2 Hz, 2H), 7.64 (d, J = 8.8 Hz, 2H), 7.54 (d, J = 9.5 Hz, 1H), 7.46 (s, 1H), 7.16 (dd, J = 9.5, 2.2 Hz, 1H), 7.13-7.14 (m, 1H), 3.35 (s, 3H), 2.59 (s, 3H); MS m/z 424 (ESI) [M + H]$^+$ |
| 380 | 2-(6-methoxy-2-methylimidazo[1,2-a]pyridin-3-yl)-6-{[4-(trifluoromethoxy)phenyl]amino}pyridine-4-carbonitrile<br>$^1$H NMR (DMSO-d$_6$) δ 9.84 (br. s, 1H), 8.73 (d, J = 2.2 Hz, 1H), 7.70 (d, J = 9.1 Hz, 2H), 7.52 (d, J = 9.8 Hz, 1H), 7.38 (d, J = 0.9 Hz, 1H), 7.30 (d, J = 8.2 Hz, 2H), 7.14 (dd, J = 9.5, 2.5 Hz, 1H), 7.07 (d, J = 0.9 Hz, 1H), 3.36 (s, 3H), 2.58 (s, 3H); MS m/z 440 (ESI) [M + H]$^+$ |
| 381 | 2-(6-hydroxy-2-methylimidazo[1,2-a]pyridin-3-yl)-6-{[4-(trifluoromethyl)phenyl]amino}pyridine-4-carbonitrile<br>$^1$H NMR (DMSO-d$_6$) δ 10.03 (s, 1H), 9.48 (s, 1H), 8.63 (td, J = 2.2, 0.9 Hz, 1H), 7.87 (d, J = 8.5 Hz, 2H), 7.62 (d, J = 8.5 Hz, 2H), 7.48 (dd, J = 9.5, 1.6 Hz, 1H), 7.43 (d, J = 0.9 Hz, 1H), 7.15 (d, J = 1.3 Hz, 1H), 7.09 (dt, J = 9.8, 2.2 Hz, 1H), 2.55 (s, 3H); MS m/z 410 (ESI) [M + H]$^+$ |
| 396 | 2-(6-hydroxy-2-methylimidazo[1,2-a]pyridin-3-yl)-6-{[4-(trifluoromethoxy)phenyl]amino}pyridine-4-carbonitrile<br>$^1$H NMR (DMSO-d$_6$) δ 9.79 (br. s, 1H), 9.45 (s, 1H), 8.62 (td, J = 2.3, 0.8 Hz, 1H), 7.71-7.79 (m, 2H), 7.47 (dd, J = 9.6, 1.4 Hz, 1H), 7.35 (d, J = 0.9 Hz, 1H), 7.28 (d, J = 8.5 Hz, 2H), 7.06-7.10 (m, 2H), 2.53 (s, 3H); MS m/z 426 (ESI) [M + H]$^+$ |
| 512 | 2-{[4-(difluoromethoxy)phenyl]amino}-6-(2-methylpyrazolo[1,5-a]pyridin-3-yl)pyridine-4-carbonitrile<br>$^1$H NMR (Acetone-d$_6$) δ 8.62 (br. s, 1H), 8.42 (dt, J = 6.6, 0.9 Hz, 1H), 8.09 (dt, J = 9.1, 0.9 Hz, 1H), 7.59 (d, J = 9.1 Hz, 2H), 7.17 (d, J = 1.3 Hz, 1H), 7.16 (ddd, J = 9.1, 6.6, 1.3 Hz, 1H), 7.03-7.08 (m, 2H), 6.82 (d, J = 1.3 Hz, 2H), 6.81 (t, J = 75.0 Hz, 1H), 2.56 (s, 3H); MS m/z 392 (ESI) [M + H]$^+$ |
| 513 | 2-{[4-(difluoromethoxy)-3-fluorophenyl]amino}-6-(2-methylpyrazolo[1,5-a]pyridin-3-yl)pyridine-4-carbonitrile<br>$^1$H NMR (Acetone-d$_6$) δ 9.00 (br. s, 1H), 8.59 (dt, J = 6.9, 0.9 Hz, 1H), 8.23 (dt, J = 9.1, 1.2 Hz, 1H), 7.96 (d, J = 12.9, 2.8 Hz, 1H), 7.41 (ddd, J = 9.1, 2.5, 1.6 Hz, 1H), 7.39 (d, J = 0.9 Hz, 1H), 7.30-7.37 (m, 2H), 7.02 (d, J = 0.9 Hz, 1H), 6.99 (td, J = 6.9, 1.3 Hz, 1H), 6.96 (t, J = 74.1 Hz, 1H), 2.72 (s, 3H); MS m/z 410 (ESI) [M + H]$^+$ |
| 514 | 2-(2-methylpyrazolo[1,5-a]pyridin-3-yl)-6-{[4-(trifluoromethoxy)phenyl]amino}pyridine-4-carbonitrile<br>$^1$H NMR (Acetone-d$_6$) δ 8.90 (br. s, 1H), 8.58 (dt, J = 6.9, 0.9 Hz, 1H), 8.22 (dt, J = 8.8, 0.9 Hz, 1H), 7.77-7.85 (m, 2H), 7.36 (d, J = 0.9 Hz, 1H), 7.27-7.34 (m, 3H), 7.00-7.03 (m, 1H), 6.98 (td, J = 6.9, 1.6 Hz, 1H), 2.71 (s, 3H); MS m/z 410 (ESI) [M + H]$^+$ |
| 526 | 2-(2-ethylpyrazolo[1,5-a]pyridin-3-yl)-6-{[4-(trifluoromethyl)phenyl]amino}pyridine-4-carbonitrile<br>$^1$H NMR (Acetone-d$_6$) δ 9.15 (br. s, 1H), 8.62 (dt, J = 7.3, 0.9 Hz, 1H), 8.18 (dt, J = 8.8, 0.9 Hz, 1H), 7.96 (d, J = 8.5 Hz, 2H), 7.66 (d, J = 8.5 Hz, 2H), 7.40 (d, J = 0.9 Hz, 1H), 7.35 (ddd, J = 9.1, 6.6, 1.3 Hz, 1H), 7.10 (d, J = 0.9 Hz, 1H), 7.00 (td, J = 6.9, 1.3 Hz, 1H), 3.18 (q, J = 7.6 Hz, 2H), 1.38 (t, J = 7.6 Hz, 3H); MS m/z 408 (ESI) [M + H]$^+$ |
| 527 | 2-{[4-(difluoromethoxy)phenyl]amino}-6-(2-ethylpyrazolo[1,5-a]pyridin-3-yl)pyridine-4-carbonitrile<br>$^1$H NMR (Acetone-d$_6$) δ 8.79 (br. s, 1H), 8.60 (dt, J = 6.9, 0.9 Hz, 1H), 8.18 (dt, J = 9.1, 0.9 Hz, 1H), 7.74 (m, 2H), 7.31 (ddd, J = 9.1, 6.9, 1.2 Hz, 1H), 7.29 (d, J = 0.9 Hz, 1H), 7.15-7.24 (m, 2H), 6.96-7.00 (m, 2H), 6.96 (t, J = 74.7 Hz, 1H), 3.16 (q, J = 7.6 Hz, 2H), 1.37 (t, J = 7.6 Hz, 3H); MS m/z 406 (ESI) [M + H]$^+$ |
| 528 | 2-{[4-(difluoromethoxy)-3-fluorophenyl]amino}-6-(2-ethylpyrazolo[1,5-a]pyridin-3-yl)pyridine-4-carbonitrile<br>$^1$H NMR (Acetone-d$_6$) δ 9.02 (br. s, 1H), 8.62 (dt, J = 6.9, 1.2 Hz, 1H), 8.18 (dt, J = 9.1, 1.2 Hz, 1H), 7.97 (dd, J = 12.9, 2.5 Hz, 1H), 7.40 (ddd, J = 8.8, 2.5, 1.3 Hz, 1H), 7.36 (d, J = 1.3 Hz, 1H), 7.34 (ddd, J = 6.9, 2.3, 1.3 Hz, 1H), 7.32 (t, J = 8.8 Hz, 1H), 7.04 (d, J = 0.9 Hz, 1H), 6.99 (td, J = 6.6, 1.3 Hz, 1H), 6.96 (t, J = 74.1 Hz, 1H), 3.17 (q, J = 7.6 Hz, 2H), 1.38 (t, J = 7.6 Hz, 3H); MS m/z 424 (ESI) [M + H]$^+$ |
| 529 | 2-(2-ethylpyrazolo[1,5-a]pyridin-3-yl)-6-{[4-(trifluoromethoxy)phenyl]amino}pyridine-4-carbonitrile<br>$^1$H NMR (Acetone-d$_6$) δ 8.92 (br. s, 1H), 8.60 (dt, J = 6.9, 1.1 Hz, 1H), 8.17 (dt, J = 8.9, 1.2 Hz, 1H), 7.78-7.87 (m, 2H), 7.25-7.38 (m, 4H), 7.03 (d, J = 0.9 Hz, 1H), 6.98 (td, J = 6.8, 1.3 Hz, 1H), 3.16 (q, J = 7.6 Hz, 2H), 1.37 (t, J = 7.6 Hz, 3H); MS m/z 424 (ESI) [M + H]$^+$ |
| 672 | 2-(2-ethylpyrazolo[1,5-a]pyridin-3-yl)-6-{[4-(trifluoromethoxy)phenyl]amino}pyridine-4-carbonitrile<br>$^1$H NMR (Acetone-d$_6$) δ 8.98 (d, J = 1.9 Hz, 1H), 8.67 (br. s, 1H), 7.49-7.57 (m, 2H), 7.46 (dd, J = 9.8, 0.6 Hz, 1H), 7.25 (d, J = 0.9 Hz, 1H), 7.05-7.14 (m, 1H), 6.88-7.00 (m, 3H), 3.81 (s, 3H), 3.48 (s, 3H), 2.65 (s, 3H); MS m/z 386 (ESI) [M + H]$^+$ |
| 673 | 2-(6-methoxy-2-methylimidazo[1,2-a]pyridin-3-yl)-6-[(4-methylphenyl)amino]pyridine-4-carbonitrile<br>$^1$H NMR (Acetone-d$_6$) δ 8.97 (dd, J = 2.5, 0.9 Hz, 1H), 8.78 (br. s, 1H), 7.52 (d, J = 8.2 Hz, 2H), 7.47 (dd, J = 9.5, 0.9 Hz, 1H), 7.28 (d, J = 1.3 Hz, 1H), 7.16 (d, J = 7.9 Hz, 2H), 7.10 (dd, J = 9.6, 2.4 Hz, 1H), 7.01 (d, J = 1.3 Hz, 1H), 3.43 (s, 3H), 2.66 (s, 3H), 2.32 (s, 3H); MS m/z 370 (ESI) [M + H]$^+$ |
| 674 | 2-[(4-fluorophenyl)amino]-6-(6-methoxy-2-methylimidazo[1,2-a]pyridin-3-yl)pyridine-4-carbonitrile<br>$^1$H NMR (Acetone-d$_6$) δ 8.91 (dd, J = 2.2, 0.9 Hz, 1H), 8.89 (br. s, 1H), 7.64-7.71 (m, 2H), 7.47 (dd, J = 9.8, 0.9 Hz, 1H), 7.32 (d, J = 0.9 Hz, 1H), 7.09-7.16 (m, 3H), 7.02 (d, J = 0.9 Hz, 1H), 3.48 (s, 3H), 2.65 (s, 3H); MS m/z 374 (ESI) [M + H]$^+$ |
| 675 | 2-(6-methoxy-2-methylimidazo[1,2-a]pyridin-3-yl)-6-(phenylamino)pyridine-4-carbonitrile<br>$^1$H NMR (Acetone-d$_6$) δ 8.96 (dd, J = 2.2, 0.9 Hz, 1H), 8.90 (br. s, 1H), 7.67 (dd, J = 8.5, 0.9 Hz, 2H), 7.47 (dd, J = 9.6, 0.8 Hz, 1H), 7.30-7.36 (m, 3H), 7.03-7.14 (m, 3H), 3.43 (s, 3H), 2.66 (s, 3H); MS m/z 356 (ESI) [M + H]$^+$ |
| 676 | 2-[(4-chlorophenyl)amino]-6-(6-methoxy-2-methylimidazo[1,2-a]pyridin-3-yl)pyridine-4-carbonitrile<br>$^1$H NMR (Acetone-d$_6$) δ 8.90 (br. s, 1H), 8.75 (dd, J = 2.5, 0.9 Hz, 1H), 7.55-7.59 (m, 2H), 7.52 (d, J = 8.7, 1.1 Hz, 1H), 7.33-7.35 (m, 1H), 7.17-7.22 (m, 2H), 6.98 (dd, J = 9.8, 2.5 Hz, 1H), 6.92 (dd, J = 5.4, 1.3 Hz, 1H), 3.34 (s, 3H), 2.51 (s, 3H); MS m/z 390 (ESI) [M + H]$^+$ |

| Cpd | Name and Data |
|---|---|
| 677 | 2-{[4-(difluoromethoxy)phenyl]amino}-6-(6-methoxy-2-methylimidazo[1,2-a]pyridin-3-yl)pyridine-4-carbonitrile<br>$^1$H NMR (Acetone-d$_6$) δ 8.83 (br. s, 1H), 8.77 (d, J = 2.2 Hz, 1H), 7.52-7.62 (m, 2H), 7.33 (dd, J = 9.8, 0.9 Hz, 1H), 7.19 (d, J = 0.9 Hz, 1H), 7.01-7.06 (m, 2H), 6.97 (dd, J = 9.6, 2.4 Hz, 1H), 6.90 (d, J = 1.3 Hz, 1H), 6.80 (t, J = 74.7 Hz, 1H), 3.33 (s, 3H), 2.51 (s, 3H); MS m/z 422 (ESI) [M + H]$^+$ |

| Cpd | Name and Data |
|---|---|
| 207 | 4-({6-[2-(trifluoromethyl)imidazo[1,2-a]pyridin-3-yl]pyrazin-2-yl}amino)phenol<br>$^1$H NMR (DMSO-d$_6$) δ 9.50 (s, 1H), 9.15 (s, 1H), 8.73 (dt, J = 6.9, 0.9 Hz, 1H), 8.23 (s, 1H), 8.08 (s, 1H), 7.83 (dt, J = 9.1, 0.9 Hz, 1H), 7.56 (ddd, J = 9.1, 6.8, 1.1 Hz, 1H), 7.36-7.46 (m, 2H), 7.13 (td, J = 6.9, 1.3 Hz, 1H), 6.65-6.73 (m, 2H); MS m/z 372 (ESI) [M + H]$^+$ |

Example 89

2-methyl-3-(6-{[4-(trifluoromethyl)phenyl]amino}pyrazin-2-yl)imidazo[1,2-a]pyridin-6-ol (Cpd 378)

Example 90

6-[6-fluoro-2-(trifluoromethyl)imidazo[1,2-a]pyridin-3-yl]-4-nitro-N-[4-(trifluoromethyl)phenyl]pyridin-2-amine (Cpd 286)

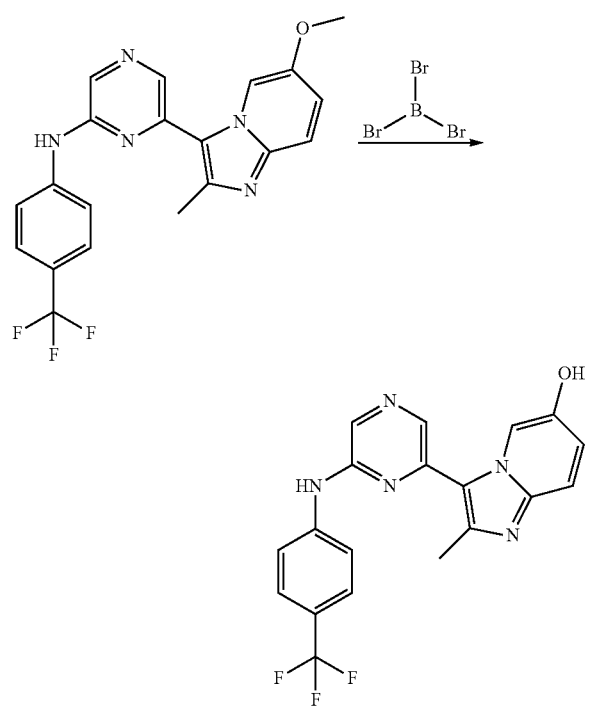

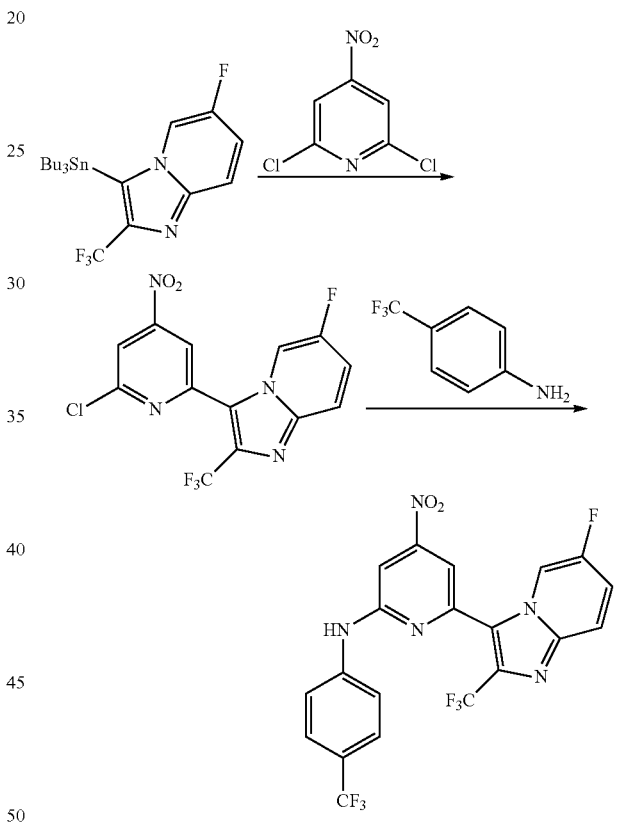

To a suspension of 6-(6-methoxy-2-methylimidazo[1,2-a]pyridin-3-yl)-N-(4-(trifluoromethyl)phenyl)pyrazin-2-amine (37 mg, 0.093 mmol) in CH$_2$Cl$_2$ (10 mL) was added boron tribromide (1.0 M in CH$_2$Cl$_2$, 0.46 mL, 0.46 mmol). The reaction mixture was stirred at room temperature for 2 hours until UPLC showed complete consumption of the starting material. The mixture was washed with a saturated aqueous solution of NaHCO$_3$ (3×5 mL) and the aqueous parts were back-extracted with CH$_2$Cl$_2$ (2×3 mL). The combined organic parts were dried over Na$_2$SO$_4$, then concentrated and purified using silica-gel chromatography to afford the title compound as a clear solid (22 mg, 58%). $^1$H NMR (DMSO-d$_6$) δ 10.11 (s, 1H), 9.63 (br. s., 1H), 8.62 (d, J=2.2 Hz, 1H), 8.32 (s, 1H), 8.25 (s, 1H), 7.91 (d, J=8.8 Hz, 2H), 7.64 (d, J=9.1 Hz, 2H), 7.54 (d, J=9.1 Hz, 1H), 7.15 (dd, J=9.1, 2.2 Hz, 1H), 2.56 (s, 3H); MS m/z 386.

Additional compounds of Formula (I) or a form thereof described herein may be prepared according to the procedure of Example 89 by substituting the appropriate starting materials, reagents and reaction conditions:

Step 1. A mixture of 6-fluoro-3-(tributylstannyl)-2-(trifluoromethyl)imidazo[1,2-a]pyridine (1.68 g, 3.39 mmol), 2,6-dichloro-4-nitropyridine (1.3 g, 6.78 mmol), APC (62 mg, 0.17 mmol), pentaphenyl(di-tert-butylphosphino)ferrocene (Q-Phos, 120 mg, 0.17 mmol) and dioxane (10 mL) was degassed by three cycles of vacuum pumping and N$_2$ purging and heated at 100° C. for 20 minutes until UPLC showed complete consumption of starting material. The reaction mixture was cooled and the solvent was evaporated. The residue was purified using silica gel column chromatography to afford 3-(6-chloro-4-nitropyridin-2-yl)-6-fluoro-2-(trifluoromethyl)imidazo[1,2-a]pyridine (620 mg, 51%) as a yellow solid. $^1$H NMR (DMSO-d$_6$) δ 8.95 (ddd, J=5.0, 2.5, 0.6 Hz, 1H), 8.49 (d, J=1.6 Hz, 1H), 8.48 (d, J=1.6 Hz, 1H), 7.98 (ddd, J=10.1, 5.0, 0.6 Hz, 1H), 7.75 (ddd, J=10.0, 8.0, 2.4 Hz, 1H)

Step 2. A mixture of the obtained product (225 mg, 0.625 mmol), 4-trifluoromethylaniline (200 mg, 1.25 mmol), 2-dicyclohexylphosphino-2',4',6'-triisopropylbiphenyl (X-Phos, 29 mg, 0.006 mmol), tris(dibenzylideneacetone) dipalladium(0) (29 mg, 0.03 mmol) and a mixture of tripotassium phosphate (265 mg, 1.25 mmol) in dioxane (4 mL) was degassed by three cycles of vacuum pumping and $N_2$ purging and heated at 170° C. in a microwave oven for 40 minutes. The reaction mixture was cooled to room temperature, then filtered via a plug of Celite and washed with EtOAc. The filtrate was concentrated and purified by silica gel column chromatography to give the title compound (244 mg, 80%) as a tan solid. $^1$H NMR (DMSO-$d_6$) δ 10.39 (br. s, 1H), 8.98 (ddd, J=5.0, 2.2, 0.9 Hz, 1H), 7.96 (ddd, J=10.1, 5.4, 0.9 Hz, 1H), 7.88 (d, J=8.5 Hz, 2H), 7.82 (d, J=1.6 Hz, 1H), 7.75 (d, J=1.9 Hz, 1H), 7.71 (ddd, J=10.1, 7.9, 2.5 Hz, 1H), 7.63 (d, J=8.8 Hz, 2H); MS m/z 485.9.

Example 91

6-[6-fluoro-2-(trifluoromethyl)imidazo[1,2-a]pyridin-3-yl]-$N^2$-[4-(trifluoromethyl)phenyl]pyridine-2,4-diamine (Cpd 287)

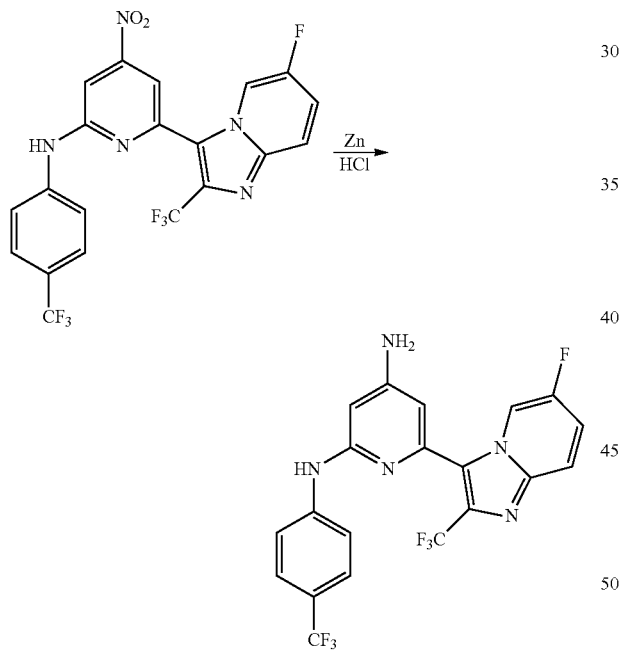

A mixture of Compound 286 (prepared using the procedure described in Example 90 and appropriate starting materials, reagents and reaction conditions) (43 mg, 0.089 mmol), EtOH (2 mL), Zn (40 mg, 0.60 mmol) and 1.0 M HCl (0.6 mL, 0.6 mmol) was stirred at room temperature for 2 hours then quenched with water (5 mL). The resulting precipitate was collected on a filter and dried to afford the title compound (18 mg, 44%) as an off-white solid. $^1$H NMR (DMSO-$d_6$) δ 9.32 (s, 1H), 8.90 (ddd, J=5.0, 2.5, 0.6 Hz, 1H), 7.88 (ddd, J=9.9, 5.2, 0.6 Hz, 1H), 7.77 (d, J=8.8 Hz, 2H), 7.64 (ddd, J=10.0, 7.8, 2.4 Hz, 1H), 7.49 (d, J=8.8 Hz, 2H), 6.48-6.51 (m, 1H), 6.32 (br. s, 2H), 6.17 (d, J=1.6 Hz, 1H); MS m/z 456.

Example 92

2-[(2-[6-fluoro-2-(trifluoromethyl)imidazo[1,2-a]pyridin-3-yl]-6-{[4-(trifluoromethyl)phenyl]amino}pyridin-4-yl)amino]ethanol (Cpd 291)

6-[6-fluoro-2-(trifluoromethyl)imidazo[1,2-a]pyridin-3-yl]-$N^4$-hydroxy-$N^2$-[4-(trifluoromethyl)phenyl]pyridine-2,4-diamine (Cpd 418)

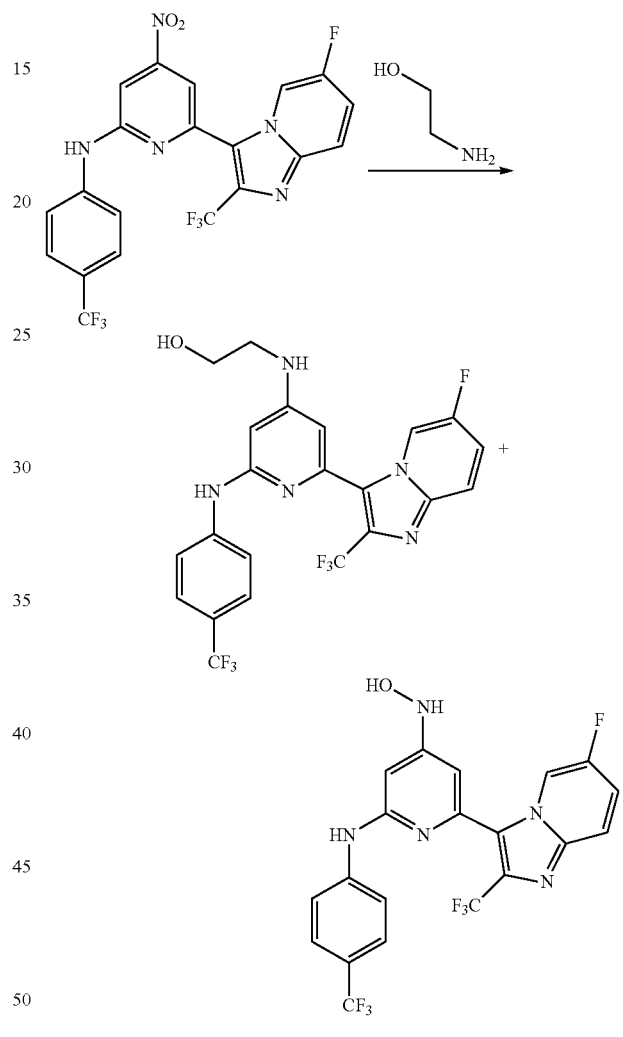

A mixture of Compound 286 (prepared using the procedure described in Example 90 and appropriate starting materials, reagents and reaction conditions) (300 mg, 0.618 mmol) in 2-aminoethanol (3.5 mL) was heated at 120° C. in a microwave oven for 15 minutes. The reaction mixture was cooled down to room temperature, diluted with water (15 mL) and extracted with EtOAc (3×30 mL). The combined organic extracts were dried over $Na_2SO_4$ and concentrated. The residue was separated using silica gel column chromatography to afford a mixture of the title Compound 291 (188 mg, 63%) as an off-white solid and the title Compound 418 (21 mg, 7%).

Compound 291: $^1$H NMR (DMSO-$d_6$) δ 9.36 (s, 1H), 8.88 (ddd, J=4.7, 2.2, 0.6 Hz, 1H), 7.89 (ddd, J=10.1, 5.4, 0.6 Hz, 1H), 7.79 (d, J=8.5 Hz, 2H), 7.64 (ddd, J=10.0, 7.8, 2.4 Hz, 1H), 7.50 (d, J=8.8 Hz, 2H), 6.87 (t, J=5.4 Hz, 1H), 6.56 (s, 1H), 6.14 (d, J=1.6 Hz, 1H), 4.83 (t, J=5.2 Hz, 1H), 3.61 (dd, J=11.5, 5.8 Hz, 2H), 3.18 (dd, J=11.3, 5.7 Hz, 2H); MS m/z 500.

Compound 418: $^1$H NMR (DMSO-d$_6$) δ 9.52 (br. s, 1H), 9.27 (s, 1H), 8.91 (ddd, J=5.0, 2.5, 0.6 Hz, 1H), 8.84 (d, J=1.3 Hz, 1H), 7.90 (ddd, J=10.1, 5.4, 0.6 Hz, 1H), 7.81 (d, J=8.5 Hz, 2H), 7.65 (ddd, J=10.1, 7.9, 2.5 Hz, 1H), 7.52 (d, J=8.8 Hz, 2H), 6.59 (s, 1H), 6.47 (d, J=1.6 Hz, 1H); MS m/z 472.

| Cpd | Name and Data |
|---|---|
| 409 | 6-(6-methoxy-2-methyl-5,6,7,8-tetrahydroimidazo[1,2-a]pyridin-3-yl)-N-[4-(trifluoromethyl)phenyl]pyrazin-2-amine<br>$^1$H NMR (DMSO-d$_6$) δ 9.98 (br. s, 1H), 8.16 (s, 1H), 8.11 (s, 1H),<br>7.88 (d, J = 8.5 Hz, 2H), 7.66 (d, J = 8.5 Hz, 2H), 4.15 (d, J = 3.8 Hz, 2H), 3.76-3.89 (m, 1H), 3.24 (s, 3H), 2.76-2.82 (m, 2H), 2.26 (s, 3H), 2.07-2.15 (m, 1H), 1.96-2.05 (m, 1H); MS m/z 404 (ESI) [M + H]$^+$ |

Example 93

6-[6-fluoro-2-(trifluoromethyl)-5,6,7,8-tetrahydroimidazo[1,2-a]pyridin-3-yl]-N-[4-(trifluoromethyl)phenyl]pyrazin-2-amine (Cpd 406)

Example 94

N-[4-(difluoromethoxy)phenyl]-6-(2-methyl-1H-indol-1-yl)pyrazin-2-amine (Cpd 163)

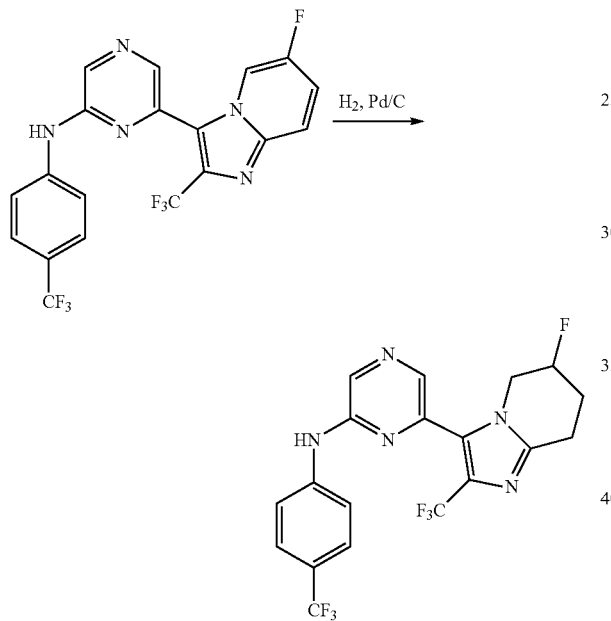

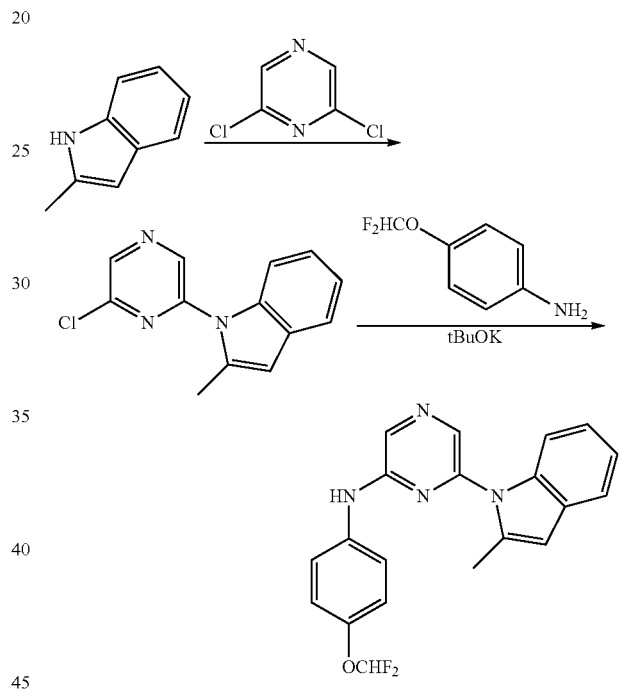

To a mixture of Compound 58 (prepared using the procedure described in Example 42 and appropriate starting materials, reagents and reaction conditions) (88 mg, 0.199 mmol) dissolved in EtOH (10 mL) was added Pd/C (5%) (catalytic). The mixture was reacted under hydrogen (50 psi) in a Parr hydrogenator for 18 hours (UPLC showed complete consumption of the starting material). The catalyst was removed by filtration via Celite plug and the filtrate was concentrated and purified using silica gel column chromatography to afford the title compound (28 mg, 32%) as tan solid. $^1$H NMR (MeOD-d$_4$) δ 8.30 (s, 1H), 8.15 (s, 1H), 7.90 (d, J=8.5 Hz, 2H), 7.61 (d, J=8.5 Hz, 2H), 5.14-5.40 (m, J=4.4, 1.9 Hz, 1H), 4.45 (tt, J=15.1, 1.6 Hz, 1H), 4.23 (ddd, J=38.1, 14.8, 2.5 Hz, 1H), 3.02-3.12 (m, 2H), 2.41-2.53 (m, 1H), 2.09-2.29 (m, 1H), NH missing from spectra; MS m/z 446.

Additional compounds of Formula (I) or a form thereof described herein may be prepared according to the procedure of Example 93 by substituting the appropriate starting materials, reagents and reaction conditions:

Step 1. To a solution of 2-methyl-1H-indole (1.0 g, 7.62 mmol) in dry DMF (10 mL) cooled to 0° C. was added NaH (609 mg, 15.2 mmol, 60% suspension in oil) (followed by gas evolution). The reaction mixture was stirred for 20 minutes at 0° C., then 2,6-dichloropyrazine (1.7 g, 11.43 mmol) was added in one portion. The reaction mixture was warmed to room temperature and stirred for 18 hours until UPLC showed complete consumption of the starting material. The reaction mixture was quenched with water and the resulting precipitate was filtered and recrystallized from MeOH to provide 1-(6-chloropyrazin-2-yl)-2-methyl-1H-indole (779 mg, 43%) as a tan solid. $^1$H NMR (DMSO-d$_6$) δ 8.99-9.02 (m, 1H), 8.87 (s, 1H), 7.51-7.57 (m, 2H), 7.13-7.19 (m, 2H), 6.55-6.57 (m, 1H), 2.49 (d, J=0.9 Hz, 3H); MS m/z 244.

Step 2. A solution of the obtained product (74 mg, 0.04 mmol) and 4-(difluoromethoxy)aniline (96 mg, 0.609 mmol) in THF (1.0 mL) was treated with potassium tert-butoxide (1.0 M in THF, 0.67 mL) at 0° C. The reaction mixture was warmed to room temperature and stirred for one hour, quenched with few drops of AcOH, then water (2 mL) and extracted with CH$_2$Cl$_2$. The organic part was separated, dried over Na$_2$SO$_4$, then concentrated and purified using silica-gel chromatography to afford the title compound (61 mg, 55%) as an off-white solid. $^1$H NMR (DMSO-d$_6$) δ 9.91H afford (s, 1H), 8.27 (s, 1H), 8.15 (s, 1H), 7.63-7.76 (m, 2H), 7.50-7.57 (m, 1H), 7.41-7.46 (m, 1H), 7.09-7.14 (m, 4H), 7.12 (t, J=74.7 Hz, 1H), 6.48-6.51 (m, 1H), 2.45 (d, J=0.9 Hz, 3H); MS m/z 367.

Additional compounds of Formula (I) or a form thereof described herein may be prepared according to the procedure of Example 94 by substituting the appropriate starting materials, reagents and reaction conditions:

| Cpd | Name and Data |
|---|---|
| 164 | N-(4-methoxyphenyl)-6-(2-methyl-1H-indol-1-yl)pyrazin-2-amine<br>$^1$H NMR (DMSO-d$_6$) δ 9.64 (s, 1H), 8.21 (s, 1H), 8.06 (s, 1H), 7.56 (d, J = 9.1 Hz, 2H), 7.51-7.54 (m, 1H), 7.39-7.47 (m, 1H), 7.07-7.13 (m, 2H), 6.83-6.92 (m, 2H), 6.45-6.49 (m, 1H), 3.71 (s, 3H), 2.44 (d, J = 0.9 Hz, 3H); MS m/z 331 (ESI) [M + H]$^+$ |
| 162 | 6-(2-methyl-1H-indol-1-yl)-N-P-(trifluoromethyl)phenyl]pyrazin-2-amine<br>$^1$H NMR (DMSO-d$_6$) δ 10.27 (s, 1H), 8.36 (s, 1H), 8.27 (s, 1H), 7.89 (d, J = 8.5 Hz, 2H), 7.64 (d, J = 8.8 Hz, 2H), 7.52-7.59 (m, 1H), 7.40-7.49 (m, 1H), 7.09-7.16 (m, 2H), 6.51-6.53 (m, 1H), 2.47 (d, J = 0.6 Hz, 3H); MS m/z 369 (ESI) [M + H]$^+$) |
| 174 | N-(4-methoxyphenyl)-6-(2-methyl-1H-indol-1-yl)pyridin-2-amine<br>$^1$H NMR (DMSO-d$_6$) δ 9.09 (s, 1H), 7.75 (dd, J = 8.4, 7.4 Hz, 1H), 7.47-7.57 (m, 3H), 7.34-7.41 (m, 1H), 7.03-7.10 (m, 2H), 6.82-6.86 (m, 2H), 6.80 (dd, J = 8.0, 2.4 Hz, 2H), 6.40-6.43 (m, 1H), 3.69 (s, 3H), 2.43 (d, J = 0.6 Hz, 3H); MS m/z 330 (ESI) [M + H]$^+$ |
| 192 | 6-(5,6-dichloro-2-methyl-1H-benzimidazol-1-yl)-N-[4-(trifluoromethoxy)phenyl]pyrazin-2-amine<br>$^1$H NMR (DMSO-d$_6$) δ 10.16 (br. s, 1H), 8.39 (s, 1H), 8.34 (s, 1H), 7.96 (s, 1H), 7.85 (s, 1H), 7.76 (d, J = 9.1 Hz, 2H), 7.32 (d, J = 9.1 Hz, 2H), 2.65 (s, 3H); MS m/z 455 (ESI) [M + H]$^+$ |
| 193 | 6-(5,6-dichloro-2-methyl-1H-benzimidazol-1-yl)-N-[4-(trifluoromethyl)phenyl]pyrazin-2-amine<br>$^1$H NMR (Acetone-d$_6$) δ 9.97 (br. s., 1H), 8.31 (d, J = 8.5 Hz, 2H), 8.12 (d, J = 1.9 Hz, 1H), 7.97 (d, J = 8.5 Hz, 2H), 7.88 (d, J = 8.5 Hz, 1H), 7.61 (s, 1H), 7.57 (dd, J = 8.7, 2.0 Hz, 1H), 3.04 (s, 3H); MS m/z 439 (ESI) [M + H]$^+$ |
| 209 | N-[3-fluoro-4-(trifluoromethyl)phenyl]-6-(2-methyl-1H-benzimidazol-1-yl)pyrazin-2-amine<br>$^1$H NMR (DMSO-d$_6$) δ 10.59 (s, 1H), 8.46 (d, J = 6.3 Hz, 2H), 7.93 (d, J = 14.2 Hz, 1H), 7.63-7.76 (m, 2H), 7.57 (dd, J = 6.9, 1.6 Hz, 1H), 7.53 (d, J = 8.5 Hz, 1H), 7.25-7.32 (m, 2H), 2.66 (s, 3H); MS m/z 388 (ESI) [M + H]$^+$ |
| 220 | 6-(6-chloro-2-methyl-1H-benzimidazol-1-yl)-N-[4-(trifluoromethoxy)phenyl]pyrazin-2-amine<br>$^1$H NMR (DMSO-d$_6$) δ 10.15 (br. s, 1H), 8.38 (s, 1H), 8.33 (s, 1H), 7.74-7.80 (m, 2H), 7.67 (d, J = 8.5 Hz, 1H), 7.61 (d, J = 1.9 Hz, 1H), 7.27-7.35 (m, 3H), 2.63 (s, 3H); MS m/z 420 (ESI) [M + H]$^+$ |
| 221 | 6-(6-chloro-2-methyl-1H-benzimidazol-1-yl)-N-[4-(difluoromethoxy)phenyl]pyrazin-2-amine<br>$^1$H NMR (DMSO-d$_6$) δ 10.02 (br. s, 1H), 8.35 (s, 1H), 8.28 (s, 1H), 7.64-7.71 (m, 3H), 7.61 (d, J = 2.2 Hz, 1H), 7.30 (dd, J = 8.7, 2.0 Hz, 1H), 7.11-7.16 (m, 2H), 7.12 (t, J = 74.4 Hz, 1H), 2.62 (s, 3H); MS m/z 402 (ESI) [M + H]$^+$ |
| 223 | 6-(5-chloro-2-methyl-1H-benzimidazol-1-yl)-N-[4-(trifluoromethoxy)phenyl]pyrazin-2-amine<br>$^1$H NMR (DMSO-d$_6$) δ 10.16 (br. s, 1H), 8.39 (s, 1H), 8.31 (s, 1H), 7.76 (d, J = 9.1 Hz, 2H), 7.73 (d, J = 1.9 Hz, 1H), 7.54 (d, J = 8.5 Hz, 1H), 7.33 (d, J = 8.5 Hz, 2H), 7.29 (dd, J = 8.7, 2.0 Hz, 1H), 2.63 (s, 3H); MS m/z 420 (ESI) [M + H]$^+$ |
| 224 | 6-(5-chloro-2-methyl-1H-benzimidazol-1-yl)-N-[4-(difluoromethoxy)phenyl]pyrazin-2-amine<br>MS m/z 402 (ESI) [M + H]$^+$ |
| 225 | N,2-dimethyl-1-(6-{[4-(trifluoromethoxy)phenyl]amino}pyrazin-2-yl)-1H-benzimidazol-6-amine<br>$^1$H NMR (DMSO-d$_6$) δ 10.08 (br. s, 1H), 8.31 (s, 1H), 8.24 (s, 1H), 7.75-7.81 (m, 2H), 7.32 (d, J = 8.2 Hz, 2H), 7.25 (d, J = 8.8 Hz, 1H), 6.69 (d, J = 2.2 Hz, 1H), 6.58 (dd, J = 8.7, 2.4 Hz, 1H), 5.47 (q, J = 5.5 Hz, 1H), 2.72 (d, J = 5.4 Hz, 3H), 2.57 (s, 3H); MS m/z 415 (ESI) [M + H]$^+$ |
| 239 | 6-(5-chloro-2-methyl-1H-benzimidazol-1-yl)-N-[4-(trifluoromethyl)phenyl]pyrazin-2-amine<br>$^1$H NMR (DMSO-d$_6$) δ 10.37 (s, 1H), 8.45 (s, 1H), 8.39 (s, 1H), 7.87 (d, J = 8.5 Hz, 2H), 7.75 (s, 1H), 7.67 (d, J = 8.5 Hz, 2H), 7.56 (d, J = 8.5 Hz, 1H), 7.31 (d, J = 8.8 Hz, 1H), 2.65 (s, 3H); MS m/z 404 (ESI) [M + H]$^+$ |
| 240 | 6-(6-chloro-2-methyl-1H-benzimidazol-1-yl)-N-[4-(trifluoromethyl)phenyl]pyrazin-2-amine<br>$^1$H NMR (DMSO-d$_6$) δ 10.36 (s, 1H), 8.44 (s, 1H), 8.40 (s, 1H), 7.88 (d, J = 8.5 Hz, 2H), 7.67 (t, J = 8.8 Hz, 3H), 7.63 (d, J = 1.6 Hz, 1H), 7.31 (dd, J = 8.7, 2.0 Hz, 1H), 2.64 (s, 3H); MS m/z 404 (ESI) [M + H]$^+$ |
| 274 | N,2-dimethyl-1-(6-{[4-(trifluoromethyl)phenyl]amino}pyrazin-2-yl)-1H-benzimidazol-6-amine<br>$^1$H NMR (DMSO-d$_6$) δ 10.33 (br. s, 1H), 8.39 (s, 1H), 8.33 (s, 1H), 7.91 (d, J = 8.5 Hz, 2H), 7.66 (d, J = 8.5 Hz, 2H), 7.35 (d, J = 8.8 Hz, 1H), 6.58 (dd, J = 8.5, 2.2 Hz, 1H), 6.55 (s, 1H), 5.64 (q, J = 5.4 Hz, 1H), 2.59 (d, J = 5.4 Hz, 3H), 2.54 (s, 3H); MS m/z 399 (ESI) [M + H]$^+$ |
| 275 | N-benzyl-2-methyl-1-(6-{[4-(trifluoromethyl)phenyl]amino}pyrazin-2-yl)-1H-benzimidazol-6-amine<br>$^1$H NMR (DMSO-d$_6$) δ 10.31 (br. s., 1H), 8.37 (s, 1H), 8.22 (s, 1H), 7.84-7.94 (m, 2H), 7.62-7.70 (m, 2H), 7.21-7.35 (m, 5H), 7.13-7.20 (m, 1H), 6.61-6.68 (m, 2H), 6.18 (t, J = 6.0 Hz, 1H), 4.18 (d, J = 6.0 Hz, 2H), 2.53 (s, 3H); MS m/z 475 (ESI) [M + H]$^+$ |
| 285 | 2-methyl-1-(6-{[4-(trifluoromethyl)phenyl]amino}pyrazin-2-yl)-1H-benzimidazol-6-amine<br>$^1$H NMR (DMSO-d$_6$) δ 10.31 (s, 1H), 8.39 (s, 1H), 8.29 (s, 1H), 7.89 (d, J = 8.5 Hz, 2H), 7.67 (d, J = 8.8 Hz, 2H), 7.29 (d, J = 8.5 Hz, 1H), 6.65 (d, J = 1.9 Hz, 1H), 6.56 (dd, J = 8.4, 2.0 Hz, 1H), 5.01 (br. s, 2H), 2.53 (s, 3H); MS m/z 385 (ESI) [M + H]$^+$ |
| 306 | 6-(2-methyl-1H-benzimidazol-1-yl)-N-[4-(2,2,2-trifluoroethoxy)phenyl]pyrazin-2-amine<br>$^1$H NMR (DMSO-d$_6$) δ 9.85 (br. s, 1H), 8.30 (s, 1H), 8.21 (s, 1H), 7.65 (dd, J = 6.3, 2.2 Hz, 1H), 7.61 (d, J = 8.8 Hz, 2H), 7.51 (d, J = 6.6 Hz, 1H), 7.18-7.33 (m, 2H), 7.02 (d, J = 8.8 Hz, 2H), 4.69 (q, J = 8.8 Hz, 2H), 2.61 (s, 3H); MS m/z 400 (ESI) [M + H]$^+$ |
| 307 | 6-(2-methyl-1H-benzimidazol-1-yl)-N-[4-(1,1,2,2-tetrafluoroethoxy)phenyl]pyrazin-2-amine<br>$^1$H NMR (DMSO-d$_6$) δ 10.10 (s, 1H), 8.37 (s, 1H), 8.30 (s, 1H), 7.75 (d, J = 8.8 Hz, 2H), 7.64-7.68 (m, 1H), 7.49-7.53 (m, 1H), 7.24-7.29 (m, 2H), 7.22 (s, 2H), 6.77 (tt, J = 51.7, 2.8 Hz, 1H), 2.63 (s, 3H); MS m/z 418 (ESI) [M + H]$^+$ |
| 324 | N-[4-(difluoromethoxy)-3-fluorophenyl]-6-(2-methyl-1H-benzimidazol-1-yl)pyrazin-2-amine<br>$^1$H NMR (DMSO-d$_6$) δ 10.23 (s, 1H), 8.37 (s, 1H), 8.35 (s, 1H), 7.85 (dd, J = 13.4, 2.4 Hz, 1H), 7.65-7.69 (m, 1H), 7.55 (dd, J = 7.4, 1.1 Hz, 1H), 7.37-7.41 (m, 1H), 7.33 (d, J = 8.8 Hz, 1H), 7.25-7.31 (m, 2H), 7.13 (t, J = 74.0 Hz, 1H), 2.64 (s, 3H); MS m/z 386 (ESI) [M + H]$^+$ |
| 397 | 2-{[2-methyl-1-(6-{[4-(trifluoromethyl)phenyl]amino}pyrazin-2-yl)-1H-benzimidazol-6-yl]amino}ethanol<br>$^1$H NMR (DMSO-d$_6$) δ 10.31 (s, 1H), 8.39 (s, 1H), 8.32 (s, 1H), 7.90 (d, J = 8.5 Hz, 2H), 7.66 (d, J = 8.5 Hz, 2H), 7.34 (d, J = 8.5 Hz, 1H), 6.57-6.68 (m, 2H), 5.46 (t, J = 5.9 Hz, 1H), 4.62 (t, J = 5.9 Hz, 1H), 3.52 (q, J = 5.6 Hz, 2H), 3.01 (q, J = 5.9 Hz, 2H), 2.55 (s, 3H); MS m/z 429 (ESI) [M + H]$^+$ |

Example 95

6-(2-methyl-1H-benzimidazol-1-yl)-N²-[4-(trifluoromethyl)phenyl]pyridine-2,3-diamine (Cpd 465)

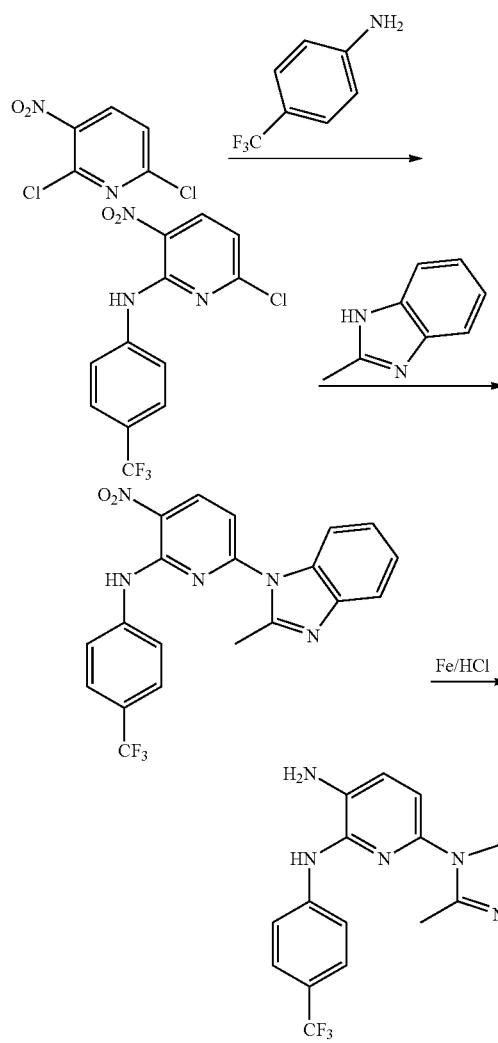

Step 1. To a solution of 2,6-dichloro-3-nitropyridine (1.0 g, 6.12 mmol) and 4-(trifluoromethyl)aniline (988 mg, 6.12 mmol) in acetonitrile (15 mL) was added $Cs_2CO_3$ (3.9 g, 12.24 mmol). The reaction mixture was stirred at room temperature for 14 hours, then quenched with water. The resulting precipitate was filtered and purified by chromatography on silica gel to provide 6-chloro-3-nitro-N-(4-(trifluoromethyl)phenyl)pyridin-2-amine (214 mg, 11%) as yellow solid.

Step 2. To a solution of the obtained intermediate (60 mg, 0.185 mmol) in acetonitrile (3 mL) was added 2-methyl-1H-benzo[d]imidazole (25 mg, 0.185 mmol) and $Cs_2CO_3$ (120 mg, 0.37 mmol). The reaction mixture was heated at 60° C. for 16 hours, until UPLC analysis showed complete conversion of the starting material, then quenched with water (5 mL) and the resulting precipitate was collected on a filter. The residue was dried to give 6-(2-methyl-1H-benzo[d]imidazol-1-yl)-3-nitro-N-(4-(trifluoromethyl)phenyl)pyridin-2-amine (59 mg, 77%) as a bright yellow solid. Regiochemistry was established by NOESY analysis. $^1$H NMR (Acetone-$d_6$) δ 10.36 (br. s., 1H), 8.78 (d, J=8.5 Hz, 1H), 7.88 (d, J=8.5 Hz, 2H), 7.60 (d, J=8.8 Hz, 2H), 7.50 (d, J=8.5 Hz, 2H), 7.24 (d, J=8.8 Hz, 1H), 7.16 (td, J=7.9, 1.3 Hz, 1H), 7.12 (td, J=7.9, 1.3 Hz, 1H), 2.51 (s, 3H); MS m/z 414.

Step 3. To a solution of the obtained intermediate (50 mg, 0.12 mmol) in EtOH (3 mL) was added iron (34 mg, 0.60 mmol) and 1.0 M HCl (0.6 mL, 0.6 mmol). The reaction mixture was stirred at room temperature for 3 hours, then quenched with a saturated aqueous solution of $NaHCO_3$ (5 mL). The resulting precipitate was collected on a filter and purified using silica-gel chromatography to afford the title compound as an off-white solid (36 mg, 78%). $^1$H NMR (Acetone-$d_6$) δ 7.89 (br. s., 1H), 7.88 (d, J=8.5 Hz, 2H), 7.59-7.65 (m, 1H), 7.55 (d, J=8.8 Hz, 2H), 7.41 (d, J=7.9 Hz, 1H), 7.34-7.39 (m, 1H), 7.21 (dddd, J=13.0, 7.8, 7.6, 1.6 Hz, 2H), 7.02 (d, J=7.9 Hz, 1H), 5.05 (br. s., 2H), 2.57 (s, 3H); MS m/z 384.

Example 96

N-[4-(methylsulfonyl)phenyl]-6-[2-(trifluoromethyl)imidazo[1,2-a]pyridin-3-yl]pyrazin-2-amine (Cpd 68)

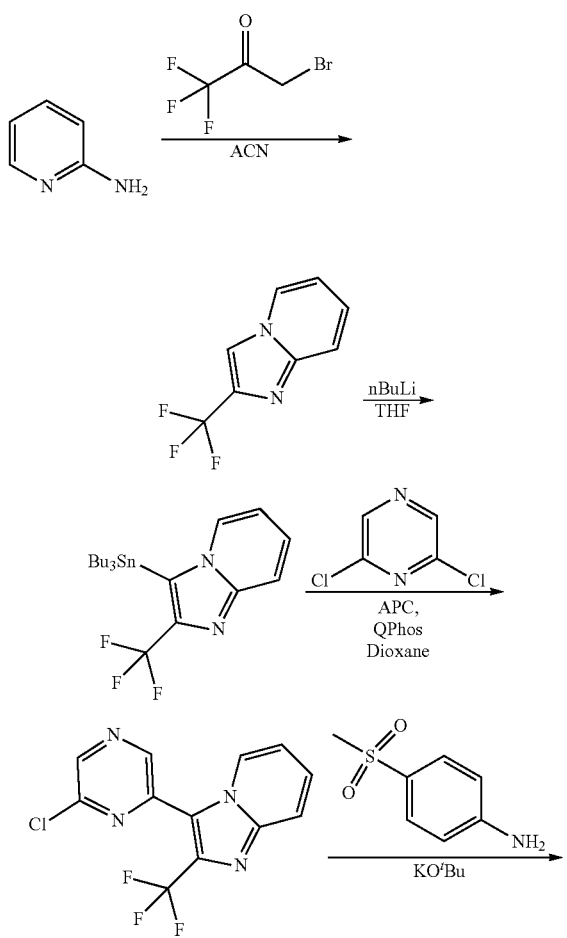

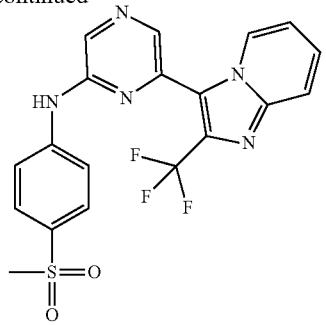

Step 1. To 2-aminopyrindine (6.9 g, 73.31 mmol) was added 3-bromo-1,1,1-trifluoropropan-2-one (14.0 g, 73.31 mmol) portion wise at 0° C. The mixture was diluted with acetonitrile (25 mL), then heated at reflux overnight, cooled and diluted with ethyl acetate (300 mL), then washed with a saturated $NaHCO_3$ solution (200 mL), water (200 mL) and brine (200 mL). The residue was dried over magnesium sulfate, then filtered and evaporated. The product was filtered by a pad of silica gel, while washing with a 25% ethyl acetate:hexane mixture to afford 2-(trifluoromethyl)imidazo[1,2-a]pyridine (8.7 g, 64%).

Step 2. To a solution of the obtained intermediate (2.61 g, 14.02 mmol) in THF (25 mL) was added n-BuLi (2.5 M in hexane, 6.73 mL, 16.83 mmol) dropwise at −78° C. The reaction mixture was stirred at −78° C. for 15 minutes, then tributyltin iodide was added. The reaction mixture was stirred at room temperature for 2 hours, then diluted with ethanol (50 mL), filtered through a plug of potassium fluoride (5 g)/Celite (100 g) and washed with ethanol. The solvent was evaporated and the residue separated by silica gel column chromatography (1:5 ethyl acetate-hexane) to afford 3-(tributylstannyl)-2-(trifluoromethyl)imidazo[1,2-a]pyridine (5.76 g, 86%) as an oil.

Step 3. A mixture of the obtained intermediate (2.11 g, 4.43 mmol), 2,6-dichloropyrazine (0.60 g, 4.03 mmol), APC (44.2 mg, 0.12 mmol), pentaphenyl(di-tert-butylphosphino)ferrocene (Q-Phos, 85.9 mg, 0.12 mmol) and dioxane (10 mL) was degassed by three cycles of vacuum pumping and $N_2$ purging. The reaction mixture was heated at reflux for 2 hours, then cooled and the solvent evaporated. The residue was separated by column chromatography, eluting with 20% ethyl acetate in hexane to afford 3-(6-chloropyrazin-2-yl)-2-(trifluoromethyl)imidazo[1,2-a]pyridine (535.0 mg, 46%) as an off-white solid.

Step 4. A solution of the obtained intermediate (105.0 mg, 0.35 mmol) and 4-(methylsulfonyl)aniline (120.4 mg, 0.70 mmol) in THF (1.0 mL) was treated with potassium tert-butoxide (1.0 M in THF, 1.1 mL, 1.05 mmol) at 0° C. The reaction mixture was stirred at room temperature for one hour, then diluted with 20% ethyl acetate:dichloromethane, filtered through a pad of silica gel/Celite and the solvent evaporated. The residue was separated by column chromatography, eluting with 20% ethyl acetate:hexane, then 10% methanol:dichloromethane to afford the title compound (120.0 mg, 79%) as a yellow solid. m.p. 256-258° C.; $^1$H NMR (500 MHz, Acetone-$d_6$) δ 9.56 (s, 1H), 8.82-8.93 (m, 1H), 8.44 (s, 1H), 8.40 (s, 1H), 8.01 (d, J=9.14 Hz, 2H), 7.83 (dd, J=9.14 Hz, 2H), 7.77-7.81 (m, 1H), 7.55-7.65 (m, 1H), 7.18 (d, J=1.26 Hz, 1H), 3.06 (s, 3H). MS (ES+): m/e 434.2 (100), 435.2 (20).

Additional compounds of Formula (I) or a form thereof described herein may be prepared according to the procedure of Example 96 by substituting the appropriate starting materials, reagents and reaction conditions:

| Cpd | Name and Data |
|---|---|
| 69 | N-[4-(methylsulfanyl)phenyl]-6-[2-(trifluoromethyl)imidazo[1,2-a]pyridin-3-yl]pyrazin-2-amine <br> $^1$H NMR (500 MHz, Acetone-$d_6$) δ 9.04 (br. s, 1H), 8.83-8.90 (m, 1H), 8.33 (s, 1H), 8.25 (s, 1H), 7.75-7.80 (m, 1H), 7.68-7.74 (d, J = 8.20 Hz, 2H), 7.53-7.64 (m, 1H), 7.22-7.28 (d, J = 8.20 Hz, 2H), 7.14 (d, J = 0.95 Hz, 1H), 2.45 (s, 3H); m.p. 202-204° C.; MS m/z 402.2 (ESI) [M + H]$^+$ |
| 96 | N-(4-methyl-1,3-thiazol-2-yl)-6-[2-(trifluoromethyl)imidazo[1,2-a]pyridin-3-yl]pyrazin-2-amine <br> $^1$H NMR (500 MHz, DMSO-$d_6$) δ 11.96 (br. s, 1H), 8.91 (s, 1H), 8.61 (d, J = 4.10 Hz, 2H), 7.88 (d, J = 8.83 Hz, 1H), 7.59-7.64 (m, 1H), 7.55-7.58 (m, 1H), 6.65 (s, 1H), 2.27 (s, 3H); m.p. 317-319° C.; MS m/z 377.1 (ESI) [M + H]$^+$ |
| 97 | N-(3-methyl-1,2-oxazol-5-yl)-6-[2-(trifluoromethyl)imidazo[1,2-a]pyridin-3-yl]pyrazin-2-amine <br> $^1$H NMR (500 MHz, DMSO-$d_6$) δ 11.53 (s, 1H), 8.60-8.83 (m, 1H), 8.47 (s, 1H), 8.39 (s, 1H), 7.82-7.91 (m, 1H), 7.53-7.66 (m, 1H), 7.12-7.27 (m, 1H), 6.03 (s, 1H), 2.11 (s, 3H); m.p. 216-218° C.; MS m/z 361.2 (ESI) [M + H]$^+$ |
| 118 | 6-[6-(trifluoromethyl)imidazo[2,1-b][1,3]thiazol-5-yl]-N-[4-(trifluoromethyl)phenyl]pyrazin-2-amine <br> $^1$H NMR (500 MHz, Acetone-$d_6$) δ 9.28-9.50 (m, 1H), 8.34-8.48 (m, 2H), 8.26 (d, J = 4.73 Hz, 1H), 7.99 (d, J = 8.51 Hz, 2H), 7.67 (d, J = 8.51 Hz, 2H), 7.54 (d, J = 4.73 Hz, 1H); m.p. 195-197° C. |
| 119 | N-(4-methoxyphenyl)-6-[6-(trifluoromethyl)imidazo[2,1-b][1,3]thiazol-5-yl]pyrazin-2-amine <br> $^1$H NMR (500 MHz, Acetone-$d_6$) δ 8.75 (br. s., 1H), 8.25 (d, J = 4.41 Hz, 1H), 8.24 (s, 1H), 8.21 (s, 1H), 7.60 (d, J = 9.14 Hz, 2H), 7.47 (d, J = 4.73 Hz, 1H), 6.93-7.00 (d, J = 9.14 Hz, 2H), 3.81 (s, 3H); MS m/z 392.2 (ESI) [M + H]$^+$ |
| 120 | N-[4-(trifluoromethoxy)phenyl]-6-[6-(trifluoromethyl)imidazo[2,1-b][1,3]thiazol-5-yl]pyrazin-2-amine <br> $^1$H NMR (500 MHz, Acetone-$d_6$) δ 9.20 (br. s, 1H), 8.30-8.35 (m, 2H), 8.24 (d, J = 4.73 Hz, 1H), 7.87 (d, J = 9.46 Hz, 2H), 7.50 (d, J = 4.41 Hz, 1H), 7.33 (d, J = 9.46 Hz, 2H); m.p. 177-178° C. |
| 121 | N-[4-(difluoromethoxy)phenyl]-6-[6-(trifluoromethyl)imidazo[2,1-b][1,3]thiazol-5-yl]pyrazin-2-amine <br> $^1$H NMR (500 MHz, Acetone-$d_6$) δ 9.06 (br. s, 1H), 8.27-8.33 (m, 2H), 8.24 (d, J = 4.41 Hz, 1H), 7.76-7.83 (d, J = 9.14 Hz, 2H), 7.50 (d, J = 4.73 Hz, 1H), 7.20 (d, J = 9.14 Hz, 2H); m.p. 189-190° C. |
| 122 | N-phenyl-6-[6-(trifluoromethyl)imidazo[2,1-b][1,3]thiazol-5-yl]pyrazin-2-amine <br> $^1$H NMR (500 MHz, Acetone-$d_6$) δ 8.98 (br. s., 1H), 8.24-8.32 (m, 3H), 7.73 (d, J = 8.51 Hz, 2H), 7.49 (d, J = 4.41 Hz, 1H), 7.32-7.41 (m, 2H), 7.03-7.13 (m, 1H); MS m/z 362.1 (ESI) [M + H]$^+$ |
| 165 | N-(4-cyclopropylphenyl)-6-[2-(trifluoromethyl)imidazo[1,2-a]pyridin-3-yl]pyrazin-2-amine <br> $^1$H NMR (500 MHz, Acetone-$d_6$) δ 9.27 (s, 1H), 8.74-8.91 (m, 1H), 8.32 (s, 1H), 8.17 (s, 1H), 7.76 (d, J = 11.00 Hz, 1H), 7.61 (d, J = 8.83 Hz, 2H), 7.52-7.58 (m, 1H), 7.07-7.15 (m, 1H), 7.00 (d, J = 8.83 Hz, 2H), 1.81-1.89 (m, 1H), 0.84-0.91 (m, 2H), 0.56-0.64 (m, 2H); m.p. 317-320° C.; MS m/z 396.2 (ESI) [M + H]$^+$ |

Example 97

6-(2-cyclopropylimidazo[1,2-a]pyridin-3-yl)-N-[4-(trifluoromethyl)phenyl]pyrazin-2-amine (Cpd 129)

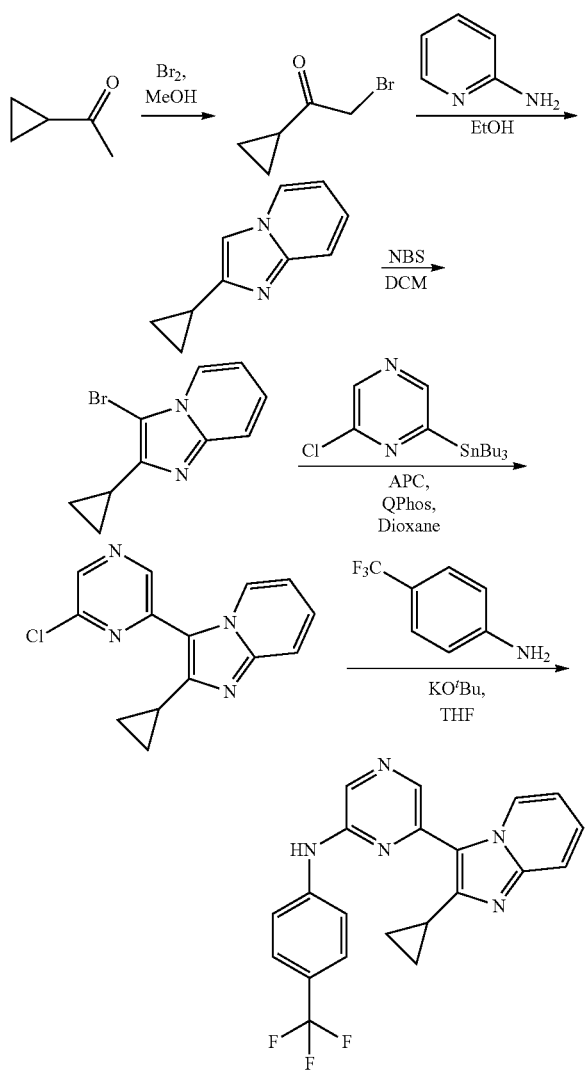

Step 1. To a solution of cyclopropyl methyl ketone (10.0 g, 0.12 mol) in methanol (80 mL) was added bromine (19.0 g, 0.12 mol) dropwise at 0° C. The resulting mixture was allowed to cool below 10° C. for 30 minutes, followed by continued stirring at room temperature for 30 minutes. The reaction was quenched with water (150 mL) and extracted with ethyl ether (3×150 mL). The extract was sequentially washed with $Na_2CO_3$ (10%, 100 mL), water (100 mL) and brine (100 mL), then dried over $MgSO_4$, filtered and evaporated to afford 2-bromo-1-cyclopropylethanone (19.0 g, 98%) as a clear oil.

Step 2. The obtained intermediate (12.99 g, 71.67 mmol) and 2-aminopyridine (6.85 g, 72.78 mmol) were pre-mixed and stirred in a 250 mL round bottom flask at room temperature for 15 minutes. The resulting mixture was diluted with ethanol (80 mL) and stirred at reflux overnight. The solvent was evaporated and the residue partitioned between ethyl acetate (300 mL) and $NaHCO_3$ (250 mL). The organic layer was separated, then dried over $MgSO_4$, filtered and evaporated. The residue was separated by silica gel column chromatography (3:2 dichloromethane-hexane) to afford 2-cyclopropylimidazo[1,2-a]pyridine (4.95 g, 45%) as a clear oil. $^1$H NMR (500 MHz, Acetone-$d_6$) δ 8.39 (ddd, J=0.95, 1.10, 6.78 Hz, 1H), 7.69 (s, 1H), 7.41 (dd, J=0.79, 8.98 Hz, 1H), 7.17 (ddd, J=1.26, 6.62, 9.14 Hz, 1H), 6.81 (dt, J=1.26, 6.78 Hz, 1H), 1.96-2.11 (m, 1H), 0.87-1.04 (m, 4H).

Step 3. To a solution of the obtained intermediate (5.02 g, 31.73 mmol) in dichloromethane (35 mL) was added N-bromosuccinimide (5.72 g, 31.73 mmol) portion wise at 0° C. The mixture was stirred at room temperature for 10 minutes, then $NaHCO_3$ (200 mL) was added. The mixture was extracted with ethyl acetate (200 mL), washed with brine, dried over $MgSO_4$, then filtered and evaporated. The residue was separated by silica gel column chromatography, eluting with 20% ethyl acetate:hexane to afford 3-bromo-2-cyclopropylimidazo[1,2-a]pyridine (6.45 g, 86%) as a pale white solid. $^1$H NMR (500 MHz, DMSO-$d_6$) δ 8.73 (d, J=6.94 Hz, 1H), 7.98 (d, J=8.83 Hz, 1H), 7.70-7.83 (m, 1H), 7.50 (dt, J=0.95, 6.78 Hz, 1H), 2.45-2.53 (m, 1H), 1.37-1.53 (m, 4H).

Step 4. A mixture of the obtained intermediate (756.0 mg, 3.18 mmol), 2-chloro-6-(tributylstannyl)pyrazine (1.35 g, 3.34 mmol), APC (35.0 mg, 0.10 mmol), pentaphenyl(di-tert-butylphosphino)ferrocene (Q-Phos, 68.0 mg, 0.10 mmol) and dioxane (5 mL) was degassed by three cycles of vacuum pumping and $N_2$ purging. The reaction mixture was heated at reflux for 3 hours, cooled and the solvent was evaporated. The residue was separated by column chromatography, eluting with 20% ethyl acetate:hexane to afford 3-(6-chloropyrazin-2-yl)-2-cyclopropylimidazo[1,2-a]pyridine (210.0 mg, 25%) as a light yellow solid. MS (ES+): m/e 245.1 (100), 247.1 (20).

Step 5. A solution of the obtained intermediate (40.0 mg, 0.15 mmol), 4-(trifluoromethyl)aniline (59.6 mg, 0.37 mmol) in THF (1.0 mL) was treated with potassium tert-butoxide (1.0 M in THF, 0.52 mL, 0.52 mmol) at 0° C. The reaction mixture was stirred at room temperature for one hour. The mixture was diluted with 20% ethyl acetate in dichloromethane, and filtered through a pad of silica gel/Celite. The solvent was evaporated and the resulting residue was washed with 20% ethyl acetate in hexane, followed by 10% methanol in dichloromethane to afford the title compound (40.9 mg, 71%) as a yellow solid. m.p. 215-217° C.; H NMR (500 MHz, Acetone-$d_6$) δ 9.30 (s, 1H), 9.13 (ddd, J=0.95, 1.10, 7.09 Hz, 1H), 8.52 (s, 1H), 8.23 (s, 1H), 7.97 (d, J=8.51 Hz, 2H), 7.63 (d, J=8.51 Hz, 2H), 7.51 (ddd, J=1.10, 1.26, 8.98 Hz, 1H), 7.33 (ddd, J=1.26, 6.78, 8.98 Hz, 1H), 6.90 (dt, J=1.26, 6.94 Hz, 1H), 2.29-2.41 (m, 1H), 1.13-1.18 (m, 2H), 1.00-1.08 (m, 2H); MS (ES+): MS (ES+): m/e 396.3 (100), 397.3 (30).

Additional compounds of Formula (I) or a form thereof described herein may be prepared according to the procedure of Example 97 by substituting the appropriate starting materials, reagents and reaction conditions:

| Cpd | Name and Data |
|---|---|
| 130 | 6-(2-cyclopropylimidazo[1,2-a]pyridin-3-yl)-N-[4-(difluoromethoxy)phenyl]pyrazin-2-amine<br>$^1$H NMR (500 MHz, Acetone-$d_6$) δ 9.16 (d, J = 6.94 Hz, 1H), 8.94 (br. s, 1H), 8.46 (s, 1H), 8.16 (s, 1H), 7.76-7.84 (d, J = 9.14 Hz, 2H), 7.50 (dd, J = 1.00, 11.35 Hz, 1H), 7.29-7.37 (m, 1H), 7.17 (d, J = 9.14 Hz, 2H), 6.78-7.08 (t, J = 75.00 Hz, 1H), 6.89 (s, 1H), 2.31-2.39 (m, 1H), 1.13-1.19 (m, 2H), 1.05 (m, 2H); m.p. 208-210° C.; MS m/z 394.3 (ESI) [M + H]$^+$ |

-continued

| Cpd | Name and Data |
|---|---|
| 131 | 6-(2-cyclobutylimidazo[1,2-a]pyridin-3-yl)-N-[4-(trifluoromethyl)phenyl]pyrazin-2-amine<br>$^1$H NMR (500 MHz, Acetone-$d_6$) δ 9.29 (s, 1H), 9.12 (td, J = 1.10, 6.94 Hz, 1H), 8.26 (s, 1H), 8.22 (s, 1H), 7.97 (d, J = 8.51 Hz, 2H), 7.60-7.70 (m, 3H), 7.38 (ddd, J = 1.26, 6.62, 8.83 Hz, 1H), 6.95 (dt, J = 1.10, 6.86 Hz, 1H), 4.00 (t, J = 8.35 Hz, 1H), 2.56-2.71 (m, 2H), 2.39 (ddd, J = 3.00, 3.15, 8.35 Hz, 2H), 1.92-2.18 (m, 2H); m.p. 218-219° C. |
| 166 | 6-(2-methyl-1H-imidazo[4,5-c]pyridin-1-yl)-N-[4-(trifluoromethyl)phenyl]pyrazin-2-amine<br>$^1$H NMR (500 MHz, Acetone-$d_6$) δ 10.03 (br. s., 1H), 8.93 (d, J = 0.95 Hz, 1H), 8.49 (s, 1H), 8.32-8.43 (m, 2H), 7.98 (d, J = 8.51 Hz, 2H), 7.64 (d, J = 8.51 Hz, 2H), 7.56 (dd, J = 0.95, 5.67 Hz, 1H), 2.74 (s, 3H); MS m/z 371.2 (ESI) [M + H]$^+$ |
| 178 | methyl 3-(6-{[4-(difluoromethoxy)phenyl]amino}pyrazin-2-yl)-2-(trifluoromethyl)imidazo[1,2-a]pyridine-6-carboxylate<br>$^1$H NMR (500 MHz, Acetone-$d_6$) δ 9.55-9.65 (m, 1H), 9.14 (s, 1H), 8.35 (s, 1H), 8.29 (s, 1H), 7.98 (dd, J = 1.73, 9.62 Hz, 1H), 7.74-7.87 (m, 3H), 7.12 (d, J = 10.10 Hz, 2H), 6.89 (td, J = 74.72 Hz, 1H), 3.80 (s, 3H); m.p. 227-229° C.; MS m/z 480.1 (ESI) [M + H]$^+$ |

Example 98

6-[2-cyclopropyl-6-(trifluoromethyl)imidazo[1,2-a]pyridin-3-yl]-N-[4-(trifluoromethyl)phenyl]pyrazin-2-amine (Cpd 250)

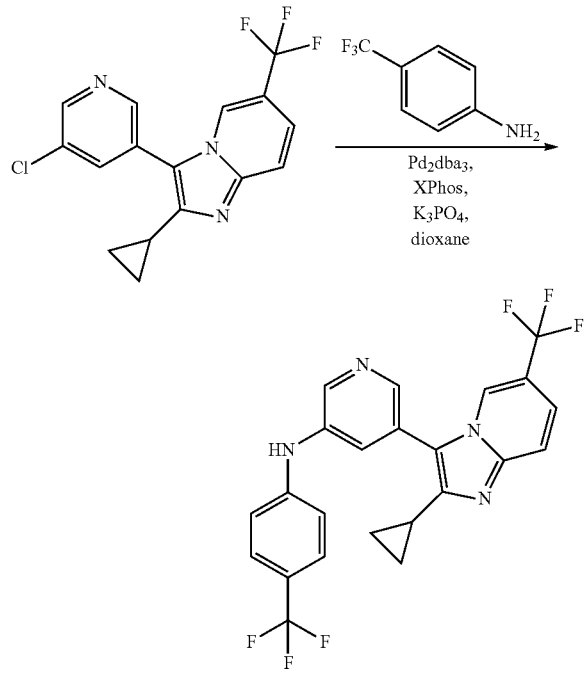

A mixture of 3-(6-chloropyrazin-2-yl)-2-cyclopropyl-6-(trifluoromethyl)imidazo[1,2-a]pyridine (100 mg, 0.295 mmol), 4-trifluoromethylaniline (143.0 mg, 0.89 mmol), 2-dicyclohexylphosphino-2',4',6'-triisopropylbiphenyl (XPhos, 16.9 mg, 0.036 mmol), tris(dibenzylideneacetone) dipalladium(0) (16.3 mg, 0.018 mmol) and a solution of tripotassium phosphate (188.5 mg, 0.89 mmol) in dioxane (2 mL) was degassed by three cycles of vacuum pumping and N$_2$ purging. The mixture was heated at 100° C. for 1 hour, cooled and poured into water (50 mL), then extracted with dichloromethane. The extract was dried over MgSO$_4$, then filtered and evaporated and was separated by column chromatography to afford 6-[2-cyclopropyl-6-(trifluoromethyl)imidazo[1,2-a]pyridin-3-yl]-N-[4-(trifluoromethyl)phenyl]pyrazin-2-amine (58.0 mg, 43%). m.p. 240-241° C.; $^1$H NMR (500 MHz, CHLOROFORM-d) δ 9.55 (br. s., 1H), 8.67 (s, 1H), 8.21 (s, 1H), 7.53-7.81 (m, 5H), 7.42 (d, J=8.51 Hz, 1H), 7.07 (br. s., 1H), 2.25-2.45 (m, 1H), 1.23-1.41 (m, 2H), 1.12-1.21 (m, 2H); MS (ES+): m/e 464.0 (100), 465.0 (20).

Additional compounds of Formula (I) or a form thereof described herein may be prepared according to the procedure of Example 98 by substituting the appropriate starting materials, reagents and reaction conditions:

| Cpd | Name and Data |
|---|---|
| 191 | 6-[2-(methylsulfanyl)imidazo[1,2-a]pyridin-3-yl]-N-[4-(trifluoromethyl)phenyl]pyrazin-2-amine<br>$^1$H NMR (Acetone-$d_6$) δ 9.24 (dt, J = 6.9, 0.9 Hz, 1H), 9.14 (br. s., 1H), 8.39 (s, 1H), 8.07 (s, 1H), 7.81 (d, J = 8.5 Hz, 2H), 7.53 (d, J = 8.5 Hz, 2H), 7.49 (dt, J = 9.1, 0.9 Hz, 1H), 7.29 (ddd, J = 9.0, 6.8, 1.3 Hz, 1H), 6.85 (td, J = 6.9, 1.3 Hz, 1H), 2.72 (s, 3H); MS m/z 402 (ESI) [M + H]$^+$ |
| 244 | 6-(6-fluoro-2-methylimidazo[1,2-a]pyridin-3-yl)-N-[4-(trifluoromethyl)phenyl]pyrazin-2-amine<br>$^1$H NMR (500 MHz, CHLOROFORM-d) δ 9.12 (m, 1H), 8.48 (br. s., 1H), 8.36 (s, 1H), 8.19 (s, 1H), 7.92 (dd, J = 4.73, 9.77 Hz, 1H), 7.62 (d, J = 8.83 Hz, 2H), 7.54-7.59 (d, J = 8.83 Hz, 2H), 7.35-7.42 (m, 1H), 2.68 (s, 3H); m.p. 160-162° C.; MS m/z 388.0 (ESI) [M + H]$^+$ |
| 245 | N-[4-(difluoromethoxy)phenyl]-6-(6-fluoro-2-methylimidazo[1,2-a]pyridin-3-yl)pyrazin-2-amine<br>$^1$H NMR (500 MHz, DMSO-$d_6$) δ 9.64 (br. s., 1H), 9.18 (m, 1H), 8.19 (s, 1H), 8.07 (s, 1H), 7.58 (d, J = 8.82 Hz, 2H), 7.36 (m, 1H), 7.06 (d, J = 8.82 Hz, 2H), 6.90-7.20 (t, J = 75.00 HZ, 1H), 2.66 (s, 3H); m.p. 171-173° C.; MS m/z 386.0 (ESI) [M + H]$^+$ |
| 246 | 6-(6-fluoro-2-methylimidazo[1,2-a]pyridin-3-yl)-N-[4-(trifluoromethoxy)phenyl]pyrazin-2-amine<br>$^1$H NMR (500 MHz, CHLOROFORM-d) δ 9.13-9.42 (m, 1H), 8.36 (s, 1H), 8.12 (s, 1H), 7.59 (dd, J = 5.20, 9.62 Hz, 1H), 7.53 (d, J = 8.83 Hz, 2H), 7.28 (d, J = 8.83 Hz, 2H), (7.17-7.24 (m, 1H), 6.76 (s, 1H), 2.75 (s, 3H); m.p. 163-165° C.; MS m/z 404.0 (ESI) [M + H]$^+$ |
| 251 | 6-[2-cyclopropyl-6-(trifluoromethyl)imidazo[1,2-a]pyridin-3-yl]-N-[4-(difluoromethoxy)phenyl]pyrazin-2-amine<br>$^1$H NMR (500 MHz, CHLOROFORM-d) δ 9.52 (s, 1H), 8.58 (s, 1H), 8.12 (s, 1H), 7.66 (d, J = 9.46 Hz, 1H), 7.50 (d, J = 8.83 Hz, 2H), 7.38 (dd, J = 1.89, 9.46 Hz, 1H), 7.14 (d, J = 8.83 Hz, 2H), 6.71 (s, 1H), 6.34-6.64 (t, J = 75.00 Hz, 1H), 2.32 (m, 1H), 1.23-1.30 (m, 2H), 1.10-1.18 (m, 2H); m.p. 212-213° C.; MS m/z 462.0 (ESI) [M + H]$^+$ |
| 252 | 6-[2-cyclopropyl-6-(trifluoromethyl)imidazo[1,2-a]pyridin-3-yl]-N-[4-(trifluoromethoxy)phenyl]pyrazin-2-amine<br>$^1$H NMR (500 MHz, CHLOROFORM-d) δ 9.52 (s, 1H), 8.60 (s, 1H), 8.14 (s, 1H), 7.67 (d, J = 9.14 Hz, 1H), 7.51-7.60 (d, J = 8.51 Hz, 2H), 7.39 (dd, J = 1.58, 9.46 Hz, 1H), 7.22 (d, J = 8.51 Hz, 2H), 6.78 (s, 1H), 2.26-2.39 (m, 1H), 1.22-1.29 (m, 2H), 1.10-1.19 (m, 2H); m.p. 213-215° C.; MS m/z 480.0 (ESI) [M + H]$^+$ |
| 308 | 6-(6-fluoroimidazo[1,2-a]pyridin-3-yl)-N-[4-(trifluoromethyl)phenyl]pyrazin-2-amine<br>$^1$H NMR (DMSO-$d_6$) δ 10.04 (br. s, 1H), 9.67 (dd, J = 5.4, 2.2 Hz, 1H), 8.76 (s, 1H), 8.59 (s, 1H), 8.18 (s, 1H), 7.84 (dd, J = 9.6, 5.5 Hz, 1H), 7.78 (d, J = 8.5 Hz, 2H), 7.71 (d, J = 8.5 Hz, 2H), 7.54 (ddd, J = 9.9, 7.7, 2.5 Hz, 1H); MS m/z 374 (ESI) [M + H]$^+$ |
| 321 | N-[4-(2,2,2-trifluoroethoxy)phenyl]-6-[2-(trifluoromethyl)imidazo[1,2-a]pyridin-3-yl]pyrazin-2-amine<br>$^1$H NMR (DMSO-$d_6$) δ 9.77 (br. s, 1H), 8.73 (d, J = 6.9 Hz, 1H), 8.30 (s, 1H), 8.15 (s, 1H), 7.84 (d, J = 9.1 Hz, 1H), 7.61 (d, J = 8.8 Hz, 2H), 7.57 (dd, J = 7.9, 6.9 Hz, 1H), 7.15 (t, J = 6.8 Hz, 1H), 7.00 (d, J = 8.8 Hz, 2H), 4.69 (q, J = 9.0 Hz, 2H); MS m/z 454 (ESI) [M + H]$^+$ |

-continued

| Cpd | Name and Data |
|---|---|
| 322 | N-[4-(1,1,2,2-tetrafluoroethoxy)phenyl]-6-[2-(trifluoromethyl)imidazo[1,2-a]pyridin-3-yl]pyrazin-2-amine<br>$^1$H NMR (DMSO-d$_6$) δ 10.04 (br. s, 1H), 8.73 (dt, J = 6.9, 0.9 Hz, 1H), 8.37 (s, 1H), 8.23 (s, 1H), 7.84 (dt, J = 9.1, 0.9 Hz, 1H), 7.76 (d, J = 9.1 Hz, 2H), 7.57 (ddd, J = 8.4, 7.3, 0.9 Hz, 1H), 7.19 (d, J = 9.1 Hz, 2H), 7.15 (td, J = 6.8, 0.9 Hz, 1H), 6.77 (tt, J = 52.3, 2.8 Hz, 1H); MS m/z 472 (ESI) [M + H]$^+$ |
| 323 | N-[4-(difluoromethoxy)-3-fluorophenyl]-6-[2-(trifluoromethyl)imidazo[1,2-a]pyridin-3-yl]pyrazin-2-amine<br>$^1$H NMR (DMSO-d$_6$) δ 10.14 (br. s, 1H), 8.75 (dt, J = 7.3, 0.9 Hz, 1H), 8.37 (s, 1H), 8.28 (s, 1H), 7.90 (dd, J = 13.4, 2.4 Hz, 1H), 7.85 (dt, J = 9.1, 0.9 Hz, 1H), 7.59 (ddd, J = 9.1, 6.8, 1.1 Hz, 1H), 7.35 (ddd, J = 9.1, 2.8, 0.9 Hz, 1H), 7.30 (t, J = 8.8 Hz, 1H), 7.16 (td, J = 6.9, 1.1 Hz, 1H), 7.13 (t, J = 73.5 Hz, 1H); MS m/z 440 (ESI) [M + H]$^+$ |
| 376 | 6-(6-methoxy-2-methylimidazo[1,2-a]pyridin-3-yl)-N-[4-(trifluoromethyl)phenyl]pyrazin-2-amine<br>$^1$H NMR (DMSO-d$_6$) δ 10.11 (s, 1H), 8.70 (d, J = 2.2 Hz, 1H), 8.35 (s, 1H), 8.23 (s, 1H), 7.88 (d, J = 9.1 Hz, 2H), 7.66 (d, J = 9.1 Hz, 2H), 7.55 (d, J = 9.1 Hz, 1H), 7.16 (dd, J = 9.8, 2.5 Hz, 1H), 3.46 (s, 3H), 2.59 (s, 3H); MS m/z 400 (ESI) [M + H]$^+$ |
| 377 | 6-(6-methoxy-2-methylimidazo[1,2-a]pyridin-3-yl)-N-[4-(trifluoromethoxy)phenyl]pyrazin-2-amine<br>$^1$H NMR (DMSO-d$_6$) δ 9.84 (br. s, 1H), 8.65 (d, J = 2.5 Hz, 1H), 8.23 (s, 1H), 8.12 (s, 1H), 7.69-7.76 (m, 2H), 7.48 (d, J = 9.8 Hz, 1H), 7.27 (d, J = 8.5 Hz, 2H), 7.09 (dd, J = 9.5, 2.5 Hz, 1H), 3.39 (s, 3H), 2.53 (s, 3H); MS m/z 416 (ESI) [M + H]$^+$ |
| 667 | 6-[6-fluoro-2-(trifluoromethyl)imidazo[1,2-a]pyridin-3-yl]-N-phenylpyrazin-2-amine<br>$^1$H NMR (DMSO-d$_6$) δ 9.88 (br. s, 1H), 8.99 (dd, J = 5.2, 2.2 Hz, 1H), 8.37 (s, 1H), 8.21 (s, 1H), 7.96 (dd, J = 9.9, 5.2 Hz, 1H), 7.70 (d, J = 7.6 Hz, 2H), 7.31 (s, 2H), 7.01 (t, J = 7.3 Hz, 1H); MS m/z 374 (ESI) [M + H]$^+$ |
| 668 | 4-({6-[6-fluoro-2-(trifluoromethyl)imidazo[1,2-a]pyridin-3-yl]pyrazin-2-yl}amino)benzonitrile<br>$^1$H NMR (DMSO-d$_6$) δ 10.40 (s, 1H), 8.94 (dd, J = 4.6, 2.0 Hz, 1H), 8.44 (s, 1H), 8.34 (s, 1H), 7.96 (dd, J = 9.9, 5.2 Hz, 1H), 7.81-7.92 (m, 2H), 7.72 (d, J = 8.5 Hz, 3H); MS m/z 399 (ESI) [M + H]$^+$ |
| 669 | N-(4-fluorophenyl)-6-[6-fluoro-2-(trifluoromethyl)imidazo[1,2-a]pyridin-3-yl]pyrazin-2-amine<br>$^1$H NMR (DMSO-d$_6$) δ 9.87 (br. s, 1H), 8.94 (dd, J = 4.7, 2.2 Hz, 1H), 8.32 (s, 1H), 8.19 (s, 1H), 7.94 (dd, J = 9.8, 5.0 Hz, 1H), 7.65-7.70 (m, 3H), 7.13 (s, 2H); MS m/z 392 (ESI) [M + H]$^+$ |
| 670 | N-(4-chlorophenyl)-6-[6-fluoro-2-(trifluoromethyl)imidazo[1,2-a]pyridin-3-yl]pyrazin-2-amine<br>$^1$H NMR (DMSO-d$_6$) δ 10.00 (s, 1H), 8.94 (ddd, J = 5.0, 2.5, 0.8 Hz, 1H), 8.35 (s, 1H), 8.23 (s, 1H), 7.95 (ddd, J = 9.9, 5.2, 0.9 Hz, 1H), 7.63-7.75 (m, 3H), 7.29-7.36 (m, 2H); MS m/z 408 (ESI) [M + H]$^+$ |
| 671 | 6-[6-fluoro-2-(trifluoromethyl)imidazo[1,2-a]pyridin-3-yl]-N-(4-methylphenyl)pyrazin-2-amine<br>$^1$H NMR (DMSO-d$_6$) δ 9.75 (br. s, 1H), 8.97 (ddd, J = 5.0, 2.5, 0.6 Hz, 1H), 8.31 (s, 1H), 8.15 (s, 1H), 7.94 (dd, J = 10.1, 5.4 Hz, 1H), 7.70 (ddd, J = 10.4, 8.2, 2.5 Hz, 1H), 7.55 (d, J = 8.5 Hz, 2H), 7.10 (d, J = 8.5 Hz, 2H), 2.25 (s, 3H); MS m/z 388 (ESI) [M + H]$^+$ |

Example 99

6-(2-cyclopropylimidazo[1,2-a]pyridin-5-yl)-N-[4-(difluoromethoxy)phenyl]pyrazin-2-amine (Cpd 90)

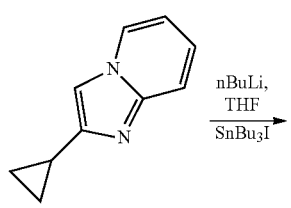

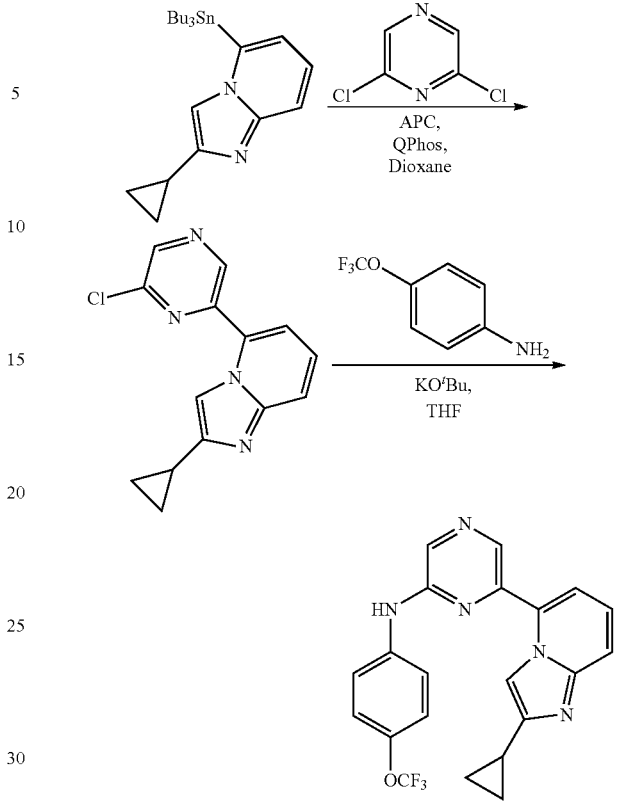

Step 1. To a solution of 2-cyclopropylimidazo[1,2-a]pyridine (4.93 g, 31.16 mmol) in THF (50 mL) was added a solution of n-butyl lithium (2.5 M in hexane, 14.3 mL) dropwise at −78° C. The mixture was stirred at −78° C. for 20 minutes, then tributyltin iodide (15.59 g, 37.40 mmol) was added. The reaction mixture was stirred at room temperature for 2 hours, diluted with DCM, then filtered through a Celite pad using KF (5:1). The solvent was evaporated and the residue purified by silica gel column chromatography (1:4 ethyl acetate:hexane) to afford 2-cyclopropyl-5-(tributylstannyl)imidazo[1,2-a]pyridine (9.28 g, 67%) as an oil.

Step 2. The obtained intermediate was carried forward (using the procedure described in Example 97 and appropriate starting materials, reagents and reaction conditions) to provide the product 5-(6-chloropyrazin-2-yl)-2-cyclopropylimidazo[1,2-a]pyridine (46%). $^1$H NMR (500 MHz, Acetone-d$_6$) δ 9.20 (d, J=0.63 Hz, 1H), 8.80 (s, 1H), 8.48 (s, 1H), 7.54-7.61 (m, 1H), 7.47 (dd, J=0.95, 7.25 Hz, 1H), 7.32 (dd, J=7.09, 8.99 Hz, 1H), 2.06-2.11 (m, 1H), 0.90-0.96 (m, 4H).

Step 3. The obtained intermediate was carried forward (using the procedure described in Example 97 and appropriate starting materials, reagents and reaction conditions) to provide the title compound. m.p. 212-213° C.; $^1$H NMR (500 MHz, MeOD-d$_4$) δ 8.40 (s, 1H), 8.30 (s, 1H), 8.25 (s, 1H), 7.70-7.77 (m, 2H), 7.55 (d, J=0.63 Hz, 1H), 7.32-7.42 (m, 2H), 7.13 (d, J=8.83 Hz, 2H), 6.61-6.91 9t, J=75.00 Hz, 1H), 1.92-2.08 (m, 1H), 0.97 (m, 2H), 0.72-0.88 (m, 2H).

Additional compounds of Formula (I) or a form thereof described herein may be prepared according to the procedure of Example 99 by substituting the appropriate starting materials, reagents and reaction conditions:

| Cpd | Name and Data |
|---|---|
| 15 | N-[4-(trifluoromethyl)phenyl]-6-[2-(trifluoromethyl)pyrazolo[1,5-a]pyridin-7-yl]pyrazin-2-amine<br>$^1$H NMR (500 MHz, CHLOROFORM-d) δ 8.58 (d, J = 6.94 Hz, 1H), 8.42 (s, 1H), 8.22 (s, 1H), 8.07 (d, J = 9.14 Hz, 1H), 7.71 (d, J = 8.51 Hz, 2H), 7.58 (d, J = 8.51 Hz, 2H), 7.35 (ddd, J = 1.50, 6.90, 8.20 Hz, 1H), 7.06 (t, J = 6.94 Hz, 1H), 6.95 (s, 1H); MS m/z 424 (ESI) [M + H]$^+$ |
| 86 | 6-(2-cyclopropylimidazo[1,2-a]pyridin-5-yl)-N-(4-methoxyphenyl)pyrazin-2-amine<br>$^1$H NMR (500 MHz, Acetone-d$_6$) δ 8.74-8.81 (s, 1H), 8.41 (s, 1H), 8.38 (s, 1H), 8.27 (s, 1H), 7.61-7.71 (d, J = 6.94 Hz, 2H), 7.50 (s, 1H), 7.28-7.34 (m, 2H), 6.95 (d, J = 6.94 Hz, 2H), 3.80 (s, 3H), 2.01 (m, 1H), 0.82-0.99 (m, 4H); m.p. 234-236° C. |
| 87 | 6-(2-cyclopropylimidazo[1,2-a]pyridin-5-yl)-N-[4-(trifluoromethoxy)phenyl]pyrazin-2-amine<br>$^1$H NMR (500 MHz, Acetone-d$_6$) δ 9.25 (br. s., 1H), 8.53 (s, 1H), 8.39 (s, 1H), 8.35 (s, 1H), 7.93 (d, J = 9.14 Hz, 2H), 7.50-7.59 (m, 1H), 7.27-7.36 (m, 4H), 1.99-2.05 (m, 1H), 0.70-1.00 (m, 4H); m.p. 225-227° C. |
| 88 | 6-(2-cyclopropylimidazo[1,2-a]pyridin-5-yl)-N-(2,2-difluoro-1,3-benzodioxol-5-yl)pyrazin-2-amine<br>$^1$H NMR (500 MHz, MeOD-d$_4$) δ 8.54 (s, 1H), 8.37 (d, J = 9.14 Hz, 2H), 7.98 (d, J = 1.89 Hz, 1H), 7.64 (d, J = 8.51 Hz, 1H), 7.41-7.50 (m, 2H), 7.35-7.40 (m, 1H), 7.31 (d, J = 10.09 Hz, 1H), 1.94-2.15 (m, 1H), 0.65-1.11 (m, 4H); m.p. 259-260° C. |
| 89 | 6-(2-cyclopropylimidazo[1,2-a]pyridin-5-yl)-N-[4-(trifluoromethyl)phenyl]pyrazin-2-amine<br>m.p. 266-268° C.; MS m/z 396.4 (ESI) [M + H]$^+$ |
| 91 | N-(2,2-difluoro-1,3-benzodioxol-5-yl)-6-[2-(trifluoromethyl)imidazo[1,2-a]pyridin-3-yl]pyrazin-2-amine<br>$^1$H NMR (500 MHz, Acetone-d$_6$) δ 9.24 (br. s., 1H), 9.04 (s, 1H), 8.60 (s, 1H), 8.40 (s, 1H), 7.86-7.96 (m, 1H), 7.80 (dd, J = 3.63, 6.46 Hz, 1H), 7.58-7.67 (m, 2H), 7.39 (dd, J = 1.89, 8.51 Hz, 1H), 7.25 (d, J = 8.83 Hz, 1H); m.p. 232-234° C. |
| 114 | 6-(2-cyclobutylimidazo[1,2-a]pyridin-5-yl)-N-[4-(trifluoromethyl)phenyl]pyrazin-2-amine<br>$^1$H NMR (500 MHz, DMSO-d$_6$) δ 10.26 (s, 1H), 8.60 (s, 1H), 8.42 (s, 1H), 8.35 (s, 1H), 7.92 (d, J = 8.51 Hz, 2H), 7.59-7.69 (m, 3H), 7.39-7.44 (m, 1H), 7.35 (d, J = 6.94, 8.83 Hz, 1H), 3.58 (s, 1H), 2.20-2.31 (m, 2H), 2.10-2.18 (m, 2H), 1.74-2.02 (m, 2H); m.p. 288-290° C. |
| 115 | 6-(2-cyclobutylimidazo[1,2-a]pyridin-5-yl)-N-[4-(difluoromethoxy)phenyl]pyrazin-2-amine<br>$^1$H NMR (500 MHz, DMSO-d$_6$) δ 9.92 (s, 1H), 8.49 (s, 1H), 8.33 (d, J = 4.41 Hz, 2H), 7.74 (d, J = 8.83 Hz, 2H), 7.57-7.68 (m, 1H), 7.28-7.40 (m, 2H), 7.13 (d, J = 8.83 Hz, 2H), 3.53-3.65 (m, 1H), 2.22-2.33 (m, 2H), 2.13-2.21 (m, 2H), 1.72-2.04 (m, 2H); m.p. 252-253° C. |
| 116 | 6-(2-cyclobutylimidazo[1,2-a]pyridin-5-yl)-N-(4-methoxyphenyl)pyrazin-2-amine<br>m.p. 223-225° C.; MS m/z 372.3 (ESI) [M + H]$^+$ |
| 117 | 6-(2-cyclobutylimidazo[1,2-a]pyridin-5-yl)-N-(2,2-difluoro-1,3-benzodioxol-5-yl)pyrazin-2-amine<br>$^1$H NMR (500 MHz, DMSO-d$_6$) δ 10.04 (s, 1H), 8.51 (s, 1H), 8.32 (d, J = 8.20 Hz, 1H), 8.03 (d, J = 2.21 Hz, 1H), 7.64 (dd, J = 0.63, 8.83 Hz, 2H), 7.31-7.39 (m, 3H), 7.24 (dd, J = 2.05, 8.67 Hz, 1H), 3.57 (t, J = 8.35 Hz, 1H), 2.19-2.31 (m, 2H), 2.12-2.19 (m, 2H), 1.76-2.02 (m, 2H); m.p. 302-305° C. |

Example 100

6-(6-fluoro-2-methylimidazo[1,2-a]pyridin-3-yl)-N-phenylpyrazin-2-amine (Cpd 590)

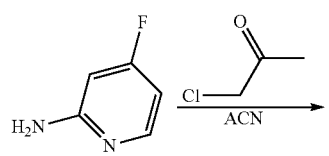

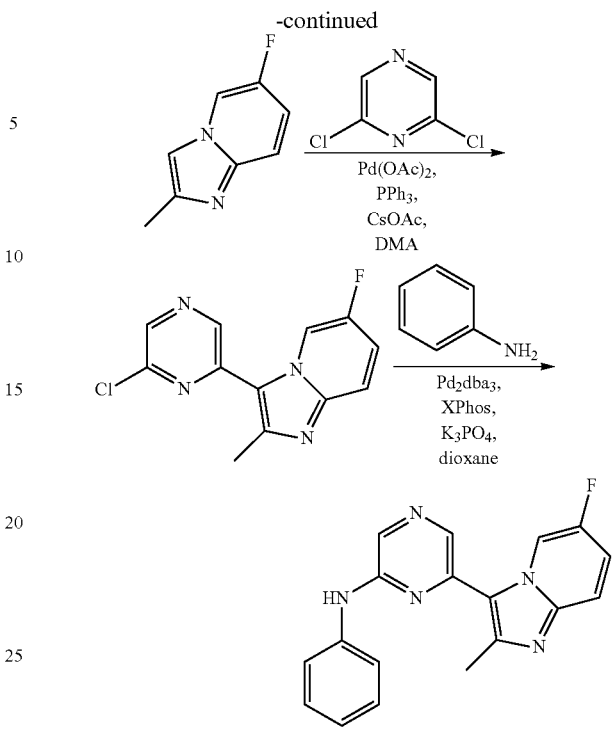

Step 1. In a 250 mL round bottom flask, 4-fluoropyridin-2-amine (8.57 g, 76.44 mmol) and chloroacetone (12.99 g, 71.67 mmol) were pre-mixed and stirred at 0° C. for 15 minutes. The mixture was diluted with acetonitrile (80 mL) and stirred at reflux overnight. The solvent was evaporated, ethyl ether (200 mL) was added and the resulting precipitate was collected by filtration. The solid was partitioned between dichloromethane (300 mL) and NaHCO$_3$ (250 mL) and the organic layer was separated, dried over MgSO$_4$, then filtered and evaporated. The residue was separated by silica gel column chromatography (1:1 ethyl acetate:hexane) to afford 6-fluoro-2-methylimidazo[1,2-a]pyridine (5.20 g, 46%) as a glassy solid. $^1$H NMR (500 MHz, CHLOROFORM-d) δ 7.95-7.99 (m, 1H), 7.46 (dd, J=5.04, 9.77 Hz, 1H), 7.34 (s, 1H), 6.99-7.06 (m, 1H), 2.44 (d, J=0.63 Hz, 3H); MS (ES+): m/e 151.0 (100).

Step 2. A mixture of the obtained intermediate (2.37 g, 15.79 mmol), 2,6-pyrazine (3.77 g, 25.28 mmol), palladium (II) acetate (178.0 mg, 0.790 mmol), triphenylphosphane (414.0 mg, 0.158 mmol) and a solution of cesium acetate (6.1 g, 31.58 mmol) in DMA (15 mL) was degassed by three cycles of vacuum pumping and N$_2$ purging. The reaction mixture was heated at 100° C. overnight, cooled and poured into water (150 mL). The mixture was extracted with dichloromethane, dried over MgSO$_4$, then filtered and evaporated. The residue was triturated with ethyl ether to afford 3-(6-chloropyrazin-2-yl)-6-fluoro-2-methylimidazol[1,2-a]pyridine (2.27 g, 55%) as a pale white solid. $^1$H NMR (500 MHz, DMSO-d$_6$) δ 9.21-9.32 (m, 1H), 8.98 (s, 1H), 8.70 (s, 1H), 7.69-7.83 (m, 1H), 7.51-7.64 (m, 1H), 2.66 (s, 3H); MS (ES+): m/e 262.7 (50), 265.1 (100), 266.1 (30)

Step 3: The obtained intermediate was carried forward (using the procedure described in Example 97 and appropriate starting materials, reagents and reaction conditions) to provide the title compound. m.p 216-218° C.; $^1$H NMR (00 MHz, DMSO-d$_6$) δ 9.68 (s, 1H), 9.32 (s, 1H), 8.26 (s, 1H), 8.17 (s, 1H), 7.64 (m, J=7.90 Hz, 3H), 7.41-7.53 (m, 1H), 7.24-7.39 (m, 2H), 6.96-7.10 (m, 1H), 2.62 (s, 3H); MS (ES+): m/e 321.6

Additional compounds of Formula (I) or a form thereof described herein may be prepared according to the procedure of Example 100 by substituting the appropriate starting materials, reagents and reaction conditions:

| Cpd | Name and Data |
|---|---|
| 202 | 6-(2-methylimidazo[1,2-a]pyridin-3-yl)-N-[4-(trifluoromethyl)phenyl]pyrazin-2-amine<br>$^1$H NMR (500 MHz, Acetone-d$_6$) δ 9.28 (br. s, 1H), 9.18-9.24 (m, 1H), 8.38 (s, 1H), 8.24 (s, 1H), 7.96 (d, J = 8.51 Hz, 2H), 7.65 (d, J = 8.51 Hz, 2H), 7.59 (d, J = 8.83 Hz, 1H), 7.32-7.40 (m, 1H), 6.91-6.97 (m, 1H), 3.41 (m, 1H), 2.67 (s, 3H), 2.06 (m, 4H); m.p. 180-182° C.; MS m/z 370.2 (ESI) [M + H]$^+$ |
| 247 | 2-(6-fluoro-2-methylimidazo[1,2-a]pyridin-3-yl)-6-{[4-(trifluoromethyl)phenyl]amino}pyridine-4-carbonitrile<br>$^1$H NMR (500 MHz, CHLOROFORM-d) δ 9.28 (dd, J = 2.05, 5.20 Hz, 1H), 8.60 (s, 1H), 7.63 (d, J = 8.20 Hz, 2H), 7.52-7.59 (m, 3H), 7.16-7.22 (m, 1H), 7.15 (d, J = 0.95 Hz, 1H), 6.99 (d, J = 0.95 Hz, 1H), 2.69 (s, 3H); m.p. 241-243° C.; MS m/z 412.0 (ESI) [M + H]$^+$ |
| 248 | 2-{[4-(difluoromethoxy)phenyl]amino}-6-(6-fluoro-2-methylimidazo[1,2-a]pyridin-3-yl)pyridine-4-carbonitrile<br>$^1$H NMR (500 MHz, CHLOROFORM-d) δ 9.30 (dd, J = 1.89, 5.36 Hz, 1H), 7.57 (dd, J = 5.36, 9.77 Hz, 1H), 7.40 (d, J = 9.14 Hz, 2H), 7.15-7.24 (m, 4H), 6.82 (s, 1H), 6.80 (s, 1H), 6.39-6.68 (t, J = 72.50 Hz, 1H), (s, 3H); m.p. 221-223° C.; MS m/z 410.0 (ESI) [M + H]$^+$ |
| 249 | 2-(6-fluoro-2-methylimidazo[1,2-a]pyridin-3-yl)-6-{[4-(trifluoromethoxy)phenyl]amino}pyridine-4-carbonitrile<br>$^1$H NMR (500 MHz, CHLOROFORM-d) δ 9.26 (dd, J = 2.21, 5.04 Hz, 1H), 8.36 (s, 1H), 8.12 (s, 1H), 7.59 (dd, J = 5.20, 9.62 Hz, 1H), 7.53 (d, J = 8.83 Hz, 2H), 7.24-7.29 (d, J = 8.83 Hz, 2H), 7.17-7.24 (m, 1H), 6.76 (s, 1H), 2.75 (s, 3H); m.p. 209-210° C.; MS m/z 428.0 (ESI) [M + H]$^+$ |
| 261 | 2-(6-fluoro-2-methyl-1H-benzimidazol-1-yl)-6-{[4-(trifluoromethyl)phenyl]amino}pyridine-4-carbonitrile<br>$^1$H NMR (500 MHz, DMSO-d$_6$) δ 10.25 (s, 1H), 7.82 (d, J = 8.83 Hz, 2H), 7.62-7.68 (m, 3H), 7.58 (d, J = 0.95 Hz, 1H), 7.40-7.45 (m, 1H), 7.36 (d, J = 0.63 Hz, 1H), 7.06-7.17 (m, 1H), 2.61 (s, 3H); m.p. 223-225° C.; MS m/z 412.0 (ESI) [M + H]$^+$ |
| 262 | 2-{[4-(difluoromethoxy)phenyl]amino}-6-(6-fluoro-2-methyl-1H-benzimidazol-1-yl)pyridine-4-carbonitrile<br>$^1$H NMR (500 MHz, DMSO-d$_6$) δ 9.91 (s, 1H), 7.58-7.68 (m, 3H), 7.45 (d, J = 0.95 Hz, 1H), 7.38-7.43 (m, 1H), 7.25 (d, J = 0.95 Hz, 1H), 7.10-7.15 (m, 3H), 6.98-7.28 (t, J = 75.00 Hz, 1H), 2.60 (s, 3H); m.p. 231-232° C.; MS m/z 410.0 (ESI) [M + H]$^+$ |
| 309 | N-[4-(difluoromethoxy)-3-fluorophenyl]-6-(6-fluoro-2-methylimidazo[1,2-a]pyridin-3-yl)pyrazin-2-amine<br>$^1$H NMR (500 MHz, DMSO-d$_6$) δ 9.85 (s, 1H), 9.06-9.20 (m, 1H), 8.22 (s, 1H), 8.08 (s, 1H), 7.69-7.83 (m, 1H), 7.52-7.62 (m, 1H), 7.31-7.44 (m, 1H), 7.23 (m, 2H), 6.89-7.18 (d, J = 72.50 Hz, 1H), 2.50 (s, 3H); MS m/z 404.5 (ESI) [M + H]$^+$ |
| 310 | 6-(6-fluoro-2-methylimidazo[1,2-a]pyridin-3-yl)-N-[3-fluoro-4-(trifluoromethyl)phenyl]pyrazin-2-amine<br>m.p. 216-218° C.; MS m/z 406.0 (ESI) [M + H]$^+$ |
| 311 | 2-{[4-(difluoromethoxy)-3-fluorophenyl]amino}-6-(6-fluoro-2-methylimidazo[1,2-a]pyridin-3-yl)pyridine-4-carbonitrile<br>$^1$H NMR (500 MHz, DMSO-d$_6$) δ 9.88 (s, 1H), 9.15-9.31 (m, 1H), 7.73-7.84 (m, 1H), 7.62-7.71 (m, 1H), 7.43-7.48 (m, 1H), 7.42 (d, J = 0.95 Hz, 1H), 7.26-7.30 (m, 2H), 7.08 (d, J = 0.95 Hz, 1H), 6.99-7.27 (t, J = 70.00 Hz, 1H), 2.59 (s, 3H); m.p. 231-233° C.; MS m/z 428.5 (ESI) [M + H]$^+$ |
| 312 | 2-(6-fluoro-2-methylimidazo[1,2-a]pyridin-3-yl)-6-{[3-fluoro-4-(trifluoromethyl)phenyl]amino}pyridine-4-carbonitrile<br>$^1$H NMR (500 MHz, DMSO-d$_6$) δ 10.27 (s, 1H), 9.24 (dd, J = 2.21, 5.36 Hz, 1H), 7.92 (d, J = 14.19 Hz, 1H), 7.63-7.76 (m, 2H), 7.55 (d, J = 0.95 Hz, 1H), 7.48 (d, J = 2.21 Hz, 1H), 7.41 (d, J = 8.51 Hz, 1H), 7.18 (d, J = 0.95 Hz, 1H), 2.60 (s, 3H); m.p. 245-249° C.; MS m/z 430.5 (ESI) [M + H]$^+$ |
| 313 | 2-[(3,5-difluoro-4-methoxyphenyl)amino]-6-(6-fluoro-2-methylimidazo[1,2-a]pyridin-3-yl)pyridine-4-carbonitrile<br>$^1$H NMR (500 MHz, DMSO-d$_6$) δ 9.84 (s, 1H), 9.19-9.33 (m, 1H), 7.63-7.74 (m, 1H), 7.44 (s, 2H), 7.37 (m, 2H), 7.07 (s, 1H), 3.85 (s, 3H), 2.60 (s, 3H); MS m/z 410.5 (ESI) [M + H]$^+$ |
| 314 | 2-[(4-fluoro-3-methoxyphenyl)amino]-6-(6-fluoro-2-methylimidazo[1,2-a]pyridin-3-yl)pyridine-4-carbonitrile<br>$^1$H NMR (500 MHz, DMSO-d$_6$) δ 9.60 (s, 1H), 9.29 (dd, J = 2.36, 5.52 Hz, 1H), 7.60-7.78 (m, 1H), 7.39-7.48 (m, 1H), 7.30-7.38 (m, 2H), 7.12-7.19 (m, 1H), 7.08 (br. s, 1H), 7.02 (d, J = 0.63 Hz, 1H), 3.67 (s, 3H), 2.61 (s, 3H); m.p. 233-237° C.; MS m/z 392.5 (ESI) [M + H]$^+$ |
| 315 | N$^2$-[4-(difluoromethoxy)-3-fluorophenyl]-6-(6-fluoro-2-methylimidazo[1,2-a]pyridin-3-yl)pyridine-2,4-diamine<br>$^1$H NMR (500 MHz, DMSO-d$_6$) δ 9.29 (dd, J = 1.89, 5.67 Hz, 1H), 9.04 (s, 1H), 7.77-7.85 (m, 1H), 7.61 (dd, J = 5.67, 9.77 Hz, 1H), 7.32-7.40 (m, 1H), 7.17-7.25 (m, 2H), 6.93-7.21 (t, J = 70.00 Hz, 1H), 6.46 (d, J = 1.58 Hz, 1H), 6.12 (s, 2H), 6.00 (d, J = 1.89 Hz, 1H), 2.55 (s, 3H); m.p. 182-183° C.; MS m/z 418.4 (ESI) [M + H]$^+$ |
| 336 | 6-(2-cyclopropyl-6-fluoroimidazo[1,2-a]pyridin-3-yl)-N-[4-(trifluoromethyl)phenyl]pyrazin-2-amine<br>$^1$H NMR (500 MHz, Acetone-d$_6$) δ 9.07 (br. s, 1H), 8.93-9.00 (m, 1H), 8.30 (s, 1H), 7.99 (s, 1H), 7.68 (d, J = 8.51 Hz, 2H), 7.38 (d, J = 8.51 Hz, 2H), 7.22-7.31 (m, 1H), 7.06 (ddd, J = 2.36, 7.88, 9.93 Hz, 1H), 2.00-2.13 (m, 1H), 0.84-0.91 (m, 2H), 0.74-0.82 (m, 2H); m.p. 183-185° C.; MS m/z 414.5 (ESI) [M + H]$^+$ |
| 337 | 6-(2-cyclopropyl-6-fluoroimidazo[1,2-a]pyridin-3-yl)-N-[4-(difluoromethoxy)phenyl]pyrazin-2-amine<br>$^1$H NMR (500 MHz, Acetone-d$_6$) δ 9.27 (dd, J = 2.21, 5.36 Hz, 1H), 8.93 (s, 1H), 8.50 (s, 1H), 8.17 (s, 1H), 7.76 (d, J = 8.83 Hz, 2H), 7.53 (dd, J = 5.36, 9.77 Hz, 1H), 7.32 (ddd, J = 2.52, 7.80, 9.85 Hz, 1H), 7.19 (d, J = 8.83 Hz, 2H), 6.76-7.06 (t, J = 75.00 Hz, 1H), 2.29-2.40 (m, 1H), 2.00-2.08 (m, 4H); m.p. 183-185° C.; MS m/z 412.3 (ESI) [M + H]$^+$ |
| 338 | 6-(2-cyclopropyl-6-fluoroimidazo[1,2-a]pyridin-3-yl)-N-[4-(difluoromethoxy)-3-fluorophenyl]pyrazin-2-amine<br>$^1$H NMR (500 MHz, Acetone-d$_6$) δ 9.20-9.25 (m, 1H), 9.14 (s, 1H), 8.53 (s, 1H), 8.19 (s, 1H), 7.90 (dd, J = 2.52, 13.24 Hz, 1H), 7.55 (dd, J = 5.36, 9.77 Hz, 1H), 7.42-7.50 (m, 1H), 7.27-7.39 (m, 2H), 6.78-7.07 (t, J = 72.50 Hz, 1H), 2.27-2.41 (m, 1H), 2.01-2.08 (m, 4H); m.p. 173-175° C.; MS m/z 430.5 (ESI) [M +H]$^+$ |
| 346 | 2-(2-cyclopropyl-6-fluoroimidazo[1,2-a]pyridin-3-yl)-6-{[4-(trifluoromethyl)phenyl]amino}pyridine-4-carbonitrile<br>$^1$H NMR (500 MHz, DMSO-d$_6$) δ 10.18 (s, 1H), 9.32 (dd, J = 2.21, 5.36 Hz, 1H), 7.96 (d, J = 8.51 Hz, 2H), 7.74-7.81 (m, 3H), 7.72 (s, 1H), 7.57 (ddd, J = 2.52, 7.80, 9.85 Hz, 1H), 7.30 (s, 1H), 3.53 (q, J = 6.94 Hz, 1H), 1.15-1.22 (m, 4H); m.p. 245-247° C.; MS m/z 438.5 (ESI) [M +H]$^+$ |
| 347 | 2-(2-cyclopropyl-6-fluoroimidazo[1,2-a]pyridin-3-yl)-6-{[3-fluoro-4-(trifluoromethyl)phenyl]amino}pyridine-4-carbonitrile<br>$^1$H NMR (500 MHz, DMSO-d$_6$) δ 10.27 (s, 1H), 9.14 (dd, J = 2.21, 5.36 Hz, 1H), 7.98 (dd, J = 1.42, 14.03 Hz, 1H), 7.57-7.73 (m, 3H), 7.37-7.52 (m, 2H), 7.19 (d, J = 0.95 Hz, 1H), 2.31-2.41 (m, 1H), 1.00-1.06 (m, 4H); m.p. 256-258° C.; MS (ES + ): m/e 456.5 (100), 457.4 (60), 458.5 (10) |
| 348 | 2-(2-cyclopropyl-6-fluoroimidazo[1,2-a]pyridin-3-yl)-6-{[4-(difluoromethoxy)phenyl]amino}pyridine-4-carbonitrile<br>$^1$H NMR (500 MHz, DMSO-d$_6$) δ 9.67 (s, 1H), 9.19 (dd, J = 2.21, 5.36 Hz, 1H), 7.55-7.73 (m, 3H), 7.47 (d, J = 0.95 Hz, 1H), 7.41 (ddd, J = 2.52, 7.80, 9.85 Hz, 1H), 6.98-7.28 (t, J = 75.00 Hz, 1H), 7.14 (d, J = 9.10 Hz, 2H), 7.04 (d, J = 0.63 Hz, 1H), 2.30-2.39 (m, 1H), 0.97-1.06 (m, 4H); m.p. 199-200° C.; MS m/z 436.5 (ESI) [M + H]$^+$ |
| 349 | 2-(2-cyclopropyl-6-fluoroimidazo[1,2-a]pyridin-3-yl)-6-{[4-(difluoromethoxy)-3-fluorophenyl]amino}pyridine-4-carbonitrile<br>$^1$H NMR (500 MHz, DMSO-d$_6$) δ 9.90 (s, 1H), 9.16 (dd, J = 2.05, 5.20 Hz, 1H), 7.83-7.92 (m, 1H), 7.64 (dd, J = 5.36, 9.77 Hz, 1H), 7.55 (d, J = 0.95 Hz, 1H), 7.44 (ddd, J = 2.36, 7.88, 9.93 Hz, 1H), 7.29-7.33 (m, 2H), 6.99-7.28 (t, J = 72.50 Hz, 1H), 7.11 (d, J = 0.95 Hz, 1H), 2.31-2.41 (m, 1H), 1.03 (d, J = 6.31 Hz, 4H); m.p. 185-186° C.; MS m/z 454.5 (ESI) [M + H]$^+$ |
| 350 | 2-(2-cyclopropyl-6-fluoroimidazo[1,2-a]pyridin-3-yl)-6-{[4-(trifluoromethoxy)phenyl]amino}pyridine-4-carbonitrile<br>$^1$H NMR (500 MHz, DMSO-d$_6$) δ 9.80 (s, 1H), 9.18 (dd, J = 2.21, 5.36 Hz, 1H), 7.69 (d, J = 8.51 Hz, 2H), 7.61 (dd, J = 5.36, 9.77 Hz, 1H), 7.51 (d, J = 0.63 Hz, 1H), 7.41 (ddd, J = |

| Cpd | Name and Data |
|---|---|
| | 2.52, 7.80, 9.85 Hz, 1H), 7.29 (d, J = 8.51 Hz, 2H), 7.08 (d, J = 0.63 Hz, 1H), 2.30-2.40 (m, 1H), 1.03 (d, J = 6.31 Hz, 4H); m.p. 194-195° C.; MS m/z 454.5 (ESI) [M + H]+ |
| 351 | 2-(2-cyclopropyl-6-fluoroimidazo[1,2-a]pyridin-3-yl)-6-[[(3,5-difluoro-4-methoxyphenyl)amino}pyridine-4-carbonitrile<br>1H NMR (500 MHz, DMSO-d6) δ 9.84 (s, 1H), 9.16 (dd, J = 2.21, 5.36 Hz, 1H), 7.63 (dd, J = 5.52, 9.62 Hz, 1H), 7.54 (d, J = 0.63 Hz, 1H), 7.35-7.47 (m, 3H), 7.07 (s, 1H), 3.84 (s, 3H), 2.29-2.39 (m, 1H), 1.03 (d, J = 6.31 Hz, 4H); m.p. 230-232° C.; MS m/z 436.5 (ESI) [M + H]+ |
| 437 | 2-(6-fluoro-2-methylimidazo[1,2-a]pyrimidin-3-yl)-6-{[4-(trifluoromethyl)phenyl]amino}pyridine-4-carbonitrile<br>1H NMR (500 MHz, DMSO-d6) δ 10.05 (s, 1H), 9.63 (dd, J = 2.84, 5.36 Hz, 1H), 8.78 (d, J = 3.15 Hz, 1H), 7.76 (d, J = 8.51 Hz, 2H), 7.64 (d, J = 8.83 Hz, 2H), 7.52 (d, J = 0.95 Hz, 1H), 7.17 (d, J = 0.95 Hz, 1H), 2.66 (s, 3H); m.p. 290-292° C. |
| 438 | 2-(6-fluoro-2-methylimidazo[1,2-a]pyrimidin-3-yl)-6-{[4-(trifluoromethoxy)phenyl]amino}pyridine-4-carbonitrile<br>1H NMR (500 MHz, DMSO-d6) δ 9.82 (s, 1H), 9.64 (dd, J = 2.84, 5.36 Hz, 1H), 8.77 (d, J = 3.15 Hz, 1H), 7.61-7.71 (d, J = 8.51 Hz, 2H), 7.45 (d, J = 0.95 Hz, 1H), 7.32 (d, J = 8.51 Hz, 2H), 7.10 (d, J = 1.26 Hz, 1H), 2.67 (s, 3H); m.p. 275-277° C.; MS m/z 429.2 (ESI) [M + H]+ |
| 439 | 2-{[4-(difluoromethoxy)-3-fluorophenyl]amino}-6-(6-fluoro-2-methylimidazo[1,2-a]pyrimidin-3-yl)pyridine-4-carbonitrile<br>1H NMR (500 MHz, DMSO-d6) δ 9.90 (s, 1H), 9.66 (dd, J = 2.99, 5.20 Hz, 1H), 8.80 (d, J = 3.15 Hz, 1H), 7.74 (s, 1H), 7.49 (d, J = 0.95 Hz, 1H), 7.25-7.40 (m, 2H), 7.12 (d, J = 0.95 Hz, 1H), 2.66 (s, 3H); m.p. 268-270° C.; MS m/z 429.2 (ESI) [M + H]+ |
| 441 | 2-(6,8-difluoro-2-methylimidazo[1,2-a]pyridin-3-yl)-6-{[4-(trifluoromethyl)phenyl]amino}pyridine-4-carbonitrile<br>1H NMR (500 MHz, DMSO-d6) δ 10.04 (s, 1H), 9.12 (dd, J = 1.58, 5.04 Hz, 1H), 7.77 (d, J = 8.51 Hz, 2H), 7.62 (d, J = 8.51 Hz, 3H), 7.49 (d, J = 0.95 Hz, 1H), 7.18 (d, J = 0.95 Hz, 1H), 2.61 (s, 3H); m.p. 243-245° C.; MS m/z 430.2 (ESI) [M + H]+ |
| 442 | 2-{[4-(fluoromethoxy)phenyl]amino}-6-(6,8-difluoro-2-methylimidazo[1,2-a]pyridin-3-yl)pyridine-4-carbonitrile<br>1H NMR (500 MHz, DMSO-d6) δ 9.68 (s, 1H), 9.03-9.24 (m, 1H), 7.60-7.66 (m, 1H), 7.58 (d, J = 9.14 Hz, 2H), 7.37 (d, J = 0.95 Hz, 1H), 7.01-7.27 (t, J = 67.50, 1H), 7.11-7.16 (m, J = 9.14 Hz, 2H), 7.06 (d, J = 0.95 Hz, 1H), 2.60 (s, 3H); m.p. 236-238° C.; MS m/z 428.2 (ESI) [M + H]+ |
| 443 | 2-(6,8-difluoro-2-methylimidazo[1,2-a]pyridin-3-yl)-6-{[4-(trifluoromethoxy)phenyl]amino}pyridine-4-carbonitrile<br>1H NMR (500 MHz, DMSO-d6) δ 9.82 (s, 1H), 8.96-9.27 (m, 1H), 7.65-7.69 (d, J = 8.20 Hz, 2H), 7.60-7.64 (m, 1H), 7.42 (d, J = 0.95 Hz, 1H), 7.30 (d, J = 8.20 Hz, 2H), 7.11 (d, J = 1.26 Hz, 1H), 2.62 (s, 3H); m.p. 213-216° C.; MS m/z 446.2 (ESI) [M + H]+ |
| 444 | 2-{[4-(difluoromethoxy)-3-fluorophenyl]amino}-6-(6,8-difluoro-2-methylimidazo[1,2-a]pyridin-3-yl)pyridine-4-carbonitrile<br>1H NMR (500 MHz, DMSO-d6) δ 9.91 (s, 1H), 9.13 (dd, J = 1.73, 4.89 Hz, 1H), 7.78 (dd, J = 2.05, 13.08 Hz, 1H), 7.60-7.71 (m, 1H), 7.46 (d, J = 0.95 Hz, 1H), 6.97-7.31 (t, J = 85.00, 1H), 7.26-7.36 (m, 2H), 7.13 (m, 1H), 2.61 (s, 3H); m.p. 238-241° C.; MS m/z 446.2 (ESI) [M + H]+ |
| 466 | 2-[2-(difluoromethyl)-6-fluoroimidazo[1,2-a]pyridin-3-yl]-6-{[4-(trifluoromethyl)phenyl]amino}pyridine-4-carbonitrile<br>1H NMR (500 MHz, DMSO-d6) δ 10.15 (s, 1H), 9.08-9.15 (m, 1H), 7.86-7.91 (m, 1H), 7.84 (d, J = 8.51 Hz, 2H), 7.59-7.65 (m, J = 8.80 Hz, 3H), 7.51 (d, J = 0.95 Hz, 1H), 7.41 (t, J = 53.60 Hz, 1H), 7.30 (d, J = 0.95 Hz, 1H); m.p. 249-251° C.; MS m/z 448.2 (ESI) [M + H]+ |
| 467 | 2-{[4-(difluoromethoxy)phenyl]amino}-6-[2-(difluoromethyl)-6-fluoroimidazo[1,2-a]pyridin-3-yl]pyridine-4-carbonitrile<br>1H NMR (500 MHz, DMSO-d6) δ 9.80 (s, 1H), 9.04-9.15 (m, 1H), 7.82-7.91 (m, 1H), 7.62-7.67 (m, 3H), 7.25-7.47 (t, J = 55.00 Hz, 1H), 7.39 (d, J = 0.95 Hz, 1H), 6.99-7.29 (t, J = 75.00 Hz, 1H), 7.20 (d, J = 0.95 Hz, 1H), 7.09-7.16 (m, 2H); m.p. 215-217° C.; MS m/z 446.2 (ESI) [M + H]+ |
| 468 | 2-{[6-(difluoromethoxy)-5-methylpyridin-3-yl]amino}-6-[2-(difluoromethyl)-6-fluoroimidazo[1,2-a]pyridin-3-yl]pyridine-4-carbonitrile<br>1H NMR (500 MHz, DMSO-d6) δ 9.84 (s, 1H), 9.04-9.12 (m, 1H), 8.10-8.20 (m, 2H), 7.84-7.93 (m, 1H), 7.48-7.77 (t, J = 72.50 Hz, 1H), 7.60-7.68 (m, 1H), 7.23-7.44 (t, J = 52.50 Hz, 1H), 7.42 (s, 1H), 7.22 (d, J = 0.95 Hz, 1H), 3.35 (s, 3H); m.p. 239-241° C.; MS m/z 461.2 (ESI) [M + H]+ |
| 469 | 2-[2-(difluoromethyl)-6-fluoroimidazo[1,2-a]pyridin-3-yl]-6-{[6-(trifluoromethyl)pyridin-3-yl]amino}pyridine-4-carbonitrile<br>1H NMR (500 MHz, DMSO-d6) δ 10.40 (s, 1H), 9.04-9.09 (m, 1H), 8.90 (s, 1H), 8.35-8.42 (m, 1H), 7.86-7.95 (m, 1H), 7.73-7.82 (m, 1H), 7.61-7.70 (m, 1H), 7.58 (s, 1H), 7.37 (s, 1H), 7.24-7.45 (t, J = 52.50 Hz, 1H); m.p. 285-288° C.; MS m/z 449.2 (ESI) [M + H]+ |
| 470 | 2-{[6-(difluoromethoxy)-5-methylpyridin-3-yl]amino}-6-(6-fluoro-2-methylimidazo[1,2-a]pyridin-3-yl)pyridine-4-carbonitrile<br>1H NMR (500 MHz, DMSO-d6) δ 9.71 (s, 1H), 9.16-9.22 (m, 1H), 8.15 (dd, J = 1.00, 2.21 Hz, 1H), 8.10 (dd, J = 1.00, 4.10 Hz, 1H), 7.49-7.78 (t, J = 72.50 Hz, 1H), 7.64-7.69 (m, 1H), 7.43-7.48 (m, 1H), 7.39 (d, J = 0.95 Hz, 1H), 7.04 (d, J = 1.00 Hz, 1H), 2.60 (s, 3H), 2.15 (s, 3H); m.p. 219-222° C.; MS m/z 425.2 (ESI) [M + H]+ |
| 471 | 2-{[6-(difluoromethoxy)-5-methylpyridin-3-yl]amino}-6-(6,8-difluoro-2-methylimidazo[1,2-a]pyridin-3-yl)pyridine-4-carbonitrile<br>1H NMR (500 MHz, DMSO-d6) δ 9.73 (s, 1H), 9.06 (d, J = 3.47 Hz, 1H), 8.13 (d, J = 2.52 Hz, 1H), 8.09 (d, J = 1.89 Hz, 1H), 7.48-7.78 (t, J = 75.00 Hz, 1H), 7.61-7.67 (m, 1H), 7.41 (d, J = 1.26 Hz, 1H), 7.08 (d, J = 0.95 Hz, 1H), 2.60 (s, 3H), 2.15 (s, 3H); m.p. 236-238° C.; MS m/z 443.2 (ESI) [M + H]+ |
| 472 | 6-[2-(difluoromethyl)-6-fluoroimidazo[1,2-a]pyridin-3-yl]-N-[4-(trifluoromethyl)phenyl]pyrazin-2-amine<br>1H NMR (500 MHz, DMSO-d6) δ 10.22 (s, 1H), 9.09 (dd, J = 2.52, 5.04 Hz, 1H), 8.35 (d, J = 8.51 Hz, 2H), 7.84-7.92 (m, 3H), 7.59-7.69 (m, 3H), 7.22-7.43 (t, J = 52.50 Hz, 1H); m.p. 180-182° C.; MS m/z 424.3 (ESI) [M + H]+ |
| 473 | N-[4-(difluoromethoxy)phenyl]-6-[2-(difluoromethyl)-6-fluoroimidazo[1,2-a]pyridin-3-yl]pyrazin-2-amine<br>1H NMR (500 MHz, DMSO-d6) δ 9.86 (s, 1H), 9.09 (dd, J = 2.05, 4.89 Hz, 1H), 8.27 (s, 1H), 8.24 (s, 1H), 7.86 (d, J = 5.36 Hz, 1H), 7.67-7.72 (m, 1H), 7.62 (s, 1H), 7.21-7.42 (t, J = 52.50 Hz, 1H), 7.13 (dd, J = 1.00, 4.10 Hz, 2H), 6.98-7.28 (t, J = 75.00 Hz, 1H); m.p. 167-169° C.; MS m/z 422.3 (ESI) [M + H]+ |
| 479 | N-[6-(difluoromethoxy)pyridin-3-yl]-6-[2-(difluoromethyl)-6-fluoroimidazo[1,2-a]pyridin-3-yl]pyrazin-2-amine<br>1H NMR (500 MHz, DMSO-d6) δ 9.62 (br. s, 1H), 9.52-9.58 (m, 1H), 9.00 (d, J = 2.52 Hz, 1H), 8.86 (s, 1H), 8.80 (dd, J = 2.84, 8.83 Hz, 1H), 8.79 (s, 1H), 8.24-8.29 (m, 1H), 7.88-8.18 (t, J = 75.00 Hz, 1H), 8.00 (s, 1H), 7.54-7.75 (t, J = 52.50 Hz, 1H), 7.48 (d, J = 8.83 Hz, 1H); m.p. 225-227° C.; MS m/z 423.3 (ESI) [M + H]+ |
| 480 | N-[6-(difluoromethoxy)pyridin-3-yl]-6-(6-fluoro-2-methylimidazo[1,2-a]pyridin-3-yl)pyrazin-2-amine<br>1H NMR (500 MHz, DMSO-d6) δ 9.65-9.78 (m, 1H), 9.49 (s, 1H), 8.86 (d, J = 2.84 Hz, 1H), 8.67 (dd, J = 2.84, 8.83 Hz, 1H), 7.88-8.18 (t, J = 75.00 Hz, 1H), 8.00-8.06 (m, 1H), 7.83 (d, J = 0.95 Hz, 1H), 7.76-7.82 (m, 1H), 7.53 (d, J = 0.95 Hz, 1H), 7.49 (d, J = 8.83 Hz, 1H), 3.12 (s, 3H); m.p. 204-207° C. |
| 487 | 2-{[4-(trifluoromethyl)phenyl]amino}-6-(2,6,8-trimethylimidazo[1,2-a]pyrazin-3-yl)pyridine-4-carbonitrile<br>m.p. 237-238° C.; MS m/z 423.4 (ESI) [M + H]+ |
| 488 | N-[4-(trifluoromethyl)phenyl]-6-(2,6,8-trimethylimidazo-[1,2-a]pyrazin-3-yl)pyrazin2-amine<br>1H NMR (500 MHz, DMSO-d6) δ 10.13 (d, J = 1.00 Hz, 1H), 8.74 (s, 1H), 8.39 (s,1H), 8.26 (s, 1H), 7.86 (none, 1H), 7.85 (d, J = 8.51 Hz, 2H), 7.67 (d, J = 8.51 Hz,2H), 2.73 (s, 3H), 2.64 (s, 3H), 2.29 (s, 3H); m.p. 102-105° C. |
| 489 | N-[4-(difluoromethoxy)phenyl]-6-(2,6,8-trimethylimidazo[1,2-a]pyrazin-3-yl)pyrazin-2-amine<br>1H NMR (500 MHz, DMSO-d6) δ 10.14 (s, 1H), 8.75 (s, 1H), 8.40 (s, 1H), 8.27 (s, 1H), 7.86 (d, J = 8.83 Hz, 2H), 7.68 (d, |

| Cpd | Name and Data |
|---|---|
| | J = 8.51 Hz, 2H), 2.74 (s, 3H), 2.65 (s, 3H), 2.30 (s, 3H); m.p. 140-141° C. |
| 491 | 2-(2-cyclopropyl-6,8-dimethylimidazo[1,2-a]pyrazin-3-yl)-6-{[4-(trifluoromethyl)phenyl]amino}pyridine-4-carbonitrile<br>¹H NMR (500 MHz, DMSO-d₆) δ 10.02-10.20 (m, 1H), 8.60-8.73 (m, 1H), 7.80-7.88 (d, J = 8.2 Hz, 2H), 7.56-7.69 (m, 3H), 7.11-7.26 (m, 1H), 2.69 (s, 3H), 2.35-2.44 (m, 1H), 2.24 (s, 3H), 1.03-1.11 (m, 4H); m.p. 150-152° C.; MS m/z 449.5 (ESI) [M + H]⁺ |
| 591 | 6-(6-fluoro-2-methylimidazo[1,2-a]pyridin-3-yl)-N-(4-fluorophenyl)pyrazin-2-amine<br>¹H NMR (500 MHz, DMSO-d₆) δ 9.66 (s, 1H), 9.25 (dd, J = 5.52, 2.05 Hz, 1H), 8.25 (s, 1H), 8.13 (s, 1H), 7.57-7.74 (m, 3H), 7.44 (t, J = 1.00 Hz, 1H), 7.17 (t, J = 8.83 Hz, 2H), 2.61 (s, 3H); m.p. 208-210° C.; MS m/z 339.2 (ESI) [M + H]⁺ |
| 592 | 6-(6-fluoro-2-methylimidazo[1,2-a]pyridin-3-yl)-N-(4-methoxyphenyl)pyrazin-2-amine<br>¹H NMR (500 MHz, DMSO-d₆) δ 9.44 (s, 1H), 9.30 (d, J = 3.15 Hz, 1H), 8.19 (s, 1H), 8.07 (s, 1H), 7.65 (dd, J = 5.20, 9.62 Hz, 1H), 7.50 (d, J = 8.83 Hz, 2H), 7.39-7.46 (m, 1H), 6.92 (d, J = 8.83 Hz, 2H), 3.73 (s, 3H), 2.61 (s, 3H); m.p. 136-166° C.; MS m/z 350.3 (ESI) [M + H]⁺ |
| 593 | N-(4-chlorophenyl)-6-(6-fluoro-2-methylimidazo[1,2-a]pyridin-3-yl)pyrazin-2-amine<br>¹H NMR (500 MHz, DMSO-d₆) 9.80 (s, 1H), 9.16-9.28 (m, 1H), 8.29 (s, 1H), 8.17 (s, 1H), 7.62-7.72 (m, 4H), 7.41-7.50 (m, 1H), 7.29-7.39 (m, 2H), δ 2.61 (s, 3H); m.p. 215-218° C.; MS m/z 354.2 (ESI) [M + H]⁺ |
| 594 | 6-(6-fluoro-2-methylimidazo[1,2-a]pyridin-3-yl)-N-[3-(trifluoromethyl)phenyl]pyrazin-2-amine<br>¹H NMR (500 MHz, DMSO-d₆) δ 10.06 (br. s., 1H), 9.14 (br. s., 1H), 8.12-8.40 (m, 3H), 7.75 (d, J = 7.88 Hz, 1H), 7.67 (dd, J = 5.04, 9.14 Hz, 1H), 7.54 (t, J = 7.57 Hz, 1H), 7.44 (t, J = 8.04 Hz, 1H), 7.31 (d, J = 7.25 Hz, 1H), 2.59 (s, 3H); m.p. 188-190° C.; MS m/z 389.2 (ESI) [M + H]⁺ |
| 595 | 6-(6-fluoro-2-methylimidazo[1,2-a]pyridin-3-yl)-N-(3-fluorophenyl)pyrazin-2-amine<br>¹H NMR (500 MHz, DMSO-d₆) δ 9.91 (s, 1H), 9.26 (dd, J = 1.89, 5.36 Hz, 1H), 8.32 (s, 1H), 8.20 (s, 1H), 7.65-7.75 (m, 2H), 7.42-7.53 (m, 1H), 7.25-7.38 (m, 2H), 6.74-6.92 (m, 1H), 2.61 (s, 3H); m.p. 270-273° C.; MS m/z 339.2 (ESI) [M + H]⁺ |
| 596 | 6-(6-fluoro-2-methylimidazo[1,2-a]pyridin-3-yl)-N-(3-methoxyphenyl)pyrazin-2-amine<br>¹H NMR (500 MHz, DMSO-d₆) δ 9.67 (s, 1H), 9.30 (d, J = 2.21, 5.04 Hz, 1H), 8.26 (s, 1H), 8.17 (s, 1H), 7.67 (s, 1H), 7.38-7.50 (m, 1H), 7.10-7.35 (m, 3H), 6.60 (d, J = 7.88 Hz, 1H), 3.67 (s, 3H), 2.61 (s, 3H); m.p. 270-273° C.; MS m/z 349.9 (ESI) [M + H]⁺ |
| 597 | N-(3-chlorophenyl)-6-(6-fluoro-2-methylimidazo[1,2-a]pyridin-3-yl)pyrazin-2-amine<br>¹H NMR (500 MHz, DMSO-d₆) δ 9.92 (s, 1H), 9.14-9.30 (m, 1H), 8.32 (s, 1H), 8.19 (s, 1H), 8.00 (t, J = 2.05 Hz, 1H), 7.69 (dd, J = 5.36, 9.77 Hz, 1H), 7.40-7.53 (m, 2H), 7.34 (t, J = 8.04 Hz, 1H), 7.04 (ddd, J = 0.79, 2.05, 7.88 Hz, 1H), 2.61 (s, 3H); m.p. 272-275° C.; MS m/z 354.2 (ESI) [M + H]⁺ |
| 598 | 6-(6-fluoro-2-methylimidazo[1,2-a]pyridin-3-yl)-N-(2-fluorophenyl)pyrazin-2-amine<br>¹H NMR (500 MHz, DMSO-d₆) δ 9.41 (br. s., 1H), 9.20 (m, 1H), 8.28 (s, 1H), 8.22 (s, 1H), 7.80 (m, 1H), 7.64 (dd, J = 5.52, 9.30 Hz, 1H), 7.36-7.48 (m, 1H), 7.30 (m, 1H), 7.18 (m, 2H), 2.60 (s, 3H); m.p. 218-220° C.; MS m/z 337.9 (ESI) [M + H]⁺ |
| 646 | 2-(6-fluoro-2-methylimidazo[1,2-a]pyridin-3-yl)-6-(phenylamino)pyridine-4-carbonitrile<br>¹H NMR (500 MHz, DMSO-d₆) δ 9.61 (s, 1H), 9.32 (d, J = 3.15 Hz, 1H), 7.64 (dd, J = 5.36, 9.46 Hz, 1H), 7.55 (d, J = 7.88 Hz, 2H), 7.38-7.50 (m, 1H), 7.25-7.35 (m, 3H), 7.00-7.09 (m, 2H), 2.59 (s, 3H); m.p. 176-178° C.; MS m/z 344.5 (ESI) [M + H]⁺ |
| 647 | 2-[(4-chlorophenyl)amino]-6-(6-fluoro-2-methylimidazo[1,2-a]pyridin-3-yl)pyridine-4-carbonitrile<br>¹H NMR (500 MHz, DMSO-d₆) δ 9.74 (s, 1H), 9.26 (dd, J = 2.05, 5.52 Hz, 1H), 7.66 (dd, J = 5.52, 9.62 Hz, 1H), 7.59 (d, J = 8.83 Hz, 2H), 7.41-7.48 (m, 2H), 7.38 (s, 1H), 7.34 (d, J = 8.83 Hz, 2H), 7.05 (s, 1H), 2.60 (s, 3H); m.p. 148-151° C.; MS m/z 377.9 (ESI) [M + H]⁺ |
| 648 | 2-(6-fluoro-2-methylimidazo[1,2-a]pyridin-3-yl)-6-[(4-methylphenyl)amino}pyridine-4-carbonitrile<br>¹H NMR (500 MHz, DMSO-d₆) δ 9.50 (s, 1H), 9.32 (d, J = 3.47 Hz, 1H), 7.57-7.72 (m, 1H), 7.39-7.47 (m, 3H), 7.28 (s, 1H), 7.13 (d, J = 8.20 Hz, 2H), 6.99 (s, 1H), 2.60 (s, 3H), 2.27 (s, 3H); m.p. 185-188° C.; MS m/z 358.2 (ESI) [M + H]⁺ |
| 649 | 2-(6-fluoro-2-methylimidazo[1,2-a]pyridin-3-yl)-6-[(4-methoxyphenyl)amino}pyridine-4-carbonitrile<br>¹H NMR (500 MHz, DMSO-d₆) δ 9.38 (s, 1H), 9.32 (dd, J = 2.21, 5.36 Hz, 1H), 7.63 (dd, J = 5.36, 9.77 Hz, 1H), 7.38-7.46 (m, 3H), 7.24 (s, 1H), 6.88-6.96 (m, 3H), 3.33 (s, 3H), 2.60 (s, 3H); m.p. 190-192° C.; MS m/z 373.9 (ESI) [M + H]⁺ |
| 650 | 2-(6-fluoro-2-methylimidazo[1,2-a]pyridin-3-yl)-6-[(3-methoxyphenyl)amino}pyridine-4-carbonitrile<br>m.p. 247-250° C.; MS m/z 374.2 (ESI) [M + H]⁺ |
| 651 | 2-(6-fluoro-2-methylimidazo[1,2-a]pyridin-3-yl)-6-[(3-fluorophenyl)amino}pyridine-4-carbonitrile<br>¹H NMR (500 MHz, DMSO-d₆) δ 10.00 (s, 1H), 9.06-9.25 (m, 1H), 8.19 (s, 1H), 7.71-7.75 (m, 1H), 7.64-7.69 (m, 1H), 7.51-7.57 (m, 1H), 7.41-7.48 (m, J = 0.90 Hz, 2H), 7.29-7.35 (m, 1H), 7.13 (d, J = 0.95 Hz, 1H), 2.59 (s, 3H); m.p. 250-253° C.; MS m/z 361.9 (ESI) [M + H]⁺ |

Example 101

6-(6-fluoro-2-methylimidazo[1,2-a]pyridin-3-yl)-N²-[4-(trifluoromethyl)phenyl]pyridine-2,4-diamine (Cpd 316)

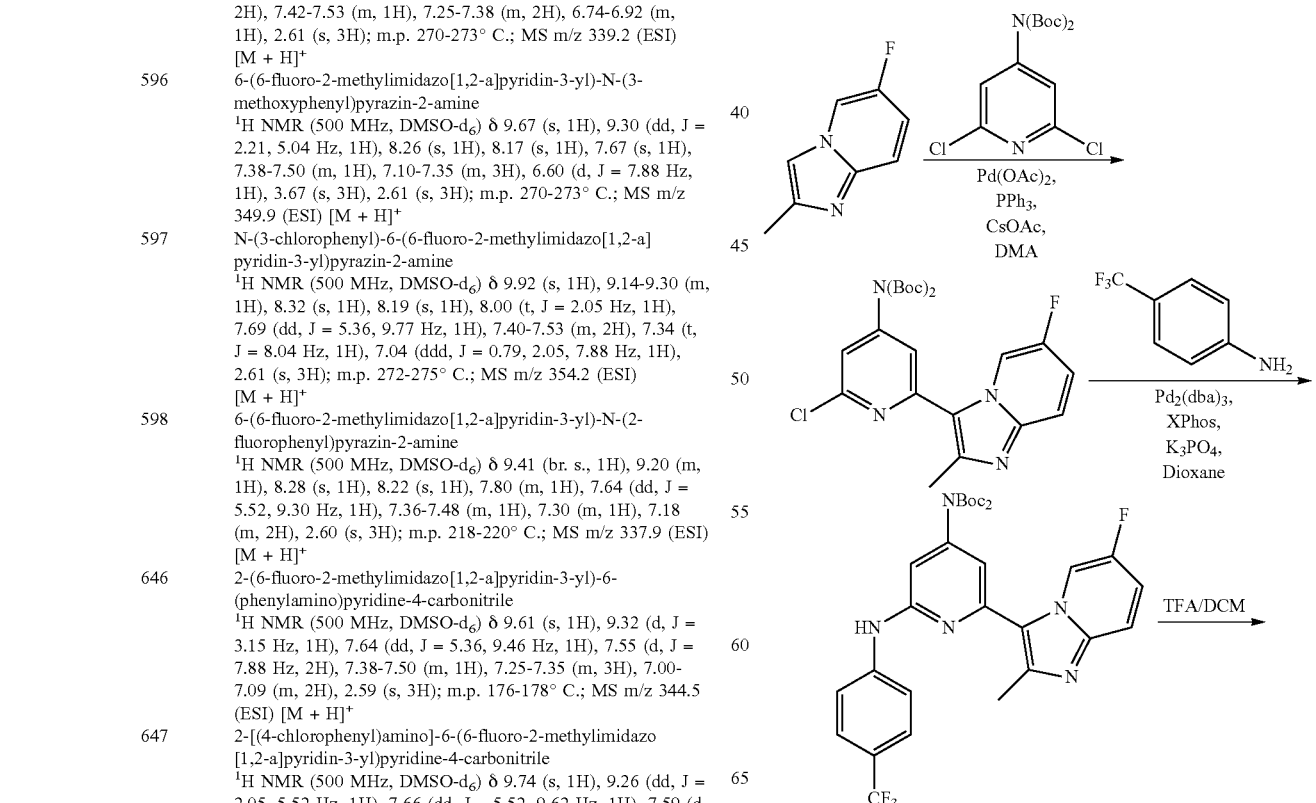

-continued

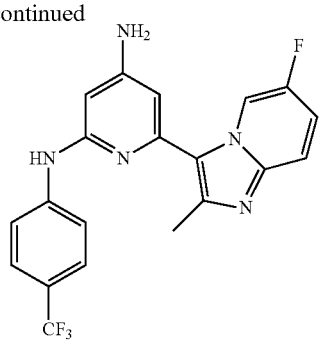

Step 1. Using the procedure described in Example 99 and appropriate reagents and reaction conditions, 6-fluoro-2-methylimidazo[1,2-a]pyridine (1.08 g, 7.2 mmol) and di-tert-butyl 2,6-dichloropyridin-4-yliminodicarbonate (3.92 g, 10.80 mmol) were reacted to provide di-tert-butyl 2-chloro-6-(6-fluoro-2-methylimidazo[1,2-a]pyridin-3-yl)pyridin-4-yliminodicarbonate (830.0 mg, 21%).

Step 2. Using the procedure described in Example 97 and appropriate reagents and reaction conditions, the obtained intermediate (468.0 mg, 0.98 mmol) and 4-trifluoroaniline (316.0 mg, 1.96 mmol) were reacted to provide di-tert-butyl 2-(6-fluoro-2-methylimidazo[1,2-a]pyridin-3-yl)-6-(4-(trifluoromethyl)phenylamino)pyridin-4-yliminodicarbonate (350.1 mg, 60%).

Step 3. A solution of the obtained intermediate (350.1 mg, 0.58 mmol) in dichloromethane (2 mL) was treated with TFA (0.8 mL) at 0° C. The resulting mixture was stirred at room temperature for 5 hours, then the solvent was evaporated and the product partitioned between ethyl acetate and saturated NaHCO$_3$. The organic phase was washed with brine, dried over magnesium sulfate, then filtered and evaporated. The residue was triturated with ethyl ether to afford the title compound (187.0 mg, 90%) as a white solid. m.p. 161-163° C.; $^1$H NMR (500 MHz, DMSO-d$_6$) δ 9.34 (dd, J=2.36, 5.52 Hz, 1H), 9.20 (s, 1H), 7.73 (d, J=8.51 Hz, 2H), 7.60 (dd, J=5.36, 9.77 Hz, 1H), 7.51 (d, J=8.51 Hz, 2H), 7.32-7.39 (m, 1H), 6.49 (d, J=1.58 Hz, 1H), 6.14 (s, 2H), 6.06 (d, J=1.58 Hz, 1H), 2.56 (s, 3H); MS (ES+): m/e 402.5 (100).

Additional compounds of Formula (I) or a form thereof described herein may be prepared according to the procedure of Example 101 by substituting the appropriate starting materials, reagents and reaction conditions:

| Cpd | Name and Data |
|---|---|
| 363 | 6-(2-cyclopropyl-6-fluoroimidazo[1,2-a]pyridin-3-yl)-N$^2$-[4-(trifluoromethyl)phenyl]pyridine-2,4-diamine<br>$^1$H NMR (500 MHz, DMSO-d$_6$) δ 9.22 (s, 1H), 9.18-9.21 (m, 1H), 7.77 (d, J = 8.83 Hz, 2H), 7.55-7.61 (m, 1H), 7.51 (d, J = 8.83 Hz, 2H), 7.30-7.40 (m, 1H), 6.67 (d, J = 1.58 Hz, 1H), 6.13-6.25 (m, 2H), 6.08 (d, J = 1.58 Hz, 1H), 2.26-2.34 (m, 1H), 0.98-1.05 (m, 4H); m.p. 160-162° C.; MS m/z 428.0 (ESI) [M + H]$^+$ |
| 364 | 6-(2-cyclopropyl-6-fluoroimidazo[1,2-a]pyridin-3-yl)-N$^2$-[3-fluoro-4-(trifluoromethyl)phenyl]pyridine-2,4-diamine<br>$^1$H NMR (500 MHz, DMSO-d$_6$) δ 9.51 (s, 1H), 9.06-9.19 (m, 1H), 7.95-8.13 (m, 1H), 7.57-7.62 (m, 1H), 7.51-7.56 (m, 1H), 7.34 (s, 2H), 6.70 (d, J = 1.58 Hz, 1H), 6.25 (s, 2H), 6.09 (d, J = 1.89 Hz, 1H), 2.27-2.34 (m, 1H), 0.98-1.06 (m, 4H); m.p. 223-225° C.; MS m/z 446.0 (ESI) [M + H]$^+$ |
| 365 | 6-(2-cyclopropyl-6-fluoroimidazo[1,2-a]pyridin-3-yl)-N$^2$-[4-(difluoromethoxy)phenyl]pyridine-2,4-diamine<br>$^1$H NMR (500 MHz, DMSO-d$_6$) δ 9.24 (br. s., 1H), 8.77 (br. s., 1H), 7.48-7.70 (m, 3H), 7.27-7.42 (m, 1H), 6.92-7.22 (t, J = 75.00 Hz, 1H), 6.98-7.14 (m, 2H), 6.60 (s, 1H), 5.85-6.18 (m, 3H), 2.20-2.40 (m, 1H), 0.88-1.20 (m, 4H); m.p. 185-186° C.; MS m/z 426.0 (ESI) [M + H]$^+$ |
| 366 | 6-(2-cyclopropyl-6-fluoroimidazo[1,2-a]pyridin-3-yl)-N$^2$-[4-(difluoromethoxy)-3-fluorophenyl]pyridine-2,4-diamine<br>$^1$H NMR (500 MHz, DMSO-d$_6$) δ 9.13 (dd, J = 2.21, 5.36 Hz, 1H), 9.04 (s, 1H), 7.87 (dd, J = 2.05, 14.03 Hz, 1H), 7.56 (dd, J = 5.36, 9.77 Hz, 1H), 7.34 (d, J = 1.89 Hz, 1H), 7.15-7.24 (m, 2H), 6.91-7.22 (t, J = 77.50 Hz, 1H), 6.62 (d, J = 1.58 Hz, 1H), 6.12 (s, 2H), 6.00 (d, J = 1.58 Hz, 1H), 2.24-2.34 (m, 1H), 0.92-1.04 (m, 4H); m.p. 169-170° C.; MS m/z 444.0 (ESI) [M + H]$^+$ |
| 367 | 6-(2-cyclopropyl-6-fluoroimidazo[1,2-a]pyridin-3-yl)-N$^2$-[4-(trifluoromethoxy)phenyl]pyridine-2,4-diamine<br>$^1$H NMR (500 MHz, DMSO-d$_6$) δ 9.23 (dd, J = 2.21, 5.36 Hz, 1H), 8.93 (s, 1H), 7.65(d, J = 8.83 Hz, 2H), 7.56 (dd, J = 5.52, 9.62 Hz, 1H), 7.29-7.38 (m, 1H), 7.19 (d, J = 8.83 Hz, 2H), 6.63 (d, J = 1.58 Hz, 1H), 6.09 (br. s., 2H), 6.01 (d, J = 1.58 Hz, 1H), 2.30 (s, 1H), 0.96-1.05 (m, 4H); m.p. 166-168° C.; MS m/z 444.0 (ESI) [M + H]$^+$ |

Example 102

N-[2-(2-cyclopropyl-6-fluoroimidazo[1,2-a]pyridin-3-yl)-6-{[4-(trifluoromethyl)phenyl]amino}pyridin-4-yl]sulfuric diamide (Cpd 368)

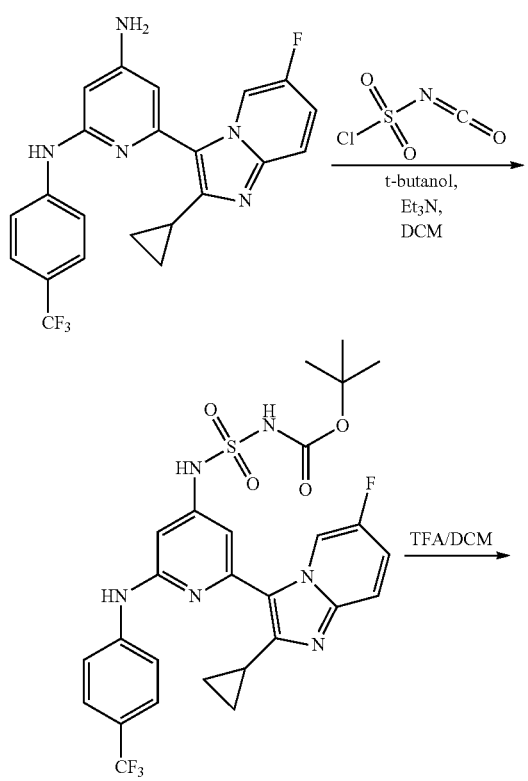

421

-continued

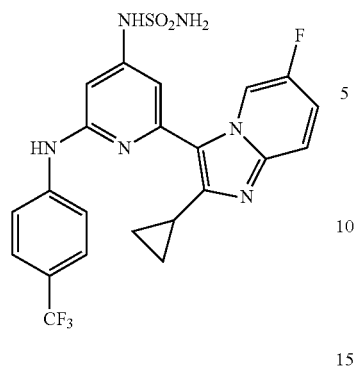

Step 1. To a solution of t-butanol (19.1 mg, 0.26 mmol) in dichloromethane (1 mL) was added sulfurisocyanatidic chloride (36.4 mL) in DCM (0.6 mL) at 0° C. dropwise. The reaction mixture was stirred at 0° C. for 10 minutes, then a mixture of Compound 364 (prepared using the procedure described in Example 101 and appropriate starting materials, reagents and reaction conditions) (100.0 mg, 0.23 mmol) in DCM (1 mL) and triethylamine (28.7 mg, 0.27 mmol) was added. The resulting mixture was stirred at room temperature for 1 hour, then partitioned between ethyl acetate and saturated water. The organic phase was washed with brine, dried over magnesium sulfate, then filtered and evaporated. The obtained product tert-butyl N-(2-(2-cyclopropyl-6-fluoroimidazo[1,2-a]pyridin-3-yl)-6-(4-(trifluoromethyl)phenylamino)pyridin-4-yl)sulfamoylcarbamate was used in the next step without further purification.

Step 2. The obtained product was carried forward (using the procedure described in Example 101 and appropriate starting materials, reagents and reaction conditions) to provide the title compound. m.p. 158-160° C.; $^1$H NMR (500 MHz, DMSO-$d_6$) δ 10.33 (s, 1H), 9.66 (s, 1H), 9.29 (d, J=2.84 Hz, 1H), 7.82 (d, J=8.51 Hz, 2H), 7.66 (dd, J=4.89, 9.62 Hz, 1H), 7.56 (d, J=8.51 Hz, 2H), 7.43-7.53 (m, 1H), 7.39 (s, 2H), 7.26 (d, J=1.26 Hz, 1H), 6.72 (d, J=1.26 Hz, 1H), 2.33 (m, 1H), 1.00-1.12 (m, 4H); MS (ES+): m/e 507.4 (100), 508.4 (40), 509.4 (10); MS (ES+): m/e 507.4 (100).

Example 103

1-[2-(2-cyclopropyl-6-fluoroimidazo[1,2-a]pyridin-3-yl)-6-{[4-(trifluoromethyl)phenyl]amino}pyridin-4-yl]urea (Cpd 369)

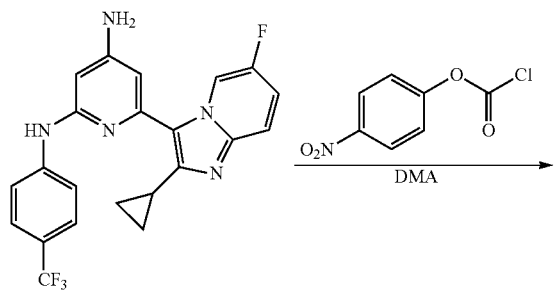

422

-continued

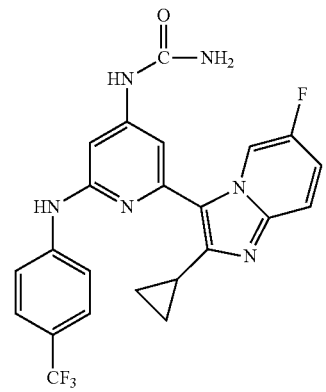

A mixture of Compound 364 (prepared using the procedure described in Example 101 and appropriate starting materials, reagents and reaction conditions) (123.0 mg, 0.29 mmol) 4-nitrophenylchloroformate 961.0 mg, 0.29 mmol), dimethylacetamide (1 mL) and THF (1 mL) was stirred at room temperature for 2 hours, then ammonia (0.5 mL) was added. The reaction mixture was stirred at room temperature for 30 minutes, then partitioned between ethyl acetate and water. The organic phase was washed with brine, dried over magnesium sulfate, then filtered and evaporated. The residue was separated by column chromatography, eluting with 0-5% methanol:dichloromethane to afford the title compound (45.0 mg, 33%). m.p. 232-235° C.; $^1$H NMR (500 MHz, DMSO-$d_6$) δ 9.59 (s, 1H), 9.16-9.24 (m, 1H), 9.08 (s, 1H), 7.83 (d, J=8.51 Hz, 2H), 7.57-7.62 (m, 1H), 7.54 (d, J=8.51 Hz, 2H), 7.34-7.40 (m, 1H), 7.29 (d, J=1.58 Hz, 1H), 7.26 (d, J=1.58 Hz, 1H), 6.16 (br. s, 2H), 2.28-2.37 (m, 1H), 0.99-1.07 (m, 4H); MS (ES+): m/e 471.0 (100), 472.0 (20); MS (ES+): m/e 471.0 (100).

Example 104

6-(6-fluoro-2-methyl-1H-benzimidazol-1-yl)-N-[4-(trifluoromethyl)phenyl]pyrazin-2-amine (Cpd 228)

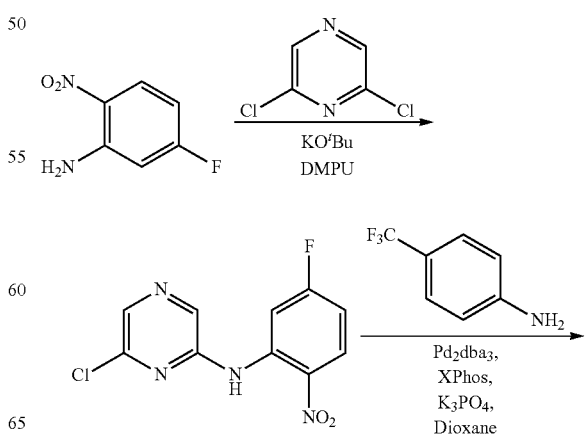

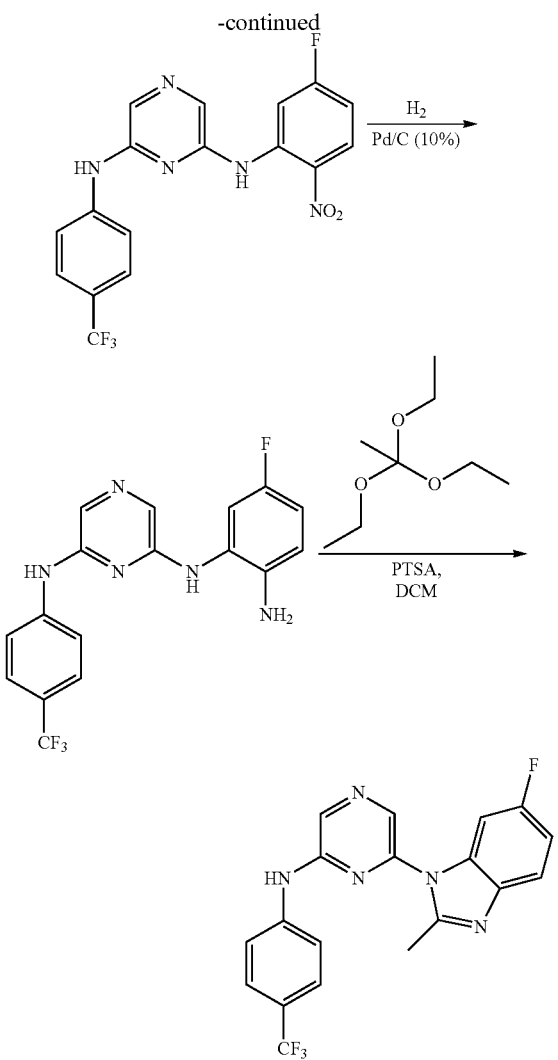

Step 1. A mixture of 5-fluoro-2-nitroaniline (4.4 g, 28.19 mmol) and 2,6-dichloropyrazine (4.0 g, 26.85 mmol) in N,N'-dimethyl-N,N'-trimethyleneurea (DMPU) (10 mL) was treated with potassium tert-butoxide (1M in THF, 59.1 mL, 59.1 mmol) at 80° C. The reaction mixture was stirred at 80° C. for 2 hours, cooled, then poured into ice-water (200 mL) and extracted with ethyl acetate (200 mL). The organic phase was washed with brine (200 mL), dried over magnesium sulfate, then filtered and evaporated. The residue was separated by silica gel column chromatography (1:1 dichloromethane:hexane) to afford 6-chloro-N-(5-fluoro-2-nitrophenyl)pyrazin-2-amine (6.0 g, 78%). $^1$H NMR (500 MHz, DMSO-d$_6$) δ 10.08 (s, 1H), 8.30 (s, 1H), 8.09 (s, 1H), 7.97 (dd, J=2.99, 8.67 Hz, 1H), 7.80 (dd, J=5.04, 9.14 Hz, 1H), 7.67 (ddd, J=3.15, 7.88, 9.14 Hz, 1H); MS (ES+): m/e 269.0 (100).

Step 2. A mixture of the obtained intermediate (495.0 mg, 1.84 mmol), 4-(trifluoromethyl)aniline (895.9 mg, 5.53 mmol), 2-dicyclohexylphosphino-2',4',6'-triisopropylbiphenyl (XPhos, 52.7 mg, 0.11 mmol), tris(dibenzylideneacetone) dipalladium(0) (50.7 mg, 0.055 mmol) and a solution of tripotassium phosphate (1.18 g, 5.52 mmol) in dioxane (3 mL) was degassed by three cycles of vacuum pumping and N$_2$ purging. The reaction mixture was heated at 100° C. for 1 hour, cooled, then poured into water (50 mL) and extracted with dichloromethane. The extract was dried over MgSO$_4$, then filtered and evaporated. The residue was separated by column chromatography, eluting with 1:1 dichloromethane:hexane, then 1:2 ethyl acetate:hexane to afford N-(5-fluoro-2-nitrophenyl)-N-[4-(trifluoromethyl)phenyl]pyrazine-2,6-diamine (427.0 mg, 59%). MS (ES+): m/e 394.0 (100).

Step 3. A pressure reaction vessel charged with the obtained intermediate (427.0 mg), Pd/C (10%, wet, 43.0 mg) and 1:1 ethyl acetate:methanol (5 mL) was shaken while degassing with three cycles of vacuum pumping and N$_2$ purging. The vessel was charged with hydrogen (40 psi) and shaken for 2 hours. The charcoal was filtered off and the solvent was evaporated to provide N-(2-amino-5-fluorophenyl)-N-[4-(trifluoromethyl)phenyl]pyrazine-2,6-diamine used in the next step without further purification. MS (ES+): m/e 364.1 (100), 365.1 (20).

Step 4. A mixture of the obtained intermediate (177.0 mg, 0.49 mmol), triethyl orthoacetate (237.0 mg, 1.46 mmol), p-toluenesulfonic acid (5.0 mg, 0.025 mmol) and ethanol (2.0 mL) was heated at reflux for 2 hours. The reaction mixture was cooled and partitioned between dichloromethane (20 mL) and saturated NaHCO$_3$ solution (10 mL). The organic phase was washed with brine (10 mL), dried over MgSO$_4$, then filtered and evaporated. The product was obtained as an oil and was triturated with ethyl ether to afford the title compound (107.0 mg, 56%). m.p. 243-245° C.; $^1$H NMR (500 MHz, DMSO-d$_6$) δ 10.71 (s, 1H), 8.59 (s, 1H), 8.42 (s, 1H), 7.90 (d, J=8.51 Hz, 2H), 7.83 (dd, J=4.73, 8.83 Hz, 1H), 7.59-7.68 (m, 3H), 7.35 (d, J=2.21 Hz, 1H), 2.77 (s, 3H); MS (ES+): m/e 388.1 (100), 389.1 (30)

Additional compounds of Formula (I) or a form thereof described herein may be prepared according to the procedure of Example 104 by substituting the appropriate starting materials, reagents and reaction conditions:

| Cpd | Name and Data |
| --- | --- |
| 204 | 6-(5-fluoro-2-methyl-1H-benzimidazol-1-yl)-N-[4-(trifluoromethyl)phenyl]pyrazin-2-amine<br>° C. $^1$H NMR (500 MHz, MeOD-d$_4$) δ 8.41 (s, 1H), 8.31 (s, 1H), 7.89 (d, J = 8.51 Hz, 2H), 7.61 (d, J = 8.51 Hz, 2H), 7.54 (dd, J = 4.57, 8.98 Hz, 1H), 7.39 (dd, J = 2.52, 9.14 Hz, 1H), 7.12 (d, J = 2.52 Hz, 1H), 2.71 (s, 3H); m.p. 272-275° C.; MS m/z 388.0 (ESI) [M + H]$^+$ |
| 205 | N-[4-(difluoromethoxy)phenyl]-6-(5-fluoro-2-methyl-1H-benzimidazol-1-yl)pyrazin-2-amine<br>$^1$H NMR (500 MHz, DMSO-d$_6$) δ 10.01 (s, 1H), 8.34 (s, 1H), 8.26 (s, 1H), 7.68 (d, J = 9.14 Hz, 2H), 7.51 (dd, J = 4.89, 8.98 Hz, 1H), 7.47 (dd, J = 2.36, 9.62 Hz, 1H), 7.10-7.17 (m, 3H), 6.97-7.26 (t, J = 72.50 Hz, 1H), 2.61 (s, 3H); m.p. 239-241° C.; MS m/z 386.0 (ESI) [M + H]$^+$ |
| 206 | 6-(5-fluoro-2-methyl-1H-benzimidazol-1-yl)-N-[4-(trifluoromethoxy)phenyl]pyrazin-2-amine<br>$^1$H NMR (500 MHz, DMSO-d$_6$) δ 10.14 (s, 1H), 8.37 (s, 1H), 8.30 (s, 1H), 7.75 (d, J = 8.51 Hz, 2H), 7.51 (dd, J = 4.57, 8.99 Hz, 1H), 7.47 (dd, J = 2.36, 9.62 Hz, 1H), 7.31 (d, J = 8.51 Hz, 2H), 7.11 (d, J = 1.89 Hz, 1H), 2.62 (s, 3H); m.p. 248-250° C.; MS m/z 404.1 (ESI) [M + H]$^+$ |
| 227 | 6-(2-cyclopropyl-5-fluoro-1H-benzimidazol-1-yl)-N-[4-(difluoromethoxy)phenyl]pyrazin-2-amine<br>$^1$H NMR (500 MHz, Acetone-d$_6$) δ 9.24 (s, 1H), 8.37 (s, 1H), 8.32 (s, 1H), 7.82 (d, J = 8.83 Hz, 2H), 7.49-7.58 (m, 1H), 7.29-7.35 (m, 1H), 7.14 (d, J = 8.83 Hz, 2H), 6.99-7.07 (m, 1H), 2.25-2.38 (m, 1H), 2.23-2.34 (m, 1H), 1.32 (s, 2H), 1.29-1.37 (m, 2H), 1.08-1.17 (m, 2H); m.p. 188-190° C.; MS m/z 412.0 (ESI) [M + H]$^+$ |
| 229 | N-[4-(difluoromethoxy)phenyl]-6-(6-fluoro-2-methyl-1H-benzimidazol-1-yl)pyrazin-2-amine<br>$^1$H NMR (500 MHz, DMSO-d$_6$) δ 10.02 (s, 1H), 8.35 (s, 1H), 8.28 |

| Cpd | Name and Data |
|---|---|
| | (s, 1H), 7.70 (d, J = 8.83 Hz, 2H), 7.68 (dd, J = 4.73, 8.83 Hz, 1H), 7.35 (dd, J = 2.52, 9.46 Hz, 1H), 7.10-7.15 (m, 3H), 6.98-7.28 (t, J = 75.00 Hz, 1H), 2.61 (s, 3H); m.p. 200-202° C.; MS m/z 386.1 (ESI) [M + H]⁺ |
| 230 | 6-(6-fluoro-2-methyl-1H-benzimidazol-1-yl)-N-[4-(trifluoromethoxy)phenyl]pyrazin-2-amine<br>¹H NMR (500 MHz, DMSO-d₆) δ 10.13 (s, 1H), 8.37 (s, 1H), 8.30 (s, 1H), 7.75 (d, J = 8.83 Hz, 2H), 7.65 (dd, J = 4.73, 8.83 Hz, 1H), 7.35 (dd, J = 2.52, 9.46 Hz, 1H), 7.30 (d, J = 8.51 Hz, 2H), 7.07-7.16 (m, 1H), 2.60 (s, 3H); m.p. 215-217° C.; MS m/z 404.1 (ESI) [M + H]⁺ |
| 259 | 6-(2-ethyl-6-fluoro-1H-benzimidazol-1-yl)-N-[4-(trifluoromethyl)phenyl]pyrazin-2-amine<br>¹H NMR (500 MHz, DMSO-d₆) δ 10.37 (s, 1H), 8.44 (s, 1H), 8.36 (s, 1H), 7.85 (d, J = 8.51 Hz, 2H), 7.70 (dd, J = 4.73, 8.83 Hz, 1H), 7.65 (d, J = 8.51 Hz, 2H), 7.33 (dd, J = 2.52, 9.14 Hz, 1H), 7.13 (d, J = 1.58 Hz, 1H), 2.95 (q, J = 7.57 Hz, 2H), 1.27 (t, J = 7.41 Hz, 3H); m.p. 267-269° C. |
| 260 | N-[4-(difluoromethoxy)phenyl]-6-(2-ethyl-6-fluoro-1H-benzimidazol-1-yl)pyrazin-2-amine<br>¹H NMR (500 MHz, DMSO-d₆) δ 10.02 (s, 1H), 8.35 (s, 1H), 8.25 (s, 1H), 7.62-7.74 (m, 3H), 7.31 (dd, J = 2.36, 9.30 Hz, 1H), 7.07-7.21 (m, 3H), 6.97-7.26 (t, J = 72.5 Hz, 1H), 2.93 (q, J = 7.46 Hz, 2H), 1.26 (t, J = 7.57 Hz, 3H); m.p. 205-207° C.; |
| 320 | N-[4-(difluoromethoxy)-3-fluorophenyl]-6-(6-fluoro-2-methyl-1H-benzimidazol-1-yl)pyrazin-2-amine<br>¹H NMR (500 MHz, DMSO-d₆) δ 10.24 (s, 1H), 8.36 (d, J = 11.03 Hz, 2H), 7.84 (dd, J = 2.52, 13.24 Hz, 1H), 7.65 (dd, J = 5.04, 8.83 Hz, 1H), 7.35-7.43 (m, 2H), 7.26-7.34 (m, 1H), 7.08-7.16 (m, 1H), 6.98-7.27 (t, J = 72.50 Hz, 1H), 2.61 (s, 3H); m.p. 230-231° C.; MS m/z 404.4 (ESI) [M + H]⁺ |
| 362 | 6-(2-cyclopropyl-6-fluoro-1H-benzimidazol-1-yl)-N-[4-(trifluoromethyl)phenyl]pyrazin-2-amine<br>¹H NMR (500 MHz, DMSO-d₆) δ 10.38 (s, 1H), 8.44 (s, 1H), 8.41 (s, 1H), 7.91 (d, J = 8.83 Hz, 2H), 7.65 (d, J = 8.51 Hz, 2H), 7.61 (dd, J = 5.04, 8.83 Hz, 1H), 7.34 (dd, J = 2.36, 9.30 Hz, 1H), 7.10 (dt, J = 2.36, 9.22 Hz, 1H), 2.15-2.26 (m, 1H), 1.14-1.21 (m, 2H), 1.02-1.12 (m, 2H); m.p. 263-265° C.; MS m/z 414.3 (ESI) [M + H]⁺ |
| 410 | 2-(2-cyclopropyl-6-fluoro-1H-benzimidazol-1-yl)-6-{[4-(trifluoromethyl)phenyl]amino}pyridine-4-carbonitrile<br>¹H NMR (500 MHz, DMSO-d₆) δ 10.22-10.35 (m, 1H), 7.88 (d, J = 8.51 Hz, 2H), 7.64 (d, J = 8.51 Hz, 2H), 7.59 (m, 2H), 7.38 (s, 2H), 7.06-7.13 (m, 1H), 2.20-2.31 (m, 1H), 1.13-1.20 (m, 2H), 0.97-1.10 (m, 2H); m.p. 291-293° C.; MS m/z 438.1 (ESI) [M + H]⁺ |
| 501 | 6-(5,6-difluoro-2-methyl-1H-benzimidazol-1-yl)-N-[4-(difluoromethyl)phenyl]pyrazin-2-amine<br>¹H NMR (500 MHz, DMSO-d₆) δ 10.22 (s, 1H), 8.41 (s, 1H), 8.34 (s, 1H), 7.79 (d, J = 8.51 Hz, 2H), 7.72-7.77 (m, 1H), 7.64-7.68 (m, 1H), 7.51 (d, J = 8.51 Hz, 2H), 6.83-7.05 (t, J = 55.00 Hz, 1H), 2.62 (s, 3H); m.p. 209-211° C.; MS m/z 388.4 (ESI) [M + H]⁺ |
| 502 | 4-{[6-(5,6-difluoro-2-methyl-1H-benzimidazol-1-yl)pyrazin-2-yl]amino}benzaldehyde<br>¹H NMR (500 MHz, DMSO-d₆) δ 10.49 (s, 1H), 9.82 (s, 1H), 8.46 (s, 1H), 8.42 (s, 1H), 7.86 (d, J = 8.83 Hz, 2H), 7.85 (d, J = 8.83 Hz, 2H), 7.72-7.79 (m, 1H), 7.65-7.71 (m, 1H), 2.63 (s, 3H); m.p. 202-204° C.; MS m/z 366.3 (ESI) [M + H]⁺ |
| 552 | 6-(6-fluoro-2-methyl-1H-benzimidazol-1-yl)-N-(4-methoxyphenyl)pyrazin-2-amine<br>¹H NMR (500 MHz, DMSO-d₆) δ 9.75 (s, 1H), 8.27 (s, 1H), 8.17 (s, 1H), 7.64 (dd, J = 8.67, 4.89 Hz, 1H), 7.55 (d, J = 8.83 Hz, 2H), 7.34 (dd, J = 9.30, 2.36 Hz, 1H), 7.11 (d, J = 1.58 Hz, 1H), 6.89 (d, J = 9.14 Hz, 2H), 3.71 (s, 3H), 2.59 (s, 3H); m.p. 184-186° C.; MS m/z 350.1 (ESI) [M + H]⁺ |
| 553 | 6-(6-fluoro-2-methyl-1H-benzimidazol-1-yl)-N-(4-methoxyphenyl)pyrazin-2-amine<br>¹H NMR (500 MHz, DMSO-d₆) δ 9.84 (s, 1H), 8.32 (s, 1H), 8.22 (s, 1H), 7.65 (dd, J = 8.83, 5.04 Hz, 1H), 7.48-7.57 (m, 1H), 7.36 (dd, J = 9.14, 2.52 Hz, 1H), 7.05-7.19 (m, 3H), 2.61 (s, 3H), 2.24 (s, 3H); m.p. 200-202° C.; MS m/z 334.1 (ESI) [M + H]⁺ |
| 554 | N-(4-chlorophenyl)-6-(6-fluoro-2-methyl-1H-benzimidazol-1-yl)pyrazin-2-amine<br>¹H NMR (500 MHz, Acetone-d₆) δ 9.95 (s, 1H), 8.42 (s, 1H), 8.26 (s, 1H), 7.80 (d, J = 8.55 Hz, 2H), 7.64 (dd, J = 8.83, 5.04 Hz, 1H), 7.28-7.38 (m, 3H), 6.99-7.12 (m, 1H), 2.65 (s, 3H); m.p. 243-245° C.; MS m/z 354.1 (ESI) [M + H]⁺ |
| 555 | 4-{[6-(6-fluoro-2-methyl-1H-benzimidazol-1-yl)pyrazin-2-yl]amino}benzonitrile<br>¹H NMR (500 MHz, DMSO-d₆) δ 10.46 (s, 1H), 8.44 (s, 1H), 8.41 (s, 1H), 7.83 (d, J = 8.50 Hz, 2H), 7.73 (d, J = 8.50 Hz, 2H), 7.65 (dd, J = 4.89, 8.67 Hz, 1H), 7.36 (dd, J = 9.14, 2.52 Hz, 1H), 7.08-7.16 (m, 1H), 2.60 (s, 3H); m.p. 300-303° C.; MS m/z 345.1 (ESI) [M + H]⁺ |
| 556 | methyl 4-{[6-(6-fluoro-2-methyl-1H-benzimidazol-1-yl)pyrazin-2-yl]amino}benzoate<br>¹H NMR (500 MHz, DMSO-d₆) δ 10.37 (s, 1H), 8.43 (s, 1H), 8.38 (s, 1H), 7.89 (d, J = 8.50 Hz, 2H), 7.80 (d, J = 8.50 Hz, 2H), 7.66 (dd, J = 8.83, 5.04 Hz, 1H), 7.39 (dd, J = 9.30, 2.36 Hz, 1H), 7.08-7.17 (m, 1H), 3.79 (s, 3H), 2.63 (s, 3H); m.p. 198-200° C.; MS m/z 378.2 (ESI) [M + H]⁺ |
| 558 | N-[6-(6-fluoro-2-methyl-1H-benzimidazol-1-yl)pyrazin-2-yl]benzene-1,4-diamine<br>¹H NMR (500 MHz, DMSO-d₆) δ 9.44 (s, 1H), 8.18 (s, 1H), 8.08 (s, 1H), 7.62 (dd, J = 8.83, 4.73 Hz, 1H), 7.34 (dd, J = 9.14, 2.52 Hz, 1H), 7.24 (d, J = 8.50 Hz, 2H), 6.99-7.14 (m, 1H), 6.53 (d, J = 8.50 Hz, 2H), 4.89 (s, 2H), 2.59 (s, 3H); m.p. 189-191° C.; MS m/z 335.1 (ESI) [M + H]⁺ |
| 559 | 6-(6-fluoro-2-methyl-1H-benzimidazol-1-yl)-N-(3-methoxyphenyl)pyrazin-2-amine<br>¹H NMR (500 MHz, DMSO-d₆) δ 9.95 (s, 1H), 8.35 (s, 1H), 8.27 (s, 1H), 7.65 (dd, J = 4.89, 8.67 Hz, 1H), 7.36-7.44 (m, 2H), 7.04-7.25 (m, 3H), 6.57 (d, J = 7.25 Hz, 1H), 3.63 (s, 3H), 2.61 (s, 3H); m.p. 173-174° C.; MS m/z 350.1 (ESI) [M + H]⁺ |
| 560 | 6-(6-fluoro-2-methyl-1H-benzimidazol-1-yl)-N-(3-methylphenyl)pyrazin-2-amine<br>¹H NMR (500 MHz, Acetone-d₆) δ 9.22-9.48 (s, 1H), 8.36 (s, 1H), 8.22 (s, 1H), 7.59-7.66 (m, 2H), 7.44-7.53 (m, 1H), 7.33-7.42 (m, 1H), 7.14-7.24 (m, 1H), 7.03-7.12 (m, 1H), 6.80-6.95 (m, 1H), 2.83-2.97 (m, 3H), 2.67 (s, 3H); m.p. 173-174° C.; MS m/z 334.1 (ESI) [M + H]⁺ |
| 620 | 6-(2-ethyl-6-fluoro-1H-benzimidazol-1-yl)-N-phenylpyrazin-2-amine<br>¹H NMR (500 MHz, DMSO-d₆) δ 9.75 (br. s., 1H), 8.28 (s, 1H), 8.15 (s, 1H), 7.67 (dd, J = 4.73, 8.20 Hz, 1H), 7.53 (d, J = 8.51 Hz, 2H), 7.29 (d, J = 8.20 Hz, 1H), 7.10 (t, J = 8.20 Hz, 1H), 6.88 (d, J = 8.51 Hz, 2H), 6.41-6.70 (m, 1H), 2.93 (q, J = 7.15 Hz, 2H), 1.26 (t, J = 7.25 Hz, 3H); MS m/z 334.1 (ESI) [M + H]⁺ |
| 621 | 6-(2-ethyl-6-fluoro-1H-benzimidazol-1-yl)-N-(4-methoxyphenyl)pyrazin-2-amine<br>¹H NMR (500 MHz, Acetone-d₆) δ 9.74 (s, 1H), 8.39 (d, J = 0.63 Hz, 1H), 8.16 (s, 1H), 7.66 (dd, J = 4.89, 8.67 Hz, 1H), 7.62 (d, J = 8.51 Hz, 2H), 7.28 (dd, J = 2.36, 9.30 Hz, 1H), 7.10 (d, J = 8.51 Hz, 2H), 7.04-7.08 (m, 1H), 3.00 (q, J = 7.57 Hz, 2H), 2.25 9 (s, 3H), 2.05 (td, J = 2.21, 4.41 Hz, 3H); m.p. 218-220° C.; MS m/z 363.9 (ESI) [M + H]⁺ |
| 622 | 6-(2-ethyl-6-fluoro-1H-benzimidazol-1-yl)-N-(4-methylphenyl)pyrazin-2-amine<br>¹H NMR (500 MHz, Acetone-d₆) δ 9.50 (br. s., 1H), 8.32 (s, 1H), 8.12 (s, 1H), 7.57-7.69 (m, 3H), 7.27 (dd, J = 2.36, 9.30 Hz, 1H), 7.06 (d, J = 1.58 Hz, 1H), 6.88 (d, J = 8.83 Hz, 2H), 3.74 (s, 3H), 2.95-3.05 (m, 2H), 1.32 (t, J = 7.41 Hz, 2H); m.p. 223-226° C. |
| 623 | N-(4-chlorophenyl)-6-(2-ethyl-6-fluoro-1H-benzimidazol-1-yl)pyrazin-2-amine<br>¹H NMR (500 MHz, Acetone-d₆) δ 9.99 (br. s., 1H), 8.42 (s, 1H), 8.23 (s, 1H), 7.78 (d, J = 9.77 Hz, 2H), 7.65 (dd, J = 4.89, 8.67 Hz, 1H), 7.29-7.32 (d, J = 9.77 Hz, 2H), 7.27 (dd, J = 2.52, 9.14 Hz, |

| Cpd | Name and Data |
|---|---|
| | 1H), 7.07 (ddd, J = 2.52, 8.83, 9.77 Hz, 1H), 2.99 (q, J = 7.57 Hz, 2H), 1.32 (t, J = 7.41 Hz, 3H); m.p. 252-255° C.; MS m/z 368.5 (ESI) [M + H]+ |
| 624 | 6-(2-ethyl-6-fluoro-1H-benzimidazol-1-yl)-N-(3-methoxyphenyl)pyrazin-2-amine<br>1H NMR (500 MHz, Acetone-d6) δ 9.73 (s, 1H), 8.42 (s, 1H), 8.23 (s, 1H), 7.67 (dd, J = 5.04, 8.83 Hz, 1H), 7.48 (t, J = 2.05 Hz, 1H), 7.33 (dd, J = 2.52, 9.14 Hz, 1H), 7.24-7.30 (m, 1H), 7.18-7.24 (m, 1H), 7.05-7.13 (m, 1H), 6.57-6.63 (m, 1H), 3.70 (s, 3H), 3.04-3.08 (m, 2H), 1.35 (t, J = 7.41 Hz, 3H; MS (ES+): m/e 363.8 (50), 365.2 (100); m.p. 179-181° C. |
| 625 | N-(3-chlorophenyl)-6-(2-ethyl-6-fluoro-1H-benzimidazol-1-yl)pyrazin-2-amine<br>1H NMR (500 MHz, Acetone-d6) δ 9.88 (br. s., 1H), 8.42 (s, 1H), 8.28 (s, 1H), 8.00 (t, J = 1.89 Hz, 1H), 7.66 (dd, J = 4.73, 8.83 Hz, 1H), 7.59 (dd, J = 1.26, 8.20 Hz, 1H), 7.27-7.36 (m, 2H), 7.05-7.12 (m, 1H), 7.01 (dd, J = 1.26, 7.88 Hz, 1H), 3.04 (q, J = 7.57 Hz, 2H), 1.36 (t, J = 7.41 Hz, 3H); m.p. 192-195° C.; MS m/z 367.8 (ESI) [M + H]+ |
| 626 | 6-(2-ethyl-6-fluoro-1H-benzimidazol-1-yl)-N-(3-fluorophenyl)pyrazin-2-amine<br>1H NMR (500 MHz, Acetone-d6) δ 10.13 (s, 1H), 8.44 (s, 1H), 8.28 (s, 1H), 7.73 (td, J = 2.21, 11.98 Hz, 1H), 7.67 (dd, J = 4.89, 8.67 Hz, 1H), 7.44 (dd, J = 1.26, 8.20 Hz, 1H), 7.28-7.36 (m, 2H), 7.04-7.14 (m, 1H), 6.72-6.80 (m, 1H), 3.01 (q, J = 7.36 Hz, 2H), 1.33 (t, J = 7.57 Hz, 3H); m.p. 228-230° C.; MS m/z 351.7 (ESI) [M + H]+ |
| 654 | N-(4-chloro-3-fluorophenyl)-6-(6-fluoro-2-methyl-1H-benzimidazol-1-yl)pyrazin-2-amine<br>1H NMR (500 MHz, DMSO-d6) δ 10.30 (s, 1H), 8.38 (d, J = 2.52 Hz, 2H), 7.88 (dd, J = 2.21, 12.30 Hz, 1H), 7.66 (dd, J = 5.04, 8.83 Hz, 1H), 7.50 (t, J = 8.67 Hz, 1H), 7.35-7.44 (m, 2H), 7.07-7.17 (m, 1H), 2.62 (s, 3H); MS m/z 372.2 (ESI) [M + H]+ |

Example 105

6-(2-cyclopropyl-4,6-difluoro-1H-benzimidazol-1-yl)-N-[4-(trifluoromethyl)phenyl]pyrazin-2-amine (Cpd 461)

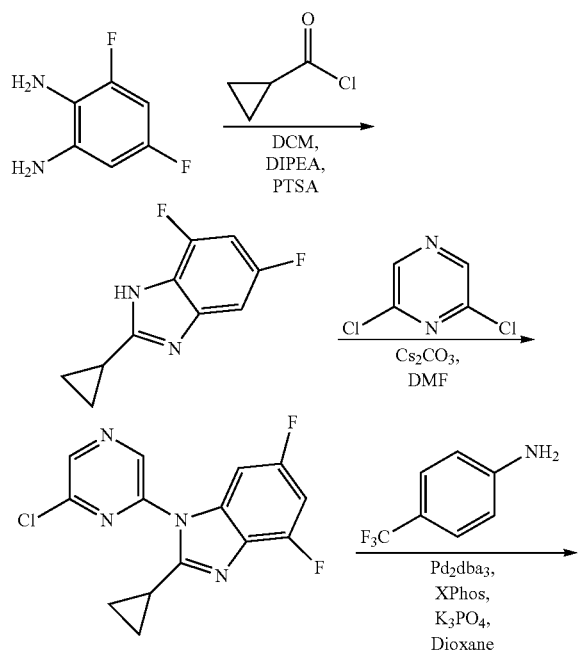

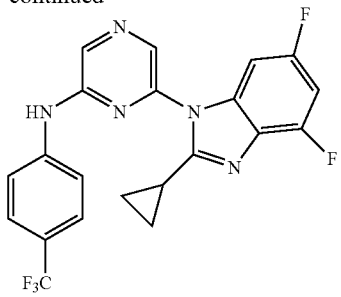

Step 1. To a mixture of 3,5-difluorobenzene-1,2-diamine (1.0 g, 6.94 mmol) in dichloromethane (15 mL) was added cyclopropanecarbonyl chloride (726 mg, 6.94 mmol) dropwise at 0° C., then DIPEA (2.3 mL, 13.88 mmol). The reaction mixture was stirred at room temperature for 2 hours and the solvent was evaporated. To the residue in a microwave reaction vial was added acetonitrile (4 mL), then p-toluenesulfonic acid (cat. 10%). The reaction mixture was heated at 180° C. for 30 minutes in a microwave oven, then partitioned between 10% MeOH:ethyl acetate and saturated NaHCO3. The aqueous phase was extracted with ethyl acetate (2×) and the combined organic extract was washed with brine, dried over MgSO4, then filtered and evaporated. The residue was separated by column chromatography, eluting with 0-10% dichloromethane:hexane to provide 2-cyclopropyl-5,7-difluoro-1H-benzo[d]imidazole (630.0 mg, 47%) as a brown solid.

Step 2. A mixture of the obtained intermediate (106.0 mg, 0.55 mmol), 2,6-dichloropyrazine (163.0 mg, 1.09 mmol), cesium carbonate (356.0 mg, 1.10 mmol) and DMF (1 mL) was heated at 80° C. for 6 hours. The reaction mixture was cooled, then partitioned between ethyl acetate and water and the organic phase was sequentially washed with water and brine. The product was dried over MgSO4, filtered and evaporated, then separated by column chromatography, eluting with 20% ethyl acetate:hexane to afford 1-(6-chloropyrazin-2-yl)-2-cyclopropyl-4,6-difluoro-1H-benzo[d]imidazole (55.0 mg, 37%).

Step 3. The obtained intermediate was carried forward (using the procedure described in Example 100 and appropriate starting materials, reagents and reaction conditions) to provide the title compound. m.p. 247-249° C.; 1H NMR (500 MHz, DMSO-d6) δ 10.41 (s, 1H), 8.46 (s, 1H), 8.41 (s, 1H), 7.90 (d, J=8.83 Hz, 2H), 7.65 (d, J=8.83 Hz, 2H), 7.21-7.29 (m, 1H), 7.06-7.20 (m, 1H), 2.15-2.26 (m, 1H), 1.20 (m, 2H), 1.04-1.12 (m, 2H); MS (ES+): m/e 432.3 (100), 433.3 (20).

Additional compounds of Formula (I) or a form thereof described herein may be prepared according to the procedure of Example 105 by substituting the appropriate starting materials, reagents and reaction conditions:

| Cpd | Name and Data |
|---|---|
| 462 | 6-(2-cyclopropyl-4,6-difluoro-1H-benzimidazol-1-yl)-N-[4-(difluoromethoxy)phenyl]pyrazin-2-amine<br>1H NMR (500 MHz, DMSO-d6) δ 10.06 (s, 1H), 8.38 (s, 1H), 8.30 (s, 1H), 7.72 (d, J = 9.77 Hz, 2H), 6.98-7.27 (t, J = 72.50 Hz, 1H), 7.22 (dd, J = 2.21, 8.83 Hz, 1H), 7.09-7.18 (m, 3H), 2.12-2.29 (m, 1H), 1.16-1.21 (m, 2H), 1.03-1.12 (m, 2H); m.p. 202-203° C.; MS m/z 430.4 (ESI) [M + H]+ |
| 463 | 6-(2-cyclopropyl-4,6-difluoro-1H-benzimidazol-1-yl)-N-[4-(trifluoromethoxy)phenyl]pyrazin-2-amine |

| Cpd | Name and Data |
|---|---|
|  | ¹H NMR (500 MHz, DMSO-d₆) δ 10.39 (s, 1H), 8.46 (s, 1H), 8.41 (s, 1H), 7.89 (d, J = 8.51 Hz, 2H), 7.65 (d, J = 8.51 Hz, 2H), 7.21-7.26 (m, 1H), 2.15-2.26 (m, 1H), 7.10-7.19 (m, 1H), 2.15-2.26 (m, 1H), 1.16-1.22 (m, 2H), 1.03-1.13 (m, 2H); m.p. 218-220° C.; MS m/z 448.4 (ESI) [M + H]⁺ |
| 464 | 6-(2-cyclopropyl-4,6-difluoro-1H-benzimidazol-1-yl)-N-[6-(trifluoromethyl)pyridin-3-yl]pyrazin-2-amine<br>¹H NMR (500 MHz, DMSO-d₆) δ 10.64 (s, 1H), 8.94-9.01 (m, 1H),<br>8.51 (s, 1H), 8.48 (s, 1H), 8.38-8.42 (m, 1H), 7.84 (s, 1H), 7.24-7.30 (m, 1H), 7.10-7.20 (m, 1H), 2.14-2.24 (m, 1H), 1.17-1.22 (m, 2H), 1.03-1.12 (m, 2H); m.p. 267-270° C.; MS m/z 433.2 (ESI) [M + H]⁺ |
| 474 | 2-(2-cyclopropyl-4,6-difluoro-1H-benzimidazol-1-yl)-6-{[4-(trifluoromethyl)phenyl]amino}pyridine-4-carbonitrile<br>¹H NMR (500 MHz, DMSO-d₆) δ 10.30 (s, 1H), 7.86 (d, J = 8.51 Hz, 2H), 7.63 (d, J = 8.51 Hz, 2H), 7.58-7.60 (m, 1H), 7.39 (d, J = 0.63 Hz, 1H), 7.29 (dd, J = 2.21, 8.83 Hz, 1H), 7.14 (dt, J = 2.21, 10.40 Hz, 1H), 2.19-2.27 (m, 1H), 1.16-1.22 (m, 2H), 1.02-1.09 (m, 2H); m.p. 233-235° C.; MS m/z 456.2 (ESI) [M + H]⁺ |
| 475 | 2-(2-cyclopropyl-4,6-difluoro-1H-benzimidazol-1-yl)-6-{[4-(difluoromethoxy)phenyl]amino}pyridine-4-carbonitrile<br>¹H NMR (500 MHz, DMSO-d₆) δ 9.97 (s, 1H), 7.67 (dd, J = 1.00, 9.14 Hz, 2H), 7.47 (d, J = 0.95 Hz, 1H), 7.24-7.32 (m, 2H), 7.08-7.15 (m, 3H), 6.98-7.28 (t, J = 75.00 Hz, 1H), 2.18-2.29 (m, 1H), 1.15-1.21 (m, 2H), 1.03-1.10 (m, 2H); m.p. 168-170° C.; MS m/z 454.2 (ESI) [M + H]⁺ |
| 476 | 2-(2-cyclopropyl-4,6-difluoro-1H-benzimidazol-1-yl)-6-{[4-(difluoromethoxy)-3-fluorophenyl]amino}pyridine-4-carbonitrile<br>¹H NMR (500 MHz, DMSO-d₆) δ 9.76 (s, 1H), 9.00 (d, J = 2.84 Hz,<br>1H), 8.74 (dd, J = 2.84, 8.83 Hz, 1H), 7.96 (d, J = 0.63 Hz, 1H), 7.86-8.15 (t, J = 72.50 Hz, 1H), 7.82 (d, J = 0.63 Hz, 1H), 7.65-7.72<br>(m, 1H), 7.46 (d, J = 8.83 Hz, 1H), 7.39 (dt, J = 2.21, 10.40 Hz, 1H), 2.72-2.81 (m, 1H), 1.69-1.76 (m, 2H), 1.52-1.59 (m, 2H); m.p. 183-184° C.; MS m/z 472.2 (ESI) [M + H]⁺ |
| 478 | 2-(2-cyclopropyl-4,6-difluoro-1H-benzimidazol-1-yl)-6-{[6-(difluoromethoxy)pyridin-3-yl]amino}pyridine-4-carbonitrile<br>¹H NMR (500 MHz, DMSO-d₆) δ 9.76 (s, 1H), 9.00 (d, J = 2.84 Hz,<br>1H), 8.74 (dd, J = 2.84, 8.83 Hz, 1H), 7.86-8.15 (t, J = 72.50 Hz, 1H), 7.95 (d, J = 0.63 Hz, 1H), 7.82 (d, J = 0.63 Hz, 1H), 7.66-7.72<br>(m, 1H), 7.46 (d, J = 8.83 Hz, 1H), 7.38 (dt, J = 2.21, 10.40 Hz, 1H), 2.71-2.82 (m, 1H), 2.47-2.53 (m, 4H); m.p. 207-209° C.; MS m/z 455.4 (ESI) [M + H]⁺ |
| 481 | 6-[2-(difluoromethyl)-1H-benzimidazol-1-yl]-N-[4-(trifluoromethyl)phenyl]pyrazin-2-amine<br>m.p. 229-231° C.; MS m/z 406.3 (ESI) [M + H]⁺ |
| 482 | N-[4-(difluoromethoxy)phenyl]-6-[2-(difluoromethyl)-1H-benzimidazol-1-yl]pyrazin-2-amine<br>¹H NMR (500 MHz, DMSO-d₆) δ 10.10 (s, 1H), 8.40 (s, 1H), 8.30 (s, 1H), 7.89-7.93 (m, 1H), 7.69 (d, J = 9.14 Hz, 2H), 7.64-7.67 (m,<br>1H), 7.34-7.55 (t, J = 52.50 Hz, 1H), 7.42-7.50 (m, 2H), 7.12 (d, J =<br>9.14 Hz, 2H), 6.98-7.28 (t, J = 75.00 Hz, 1H); m.p. 213-216° C.; MS m/z 404.3 (ESI) [M + H]⁺ |
| 483 | N-[4-(difluoromethoxy)-3-fluorophenyl]-6-[2-(difluoromethyl)-1H-benzimidazol-1-yl]pyrazin-2-amine<br>¹H NMR (500 MHz, DMSO-d₆) δ 10.31 (s, 1H), 8.43 (s, 1H), 8.38 (s, 1H), 7.90-7.94 (m, 1H), 7.84-7.90 (m, 1H), 7.65-7.70 (m, 1H), 7.46 (d, J = 11.66 Hz, 2H), 7.34-7.55 (t, J = 52.50 Hz, 1H), 7.28-7.37 (m, 2H), 6.99-7.28 (t, J = 75.00 Hz, 1H); m.p. 220-222° C.; MS m/z 422.3 (ESI) [M + H]⁺ |
| 484 | 2-[2-(difluoromethyl)-1H-benzimidazol-1-yl]-6-{[4-(trifluoromethyl)phenyl]amino}pyridine-4-carbonitrile<br>¹H NMR (500 MHz, DMSO-d₆) δ 10.32 (s, 1H), 10.30 (s, 1H), 7.91<br>(dd, J = 1.00, 6.94 Hz, 1H), 7.82 (dd, J = 1.00, 8.20 Hz, 2H), 7.71 (dd, J = 1.00, 7.25 Hz, 1H), 7.60-7.66 (m, 3H), 7.41-7.52 (m, 3H), 7.36-7.57 (t, J = 52.50 Hz, 1H); m.p. 225-227° C.; MS m/z 430.4 (ESI) [M + H]⁺ |
| 485 | 6-(2-cyclobutyl-6-fluoro-1H-benzimidazol-1-yl)-N-[4-(trifluoromethyl)phenyl]pyrazin-2-amine<br>¹H NMR (500 MHz, DMSO-d₆) δ 10.37 (s, 1H), 8.44 (s, 1H), 8.26 (s, 1H), 7.85 (d, J = 8.51 Hz, 2H), 7.72 (d, J = 4.89, 8.67 Hz, 1H), |
|  | 7.64 (d, J = 8.83 Hz, 2H), 7.31 (dd, J = 2.36, 9.30 Hz, 1H), 7.07-7.18 (m, 1H), 3.85 (t, J = 8.35 Hz, 1H), 2.42 (dt, J = 2.21, 9.14 Hz, 2H), 2.13-2.26 (m, 2H), 1.79-2.01 (m, 2H); m.p. 289-291° C.; MS m/z 428.4 (ESI) [M + H]⁺ |
| 486 | 6-[2-(difluoromethyl)-6-fluoro-1H-benzimidazol-1-yl]-N-[4-(trifluoromethyl)phenyl]pyrazin-2-amine<br>¹H NMR (500 MHz, DMSO-d₆) δ 10.42 (s, 1H), 8.48 (s, 1H), 8.40 (s, 1H), 7.94 (dd, J = 5.04, 8.83 Hz, 1H), 7.85 (d, J = 8.83 Hz, 2H),<br>7.63 (d, J = 8.51 Hz, 2H), 7.51-7.58 (m, 1H), 7.33-7.53 (t, J = 47.5 Hz, 1H), 7.32 (dt, J = 2.52, 9.30 Hz, 1H); m.p. 197-199° C.; MS m/z 424.4 (ESI) [M + H]⁺ |

Example 106

6-(2-ethyl-5-fluoropyrazolo[1,5-a]pyridin-3-yl)-N-[4-(trifluoromethyl)phenyl]pyrazin-2-amine (Cpd 551)

431
-continued

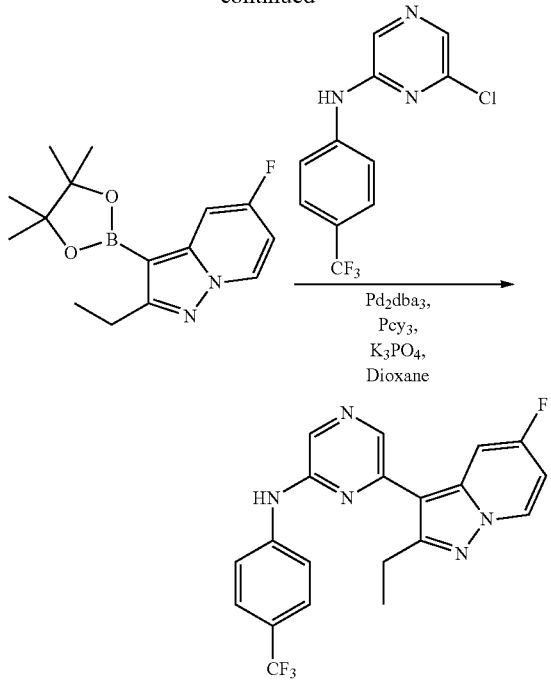

Step 1. A mixture of 2-chloro-4-fluoropyridine (2.0 g, 15.2 mmol), (1.86 g, 33.29 mmol), Bis(acetonitrile)dichloropalladium(II) (196.8 mg, 0.76 mmol), 2-dicyclohexylphosphino-2',4',6'-triisopropylbiphenyl (XPhos, 731.2 mg, 0.15 mmol) and N-methyl-2-pyrrolidone (NMP) (15 mL) was degassed by three cycles of vacuum pumping and $N_2$ purging, then triethylamine (4.3 mL, 30.4 mmol) was added. The mixture was degassed and purged with $N_2$, heated at 50° C. overnight, then cooled, poured into water (100 mL) and extracted with ethyl acetate (150 mL). The residue was dried using $MgSO_4$, filtered and evaporated, then separated by column chromatography, eluting with 0-10% dichloromethane-hexane, to provide 2-(but-1-ynyl)-4-fluoropyridine (1.35 g, 59%) as an oil.

Step 2. To a solution of the obtained intermediate (1.10 g, 7.38 mmol) in dichloromethane (15 mL) was added 2-[(aminooxy)sulfonyl]-1,3,5-trimethylbenzene (1.60 g, 7.44 mmol) portion wise at 0° C. The reaction mixture was stirred at room temperature for 2 days and the solvent was evaporated using an $N_2$ stream. To the crude mixture, carried forward without further purification, was sequentially added DMF (3 mL), then $K_2CO_3$ (825.0 mg, 5.97 mmol) at 0° C. The reaction mixture was stirred at room temperature for 24 hours, then partitioned between ethyl acetate and water. The organic phase was sequentially washed with water and brine, dried over $MgSO_4$, then filtered and evaporated to provide 2-ethyl-5-fluoropyrazolo[1,5-a]pyridine, used in the next step without further purification.

Step 3. A mixture of the obtained intermediate, N-iodosuccinimide (NIS) (1.6 g, 7.10 mmol) and chloroform (10 mL) was stirred at room temperature for 2 hours, then partitioned between ethyl acetate and water. The organic phase was sequentially washed with water and brine, dried over $MgSO_4$, then filtered and evaporated. The residue was separated by silica gel column chromatography, eluting with 1:1 dichloromethane:hexane, then 1% methanol in 1:4 ethyl acetate:dichloromethane to afford 2-ethyl-5-fluoro-3-iodopyrazolo[1,5-a]pyridine (435.0 mg, 46%) as an oil.

Step 4. To a solution of the obtained intermediate (302.0 mg, 1.04 mmol) in THF (5 mL) was added a solution of an isopropylmagnesium chloride:lithium chloride complex (1.3 M in THF, 0.80 mL, 1.04 mmol) at −78° C. dropwise. The reaction mixture was warmed to 0° C. and stirred at 0° C. for 30 minutes, then 2-isopropoxy-4,4,5,5-tetramethyl-1,3,2-dioxaborolane (212.8 mg, 1.14 mmol) at −78° C. was added in one portion. The reaction mixture was stirred at 0° C. for one hour, then partitioned between ethyl acetate and water. The organic phase was washed with brine, dried over $MgSO_4$, then filtered and evaporated. The residue was separated by silica gel column chromatography, eluting with 1:9 ethyl acetate:hexane to afford 2-ethyl-5-fluoro-3-(4,4,5,5-tetramethyl-1,3,2-dioxaborolan-2-yl)pyrazolo[1,5-a]pyridine.

Step 5. A mixture of the obtained intermediate, 6-chloro-N-(4-(trifluoromethyl)phenyl)pyrazin-2-amine (341.2 mg, 1.25 mmol), tris(dibenzylideneacetone)dipalladium(0) (47.6 mg, 5%), tricyclohexylphosphine (26.0 mg, 10%) and a solution of tripotassium phosphate (426.0 mg, 2.0 mmol) in dioxane (2.0 mL) and water (0.3 mL) was degassed and purged with $N_2$. The reaction mixture was heated at 80° C. for 3 hours, cooled and poured into water (100 mL), then extracted with ethyl acetate (150 mL). The extract was dried over $MgSO_4$, then filtered and evaporated. The residue was separated by column chromatography, eluting with 0-40% dichloromethane:hexane, then 50% ethyl acetate:dichloromethane to provide the title compound as a white solid (220.0 mg, 53%). m.p. 129-131° C.; $^1$H NMR (500 MHz, Acetone-$d_6$) δ 9.10 (br. s., 1H), 8.58-8.73 (m, 1H), 8.33 (s, 1H), 8.16 (s, 1H), 7.95 (d, J=8.51 Hz, 2H), 7.85 (dd, J=2.36, 9.93 Hz, 1H), 7.66 (d, J=8.51 Hz, 2H), 6.91 (d, J=2.84 Hz, 1H), 3.15 (q, J=7.57 Hz, 2H), 1.38 (t, J=7.57 Hz, 3H); MS (ES+): m/e 402.2 (100).

Additional compounds of Formula (I) or a form thereof described herein may be prepared according to the procedure of Example 106 by substituting the appropriate starting materials, reagents and reaction conditions:

| Cpd | Name and Data |
| --- | --- |
| 535 | 6-(2-cyclopropyl-5-fluoropyrazolo[1,5-a]pyridin-3-yl)-N-[4-(trifluoromethyl)phenyl]pyrazin-2-amine<br>$^1$H NMR (500 MHz, Acetone-$d_6$) δ 9.11 (br. s., 1H), 8.47-8.66 (m, 2H), 8.16 (s, 1H), 7.98 (d, J = 8.51 Hz, 2H), 7.79-7.90 (m, 1H), 7.65 (d, J = 8.51 Hz, 2H), 6.77-6.98 (m, 1H), 2.35-2.54 (m, 1H), 1.04-1.24 (m, 4H); m.p. 122-125° C.; MS m/z 414.4 (ESI) [M + H]$^+$ |

Example 107

6-(2-cyclopropyl-5-fluoropyrazolo[1,5-a]pyridin-3-yl)-N-[4-(trifluoromethyl)phenyl]pyrazin-2-amine 4-oxide (Cpd 536)

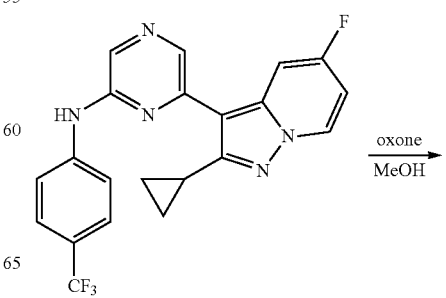

-continued

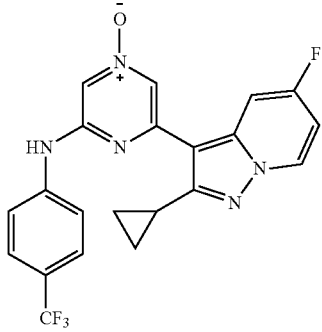

A suspension of oxone (1.17 g, 1.90 mmol) and water (4 mL) was added to a solution of Compound 535 (prepared using the procedure described in Example 106 and appropriate starting materials, reagents and reaction conditions) (80.0 mg, 0.19 mmol) in MeOH (2 mL). The reaction mixture was stirred at room temperature overnight, then partitioned between ethylacetate and water. The organic phase was washed with brine, dried over MgSO$_4$, then filtered and evaporated. The residue was separated by column chromatography, eluting with 0-2% methanol:dichloromethane to provide the title compound as a white solid (15.0 mg, 18%). m.p. 183-186° C.; $^1$H NMR (500 MHz, Acetone-d$_6$) δ 9.00-9.23 (m, 1H), 8.54-8.68 (m, 1H), 8.19 (s, 1H), 7.84-8.02 (m, 3H), 7.77 (s, 1H), 7.69 (d, J=8.51 Hz, 2H), 6.89-6.99 (m, 1H), 2.34-2.43 (m, 1H), 1.05-1.19 (m, 4H); MS (ES+): m/e 430.4 (100).

Example 108

N-[4-(trifluoromethoxy)phenyl]-6-(1,3,5-trimethyl-1H-pyrazol-4-yl)pyrazin-2-amine (Cpd 105)

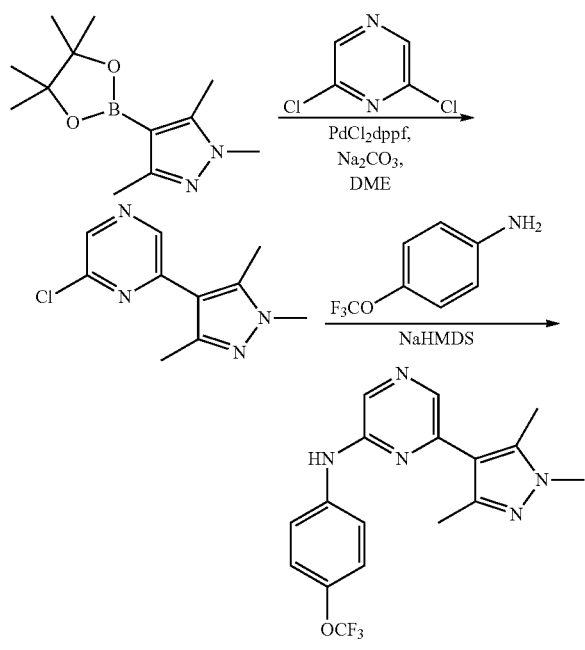

Step 1. A mixture of 2,6-dichloropyrazine (1.798 g, 12.1 mmol), 1,3,5-trimethylpyrazole-4-boronic acid pinacol ester (0.946 g, 4.01 mmol), a 1,1'-bis(diphenylphosphino)ferrocene) dichloropalladium (II)-dichloromethane complex (147 mg, 0.201 mmol) and a solution of sodium carbonate (2.0 mL of a 2 N aqueous solution, 4.0 mmol) in 1,2-dimethoxyethane (10 mL) was degassed by three successive cycles of vacuum pumping and purging with dry nitrogen gas. The reaction mixture was heated at reflux for 8 hours, cooled and filtered through Celite. A solution of the filtrate in dichloromethane (100 mL) was washed three times with water, then with saturated aqueous brine, dried over anhydrous MgSO$_4$, then filtered and evaporated. The residue was separated on a silica gel column (30:70 ethyl acetate:hexane) to afford 2-chloro-6-(1,3,5-trimethyl-1H-pyrazol-4-yl)pyrazine (623 mg, 2.82 mmol, 70%) as a waxy solid. m.p. 60-61° C.; $^1$H NMR (500 MHz, CDCl$_3$): δ 8.52 (1H, s), 8.38 (1H, s), 3.80 (3H, s), 2.48 (3H, s), 2.42 (3H, s); MS (ES+): m/e 225.1 (50), 223.1 (100).

Step 2. The obtained intermediate (96 mg, 0.431 mmol) was added to a solution of 4-trifluoromethoxyaniline (0.18 mL, 1.29 mmol) in THF (2 mL). The reaction mixture was cooled to −78° C. and treated with a solution of sodium hexamethyldisilazide (0.65 mL, 2.0 M, 1.30 mmol) in THF by syringe. The reaction mixture was stirred and allowed to warm to 0° C. over 20 minutes, then partitioned between 1:1 water:dichloromethane (20 mL each). The organic phase was separated, dried over MgSO$_4$, then filtered and evaporated. The residue was separated by column chromatography to afford the title compound (69 mg, 0.190 mmol, 44%). $^1$H NMR (500 MHz, CDCl$_3$): δ 8.09 (1H, s), 8.05 (1H, s), 7.55 (2H, d, J=8.9 Hz), 7.19 (2H, d, J=8.9 Hz), 6.95 (1H, br s), 3.80 (3H, s), 2.43 (3H, s), 2.41 (3H, s); MS (ES+): m/e 365.2 (20), 364.2 (100); MS (ES−): m/e 363.3 (20), 362.2 (100).

Additional compounds of Formula (I) or a form thereof described herein may be prepared according to the procedure of Example 108 by substituting the appropriate starting materials, reagents and reaction conditions:

| Cpd | Name and Data |
|---|---|
| 106 | N-(4-bromophenyl)-6-(1,3,5-trimethyl-1H-pyrazol-4-yl)pyrazin-2-amine<br>$^1$H NMR (500 MHz, CDCl$_3$): δ 8.09 (1H, s), 8.03 (1H, s), 7.44 (2H, s), 6.96 (1H, br s), 3.80 (3H, s), 2.43 (3H, s), 2.41 (3H, s); MS m/z 360.1 (ESI) [M + H]$^+$ |
| 143 | N-[4-(difluoromethoxy)phenyl]-6-(1,3,5-trimethyl-1H-pyrazol-4-yl)pyrazin-2-amine<br>$^1$H NMR (500 MHz, CDCl$_3$): δ 8.18 (1H, s), 7.98 (1H, s), 7.54 (2H, d, J = 8.9 Hz), 7.48 (1H, br s), 7.12 (2H, d, J = 8.9 Hz), 6.48 (1H, t, J = 74.0 Hz), 3.81 (3H, s), 2.44 (3H, s), 2.41 (3H, s); m.p. 158-159° C.; MS m/z 346.2 (ESI) [M + H]$^+$ |
| 144 | N-[4-(trifluoromethoxy)phenyl]-6-(1,3,5-trimethyl-1H-pyrazol-4-yl)pyridin-2-amine<br>$^1$H NMR (500 MHz, CDCl$_3$): δ 7.65-7.58 (1H, m), 7.42 (2H, d, J = 8.9 Hz), 7.19 (2H, d, J = 8.9 Hz), 6.77 (1H, dd, J = 7.4, 0.5 Hz), 6.71 (1H, d, J = 8.3 Hz), 3.78 (3H, s), 2.45 (3H, s), 2.37 (3H, s); MS m/z 363.3 (ESI) [M + H]$^+$ |
| 145 | N-[4-(trifluoromethyl)phenyl]-6-(1,3,5-trimethyl-1H-pyrazol-4-yl)pyridin-2-amine<br>TLC R$_F$ 0.21 (50:50 ethyl acetate-hexane); $^1$H NMR (500 MHz, CDCl$_3$): δ 7.60 (1H, dd, J = 8.1, 7.7 Hz), 7.53 (4H, s), 7.13 (1H, br s), 6.84 (1H, dd, J = 7.7, 0.5 Hz), 6.75 (1H, dd, J = 8.1, 0.5 Hz), 3.78 (3H, s), 2.43 (3H, s), 2.38 (3H, s); m.p. 48-50° C.; MS m/z 347.2 (ESI) [M + H]$^+$ |
| 146 | N-[4-(difluoromethoxy)phenyl]-6-(1,3,5-trimethyl-1H-pyrazol-4-yl)pyridin-2-amine<br>$^1$H NMR (500 MHz, CDCl$_3$): δ 7.54 (1H, t, J = 7.9 Hz), 7.37 (2H, d, J = 8.9 Hz), 7.09 (2H, d, J = 8.9 Hz), 6.99 (1H, br s), 6.75 (1H, dd, J = 7.4, 0.6 Hz), 6.65 (1H, d, J = 8.4 Hz), 6.47 (1H, t, J = 74.1 Hz), 3.76 (3H, s), 2.42 (3H, s), 2.37 (3H, s); m.p. 71-72° C.; MS m/z 345.2 (ESI) [M + H]$^+$ |

-continued

| Cpd | Name and Data |
|---|---|
| 263 | 2-{[4-(trifluoromethyl)phenyl]amino}-6-(1,3,5-trimethyl-1H-pyrazol-4-yl)pyridine-4-carbonitrile<br>$^1$H NMR (500 MHz, CDCl$_3$): δ 7.60 (2H, d, J = 8.6 Hz), 7.54 (2H, d, J = 8.6 Hz), 7.17 (1H, v br), 6.98 (1H, d, J = 1.0 Hz), 6.89 (1H, d, J = 1.0 Hz), 3.80 (3H, s), 2.44 (3H, s), 2.39 (3H, s); m.p. 182-183° C.; MS m/z 372.1 (ESI) [M + H]$^+$ |
| 264 | 2-{[4-(difluoromethoxy)phenyl]amino}-6-(1,3,5-trimethyl-1H-pyrazol-4-yl)pyridine-4-carbonitrile<br>$^1$H NMR (500 MHz, CDCl$_3$): δ 7.36 (2H, d, J = 8.9 Hz), 7.15 (2H, d, J = 8.9 Hz), 6.89 (1H, d, J = 1.0 Hz), 6.77 (1H, d, J = 1.0 Hz), 6.51 (1H, t, J = 73.7 Hz), 3.78 (3H, s), 2.43 (3H, s), 2.38 (3H, s); m.p. 144-145° C.; MS m/z 370.2 (ESI) [M + H]$^+$ |
| 265 | 2-{[4-(trifluoromethoxy)phenyl]amino}-6-(1,3,5-trimethyl-1H-pyrazol-4-yl)pyridine-4-carbonitrile<br>$^1$H NMR (500 MHz, CDCl$_3$): δ 7.40 (2H, d, J = 8.9 Hz), 7.22 (2H, d, J = 8.9 Hz), 6.92 (1H, d, J = 1.0 Hz), 6.80 (1H, d, J = 1.0 Hz), 3.78 (3H, s), 2.42 (3H, s), 2.38 (3H, s); m.p. 135-136° C.; MS m/z 388.1 (ESI) [M + H]$^+$ |
| 635 | 6-(3,5-dimethyl-1,2-oxazol-4-yl)-N-(4-methylphenyl)pyrazin-2-amine<br>$^1$H NMR (500 MHz, CDCl$_3$): δ 8.13 (1H, s), 8.00 (1H, s), 7.34 (2H, d, J = 8.3 Hz), 7.17 (2H, d, J = 8.3 Hz), 2.60 (3H, s), 2.45 (3H, s); m.p. 186-188° C.; MS (ES+): m/e 282.5 (15), 281.5 (100). MS (ES−): m/e 280.2 (15), 279.2 (100); MS m/z 279.2 (ESI) [M + H]$^+$ |
| 636 | 6-(3,5-dimethyl-1,2-oxazol-4-yl)-N-(4-methoxyphenyl)pyrazin-2-amine<br>$^1$H NMR (500 MHz, CDCl$_3$): δ 8.04 (1H, s), 7.99 (1H, s), 7.36 (2H, d, J = 8.9 Hz), 6.91 (2H, d, J = 8.9 Hz), 3.82 (3H, s), 2.59 (3H, s), 2.44 (3H, s); m.p. 154-155° C.; MS m/z 296.9 (ESI) [M + H]$^+$ |
| 637 | 6-(3,5-dimethyl-1,2-oxazol-4-yl)-N-(3-fluoro-4-methoxyphenyl)pyrazin-2-amine<br>$^1$H NMR (500 MHz, CDCl$_3$): δ 8.043 (1H, s), 8.038 (1H, s), 7.38 (1H, dd, J = 12.7, 2.5 Hz), 7.10 (1H, ddd, J = 8.8, 2.3, 1.6 Hz), 6.95 (1H, t, J = 9.0 Hz), 6.60 (1H, br s), 3.90 (3H, s), 2.59 (3H, s), 2.44 (3H, s); m.p. 158-159° C.; MS m/z 313.2 (ESI) [M + H]$^+$ |
| 638 | 6-(3,5-dimethyl-1,2-oxazol-4-yl)-N-(6-methoxypyridin-3-yl)pyrazin-2-amine<br>$^1$H NMR (500 MHz, CDCl$_3$): δ 8.25 (1H, d, J = 2.6 Hz), 8.04 (1H, s), 8.02 (1H, s), 7.81 (1H, dd, J = 8.8, 2.7 Hz), 6.79 (1H, d, J = 8.8 Hz), 3.95 (3H, s), 2.57 (3H, s), 2.41 (3H, s); m.p. 173-174° C.; MS m/z 298.2 (ESI) [M + H]$^+$ |
| 639 | N-(1,3-benzodioxol-5-yl)-6-(3,5-dimethyl-1,2-oxazol-4-yl)pyrazin-2-amine<br>$^1$H NMR (500 MHz, CDCl$_3$): δ 8.08 (1H, s), 7.99 (1H, s), 7.05 (1H, d, J = 2.0 Hz), 6.83 (1H, dd, J = 8.3, 2.0 Hz), 6.80 (1H, d, J = 8.3 Hz), 6.77 (1H, br s), 5.99 (2H, s), 2.60 (3H, s), 2.44 (3H, s); m.p. 185-186° C.; MS m/z 311.1 (ESI) [M + H]$^+$ |

Example 109

6-(3,5-dimethyl-1,2-oxazol-4-yl)-N-[4-(trifluoromethyl)phenyl]pyrazin-2-amine (Cpd 127)

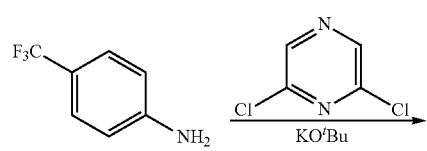

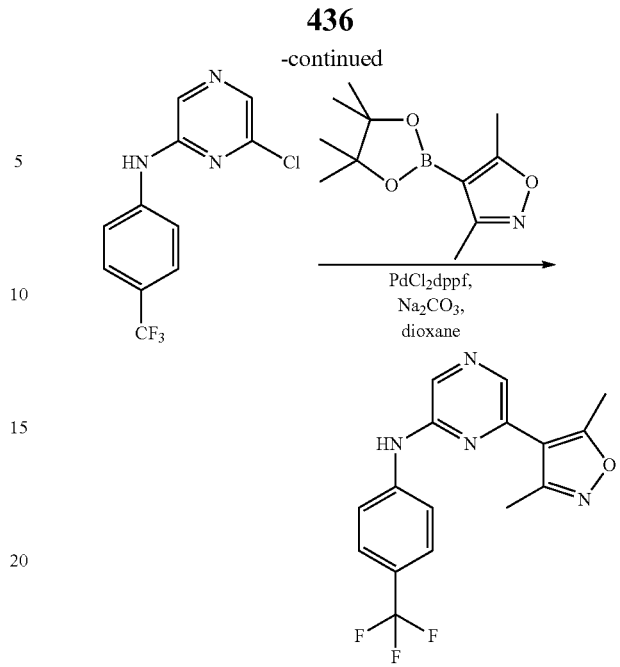

Step 1. A solution of 2,6-dichloropyrazine (8.64 g, 58 mmol) and 4-trifluoromethylaniline (4.95 mL, 39 mmol) in THF (40 mL) was cooled to −78° C. and treated with a solution of potassium tert-butoxide (40 mL, 1.0 M, 40 mmol) in THF. The reaction mixture was stirred and allowed to warm to 0° C. over 20 minutes, then partitioned between 1:1 water:dichloromethane (150 mL each). The organic phase was separated, dried over MgSO4, then filtered and evaporated. The residue was separated by column chromatography, eluting with 20:80 ethyl acetate:hexane, to afford 6-chloro-N-(4-(trifluoromethyl)phenyl)pyrazin-2-amine (3.62 g, 13.2 mmol, 34%) as a powder. m.p. 129-130° C.; TLC R$_F$ 0.10 (20:80 ethyl acetate:hexane); H NMR (500 MHz, CDCl$_3$): δ 8.18 (1H, s), 8.07 (1H, s), 7.63 (2H, d, J=9.2 Hz), 7.60 (2H, d, J=9.2 Hz), 6.89 (1H, br s); MS (ES+): m/e 276.1 (35), 274.1 (100); MS (ES−): m/e 274.2 (35), 272.1 (100).

Step 2. A mixture of the obtained intermediate (420 mg, 1.53 mmol), 3,5-dimethylisoxazole-4-boronic acid pinacol ester (369 mg, 1.65 mmol), a 1,1'-bis(diphenylphosphino)ferrocene) dichloropalladium (II)-dichloromethane complex (57 mg, 0.078 mmol) and a 2 N aqueous solution of sodium carbonate (1.65 mL, 3.30 mmol) in 1,4-dioxane (10 mL) was degassed by three successive cycles of vacuum pumping and purging with dry nitrogen gas. The reaction mixture was heated at reflux for 8 hours, then cooled and filtered through Celite. A solution of the filtrate in dichloromethane (50 mL) was washed three times with water, then with saturated aqueous brine, dried over anhydrous MgSO$_4$, then filtered and evaporated. The residue was separated on a silica gel column (30:70 ethyl acetate:hexane) to afford the title compound (266 mg, 0.796 mmol, 52%) as a powder. m.p. 208-210° C.; TLC R$_F$ 0.29 (50:50 ethyl acetate-hexane; $^1$H NMR (500 MHz, CDCl$_3$): δ 8.22 (1H, s), 8.13 (1H, s), 7.66 (2H, d, J=8.6 Hz), 7.60 (2H, d, J=8.6 Hz), 7.00 (1H, br s), 2.62 (3H, s), 2.46 (3H, s); MS (ES+): m/e 336.3 (15), 335.2 (100); MS (ES−): m/e 334.3 (15), 333.3 (100)

Additional compounds of Formula (I) or a form thereof described herein may be prepared according to the procedure of Example 109 by substituting the appropriate starting materials, reagents and reaction conditions:

| Cpd | Name and Data |
|---|---|
| 128 | N-[4-(trifluoromethyl)phenyl]-6-(1,3,5-trimethyl-1H-pyrazol-4-yl)pyrazin-2-amine<br>$^1$H NMR (500 MHz, CDCl$_3$): δ 8.12 (1H, s), 8.09 (1H, s), 7.66 (2H, d, J = 8.6 Hz), 7.57 (2H, d, J = 8.6 Hz), 6.90 (1H, br s), 3.80 (3H, s), 2.45 (3H, s), 2.42 (3H, s); m.p. 201-202° C.; MS m/z 348.2 (ESI) [M + H]$^+$ |
| 226 | 6-(3,5-dimethyl-1H-pyrazol-4-yl)-N-[4-(trifluoromethyl)phenyl]pyrazin-2-amine<br>$^1$H NMR (500 MHz, CDCl$_3$): δ 8.25 (1H, s), 8.15 (1H, s), 7.60 (4H, s), 2.73 (3H, s), 2.48 (3H, s); MS m/z 334.2 (ESI) [M + H]$^+$ |

Example 110

6-(1-ethyl-3,5-dimethyl-1H-pyrazol-4-yl)-N-[4-(trifluoromethyl)phenyl]pyrazin-2-amine (Cpd 175)

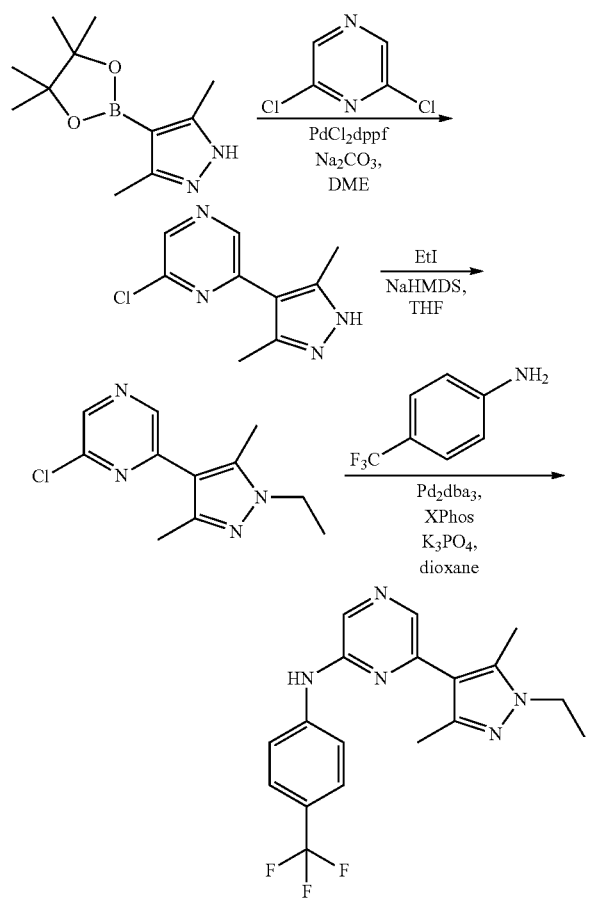

Step 1. A mixture of 2,6-dichloropyrazine (1.798 g, 12.1 mmol), 3,5-dimethyl-4-(4,4,5,5-tetramethyl-1,3,2-dioxaborolan-2-yl)-1H-pyrazole (0.897 g, 4.01 mmol), a 1,1'-bis(diphenylphosphino)ferrocene) dichloropalladium (II)-dichloromethane complex (147 mg, 0.201 mmol) and a 2 N aqueous solution of sodium carbonate (2.0 mL, 4.0 mmol) in 1,2-dimethoxyethane (10 mL) was degassed by three successive cycles of vacuum pumping and purging with dry nitrogen gas. The mixture was heated at reflux for 8 hours, then cooled and filtered through Celite. A solution of the filtrate in dichloromethane (100 mL) was washed three times with water, then with saturated aqueous brine, dried over anhydrous MgSO$_4$, then filtered and evaporated. The residue was separated on a silica gel column (30:70 ethyl acetate-hexane) to afford 2-chloro-6-(3,5-dimethyl-1H-pyrazol-4-yl)pyrazine (623 mg, 2.82 mmol, 70%) as a waxy solid. m.p. 60-61° C.; TLC R$_F$ 0.20 (50:50 ethyl acetate-hexane); $^1$H NMR (500 MHz, CDCl$_3$): δ 8.52 (1H, s), 8.38 (1H, s), 3.80 (3H, s), 2.48 (3H, s), 2.42 (3H, s); MS (ES+): m/e 225.1 (50), 223.1 (100).

Step 2. A solution of the obtained intermediate (44 mg, 0.211 mmol) in THF was cooled to −78° C. and treated with a THF solution of sodium hexamethyldisilazide (0.12 mL, 2.0 M, 0.24 mmol) by syringe. The mixture was stirred for 10 minutes, then ethyl iodide (20 μL, 0.248 mmol) was added. The mixture was allowed to warm for 4 hours, then partitioned between water and ethyl acetate. The organic layer was separated, dried over MgSO$_4$, then filtered and evaporated to afford 2-chloro-6-(1-ethyl-3,5-dimethyl-1H-pyrazol-4-yl)pyrazine in sufficiently pure form. MS (ES+): m/e 238.1 (35), 237.1 (100).

Step 3. A tube containing a mixture of the obtained intermediate (48.0 mg, 0.20 mmol), 4-trifluoromethylaniline (0.10 mL), 2-dicyclohexylphosphino-2',4',6'-triisopropylbiphenyl (12 mg), tris(dibenzylideneacetone) dipalladium(0) (11 mg) and tripotassium phosphate (120 mg) in dioxane (2 mL) was degassed by three cycles of vacuum pumping and N$_2$ purging, then heated at 100° C. for 12 hours. The reaction mixture was cooled, poured into water (20 mL) and extracted with dichloromethane. The extract was dried over MgSO$_4$, then filtered and evaporated and the residue separated by column chromatography to afford the title compound (39.1 mg, 57%). m.p. 78-79° C.; TLC R$_F$ 0.11 (50:50 ethyl acetate-hexane); H NMR (500 MHz, CDCl$_3$): δ 8.32 (1H, s), 8.04 (1H, s), 7.81 (1H, br), 7.74 (2H, d, J=8.5 Hz), 7.59 (2H, d, J=8.5 Hz), 4.16 (2H, q, J=7.3 Hz), 2.47 (3H, s), 2.45 (3H, s), 1.47 (3H, t, J=7.3 Hz); MS (ES+): m/e 363.2 (30), 362.3 (100); MS (ES−): m/e 361.3 (20), 360.2 (100)

Additional compounds of Formula (I) or a form thereof described herein may be prepared according to the procedure of Example 110 by substituting the appropriate starting materials, reagents and reaction conditions:

| Cpd | Name and Data |
|---|---|
| 84 | 6-(1-ethyl-3,5-dimethyl-1H-pyrazol-4-yl)-N-[4-(trifluoromethoxy)phenyl]pyrazin-2-amine<br>$^1$H NMR (500 MHz, CDCl$_3$): δ 8.07 (1H, s), 8.05 (1H, s), 7.55, (2H d, J = 9.0 Hz), 7.18 (2H, d, J = 9.0 Hz), 7.01 (1H, br s), 4.11 (2H, q, J = 7.3 Hz), 2.43 (3H, s), 2.41 (3H, s), 1.43 (3H, t, J = 7.3 Hz); m.p. 142-143° C.; MS m/z 378.2 (ESI) [M + H]$^+$ |
| 176 | 6-[1-(ethylsulfonyl)-3,5-dimethyl-1H-pyrazol-4-yl]-N-[4-(trifluoromethyl)phenyl]pyrazin-2-amine<br>$^1$H NMR (500 MHz, CDCl$_3$): δ 8.37 (1H, s), 8.04 (1H, s), 7.71 (2H, d, J = 8.5 Hz), 7.60 (2H, d, J = 8.5 Hz), 7.55 (1H, br), 3.57 (2H, q, J = 7.3 Hz), 2.68 (3H, s), 2.42 (3H, s), 1.38 (3H, t, J = 7.3 Hz); m.p. 70-71° C.; MS m/z 426.2 (ESI) [M + H]$^+$ |
| 277 | 1-[3,5-dimethyl-4-(6-{[4-(trifluoromethyl)phenyl]amino}pyrazin-2-yl)-1H-pyrazol-1-yl]ethanone<br>$^1$H NMR (500 MHz, CDCl$_3$): δ 8.38 (1H, s), 8.04 (1H, s), 7.73 (2H, d, J = 8.5 Hz), 7.59 (2H, d, J = 8.5 Hz), 2.74 (3H, s), 2.73 (3H, s), 2.40 (3H, s); m.p. 199-200° C.; MS m/z 376.0 (ESI) [M + H]$^+$ |
| 278 | ethyl 3,5-dimethyl-4-(6-{[4-(trifluoromethyl)phenyl]amino}pyrazin-2-yl)-1H-pyrazole-1-carboxylate<br>$^1$H NMR (500 MHz, CDCl$_3$): δ 9.00 (1H, v br), 8.71 (1H, s), 7.94 (1H, s), 7.84 (2H, d, J = 8.5 Hz), 7.61 (2H, d, J = 8.5 Hz), |

| Cpd | Name and Data |
|---|---|
| | 4.56 (2H, q, J = 7.1 Hz), 2.74 (3H, s), 2.44 (3H, s), 1.50 (3H, t, J = 7.1 Hz); m.p. 122-123° C.; MS m/z 406.5 (ESI) [M + H]⁺ |
| 279 | ethyl 4-(6-{[4-(difluoromethoxy)phenyl]amino}pyrazin-2-yl)-3,5-dimethyl-1H-pyrazole-1-carboxylate<br>¹H NMR (500 MHz, CDCl₃): δ 8.27 (1H, s), 7.98 (1H, s), 7.55 (2H, d, J = 8.9 Hz), 7.40 (1H, br), 7.12 (2H, d, J = 8.9 Hz), 6.49 (1H, t, J = 73.9 Hz), 4.54 (2H, q, J = 7.1 Hz), 2.70 (3H, s), 2.41 (3H, s), 1.49 (3H, t, J = 7.1 Hz); m.p. 92-93° C.; MS m/z 404.5 (ESI) [M + H]⁺ |
| 382 | N-[4-(difluoromethoxy)-3-fluorophenyl]-6-(1-ethyl-3,5-dimethyl-1H-pyrazol-4-yl)pyrazin-2-amine<br>¹H NMR (500 MHz, CDCl₃): δ 8.10 (1H, s), 8.01 (1H, s), 7.73 (1H, dd, J = 12.6, 2.6 Hz), 7.18 (1H, t, J = 8.7 Hz), 7.11 (1H, ddd, J = 8.9, 2.4, 1.2 Hz), 6.90 (1H, br s), 6.50 (1H, t, J = 73.7 Hz), 4.11 (2H, q, J = 7.3 Hz), 2.45 (3H, s), 2.42 (3H, s), 1.44 (3H, t, J = 7.3 Hz); m.p. 129-130° C.; MS m/z 378.0 (ESI) [M + H]⁺ |
| 399 | 6-[1-(2-methoxyethyl)-3,5-dimethyl-1H-pyrazol-4-yl]-N-[4-(trifluoromethyl)phenyl]pyrazin-2-amine<br>¹H NMR (500 MHz, CDCl₃): δ 8.12 (1H, s), 8.08 (1H, s), 7.66 (2H, d, J = 8.4 Hz), 7.56 (2H, d, J = 8.4 Hz), 6.94 (1H, br s), 4.23 (2H, t, J = 5.0 Hz), 3.77 (2H, t, J = 5.0 Hz), 3.33 (3H, s), 2.47 (3H, s), 2.42 (3H, s); MS m/z 392.2 (ESI) [M + H]⁺ |
| 400 | 6-[3,5-dimethyl-1-(pyridin-2-ylmethyl)-1H-pyrazol-4-yl]-N-[4-(trifluoromethyl)phenyl]pyrazin-2-amine<br>¹H NMR (500 MHz, CDCl₃): δ 8.57 (1H, ddd, J = 4.9, 1.6, 0.8 Hz), 8.13 (1H, s), 8.08 (1H, s), 7.68-7.63 (3H, m), 7.55 (2H, d, J = 8.6 Hz), 7.20 (1H, ddd, J = 7.5, 4.9, 0.8 Hz), 7.05 (1H, s), 6.98 (1H, d, J = 7.8 Hz), 5.44 (2H, s), 2.46 (3H, s), 2.43 (3H, s); m.p. 50-51° C.; MS m/z 425.2 (ESI) [M + H]⁺ |
| 401 | N-[4-(difluoromethoxy)phenyl]-6-[3,5-dimethyl-1-(pyridin-2-ylmethyl)-1H-pyrazol-4-yl]pyrazin-2-amine<br>¹H NMR (500 MHz, CDCl₃): δ 8.57 (1H, ddd, J = 4.9, 1.6, 0.9 Hz), 8.08 (1H, s), 8.02 (1H, s), 7.63 (1H, td, J = 7.7, 1.7 Hz), 7.47 (2H, d, J = 8.9 Hz), 7.20 (1H, ddd, J = 7.5, 4.9, 0.9 Hz), 7.10 (2H, d, J = 8.9 Hz), 6.96 (1H, d, J = 8.9 Hz), 6.59 (1H, br s), 6.47 (1H, t, J = 74.0 Hz), 5.43 (2H, s), 2.45 (3H, s), 2.40 (3H, s); m.p. 47-48° C.; MS m/z 423.2 (ESI) [M + H]⁺ |
| 402 | 6-[3,5-dimethyl-1-(pyridin-3-ylmethyl)-1H-pyrazol-4-yl]-N-[4-(trifluoromethyl)phenyl]pyrazin-2-amine<br>¹H NMR (500 MHz, CDCl₃): δ 8.55 (1H, dd, J = 4.8, 1.5 Hz), 8.51(1H, d, J = 1.9 Hz), 8.12 (1H, s), 8.10 (1H, s), 7.64 (2H, d, J = 8.5 Hz), 7.56 (2H, d, J = 8.5 Hz), 7.51 (1H, dt, J = 7.9, 1.9 Hz), 7.28 (1H, ddd, J = 7.9, 4.8, 0.4 Hz), 6.99 (1H, br s), 5.32 (2H, s), 2.45 (3H, s), 2.41 (3H, s); m.p. 47-48° C.; MS m/z 425.2 (ESI) [M + H]⁺ |
| 403 | 6-[3,5-dimethyl-1-(pyridin-4-ylmethyl)-1H-pyrazol-4-yl]-N-[4-(trifluoromethyl)phenyl]pyrazin-2-amine<br>¹H NMR (500 MHz, CDCl₃): δ 8.58 (1H, d, J = 6.0 Hz), 8.15 (1H, s), 8.11 (1H, s), 7.65 (2H, d, J = 8.6 Hz), 7.57 (2H, d, J = 8.6 Hz), 7.03 (2H, d, J = 6.0 Hz), 6.90 (1H, br s), 5.32 (2H, s), 2.47 (3H, s), 2.38 (3H, s); m.p. 66-67° C.; MS m/z 425.2 (ESI) [M + H]⁺ |

Example 111

6-[3,5-dimethyl-1-(2,2,2-trifluoroethyl)-1H-pyrazol-4-yl]-N-[4-(trifluoromethyl)phenyl]pyrazin-2-amine (Cpd 253)

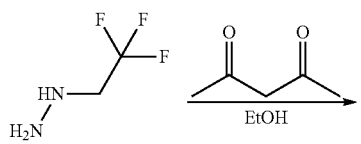

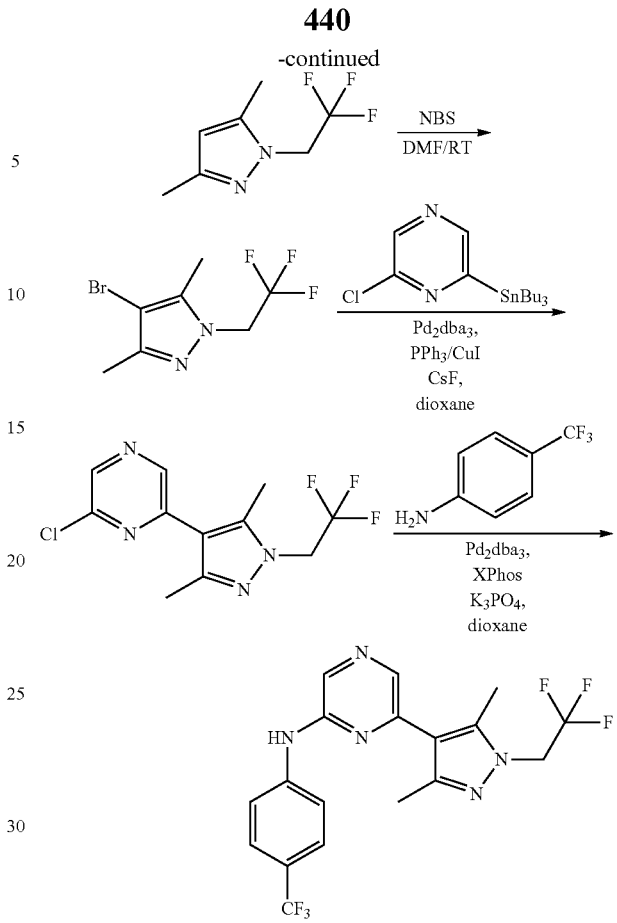

Step 1. A solution of 2,4-pentanedione (8.00 mL, 77.9 mmol) and 2,2,2-trifluoroethylhydrazine (10.0 mL, 79.4 mmol) in ethanol (100 mL) was heated at reflux overnight. The mixture was cooled, partially evaporated, then poured into water and extracted with ethyl acetate. The extract was dried over Na₂SO₄, then filtered and evaporated to afford 3,5-dimethyl-1-(2,2,2-trifluoroethyl)-1H-pyrazole (13.8 g, 77.5 mmol, 99%). ¹H NMR (500 MHz, CDCl₃): δ 5.87 (1H, s), 4.54 (2H, q, J=8.4 Hz), 2.26 (3H, s), 2.22 (3H, s).

Step 2. A solution of the obtained intermediate (7.12 g, 40.0 mmol) in dimethylformamide (80 mL) was treated with N-bromosuccinimide (7.12 g, 40.0 mmol). The reaction mixture was stirred at room temperature for 12 hours, then diluted with ethyl acetate (150 mL). The solution was washed with water (3×150 mL) and brine (50 mL), dried over MgSO₄, then filtered and evaporated. The residue was separated on a silica gel column (10:90 ethyl acetate:hexane) to afford 4-bromo-3,5-dimethyl-1-(2,2,2-trifluoroethyl)-1H-pyrazole (8.33 g, 32.4 mmol, 81%) as a waxy solid. ¹H NMR (500 MHz, CDCl₃): δ 4.56 (2H, q, J=8.3 Hz), 2.26 (3H, s), 2.20 (3H, s).

Step 3. A mixture of the obtained intermediate (678 mg, 2.64 mmol), 2-chloro-6-(tributylstannyl)pyrazine (1.00 g, 2.48 mmol), tris(dibenzylideneacetone)dipalladium(0) (70 mg), tri-tert-butylphosphine (0.75 mL, 0.40 M solution in hexane), copper(I) iodide (112 mg) and a solution of cesium fluoride (867 mg) in dioxane (10 mL) was degassed by two pump/purge cycles. The reaction mixture was heated at 100° C. for 6 hours, cooled, then filtered and evaporated. The residue was separated by column chromatography (30:70 ethyl acetate:hexane) to afford 2-chloro-6-(3,5-dimethyl-1-(2,2,2-trifluoroethyl)-1H-pyrazol-4-yl)pyrazine (70 mg, 0.24 mmol, 10%). $^1$H NMR (500 MHz, CDCl$_3$): δ 8.55 (1H, s), 8.44 (1H, s), 4.67 (2H, q, J=8.2 Hz), 2.52 (3H, s), 2.44 (3H, s); MS (ES+): m/e 293.1 (35), 291.1 (100).

Step 4. A tube containing the obtained intermediate (58 mg, 0.20 mmol), 4-trifluoromethylaniline (0.10 mL), 2-dicyclohexylphosphino-2',4',6'-triisopropylbiphenyl (12 mg), tris(dibenzylideneacetone) dipalladium(0) (11 mg) and a solution of tripotassium phosphate (120 mg) in dioxane (2 mL) was degassed by three cycles of vacuum pumping and N$_2$ purging. The reaction mixture was heated at 100° C. for 12 hours, cooled, then poured into water (20 mL) and extracted with dichloromethane. The extract was dried over MgSO$_4$, then filtered and evaporated. The residue was separated by column chromatography to afford the title compound (40 mg, 0.096 mmol, 48%). m.p. 90-91° C.; $^1$H NMR (500 MHz, CDCl$_3$): δ 8.52 (1H, s), 8.49 (1H, v br), 7.99 (1H, s), 7.78 (2H, d, J=8.5 Hz), 7.60 (2H, d, J=8.5 Hz), 4.67 (2H, q, J=8.3 Hz), 2.50 (3H, s), 2.44 (3H, s); MS (ES+): m/e 417.2 (20), 416.1 (100); MS (ES−): m/e 415.1 (20), 414.1 (100).

Additional compounds of Formula (I) or a form thereof described herein may be prepared according to the procedure of Example 111 by substituting the appropriate starting materials, reagents and reaction conditions:

| Cpd | Name and Data |
|-----|---------------|
| 332 | 6-(3,5-diethyl-1-methyl-1H-pyrazol-4-yl)-N-[4-(trifluoromethyl)phenyl]pyrazin-2-amine<br>$^1$H NMR (500 MHz, CDCl$_3$): δ 8.114 (1H, s), 8.105 (1H, s), 7.63 (2H, d, J = 8.6 Hz), 7.57 (2H, d, J = 8.6 Hz), 6.75 (1H, br s), 3.84 (3H, s), 2.83 (2H, q, J = 7.6 Hz), 2.81 (2H, q, J = 7.6 Hz), 1.23 (3H, t, J = 7.6 Hz), 1.21 (3H, t, J = 7.6 Hz); m.p. 59-60° C.; MS m/z 376.2 (ESI) [M + H]$^+$ |
| 333 | 6-(3,5-diethyl-1-methyl-1H-pyrazol-4-yl)-N-[4-(difluoromethoxy)phenyl]pyrazin-2-amine<br>$^1$H NMR (500 MHz, CDCl$_3$): δ 8.035 (1H, s), 8.028 (1H, s), 7.46 (2H, d, J = 8.9 Hz), 7.11 (2H, d, J = 8.9 Hz), 6.59 (1H, br s), 6.47 (1H, t, J = 74.0 Hz), 3.82 (3H, s), 2.81 (2H, q, J = 7.3 Hz), 2.79 (2H, q, J = 7.3 Hz), 1.22 (3H, t, J = 7.3 Hz), 1.19 (3H, t, J = 7.3 Hz); m.p. 95-96° C.; MS m/z 374.2 (ESI) [M + H]$^+$ |
| 334 | 6-(3,5-diethyl-1-methyl-1H-pyrazol-4-yl)-N-[4-(trifluoromethoxy)phenyl]pyrazin-2-amine<br>$^1$H NMR (500 MHz, CDCl$_3$): δ 8.054 (1H, s), 8.048 (1H, s), 7.50 (2H, d, J = 9.0 Hz), 7.18 (2H, d, J = 9.0 Hz), 6.68 (1H, br s), 3.83 (1H, s), 2.81 (2H, q, J = 7.6 Hz), 2.80 (2H, q, J = 7.6 Hz), 1.22 (3H, t, J = 7.6 Hz), 1.18 (3H, t, J = 7.6 Hz); m.p. 122-123° C.; MS m/z 392.2 (ESI) [M + H]$^+$ |
| 335 | 2-[3,5-dimethyl-4-(6-{[4-(trifluoromethyl)phenyl]amino}pyrazin-2-yl)-1H-pyrazol-1-yl]ethanol<br>$^1$H NMR (500 MHz, CDCl$_3$): δ 9.92 (1H, s), 8.16 (1H, s), 8.08 (1H, s), 7.97 (2H, d, J = 8.6 Hz), 7.66 (2H, d, J = 8.6 Hz), 4.96 (1H, br), 4.12 (2H, t, J = 5.6 Hz), 3.78 (2H, t, J = 5.6 Hz), 2.47 (3H, s), 2.34 (3H, s); MS m/z 378.1 (ESI) [M + H]$^+$; m.p. 172-174° C. |
| 412 | 6-(5-chloro-1,3-dimethyl-1H-pyrazol-4-yl)-N-[4-(trifluoromethyl)phenyl]pyrazin-2-amine<br>$^1$H NMR (500 MHz, CDCl$_3$): δ 8.33 (1H, s), 8.13 (1H, s), 7.69 (2H, d, J = 8.6 Hz), 7.58 (2H, d, J = 8.6 Hz), 6.81 (1H, br s), 3.87 (3H, s), 2.45 (3H, s); MS m/z 368.1 (ESI) [M + H]$^+$ |
| 413 | 6-(5-chloro-1,3-dimethyl-1H-pyrazol-4-yl)-N-[4-(difluoromethoxy)phenyl]pyrazin-2-amine<br>$^1$H NMR (500 MHz, CDCl$_3$): δ 8.26 (1H, s), 8.05 (1H, s), 7.52 (2H, d, J = 8.9 Hz), 7.12 (2H, d, J = 8.9 Hz), 6.58 (1H, br s), 6.48 (1H, t, J = 74.0 Hz), 3.86 (3H, s), 2.42 (3H, s); MS m/z 366.1 (ESI) [M + H]$^+$ |
| 414 | 6-(5-chloro-1,3-dimethyl-1H-pyrazol-4-yl)-N-[4-(trifluoromethoxy)phenyl]pyrazin-2-amine<br>$^1$H NMR (500 MHz, CDCl$_3$): δ 8.28 (1H, s), 8.08 (1H, s), 7.57 (2H, d, J = 8.9 Hz), 7.20 (2H, d, J = 8.9 Hz), 6.64 (1H, br s), 3.86 (3H, s), 2.43 (3H, s); MS m/z 384.1 (ESI) [M + H]$^+$ |
| 415 | 6-(5-chloro-1,3-dimethyl-1H-pyrazol-4-yl)-N-[4-(difluoromethoxy)-3-fluorophenyl]pyrazin-2-amine<br>$^1$H NMR (500 MHz, CDCl$_3$): δ 8.30 (1H, s), 8.06 (1H, s), 7.77 (1H, dd, J = 12.5, 2.5 Hz), 7.20 (1H, t, J = 8.6 Hz), 7.13 (1H, ddd, J = 8.8, 2.5, 1.2 Hz), 6.63 (1H, br s), 6.51 (1H, t, J = 73.7 Hz), 3.87 (3H, s), 2.44 (3H, s); MS m/z 384.1 (ESI) [M + H]$^+$ |

Example 112

N-[4-(difluoromethoxy)phenyl]-6-[1,5-dimethyl-3-(trifluoromethyl)-1H-pyrazol-4-yl]pyrazin-2-amine (Cpd 280)

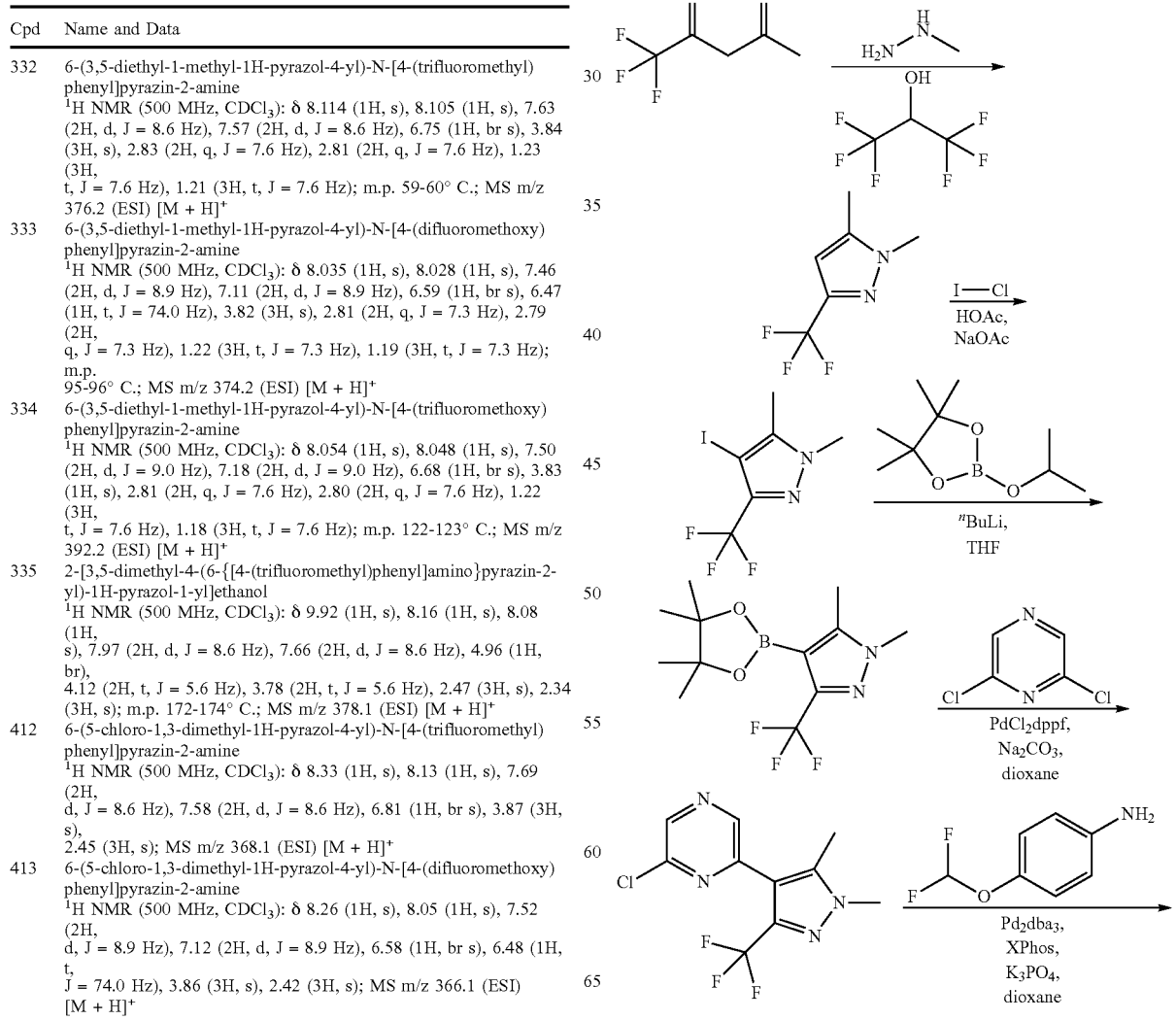

-continued

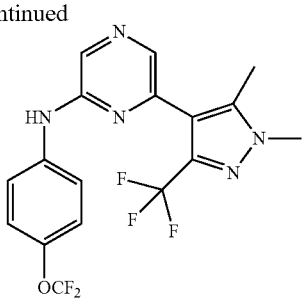

Step 1. A solution of 1,1,1-trifluoropentane-2,4-dione (4.00 mL, 32.4 mmol) and methylhydrazine (1.80 mL, 33.5 mmol) in hexafluoroisopropanol (35 mL) was warmed to 45° C. for 10 hours, then cooled and the solvent removed by short-path distillation. The crude product 1,5-dimethyl-3-(trifluoromethyl)-1H-pyrazole (5.26 g, 32.0 mmol, 99%) was used directly in the next step without further purification. $^1$H NMR (500 MHz, CDCl$_3$): δ 6.28 (1H, s), 3.81 (3H, s), 2.30 (3H, s).

Step 2. A solution of the obtained intermediate (5.26 g, 32.0 mmol) and sodium acetate (2.79 g, 34.0 mmol) in acetic acid (40 mL) was cooled to 5° C. and treated with iodine monochloride (5.46 g, 33.6 mmol). The reaction mixture was stirred overnight, poured into water (200 mL) and quenched by adding Na$_2$S$_2$O$_5$ (to destroy excess iodine monochloride) and NaHCO$_3$, then extracted with dichloromethane (2×150 mL). The combined extracts were dried over MgSO$_4$, then filtered and evaporated. The residue was triturated with ether, collected by filtration and dried under vacuum to afford 4-iodo-1,5-dimethyl-3-(trifluoromethyl)-1H-pyrazole (5.75 g, 19.8 mmol, 62%). m.p. 91-92° C.; $^1$H NMR (500 MHz, CDCl$_3$): δ 3.90 (3H, s), 2.34 (3H, s); MS (ES+): m/e 290.9 (100).

Step 3. A solution of the obtained intermediate (2.82 g, 9.71 mmol) in THF (30 mL) was cooled to −78° C., and treated with a solution of n-butyllithium in hexane (6.30 mL, 10.1 mmol). The reaction mixture was stirred for 20 minutes, then treated with 2-isopropoxy-4,4,5,5-tetramethyl-1,3,2-dioxaborolane (2.50 mL, 12.0 mmol). The reaction mixture was stirred for 4 hours, poured into a saturated aqueous ammonium chloride solution (50 mL) and extracted with dichloromethane (2×50 mL). The combined extracts were dried over MgSO$_4$, then filtered and evaporated to afford a crude product. The solid was triturated with 1:1 ether:pentane, then collected by filtration and dried under vacuum to afford 1,5-dimethyl-3-(trifluoromethyl)-1H-pyrazole-4-boronic acid pinacol ester (942 mg, 3.25 mmol, 33%). $^1$H NMR (500 MHz, CDCl$_3$): δ 3.80 (3H, s), 2.43 (3H, s), 1.31 (12H, s); MS (ES+): m/e 292.3 (10), 291.2 (100).

Step 4. A mixture of the obtained intermediate (908 mg, 3.13 mmol), 2,6-dichloropyrazine (1.41 g, 9.49 mmol), 1,1'-bis(diphenylphosphino)ferrocene) dichloropalladium (II)-dichloromethane complex (267 mg, 0.365 mmol) and an aqueous sodium carbonate solution (3.2 mL, 2.0 N, 6.4 mmol) in dioxane (15 mL) was degassed by three cycles of vacuum pumping and N$_2$ purging. The reaction mixture was heated at reflux for 12 hours, cooled and partitioned between 1:1 water:dichloromethane (75 mL each). The organic layer was separated, dried over MgSO$_4$, then filtered and evaporated. The residue was separated by silica gel column chromatography (20:80 ethyl acetate-hexane) to afford 2-chloro-6-(1,5-dimethyl-3-(trifluoromethyl)-1H-pyrazol-4-yl)pyrazine (420 mg, 1.52 mmol, 49%). $^1$H NMR (500 MHz, CDCl$_3$): δ 8.63 (1H, s), 8.52 (1H, s), 3.91 (3H, s), 2.45 (3H, s); MS (ES+): m/e 279.1 (35), 277.1 (100).

Step 5. A tube containing a mixture of the obtained intermediate (141 mg, 0.510 mmol), 4-difluoromethoxyaniline (0.20 mL, 1.58 mmol), 2-dicyclohexylphosphino-2',4',6'-triisopropylbiphenyl (33 mg, 0.069 mmol), tris(dibenzylideneacetone) dipalladium(0) (27 mg, 0.029 mmol) and a solution of tripotassium phosphate (291 mg, 1.37 mmol) in dioxane (6 mL) was degassed by three cycles of vacuum pumping and N$_2$ purging. The reaction mixture was heated at 100° C. for 12 hours, cooled and poured into water (20 mL), then extracted with dichloromethane. The extract was dried over MgSO$_4$, then filtered and evaporated. The residue was separated by silica gel column chromatography (30:70 ethyl acetate-hexane) to afford the title compound (104 mg, 0.260 mmol, 51%), m.p. 139-140° C. $^1$H NMR (500 MHz, CDCl$_3$): δ 8.21 (1H, s), 8.06 (1H, s), 7.52 (2H, d, J=8.9 Hz), 7.11 (2H, d, J=8.9 Hz), 6.48 (1H, t, J=74.0 Hz), 3.90 (3H, s), 2.40 (3H, s). MS (ES+): m/e 401.4 (20), 400.5 (100). MS (ES−): m/e 399.5 (20), 398.5 (100).

Additional compounds of Formula (I) or a form thereof described herein may be prepared according to the procedure of Example 112 by substituting the appropriate starting materials, reagents and reaction conditions:

| Cpd | Name and Data |
| --- | --- |
| 126 | benzyl-2-ethyl-4-methyl-1H-imidazol-5-yl)-N-[4-(trifluoromethyl)phenyl]pyrazin-2-amine MS m/z 438.4 (ESI) [M + H]$^+$ |
| 276 | 6-[1,5-dimethyl-3-(trifluoromethyl)-1H-pyrazol-4-yl]-N-[4-(trifluoromethyl)phenyl]pyrazin-2-amine<br>$^1$H NMR (500 MHz, CDCl$_3$): δ 8.44 (1H, s), 8.09 (1H, s), 7.82 (1H, s), 7.74 (2H, d, J = 8.5 Hz), 7.58 (2H, d, J = 8.5 Hz), 3.93 (3H, s), 2.42 (3H, s) |
| 281 | 6-[1,5-dimethyl-3-(trifluoromethyl)-1H-pyrazol-4-yl]-N-[4-(trifluoromethoxy)phenyl]pyrazin-2-amine<br>$^1$H NMR (500 MHz, CDCl$_3$): δ 8.31 (1H, s), 8.05 (1H, s), 7.60 (2H, d, J = 9.0 Hz), 7.45 (1H, br), 7.20 (2H, d, J = 9.0 Hz), 3.91 (3H, s), 2.40 (3H, s); m.p. 157-158° C.; MS m/z 418.4 (ESI) [M + H]$^+$ |
| 329 | 6-[1-ethyl-5-methyl-3-(trifluoromethyl)-1H-pyrazol-4-yl]-N-[4-(trifluoromethyl)phenyl]pyrazin-2-amine<br>$^1$H NMR (500 MHz, CDCl$_3$): δ 8.31 (1H, s), 8.13 (1H, s), 7.70 (2H, d, J = 8.6 Hz), 7.58 (2H, d, J = 8.6 Hz), 6.31 (1H, br s), 4.23 (2H, q, J = 7.3 Hz), 2.42 (3H, s), 1.51 (3H, t, J = 7.3 Hz); m.p. 150-151° C.; MS m/z 416.1 (ESI) [M + H]$^+$ |
| 330 | N-[4-(difluoromethoxy)phenyl]-6-[1-ethyl-5-methyl-3-(trifluoromethyl)-1H-pyrazol-4-yl]pyrazin-2-amine<br>$^1$H NMR (500 MHz, CDCl$_3$): δ 8.11 (1H, s), 8.09 (1H, s), 7.48 (2H, d, J = 9.0 Hz), 7.12 (2H, d, J = 9.0 Hz), 6.61 (1H, br s), 6.48 (1H, t, J = 74.0 Hz), 4.21 (2H, q, J = 7.3 Hz), 2.40 (3H, s), 1.49 (3H, t, J = 7.3 Hz); m.p. [138-139° C.; MS m/z 414.1 (ESI) [M + H]$^+$ |
| 331 | 6-[1-ethyl-5-methyl-3-(trifluoromethyl)-1H-pyrazol-4-yl]-N-[4-(trifluoromethoxy)phenyl]pyrazin-2-amine<br>$^1$H NMR (500 MHz, CDCl$_3$): δ 8.13 (1H, s), 8.11 (1H, s), 7.53 (2H, d, J = 9.0 Hz), 7.19 (2H, d, J = 9.0 Hz), 6.66 (1H, br s), 4.21 (2H, q, J = 7.3 Hz), 2.40 (3H, s), 1.49 (3H, t, J = 7.3 Hz); m.p. 128-129° C.; MS m/z 432.1 (ESI) [M + H]$^+$ |

Example 113

6-{3,5-dimethyl-1-[2-(2H-tetrazol-2-yl)ethyl]-1H-pyrazol-4-yl}-N-[4-(trifluoromethyl)phenyl]pyrazin-2-amine (Cpd 352)

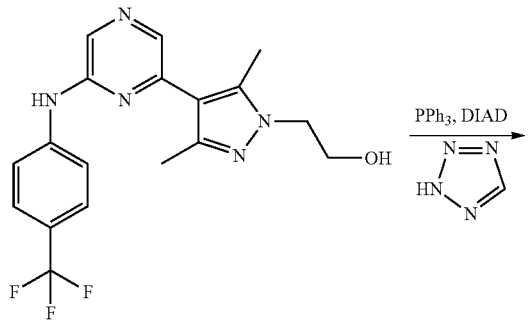

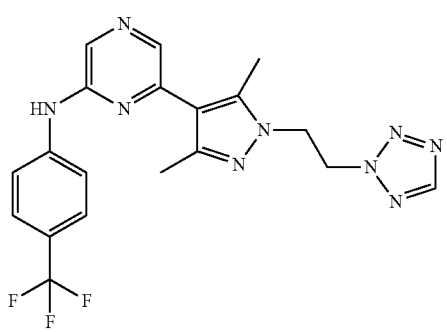

A solution of triphenylphosphine (140 mg, 0.534 mmol) in THF (5 mL) was cooled to −30° C. and treated by syringe with diisopropyl azodicarboxylate (0.10 mL, 0.482 mmol). The solution was stirred for 30 minutes, then treated with a THF solution of 2-(3,5-dimethyl-4-(6-(4-(trifluoromethyl) phenylamino) pyrazin-2-yl)-1H-pyrazol-1-yl)ethanol (90 mg, 0.238 mmol) and tetrazole (0.54 mmol) by syringe. The mixture was allowed to arm to room temperature for 12 hours, then the solvent was evaporated. The residue was separated by silica gel column chromatography (ethyl acetate) to afford the product, 6-(1-(2-(2H-tetrazol-2-yl) ethyl)-3,5-dimethyl-1H-pyrazol-4-yl)-N-(4-(trifluoromethyl)phenyl)pyrazin-2-amine (71 mg, 0.165 mmol, 69%). m.p. 138-139° C.; TLC $R_F$ 0.22 (ethyl acetate); $^1$H NMR (500 MHz, CDCl$_3$): δ 8.53 (1H, s), 8.09 (1H, s), 8.07 (1H, s), 7.63 (2H, d, J=8.7 Hz), 7.58 (2H, d, J=8.7 Hz), 6.75 (1H, br s), 5.17 (2H, t, J=6.0 Hz), 4.67 (2H, t, J=6.0 Hz), 2.41 (3H, s), 2.16 (3H, s); MS (ES+): m/e 431.2 (20), 430.1 (100); MS (ES−): m/e 429.2 (20), 428.1 (100).

Example 114

(2S)-4-[3,5-dimethyl-4-(6-{[4-(trifluoromethyl)phenyl]amino}pyrazin-2-yl)-1H-pyrazol-1-yl]butane-1,2-diol (Cpd 404)

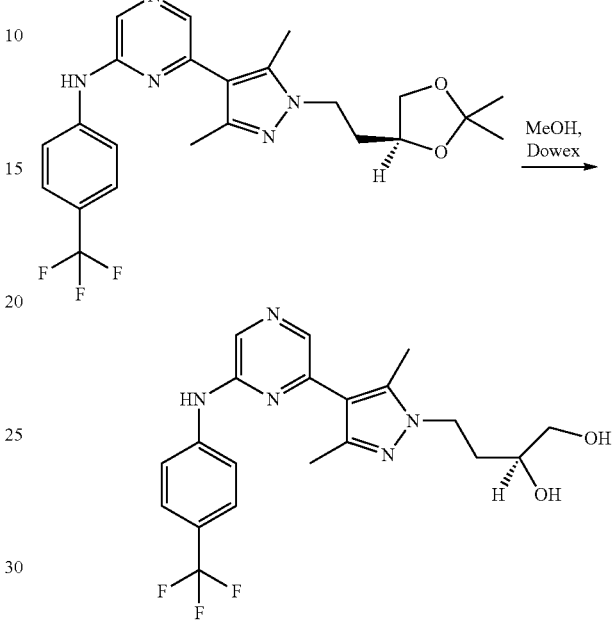

A solution of (S)-6-(1-(2-(2,2-dimethyl-1,3-dioxolan-4-yl)ethyl)-3,5-dimethyl-1H-pyrazol-4-yl)-N-(4-(trifluoromethyl)phenyl)pyrazin-2-amine (prepared using the procedure described in Example 68 and appropriate starting materials, reagents and reaction conditions as disclosed in International Publication Number WO2011/143645) (503 mg, 1.09 mmol) in methanol (10 mL) was treated with Dowex resin (100 mg). The reaction mixture was stirred for 12 hours, then the resin was filtered through Celite. The solvent was evaporated from the filtrate to afford the title compound (454 mg, 1.08 mmol, 99%). m.p. 75-77° C.; $^1$H NMR (500 MHz, DMSO-d$_6$): δ 9.89 (1H, s), 8.13 (1H, s), 8.06 (1H, s), 7.94 (2H, d, J=8.6 Hz), 7.64 (2H, d, J=8.6 Hz), 4.60 (2H, br), 4.17-4.10 (2H, m), 3.47-3.44 (1H, m), 3.35 (1H, dd, J=10.8, 5.7 Hz), 3.28 (1H, dd, J=10.8, 5.7 Hz), 2.45 (3H, s), 2.31 (3H, s), 2.03-1.96 (1H, m), 1.71-1.63 (1H, m); MS (ES+): m/e 423.2 (20), 422.1 (100); MS (ES−): m/e 421.2 (20), 420.1 (100).

Example 115

N-(5-methyl-1,3-thiazol-2-yl)-6-[2-(trifluoromethyl) imidazo[1,2-a]pyridin-3-yl]pyridin-2-amine (Cpd 147)

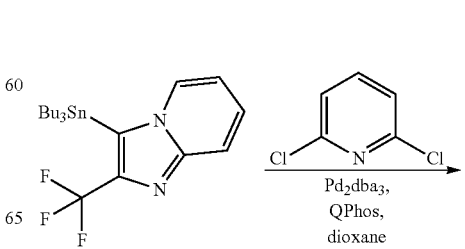

-continued

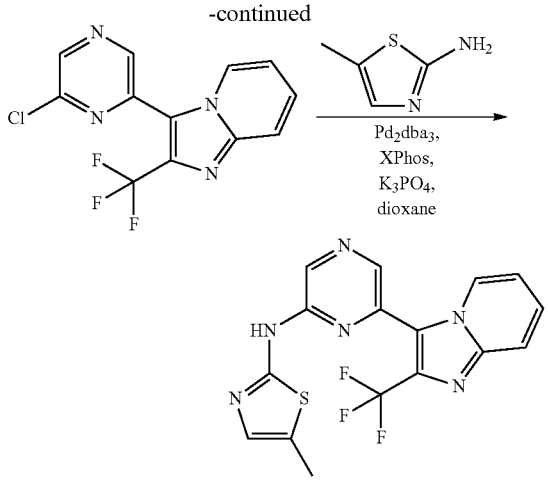

Step 1. A screwtop vial containing 2,6-dichloropyridine (7.28 g, 49.1 mmol), 3-(tributylstannyl)-2-(trifluoromethyl)imidazo[1,2-a]pyridine (5.82 g, 12.2 mmol), tris(dibenzylideneacetone) dipalladium(0) (139 mg, 0.152 mmol) and 1,2,3,4,5-pentaphenyl-1'-(di-tert-butylphosphino)ferrocene (200 mg, 0.281 mmol) in dioxane (30 mL) was degassed by two successive cycles of vacuum pumping and $N_2$ purging. The reaction mixture was heated at 100° C. for 12 hours, cooled and poured into a 1 N aqueous solution of KF, then filtered through Celite and extracted with dichloromethane. The organic extract was dried over $MgSO_4$, then filtered and evaporated. The residue was separated by column chromatography (silica gel, 10:90 ethyl acetate:hexane) to afford the product, 3-(6-chloropyridin-2-yl)-2-(trifluoromethyl)imidazo[1,2-a]pyridine, as a solid (1.984 g, 6.67 mmol, 55%). m.p. 96-97° C.; TLC $R_F$ 0.33 (30:70 ethyl acetate:hexane); $^1$H NMR (500 MHz, CDCl$_3$): δ 8.93 (1H, dt, J=7.1, 1.1 Hz), 7.84 (1H, t, J=7.8 Hz), 7.76 (1H, dt, J=9.1, 1.1 Hz), 7.64 (1H, dd, J=6.9, 0.8 Hz), 7.43-7.39 (2H, m), 7.01 (1H, td, J=6.9, 1.2 Hz).

Step 2. A vial containing a mixture of the obtained intermediate (206.5 mg, 0.694 mmol), 2-amino-5-methylthiazole (159.9 mg, 1.401 mmol), tris(dibenzylideneacetone)dipalladium(0) (34.6 mg, 0.038 mmol), 2-dicyclohexylphosphino-2',4',6'-triisopropylbiphenyl (37.1 mg, 0.078 mmol) and a solution of tripotassium phosphate (314.3 mg, 1.481 mmol) in dioxane (5 mL) was degassed by two successive cycles of vacuum pumping and $N_2$ purging. The reaction mixture was heated at 100° C. for 12 hours, cooled and poured into water, then filtered through Celite and extracted with dichloromethane. The organic extract was dried over $MgSO_4$, then filtered and evaporated. The residue was separated by column chromatography (silica gel, 50:50 ethyl acetate:hexane) to afford the title compound (161 mg, 0.429 mmol, 62%) as a powder. m.p. 270-271° C. TLC $R_F$ 0.11 (50:50 ethyl acetate:hexane); $^1$H NMR (500 MHz, CDCl$_3$): δ 8.54 (1H, dt, J=7.0, 1.0 Hz), 7.89 (1H, dd, J=8.2, 7.6 Hz), 7.81 (1H, dt, J=9.1, 1.1 Hz), 7.42 (1H, ddd, J=9.1, 6.7, 1.3 Hz), 7.37 (1H, d, J=7.5 Hz), 7.21 (1H, d, J=8.2 Hz), 7.05 (1H, d, J=1.2 Hz), 7.94 (1H, td, J=6.7, 1.1 Hz), 2.30 (3H, d, J=1.2 Hz); MS (ES+): m/e 377.2 (30), 376.2 (100); MS (ES−): m/e 375.2 (20), 374.2 (100).

Additional compounds of Formula (I) or a form thereof described herein may be prepared according to the procedure of Example 115 by substituting the appropriate starting materials, reagents and reaction conditions:

| Cpd | Name and Data |
|---|---|
| 101 | 6-[6-methoxy-2-(trifluoromethyl)imidazo[1,2-a]pyridin-3-yl]-N-[4-(trifluoromethoxy)phenyl]pyridin-2-amine<br>$^1$H NMR (DMSO-d$_6$) δ 9.61 (s, 1H), 8.38 (d, J = 1.6 Hz, 1H), 7.84 (td, J = 7.9, 0.9 Hz, 1H), 7.78 (d, J = 8.5 Hz, 2H), 7.74 (d, J = 9.8 Hz, 1H), 7.33 (dd, J = 9.8, 2.2 Hz, 1H), 7.25 (d, J = 8.5 Hz, 2H), 7.11 (d, J = 7.3 Hz, 1H), 6.98 (d, J = 8.5 Hz, 1H), 3.47 (s, 3H); MS m/z 469 (ESI) [M + H]$^+$ |
| 102 | 6-[6-methoxy-2-(trifluoromethyl)imidazo[1,2-a]pyridin-3-yl]-N-[4-(trifluoromethyl)phenyl]pyridin-2-amine<br>$^1$H NMR (DMSO-d$_6$) δ 9.85 (s, 1H), 8.35 (d, J = 2.2 Hz, 1H), 7.82-7.95 (m, 3H), 7.75 (d, J = 9.8 Hz, 1H), 7.58 (d, J = 8.5 Hz, 2H), 7.34 (dd, J = 9.8, 2.5 Hz, 1H), 7.18 (d, J = 7.3 Hz, 1H), 7.05 (d, J = 8.2 Hz, 1H), 3.50 (s, 3H); MS m/z 453 (ESI) [M + H]$^+$ |
| 103 | N-[4-(difluoromethoxy)phenyl]-6-[6-methoxy-2-(trifluoromethyl)imidazo[1,2-a]pyridin-3-yl]pyridin-2-amine<br>$^1$H NMR (DMSO-d$_6$) δ 9.47 (s, 1H), 8.37 (d, J = 1.9 Hz, 1H), 7.81 (t, J = 7.9 Hz, 1H), 7.74 (d, J = 9.8 Hz, 1H), 7.70 (d, J = 9.1 Hz, 2H), 7.33 (dd, J = 9.8, 2.2 Hz, 1H), 7.01-7.17 (m, 3H), 6.94 (d, J = 8.5 Hz, 1H), 7.10 (t, J = 74.4 Hz, 1H), 3.50 (s, 3H); MS m/z 451 (ESI) [M + H]$^+$ |
| 104 | N-(4-methoxyphenyl)-6-[6-methoxy-2-(trifluoromethyl)imidazo[1,2-a]pyridin-3-yl]pyridin-2-amine<br>$^1$H NMR (DMSO-d$_6$) δ 9.07 (s, 1H), 8.32 (dd, J = 2.5, 0.9 Hz, 1H), 7.61-7.68 (m, 2H), 7.45 (d, J = 8.8 Hz, 2H), 7.22 (dd, J = 9.8, 2.2 Hz, 1H), 6.90 (d, J = 7.3 Hz, 1H), 6.78 (dd, J = 8.5, 0.9 Hz, 1H), [6.76 (d, J = 9.1 Hz, 2H), 3.61 (s, 3H), 3.42 (s, 3H); MS m/z 415 (ESI) [M + H]$^+$ |
| 110 | 3-(6-{[4-(trifluoromethoxy)phenyl]amino}pyridin-2-yl)-2-(trifluoromethyl)imidazo[1,2-a]pyridin-6-ol<br>$^1$H NMR (DMSO-d$_6$) δ 9.85 (s, 1H), 9.57 (s, 1H), 8.13 (dd, J = 2.2, 0.9 Hz, 1H), 7.83 (dd, J = 8.5, 7.3 Hz, 1H), 7.76-7.80 (m, 2H), 7.68 (dd, J = 9.8, 0.9 Hz, 1H), 7.18-7.26 (m, 3H), 7.07 (d, J = 7.6 Hz, 1H), 6.99 (dd, J = 8.5, 0.9 Hz, 1H); MS m/z 455 (ESI) [M + H]$^+$ |
| 111 | 2-(trifluoromethyl)-3-(6-{[4-(trifluoromethyl)phenyl]amino}pyridin-2-yl)imidazo[1,2-a]pyridin-6-ol<br>$^1$H NMR (DMSO-d$_6$) δ 9.86 (s, 1H), 9.81 (br. s, 1H), 8.15 (dt, J = 2.2, 0.6 Hz, 1H), 7.85-7.92 (m, 3H), 7.70 (dd, J = 9.8, 0.9 Hz, 1H), 7.56 (d, J = 8.5 Hz, 2H), 7.25 (dd, J = 9.8, 2.5 Hz, 1H), 7.14 (d, J = 7.6 Hz, 1H), 7.06 (dd, J = 8.5, 0.9 Hz, 1H); MS m/z 439 (ESI) [M + H]$^+$ |
| 112 | 4-({6-[6-methoxy-2-(trifluoromethyl)imidazo[1,2-a]pyridin-3-yl]pyridin-2-yl}amino)phenyl formate<br>$^1$H NMR (DMSO-d$_6$) δ 9.49 (s, 1H), 8.49 (s, 1H), 8.38 (dd, J = 2.2, 0.9 Hz, 1H), 7.82 (dd, J = 8.4, 7.4 Hz, 1H), 7.72 (d, J = 9.1 Hz, 3H), 7.32 (dd, J = 9.8, 2.5 Hz, 1H), 7.06-7.11 (m, 3H), 6.96 (dd, J = 8.5, 0.9 Hz, 1H), 3.51 (s, 3H); MS m/z 429 (ESI) [M + H]$^+$ |
| 113 | 4-({6-[6-methoxy-2-(trifluoromethyl)imidazo[1,2-a]pyridin-3-yl]pyridin-2-yl}amino)phenol<br>$^1$H NMR (DMSO-d$_6$) δ 9.11 (s, 1H), 9.07 (s, 1H), 8.50 (d, J = 1.9 Hz, 1H), 7.68-7.82 (m, 2H), 7.44 (d, J = 8.8 Hz, 2H), 7.35 (dd, J = 9.8, 2.2 Hz, 1H), 7.01 (d, J = 7.3 Hz, 1H), 6.87 (d, J = 8.5 Hz, 1H), 6.72 (d, J = 8.5 Hz, 2H), 3.38 (s, 3H); MS m/z 401 (ESI) [M + H]$^+$ |
| 148 | N-(4-methyl-1,3-thiazol-2-yl)-6-[2-(trifluoromethyl)imidazo[1,2-a]pyridin-3-yl]pyridin-2-amine<br>$^1$H NMR (500 MHz, CDCl$_3$): δ 8.59 (1H, d, J = 7.0 Hz), 7.87 (1H, dd, J = 8.1, 7.7 Hz), 7.79 (1H, d, J = 9.2 Hz), 7.40 (1H, ddd, J = 9.1, 6.7, 1.2 Hz), 7.37 (1H, d, J = 7.6 Hz), 7.12 (1H, d, J = 8.2 Hz), 6.92 (1H, td, J = 7.0, 1.0 Hz), 6.32 (1H, d, J = 1.1 Hz), 2.38 (3H, d, J = 0.9 Hz); m.p. 259-261° C.; MS m/z 376.2 (ESI) [M + H]$^+$ |

-continued

| Cpd | Name and Data |
|---|---|
| 149 | N-(4,5-dimethyl-1,3-thiazol-2-yl)-6-[2-(trifluoromethyl)imidazo[1,2-a]pyridin-3-yl]pyridin-2-amine<br>$^1$H NMR (500 MHz, CDCl$_3$): δ 8.38 (1H, dt, J = 7.0, 1.1 Hz), 7.96 (1H, dd, J = 8.1, 7.7 Hz), 7.83 (1H, dt, J = 7.9, 1.2 Hz), 7.48-7.42 (2H, m), 7.36 (1H, d, J = 8.3 Hz), 6.98-6.94 (1H, m), 2.31 (3H, s), 2.17 (3H, s); m.p. 227-228° C.; MS m/z 390.2 (ESI) [M + H]$^+$ |
| 411 | 6-[6-fluoro-2-(trifluoromethyl)imidazo[1,2-a]pyridin-3-yl]-N-[4-(trifluoromethyl)phenyl]pyridin-2-amine<br>$^1$H NMR (DMSO-d$_6$) δ 9.82 (s, 1H), 8.92 (ddd, J = 4.9, 2.2, 0.9 Hz, 1H), 7.93 (ddd, J = 9.8, 5.4, 0.9 Hz, 1H), 7.84-7.91 (m, 3H), 7.67 (ddd, J = 10.1, 7.9, 2.5 Hz, 1H), 7.57 (d, J = 8.5 Hz, 2H), 7.19 (d, J = 7.3 Hz, 1H), 7.07 (dd, J = 8.5, 0.9 Hz, 1H); MS m/z 441 (ESI) [M + H]$^+$ |

Example 116

6-(6,8-difluoro-2-methylimidazo[1,2-a]pyridin-3-yl)-N-[4-(trifluoromethyl)phenyl]pyrazin-2-amine (Cpd 254)

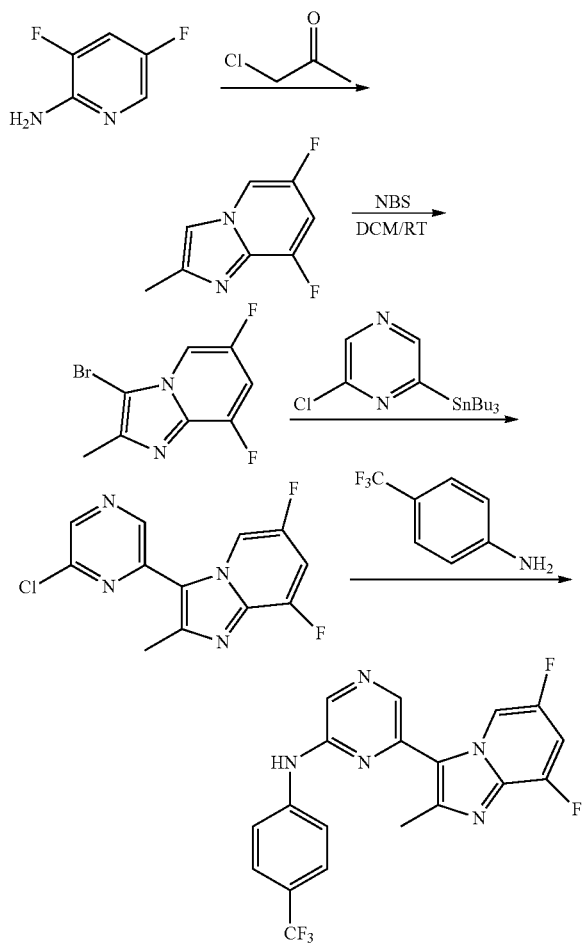

Step 1. A mixture of 2-amino-3,5-difluoropyridine (5.509 g, 42.3 mmol) and chloroacetone (4.00 mL, 54.0 mmol) was heated at 110° C. for 4 hours, then cooled. The resulting precipitate was collected by filtration, washed with ether and dried under vacuum. The residue was taken up in ethanol (50 mL) and heated at reflux overnight. The reaction mixture was allowed to cool, then poured into water (150 mL) and extracted with ethyl acetate (200 mL). The extract was washed with water (200 mL) and saturated brine (100 mL), dried over sodium sulfate, then filtered and evaporated. The residue was separated by silica gel column chromatography (20:80 ethyl acetate:hexane) to afford 6,8-difluoro-2-methylimidazo[1,2-a]pyridine (6.19 g, 36.8 mmol, 87%) as a solid. m.p. 122-123° C.; TLC R$_F$ 0.16 (30:70 ethyl acetate:hexane); H NMR (500 MHz, CDCl$_3$): δ 7.86-7.84 (1H, m), 7.39 (1H, q, J=2.4 Hz), 6.80 (1H, ddd, J=10.2, 8.8, 2.0 Hz), 2.44 (3H, d, J=0.8 Hz). MS (ES+): m/e 170.1 (10), 169.0 (100).

Step 2. A solution of the obtained intermediate (1.783 g, 10.6 mmol) in dichloromethane (20 mL) was treated with N-bromosuccinimide (1.93 g, 10.8 mmol). The reaction mixture was stirred at room temperature for 12 hours, then diluted with four volumes of ethyl acetate and washed with water and saturated brine. The residue was dried over MgSO$_4$, filtered and evaporated, then eluted through a short column of silica gel (30:70 ethyl acetate:hexane) to afford 3-bromo-6,8-difluoro-2-methylimidazo[1,2-a]pyridine (first crop from ethyl:pentane: 2.083 g, 8.43 mmol, 80%) as a waxy solid. m.p. 115-116° C.; TLC R$_F$ 0.27 (30:70 ethyl acetate:hexane); H NMR (500 MHz, CDCl$_3$): δ 7.88 (1H, ddd, J=3.6, 2.1, 1.0 Hz), 6.92 (1H, ddd, J=10.0, 8.8, 2.1 Hz), 2.48 (3H, s); MS (ES+): m/e 248.9 (100), 246.9 (99).

Step 3. A screwtop vial containing the obtained intermediate (906 mg, 3.67 mmol), 2-chloro-6-tributylstannylpyrazine (1.753 g, 4.34 mmol) and tetrakis(triphenylphosine)palladium (212 mg, 0.183 mmol) in toluene (12 mL) was degassed by two successive cycles of vacuum pumping and N$_2$ purging. The reaction mixture was heated at 100° C. for 12 hours, then cooled and poured into a 1 N aqueous solution of KF. The resulting mixture was filtered through Celite and extracted with dichloromethane. The organic extract was dried over MgSO$_4$, then filtered and evaporated. The residue was separated by column chromatography (silica gel, 30:70 ethyl acetate-hexane) to afford 3-(6-chloropyrazin-2-yl)-6,8-difluoro-2-methylimidazo[1,2-a]pyridine (80 mg, 0.285 mmol, 8%) as a powder. m.p. 160-161° C.; TLC R$_F$ 0.08 (30:70 ethyl acetate:hexane); $^1$H NMR (500 MHz, CDCl$_3$): δ 9.29-9.27 (1H, m), 8.85 (1H, s), 8.53 (1H, s), 7.12 (1H, ddd, J=9.5, 8.3, 2.0 Hz), 2.82 (3H, s); MS (ES+): m/e 283.1 (35), 281.1 (100).

Step 4. A vial containing a mixture of the obtained intermediate (50 mg, 0.178 mmol), 4-trifluoromethylaniline (70 µL, 0.55 mmol), tris(dibenzylideneacetone)dipalladium (0) (10 mg, 0.011 mmol), 2-dicyclohexylphosphino-2',4',6'-triisopropylbiphenyl (11 mg, 0.023 mmol) and a solution of tripotassium phosphate (83 mg, 0.39 mmol) in dioxane (2 mL) was degassed by two successive cycles of vacuum pumping and N$_2$ purging. The reaction mixture was heated at 100° C. for 12 hours, cooled and poured into water, then filtered through Celite and extracted with dichloromethane. The organic extract was dried over MgSO$_4$, then filtered and evaporated. The residue was separated by column chromatography (silica gel, 50:50 ethyl acetate:hexane) to afford the title compound (11 mg, 0.027 mmol, 15%) as a solid. TLC R$_F$ 0.05 (50:50 ethyl acetate-hexane); $^1$H NMR (500 MHz, CDCl$_3$): δ 9.08-9.07 (1H, m), 8.39 (1H, s), 8.25 (1H, s), 7.63 (4H, s), 7.06-7.03 (1H, m), 2.78 (3H, s); MS (ES+): m/e 407.2 (20), 406.1 (100); MS (ES-): m/e 405.1 (20), 404.1 (100).

Additional compounds of Formula (I) or a form thereof described herein may be prepared according to the procedure of Example 116 by substituting the appropriate starting materials, reagents and reaction conditions:

| Cpd | Name and Data |
|---|---|
| 255 | N-[4-(difluoromethoxy)phenyl]-6-(6,8-difluoro-2-methylimidazo[1,2-a]pyridin-3-yl)pyrazin-2-amine<br>$^1$H NMR (500 MHz, CDCl$_3$): δ 9.10 (1H, dd, J = 3.0, 1.1 Hz), 8.33 (1H, s), 8.14 (1H, s), 7.47 (2H, d, J = 8.9 Hz), 7.18 (2H, d, J = 8.9 Hz), 7.14-7.09 (1H, m), 6.71 (1H, br), 6.51 (1H, t, J = 73.8 Hz), 2.78 (3H, s); MS m/z 404.1 (ESI) [M + H]$^+$ |

Example 117

6-(2-ethyl-4-methyl-1H-imidazol-1-yl)-N-[4-(trifluoromethyl)phenyl]pyrazin-2-amine (Cpd 179)

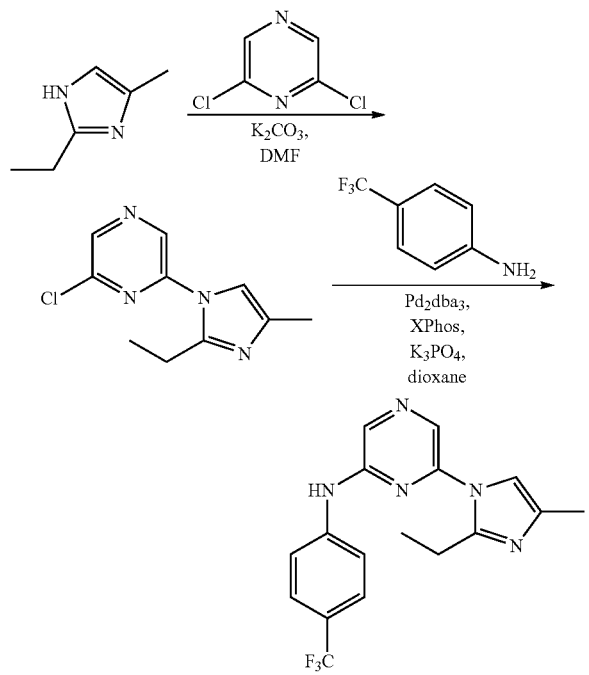

Step 1. A solution of 2,6-dichloropyrazine (3.528 g, 23.7 mmol), 2-ethyl-4-methylimidazole (2.66 g, 24.1 mmol) and potassium carbonate (3.35 g, 24.2 mmol) in DMF (30 mL) was heated at 80° C. overnight, then cooled and diluted with four volumes of ethyl acetate. The mixture was washed with water (3×100 mL) and saturated brine (100 mL), dried over sodium sulfate, then filtered and evaporated. The residue was separated by column chromatography (silica gel, 30:70 ethyl acetate:hexane) to afford 2-chloro-6-(2-ethyl-4-methyl-1H-imidazol-1-yl)pyrazine (1.453 g, 6.53 mmol, 28%) as a waxy solid. m.p. 65-66° C.; $^1$H NMR (500 MHz, CDCl$_3$): δ 8.51 (1H, d, J=0.4 Hz), 8.47 (1H, d, J=0.4 Hz), 7.00 (1H, d, J=1.0 Hz), 2.94 (2H, q, J=7.5 Hz), 2.21 (3H, d, J=1.0 Hz), 1.30 (3H, t, J=7.5 Hz); MS (ES+): m/e 225.15 (34), 223.13 (100).

Step 2. A vial containing a mixture of 2-chloro-6-(2-ethyl-4-methyl-1H-imidazol-1-yl)pyrazine (282 mg, 1.27 mmol), 4-trifluoromethylaniline (500 μL, 3.94 mmol), tris(dibenzylideneacetone)dipalladium(0) (58 mg, 0.063 mmol), 2-dicyclohexylphosphino-2',4',6'-triisopropylbiphenyl (61 mg, 0.128 mmol) and a solution of tripotassium phosphate (593 mg, 2.79 mmol) in dioxane (8 mL) was degassed by two successive cycles of vacuum pumping and N$_2$ purging. The reaction mixture was heated at 100° C. for 12 hours, cooled and poured into water, then filtered through Celite and extracted with dichloromethane. The organic extract was dried over MgSO$_4$, then filtered and evaporated. The residue was separated by column chromatography (silica gel, 50:50 ethyl acetate:hexane) to afford the title compound (300 mg, 0.864 mmol, 68%) as a powder. m.p. 207-208° C.; TLC R$_F$ 0.06 (50:50 ethyl acetate-hexane); H NMR (500 MHz, CDCl$_3$): δ 8.33 (1H, s), 8.09 (1H, s), 7.98 (1H, br), 7.70 (2H, d, J=8.5 Hz), 7.60 (2H, d, J=8.5 Hz), 7.01 (1H, d, J=1.1 Hz), 2.98 (2H, q, J=7.5 Hz), 2.31 (3H, d, J=1.1 Hz), 1.32 (3H, t, J=7.5 Hz); MS (ES+): m/e 349.3 (20), 348.5 (100); MS (ES-): m/e 347.3 (20), 346.3 (100).

Additional compounds of Formula (I) or a form thereof described herein may be prepared according to the procedure of Example 117 by substituting the appropriate starting materials, reagents and reaction conditions:

| Cpd | Name and Data |
|---|---|
| 180 | N-[4-(difluoromethoxy)phenyl]-6-(2-ethyl-4-methyl-1H-imidazol-1-yl)pyrazin-2-amine<br>$^1$H NMR (500 MHz, CDCl$_3$): δ 8.19 (1H, s), 8.02 (1H, s), 7.51 (2H, d, J = 8.9 Hz), 7.14 (2H, d, J = 8.9 Hz), 6.98 (1H, d, J = 1.0 Hz), 6.49 (1H, d, J = 73.8 Hz), 2.95 (2H, q, J = 7.5 Hz), 2.29 (3H, d, J = 1.0 Hz), 1.29 (3H, t, J = 7.5 Hz); m.p. 168-169° C.; MS m/z 346.3 (ESI) [M + H]+ |

Example 118

6-(imidazo[1,2-a]pyridin-3-yl)-N-[4-(trifluoromethyl)phenyl]pyrazin-2-amine (Cpd 235)

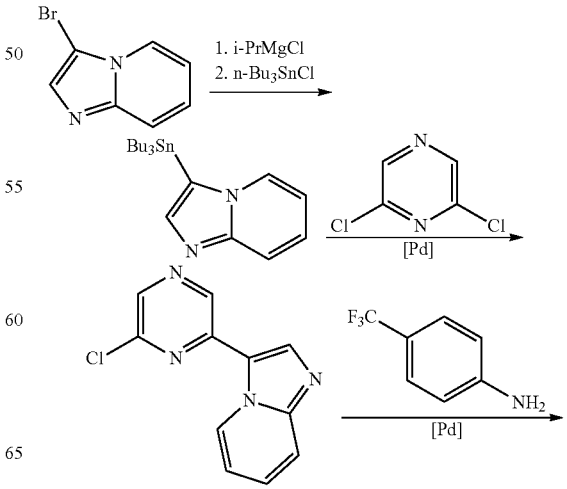

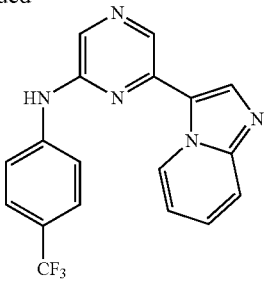

Step 1. To 3-bromoimidazo[1,2-a]pyridine (324 mg, 1.65 mmol) was added THF (3 mL). The mixture was cooled under nitrogen to −40° C. (external temperature) and a solution of i-PrMgCl×LiCl was added (14%, ~1 N solution in THF, 1.7 mL, 1.7 mmol). The mixture was reacted for 20 minutes, then n-Bu$_3$SnCl (0.46 mL, 1.7 mmol) was added. The mixture was reacted for 40 minutes at −40° C., then partially concentrated in a flow of dry nitrogen at 100° C. (oil bath) to 50% of the original volume to provide 3-(tributylstannyl)imidazo[1,2-a]pyridine in solution.

Step 2. The obtained intermediate was carried forward (using the procedure described in Example 42 and Example 44 and appropriate starting materials, reagents and reaction conditions) to provide the title compound as a green solid.

$^1$H NMR (500 MHz, DMSO-d$_6$) δ: 10.07 (s, 1H), 9.53 (dt, J=7.0, 1.2 Hz, 1H), 8.69 (s, 1H), 8.46 (s, 1H), 8.18 (s, 1H), 7.79-7.83 (m, J=8.8 Hz, 2H), 7.76 (dt, J=8.8, 2.2 Hz, 1H), 7.68-7.73 (m, J=8.8 Hz, 2H), 7.43 (ddd, J=9.1, 6.7, 1.6 Hz, 1H), 7.07 (td, J=6.9, 1.6 Hz, 1H); MS m/z 356 (ESI) [M+H]$^+$.

Additional compounds of Formula (I) or a form thereof described herein may be prepared according to the procedure of Example 118 by substituting the appropriate starting materials, reagents and reaction conditions:

| Cpd | Name and Data |
|---|---|
| 477 | N-[4-(difluoromethoxy)phenyl]-6-(imidazo[1,2-a]pyridin-3-yl)pyrazin-2-amine<br>$^1$H NMR (DMSO-d$_6$) δ: 9.63 (s, 1H), 9.56 (dt, J = 6.9, 1.1 Hz, 1H), 8.60 (s, 1H), 8.45 (s, 1H), 8.06 (s, 1H), 7.73 (dt, J = 9.1, 1.3 Hz, 1H), 7.59-7.66 (m, 2H), 7.41 (ddd, J = 9.1, 6.6, 1.3 Hz, 1H), 7.21-7.25 (m, J = 8.8 Hz, 2H), 7.20 (t, J = 74.4 Hz, 1H), 7.02 (td, J = 6.9, 1.6 Hz, 1H); MS m/z 354 (ESI) [M + H]$^+$ |

Example 119

3-methyl-6-[2-(trifluoromethyl)imidazo[1,2-a]pyridin-3-yl]-N-[4-(trifluoromethyl)phenyl]pyridin-2-amine (Cpd 269)

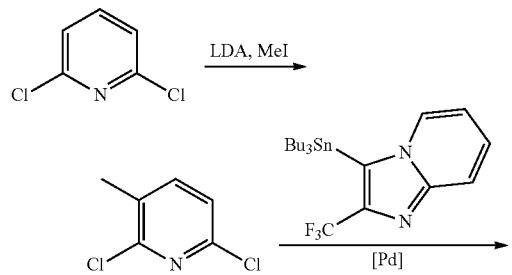

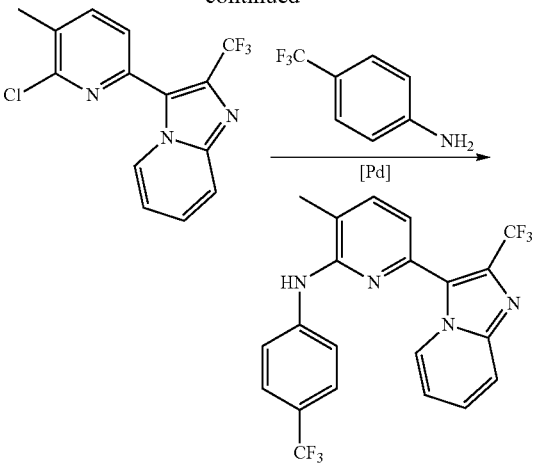

Step 1. To diisopropylamine (0.71 mL, 5 mmol) was added THF (6 mL). The mixture was cooled under nitrogen to −70° C. (external temperature) and n-BuLi (2.2 M in c-Hex, 2.2 mL, 5 mmol) was added. The mixture was allowed to stand for 2 minutes, then a solution of 2,6-dichloropyridine was added (656 mg, 4.4. mmol in 3 mL of THF) dropwise via cannula. The mixture was reacted for 1.5 hours at −70° C. (external temperature), then MeI was added (0.28 mL, 4.5 mmol). The mixture was reacted for 25 minutes, then quenched with an aqueous solution of ammonium chloride and extracted with ether. The crude material was purified by chromatography on silicagel (gradient ethyl acetate:hexane 1:10 to 1:2) and very briefly dried in vacuum to provide 2,6-dichloro-3-methylpyridine (80% pure according to H-NMR analysis) as a low-melting white wax (758 mg). $^1$H NMR (DMSO-d$_6$) δ: 7.89 (dd, J=7.9, 0.6 Hz, 1H), 7.50 (d, J=7.9 Hz, 1H), 2.32 (s, 3H).

Step 2 and 3. The obtained intermediates were carried forward (using the procedure described in Example 45 and appropriate materials, reagents and reaction conditions) to provide two isomers: 3-(6-chloro-5-methylpyridin-2-yl)-2-(trifluoromethyl)imidazo[1,2-a]pyridine (less polar using silicagel and EtOAc/hexane) and 3-(6-chloro-3-methylpyridin-2-yl)-2-(trifluoromethyl)imidazo[1,2-a]pyridine (more polar). The less polar isomer was carried forward to provide the title compound. $^1$H NMR (DMSO-d$_6$) δ: 8.63 (d, J=6.9 Hz, 1H), 8.52 (s, 1H), 7.87 (d, J=8.8 Hz, 2H), 7.75 (d, J=7.6 Hz, 1H), 7.78 (d, J=9.1 Hz, 1H), 7.47-7.59 (m, 3H), 7.15 (d, J=7.6 Hz, 1H), 7.07 (td, J=6.9, 1.3 Hz, 1H), 2.41 (s, 3H); MS m/z 437 (ESI) [M+H]$^+$.

Example 120

6-(5,6-difluoro-2-methyl-1H-benzimidazol-1-yl)-N-[3-fluoro-4-(trifluoromethoxy)phenyl]pyrazin-2-amine (Cpd 301)

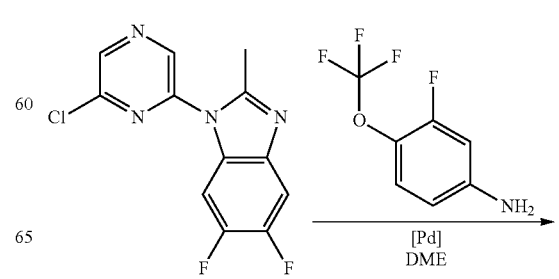

-continued

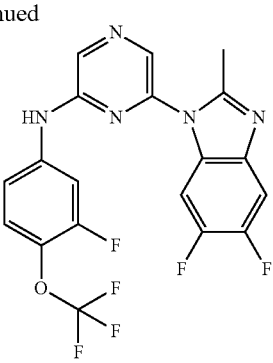

To a mixture of 1-(6-chloropyrazin-2-yl)-5,6-difluoro-2-methyl-1H-benzo[d]imidazole (140 mg, 0.5 mmol) in DME was added $K_3PO_4$ (360 mg, 0.85 mmol), $Pd_2dba_3$ (23 mg, 0.0125 mmol) and X-Phos (24 mg, 0.025 mmol). The reaction mixture was stirred at 100° C. for 4 hours, then cooled to room temperature. The product was filtered and washed with DME, then dried under reduced pressure to give the title compound as a white solid (195 mg, 92%). $^1$H NMR (500 MHz, DMSO-$d_6$) δ 10.37 (br. s., 1H), 8.40 (d, J=2.52 Hz, 2H), 7.91 (dd, J=13.24, 2.52 Hz, 1H), 7.66-7.81 (m, 2H), 7.52 (t, J=8.67 Hz, 1H), 7.44 (dt, J=8.99, 1.34 Hz, 1H), 2.58-2.70 (S, 3H); MS m/z 440.4 (ESI) [M+H]$^+$.

Example 121

N-[4-(trifluoromethyl)phenyl]-6-[2-(trifluoromethyl)pyrazolo[1,5-a]pyridin-3-yl]pyrazin-2-amine (Cpd 62)

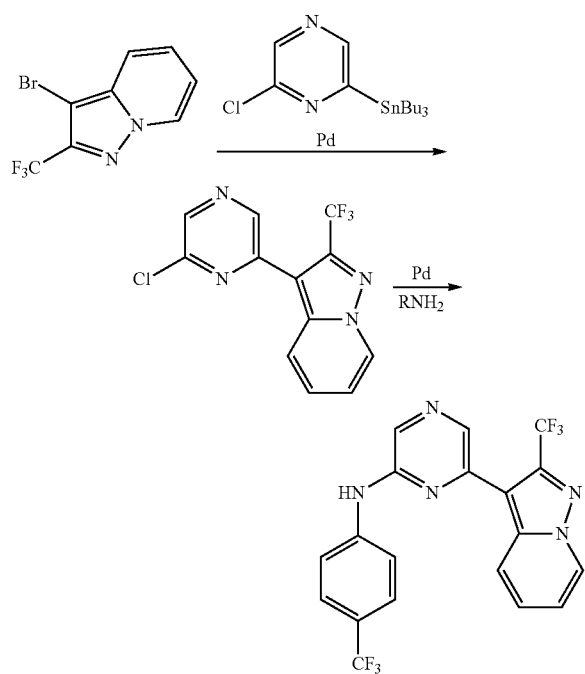

Step 1. To 3-bromo-2-(trifluoromethyl)pyrazolo[1,5-a]pyridine (500 mg, 1.88 mmol) was added 2-chloro-6-(tributylstannyl)pyrazine (1.14 g, 2.83 mmol), ACP (41 mg, 0.11 mmol), QPhos (161 mg, 0.22 mmol) and dioxane (12 mL).

The reaction tube was degassed for 10 minutes, then sealed and heated at 110° C. for 2 hours. The product 3-(6-chloropyrazin-2-yl)-2-(trifluoromethyl)pyrazolo[1,5-a]pyridine was isolated by chromatography (215 mg, 39%). $^1$H NMR (CHLOROFORM-d) δ: 8.86 (s, 1H), 8.58 (dt, J=7.1, 1.0 Hz, 1H), 8.53 (s, 1H), 8.31 (dt, J=9.1, 1.3 Hz, 1H), 7.47 (ddd, J=9.1, 6.8, 1.1 Hz, 1H), 7.10 (td, J=6.9, 1.3 Hz, 1H).

Step 2. The obtained intermediate was carried forward (using the procedure described in Example 2 and appropriate materials, reagents and reaction conditions) to provide the title compound. $^1$H NMR (500 MHz, CHLOROFORM-d) δ 8.60 (d, J=6.94 Hz, 1H), 8.49 (br. s., 1H), 8.33 (s, 1H), 8.10 (d, J=9.14 Hz, 1H), 8.04 (br. s., 1H), 7.80 (d, J=8.51 Hz, 2H), 7.59 (d, J=7.88 Hz, 2H), 7.38 (dd, J=6.62, 8.20 Hz, 1H), 7.09 (t, J=6.78 Hz, 1H); MS m/z 424 (ESI) [M+H]$^+$.

Additional compounds of Formula (I) or a form thereof described herein may be prepared according to the procedure of Example 121 by substituting the appropriate starting materials, reagents and reaction conditions:

| Cpd | Name and Data |
|---|---|
| 63 | N-[4-(trifluoromethoxy)phenyl]-6-[2-(trifluoromethyl)pyrazolo[1,5-a]pyridin-3-yl]pyrazin-2-amine<br>$^1$H NMR (500 MHz, CHLOROFORM-d) δ 8.56 (td, J = 1.06, 7.01 Hz, 1H), 8.33 (s, 1H), 8.25 (s, 1H), 8.06 (td, J = 1.10, 9.14 Hz, 1H), 7.57-7.64 (m, 2H), 7.32 (ddd, J = 1.10, 6.78, 9.14 Hz, 2H), 7.20 (dd, J = 0.79, 8.98 Hz, 2H), 7.04 (dt, J = 1.26, 6.94 Hz, 1H);<br>MS m/z 440 (ESI) [M + H]$^+$ |
| 72 | N-[4-(difluoromethoxy)phenyl]-6-[2-(trifluoromethyl)pyrazolo[1,5-a]pyridin-3-yl]pyrazin-2-amine<br>$^1$H NMR (500 MHz, CHLOROFORM-d) δ 8.57 (td, J = 0.90, 7.25 Hz, 1H), 8.34 (s, 1H), 8.18 (s, 1H), 8.07 (td, J = 0.90, 9.14 Hz, 1H), 7.55 (d, J = 7.88 Hz, 2H), 7.33 (dd, J = 6.94, 8.51 Hz, 1H), 7.14 (d, J = 8.83 Hz, 2H), 7.05 (dt, J = 0.90, 6.94 Hz, 1H), 6.84 (br. s, 1H), 6.50 (t, J = 74.40 Hz, 1H); MS m/z 422 (ESI) [M + H]$^+$ |
| 74 | N-(4-methoxyphenyl)-6-[2-(trifluoromethyl)pyrazolo[1,5-a]pyridin-3-yl]pyrazin-2-amine<br>$^1$H NMR (CHLOROFORM-d) δ: 8.55 (dt, J = 6.9, 1.1 Hz, 1H), 8.27 (s, 1H), 8.19 (s, 1H), 8.12 (dt, J = 9.1, 1.3 Hz, 1H), 7.58 (br. s, 1H), 7.43-7.49 (m, 2H), 7.33 (ddd, J = 9.1, 6.8, 1.1 Hz, 1H), 7.05 (td, J = 6.9, 1.3 Hz, 1H), 6.89-6.95 (m, 2H), 3.84 (s, 3H); MS m/z 386 (ESI) [M + H]$^+$ |
| 75 | N-(4-methylphenyl)-6-[2-(trifluoromethyl)pyrazolo[1,5-a]pyridin-3-yl]pyrazin-2-amine<br>$^1$H NMR (CHLOROFORM-d) δ: 8.57 (d, J = 6.9 Hz, 1H), 8.45 (br. s., 1H), 8.13-8.20 (m, 2H), 8.03 (br. s., 1H), 7.45-7.54 (m, J = 8.5 Hz, 2H), 7.36 (ddd, J = 9.0, 6.8, 0.9 Hz, 1H), 7.14-7.22 (m, J = 8.5 Hz, 2H), 7.07 (td, J = 6.9, 1.3 Hz, 1H), 2.36 (s, 3H); MS m/z 370 (ESI) [M + H]$^+$ |
| 92 | N-(2,2-difluoro-1,3-benzodioxol-5-yl)-6-[2-(trifluoromethyl)pyrazolo[1,5-a]pyridin-3-yl]pyrazin-2-amine<br>$^1$H NMR (CHLOROFORM-d) δ: 8.57 (d, J = 7.3 Hz, 1H), 8.36 (s, 1H), 8.11 (s, 1H), 8.05 (d, J = 9.1 Hz, 1H), 7.56 (d, J = 2.2 Hz, 1H), 7.34 (ddd, J = 9.1, 6.9, 1.1 Hz, 1H), 7.01-7.11 (m, 3H), 6.70 (br. s., 1H); MS m/z 436 (ESI) [M + H]$^+$ |

Example 122

6-(5-fluoro-2-methyl-2H-indazol-3-yl)-N-[4-(trifluoromethyl)phenyl]pyrazin-2-amine (Cpd 416)

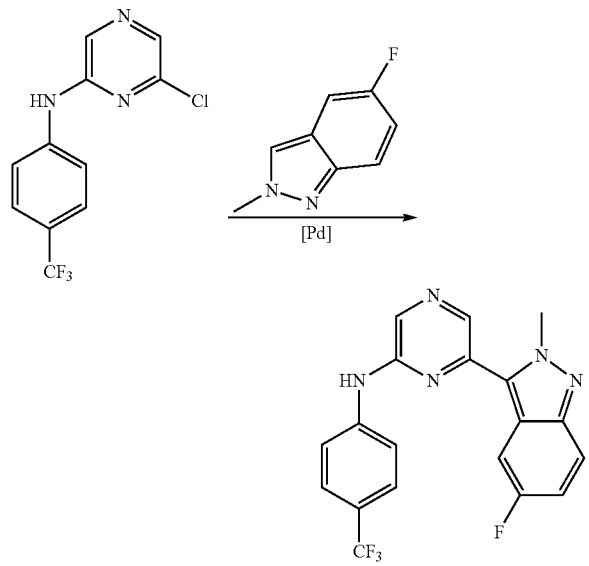

To 6-chloro-N-(4-(trifluoromethyl)phenyl)pyrazin-2-amine (164 mg, 0.6 mmol) was added 5-fluoro-2-methyl-2H-indazole (75 mg, 0.5 mmol), Pd(OAc)$_2$ (6 mg, 0.025 mmol), PPh$_3$ (16 mg, 0.06 mmol), CsOAc (112 mg, 1 mmol) and DMA (2 mL). The mixture was stirred under nitrogen at 100° C. for 16 hours. The title compound (30 mg) was isolated by chromatography (silicagel, EtOAc/hexane). MS m/z 386 (theoretical) [M+H]$^+$.

Additional compounds of Formula (I) or a form thereof described herein may be prepared according to the procedure of Example 122 by substituting the appropriate starting materials, reagents and reaction conditions:

| Cpd | Name and Data |
|---|---|
| 422 | 6-(2-cyclopropylimidazo[1,2-a]pyrimidin-3-yl)-N-[4-(trifluoromethyl)phenyl]pyrazin-2-amine<br>MS m/z 397 (theoretical) [M + H]$^+$ |
| 453 | 6-(6-fluoro-2-methylimidazo[1,2-a]pyrimidin-3-yl)-N-[4-(trifluoromethyl)phenyl]pyrazin-2-amine<br>MS m/z 389 (theoretical) [M + H]$^+$ |

BIOLOGICAL EXAMPLES

The following biological examples demonstrate the usefulness of the compounds of Formula (I) or a form thereof described herein to inhibit Bmi-1 function and reduce the level of Bmi-1.

Example 1

Sandwich ELISA Assay

Cell Seeding and Compound Treatment (Day 1):
HT-1080 cells were seeded at 8000 cells/well (50 µL) in 96-well tissue culture plates. After the cells became adherent (3-4 hours), 2× diluted stocks of test compounds in 50 µL DMEM containing 1% DMSO (final DMSO concentration was 0.5%) were added and the plates were incubated at 37° C. under 5% CO$_2$ for 40-48 hours.

ELISA Plate First Antibody Preparation (Day 2):
The First Antibody (Millipore Mouse, monoclonal to mouse Bmi-1, clone F6, catalog #05-637) diluted to 2 g/mL in PBS was added (100 µL) to each well of a Nunc MaxiSorp 96-well ELISA plate. The plate was covered with a plate seal and allowed to stand overnight.

Cell Lysate Preparation (Day 3):
Fresh Lysis buffer (1×) was prepared on the day of the assay as follows: 1 mM EDTA, 150 mM NaCl, 0.5% Triton-X 100, 10 mM NaF, 20 mM B-Glycerophosphate, 1 mM DTT (in PBS, pH 7.2-7.4) and HALT protease inhibitor cocktail (lx) (Pierce #78410).

Lysis Buffer (1×, 40 µL) was added to each well and the plate was shaken for 5-10 minutes on an orbital shaker to allow cell lysis, then diluent (1% BSA in PBS in 0.5% NP40) (100 µL) was added to each well.

A standard curve was prepared at the following Bmi-1 concentrations: 8000, 4000, 2000, 1000, 500, 250, 125 and 0 pg/mL. The Bmi-1 Recombinant Protein Standard (Novus Biologicals PCGF4 Recombinant Protein (P01), catalog # H00000648-P01) used to prepare the standard curve was stored at −80° C. On first thaw, the Recombinant Protein Standard was diluted to 10 µg/L in Blocking Buffer (1% BSA in PBS; BSA: Fisher Scientific Catalog #1600-100). Aliquots were taken and refrozen at −80° C. The aliquots may be kept at 4° C. and reused after first thaw, but only within 1-2 weeks. The Recombinant Protein Standard contains a GST-fusion tag that appears at approximately 70 Kda on Western Blot.

ELISA Assay (Day 3):
The prepared ELISA plate was washed 3× with Wash Buffer (0.05% Tween-20 in PBS). The final wash was removed from the plate and the plate was blotted dry. Blocking Buffer (300 µL) (1% BSA in PBS) was added to each well. The plate was covered with a plate seal and incubated at room temperature for 1 hour. The blocked plate was washed 3× with Wash Buffer, then the final wash was removed and the plate was blotted dry. The previously prepared samples and standards were added (100 L/well) and the plate was covered with a plate seal and incubated at 4° C. overnight.

ELISA Assay (Day 4):
The prepared ELISA plate was removed from incubation and allowed to stand at room temperature for 30 minutes, then washed and blotted dry. The Second Antibody (Cell Signaling Rabbit anti-Bmi-1, Cat #2830) diluted to 1:600 in Blocking Buffer was added (100 µL) to each well, except as needed for background control wells. The plate was covered with a plate seal and incubated for 1.5 hrs at room temperature.

The ELISA plate was washed and blotted dry as previously described. The Third Antibody (Cell Signaling HRP conjugated anti-rabbit IgG (CellSignaling, Cat #:7074) diluted to 1:300 in Blocking Buffer was added (100 µL) to each well, except as needed for background control wells. The plate was incubated for 1 hr at room temperature.

The plate was washed and blotted dry, then a previously prepared TMB substrate (TMB substrate kit, Pierce catalog #34021) (prepared by mixing kit reagents 1:1) (100 µL) was added per well. The plate was incubated for 20-30 minutes at room temperature in the dark, then Stop Solution (2 M sulfuric acid in water) (50 μL) was added per well. The plates were read at OD450 (experimental) and OD570 (reference).

As shown in Table 1, an ELISA $EC_{50}$ value for Bmi-1 protein provided by test compounds of Formula (I) or a form thereof described herein between >0.1 M and <3.0 M is indicated by one star (\*), an $EC_{50}$ value between >0.01 M to <0.1 M is indicated by two stars (\*\*), an $EC_{50}$ value between >0.001 M to <0.01 M is indicated by three stars (\*\*\*) and an $EC_{50}$ value of <0.001 M is indicated by four stars (\*\*\*\*).

TABLE 1

| Cpd | $EC_{50}$ |
|---|---|
| 1 | ** |
| 2 | ** |
| 3 | *** |
| 4 | *** |
| 5 | **** |
| 6 | *** |
| 7 | **** |
| 8 | *** |
| 9 | * |
| 10 | *** |
| 11 | ** |
| 12 | **** |
| 13 | ** |
| 14 | * |
| 15 | ** |
| 16 | ** |
| 17 | *** |
| 18 | *** |
| 19 | * |
| 20 | ** |
| 21 | *** |
| 22 | *** |
| 23 | ** |
| 24 | **** |
| 25 | *** |
| 26 | * |
| 27 | *** |
| 28 | *** |
| 29 | ** |
| 30 | *** |
| 31 | ** |
| 32 | *** |
| 33 | ** |
| 34 | * |
| 35 | ** |
| 36 | * |
| 37 | ** |
| 38 | ** |
| 39 | * |
| 40 | * |
| 41 | * |
| 42 | *** |
| 43 | *** |
| 44 | ** |
| 45 | ** |
| 46 | ** |
| 47 | *** |
| 48 | *** |
| 49 | * |
| 50 | ** |
| 51 | *** |
| 52 | ** |
| 53 | ** |
| 54 | ** |
| 55 | ** |
| 56 | *** |
| 57 | **** |
| 58 | *** |
| 59 | * |
| 60 | ** |
| 61 | *** |
| 62 | ** |
| 63 | ** |
| 64 | ** |
| 65 | * |
| 66 | * |
| 67 | ** |
| 68 | * |
| 69 | *** |
| 70 | ** |
| 71 | *** |
| 72 | *** |
| 73 | ** |
| 74 | **** |
| 75 | *** |
| 76 | * |
| 77 | ** |
| 78 | * |
| 79 | ** |
| 80 | * |
| 81 | * |
| 82 | ** |
| 83 | ** |
| 84 | *** |
| 85 | ** |
| 86 | ** |
| 87 | * |
| 88 | * |
| 89 | * |
| 90 | ** |
| 91 | * |
| 92 | * |
| 93 | ** |
| 94 | * |
| 95 | ** |
| 96 | * |
| 97 | * |
| 98 | ** |
| 99 | * |
| 100 | * |
| 101 | ** |
| 102 | ** |
| 103 | ** |
| 104 | ** |
| 105 | ** |
| 106 | **** |
| 107 | * |
| 108 | ** |
| 109 | ** |
| 110 | * |
| 111 | ** |
| 112 | * |
| 113 | * |
| 114 | * |
| 115 | ** |
| 116 | ** |
| 117 | * |
| 118 | *** |
| 119 | **** |
| 120 | ** |
| 121 | *** |
| 122 | * |
| 123 | * |
| 124 | ** |
| 125 | * |
| 126 | * |
| 127 | ** |
| 128 | *** |
| 129 | *** |
| 130 | *** |
| 131 | *** |
| 132 | ** |
| 133 | ** |
| 134 | * |
| 135 | ** |
| 136 | ** |
| 137 | * |
| 138 | ** |
| 139 | ** |
| 140 | ** |
| 141 | * |
| 142 | ** |

TABLE 1-continued

| Cpd | EC$_{50}$ |
|---|---|
| 143 | **** |
| 144 | * |
| 145 | ** |
| 146 | ** |
| 147 | * |
| 148 | ** |
| 149 | * |
| 150 | ** |
| 151 | *** |
| 152 | ** |
| 153 | *** |
| 154a | ** |
| 155 | ** |
| 156 | *** |
| 157 | * |
| 158 | ** |
| 159 | *** |
| 160 | ** |
| 161 | ** |
| 162 | * |
| 163 | * |
| 164 | ** |
| 165 | *** |
| 166 | * |
| 167 | * |
| 168 | ** |
| 169 | ** |
| 170 | * |
| 171 | ** |
| 172 | ** |
| 173 | * |
| 174 | * |
| 175 | *** |
| 176 | ** |
| 177 | ** |
| 178 | * |
| 179 | * |
| 180 | * |
| 181 | ** |
| 182 | ** |
| 183 | ** |
| 184 | * |
| 185 | * |
| 186 | * |
| 187 | *** |
| 188 | ** |
| 189 | ** |
| 190 | ** |
| 191 | *** |
| 192 | ** |
| 193 | ** |
| 194 | ** |
| 195 | * |
| 196 | ** |
| 197 | ** |
| 198 | ** |
| 199 | *** |
| 200 | * |
| 201 | *** |
| 202 | **** |
| 203 | * |
| 204 | ** |
| 205 | ** |
| 206 | * |
| 207 | * |
| 208 | ** |
| 209 | ** |
| 210 | ** |
| 211 | * |
| 212 | * |
| 213 | * |
| 214 | **** |
| 215 | *** |
| 216 | * |
| 217 | *** |
| 218 | ** |
| 219 | ** |
| 220 | ** |

TABLE 1-continued

| Cpd | EC$_{50}$ |
|---|---|
| 221 | *** |
| 222 | ** |
| 223 | * |
| 224 | ** |
| 225 | * |
| 226 | * |
| 227 | ** |
| 228 | *** |
| 229 | *** |
| 230 | ** |
| 231 | ** |
| 232 | *** |
| 233 | *** |
| 234 | ** |
| 235 | * |
| 236 | ** |
| 237 | *** |
| 238 | * |
| 239 | ** |
| 240 | ** |
| 241 | ** |
| 242 | ** |
| 243 | * |
| 244 | *** |
| 245 | *** |
| 246 | *** |
| 247 | *** |
| 248 | *** |
| 249 | ** |
| 250 | ** |
| 251 | ** |
| 252 | * |
| 253 | *** |
| 254 | *** |
| 255 | *** |
| 256 | * |
| 257 | * |
| 258 | *** |
| 259 | *** |
| 260 | *** |
| 261 | ** |
| 262 | ** |
| 263 | *** |
| 264 | *** |
| 265 | ** |
| 266 | ** |
| 267 | *** |
| 268 | ** |
| 269 | * |
| 270 | *** |
| 271 | *** |
| 272 | ** |
| 273 | *** |
| 274 | ** |
| 275 | ** |
| 276 | ** |
| 277 | * |
| 278 | * |
| 279 | * |
| 280 | ** |
| 281 | * |
| 282 | * |
| 283 | ** |
| 284 | * |
| 285 | ** |
| 286 | ** |
| 287 | ** |
| 288 | ** |
| 289a | ** |
| 290 | * |
| 291 | ** |
| 292 | *** |
| 293 | ** |
| 294 | * |
| 295 | ** |
| 296 | ** |
| 297 | * |
| 298 | * |

TABLE 1-continued

| Cpd | EC$_{50}$ |
|---|---|
| 299 | * |
| 300 | ** |
| 301 | * |
| 302 | * |
| 303 | * |
| 304 | ** |
| 305 | * |
| 306 | * |
| 307 | * |
| 308 | * |
| 309 | *** |
| 310 | ** |
| 311 | *** |
| 312 | ** |
| 313 | *** |
| 314 | * |
| 315 | *** |
| 316 | *** |
| 317 | ** |
| 318 | * |
| 319 | ** |
| 320 | ** |
| 321 | ** |
| 322 | * |
| 323 | *** |
| 324 | ** |
| 325 | ** |
| 326 | ** |
| 327 | *** |
| 328 | *** |
| 329 | ** |
| 330 | ** |
| 331 | * |
| 332 | ** |
| 333 | *** |
| 334 | ** |
| 335 | *** |
| 336 | *** |
| 337 | **** |
| 338 | *** |
| 339 | ** |
| 340 | * |
| 341 | * |
| 342 | ** |
| 343 | *** |
| 344 | * |
| 345 | ** |
| 346 | ** |
| 347 | ** |
| 348 | *** |
| 349 | ** |
| 350 | ** |
| 351 | ** |
| 352 | *** |
| 353 | * |
| 354 | * |
| 355 | * |
| 356 | * |
| 357 | * |
| 358 | ** |
| 359 | * |
| 360 | ** |
| 361 | *** |
| 362 | *** |
| 363 | * |
| 364 | ** |
| 365 | * |
| 366 | * |
| 367 | ** |
| 368 | * |
| 369 | * |
| 370 | * |
| 371 | * |
| 372 | * |
| 373 | ** |
| 374 | ** |
| 375 | * |
| 376 | ** |

TABLE 1-continued

| Cpd | EC$_{50}$ |
|---|---|
| 377 | ** |
| 378 | ** |
| 379 | ** |
| 380 | ** |
| 381 | ** |
| 382 | *** |
| 383 | ** |
| 384 | * |
| 385 | * |
| 386 | * |
| 387 | * |
| 388 | ** |
| 389 | * |
| 390 | ** |
| 391 | * |
| 392 | * |
| 393 | ** |
| 394 | ** |
| 395 | * |
| 396 | ** |
| 397 | * |
| 398 | * |
| 399 | *** |
| 400 | * |
| 401 | * |
| 402 | ** |
| 403 | ** |
| 404 | * |
| 405 | * |
| 406 | ** |
| 407 | * |
| 408 | ** |
| 409 | *** |
| 410 | ** |
| 411 | ** |
| 412 | *** |
| 413 | *** |
| 414 | ** |
| 415 | ** |
| 416 | ** |
| 417 | ** |
| 418 | ** |
| 419 | *** |
| 420 | *** |
| 421 | ** |
| 422 | ** |
| 423 | ** |
| 424 | * |
| 425 | ** |
| 426 | * |
| 427 | ** |
| 428 | *** |
| 429 | *** |
| 430 | * |
| 431 | ** |
| 432 | ** |
| 433 | * |
| 434 | ** |
| 435 | ** |
| 436 | ** |
| 437 | *** |
| 438 | ** |
| 439 | ** |
| 440 | * |
| 441 | *** |
| 442 | *** |
| 443 | ** |
| 444 | ** |
| 445 | ** |
| 446 | * |
| 447 | ** |
| 448 | ** |
| 449 | * |
| 450 | ** |
| 451 | *** |
| 452 | ** |
| 453 | ** |
| 454 | *** |

TABLE 1-continued

| Cpd | EC$_{50}$ |
|---|---|
| 455 | ** |
| 456 | * |
| 457 | * |
| 458 | * |
| 459 | ** |
| 460 | ** |
| 461 | ** |
| 462 | ** |
| 463 | * |
| 464 | ** |
| 465 | * |
| 466 | ** |
| 467 | *** |
| 468 | ** |
| 469 | ** |
| 470 | * |
| 471 | * |
| 472 | *** |
| 473 | **** |
| 474 | ** |
| 475 | ** |
| 476 | ** |
| 477 | * |
| 478 | ** |
| 479 | *** |
| 480 | * |
| 481 | ** |
| 482 | ** |
| 483 | ** |
| 484 | ** |
| 485 | * |
| 486 | ** |
| 487 | ** |
| 488 | ** |
| 489 | *** |
| 490 | ** |
| 491 | * |
| 492 | ** |
| 493 | * |
| 494 | ** |
| 495 | ** |
| 496 | ** |
| 497 | *** |
| 498 | *** |
| 499 | ** |
| 500 | ** |
| 501 | ** |
| 502 | ** |
| 503 | ** |
| 504 | ** |
| 505 | ** |
| 506 | ** |
| 507 | ** |
| 508 | ** |
| 509 | ** |
| 510 | ** |
| 511 | ** |
| 512 | ** |
| 513 | ** |
| 514 | * |
| 515 | ** |
| 516 | ** |
| 517 | * |
| 518 | ** |
| 519 | ** |
| 520 | *** |
| 521 | *** |
| 522 | ** |
| 523 | ** |
| 524 | * |
| 525 | ** |
| 526 | ** |
| 527 | ** |
| 528 | ** |
| 529 | * |
| 530 | ** |
| 531 | ** |
| 532 | ** |

TABLE 1-continued

| Cpd | EC$_{50}$ |
|---|---|
| 533 | ** |
| 534 | ** |
| 535 | ** |
| 536 | ** |
| 537 | ** |
| 538 | *** |
| 539 | ** |
| 540 | **** |
| 541 | *** |
| 542 | ** |
| 543 | * |
| 544 | **** |
| 545 | * |
| 546 | *** |
| 547 | * |
| 548 | ** |
| 549 | * |
| 550 | * |
| 551 | * |
| 552 | **** |
| 553 | *** |
| 554 | ** |
| 555 | * |
| 556 | ** |
| 557 | * |
| 558 | ** |
| 559 | * |
| 560 | * |
| 561 | *** |
| 562 | *** |
| 563 | ** |
| 564 | * |
| 565 | **** |
| 566 | *** |
| 567 | ** |
| 568 | * |
| 569 | ** |
| 570 | * |
| 571 | ** |
| 572 | *** |
| 573 | * |
| 574 | * |
| 575 | ** |
| 576 | * |
| 577 | * |
| 578 | * |
| 579 | * |
| 580 | ** |
| 581 | *** |
| 582 | *** |
| 583 | *** |
| 584 | ** |
| 585 | * |
| 586 | *** |
| 587 | *** |
| 588 | ** |
| 589 | ** |
| 590 | ** |
| 591 | * |
| 592 | **** |
| 593 | *** |
| 594 | * |
| 595 | ** |
| 596 | *** |
| 597 | ** |
| 598 | * |
| 599 | ** |
| 600 | ** |
| 601 | ** |
| 602 | ** |
| 603 | * |
| 604 | * |
| 605 | * |
| 606 | * |
| 607 | ** |
| 608 | ** |
| 609 | * |
| 610 | ** |

TABLE 1-continued

| Cpd | EC$_{50}$ |
|---|---|
| 611 | *** |
| 612 | ** |
| 613 | ** |
| 614 | ** |
| 615 | * |
| 616 | *** |
| 617 | ** |
| 618 | * |
| 619 | *** |
| 620 | * |
| 621 | **** |
| 622 | *** |
| 623 | *** |
| 624 | ** |
| 625 | * |
| 626 | * |
| 627 | **** |
| 628 | **** |
| 629 | *** |
| 630 | * |
| 631 | * |
| 632 | *** |
| 633 | ** |
| 634 | ** |
| 635 | *** |
| 636 | ** |
| 637 | ** |
| 638 | * |
| 639 | * |
| 640 | ** |
| 641 | ** |
| 642 | ** |
| 643 | * |
| 644 | ** |
| 645 | ** |
| 646 | * |
| 647 | ** |
| 648 | *** |
| 649 | *** |
| 650 | * |
| 651 | * |
| 652 | ** |
| 653 | ** |
| 654 | ** |
| 655 | * |
| 656 | ** |
| 657 | ** |
| 658 | ** |
| 659 | * |
| 660 | ** |
| 661 | ** |
| 662 | * |
| 663 | ** |
| 664 | * |
| 665 | * |
| 666 | * |
| 667 | * |
| 668 | * |
| 669 | * |
| 670 | * |
| 671 | * |
| 672 | * |
| 673 | * |
| 674 | * |
| 675 | ** |
| 676 | ** |
| 677 | * |
| 678 | ** |
| 679 | ** |
| 680 | ** |
| 681 | * |
| 682 | * |
| 683 | ** |

The following publications are incorporated by reference into the present application for any and all purposes to the same extent as if each individual publication was fully set forth herein:

1. M. J. Alkema, J. Wiegant, A. K. Raap, A. Berns, L. M. van, *Hum. Mol. Genet.* 2, 1597 (1993).
2. Y. Haupt, M. L. Bath, A. W. Harris, J. M. Adams, *Oncogene* 8, 3161-3164 (1993).
3. J. M. Adams, S. Cory, *Cancer Surv.* 15, 119 (1992).
4. Y. Haupt, G. Barri, J. M. Adams, *Mol. Biol. Rep.* 17, 17 (1992).
5. L. M. van, M. Frasch, E. Wientjens, A. Berns, *Nature* 353, 353 (1991).
6. L. M. van et al., *Cell* 65, 737 (1991).
7. J. J. Jacobs et al., *Genes Dev.* 13, 2678 (1999).
8. B. Scheijen, J. Jonkers, D. Acton, A. Berns, *J. Virol.* 71, 9 (1997).
9. J. J. Jacobs, K. Kieboom, S. Marino, R. A. DePinho, L. M. van, *Nature* 397, 164 (1999).
10. P. R. Solomon et al., *Indian J. Med. Res.* 127, 52 (2008).
11. B. Quesnel, C. Preudhomme, P. Fenaux, *Leuk. Lymphoma* 22, 11 (1996).
12. S. Faderl et al., *Cytokines Cell Mol. Ther.* 5, 159 (1999).
13. S. Faderl et al., *Clin. Cancer Res.* 5, 1855 (1999).
14. S. W. Bruggeman et al., *Cancer Cell* 12, 328 (2007).
15. S. J. Kuerbitz, J. Malandro, N. Compitello, S. B. Baylin, J. R. Graff, *Cell Growth Differ.* 10, 27 (1999).
16. S. Liu et al., *Cancer Res.* 66, 6063 (2006).
17. J. Wei, L. Zhai, J. Xu, H. Wang, *J. Biol. Chem.* 281, 22537 (2006).
18. M. Courel, L. Friesenhahn, J. A. Lees, *Dev. Dyn.* 237, 1232 (2008).
21. D. F. Dukers et al., *Am. J. Pathol.* 164, 873 (2004).
22. F. M. Raaphorst et al., *Am. J. Pathol.* 157, 709 (2000).
23. M. Sanchez-Beato et al., *J. Pathol.* 204, 528 (2004).
24. S. Bea et al., *Blood* 93, 4365 (1999).
25. M. S. Lindstrom, U. Klangby, K. G. Wiman, *Oncogene* 20, 2171 (2001).
26. F. J. van Kemenade et al., *Blood* 97, 3896 (2001).
27. F. M. Raaphorst, C. J. Meijer, A. P. Otte, *Cancer Res.* 62, 618 (2002).
28. F. M. Raaphorst et al., *Am. J. Pathol.* 164, 533 (2004).
29. V. Fernandez, E. Hartmann, G. Ott, E. Campo, A. Rosenwald, *J. Clin. Oncol.* 23, 6364 (2005).
30. B. T. Spike, K. F. Macleod, *Cell Cycle* 4, 42 (2005).
31. A. Dutton et al., *Blood* 109, 2597 (2007).
32. M. Chowdhury et al., *Leukemia* 21, 1116 (2007).
33. W. A. Dik et al., *Leukemia* 19, 1948 (2005).
34. M. Sawa et al., *Int. J. Hematol.* 82, 42-47 (2005).
35. J. Yang et al., *Proc. Natl. Acad. Sci. U.S.A* 104, 10494 (2007).
36. G. D. van et al., *Exp. Hematol.* 35, 1538 (2007).
37. J. C. van Galen et al., *J. Clin. Pathol.* 60, 167 (2007).
38. R. Kuppers, U. Klein, M. L. Hansmann, K. Rajewsky, *N. Engl. J. Med.* 341, 1520 (1999).
39. A. A. Alizadeh et al., *Nature* 403, 503 (2000).
40. C. P. Hans et al., *Blood* 103, 275 (2004).
41. W. P. de Boer, J. J. Oudejans, C. J. Meijer, J. Lankelma, *Bioinformatics.* 19, 2000 (2003).
42. S. Bea et al., *Cancer Res.* 61, 2409 (2001).
43. G. V. Glinsky, O. Berezovska, A. B. Glinskii, *J. Clin. Invest* 115, 1503-1521 (2005).
44. K. Mihara et al., *Rinsho Ketsueki* 48, 659 (2007).
45. J. B. Ames, K. Collett, L. A. Akslen, *Histopathology* 52, 370 (2008).
46. I. B. Engelsen et al., *Br. J. Cancer* 98, 1662 (2008).
47. V. Hayry et al., *Acta Neuropathol.* (2008).

48. V. Hayry et al., *Neuropathol. Appl. Neurobiol.* (2008).
49. K. H. Huang, J. H. Liu, X. X. Li, L. B. Song, M. S. Zeng, *Nan. Fang Yi. Ke. Da. Xue. Xue. Bao.* 27, 973 (2007).
50. E. M. Hurt, B. T. Kawasaki, G. J. Klarmann, S. B. Thomas, W. L. Farrar, *Br. J. Cancer* 98, 756 (2008).
51. J. H. Liu et al., *J. Surg. Oncol.* 97, 267 (2008).
52. K. Mihara et al., *Blood* 107, 305 (2006).
53. L. B. Song et al., *Cancer Res.* 66, 6225 (2006).
54. H. Vekony et al., *J. Clin. Pathol.* 61, 744 (2008).
55. H. Wang et al., *J. Cancer Res. Clin. Oncol.* 134, 535 (2008).
56. R. H. Breuer et al., *Neoplasia.* 6, 736 (2004).
57. S. Vonlanthen et al., *Br. J. Cancer* 84, 1372 (2001).
58. S. K. Li et al., *J. Biol. Chem.* (2008).
59. W. J. Guo, S. Datta, V. Band, G. P. Dimri, *Mol. Biol. Cell* 18, 536 (2007).
60. K. Nowak et al., *Nucleic Acids Res.* 34, 1745 (2006).
61. H. Cui et al., *Am. J. Pathol.* 170, 1370-1378 (2007).
62. G. P. Dimri et al., *Cancer Res.* 62, 4736 (2002).
63. M. K. Kang et al., *Br. J. Cancer* 96, 126 (2007).
64. J. H. Kim et al., *Cancer Lett.* 203, 217 (2004).
65. J. H. Kim et al., *Breast* 13, 383-388 (2004).
66. H. Koga et al., *Oncogene* 18, 3799 (1999).
67. N. Kozakowski, A. Soleiman, J. Pammer, *Pathol. Oncol. Res.* 14, 9 (2008).
68. F. Zhang, L. Sui, T. Xin, *Exp. Oncol.* 30, 70 (2008).
69. L. Liu, L. G. Andrews, T. O. Tollefsbol, *Oncogene* 25, 4370-4375 (2006).
76. Park et al., 2003, *Nature.* 423:302-305.
77. Lessard et al., 2003, *Nature* 423:255-260.
78. Wiederschain et al., 2007, *Mol Cell Biol.* 27(13):4968-4967.
79. Reinisch et al., 2006, *Histol Histopathol.* 21:1143-1149.
80. Breuer et al., 2005, *Lung Cancer.* 48:299-306.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the scope of the claims presented herein.

What is claimed is:
1. A compound of Formula (I):

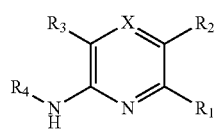

(I)

or a form thereof, wherein
R$_1$ is bicyclic heteroaryl or bicyclic heterocyclyl selected from the group consisting of 1H-indolyl, 4,5,6,7-tetrahydro-2H-indazolyl, 1H-benzimidazolyl, imidazo[2,1-b][1,3]thiazolyl, pyrazolo[1,5-a]pyridinyl, pyrazolo[1,5-c]pyrimidinyl, imidazo[1,2-a]pyridinyl, 5,6,7,8-tetrahydroimidazo[1,2-a]pyridinyl, 1H-imidazo[4,5-b]pyridinyl, 1H-imidazo[4,5-c]pyridinyl, 4,5,6,7-tetrahydro-3H-imidazo[4,5-c]pyridinyl, imidazo[1,2-a]pyrazinyl, imidazo[1,2-a]pyrimidinyl, 7H-purinyl and quinolinyl, substituted on a carbon atom ring member with one, two, three or four R$_6$ substituents or on a nitrogen atom ring member with an oxygen atom substituent to form an N-oxide;

R$_2$ and R$_3$ are independently hydrogen, cyano, halo, C$_{1-8}$ alkyl, amino, C$_{1-8}$ alkyl-amino or (C$_{1-8}$alkyl)$_2$-amino;

R$_4$ is aryl substituted with one, two, three or four R$_7$ substituents;

X is N—R$_8$;

R$_6$ is independently selected from the group consisting of cyano, halo, nitro, hydroxyl, C$_{1-8}$ alkyl, halo-C$_{1-8}$ alkyl, hydroxyl-C$_{1-8}$ alkyl, C$_{1-8}$ alkoxy-C$_{1-8}$ alkyl, halo-C$_{1-8}$ alkoxy, C$_{2-8}$ alkenyl, carboxyl, C$_{1-8}$ alkyl-amino-C$_{1-8}$ alkyl, hydroxyl-C$_{1-8}$ alkyl-amino, C$_{1-8}$ alkyl-thio, C$_{1-8}$alkyl-carbonyl, C$_{1-8}$alkyl-carbonyl-oxy-C$_{1-8}$alkyl, and C$_{3-14}$ cycloalkyl, wherein C$_{3-14}$ cycloalkyl is optionally substituted with one, two, three or four halo, C$_{1-8}$ alkyl, halo-C$_{1-8}$ alkyl, hydroxyl-C$_{1-8}$ alkyl, C$_{1-8}$ alkoxy, halo-C$_{1-8}$ alkoxy, hydroxyl-C$_{1-8}$ alkoxy or carboxyl substituents;

R$_7$ is independently selected from the group consisting of cyano, halo, hydroxyl, nitro, C$_{1-8}$ alkyl, halo-C$_{1-8}$alkyl, hydroxyl-C$_{1-8}$alkyl, C$_{1-8}$alkoxy, halo-C$_{1-8}$alkoxy, C$_{2-8}$alkenyl, C$_{2-8}$ alkynyl, formyl, C$_{1-8}$alkyl-carbonyl, halo-C$_{1-8}$alkyl-carbonyl, C$_{1-8}$ alkyl-thio, halo-C$_{1-8}$ alkyl-thio, C$_{1-8}$ alkyl-amino, C$_{1-8}$ alkoxy-carbonyl, amino-carbonyl, C$_{1-8}$alkyl-amino-carbonyl, hydroxyl-imino-C$_{1-8}$ alkyl, C$_{1-8}$ alkyl-sulfonyl, B(OR$_{10}$)$_2$, and C$_{3-14}$ cycloalkyl, wherein C$_{3-14}$ cycloalkyl is optionally substituted with one, two, three or four halo or C$_{1-8}$ alkyl substituents;

R$_8$ is absent or an oxygen atom, wherein, when present, the oxygen atom forms an N-oxide with the nitrogen atom of attachment; and, R$_{10}$ is independently hydrogen or C$_{1-8}$ alkyl;

wherein the form of the compound is selected from the group consisting of a salt, ester, hydrate, solvate, chelate, clathrate, isotopologue, stereoisomer, racemate, enantiomer, diastereomer and tautomer thereof.

2. A compound or a form thereof selected from the group consisting of:
6-(1H-benzimidazol-1-yl)-N-(4-methoxyphenyl)pyrazin-2-amine
6-(1H-benzimidazol-1-yl)-N-(4-iodophenyl)pyrazin-2-amine
N-(4-methoxyphenyl)-6-[2-(trifluoromethyl)imidazo[1,2-a]pyridin-3-yl]pyrazin-2-amine
6-[2-(trifluoromethyl)imidazo[1,2-a]pyridin-3-yl]-N-[4-(trifluoromethyl)phenyl]pyrazin-2-amine
N-(3-fluoro-4-methoxyphenyl)-6-[2-(trifluoromethyl)imidazo[1,2-a]pyridin-3-yl]pyrazin-2-amine
N-(4-fluorophenyl)-6-[2-(trifluoromethyl)imidazo[1,2-a]pyridin-3-yl]pyrazin-2-amine
N-(4-chlorophenyl)-6-[2-(trifluoromethyl)imidazo[1,2-a]pyridin-3-yl]pyrazin-2-amine
N-[4-(trifluoromethoxy)phenyl]-6-[2-(trifluoromethyl)imidazo[1,2-a]pyridin-3-yl]pyrazin-2-amine
N-(3-fluoro-4-methoxyphenyl)-6-(2-methyl-1H-benzimidazol-1-yl)pyrazin-2-amine
6-(2-methyl-1H-benzimidazol-1-yl)-N-[4-(trifluoromethyl)phenyl]pyrazin-2-amine
6-[2-(trifluoromethyl)-1H-benzimidazol-1-yl]-N-[4-(trifluoromethyl)phenyl]pyrazin-2-amine
N-[4-(trifluoromethyl)phenyl]-6-[2-(trifluoromethyl)pyrazolo[1,5-a]pyridin-7-yl]pyrazin-2-amine
6-(2-methyl-1H-benzimidazol-1-yl)-N-[4-(trifluoromethoxy)phenyl]pyrazin-2-amine N-(4-chlorophenyl)-6-(2-methyl-1H-benzimidazol-1-yl)pyrazin-2-amine
N-[4-(difluoromethoxy)phenyl]-6-(2-methyl-1H-benzimidazol-1-yl)pyrazin-2-amine
N-(3-chloro-4-methoxyphenyl)-6-[2-(trifluoromethyl)imidazo[1,2-a]pyridin-3-yl]pyrazin-2-amine
4-({6-[2-(trifluoromethyl)imidazo[1,2-a]pyridin-3-yl]pyrazin-2-yl}amino)benzonitrile
N-[4-(difluoromethoxy)phenyl]-6-[2-(trifluoromethyl)imidazo[1,2-a]pyridin-3-yl]pyrazin-2-amine
N-(4-chloro-3-fluorophenyl)-6-[2-(trifluoromethyl)imidazo[1,2-a]pyridin-3-yl]pyrazin-2-amine
N-(3,4-difluorophenyl)-6-[2-(trifluoromethyl)imidazo[1,2-a]pyridin-3-yl]pyrazin-2-amine
N-(3-chloro-4-methoxyphenyl)-6-(2-methyl-1H-benzimidazol-1-yl)pyrazin-2-amine
N-(3,4-dichlorophenyl)-6-[2-(trifluoromethyl)imidazo[1,2-a]pyridin-3-yl]pyrazin-2-amine
N-(4-bromo-3-fluorophenyl)-6-[2-(trifluoromethyl)imidazo[1,2-a]pyridin-3-yl]pyrazin-2-amine
N-(4-bromo-3-chlorophenyl)-6-[2-(trifluoromethyl)imidazo[1,2-a]pyridin-3-yl]pyrazin-2-amine
N-(4-methoxyphenyl)-6-[2-(trifluoromethyl)-1H-benzimidazol-1-yl]pyrazin-2-amine
N-[4-(difluoromethoxy)phenyl]-6-[2-(trifluoromethyl)-1H-benzimidazol-1-yl]pyrazin-2-amine
6-[6-methoxy-2-(trifluoromethyl)imidazo[1,2-a]pyridin-3-yl]-N-[4-(trifluoromethoxy)phenyl]pyrazin-2-amine
6-[6-methoxy-2-(trifluoromethyl)imidazo[1,2-a]pyridin-3-yl]-N-[4-(trifluoromethyl)phenyl]pyrazin-2-amine
N-(4-methoxyphenyl)-6-[6-methoxy-2-(trifluoromethyl)imidazo[1,2-a]pyridin-3-yl]pyrazin-2-amine
N-[4-(difluoromethoxy)phenyl]-6-[6-methoxy-2-(trifluoromethyl)imidazo[1,2-a]pyridin-3-yl]pyrazin-2-amine
4-({6-[6-methoxy-2-(trifluoromethyl)imidazo[1,2-a]pyridin-3-yl]pyrazin-2-yl}amino)benzonitrile
6-(2-ethyl-1H-benzimidazol-1-yl)-N-[4-(trifluoromethyl)phenyl]pyrazin-2-amine
6-[2-(propan-2-yl)-1H-benzimidazol-1-yl]-N-[4-(trifluoromethyl)phenyl]pyrazin-2-amine
6-(2-propyl-1H-benzimidazol-1-yl)-N-[4-(trifluoromethyl)phenyl]pyrazin-2-amine
6-[2-(methylsulfanyl)-1H-benzimidazol-1-yl]-N-[4-(trifluoromethyl)phenyl]pyrazin-2-amine
6-[6-fluoro-2-(trifluoromethyl)imidazo[1,2-a]pyridin-3-yl]-N-[4-(trifluoromethoxy)phenyl]pyrazin-2-amine
N-[4-(difluoromethoxy)phenyl]-6-[6-fluoro-2-(trifluoromethyl)imidazo[1,2-a]pyridin-3-yl]pyrazin-2-amine
6-[6-fluoro-2-(trifluoromethyl)imidazo[1,2-a]pyridin-3-yl]-N-(4-methoxyphenyl)pyrazin-2-amine
6-[6-fluoro-2-(trifluoromethyl)imidazo[1,2-a]pyridin-3-yl]-N-[4-(trifluoromethyl)phenyl]pyrazin-2-amine
N-(4-nitrophenyl)-6-[2-(trifluoromethyl)imidazo[1,2-a]pyridin-3-yl]pyrazin-2-amine
N-{6-[2-(trifluoromethyl)imidazo[1,2-a]pyridin-3-yl]pyrazin-2-yl}benzene-1,4-diamine
N-methyl-1-(6-{[4-(trifluoromethyl)phenyl]amino}pyrazin-2-yl)-1H-benzimidazol-2-amine
N-[4-(trifluoromethyl)phenyl]-6-[2-(trifluoromethyl)pyrazolo[1,5-a]pyridin-3-yl]pyrazin-2-amine
N-[4-(trifluoromethoxy)phenyl]-6-[2-(trifluoromethyl)pyrazolo[1,5-a]pyridin-3-yl]pyrazin-2-amine
6-[2-(methoxymethyl)-1H-benzimidazol-1-yl]-N-[4-(trifluoromethyl)phenyl]pyrazin-2-amine
[1-(6-{[4-(trifluoromethyl)phenyl]amino}pyrazin-2-yl)-1H-benzimidazol-2-yl]methanol
6-[2-(trifluoromethyl)imidazo[1,2-a]pyrimidin-3-yl]-N-[4-(trifluoromethyl)phenyl]pyrazin-2-amine
N-[4-(methylsulfonyl)phenyl]-6-[2-(trifluoromethyl)imidazo[1,2-a]pyridin-3-yl]pyrazin-2-amine
N-[4-(methylsulfanyl)phenyl]-6-[2-(trifluoromethyl)imidazo[1,2-a]pyridin-3-yl]pyrazin-2-amine
6-[2-(trifluoromethyl)imidazo[1,2-a]pyridin-3-yl]-N-[6-(trifluoromethyl)pyridin-3-yl]pyrazin-2-amine
N-[4-(difluoromethoxy)phenyl]-6-[2-(trifluoromethyl)pyrazolo[1,5-a]pyridin-3-yl]pyrazin-2-amine
6-(2-methyl-1H-benzimidazol-1-yl)-N-[6-(trifluoromethyl)pyridin-3-yl]pyrazin-2-amine
N-(4-methoxyphenyl)-6-[2-(trifluoromethyl)pyrazolo[1,5-a]pyridin-3-yl]pyrazin-2-amine
N-(4-methylphenyl)-6-[2-(trifluoromethyl)pyrazolo[1,5-a]pyridin-3-yl]pyrazin-2-amine
1-(6-{[4-(trifluoromethyl)phenyl]amino}pyrazin-2-yl)-1H-benzimidazol-2-amine
6-(2-methoxy-1H-benzimidazol-1-yl)-N-[4-(trifluoromethyl)phenyl]pyrazin-2-amine
(1S)-1-[1-(6-{[4-(trifluoromethyl)phenyl]amino}pyrazin-2-yl)-1H-benzimidazol-2-yl]ethyl acetate
6-[2-(ethylsulfanyl)-1H-benzimidazol-1-yl]-N-[4-(trifluoromethyl)phenyl]pyrazin-2-amine
6-(2-butyl-1H-benzimidazol-1-yl)-N-[4-(trifluoromethyl)phenyl]pyrazin-2-amine
6-(2-ethoxy-1H-benzimidazol-1-yl)-N-[4-(trifluoromethyl)phenyl]pyrazin-2-amine
6-(2-methyl-1H-imidazo[4,5-b]pyridin-1-yl)-N-[4-(trifluoromethyl)phenyl]pyrazin-2-amine
6-(2-ethyl-1H-imidazo[4,5-b]pyridin-1-yl)-N-[4-(trifluoromethyl)phenyl]pyrazin-2-amine
6-(1-ethyl-3,5-dimethyl-1H-pyrazol-4-yl)-N-[4-(trifluoromethoxy)phenyl]pyrazin-2-amine
N-[4-(difluoromethoxy)phenyl]-6-(2-methyl-1H-imidazo[4,5-b]pyridin-1-yl)pyrazin-2-amine
6-(2-cyclopropylimidazo[1,2-a]pyridin-5-yl)-N-(4-methoxyphenyl)pyrazin-2-amine
6-(2-cyclopropylimidazo[1,2-a]pyridin-5-yl)-N-[4-(trifluoromethoxy)phenyl]pyrazin-2-amine
6-(2-cyclopropylimidazo[1,2-a]pyridin-5-yl)-N-(2,2-difluoro-1,3-benzodioxol-5-yl)pyrazin-2-amine
6-(2-cyclopropylimidazo[1,2-a]pyridin-5-yl)-N-[4-(trifluoromethyl)phenyl]pyrazin-2-amine
6-(2-cyclopropylimidazo[1,2-a]pyridin-5-yl)-N-[4-(difluoromethoxy)phenyl]pyrazin-2-amine
N-(2,2-difluoro-1,3-benzodioxol-5-yl)-6-[2-(trifluoromethyl)imidazo[1,2-a]pyridin-3-yl]pyrazin-2-amine
N-(2,2-difluoro-1,3-benzodioxol-5-yl)-6-[2-(trifluoromethyl)pyrazolo[1,5-a]pyridin-3-yl]pyrazin-2-amine
6-[2-(trifluoromethyl)imidazo[1,2-a]pyrazin-3-yl]-N-[4-(trifluoromethyl)phenyl]pyrazin-2-amine
6-(8-ethyl-7H-purin-7-yl)-N-[4-(trifluoromethyl)phenyl]pyrazin-2-amine
6-(2-methyl-1H-imidazo[4,5-b]pyridin-1-yl)-N-[4-(trifluoromethoxy)phenyl]pyrazin-2-amine
N-(4-methyl-1,3-thiazol-2-yl)-6-[2-(trifluoromethyl)imidazo[1,2-a]pyridin-3-yl]pyrazin-2-amine
N-(3-methyl-1,2-oxazol-5-yl)-6-[2-(trifluoromethyl)imidazo[1,2-a]pyridin-3-yl]pyrazin-2-amine
(1S)-1-[1-(6-{[4-(trifluoromethyl)phenyl]amino}pyrazin-2-yl)-1H-benzimidazol-2-yl]ethanol
N-[4-(trifluoromethoxy)phenyl]-6-[2-(trifluoromethyl)imidazo[1,2-a]pyrimidin-3-yl]pyrazin-2-amine
N-[4-(trifluoromethoxy)phenyl]-6-(1,3,5-trimethyl-1H-pyrazol-4-yl)pyrazin-2-amine N-(4-bromophenyl)-6-(1,3,5-trimethyl-1H-pyrazol-4-yl)pyrazin-2-amine
N-[4-(difluoromethoxy)phenyl]-6-[2-(trifluoromethyl)imidazo[1,2-a]pyrimidin-3-yl]pyrazin-2-amine
6-(2-cyclobutylimidazo[1,2-a]pyridin-5-yl)-N-[4-(trifluoromethyl)phenyl]pyrazin-2-amine
6-(2-cyclobutylimidazo[1,2-a]pyridin-5-yl)-N-[4-(difluoromethoxy)phenyl]pyrazin-2-amine
6-(2-cyclobutylimidazo[1,2-a]pyridin-5-yl)-N-(4-methoxyphenyl)pyrazin-2-amine
6-(2-cyclobutylimidazo[1,2-a]pyridin-5-yl)-N-(2,2-difluoro-1,3-benzodioxol-5-yl)pyrazin-2-amine
6-[6-(trifluoromethyl)imidazo[2,1-b][1,3]thiazol-5-yl]-N-[4-(trifluoromethyl)phenyl]pyrazin-2-amine
N-(4-methoxyphenyl)-6-[6-(trifluoromethyl)imidazo[2,1-b][1,3]thiazol-5-yl]pyrazin-2-amine
N-[4-(trifluoromethoxy)phenyl]-6-[6-(trifluoromethyl)imidazo[2,1-b][1,3]thiazol-5-yl]pyrazin-2-amine
N-[4-(difluoromethoxy)phenyl]-6-[6-(trifluoromethyl)imidazo[2,1-b][1,3]thiazol-5-yl]pyrazin-2-amine
N-phenyl-6-[6-(trifluoromethyl)imidazo[2,1-b][1,3]thiazol-5-yl]pyrazin-2-amine
6-[2-(trifluoromethyl)-1H-imidazo[4,5-b]pyridin-1-yl]-N-[4-(trifluoromethyl)phenyl]pyrazin-2-amine
6-(1-benzyl-2-ethyl-4-methyl-1H-imidazol-5-yl)-N-[4-(trifluoromethyl)phenyl]pyrazin-2-amine
6-(3,5-dimethyl-1,2-oxazol-4-yl)-N-[4-(trifluoromethyl)phenyl]pyrazin-2-amine
N-[4-(trifluoromethyl)phenyl]-6-(1,3,5-trimethyl-1H-pyrazol-4-yl)pyrazin-2-amine
6-(2-cyclopropylimidazo[1,2-a]pyridin-3-yl)-N-[4-(trifluoromethyl)phenyl]pyrazin-2-amine
6-(2-cyclopropylimidazo[1,2-a]pyridin-3-yl)-N-[4-(difluoromethoxy)phenyl]pyrazin-2-amine
6-(2-cyclobutylimidazo[1,2-a]pyridin-3-yl)-N-[4-(trifluoromethyl)phenyl]pyrazin-2-amine methyl 4-{[6-(2-methyl-1H-benzimidazol-1-yl)pyrazin-2-yl]amino}benzoate
6-(2-chloro-1H-benzimidazol-1-yl)-N-[4-(trifluoromethyl)phenyl]pyrazin-2-amine
N-ethyl-1-(6-{[4-(trifluoromethyl)phenyl]amino}pyrazin-2-yl)-1H-benzimidazol-2-amine
N-[4-(trifluoromethoxy)phenyl]-6-[2-(trifluoromethyl)imidazo[1,2-a]pyrazin-3-yl]pyrazin-2-amine
N-[4-(difluoromethoxy)phenyl]-6-[2-(trifluoromethyl)imidazo[1,2-a]pyrazin-3-yl]pyrazin-2-amine
N-[4-(difluoromethoxy)phenyl]-6-(1,3,5-trimethyl-1H-pyrazol-4-yl)pyrazin-2-amine
1-[1-(6-{[4-(trifluoromethyl)phenyl]amino}pyrazin-2-yl)-1H-benzimidazol-2-yl]ethanol
[3-(6-{[4-(trifluoromethyl)phenyl]amino}pyrazin-2-yl)imidazo[1,2-a]pyridin-2-yl]methanol
(4-{[6-(2-methyl-1H-benzimidazol-1-yl)pyrazin-2-yl]amino}phenyl)methanol
1-(4-{[6-(2-methyl-1H-benzimidazol-1-yl)pyrazin-2-yl]amino}phenyl)ethanone
N-[4-(aminomethyl)phenyl]-6-(2-methyl-1H-benzimidazol-1-yl)pyrazin-2-amine
1-(4-{[6-(2-methyl-1H-benzimidazol-1-yl)pyrazin-2-yl]amino}phenyl)ethanol
N-{4-[(1E)-N-hydroxyethanimidoyl]phenyl}-6-(2-methyl-1H-benzimidazol-1-yl)pyrazin-2-amine
1-(6-{[4-(trifluoromethyl)phenyl]amino}pyrazin-2-yl)-1H-benzimidazole-2-carbonitrile
6-(2-methyl-1H-indol-1-yl)-N-[4-(trifluoromethyl)phenyl]pyrazin-2-amine
N-[4-(difluoromethoxy)phenyl]-6-(2-methyl-1H-indol-1-yl)pyrazin-2-amine
N-(4-methoxyphenyl)-6-(2-methyl-1H-indol-1-yl)pyrazin-2-amine
N-(4-cyclopropylphenyl)-6-[2-(trifluoromethyl)imidazo[1,2-a]pyridin-3-yl]pyrazin-2-amine
6-(2-methyl-1H-imidazo[4,5-c]pyridin-1-yl)-N-[4-(trifluoromethyl)phenyl]pyrazin-2-amine
6-[2-(methylsulfanyl)-1H-benzimidazol-1-yl]-N-[4-(trifluoromethoxy)phenyl]pyrazin-2-amine
N-(4-methylphenyl)-6-[2-(trifluoromethyl)imidazo[1,2-a]pyrazin-3-yl]pyrazin-2-amine
6-(1-ethyl-3,5-dimethyl-1H-pyrazol-4-yl)-N-[4-(trifluoromethyl)phenyl]pyrazin-2-amine
6-[1-(ethylsulfonyl)-3,5-dimethyl-1H-pyrazol-4-yl]-N-[4-(trifluoromethyl)phenyl]pyrazin-2-amine
6-(2-ethyl-5,6-difluoro-1H-benzimidazol-1-yl)-N-[4-(trifluoromethyl)phenyl]pyrazin-2-amine
methyl 3-(6-{[4-(difluoromethoxy)phenyl]amino}pyrazin-2-yl)-2-(trifluoromethyl)imidazo[1,2-a]pyridine-6-carboxylate
6-(2-ethyl-4-methyl-1H-imidazol-1-yl)-N-[4-(trifluoromethyl)phenyl]pyrazin-2-amine
N-[4-(difluoromethoxy)phenyl]-6-(2-ethyl-4-methyl-1H-imidazol-1-yl)pyrazin-2-amine
N-[4-(difluoromethoxy)phenyl]-6-[2-(methylsulfanyl)-1H-benzimidazol-1-yl]pyrazin-2-amine
6-(2-cyclopropyl-5,6-difluoro-1H-benzimidazol-1-yl)-N-[4-(trifluoromethyl)phenyl]pyrazin-2-amine
N-methyl-1-(6-{[4-(trifluoromethoxy)phenyl]amino}pyrazin-2-yl)-1H-benzimidazol-2-amine
1-(6-{[4-(trifluoromethoxy)phenyl]amino}pyrazin-2-yl)-1H-benzimidazole-2-carbonitrile
4-{[6-(2-methyl-1H-benzimidazol-1-yl)pyrazin-2-yl]amino}benzamide N-methyl-4-{[6-(2-methyl-1H-benzimidazol-1-yl)pyrazin-2-yl]amino}benzamide
1-(6-{[4-(difluoromethoxy)phenyl]amino}pyrazin-2-yl)-N-methyl-1H-benzimidazol-2-amine
1-(6-{[4-(difluoromethoxy)phenyl]amino}pyrazin-2-yl)-1H-benzimidazole-2-carbonitrile
6-[2-(trifluoromethyl)imidazo[1,2-a]pyridin-3-yl]-N-[5-(trifluoromethyl)pyridin-2-yl]pyrazin-2-amine
6-[2-(methylsulfanyl)imidazo[1,2-a]pyridin-3-yl]-N-[4-(trifluoromethyl)phenyl]pyrazin-2-amine
6-(5,6-dichloro-2-methyl-1H-benzimidazol-1-yl)-N-[4-(trifluoromethoxy)phenyl]pyrazin-2-amine
6-(5,6-dichloro-2-methyl-1H-benzimidazol-1-yl)-N-[4-(trifluoromethyl)phenyl]pyrazin-2-amine
N-[4-(difluoromethoxy)phenyl]-6-(5,6-difluoro-2-methyl-1H-benzimidazol-1-yl)pyrazin-2-amine
2-chloro-N-{6-[2-(trifluoromethyl)imidazo[1,2-a]pyridin-3-yl]pyrazin-2-yl}pyrimidin-5-amine
2-methoxy-N-{6-[2-(trifluoromethyl)imidazo[1,2-a]pyridin-3-yl]pyrazin-2-yl}pyrimidin-5-amine
6-(2-methylimidazo[1,2-a]pyridin-3-yl)-N-[4-(trifluoromethyl)phenyl]pyrazin-2-amine
6-(5-fluoro-2-methyl-1H-benzimidazol-1-yl)-N-[4-(trifluoromethyl)phenyl]pyrazin-2-amine
N-[4-(difluoromethoxy)phenyl]-6-(5-fluoro-2-methyl-1H-benzimidazol-1-yl)pyrazin-2-amine
6-(5-fluoro-2-methyl-1H-benzimidazol-1-yl)-N-[4-(trifluoromethoxy)phenyl]pyrazin-2-amine
4-{6-[2-(trifluoromethyl)imidazo[1,2-a]pyridin-3-yl]pyrazin-2-yl}amino)phenol
N-[3-fluoro-4-(trifluoromethyl)phenyl]-6-[2-(trifluoromethyl)imidazo[1,2-a]pyridin-3-yl]pyrazin-2-amine N-[3-fluoro-4-(trifluoromethyl)phenyl]-6-(2-methyl-1H-benzimidazol-1-yl)pyrazin-2-amine
6-[2-(trifluoromethyl)imidazo[1,2-a]pyridin-3-yl]-N-{4-[(trifluoromethyl)sulfanyl]phenyl}pyrazin-2-amine
2,2,2-trifluoro-1-[4-({6-[2-(trifluoromethyl)imidazo[1,2-a]pyridin-3-yl]pyrazin-2-yl}amino)phenyl]ethanone
[3-(6-{[4-(trifluoromethoxy)phenyl]amino}pyrazin-2-yl)imidazo[1,2-a]pyridin-2-yl]methanol
(3-{6-[(4-methylphenyl)amino]pyrazin-2-yl}imidazo[1,2-a]pyridin-2-yl)methanol
[3-(6-{[4-(difluoromethoxy)phenyl]amino}pyrazin-2-yl)imidazo[1,2-a]pyridin-2-yl]methanol
6-(6-chloro-2-methyl-1H-benzimidazol-1-yl)-N-[4-(trifluoromethoxy)phenyl]pyrazin-2-amine
6-(6-chloro-2-methyl-1H-benzimidazol-1-yl)-N-[4-(difluoromethoxy)phenyl]pyrazin-2-amine
6-(5-chloro-2-methyl-1H-benzimidazol-1-yl)-N-[4-(trifluoromethoxy)phenyl]pyrazin-2-amine
6-(5-chloro-2-methyl-1H-benzimidazol-1-yl)-N-[4-(difluoromethoxy)phenyl]pyrazin-2-amine
N,2-dimethyl-1-(6-{[4-(trifluoromethoxy)phenyl]amino}pyrazin-2-yl)-1H-benzimidazol-5-amine
6-(3,5-dimethyl-1H-pyrazol-4-yl)-N-[4-(trifluoromethyl)phenyl]pyrazin-2-amine
6-(2-cyclopropyl-5-fluoro-1H-benzimidazol-1-yl)-N-[4-(difluoromethoxy)phenyl]pyrazin-2-amine
6-(6-fluoro-2-methyl-1H-benzimidazol-1-yl)-N-[4-(trifluoromethyl)phenyl]pyrazin-2-amine
N-[4-(difluoromethoxy)phenyl]-6-(6-fluoro-2-methyl-1H-benzimidazol-1-yl)pyrazin-2-amine
6-(6-fluoro-2-methyl-1H-benzimidazol-1-yl)-N-[4-(trifluoromethoxy)phenyl]pyrazin-2-amine
N-[4-(trifluoromethyl)phenyl]-6-[2-(trifluoromethyl)-5,6,7,8-tetrahydroimidazo[1,2-a]pyridin-3-yl]pyrazin-2-amine
N-[4-(difluoromethoxy)phenyl]-6-[2-(trifluoromethyl)-5,6,7,8-tetrahydroimidazo[1,2-a]pyridin-3-yl]pyrazin-2-amine
N-[4-(trifluoromethoxy)phenyl]-6-[2-(trifluoromethyl)-5,6,7,8-tetrahydroimidazo[1,2-a]pyridin-3-yl]pyrazin-2-amine
6-(imidazo[1,2-a]pyridin-3-yl)-N-[4-(trifluoromethyl)phenyl]pyrazin-2-amine
6-(5-chloro-2-methyl-1H-benzimidazol-1-yl)-N-[4-(trifluoromethyl)phenyl]pyrazin-2-amine
6-(6-chloro-2-methyl-1H-benzimidazol-1-yl)-N-[4-(trifluoromethyl)phenyl]pyrazin-2-amine
6-(6-fluoro-2-methylimidazo[1,2-a]pyridin-3-yl)-N-[4-(trifluoromethyl)phenyl]pyrazin-2-amine
N-[4-(difluoromethoxy)phenyl]-6-(6-fluoro-2-methylimidazo[1,2-a]pyridin-3-yl)pyrazin-2-amine
6-(6-fluoro-2-methylimidazo[1,2-a]pyridin-3-yl)-N-[4-(trifluoromethoxy)phenyl]pyrazin-2-amine
6-[2-cyclopropyl-6-(trifluoromethyl)imidazo[1,2-a]pyridin-3-yl]-N-[4-(trifluoromethyl)phenyl]pyrazin-2-amine
6-[2-cyclopropyl-6-(trifluoromethyl)imidazo[1,2-a]pyridin-3-yl]-N-[4-(difluoromethoxy)phenyl]pyrazin-2-amine
6-[2-cyclopropyl-6-(trifluoromethyl)imidazo[1,2-a]pyridin-3-yl]-N-[4-(trifluoromethoxy)phenyl]pyrazin-2-amine
6-[3,5-dimethyl-1-(2,2,2-trifluoroethyl)-1H-pyrazol-4-yl]-N-[4-(trifluoromethyl)phenyl]pyrazin-2-amine
6-(6,8-difluoro-2-methylimidazo[1,2-a]pyridin-3-yl)-N-[4-(trifluoromethyl)phenyl]pyrazin-2-amine
N-[4-(difluoromethoxy)phenyl]-6-(6,8-difluoro-2-methylimidazo[1,2-a]pyridin-3-yl)pyrazin-2-amine
N-[4-(1-aminoethyl)phenyl]-6-(2-methyl-1H-benzimidazol-1-yl)pyrazin-2-amine
N-[4-(difluoromethoxy)phenyl]-6-(2-methyl-4,5,6,7-tetrahydro-1H-benzimidazol-1-yl)pyrazin-2-amine
6-(2-ethyl-6-fluoro-1H-benzimidazol-1-yl)-N-[4-(trifluoromethyl)phenyl]pyrazin-2-amine
N-[4-(difluoromethoxy)phenyl]-6-(2-ethyl-6-fluoro-1H-benzimidazol-1-yl)pyrazin-2-amine
6-(5,6-difluoro-2-methyl-1H-benzimidazol-1-yl)-N-[4-(trifluoromethoxy)phenyl]pyrazin-2-amine
6-(2-methyl-4,5,6,7-tetrahydro-1H-benzimidazol-1-yl)-N-[4-(trifluoromethyl)phenyl]pyrazin-2-amine
6-(2-methyl-4,5,6,7-tetrahydro-1H-benzimidazol-1-yl)-N-[4-(trifluoromethoxy)phenyl]pyrazin-2-amine
6-(6-fluoro-2-methyl-1H-imidazo[4,5-b]pyridin-1-yl)-N-[4-(trifluoromethyl)phenyl]pyrazin-2-amine
6-(2-ethyl-6-fluoro-1H-imidazo[4,5-b]pyridin-1-yl)-N-[4-(trifluoromethyl)phenyl]pyrazin-2-amine
N,2-dimethyl-1-(6-{[4-(trifluoromethyl)phenyl]amino}pyrazin-2-yl)-1H-benzimidazol-6-amine
N-benzyl-2-methyl-1-(6-{[4-(trifluoromethyl)phenyl]amino}pyrazin-2-yl)-1H-benzimidazol-6-amine
6-[1,5-dimethyl-3-(trifluoromethyl)-1H-pyrazol-4-yl]-N-[4-(trifluoromethyl)phenyl]pyrazin-2-amine
1-[3,5-dimethyl-4-(6-{[4-(trifluoromethyl)phenyl]amino}pyrazin-2-yl)-1H-pyrazol-1-yl]ethanone
ethyl 3,5-dimethyl-4-(6-{[4-(trifluoromethyl)phenyl]amino}pyrazin-2-yl)-1H-pyrazole-1-carboxylate
ethyl 4-(6-{[4-(difluoromethoxy)phenyl]amino}pyrazin-2-yl)-3,5-dimethyl-1H-pyrazole-1-carboxylate
N-[4-(difluoromethoxy)phenyl]-6-[1,5-dimethyl-3-(trifluoromethyl)-1H-pyrazol-4-yl]pyrazin-2-amine
6-[1,5-dimethyl-3-(trifluoromethyl)-1H-pyrazol-4-yl]-N-[4-(trifluoromethoxy)phenyl]pyrazin-2-amine
6-(2,4-dimethyl-1H-benzimidazol-1-yl)-N-[4-(trifluoromethyl)phenyl]pyrazin-2-amine
6-(2-methyl-4-nitro-1H-benzimidazol-1-yl)-N-[4-(trifluoromethyl)phenyl]pyrazin-2-amine
2-methyl-1-(6-{[4-(trifluoromethyl)phenyl]amino}pyrazin-2-yl)-1H-benzimidazol-6-amine
6-(2-cyclopropyl-6-fluoro-1H-imidazo[4,5-b]pyridin-1-yl)-N-[4-(trifluoromethyl)phenyl]pyrazin-2-amine
N-(4-chloro-3-fluorophenyl)-6-(5,6-difluoro-2-methyl-1H-benzimidazol-1-yl)pyrazin-2-amine
6-(5,6-difluoro-2-methyl-1H-benzimidazol-1-yl)-N-[3-fluoro-4-(trifluoromethyl)phenyl]pyrazin-2-amine
2-methyl-1-(6-{[4-(trifluoromethyl)phenyl]amino}pyrazin-2-yl)-1H-benzimidazol-4-amine
6-(4,5-dichloro-2-methyl-1H-imidazol-1-yl)-N-[4-(trifluoromethyl)phenyl]pyrazin-2-amine
6-(4-bromo-2-methyl-1H-imidazol-1-yl)-N-[4-(trifluoromethyl)phenyl]pyrazin-2-amine
6-(5-chloro-2,4-dimethyl-1H-imidazol-1-yl)-N-[4-(trifluoromethyl)phenyl]pyrazin-2-amine
6-(2,4-dimethyl-1H-imidazol-1-yl)-N-[4-(trifluoromethyl)phenyl]pyrazin-2-amine
6-(5,6-difluoro-2-methyl-1H-benzimidazol-1-yl)-N-[3-fluoro-4-(trifluoromethoxy)phenyl]pyrazin-2-amine
6-{2-[(methylamino)methyl]imidazo[1,2-a]pyridin-3-yl}-N-[4-(trifluoromethyl)phenyl]pyrazin-2-amine
6-[2-methyl-4-(trifluoromethyl)-1H-imidazol-1-yl]-N-[4-(trifluoromethyl)phenyl]pyrazin-2-amine
6-(5,6-difluoro-2-methyl-1H-benzimidazol-1-yl)-N-[6-(trifluoromethyl)pyridin-3-yl]pyrazin-2-amine 6-(5-chloro-2,4-dimethyl-1H-imidazol-1-yl)-N-[4-(difluoromethoxy)phenyl]pyrazin-2-amine
6-(2-methyl-1H-benzimidazol-1-yl)-N-[4-(2,2,2-trifluoroethoxy)phenyl]pyrazin-2-amine
6-(2-methyl-1H-benzimidazol-1-yl)-N-[4-(1,1,2,2-tetrafluoroethoxy)phenyl]pyrazin-2-amine
6-(6-fluoroimidazo[1,2-a]pyridin-3-yl)-N-[4-(trifluoromethyl)phenyl]pyrazin-2-amine
N-[4-(difluoromethoxy)-3-fluorophenyl]-6-(6-fluoro-2-methylimidazo[1,2-a]pyridin-3-yl)pyrazin-2-amine
6-(6-fluoro-2-methylimidazo[1,2-a]pyridin-3-yl)-N-[3-fluoro-4-(trifluoromethyl)phenyl]pyrazin-2-amine
6-(6-methoxy-2-methyl-1H-benzimidazol-1-yl)-N-[4-(trifluoromethyl)phenyl]pyrazin-2-amine
6-[2,5-dimethyl-4-(trifluoromethyl)-1H-imidazol-1-yl]-N-[4-(trifluoromethyl)phenyl]pyrazin-2-amine
N-[4-(difluoromethoxy)-3-fluorophenyl]-6-(5,6-difluoro-2-methyl-1H-benzimidazol-1-yl)pyrazin-2-amine
N-[4-(difluoromethoxy)-3-fluorophenyl]-6-(6-fluoro-2-methyl-1H-benzimidazol-1-yl)pyrazin-2-amine
N-[4-(2,2,2-trifluoroethoxy)phenyl]-6-[2-(trifluoromethyl)imidazo[1,2-a]pyridin-3-yl]pyrazin-2-amine
N-[4-(1,1,2,2-tetrafluoroethoxy)phenyl]-6-[2-(trifluoromethyl)imidazo[1,2-a]pyridin-3-yl]pyrazin-2-amine
N-[4-(difluoromethoxy)-3-fluorophenyl]-6-[2-(trifluoromethyl)imidazo[1,2-a]pyridin-3-yl]pyrazin-2-amine
N-[4-(difluoromethoxy)-3-fluorophenyl]-6-(2-methyl-1H-benzimidazol-1-yl)pyrazin-2-amine
N-[4-(difluoromethoxy)-3-fluorophenyl]-6-(2-methyl-1H-imidazo[4,5-b]pyridin-1-yl)pyrazin-2-amine
6-(6-chloro-2-ethyl-1H-imidazo[4,5-b]pyridin-1-yl)-N-[4-(trifluoromethyl)phenyl]pyrazin-2-amine
[6-fluoro-3-(6-{[4-(trifluoromethyl)phenyl]amino}pyrazin-2-yl)imidazo[1,2-a]pyridin-2-yl]methanol
6-[1-ethyl-5-methyl-3-(trifluoromethyl)-1H-pyrazol-4-yl]-N-[4-(trifluoromethyl)phenyl]pyrazin-2-amine
N-[4-(difluoromethoxy)phenyl]-6-[1-ethyl-5-methyl-3-(trifluoromethyl)-1H-pyrazol-4-yl]pyrazin-2-amine
6-[1-ethyl-5-methyl-3-(trifluoromethyl)-1H-pyrazol-4-yl]-N-[4-(trifluoromethoxy)phenyl]pyrazin-2-amine
6-(3,5-diethyl-1-methyl-1H-pyrazol-4-yl)-N-[4-(trifluoromethyl)phenyl]pyrazin-2-amine
6-(3,5-diethyl-1-methyl-1H-pyrazol-4-yl)-N-[4-(difluoromethoxy)phenyl]pyrazin-2-amine
6-(3,5-diethyl-1-methyl-1H-pyrazol-4-yl)-N-[4-(trifluoromethoxy)phenyl]pyrazin-2-amine
2-[3,5-dimethyl-4-(6-{[4-(trifluoromethyl)phenyl]amino}pyrazin-2-yl)-1H-pyrazol-1-yl]ethanol
6-(2-cyclopropyl-6-fluoroimidazo[1,2-a]pyridin-3-yl)-N-[4-(trifluoromethyl)phenyl]pyrazin-2-amine
6-(2-cyclopropyl-6-fluoroimidazo[1,2-a]pyridin-3-yl)-N-[4-(difluoromethoxy)phenyl]pyrazin-2-amine
6-(2-cyclopropyl-6-fluoroimidazo[1,2-a]pyridin-3-yl)-N-[4-(difluoromethoxy)-3-fluorophenyl]pyrazin-2-amine
6-(4-fluoro-2-methyl-1H-benzimidazol-1-yl)-N-[4-(trifluoromethyl)phenyl]pyrazin-2-amine
6-[2-methyl-6-(trifluoromethyl)-1H-benzimidazol-1-yl]-N-[4-(trifluoromethyl)phenyl]pyrazin-2-amine
6-(4-bromo-2,5-dimethyl-1H-imidazol-1-yl)-N-[4-(trifluoromethyl)phenyl]pyrazin-2-amine
N-[4-(trifluoromethyl)phenyl]-6-(2,4,5-trimethyl-1H-imidazol-1-yl)pyrazin-2-amine
6-(2,6-dimethyl-1H-benzimidazol-1-yl)-N-[4-(trifluoromethyl)phenyl]pyrazin-2-amine
6-{3,5-dimethyl-1-[2-(2H-tetrazol-2-yl)ethyl]-1H-pyrazol-4-yl}-N-[4-(trifluoromethyl)phenyl]pyrazin-2-amine
6-(2-methylpyridin-4-yl)-N-[4-(trifluoromethyl)phenyl]pyrazin-2-amine
6-(2'-chloro-2,4'-bipyridin-4-yl)-N-[4-(trifluoromethyl)phenyl]pyrazin-2-amine
6-(2,5-dimethyl-1H-imidazol-1-yl)-N-[4-(trifluoromethyl)phenyl]pyrazin-2-amine
6-[2-methyl-5-(trifluoromethoxy)-1H-benzimidazol-1-yl]-N-[4-(trifluoromethyl)phenyl]pyrazin-2-amine
6-[2-methyl-6-(trifluoromethoxy)-1H-benzimidazol-1-yl]-N-[4-(trifluoromethyl)phenyl]pyrazin-2-amine
6-(7-fluoro-2-methyl-1H-benzimidazol-1-yl)-N-[4-(trifluoromethyl)phenyl]pyrazin-2-amine
N-[3-fluoro-4-(trifluoromethyl)phenyl]-6-(2-methyl-1H-imidazo[4,5-b]pyridin-1-yl)pyrazin-2-amine
6-(6-chloro-2-methyl-1H-imidazo[4,5-b]pyridin-1-yl)-N-[4-(trifluoromethyl)phenyl]pyrazin-2-amine
6-(2-cyclopropyl-6-fluoro-1H-benzimidazol-1-yl)-N-[4-(trifluoromethyl)phenyl]pyrazin-2-amine
6-(2-ethyl-1H-imidazo[4,5-c]pyridin-1-yl)-N-[4-(trifluoromethyl)phenyl]pyrazin-2-amine
6-(8-methyl-7H-purin-7-yl)-N-[4-(trifluoromethyl)phenyl]pyrazin-2-amine
6-(5-ethyl-2-methyl-1H-imidazol-1-yl)-N-[4-(trifluoromethyl)phenyl]pyrazin-2-amine
6-(6-fluoro-2-methyl-1H-imidazo[4,5-b]pyridin-1-yl)-N-[3-fluoro-4-(trifluoromethyl)phenyl]pyrazin-2-amine
6-(2-ethyl-6-fluoro-1H-imidazo[4,5-b]pyridin-1-yl)-N-[3-fluoro-4-(trifluoromethyl)phenyl]pyrazin-2-amine
6-[2-methyl-5-(prop-2-en-1-yl)-4,5,6,7-tetrahydro-1H-imidazo[4,5-c]pyridin-1-yl]-N-[4-(trifluoromethyl)phenyl]pyrazin-2-amine
6-(6-methoxy-2-methylimidazo[1,2-a]pyridin-3-yl)-N-[4-(trifluoromethyl)phenyl]pyrazin-2-amine
6-(6-methoxy-2-methylimidazo[1,2-a]pyridin-3-yl)-N-[4-(trifluoromethoxy)phenyl]pyrazin-2-amine
2-methyl-3-(6-{[4-(trifluoromethyl)phenyl]amino}pyrazin-2-yl)imidazo[1,2-a]pyridin-6-ol
N-[4-(difluoromethoxy)-3-fluorophenyl]-6-(1-ethyl-3,5-dimethyl-1H-pyrazol-4-yl)pyrazin-2-amine
6-(quinolin-4-yl)-N-[4-(trifluoromethyl)phenyl]pyrazin-2-amine
6-(7-chloroquinolin-4-yl)-N-[4-(trifluoromethyl)phenyl]pyrazin-2-amine
N-[4-(trifluoromethyl)phenyl]-6-(2,5,6-trimethyl-1H-benzimidazol-1-yl)pyrazin-2-amine
N-[4-(trifluoromethoxy)phenyl]-6-(2,5,6-trimethyl-1H-benzimidazol-1-yl)pyrazin-2-amine
6-(6-bromo-2-methyl-1H-benzimidazol-1-yl)-N-[4-(trifluoromethyl)phenyl]pyrazin-2-amine
N-[3-chloro-4-(trifluoromethyl)phenyl]-6-(2-methyl-1H-benzimidazol-1-yl)pyrazin-2-amine
6-{4-[(Z)-2-ethoxyethenyl]-2-methyl-1H-imidazol-1-yl}-N-[4-(trifluoromethyl)phenyl]pyrazin-2-amine
6-(6-ethyl-2-methyl-1H-benzimidazol-1-yl)-N-[4-(trifluoromethyl)phenyl]pyrazin-2-amine
2-{[2-methyl-1-(6-{[4-(trifluoromethyl)phenyl]amino}pyrazin-2-yl)-1H-benzimidazol-6-yl]amino}ethanol
6-(2-ethyl-5-methyl-4,5,6,7-tetrahydro-3H-imidazo[4,5-c]pyridin-3-yl)-N-[4-(trifluoromethyl)phenyl]pyrazin-2-amine
6-[1-(2-methoxyethyl)-3,5-dimethyl-1H-pyrazol-4-yl]-N-[4-(trifluoromethyl)phenyl]pyrazin-2-amine 6-[3,5-dimethyl-1-(pyridin-2-ylmethyl)-1H-pyrazol-4-yl]-N-[4-(trifluoromethyl)phenyl]pyrazin-2-amine
N-[4-(difluoromethoxy)phenyl]-6-[3,5-dimethyl-1-(pyridin-2-ylmethyl)-1H-pyrazol-4-yl]pyrazin-2-amine
6-[3,5-dimethyl-1-(pyridin-3-ylmethyl)-1H-pyrazol-4-yl]-N-[4-(trifluoromethyl)phenyl]pyrazin-2-amine
6-[3,5-dimethyl-1-(pyridin-4-ylmethyl)-1H-pyrazol-4-yl]-N-[4-(trifluoromethyl)phenyl]pyrazin-2-amine
(2S)-4-[3,5-dimethyl-4-(6-{[4-(trifluoromethyl)phenyl]amino}pyrazin-2-yl)-1H-pyrazol-1-yl]butane-1,2-diol
N-(6-chloropyridin-3-yl)-6-(5,6-difluoro-2-methyl-1H-benzimidazol-1-yl)pyrazin-2-amine
6-[6-fluoro-2-(trifluoromethyl)-5,6,7,8-tetrahydroimidazo[1,2-a]pyridin-3-yl]-N-[4-(trifluoromethyl)phenyl]pyrazin-2-amine
6-(1H-indol-4-yl)-N-[4-(trifluoromethyl)phenyl]pyrazin-2-amine
6-(2-methyl-1H-benzimidazol-1-yl)-N-[3-methyl-4-(trifluoromethyl)phenyl]pyrazin-2-amine
6-(6-methoxy-2-methyl-5,6,7,8-tetrahydroimidazo[1,2-a]pyridin-3-yl)-N-[4-(trifluoromethyl)phenyl]pyrazin-2-amine
6-(5-chloro-1,3-dimethyl-1H-pyrazol-4-yl)-N-[4-(trifluoromethyl)phenyl]pyrazin-2-amine
6-(5-chloro-1,3-dimethyl-1H-pyrazol-4-yl)-N-[4-(difluoromethoxy)phenyl]pyrazin-2-amine
6-(5-chloro-1,3-dimethyl-1H-pyrazol-4-yl)-N-[4-(trifluoromethoxy)phenyl]pyrazin-2-amine
6-(5-chloro-1,3-dimethyl-1H-pyrazol-4-yl)-N-[4-(difluoromethoxy)-3-fluorophenyl]pyrazin-2-amine
6-(5-fluoro-2-methyl-2H-indazol-3-yl)-N-[4-(trifluoromethyl)phenyl]pyrazin-2-amine
6-(4,6-difluoro-2-methyl-1H-benzimidazol-1-yl)-N-[4-(trifluoromethyl)phenyl]pyrazin-2-amine
N-[6-(2-methyl-1H-benzimidazol-1-yl)pyrazin-2-yl]-1,3-benzothiazol-2-amine
N-[4-(trifluoromethyl)phenyl]-6-(2,4,6-trimethyl-1H-benzimidazol-1-yl)pyrazin-2-amine
6-(2-cyclopropylimidazo[1,2-a]pyrimidin-3-yl)-N-[4-(trifluoromethyl)phenyl]pyrazin-2-amine
6-(5,6-difluoro-2-methyl-1H-benzimidazol-1-yl)-N-[6-(morpholin-4-yl)pyridin-3-yl]pyrazin-2-amine
N-(2,3-dihydro-1H-inden-2-yl)-6-(2-methyl-1H-benzimidazol-1-yl)pyrazin-2-amine
2-[(5-{[6-(5,6-difluoro-2-methyl-1H-benzimidazol-1-yl)pyrazin-2-yl]amino}pyridin-2-yl)amino]ethanol
N-(6-chloropyridin-3-yl)-6-(5-fluoro-2-methyl-1H-benzimidazol-1-yl)pyrazin-2-amine
N-(6-chloropyridin-3-yl)-6-(6-fluoro-2-methyl-1H-benzimidazol-1-yl)pyrazin-2-amine
$N^5$-[6-(5,6-difluoro-2-methyl-1H-benzimidazol-1-yl)pyrazin-2-yl]-$N^2$-[2-(dimethylamino)ethyl]pyridine-2,5-diamine
6-(5-fluoro-2-methyl-1H-benzimidazol-1-yl)-N-[6-(trifluoromethyl)pyridin-3-yl]pyrazin-2-amine
6-(6-fluoro-2-methyl-1H-benzimidazol-1-yl)-N-[6-(trifluoromethyl)pyridin-3-yl]pyrazin-2-amine
6-(2-methyl-1H-benzimidazol-1-yl)-N-[4-(4,4,5,5-tetramethyl-1,3,2-dioxaborolan-2-yl)phenyl]pyrazin-2-amine
(4-{[6-(2-methyl-1H-benzimidazol-1-yl)pyrazin-2-yl]amino}phenyl)boronic acid
N-[6-(2-methyl-1H-benzimidazol-1-yl)pyrazin-2-yl]-6-(trifluoromethyl)-1,3-benzothiazol-2-amine
6-(6-fluoro-2-methylimidazo[1,2-a]pyrimidin-3-yl)-N-[4-(trifluoromethyl)phenyl]pyrazin-2-amine
6-(2-methyl-4,5,6,7-tetrahydro-2H-indazol-3-yl)-N-[4-(trifluoromethyl)phenyl]pyrazin-2-amine
6-(2-cyclopropyl-6-fluoro-1H-imidazo[4,5-b]pyridin-1-yl)-N-[4-(difluoromethoxy)phenyl]pyrazin-2-amine
6-(2-cyclopropyl-6-fluoro-1H-imidazo[4,5-b]pyridin-1-yl)-N-[4-(trifluoromethoxy)phenyl]pyrazin-2-amine
6-(2-methyl-1H-benzimidazol-1-yl)-N-[5-(trifluoromethyl)pyridin-2-yl]pyrazin-2-amine
6-(2-cyclopropyl-6-fluoro-1H-imidazo[4,5-b]pyridin-1-yl)-N-[6-(trifluoromethyl)pyridin-3-yl]pyrazin-2-amine
6-(2-cyclopropyl-6-fluoro-1H-imidazo[4,5-b]pyridin-1-yl)-N-[4-(difluoromethoxy)-3-fluorophenyl]pyrazin-2-amine
6-(2-cyclopropyl-5,6-difluoro-1H-benzimidazol-1-yl)-N-[4-(difluoromethoxy)phenyl]pyrazin-2-amine
6-(2-cyclopropyl-4,6-difluoro-1H-benzimidazol-1-yl)-N-[4-(trifluoromethyl)phenyl]pyrazin-2-amine
6-(2-cyclopropyl-4,6-difluoro-1H-benzimidazol-1-yl)-N-[4-(difluoromethoxy)phenyl]pyrazin-2-amine
6-(2-cyclopropyl-4,6-difluoro-1H-benzimidazol-1-yl)-N-[4-(trifluoromethoxy)phenyl]pyrazin-2-amine
6-(2-cyclopropyl-4,6-difluoro-1H-benzimidazol-1-yl)-N-[6-(trifluoromethyl)pyridin-3-yl]pyrazin-2-amine
6-[2-(difluoromethyl)-6-fluoroimidazo[1,2-a]pyridin-3-yl]-N-[4-(trifluoromethyl)phenyl]pyrazin-2-amine
N-[4-(difluoromethoxy)phenyl]-6-[2-(difluoromethyl)-6-fluoroimidazo[1,2-a]pyridin-3-yl]pyrazin-2-amine
N-[4-(difluoromethoxy)phenyl]-6-(imidazo[1,2-a]pyridin-3-yl)pyrazin-2-amine
N-[6-(difluoromethoxy)pyridin-3-yl]-6-[2-(difluoromethyl)-6-fluoroimidazo[1,2-a]pyridin-3-yl]pyrazin-2-amine
N-[6-(difluoromethoxy)pyridin-3-yl]-6-(6-fluoro-2-methylimidazo[1,2-a]pyridin-3-yl)pyrazin-2-amine
6-[2-(difluoromethyl)-1H-benzimidazol-1-yl]-N-[4-(trifluoromethyl)phenyl]pyrazin-2-amine
N-[4-(difluoromethoxy)phenyl]-6-[2-(difluoromethyl)-1H-benzimidazol-1-yl]pyrazin-2-amine
N-[4-(difluoromethoxy)-3-fluorophenyl]-6-[2-(difluoromethyl)-1H-benzimidazol-1-yl]pyrazin-2-amine
6-(2-cyclobutyl-6-fluoro-1H-benzimidazol-1-yl)-N-[4-(trifluoromethyl)phenyl]pyrazin-2-amine
6-[2-(difluoromethyl)-6-fluoro-1H-benzimidazol-1-yl]-N-[4-(trifluoromethyl)phenyl]pyrazin-2-amine
N-[4-(trifluoromethyl)phenyl]-6-(2,6,8-trimethylimidazo[1,2-a]pyrazin-3-yl)pyrazin-2-amine
N-[4-(difluoromethoxy)phenyl]-6-(2,6,8-trimethylimidazo[1,2-a]pyrazin-3-yl)pyrazin-2-amine
6-(5,6-difluoro-2-methyl-1H-benzimidazol-1-yl)-N-[4-(trifluoromethyl)phenyl]pyrazin-2-amine 4-oxide
6-(2-methylpyrazolo[1,5-a]pyridin-3-yl)-N-[4-(trifluoromethyl)phenyl]pyrazin-2-amine
N-[4-(difluoromethoxy)phenyl]-6-(2-methylpyrazolo[1,5-a]pyridin-3-yl)pyrazin-2-amine
6-(2-methylpyrazolo[1,5-a]pyridin-3-yl)-N-[4-(trifluoromethoxy)phenyl]pyrazin-2-amine
6-(5,6-difluoro-2-methyl-1H-benzimidazol-1-yl)-N-[4-(difluoromethyl)phenyl]pyrazin-2-amine
4-{[6-(5,6-difluoro-2-methyl-1H-benzimidazol-1-yl)pyrazin-2-yl]amino}benzaldehyde
$N^1$-[6-(2-methyl-1H-benzimidazol-1-yl)pyrazin-2-yl]-4-(trifluoromethyl)benzene-1,3-diamine
N-[4-(difluoromethyl)phenyl]-6-(2-methyl-1H-benzimidazol-1-yl)pyrazin-2-amine
N-[4-(difluoromethyl)-3-fluorophenyl]-6-(2-methyl-1H-benzimidazol-1-yl)pyrazin-2-amine N-[4-(difluoromethoxy)phenyl]-6-(5,6-difluoro-2-methyl-1H-benzimidaz-1-yl)pyrazin-2-amine 4-oxide
5-{[6-(2-methyl-1H-benzimidazol-1-yl)pyrazin-2-yl]amino}-2-(trifluoromethyl)benzonitrile
[5-{[6-(2-methyl-1H-benzimidazol-1-yl)pyrazin-2-yl]amino}-2-(trifluoromethyl)phenyl]methanol
6-(2-ethylpyrazolo[1,5-a]pyridin-3-yl)-N-[4-(trifluoromethyl)phenyl]pyrazin-2-amine
N-[4-(difluoromethoxy)phenyl]-6-(2-ethylpyrazolo[1,5-a]pyridin-3-yl)pyrazin-2-amine
N-[4-(difluoromethoxy)-3-fluorophenyl]-6-(2-ethylpyrazolo[1,5-a]pyridin-3-yl)pyrazin-2-amine
6-(2-ethylpyrazolo[1,5-a]pyridin-3-yl)-N-[4-(trifluoromethoxy)phenyl]pyrazin-2-amine
N-[3-(aminomethyl)-4-(trifluoromethyl)phenyl]-6-(2-methyl-1H-benzimidazol-1-yl)pyrazin-2-amine
6-(2-methyl-1H-benzimidazol-1-yl)-N-[4-(trifluoromethyl)phenyl]pyrazin-2-amine 4-oxide
6-(2-cyclopropyl-5,6-difluoro-1H-benzimidazol-1-yl)-N-[4-(difluoromethoxy)phenyl]pyrazin-2-amine 4-oxide
N-[4-(difluoromethoxy)phenyl]-6-(2-methyl-1H-benzimidazol-1-yl)pyrazin-2-amine 4-oxide
6-(6-fluoro-2-methyl-1H-benzimidazol-1-yl)-N-[4-(trifluoromethyl)phenyl]pyrazin-2-amine 4-oxide
6-(2-cyclopropyl-6-fluoro-1H-imidazo[4,5-b]pyridin-1-yl)-N-[4-(trifluoromethyl)phenyl]pyrazin-2-amine 4-oxide
6-[2-(trifluoromethyl)imidazo[1,2-a]pyridin-3-yl]-N-[4-(trifluoromethyl)phenyl]pyrazin-2-amine 4-oxide
6-(2-cyclopropyl-5-fluoropyrazolo[1,5-a]pyridin-3-yl)-N-[4-(trifluoromethyl)phenyl]pyrazin-2-amine
6-(2-cyclopropyl-5-fluoropyrazolo[1,5-a]pyridin-3-yl)-N-[4-(trifluoromethyl)phenyl]pyrazin-2-amine 4-oxide
6-(5-fluoro-2-methylpyrazolo[1,5-a]pyridin-3-yl)-N-[4-(trifluoromethyl)phenyl]pyrazin-2-amine
6-[6-fluoro-2-(trifluoromethyl)imidazo[1,2-a]pyridin-3-yl]-N-[4-(trifluoromethyl)phenyl]pyrazin-2-amine 4-oxide
6-(5-chloro-2-ethylpyrazolo[1,5-a]pyridin-3-yl)-N-[4-(trifluoromethyl)phenyl]pyrazin-2-amine
6-(6-chloro-2-methyl-1H-imidazo[4,5-b]pyridin-1-yl)-N-[4-(difluoromethoxy)phenyl]pyrazin-2-amine
6-(6-chloro-2-methyl-1H-imidazo[4,5-b]pyridin-1-yl)-N-[4-(difluoromethoxy)-3-fluorophenyl]pyrazin-2-amine
6-(6-chloro-2-methyl-1H-imidazo[4,5-b]pyridin-1-yl)-N-[4-(trifluoromethoxy)phenyl]pyrazin-2-amine
6-(6-chloro-2-methyl-1H-imidazo[4,5-b]pyridin-1-yl)-N-phenylpyrazin-2-amine
6-(6-chloro-2-ethyl-1H-imidazo[4,5-b]pyridin-1-yl)-N-[4-(difluoromethoxy)phenyl]pyrazin-2-amine
N-[4-(difluoromethoxy)phenyl]-1-(6-{[4-(difluoromethoxy)phenyl]amino}pyrazin-2-yl)-2-ethyl-1H-imidazo[4,5-b]pyridin-6-amine
6-(6-chloro-2-ethyl-1H-imidazo[4,5-b]pyridin-1-yl)-N-[4-(difluoromethoxy)-3-fluorophenyl]pyrazin-2-amine
N-[4-(difluoromethoxy)phenyl]-1-(6-{[4-(difluoromethoxy)phenyl]amino}pyrazin-2-yl)-2-methyl-1H-imidazo[4,5-b]pyridin-6-amine
6-(6-chloro-2-ethyl-1H-imidazo[4,5-b]pyridin-1-yl)-N-[4-(trifluoromethoxy)phenyl]pyrazin-2-amine
6-(6-chloro-2-ethyl-1H-imidazo[4,5-b]pyridin-1-yl)-N-phenylpyrazin-2-amine
N-[4-(difluoromethoxy)-3-fluorophenyl]-1-(6-{[4-(difluoromethoxy)-3-fluorophenyl]amino}pyrazin-2-yl)-2-ethyl-1H-imidazo[4,5-b]pyridin-6-amine
6-(2-ethyl-5-fluoropyrazolo[1,5-a]pyridin-3-yl)-N-[4-(trifluoromethyl)phenyl]pyrazin-2-amine
6-(6-fluoro-2-methyl-1H-benzimidazol-1-yl)-N-(4-methoxyphenyl)pyrazin-2-amine
6-(6-fluoro-2-methyl-1H-benzimidazol-1-yl)-N-(4-methylphenyl)pyrazin-2-amine
N-(4-chlorophenyl)-6-(6-fluoro-2-methyl-1H-benzimidazol-1-yl)pyrazin-2-amine
4-{[6-(6-fluoro-2-methyl-1H-benzimidazol-1-yl)pyrazin-2-yl]amino}benzonitrile methyl 4-{[6-(6-fluoro-2-methyl-1H-benzimidazol-1-yl)pyrazin-2-yl]amino}benzoate N-(3-methoxyphenyl)-6-(2-methyl-1H-benzimidazol-1-yl)pyrazin-2-amine
N-[6-(6-fluoro-2-methyl-1H-benzimidazol-1-yl)pyrazin-2-yl]benzene-1,4-diamine
6-(6-fluoro-2-methyl-1H-benzimidazol-1-yl)-N-(3-methoxyphenyl)pyrazin-2-amine
6-(6-fluoro-2-methyl-1H-benzimidazol-1-yl)-N-(3-methylphenyl)pyrazin-2-amine
N-(4-methoxyphenyl)-6-(2-methyl-1H-benzimidazol-1-yl)pyrazin-2-amine
6-(2-methyl-1H-benzimidazol-1-yl)-N-(4-methylphenyl)pyrazin-2-amine
4-methyl-N$^1$-[6-(2-methyl-1H-benzimidazol-1-yl)pyrazin-2-yl]benzene-1,2-diamine
6-(2-methylpyrazolo[1,5-a]pyridin-3-yl)-N-phenylpyrazin-2-amine
N-(4-methoxyphenyl)-6-(2-methylpyrazolo[1,5-a]pyridin-3-yl)pyrazin-2-amine
N-(4-methylphenyl)-6-(2-methylpyrazolo[1,5-a]pyridin-3-yl)pyrazin-2-amine
N-(4-chlorophenyl)-6-(2-methylpyrazolo[1,5-a]pyridin-3-yl)pyrazin-2-amine
N-(4-fluorophenyl)-6-(2-methylpyrazolo[1,5-a]pyridin-3-yl)pyrazin-2-amine
N-(3-methoxyphenyl)-6-(2-methylpyrazolo[1,5-a]pyridin-3-yl)pyrazin-2-amine
N-(3-chlorophenyl)-6-(2-methylpyrazolo[1,5-a]pyridin-3-yl)pyrazin-2-amine
4-{[6(2-methylpyrazolo[1,5-a]pyridin-3-yl)pyrazin-2-yl]amino}benzonitrile
methyl 4-{[6(2-methylpyrazolo[1,5-a]pyridin-3-yl)pyrazin-2-yl]amino}benzoate
6-(5,6-difluoro-2-methyl-1H-benzimidazol-1-yl)-N-(4-methoxyphenyl)pyrazin-2-amine
6-(5,6-difluoro-2-methyl-1H-benzimidazol-1-yl)-N-(4-methylphenyl)pyrazin-2-amine
N-(4-chlorophenyl)-6-(5,6-difluoro-2-methyl-1H-benzimidazol-1-yl)pyrazin-2-amine
N-(2-methoxy-4-methylphenyl)-6-(2-methyl-1H-benzimidazol-1-yl)pyrazin-2-amine
6-(5,6-difluoro-2-methyl-1H-benzimidazol-1-yl)-N-(3-methoxyphenyl)pyrazin-2-amine
N-(2,2-difluoro-1,3-benzodioxol-5-yl)-6-(5,6-difluoro-2-methyl-1H-benzimidazol-1-yl)pyrazin-2-amine
5-methyl-2-{[6-(2-methyl-1H-benzimidazol-1-yl)pyrazin-2-yl]amino}phenol 6-(6-fluoro-2-methylimidazo[1,2-a]pyridin-3-yl)-N-phenylpyrazin-2-amine
6-(6-fluoro-2-methylimidazo[1,2-a]pyridin-3-yl)-N44-fluorophenyl)pyrazin-2-amine
6-(6-fluoro-2-methylimidazo[1,2-a]pyridin-3-yl)-N44-methoxyphenyl)pyrazin-2-amine
N-(4-chlorophenyl)-6-(6-fluoro-2-methylimidazo[1,2-a]pyridin-3-yl)pyrazin-2-amine
6-(6-fluoro-2-methylimidazo[1,2-a]pyridin-3-yl)-N-[3-(trifluoromethyl)phenyl]pyrazin-2-amine 6-(6-fluoro-2-methylimidazo[1,2-a]pyridin-3-yl)-N43-fluorophenyl)pyrazin-2-amine
6-(6-fluoro-2-methylimidazo[1,2-a]pyridin-3-yl)-N43-methoxyphenyl)pyrazin-2-amine
N-(3-chlorophenyl)-6-(6-fluoro-2-methylimidazo[1,2-a]pyridin-3-yl)pyrazin-2-amine
6-(6-fluoro-2-methylimidazo[1,2-a]pyridin-3-yl)-N-(2-fluorophenyl)pyrazin-2-amine
N-(4-iodophenyl)-6-(2-methyl-1H-benzimidazol-1-yl)pyrazin-2-amine
6-(2-ethyl-6-fluoro-1H-benzimidazol-1-yl)-N-phenylpyrazin-2-amine
6-(2-ethyl-6-fluoro-1H-benzimidazol-1-yl)-N-(4-methoxyphenyl)pyrazin-2-amine
6-(2-ethyl-6-fluoro-1H-benzimidazol-1-yl)-N-(4-methylphenyl)pyrazin-2-amine
N-(4-chlorophenyl)-6-(2-ethyl-6-fluoro-1H-benzimidazol-1-yl)pyrazin-2-amine
6-(2-ethyl-6-fluoro-1H-benzimidazol-1-yl)-N-(3-methoxyphenyl)pyrazin-2-amine
N-(3-chlorophenyl)-6-(2-ethyl-6-fluoro-1H-benzimidazol-1-yl)pyrazin-2-amine
6-(2-ethyl-6-fluoro-1H-benzimidazol-1-yl)-N-(3-fluorophenyl)pyrazin-2-amine
6-(2-ethylpyrazolo[1,5-a]pyridin-3-yl)-N-(4-methoxyphenyl)pyrazin-2-amine
6-(2-ethylpyrazolo[1,5-a]pyridin-3-yl)-N-(4-methylphenyl)pyrazin-2-amine
N-(4-chlorophenyl)-6-(2-ethylpyrazolo[1,5-a]pyridin-3-yl)pyrazin-2-amine
6-(2-ethylpyrazolo[1,5-a]pyridin-3-yl)-N-(4-fluorophenyl)pyrazin-2-amine
6-(2-ethylpyrazolo[1,5-a]pyridin-3-yl)-N-phenylpyrazin-2-amine
6-(3,5-dimethyl-1,2-oxazol-4-yl)-N-(4-methylphenyl)pyrazin-2-amine
6-(3,5-dimethyl-1,2-oxazol-4-yl)-N-(4-methoxyphenyl)pyrazin-2-amine
6-(3,5-dimethyl-1,2-oxazol-4-yl)-N-(3-fluoro-4-methoxyphenyl)pyrazin-2-amine
6-(3,5-dimethyl-1,2-oxazol-4-yl)-N-(6-methoxypyridin-3-yl)pyrazin-2-amine
N-(1,3-benzodioxol-5-yl)-6-(3,5-dimethyl-1,2-oxazol-4-yl)pyrazin-2-amine
6-(2-ethylpyrazolo[1,5-a]pyridin-3-yl)-N-(3-methoxyphenyl)pyrazin-2-amine
4-{[6-(2-ethylpyrazolo[1,5-a]pyridin-3-yl)pyrazin-2-yl]amino}benzonitrile
methyl 4-{[6-(2-ethylpyrazolo[1,5-a]pyridin-3-yl)pyrazin-2-yl]amino}benzoate
N-(3-chlorophenyl)-6-(2-ethylpyrazolo[1,5-a]pyridin-3-yl)pyrazin-2-amine
N-[2-fluoro-4-(trifluoromethyl)phenyl]-6-(2-methyl-1H-benzimidazol-1-yl)pyrazin-2-amine
N-[3,5-difluoro-4-(trifluoromethyl)phenyl]-6-(2-methyl-1H-benzimidazol-1-yl)pyrazin-2-amine
N-(4-chloro-3-fluorophenyl)-6-(6-fluoro-2-methyl-1H-benzimidazol-1-yl)pyrazin-2-amine
N-(4-tert-butylphenyl)-6-(2-methyl-1H-benzimidazol-1-yl)pyrazin-2-amine
6-(2-methyl-1H-benzimidazol-1-yl)-N-[4-(propan-2-yloxy)phenyl]pyrazin-2-amine
6-(2-methyl-1H-benzimidazol-1-yl)-N-[4-(propan-2-yl)phenyl]pyrazin-2-amine
N-(4-ethylphenyl)-6-(2-methyl-1H-benzimidazol-1-yl)pyrazin-2-amine
6-(2-methyl-1H-benzimidazol-1-yl)-N-(4-propylphenyl)pyrazin-2-amine
N-(4-ethoxyphenyl)-6-(2-methyl-1H-benzimidazol-1-yl)pyrazin-2-amine
N-(4-ethynylphenyl)-6-(2-methyl-1H-benzimidazol-1-yl)pyrazin-2-amine
N-(4-ethenylphenyl)-6-(2-methyl-1H-benzimidazol-1-yl)pyrazin-2-amine
6-[6-fluoro-2-(trifluoromethyl)imidazo[1,2-a]pyridin-3-yl]-N-phenylpyrazin-2-amine
4-({6-[6-fluoro-2-(trifluoromethyl)imidazo[1,2-a]pyridin-3-yl]pyrazin-2-yl}amino)benzonitrile N-(4-fluorophenyl)-6-[6-fluoro-2-(trifluoromethyl)imidazo[1,2-a]pyridin-3-yl]pyrazin-2-amine
N-(4-chlorophenyl)-6-[6-fluoro-2-(trifluoromethyl)imidazo[1,2-a]pyridin-3-yl]pyrazin-2-amine
6-[6-fluoro-2-(trifluoromethyl)imidazo[1,2-a]pyridin-3-yl]-N-(4-methylphenyl)pyrazin-2-amine
6-[6-methoxy-2-(trifluoromethyl)imidazo[1,2-a]pyridin-3-yl]-N-phenylpyrazin-2-amine
N-(4-chlorophenyl)-6-[6-methoxy-2-(trifluoromethyl)imidazo[1,2-a]pyridin-3-yl]pyrazin-2-amine
N-(4-bromophenyl)-6-[6-methoxy-2-(trifluoromethyl)imidazo[1,2-a]pyridin-3-yl]pyrazin-2-amine
N-(4-fluorophenyl)-6-[6-methoxy-2-(trifluoromethyl)imidazo[1,2-a]pyridin-3-yl]pyrazin-2-amine
6-[6-methoxy-2-(trifluoromethyl)imidazo[1,2-a]pyridin-3-yl]-N-(4-methylphenyl)pyrazin-2-amine; and,
6-(5,6-difluoro-2-methyl-1H-benzimidazol-1-yl)-N-[4-(trifluoromethyl)phenyl]pyrazin-2-amine,
wherein the form of the compound is selected from the group consisting of a salt, ester, hydrate, solvate, chelate, clathrate, isotopologue, stereoisomer, racemate, enantiomer, diastereomer and tautomer thereof.

3. The compound of claim 2, or form thereof, comprising: N-[4-(aminomethyl)phenyl]-6-(2-methyl-1H-benzimidazol-1-yl)pyrazin-2-amine trifluoroacetate.

4. A method of inhibiting Bmi-1 function and reducing the level of Bmi-1 to treat a cancer mediated by Bmi-1 in a subject in need thereof comprising administering to the subject an effective amount of the compound of claim 1, or form thereof.

5. The method of claim 4, further comprising contacting a cell having elevated Bmi-1 levels from the subject with an amount of the compound, or form thereof, wherein the cell is selected from the group consisting of a cancer cell, tumor cell, cancer stem cell and tumor stem cell, determining an effective amount of the compound that inhibits Bmi-1 function in the cell and subsequently administering the effective amount of the compound to the subject.

6. The method of claim 5, wherein the effective amount of the compound or form thereof determined to inhibit Bmi-1 function in the contacted cell reduces Bmi-1 levels in the contacted cell.

7. The method of claim 6, wherein the effective amount of the compound or form thereof is in a range of from about 0.001 mg/Kg/day to about 500 mg/Kg/day.

8. The method of claim 6, wherein the effective amount of the compound or form thereof is in a range of from about 0.1 ng to about 3500 mg.

9. The method of claim 4, comprising administering the compound or form thereof in combination with one or more additional agents selected from the group consisting of anti-cancer agents, anti-proliferative agents, chemotherapeutic agents, immunomodulatory agents, anti-angiogenic agents, anti-inflammatory agents, alkylating agents, steroidal and non-steroidal anti-inflammatory agents, pain relievers, leukotriene antagonists, β2-agonists, anticholinergic agents, hormonal agents, biological agents, tubulin binding agents, glucocorticoids, corticosteroid agents, antibacterial agents, antihistamines, anti-malarial agents, anti-viral agents and antibiotics; and, optionally with radiation therapy.

10. A method of inhibiting Bmi-1 function and reducing the level of Bmi-1 to treat a cancer mediated by Bmi-1 in a subject in need thereof comprising administering to the subject an effective amount of the compound of claim 2, or form thereof.

11. The method of claim 10, further comprising contacting a cell having elevated Bmi-1 levels from the subject with an amount of the compound, or form thereof, wherein the cell is selected from the group consisting of a cancer cell, tumor cell, cancer stem cell and tumor stem cell, determining an effective amount of the compound that inhibits Bmi-1 function in the cell and subsequently administering the effective amount of the compound to the subject.

12. The method of claim 11, wherein the effective amount of the compound or form thereof determined to inhibit Bmi-1 function in the contacted cell reduces Bmi-1 levels in the contacted cell.

13. The method of claim 12, wherein the effective amount of the compound or form thereof is in a range of from about 0.001 mg/Kg/day to about 500 mg/Kg/day.

14. The method of claim 12, wherein the effective amount of the compound or form thereof is in a range of from about 0.1 ng to about 3500 mg.

15. The method of claim 12, comprising administering the compound or form thereof in combination with one or more additional agents selected from the group consisting of anti-cancer agents, anti-proliferative agents, chemotherapeutic agents, immunomodulatory agents, anti-angiogenic agents, anti-inflammatory agents, alkylating agents, steroidal and non-steroidal anti-inflammatory agents, pain relievers, leukotriene antagonists, β2-agonists, anticholinergic agents, hormonal agents, biological agents, tubulin binding agents, glucocorticoids, corticosteroid agents, antibacterial agents, antihistamines, anti-malarial agents, anti-viral agents and antibiotics; and, optionally with radiation therapy.

16. A pharmaceutical composition for use in treating a cancer mediated by Bmi-1 comprising an effective amount of the compound of claim 1, or form thereof, in admixture with a pharmaceutically acceptable excipient.

17. A pharmaceutical composition for use in treating a cancer mediated by Bmi-1 comprising an effective amount of the compound of claim 2, or form thereof, in admixture with a pharmaceutically acceptable excipient.

* * * * *